(12) United States Patent
Babaoglu et al.

(10) Patent No.: US 9,284,323 B2
(45) Date of Patent: *Mar. 15, 2016

(54) NAPHTHALENE ACETIC ACID DERIVATIVES AGAINST HIV INFECTION

(71) Applicant: Gilead Sciences, Inc., Foster City, CA (US)

(72) Inventors: Kerim Babaoglu, Lansdale, PA (US); Gediminas Brizgys, Menlo Park, CA (US); Hongyan Guo, San Mateo, CA (US); Paul Hrvatin, Davis, CA (US); Eric Lansdon, San Jose, CA (US); John O. Link, San Francisco, CA (US); Hongtao Liu, Cupertino, CA (US); Ryan McFadden, Foster City, CA (US); Michael L. Mitchell, Castro Valley, CA (US); Yingmei Qi, Foster City, CA (US); Paul A. Roethle, San Francisco, CA (US); Randall W. Vivian, San Mateo, CA (US); Lianhong Xu, Palo Alto, CA (US); Hong Yang, Fremont, CA (US)

(73) Assignee: GILEAD SCIENCES, INC., Foster City, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/370,466

(22) PCT Filed: Jan. 3, 2013

(86) PCT No.: PCT/US2013/020172
§ 371 (c)(1),
(2) Date: Jul. 2, 2014

(87) PCT Pub. No.: WO2013/103738
PCT Pub. Date: Jul. 11, 2013

(65) Prior Publication Data
US 2015/0111891 A1  Apr. 23, 2015

Related U.S. Application Data

(60) Provisional application No. 61/583,136, filed on Jan. 4, 2012.

(51) Int. Cl.
| | | |
|---|---|---|
| *C07D 491/06* | (2006.01) | |
| *A61K 45/06* | (2006.01) | |
| *C07C 59/64* | (2006.01) | |
| *C07D 213/55* | (2006.01) | |
| *C07D 231/56* | (2006.01) | |
| *C07D 491/04* | (2006.01) | |
| *C07D 277/34* | (2006.01) | |
| *A61K 31/192* | (2006.01) | |
| *A61K 31/426* | (2006.01) | |
| *A61K 31/436* | (2006.01) | |
| *A61K 31/4402* | (2006.01) | |
| *A61K 31/4406* | (2006.01) | |
| *A61K 31/4409* | (2006.01) | |
| *A61K 31/506* | (2006.01) | |
| *A61K 31/5377* | (2006.01) | |
| *C07D 277/30* | (2006.01) | |

(52) U.S. Cl.
CPC ............ *C07D 491/06* (2013.01); *A61K 31/192* (2013.01); *A61K 31/426* (2013.01); *A61K 31/436* (2013.01); *A61K 31/4402* (2013.01); *A61K 31/4406* (2013.01); *A61K 31/4409* (2013.01); *A61K 31/506* (2013.01); *A61K 31/5377* (2013.01); *A61K 45/06* (2013.01); *C07C 59/64* (2013.01); *C07D 213/55* (2013.01); *C07D 231/56* (2013.01); *C07D 277/30* (2013.01); *C07D 277/34* (2013.01); *C07D 491/04* (2013.01)

(58) Field of Classification Search
CPC .. C07D 205/04; C07D 215/04; C07D 309/10; C07D 493/04; C07D 241/12
See application file for complete search history.

(56) References Cited

U.S. PATENT DOCUMENTS

| | | | |
|---|---|---|---|
| 3,895,028 | A | 7/1975 | Wada et al. |
| 3,900,486 | A | 8/1975 | Suzuki et al. |
| 4,816,570 | A | 3/1989 | Farquhar |
| 4,968,788 | A | 11/1990 | Farquhar |
| 5,434,188 | A | 7/1995 | Boschelli et al. |

(Continued)

FOREIGN PATENT DOCUMENTS

| | | | |
|---|---|---|---|
| CA | 1144556 A1 | 4/1983 | |
| CN | 1123275 A | 5/1996 | |

(Continued)

OTHER PUBLICATIONS

Al-Mawsawi, L.Q. et al. (Feb. 7, 2011; e-pub. Jan. 12, 2011). "Allosteric inhibitor development targeting HIV-1 integrase," *ChemMedChem.* 6(2):228-241.

(Continued)

*Primary Examiner* — Rita Desai
(74) *Attorney, Agent, or Firm* — Gilead Sciences, Inc.

(57) ABSTRACT

The invention provides compounds and salts thereof as d herein. The invention also provides pharmaceutical compositions comprising a compound disclosed herein, processes for preparing compounds disclosed herein, intermediates useful for preparing compounds disclosed herein and therapeutic methods for treating an HIV infection, treating the proliferation of the HIV virus, treating AIDS or delaying the onset of AIDS or ARC symptoms in a mammal using compounds disclosed herein.

10 Claims, No Drawings

(56) References Cited

U.S. PATENT DOCUMENTS

| | | |
|---|---|---|
| 5,663,159 A | 9/1997 | Starrett, Jr. et al. |
| 5,733,906 A | 3/1998 | Jungheim et al. |
| 5,738,985 A | 4/1998 | Miles et al. |
| 5,792,756 A | 8/1998 | Starrett, Jr. et al. |
| 5,798,365 A | 8/1998 | Kirsch et al. |
| 7,514,233 B2 | 4/2009 | Debyser et al. |
| 8,008,470 B2 | 8/2011 | Debyser et al. |
| 2005/0165052 A1 | 7/2005 | Fakhfakh et al. |
| 2005/0239819 A1 | 10/2005 | Satoh et al. |
| 2005/0261336 A1 | 11/2005 | Mousnier et al. |
| 2006/0035926 A1 | 2/2006 | Lee et al. |
| 2006/0094755 A1 | 5/2006 | Rajagopalan et al. |
| 2006/0275748 A1 | 12/2006 | Debyser et al. |
| 2009/0197862 A1 | 8/2009 | Steinig et al. |
| 2009/0203742 A1 | 8/2009 | Surleraux et al. |
| 2010/0311735 A1 | 12/2010 | Tsantrizos et al. |
| 2011/0223131 A1 | 9/2011 | Jin et al. |
| 2012/0329780 A1 | 12/2012 | Thormann et al. |
| 2012/0329785 A1 | 12/2012 | Thormann et al. |
| 2013/0203727 A1 | 8/2013 | Babaoglu et al. |
| 2013/0210801 A1 | 8/2013 | Babaoglu et al. |
| 2013/0231331 A1 | 9/2013 | Pendri et al. |
| 2013/0281433 A1 | 10/2013 | Babaoglu et al. |
| 2013/0281434 A1 | 10/2013 | Babaoglu et al. |
| 2014/0031338 A1 | 1/2014 | Chasset et al. |
| 2014/0045818 A1 | 2/2014 | Mitchell et al. |
| 2014/0120087 A1 | 5/2014 | Schulze et al. |

FOREIGN PATENT DOCUMENTS

| | | |
|---|---|---|
| CN | 1044117 C | 7/1999 |
| CN | 1466576 A | 1/2004 |
| DE | 24 03 682 A1 | 7/1974 |
| EP | 0 017 543 A1 | 10/1980 |
| EP | 1 441 228 A1 | 7/2004 |
| EP | 1 541 558 A1 | 6/2005 |
| EP | 1 565 471 B1 | 10/2006 |
| EP | 1 873 238 A1 | 1/2008 |
| EP | 1 873 238 B1 | 1/2008 |
| GB | 2 154 583 A | 9/1985 |
| JP | 3-287558 A | 12/1991 |
| WO | WO-91/19721 A1 | 12/1991 |
| WO | WO-94/23041 A2 | 10/1994 |
| WO | WO-94/23041 A3 | 10/1994 |
| WO | WO-99/52850 A1 | 10/1999 |
| WO | WO-00/63152 A1 | 10/2000 |
| WO | WO-02/18341 A2 | 3/2002 |
| WO | WO-02/18341 A3 | 3/2002 |
| WO | WO-2004/014371 A1 | 2/2004 |
| WO | WO-2004/046115 A1 | 6/2004 |
| WO | WO-2004/087153 A2 | 10/2004 |
| WO | WO-2004/087153 A3 | 10/2004 |
| WO | WO-2005/120508 A1 | 12/2005 |
| WO | WO-2006/001958 A2 | 1/2006 |
| WO | WO-2006/001958 A3 | 1/2006 |
| WO | WO-2006/002185 A1 | 1/2006 |
| WO | WO-2006/116412 A2 | 11/2006 |
| WO | WO-2006/116412 A3 | 11/2006 |
| WO | WO-2006/124780 A2 | 11/2006 |
| WO | WO-2006/124780 A3 | 11/2006 |
| WO | WO-2007/016392 A2 | 2/2007 |
| WO | WO-2007/016392 A3 | 2/2007 |
| WO | WO-2007/131350 A1 | 11/2007 |
| WO | WO-2007/138472 A2 | 12/2007 |
| WO | WO-2007/138472 A3 | 12/2007 |
| WO | WO-2007/147884 A1 | 12/2007 |
| WO | WO-2008/053478 A2 | 5/2008 |
| WO | WO-2008/053478 A3 | 5/2008 |
| WO | WO-2008/071587 A2 | 6/2008 |
| WO | WO-2008/071587 A3 | 6/2008 |
| WO | WO-2009/062285 A1 | 5/2009 |
| WO | WO-2009/062288 A1 | 5/2009 |
| WO | WO-2009/062289 A1 | 5/2009 |
| WO | WO-2009/062308 A1 | 5/2009 |
| WO | WO-2009/095500 A1 | 8/2009 |
| WO | WO-2010/059658 A1 | 5/2010 |
| WO | WO-2010/130034 A1 | 11/2010 |
| WO | WO-2010/130842 A1 | 11/2010 |
| WO | WO-2011/002635 A1 | 1/2011 |
| WO | WO-2011/015641 A1 | 2/2011 |
| WO | WO-2011/047129 A1 | 4/2011 |
| WO | WO-2011/076765 A1 | 6/2011 |
| WO | WO-2011/106445 A1 | 9/2011 |
| WO | WO-2011/149950 A2 | 12/2011 |
| WO | WO-2011/149950 A3 | 12/2011 |
| WO | WO-2012/003497 A1 | 1/2012 |
| WO | WO-2012/003498 A1 | 1/2012 |
| WO | WO-2012/033735 A1 | 3/2012 |
| WO | WO-2012/065963 A2 | 5/2012 |
| WO | WO-2012/065963 A3 | 5/2012 |
| WO | WO-2012/066442 A1 | 5/2012 |
| WO | WO-2012/088365 A1 | 6/2012 |
| WO | WO-2012/102985 A1 | 8/2012 |
| WO | WO-2012/137181 A1 | 10/2012 |
| WO | WO-2012/138669 A1 | 10/2012 |
| WO | WO-2012/138670 A1 | 10/2012 |
| WO | WO-2012/140243 A1 | 10/2012 |
| WO | WO-2012/145728 A1 | 10/2012 |
| WO | WO-2013/002357 A1 | 1/2013 |
| WO | WO-2013/025584 A1 | 2/2013 |
| WO | WO-2013/043553 A1 | 3/2013 |
| WO | WO-2013/058448 A1 | 4/2013 |
| WO | WO-2013/062028 A1 | 5/2013 |
| WO | WO-2013/103724 A1 | 7/2013 |
| WO | WO-2013/106643 A2 | 7/2013 |
| WO | WO-2013/106643 A3 | 7/2013 |
| WO | WO-2013/123148 A1 | 8/2013 |
| WO | WO-2013/134113 A1 | 9/2013 |
| WO | WO-2013/134142 A1 | 9/2013 |
| WO | WO-2013/157622 A1 | 10/2013 |
| WO | WO-2013/159064 A1 | 10/2013 |
| WO | WO-2014/009794 A1 | 1/2014 |
| WO | WO-2014/028384 A1 | 2/2014 |
| WO | WO-2014/055603 A1 | 4/2014 |
| WO | WO-2014/055618 A1 | 4/2014 |

OTHER PUBLICATIONS

Balakrishnan, M. et al. (Sep. 9, 2013). "Non-catalytic site HIV-1 integrase inhibitors disrupt core maturation and induce a reverse transcription block in target cells," *PloS One* 8(9):e74163, Twelve Total Pages.

Bartholomeeusen, K. et al. (Apr. 24, 2009; e-pub. Feb. 25, 2009). "Lens epithelium-derived growth factor/p75 interacts with the transposase-derived DDE domain of PogZ," *J. Biol. Chem.* 284(17):11467-11477.

Benzaria, S. et al. (Dec. 6, 1996). "Synthesis, In Vitro Antiviral Evaluation, and Stability Studies of Bis(S-Acyl-2-Thioethyl) Ester Derivatives of 9-[2-(Phosphonomethoxy)Ethyl]adenine (PMEA) as Potential PMEA Prodrugs with Improved Oral Bioavailability," *J. Med. Chem.* 39(25):4958-4965.

Bundgaard, H. (1991). "Design and Application of Prodrugs," Chapter 5 in *A Textbook of Drug Design and Development*, Krogsgaard-Larsen, P. et al. eds., Harwood Academic Publishers, Chur, Switzerland, pp. 113-191.

Busschots, K. et al. (Feb. 2, 2007; e-pub. Nov. 3, 2006). "Identification of the LEDGF/p75 binding site in HIV-1 integrase," *J. Mol. Biol.* 365(5):1480-1492.

Busschots, K. et al. (Jan. 2009; e-pub. Oct. 16, 2008). "In search of small molecules blocking interactions between HIV proteins and intracellular cofactors," *Mol. Biosyst.* 5(1):21-31.

Chakraborty, A. et al. (Mar. 1, 2013; e-pub. Dec. 25, 2012). "Biochemical interactions between HIV-1 integrase and reverse transcriptase," *FEBS Letters* 587(5):425-429.

Chen, S. et al. (2009, e-pub. Jan. 23, 2009). "Design, Synthesis, and Biological Evaluation of Novel Quinoline Derivatives as HIV-1 Tat-TAR Interaction Inhibitors," *Bioorganic & Medicinal Chem.* 17:1948-1956.

Cherepanov, P. et al. (Jun. 2005; e-pub. May 15, 2005). "Solution structure of the HIV-1 integrase-binding domain in LEDGF/p75," *Nat. Struct. Mol. Biol.* 12(6):526-532.

(56) References Cited

OTHER PUBLICATIONS

Cherepanov, P. et al. (Nov. 29, 2005; e-pub. Oct. 31, 2005). "Structural basis for the recognition between HIV-1 integrase and transcriptional coactivator p75," *PNAS* 102(48):17308-17313.

Christ, F. et al. (Aug. 2012; e-pub. Jun. 4, 2012). "Small-molecule inhibitors of the LEDGF/p75 binding site of integrase block HIV replication and modulate integrase multimerization," *Antimicrob. Agents Chemother.* 56(8):4365-4374.

Christ, F. et al. (Jun. 2010; e-pub. May 16, 2010). "Rational design of small-molecule inhibitors of the LEDGF/p75-integrase interaction and HIV replication," *Nat. Chem. Bio.*, Twenty-Five Total Pages.

De Lombaert, S. et al. (Feb. 18, 1994). "*N*-Phosphonomethyl Dipeptides and Their Phosphonate Prodrugs, a New Generation of Neutral Endopeptidase (NEP, EC 3.4.24.11) Inhibitors," *J. Med. Chem.* 37(4):498-511.

De Luca, L. et al. (Feb. 2011; e-pub. Dec. 21, 2010). "HIV-1 integrase strand-transfer inhibitors: design, synthesis and molecular modeling investigation," *Eur. J. Med. Chem.* 46(2):756-764.

De Luca, L. et al. (Jul. 2011). "Inhibition of the interaction between HIV-1 integrase and its cofactor LEDGF/p75: a promising approach in anti-retroviral therapy," *Mini Rev. Med. Chem.* vol. 11, Fourteen Total Pages.

Desimmie, B.A. et al. (May 30, 2013). "LEDGINs inhibit late stage HIV-1 replication by modulating integrase multimerization in the virions," *Retrovirology* 10:57, Sixteen Total Pages.

Engelman, A. et al. (Mar. 28, 2008). "The lentiviral integrase binding protein LEDGF/p75 and HIV-1 replication," *PloS Pathog.* 4(3):e1000046, Nine Total Pages.

Farquhar, D. et al. (Mar. 1983). "Biologically Reversible Phosphate-Protective Groups," *J. Pharm. Sci.* 72(3):324-325.

Graham, R.L.J. et al. (2011). "Proteomic Analysis of LEDGF/p75 Interactions with Nuclear Proteins," ASMS Poster, one page.

Hauser, F.M. et al. (1978). "New Synthetic Methods for the Regioselective Annelation of Aromatic Rings: 1-Hydroxy-2,3-Disubstituted Naphthalenes and 1,4-Dihydroxy-2,3-Disubstituted Naphthalenes," *J. Org. Chem.* 43(1):178-180.

Hayouka, Z. et al. (2010). "Cyclic Peptide Inhibitors of HIV-1 Integrase Derived from the LEDGF/p75 Protein," *Bioorganic & Medicinal Chemistry* 18:8388-8395.

Hombrouck, A. et al. (Mar. 2007). "Virus Evolution Reveals an Exclusive Role for LEDGF/p75 in Chromosomal Tethering," *PloS* 3(3):e47, Thirteen Total Pages.

Huang, X. et al. (2007). "A Novel Multicomponent Reaction of Arynes, β-Keto Sulfones, and Michael-Type Acceptors: A Direct Synthesis of Polysubstituted Naphthols and Naphthalenes," *J. Org. Chem.* 72:3965-3968.

Johns, B.A. et al. (2013). "HIV Integrase Inhibitors," Chapter 6 *in Successful Strategies for the Discovery of Antiviral Drugs*, Desai, M.C. et al. eds., RSC Publishing, pp. 149-188.

Jurado, K.A. et al. (2013). "Allosteric Integrase Inhibitor Potency is Determined through the Inhibition of HIV-1 Particle Maturation," *PNAS* 110(21):8690-8695.

Kessl, J.J. et al. (2011). "FRET Analysis Reveals Distinct Conformations of IN Tetramers in the Presence of Viral DNA or LEDGF/p75," *Nuc. Acids Res.*, pp. 1-14.

Khamnei, S. et al. (Sep. 27, 1996). "Neighboring Group Catalysis in the Design of Nucleotide Prodrugs," *J. Med. Chem.* 39(20):4109-4115.

Kocienski, P.J. (May 1994). "Protecting Groups: An Overview," Chapter 1 *in Protecting Groups*, Thieme Publishing Group: New York, NY, pp. 1-20.

Kocienski, P.J. (May 1994). "Hydroxyl Protecting Groups," Chapter 2 *in Protecting Groups*, Thieme Publishing Group: New York, NY, pp. 21-94.

Kocienski, P.J. (May 1994). "Diol Protecting Groups," Chapter 3 *in Protecting Groups*, Thieme Publishing Group: New York, NY, pp. 95-117.

Kocienski, P.J. (May 1994). "Carboxyl Protecting Groups," Chapter 4 *in Protecting Groups*, Thieme Publishing Group: New York, NY, pp. 118-154.

Kocienski, P.J. (May 1994). "Carbonyl Protecting Groups," Chapter 5 *in Protecting Groups*, Thieme Publishing Group: New York, NY, pp. 155-184.

Llano, M. et al. (Sep. 2004). "LEDGF/p75 determines cellular trafficking of diverse lentiviral but not murine oncoretroviral integrase proteins and is a component of functional lentiviral preintegration complexes," *J. Virol.* 78(17):9524-9537.

Llano, M. et al. (Oct. 20, 2006; e-pub. Sep. 7, 2006). "An essential role for LEDGF/p75 in HIV integration," *Science* 314(5798):461-464.

McGinnity, D.F. et al. (Nov. 2004, e-pub. Jul. 30, 2004). "Evaluation of Fresh and Cryopreserved Hepatocytes as in Vitro Drug Metabolism Tools for the Prediction of Metabolic Clearance," *Drug Metab. Dispos.* 32(11):1247-1253.

Mekouar, K. et al. (Jul. 16, 1998; e-pub. Jun. 25, 1998). "Styrylquinoline Derivatives: A New Class of Potent HIV-1 Integrase Inhibitors That Block HIV-1 Replication in CEM Cells," *J. Med. Chem.* 41(15):2846-2857.

Mitchell, A.G. et al. (1992). "Bioreversible Protection for the Phospho Group: Bioactivation of the Di(4-Acyloxybenzyl) and Mono(4-acyloxybenzyl) Phosphoesters of Methylphosphonate and Phosphonoacetate," *J. Chem. Soc. Perkin Trans. I* 2345-2353.

Obach, R.S. et al. (Oct. 1997). "The Prediction of Human Pharmacokinetic Parameters from Preclinical and In Vitro Metabolism Data," *J. Pharmacol. Exp. Ther.* 283(1):46-58.

Palella, F.J. et al. (Mar. 26, 1998). "Declining Morbidity and Mortality Among Patients with Advanced Human Immunodeficiency Virus Infection," *N. Engl. J. Med.* 338(13):853-860.

Pauwels, R. et al. (Jun. 1987). "Sensitive and Rapid Assay on MT-4 Cells for Detection of Antiviral Compounds Against the AIDS Virus," *J. Virol. Methods* 16(3):171-185.

Pendri, A. et al. (Aug. 2011, e-pub. May 20, 2011). "New First and Second Generation Inhibitors of Human Immunodeficiency Virus-1 Integrase," *Expert Opin. Ther. Pat.* 21(8):1173-1189.

Poeschla, E.M. et al. (2008). "Integrase, LEDGF/p75 and HIV Replication," *Cell. Mol. Life Sci.* 65:1403-1424.

Porto, S. et al. (2007). "Chiral Thiols: The Assignment of Their Absolute Configuration by $^1$H NMR," *Organic Letters* 9(24):5015-5018.

Puech, F. et al. (Oct. 1993). "Intracellular Delivery of Nucleoside Monophosphates Through a Reductase-Mediated Activation Process," *Antiviral Res.* 22(2-3):155-174.

Rain, J.C. et al. (2009). "Yeast-Two Hybrid Detection of Integrase-Host Factor Interactions," *Methods*, Seven Total Pages.

Rhodes, D.I. et al. (Oct. 17, 2011; e-pub. Aug. 17, 2011). "Crystal structures of novel allosteric peptide inhibitors of HIV integrase identify new interactions at the LEDGF binding site," *Chembiochem.* 12(15):2311-2315.

Richman, D.D. (Apr. 19, 2001). "HIV Chemotherapy," *Nature* 410:995-1001.

Sagar, K.S. et al. (Aug. 1, 2004, e-pub. Jun. 19, 2004). "Preparation and Anti-HIV Activities of Retrojusticidin B Analogs and Azalignans," *Bioorg. Med .Chem.* 12(15):4045-4054.

Shun, M.C. et al. (Jul. 15, 2007). "LEDGF/p75 functions downstream from preintegration complex formation to effect gene-specific HIV-1 integration," *Genes Dev.* 21(14):1767-1778.

Spivey, A.C. et al. (1999, e-pub. Dec. 4, 1999). "Configurationally Stable Biaryl Analogues of 4-(Dimethylamino) Pyridine: A Novel Class of Chiral Nucleophilic Catalysts," *J. Org. Chem.* 64(26):9430-9443.

Suzuki, Y. et al. (Mar. 2007). "The Road to Chromatin—Nuclear Entry of Retroviruses," *Nat. Rev. Microbiol.* 5(3):187-196.

Tsiang, M. et al. (Jun. 15, 2012; e-pub. Apr. 25, 2012). "New class of HIV-1 integrase (IN) inhibitors with a dual mode of action," *J. Biol. Chem.* 287(25):21189-21203.

Vandekerckhove, L. et al. (Feb. 2006). "Transient and stable knockdown of the integrase cofactor LEDGF/p75 reveals its role in the replication cycle of human immunodeficiency virus," *J. Virol.* 80(4):1886-1896.

Walker, M.A. (2009). "New approaches for inhibiting HIV integrase: a journey beyond the active site," *Curr. Opin. Investig. Drugs* 10(2):129-136.

(56) References Cited

OTHER PUBLICATIONS

Wang, C.Y. et al. (Dec. 2004). "Pharmacokinetic and Metabolic Studies of Retrojusticidin B, A Potential Anti-Viral Lignan, in Rats," *Planta Medica* 70(12):1161-1165.
Wenhua, Z. et al. (2003). "Advances on Effects of Natural Products Against AIDS Virus," *Chinese Traditional Patent Medicine* 25(9):750-752 (with English Translation).
Willgerodt, C. et al. (1900). "Regarding Quino-α:p-α-Phenyl and Quino-α:p-α Methyl Quinoline-γ-Hydroxy Acid," *Reports of the German Chemical Society* 33(3):2927-2935 (with full English Translation).
Zhan, P. et al. (2009). "Synthesis and Anti-HIV Activity Evaluation of 2-(4-(Naphthalen-2-yl)-1,2,3-thiadiazol-5-ylthio)-*N*-Acetamides as Novel Non-Nucleoside HIV-1 Reverse Transcriptase Inhibitors," *European Journal of Medicinal Chem.* 44:4648-4653.
Zouhiri, F. et al. (2001). "HIV-1 Replication Inhibitors of the Styrylquinoline Class: Incorporation of a Masked Diketo Acid Pharmacophore," *Tetrahedron Letters* 42:8189-8192.
Restriction Requirement mailed on Nov. 8, 2013 for U.S. Appl. No. 13/866,997, filed Apr. 19, 2013, eight pages.
Restriction Requirement mailed on Apr. 24, 2014, for U.S. Appl. No. 14/112,473, filed Oct. 17, 2013, eight pages.
Non-Final Office Action mailed on May 23, 2014, for U.S. Appl. No. 13/866,997, filed Apr. 19, 2013, eight pages.
Non-Final Office Action mailed on Nov. 4, 2014, for U.S. Appl. No. 13/867,016, filed Apr. 19, 2013, seven pages.
Notice of Allowance mailed on Aug. 15, 2014, for U.S. Appl. No. 14/112,473, filed Oct. 17, 2013, seven pages.
Notice of Allowance mailed on Nov. 7, 2014, for U.S. Appl. No. 13/866,997, filed Apr. 19, 2013, eight pages.
Australian Office Action mailed on Feb. 26, 2014, for Australian Patent Application No. 2011274323, filed on Jul. 1, 2011, three pages.
Australian Office Action mailed on Mar. 7, 2014, for Australian Patent Application No. 2011274322 filed on Jul. 1, 2011, three pages.
Bolivian Opposition submitted to the Bolivian Patent Office for Bolivian Patent Application No. SP-0194-2011, filed on Jul. 1, 2011, two pages.
Chinese Office Action mailed on Mar. 3, 2014, for Chinese Patent Application No. 201180038442.X filed on Jul. 1, 2011, eight pages.
Chinese Office Action mailed on Mar. 25, 2014 for Chinese Patent Application No. 201180038443.4, filed on Jul. 1, 2011, eight pages.
Costa Rican Opposition filed Apr. 28, 2014 against Costa Rican Patent Application No. 201320102, filed Jul. 1, 2011, sixteen pages.
Bolivian Opposition submitted to the Bolivian Patent Office for Bolivian Patent Application No. SP-0195-2011, filed on Jul. 1, 2011, two pages.
Columbian Office Action mailed on Feb. 20, 2014, for Columbian Patent Application No. 12236161 filed on Jul. 1, 2011, ten pages.
Columbian Office Action mailed on Jun. 12, 2014 for Columbian Patent Application No. 12236158, filed on Jul. 1, 2011, twelve pages.
Columbian Office Action mailed on Oct. 17, 2014 for Columbian Patent Application No. 12236158, filed on Jul. 1, 2011, thirteen pages.
Costa Rican Office Action mailed on Aug. 23, 2013 for Costa Rican Patent Application No. 20130045, filed on Jul. 1, 2011, three pages.
Costa Rican Opposition submitted to the Costa Rican Patent Office for Costa Rican Patent Application No. 20130043, filed on Jul. 1, 2011, three pages.
Eurasian Office Action mailed on Mar. 19, 2014, for Eurasian Patent Application No. 201291300 filed on Jul. 1, 2011, four pages.
Eurasian Office Action mailed in Apr. 9, 2014, for Eurasian Patent Application No. 201291301, filed on Jul. 1, 2011, three pages.
International Search Report mailed on Feb. 21, 2013, for PCT Patent Application No. PCT/US2013/020172 filed on Jan. 3, 2013, four pages.
International Search Report mailed on Sep. 1, 2011, for PCT Patent Application No. PCT/US2011/042880 filed on Jul. 1, 2011, four pages.
International Search Report mailed on Sep. 14, 2011, for PCT Patent Application No. PCT/US2011/042881 filed on Jul. 1, 2011, seven pages.
International Search Report mailed on Mar. 26, 2013, for PCT Patent Application No. PCT/US2013/020151 filed on Jan. 3, 2013, five pages.
International Search Report mailed on Jul. 2, 2012, for PCT Patent Application No. PCT/US2012/034593 filed on Apr. 20, 2012, five pages.
International Search Report mailed on Aug. 5, 2013, for PCT Patent Application No. PCT/US2013/037483 filed on Apr. 19, 2013, three pages.
Israeli Office Action mailed on Mar. 3, 2014 for Israeli Patent Application No. 223558, filed on Jul. 1, 2011, two pages.
New Zealand Office Action mailed on Aug. 22, 2013 for New Zealand Patent Application No. 604598, filed on Jul. 1, 2011, two pages.
Ecuadoran Opposition filed Apr. 23, 2014 against Ecuadoran Patent Application No. SP1312418, filed Jul. 1, 2011, ten pages.
Ecuadoran Opposition from Jun. Of 2014, against Ecuadoran Patent Application No. SP1312417, filed Jul. 1, 2011, nine pages.
Philippine Office Action mailed on Aug. 1, 2014, for Philippine Patent Application No. 12013500011, filed on Jul. 1, 2011, two pages.
Written Opinion of the International Searching Authority mailed on Sep. 1, 2011, for PCT Patent Application No. PCT/US2011/042880 filed on Jul. 1, 2011, six pages.
Written Opinion of the International Searching Authority mailed on Sep. 14, 2011, for PCT Patent Application No. PCT/US2011/042881 filed on Jul. 1, 2011, twelve pages.
Written Opinion of the International Searching Authority mailed on Jul. 2, 2012, for PCT Patent Application No. PCT/US2012/034593 filed on Apr. 20, 2012, six pages.
Written Opinion of the International Searching Authority mailed on Aug. 5, 2013, for PCT Patent Application No. PCT/US2013/037483 filed on Apr. 19, 2013, seven pages.
Written Opinion of the International Searching Authority mailed on Jul. 17, 2014, for PCT Patent Application No. PCT/US2013/020151 filed on Jan. 3, 2013, six pages.
Written Opinion of the International Searching Authority mailed on Jul. 17, 2014, for PCT Patent Application No. PCT/US2013/020172, filed on Jan. 3, 2013, seven pages.
International Preliminary Report on Patentability mailed on Jan. 17, 2013, for PCT Patent Application No. PCT/US2011/042880 filed on Jul. 1, 2011, seven pages.
European Communication mailed on Oct. 15, 2013, for European Patent Application No. 11738878.5 filed on Jul. 1, 2011, four pages.
European Communication mailed on Feb. 8, 2013, for European Patent Application No. 11738878.5 filed on Jul. 1, 2011, two pages.
European Communication mailed on Mar. 12, 2014, for European Patent Application No. 11738878.5 filed on Jul. 1, 2011, eight pages.
European Communication mailed on Feb. 15, 2013, for European Patent Application No. 11738339.8, filed on Jul. 1, 2011, two pages.
European Office Action mailed on Oct. 20, 2014, for European Patent Application No. 13719355.3, filed on Apr. 19, 2013, four pages.
Pakistani Office Action mailed on Nov. 10, 2012, for Pakistani Patent Application No. 4932011, filed on Jul. 1, 2011, two pages.
Pakistani Office Action mailed on Nov. 10, 2012, for Pakistani Patent Application No. 4942011, filed on Jul. 1, 2011, two pages.
Philippines Office Action mailed on Mar. 14, 2014, for Philippine Patent Application No. 1/2013/500011, filed on Jul. 1, 2011, two pages.
Taiwanese Office Action mailed on Nov. 5, 2013, for Taiwanese Patent Application No. 100123357, filed on Jul. 1, 2011, nine pages.
Mexican Office Action mailed on Mar. 13, 2014, for Mexican Patent Application No. MX/a/2012/015293, filed on Jul. 1, 2011, seven pages.
Vietnamese Office Action mailed on Jul. 28, 2014, for Vietnamese Patent Application No. 1-201300326, filed on Jul. 1, 2011, two pages.

NAPHTHALENE ACETIC ACID DERIVATIVES AGAINST HIV INFECTION

CROSS REFERENCE TO RELATED APPLICATIONS

This patent application is a National Phase filing under 35 U.S.C. §371 of International Application No. PCT/US2013/020172, having an international filing date of Jan. 3, 2013, which claims the benefit of priority of U.S. Application Ser. No. 61/583,136, filed Jan. 4, 2012. The contents of these applications are hereby incorporated herein by reference in their entirety.

BACKGROUND OF THE INVENTION

Human immunodeficiency virus (HIV) infection and related diseases are a major public health problem worldwide. Human immunodeficiency virus type 1 (HIV-1) encodes three enzymes which are required for viral replication: reverse transcriptase, protease, and integrase. Although drugs targeting reverse transcriptase and protease are in wide use and have shown effectiveness, particularly when employed in combination, toxicity and development of resistant strains have limited their usefulness (Palella, et al *N. Engl. J. Med.* (1998) 338:853-860; Richman, D. D. *Nature* (2001) 410:995-1001). Accordingly, there is a need for new agents that inhibit the replication of HIV. There is also a need for agents that are directed against alternate sites in the viral life cycle including agents that target the inhibition of integrase.

SUMMARY

Compounds and methods for the treatment of an HIV infection are disclosed.

Accordingly, one embodiment provides a compound selected from:

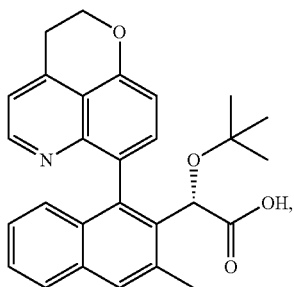

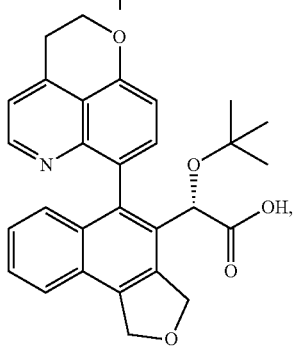

-continued

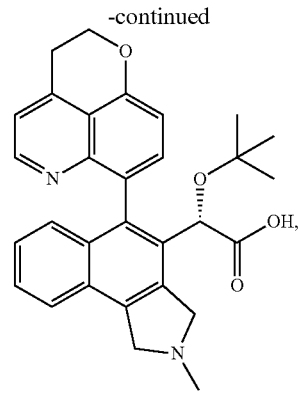

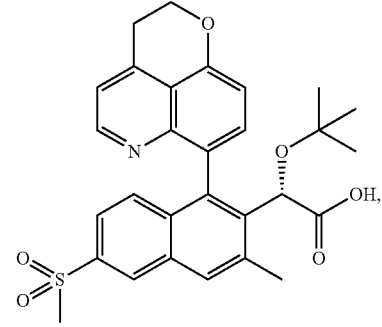

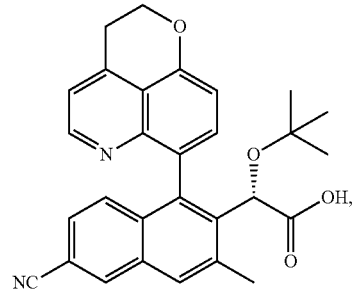

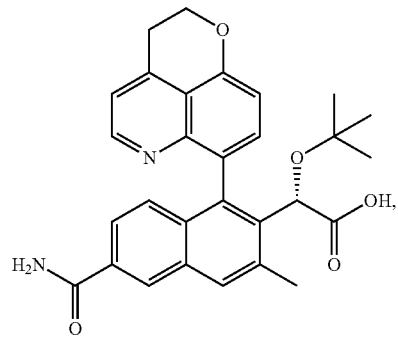

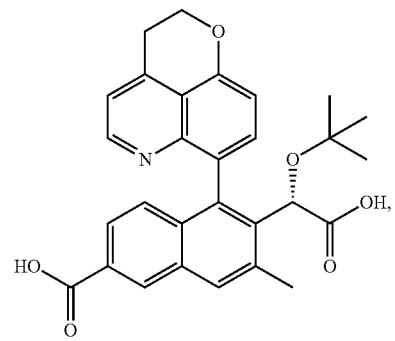

-continued
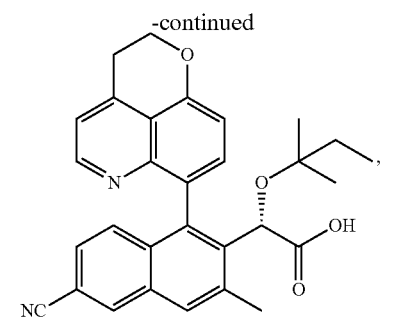
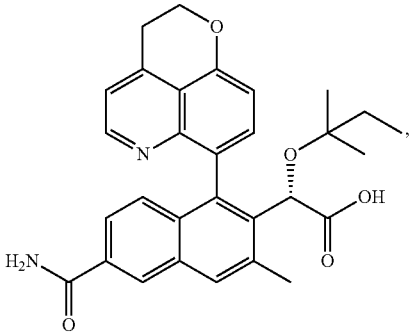
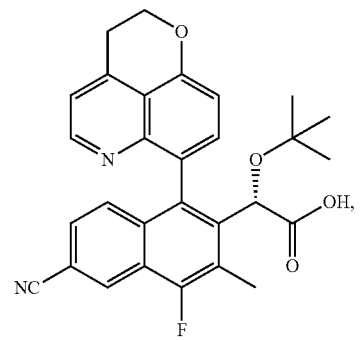
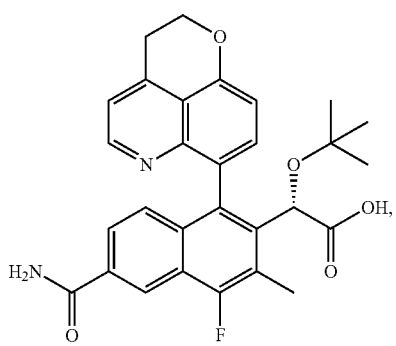
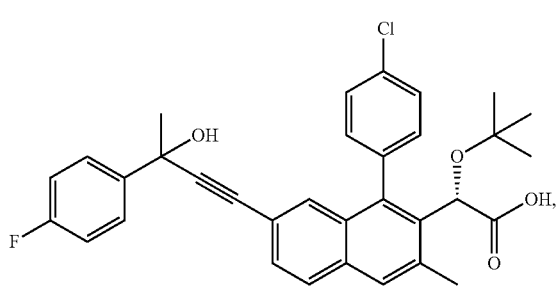
-continued
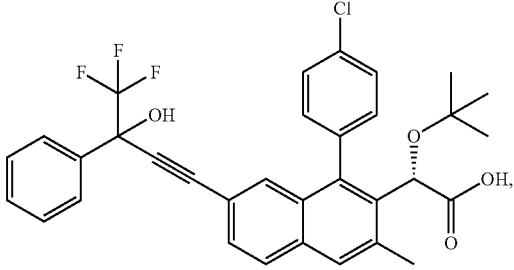
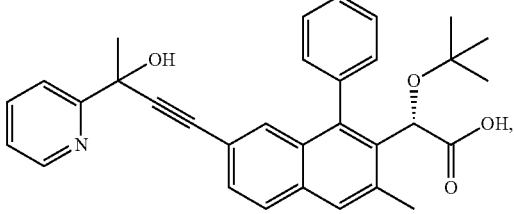
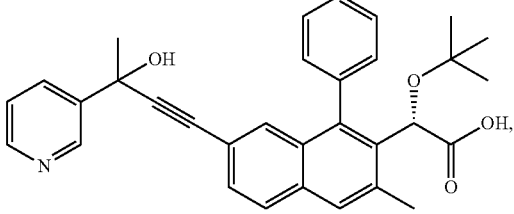
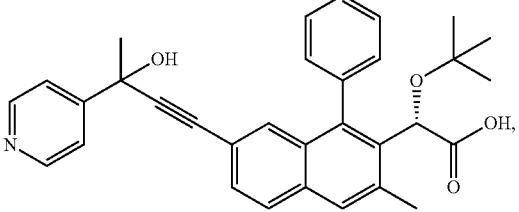
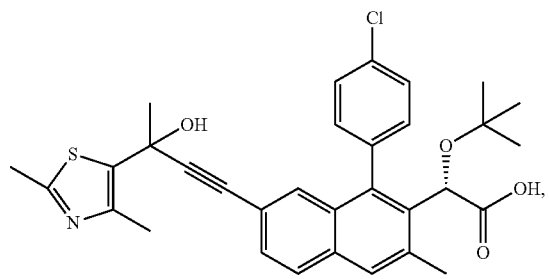
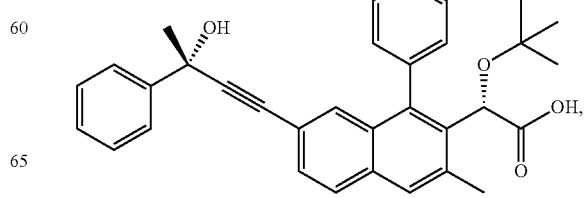

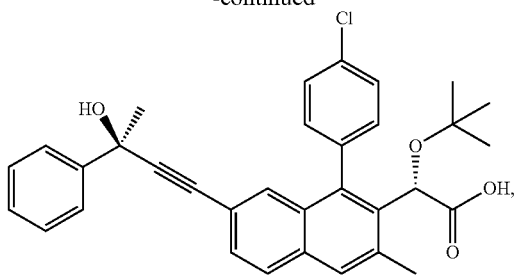
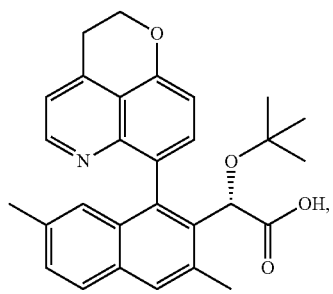
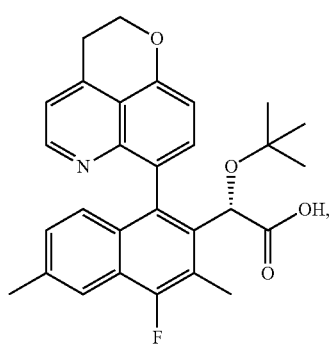
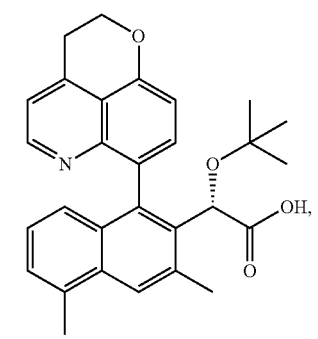
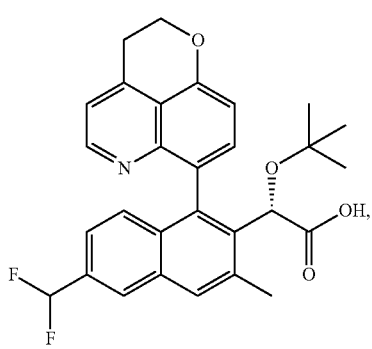
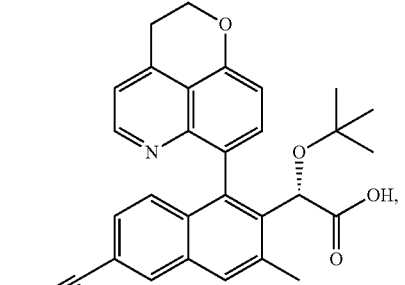
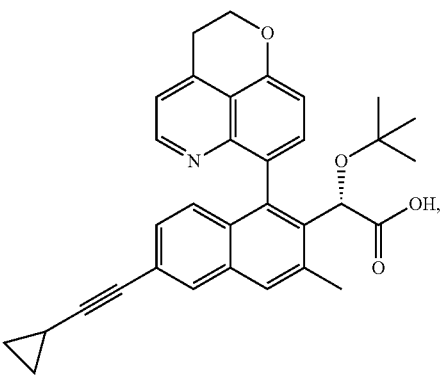
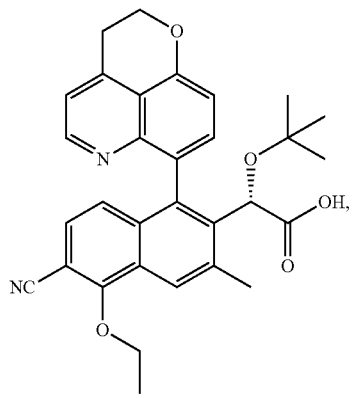
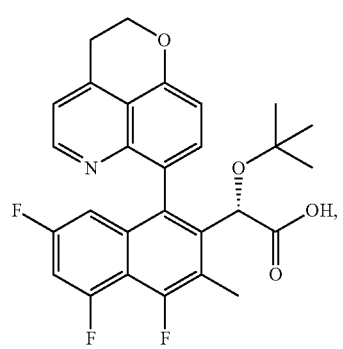

-continued
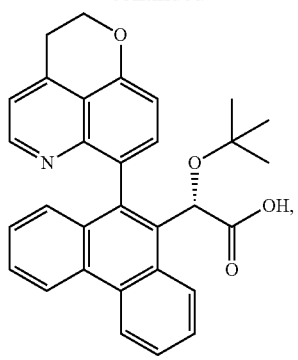
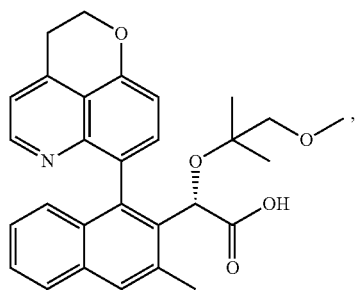
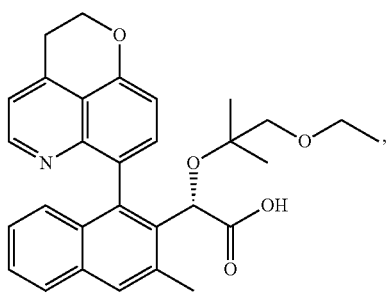
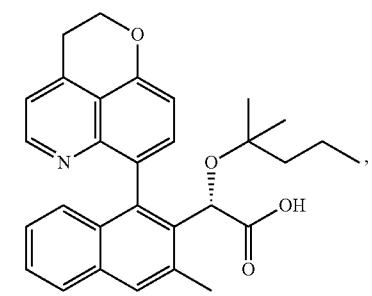
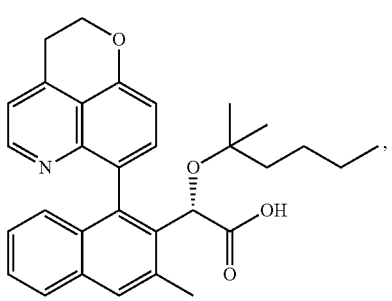
-continued
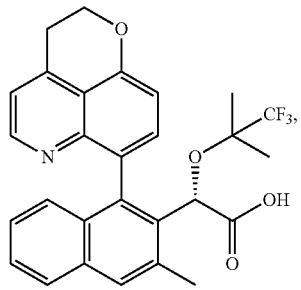
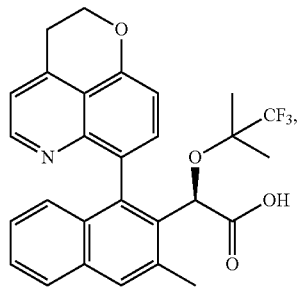
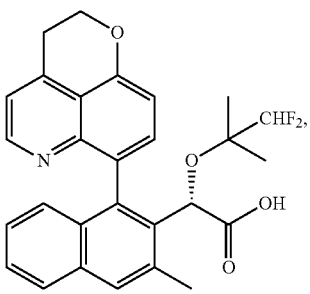
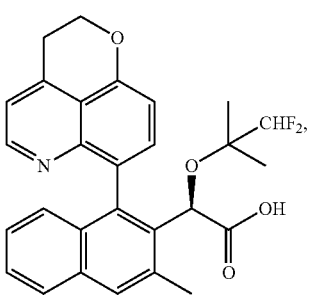
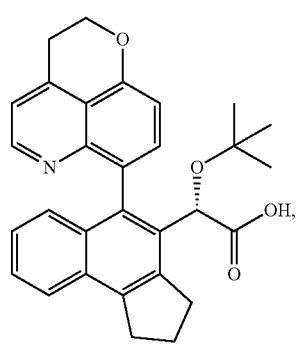

9
-continued
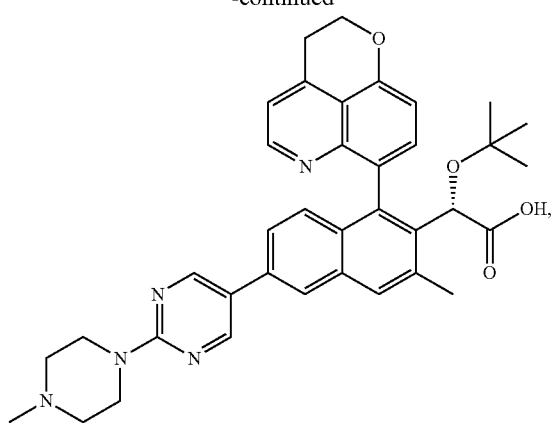
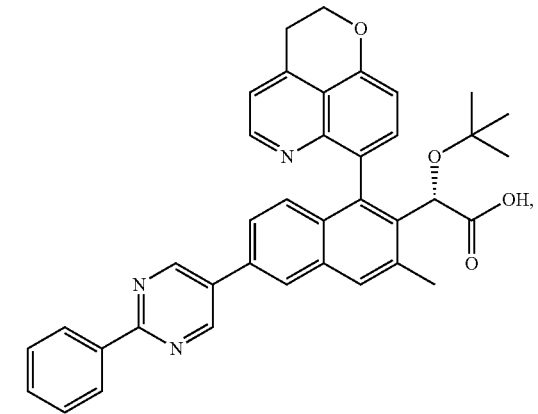
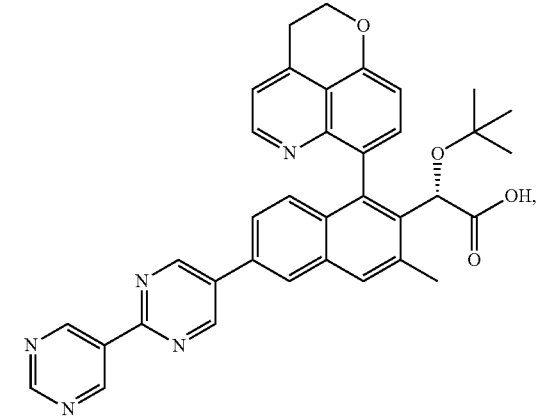
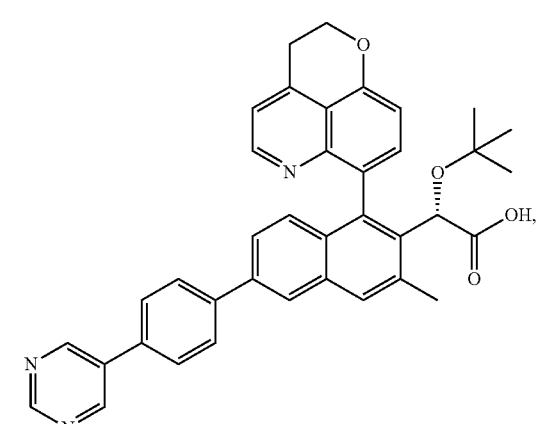
10
-continued
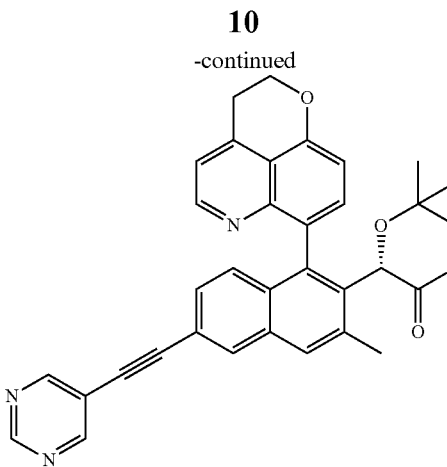
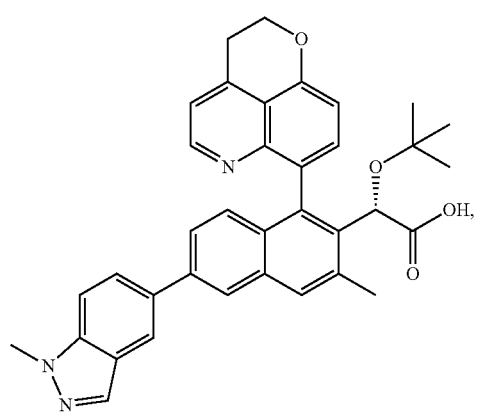
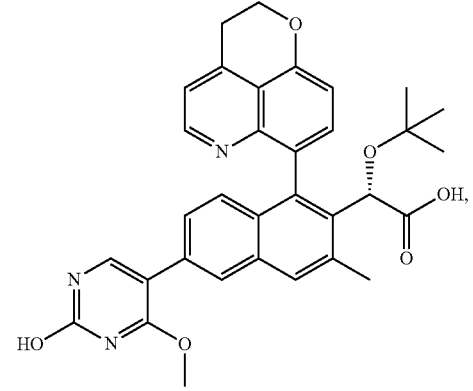
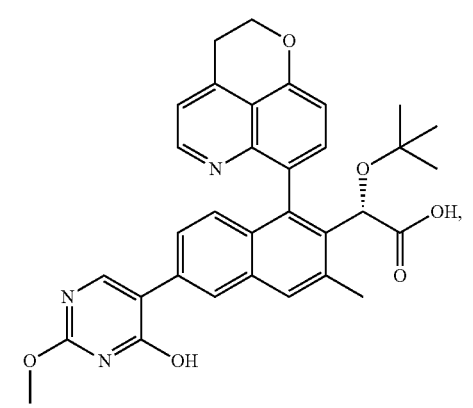

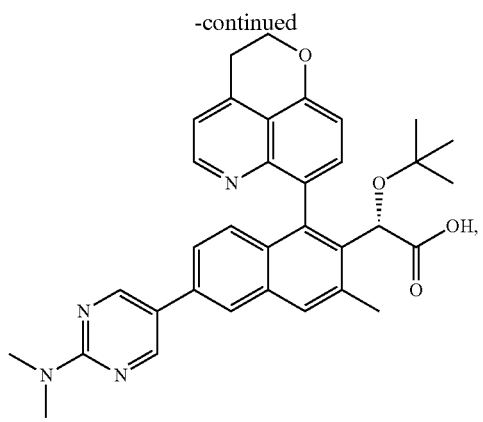
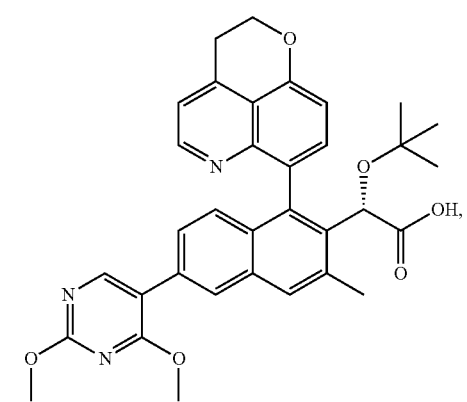
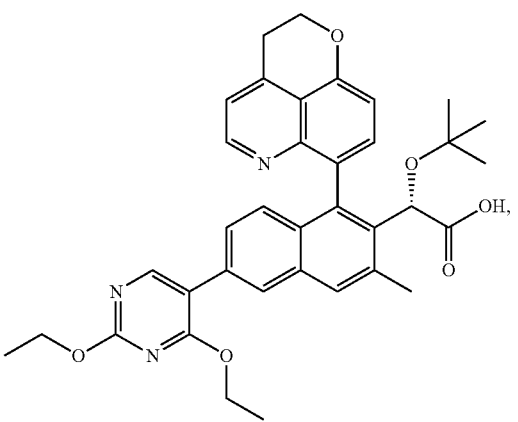
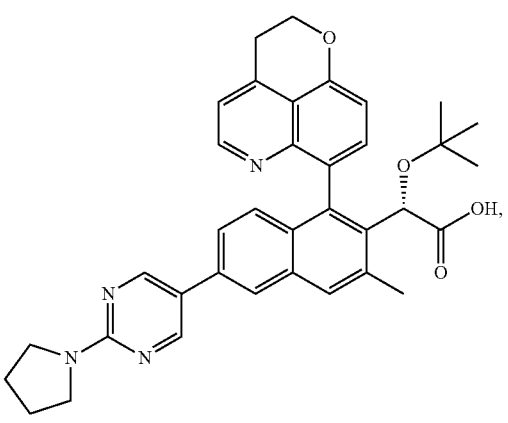
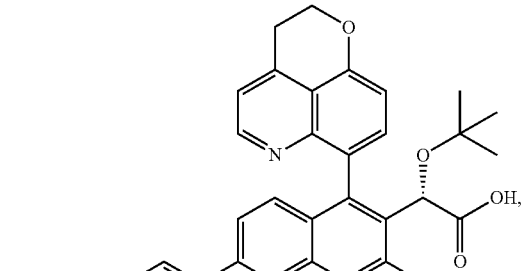
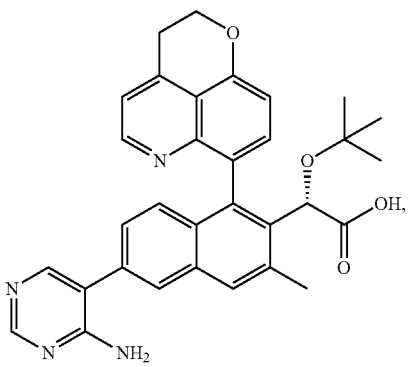
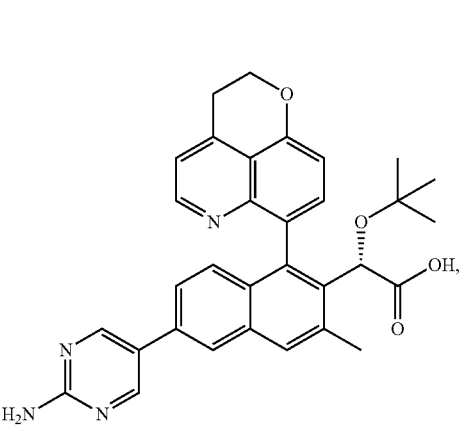
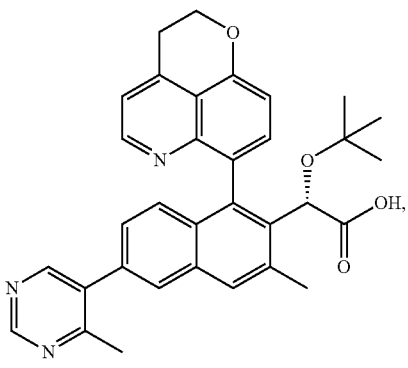

-continued
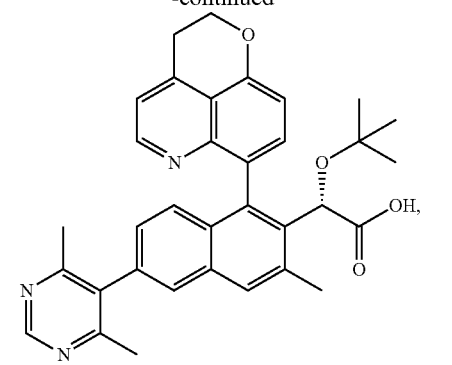
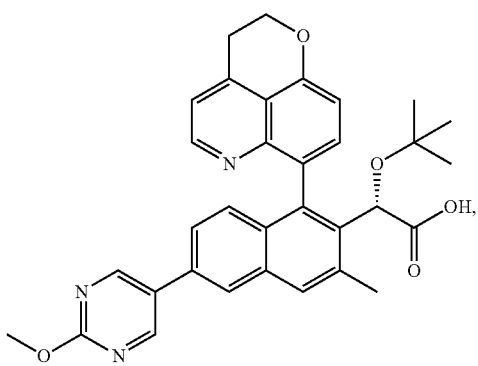
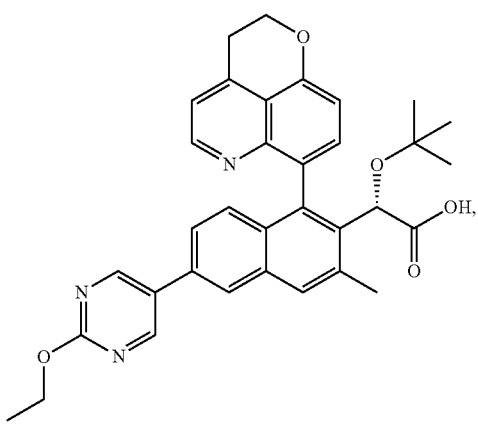
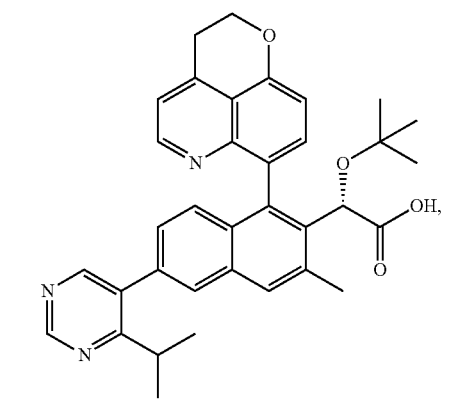
-continued
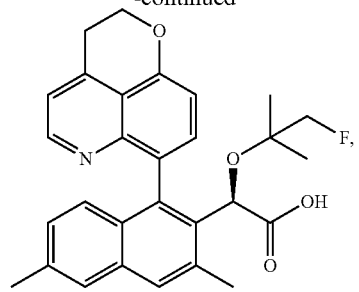
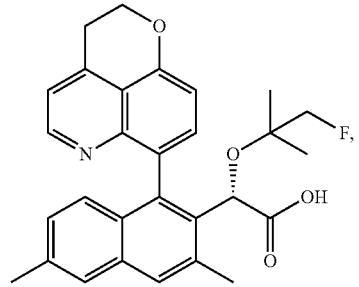
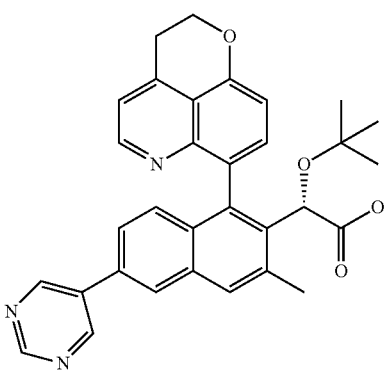

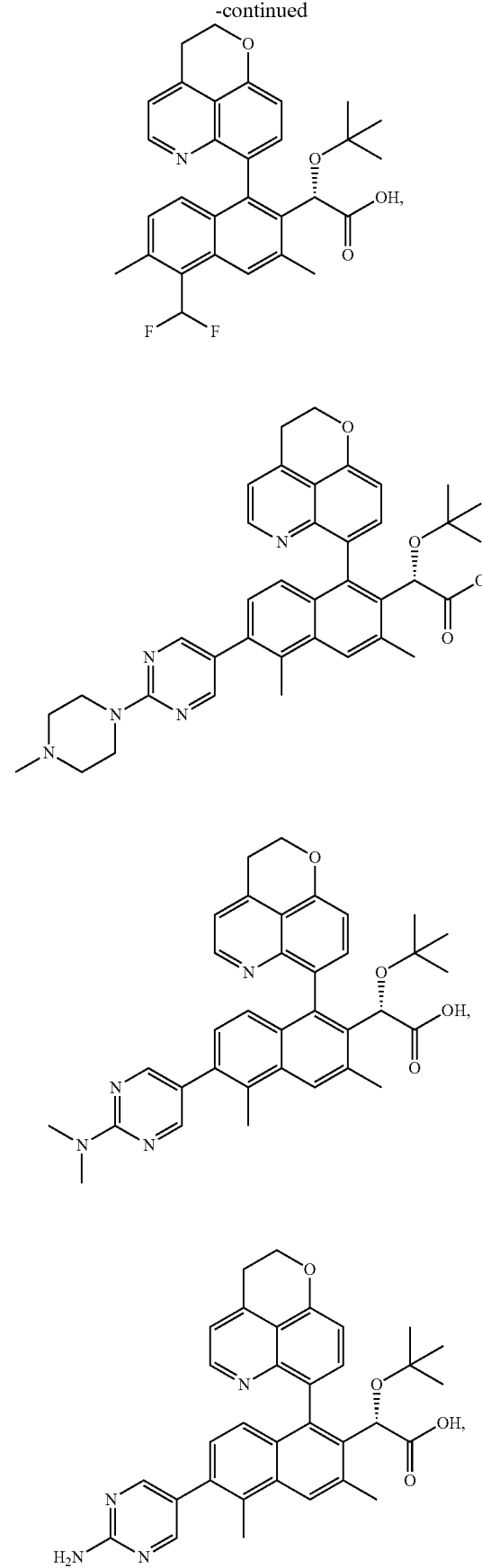
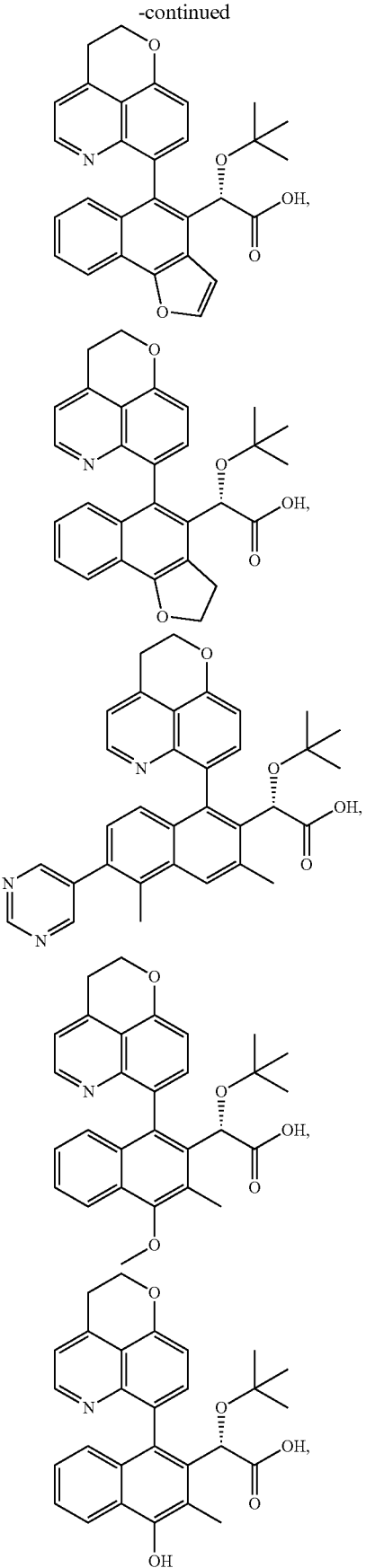

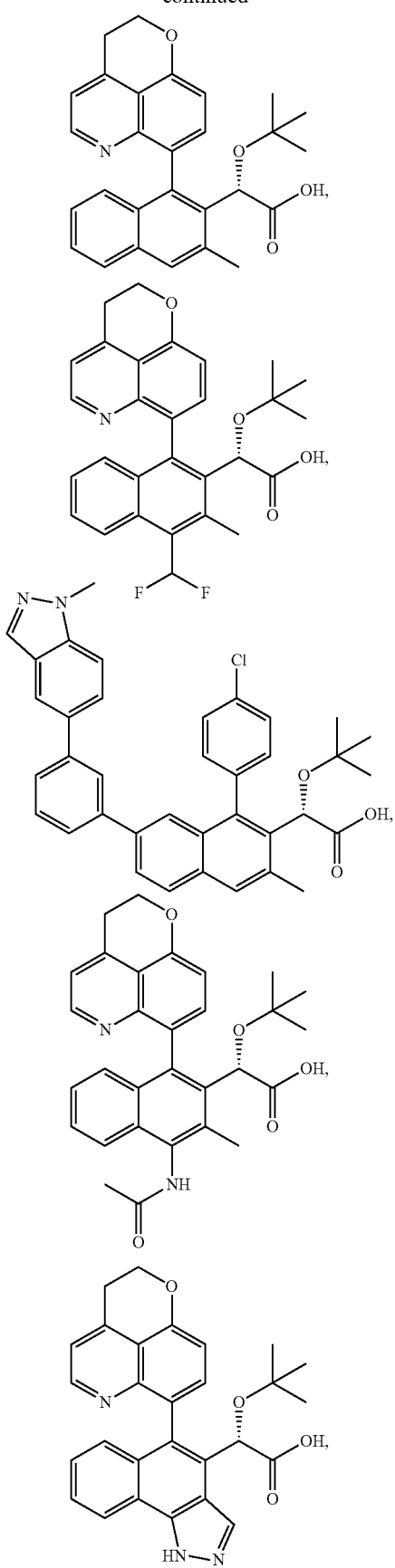
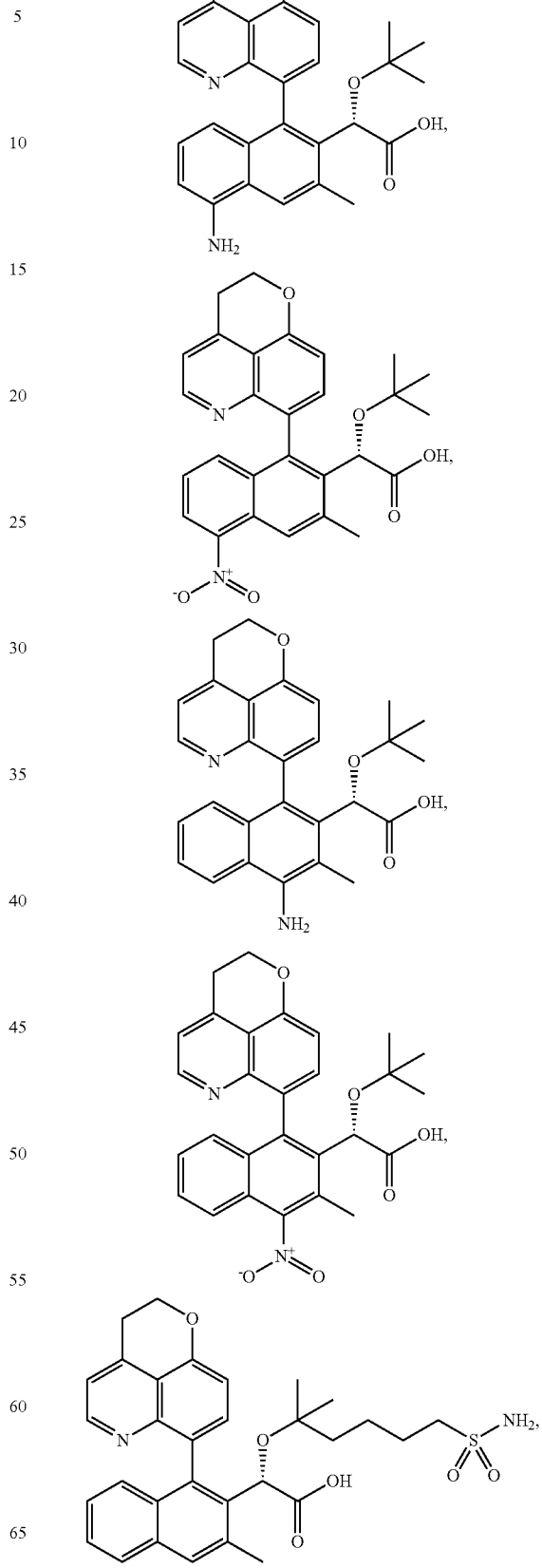

-continued
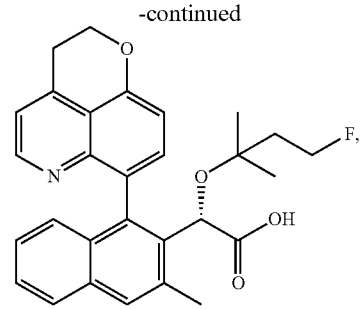
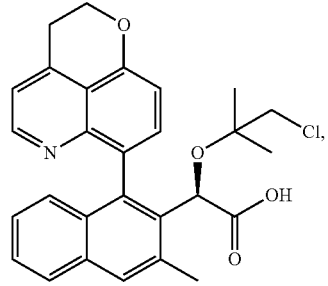
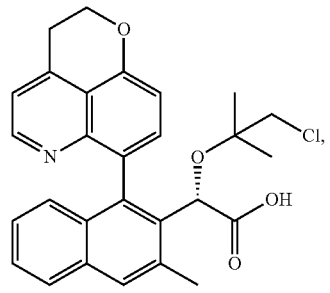
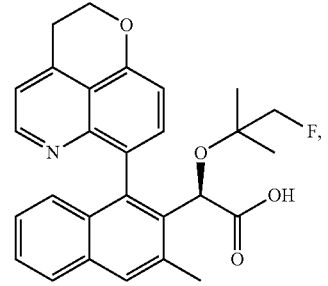

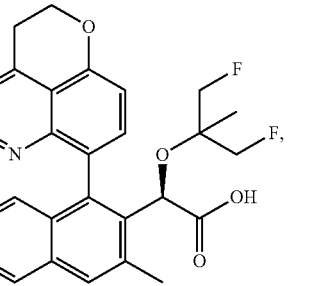
-continued
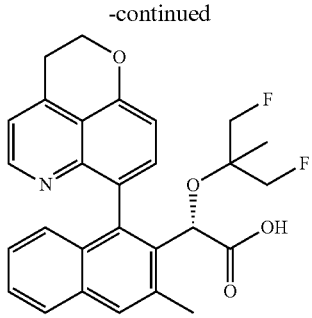
and salts thereof.
Another embodiment provides a compound selected from:
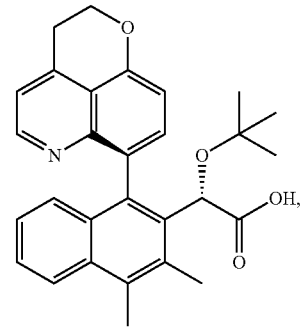
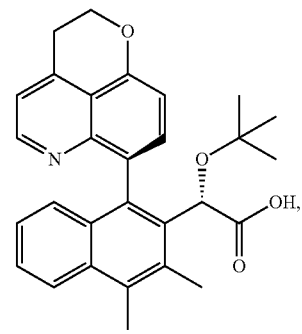
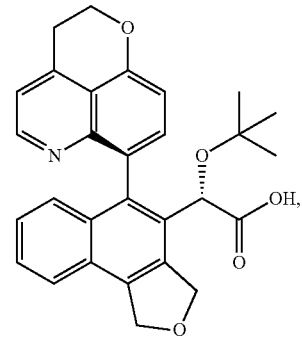

-continued
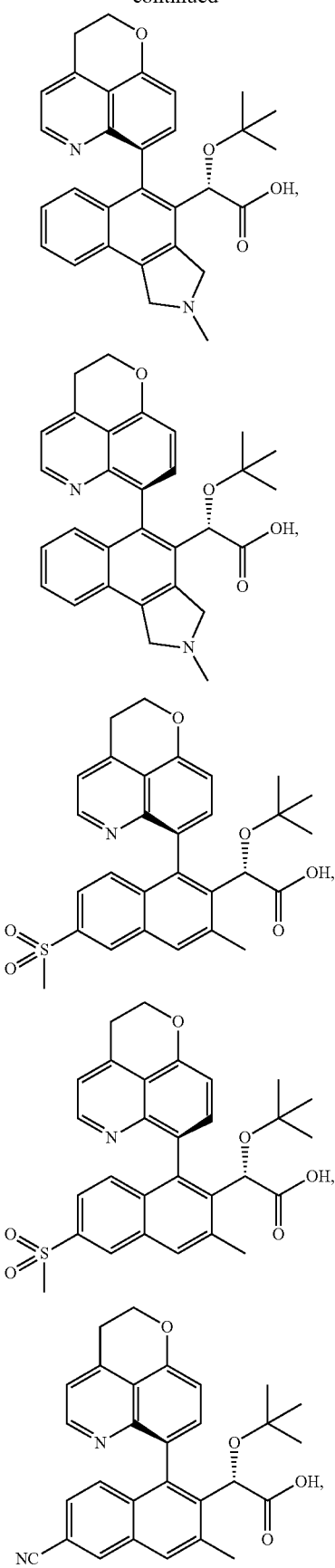
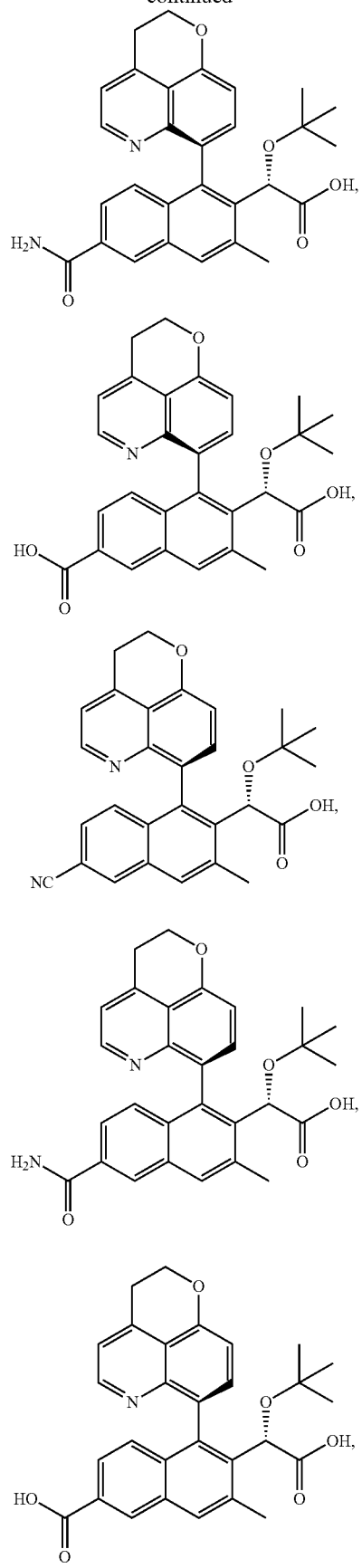

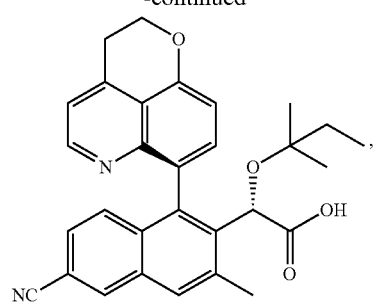
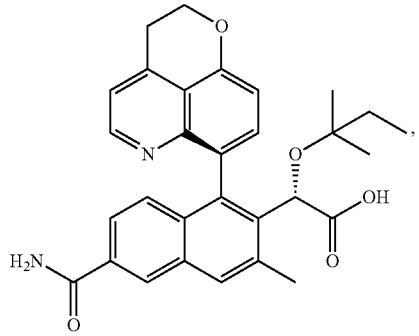
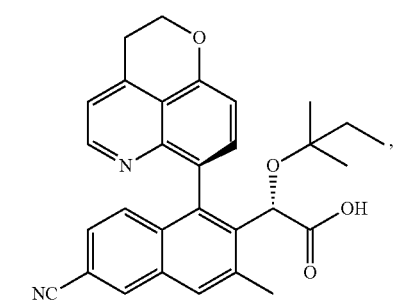
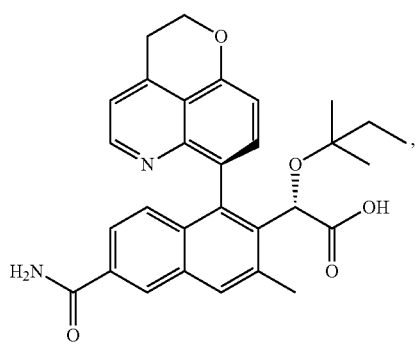
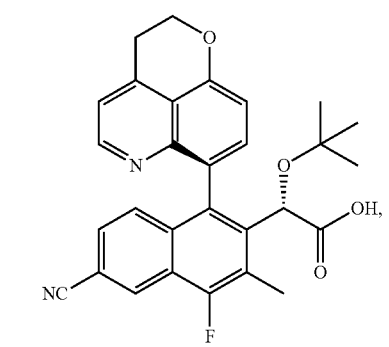
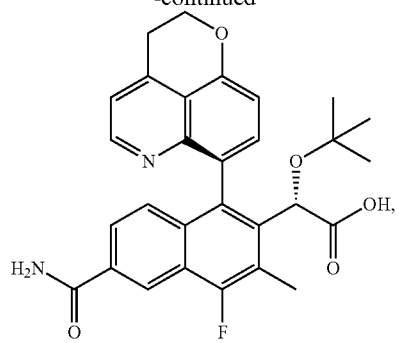
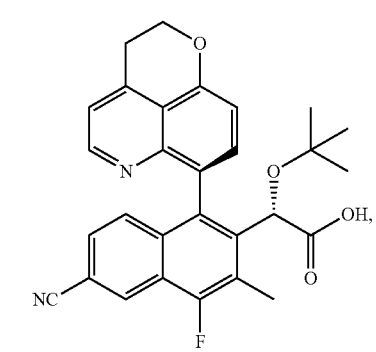
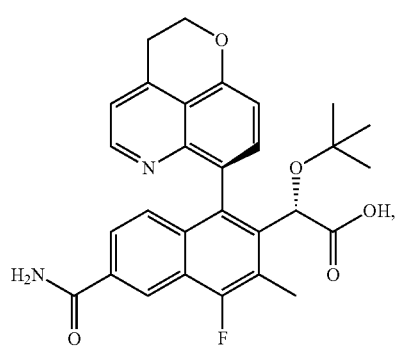
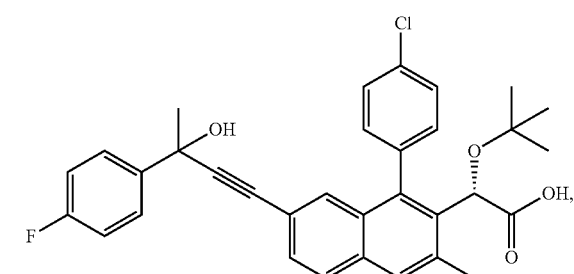

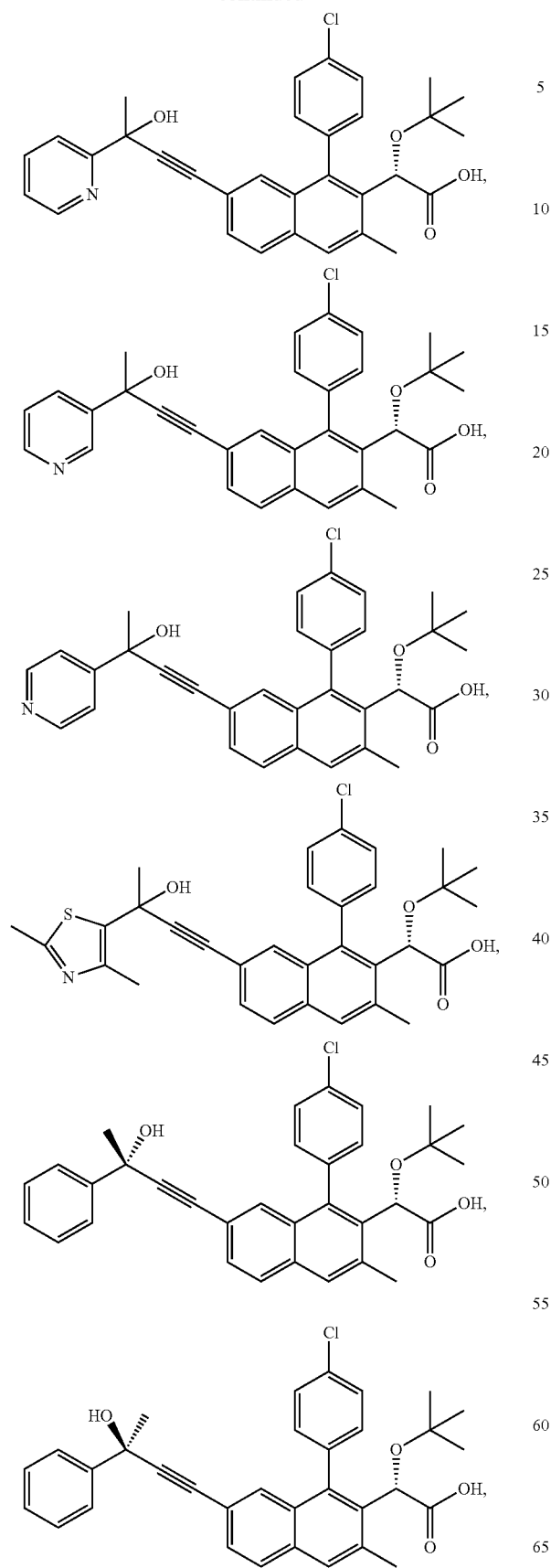
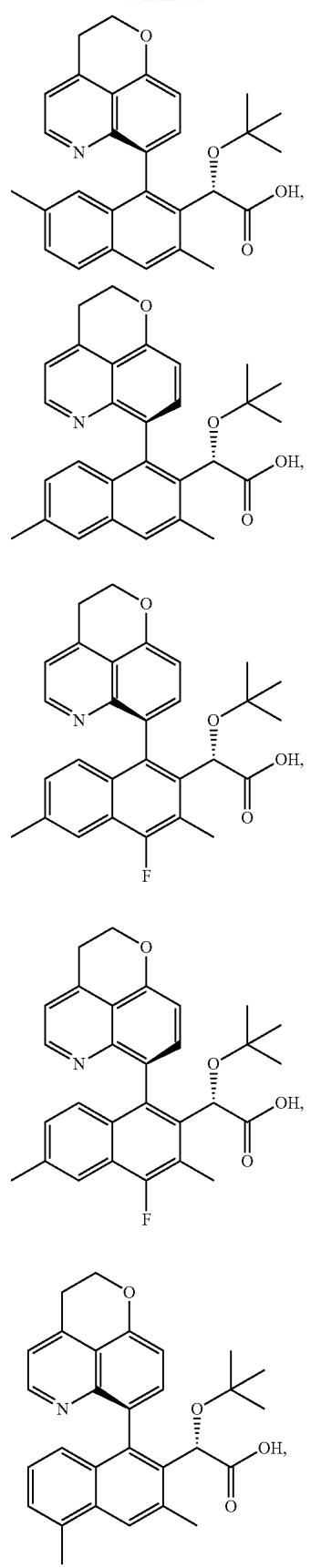

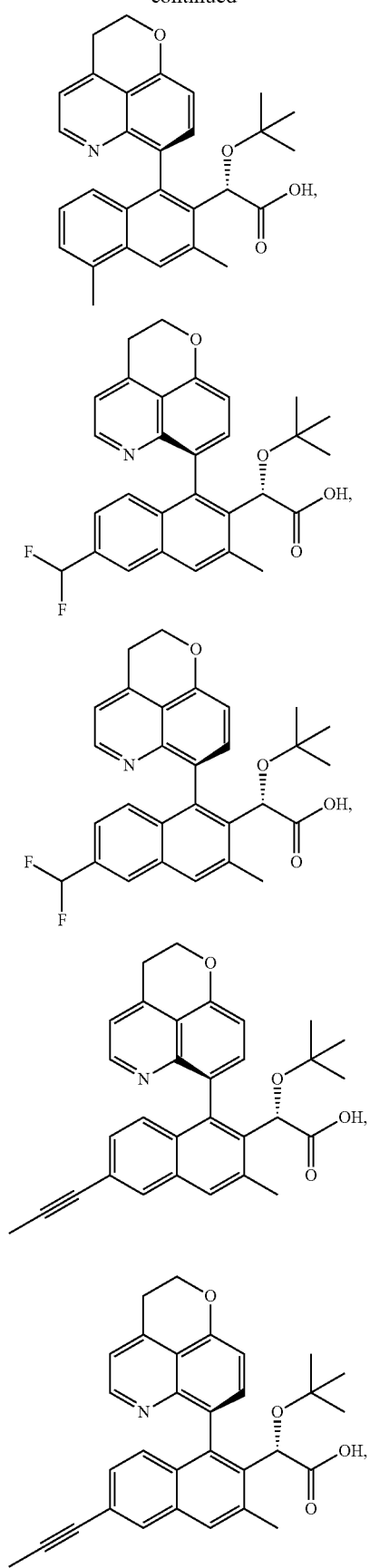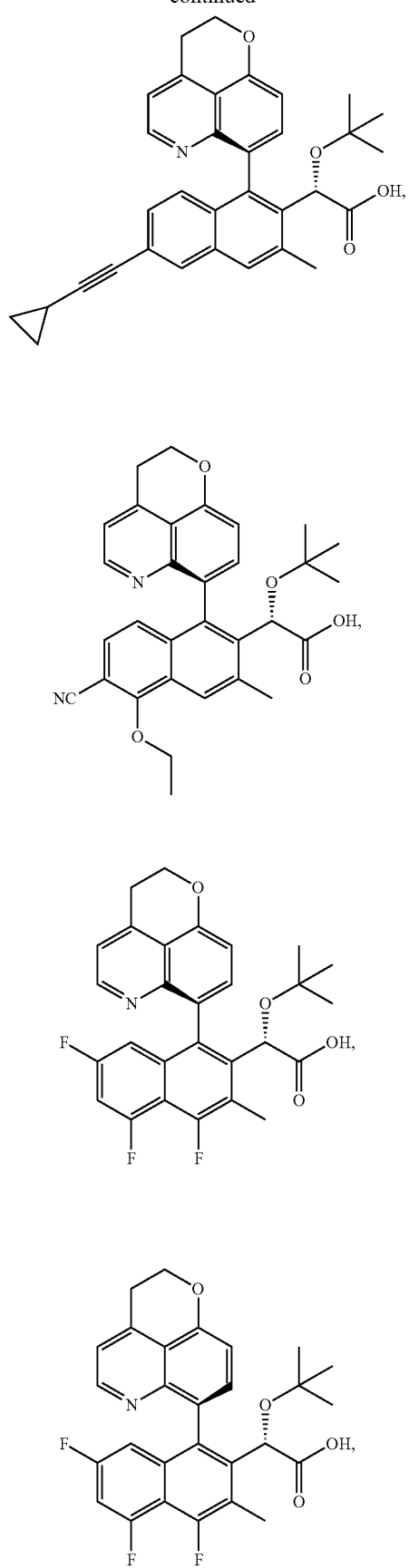

29
-continued
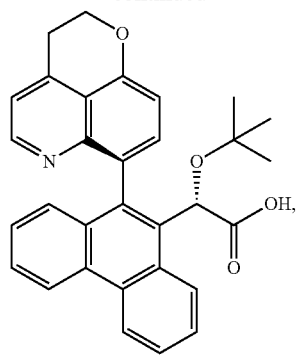
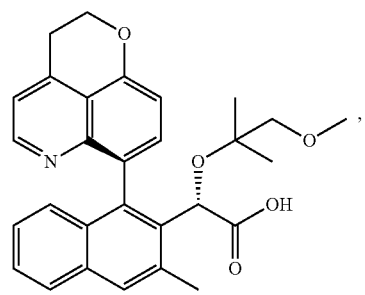
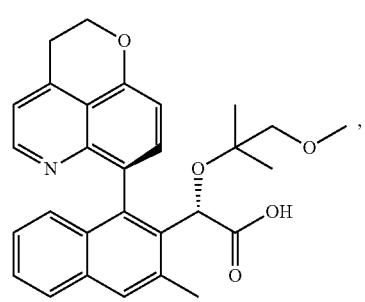
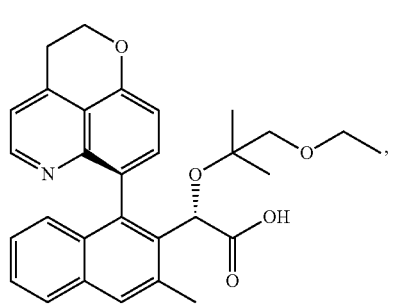
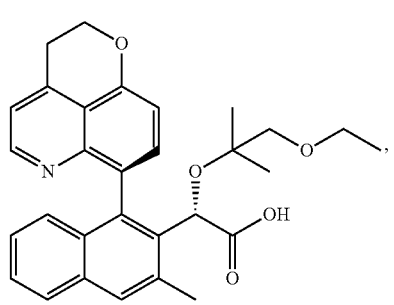
30
-continued
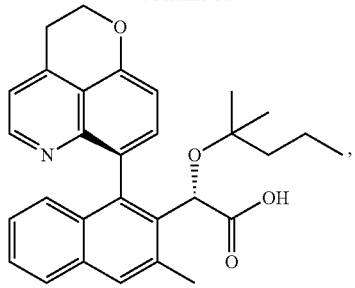
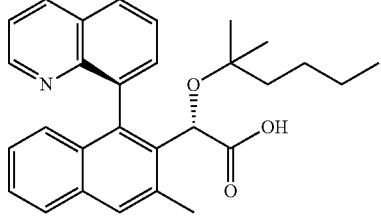
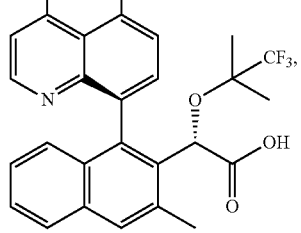
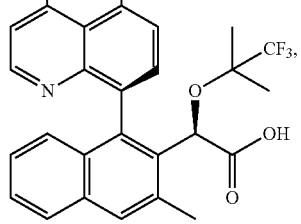
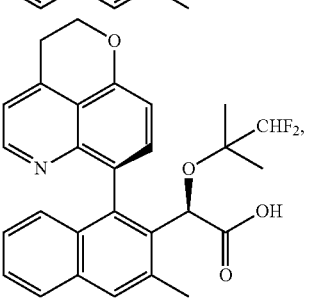

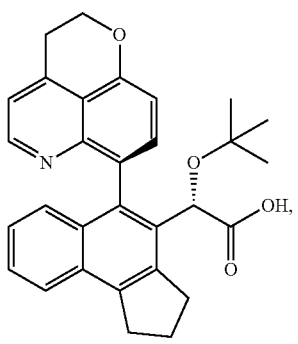
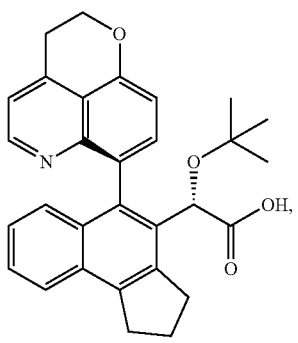
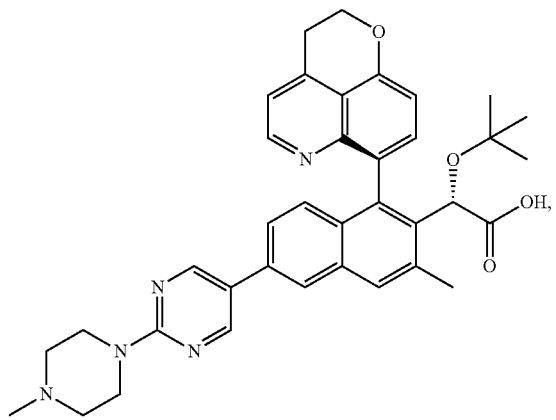
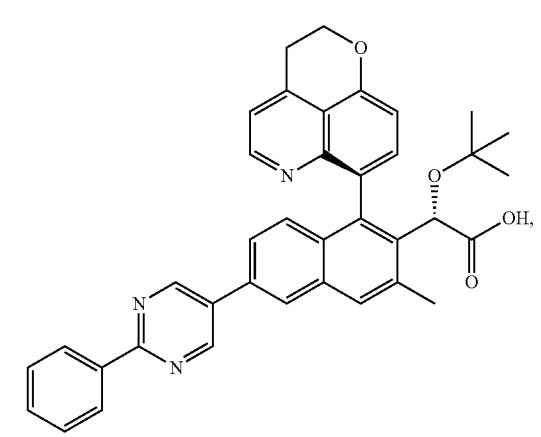
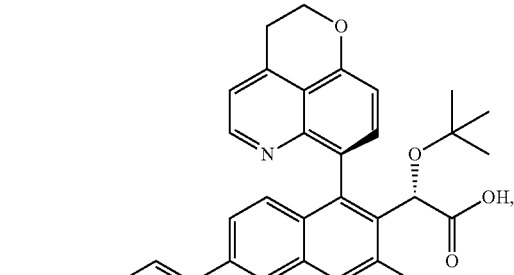
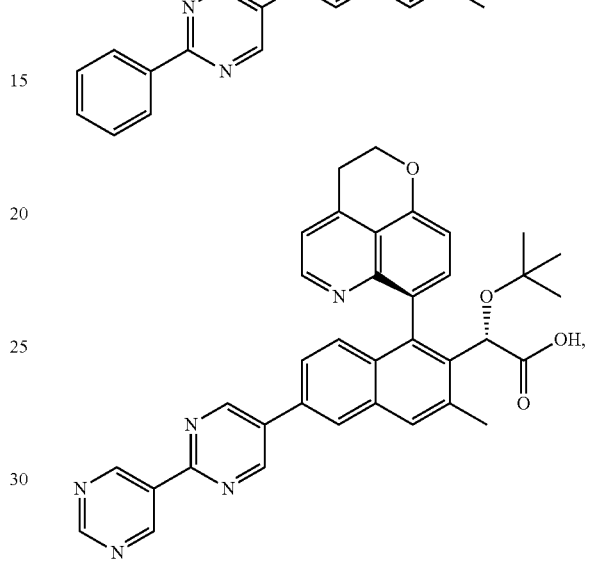
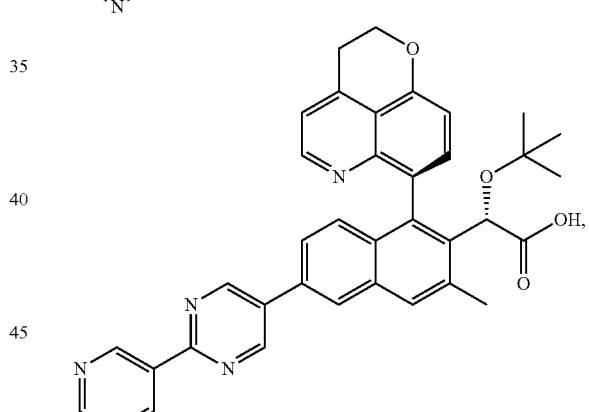

33
-continued
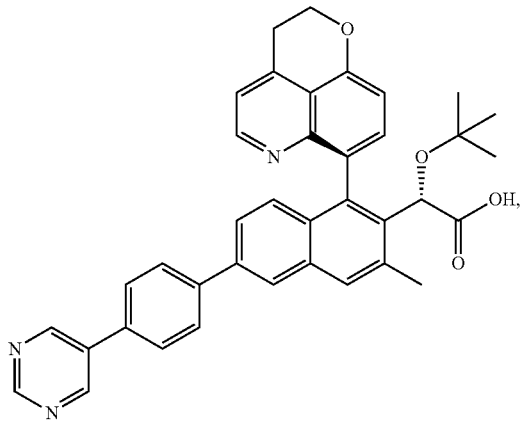
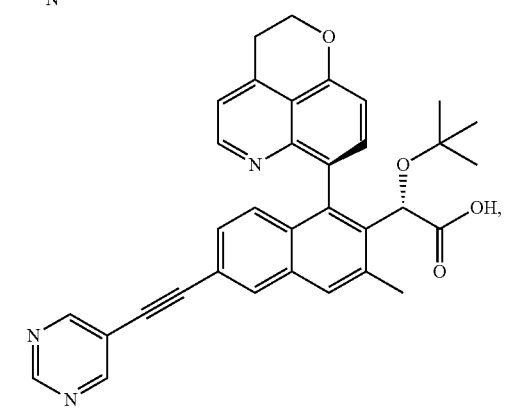
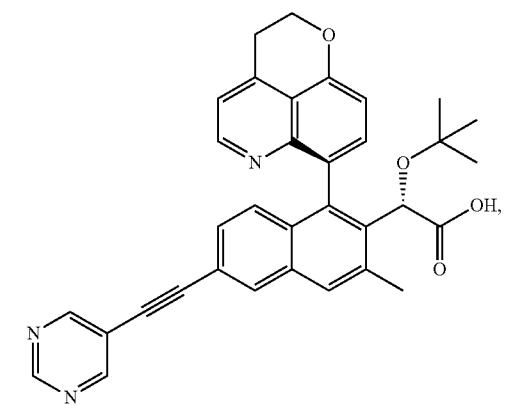
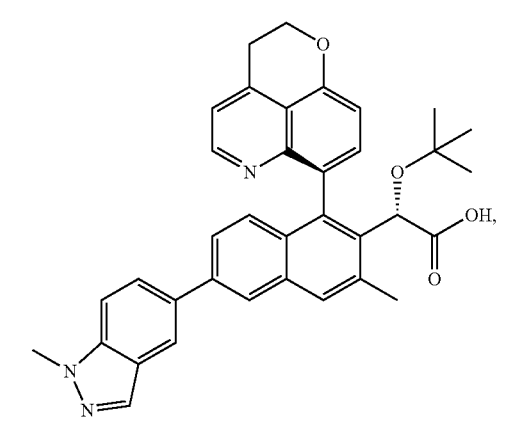
34
-continued
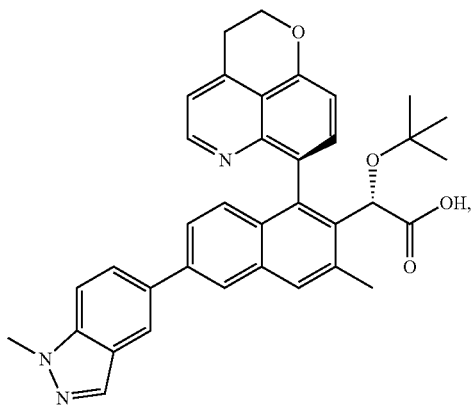
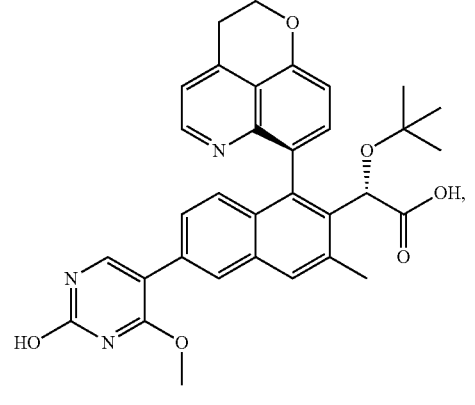
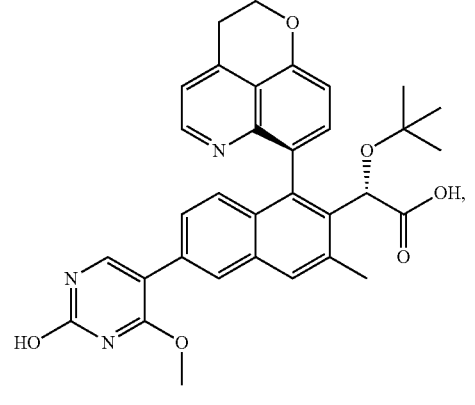
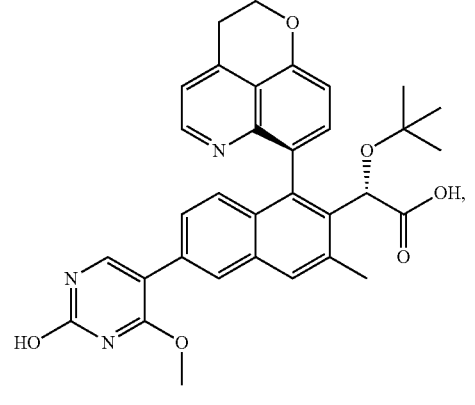

35
-continued
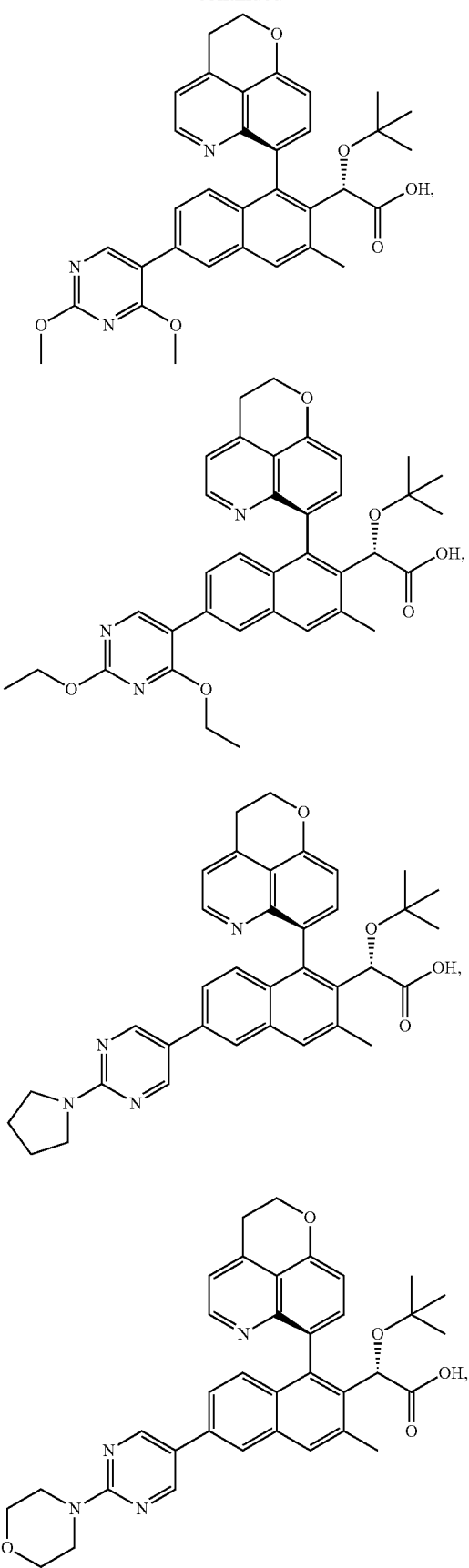
36
-continued
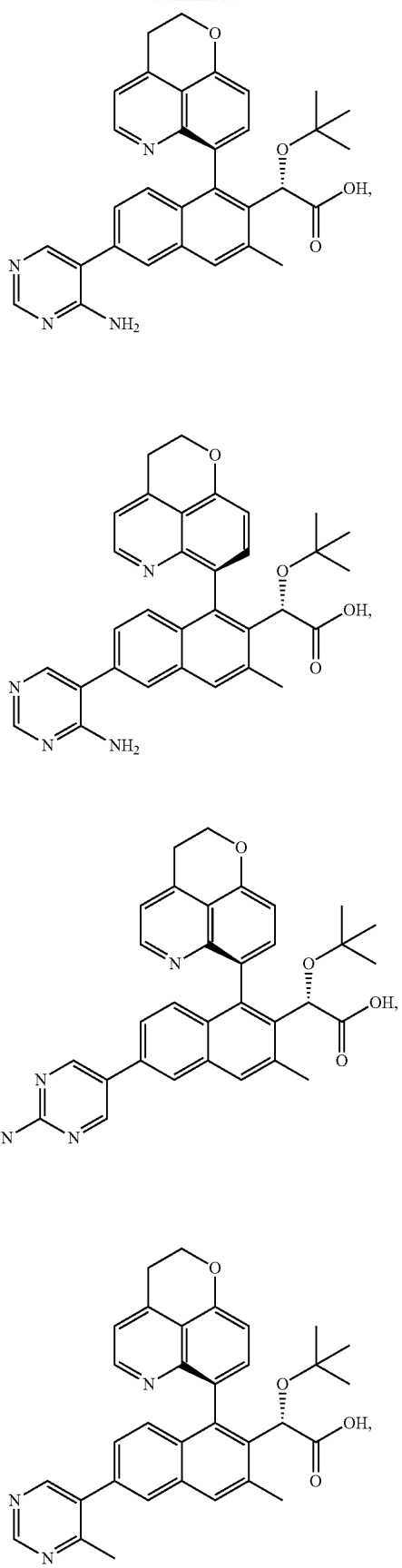

37
-continued
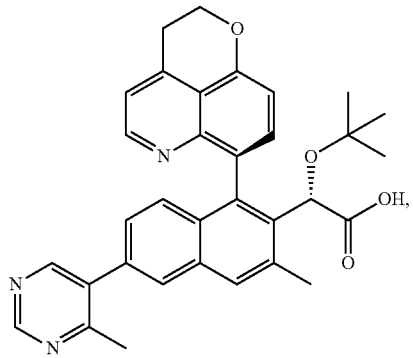
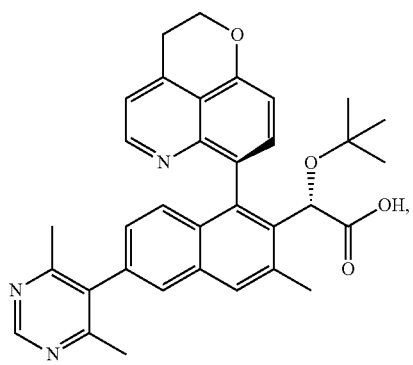
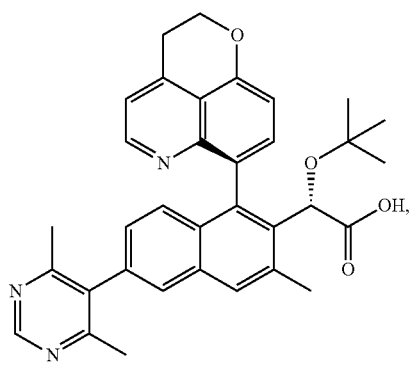
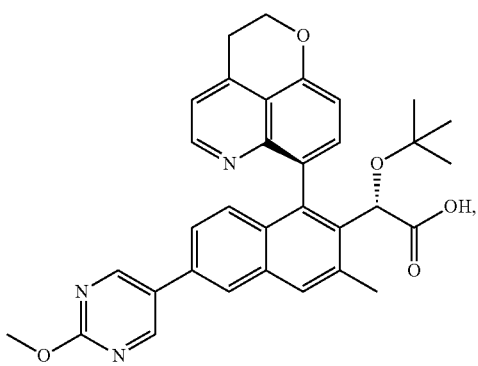
38
-continued
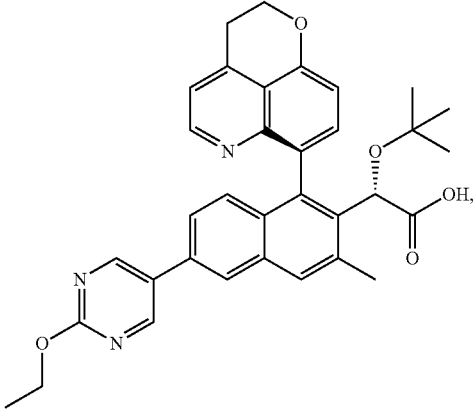

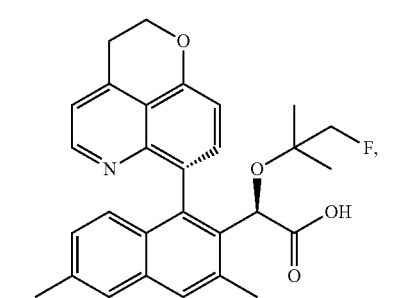
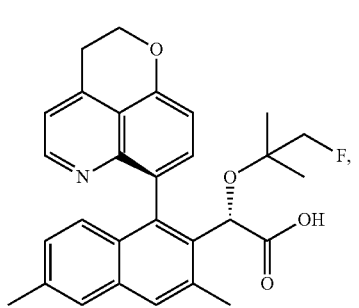

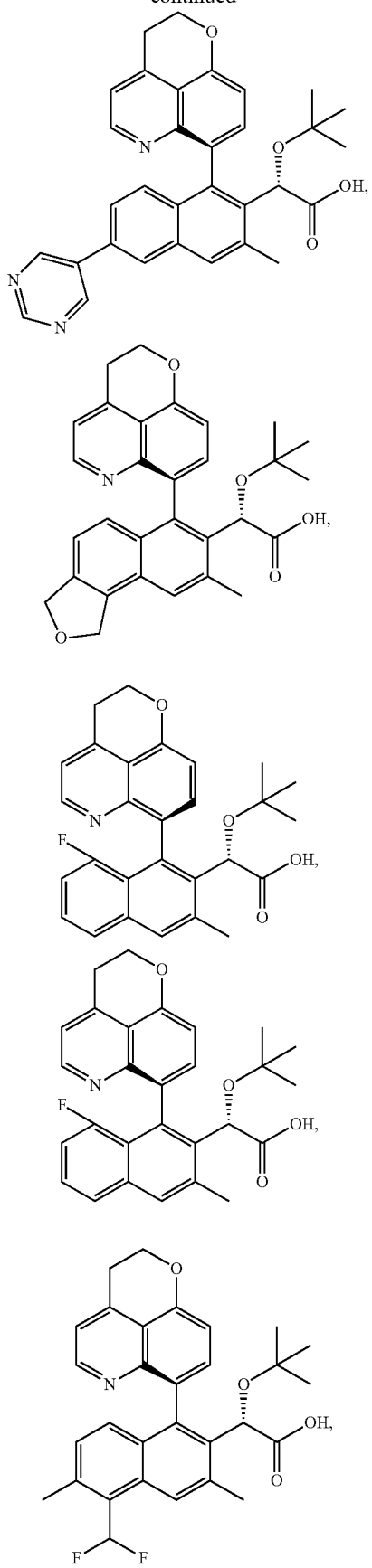
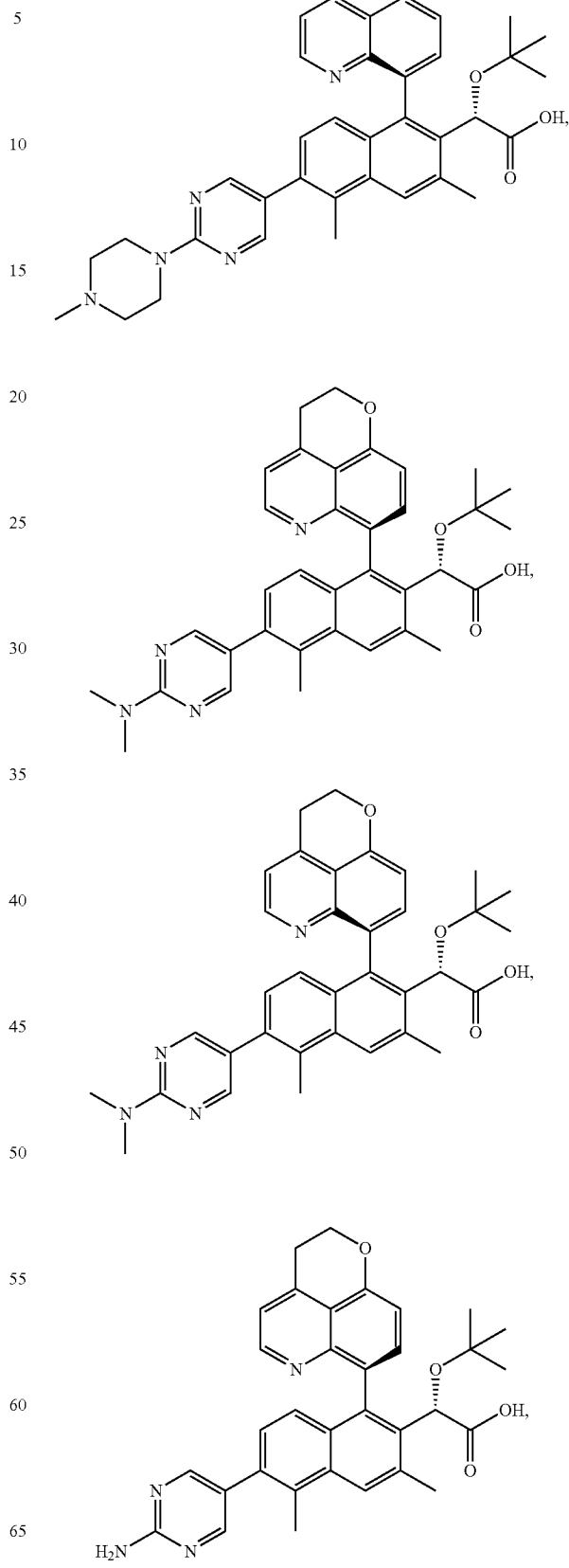

-continued
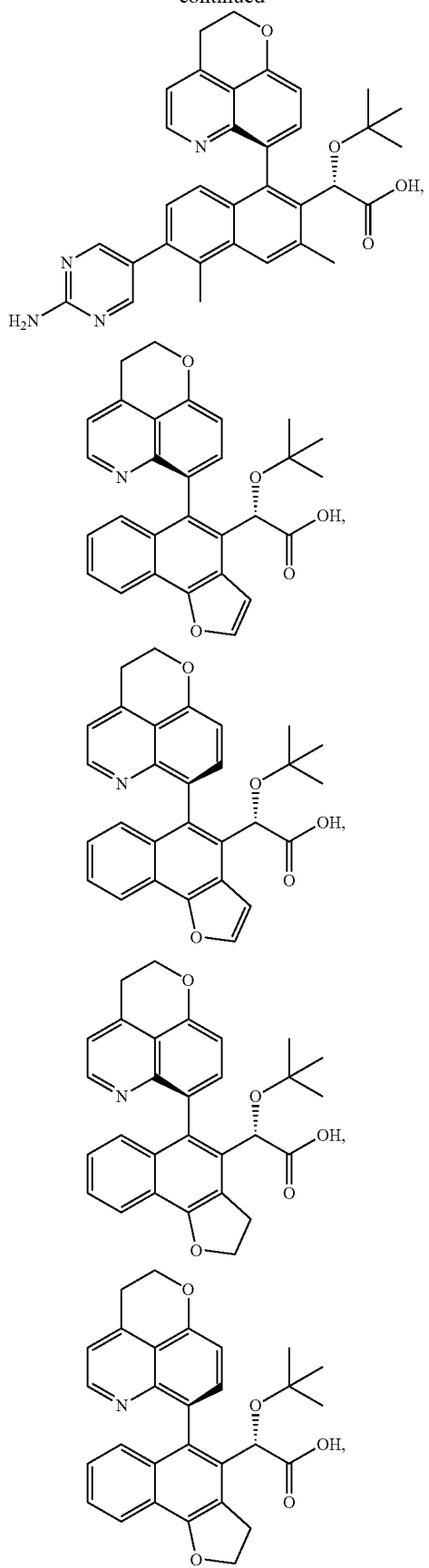
-continued
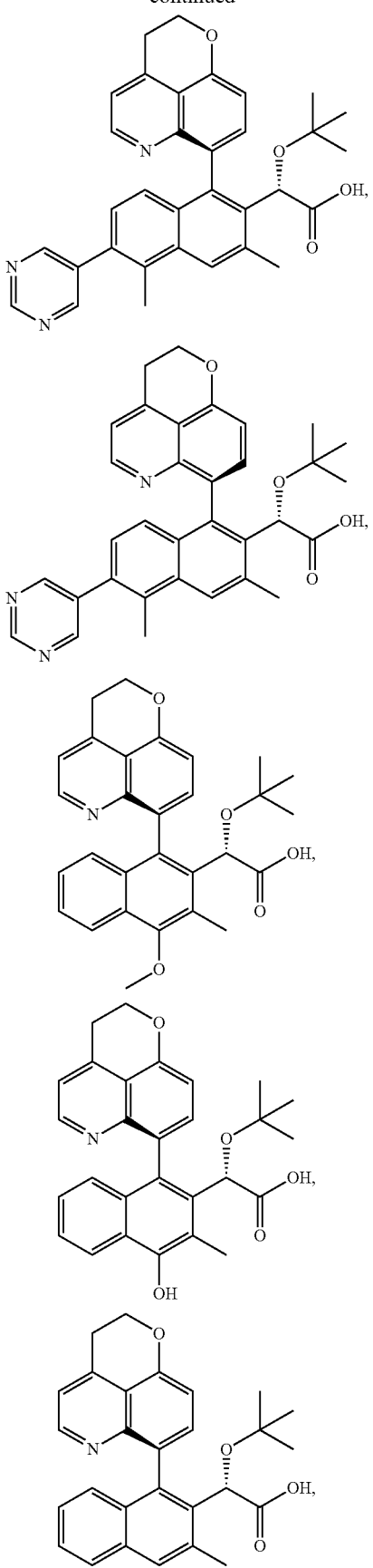

-continued
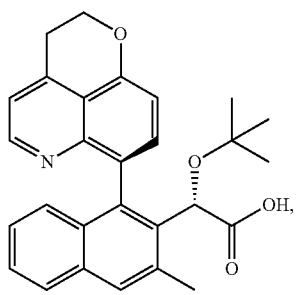
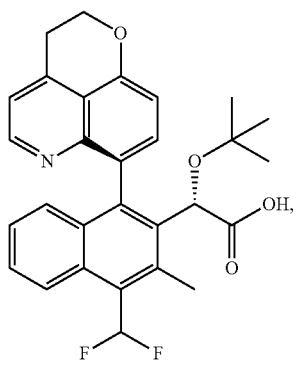
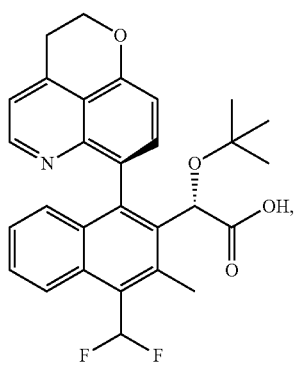
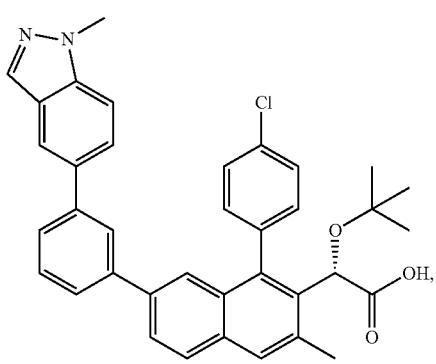
-continued
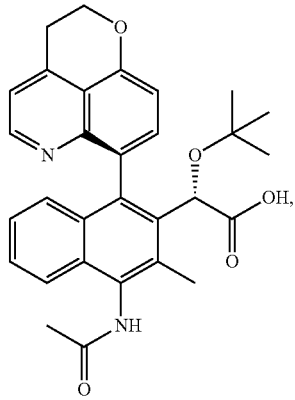
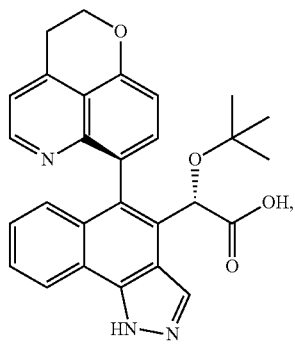
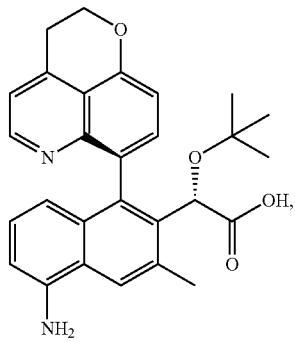
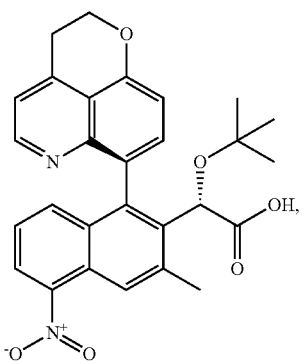

45
-continued
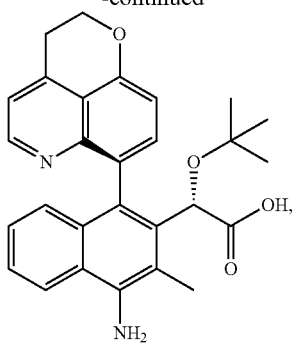
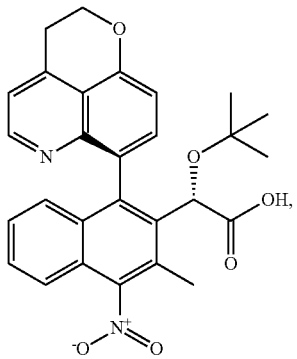
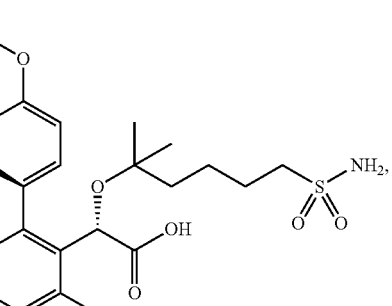
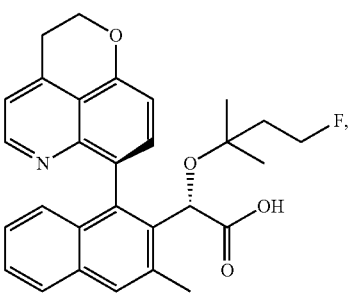
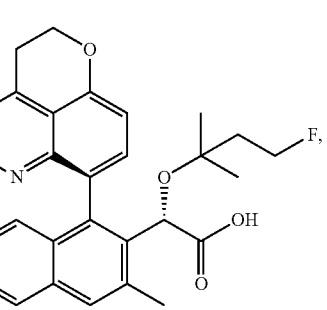
46
-continued
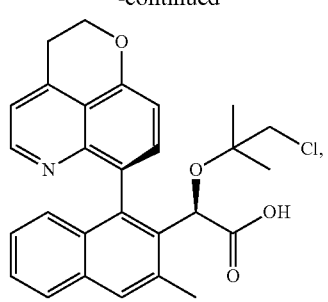
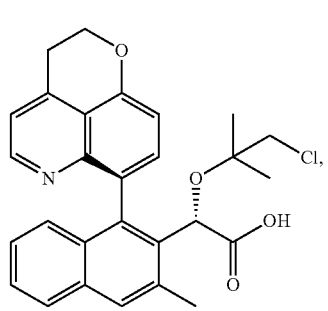
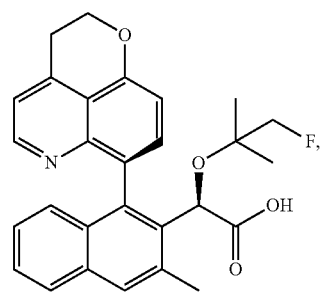
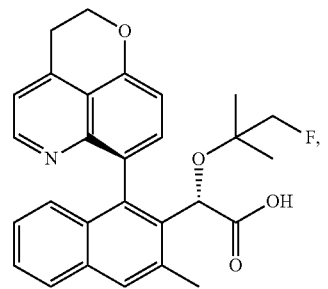
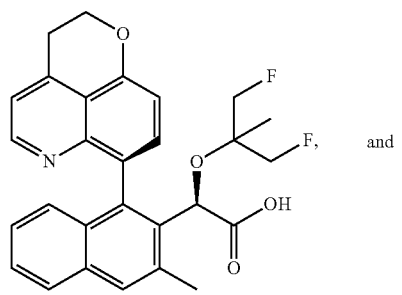
and

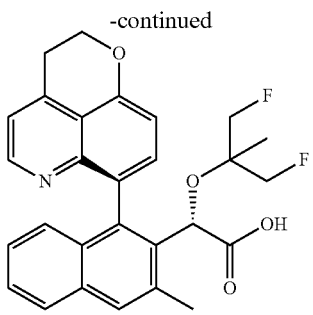

and salts thereof.

Another embodiment provides a compound as described in any one of the Examples disclosed herein or a non-salt thereof or a salt thereof or an alternative salt thereof.

Another embodiment provides a pharmaceutical composition comprising a compound disclosed herein, or a pharmaceutically acceptable salt thereof, and a pharmaceutically acceptable carrier.

Another embodiment provides a method for treating (e.g., preventing, mediating or inhibiting) the proliferation of the HIV virus, treating AIDS or delaying the onset of AIDS or ARC symptoms in a mammal (e.g., a human), comprising administering a compound disclosed herein, or a pharmaceutically acceptable salt thereof, to the mammal.

Another embodiment provides a method for treating an HIV infection in a mammal (e.g., a human) comprising administering one or more of the compounds disclosed herein, or a pharmaceutically acceptable salt thereof, to the mammal.

Another embodiment provides a method for treating an HIV infection in a mammal (e.g., a human) comprising administering to the mammal in need thereof a therapeutically effective amount of a compound disclosed herein, or a pharmaceutically acceptable salt thereof, in combination with a therapeutically effective amount of one or more additional therapeutic agents selected from the group consisting HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drugs for treating HIV, and combinations thereof.

Another embodiment provides a compound disclosed herein, or a pharmaceutically acceptable salt thereof for use in medical therapy (e.g., for use in treating (e.g., preventing, mediating or inhibiting) the proliferation of the HIV virus or AIDS or delaying the onset of AIDS or ARC symptoms in a mammal (e.g., a human)).

Another embodiment provides a compound disclosed herein, or a pharmaceutically acceptable salt thereof for use in medical therapy (e.g., for use in treating e.g., preventing, mediating or inhibiting) an HIV infection in a mammal (e.g., a human)).

Another embodiment provides a compound disclosed herein, or a pharmaceutically acceptable salt thereof for use in the manufacture of a medicament for treating (e.g., preventing, mediating or inhibiting) the proliferation of the HIV virus or AIDS or delaying the onset of AIDS or ARC symptoms in a mammal (e.g., a human).

Another embodiment provides a compound disclosed herein, or a pharmaceutically acceptable salt thereof, for use in the prophylactic or therapeutic treatment (e.g., prevention, mediation or inhibition) of the proliferation of the HIV virus or AIDS or for use in the therapeutic treatment of delaying the onset of AIDS or ARC symptoms.

Another embodiment provides a compound disclosed herein, or a pharmaceutically acceptable salt thereof, for the manufacture of a medicament for treating an HIV infection in a mammal e.g., a human).

Another embodiment provides a compound disclosed herein, or a pharmaceutically acceptable salt thereof, for use in the prophylactic or therapeutic treatment of an HIV infection.

Another embodiment provides processes and intermediates disclosed herein that are useful for preparing compounds disclosed herein or salts thereof.

Other embodiments, objects, features and advantages will be set forth in the detailed description of the embodiments that follows, and in part will be apparent from the description, or may be learned by practice, of the claimed invention. These objects and advantages will be realized and attained by the processes and compositions particularly pointed out in the written description and claims hereof. The foregoing Summary has been made with the understanding that it is to be considered as a brief and general synopsis of some of the embodiments disclosed herein, is provided solely for the benefit and convenience of the reader, and is not intended to limit in any manner the scope, or range of equivalents, to which the appended claims are lawfully entitled.

DETAILED DESCRIPTION

While the present invention is capable of being embodied in various forms, the description below of several embodiments is made with the understanding that the present disclosure is to be considered as an exemplification of the claimed subject matter, and is not intended to limit the appended claims to the specific embodiments illustrated. The headings used throughout this disclosure are provided for convenience only and are not to be construed to limit the claims in any way. Embodiments illustrated under any heading may be combined with embodiments illustrated under any other heading.

Definitions

Unless stated otherwise, the following terms and phrases as used herein are intended to have the following meanings:

When trade names are used herein, applicants intend to independently include the tradename product and the active pharmaceutical ingredient(s) of the tradename product.

The modifier "about" used in connection with a quantity is inclusive of the stated value and has the meaning dictated by the context (e.g., includes the degree of error associated with measurement of the particular quantity). The word "about" may also be represented symbolically by "~" in the context of a chemical measurement (e.g., ~50 mg or pH~7).

The term "treatment" or "treating," to the extent it relates to a disease or condition includes preventing the disease or condition from occurring, inhibiting the disease or condition, eliminating the disease or condition, and/or relieving one or more symptoms of the disease or condition.

Stereoisomers

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers or axes of chirality and whose molecules are not mirror images of one another. Diastereomers typically have different physical properties, e.g., melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

The compounds disclosed herein may have chiral centers, e.g., chiral carbon atoms. Such compounds thus include racemic mixtures of all stereoisomers, including enantiomers, diastereomers and atropisomers. In addition, the compounds disclosed herein include enriched or resolved optical isomers at any or all asymmetric, chiral atoms. In other words, the chiral centers apparent from the depictions are provided as the chiral isomers or racemic mixtures. Both racemic and diastereomeric mixtures, as well as the individual optical isomers isolated or synthesized, substantially free of their enantiomeric or diastereomeric partners, are all within the scope of the invention. The racemic mixtures can be separated into their individual, substantially optically pure isomers through well-known techniques such as, for example, the separation of diastereomeric salts formed with optically active adjuncts, e.g., acids or bases followed by conversion back to the optically active substances. The desired optical isomer can also be synthesized by means of stereospecific reactions, beginning with the appropriate stereoisomer of the desired starting material.

It is to be understood that for compounds disclosed herein when a bond is drawn in a non-stereochemical manner (e.g., flat) the atom to which the bond is attached includes all stereochemical possibilities. It is also to be understood that when a bond is drawn in a stereochemical manner (e.g., bold, bold-wedge, dashed or dashed-wedge) the atom to which the stereochemical bond is attached has the stereochemistry as shown unless otherwise noted. Accordingly, in one embodiment, a compound disclosed herein is greater than 50% a single enantiomer. In another embodiment, a compound disclosed herein is at least 80% a single enantiomer. In another embodiment, a compound disclosed herein is at least 90% a single enantiomer. In another embodiment, a compound disclosed herein is at least 98% a single enantiomer. In another embodiment, a compound disclosed herein is at least 99% a single enantiomer. In another embodiment, a compound disclosed herein is greater than 50% a single diastereomer. In another embodiment, a compound disclosed herein is at least 80% a single diastereomer. In another embodiment, a compound disclosed herein is at least 90% a single diastereomer. In another embodiment, a compound disclosed herein is at least 98% a single diastereomer. In another embodiment, a compound disclosed herein is at least 99% a single diastereomer.

Tautomers

The compounds disclosed herein can also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Salts and Hydrates

Examples of pharmaceutically acceptable salts of the compounds disclosed herein include salts derived from an appropriate base, such as an alkali metal (for example, sodium), an alkaline earth metal (for example, magnesium), ammonium and $NX_4^+$ (wherein X is $C_1$-$C_4$ alkyl). Pharmaceutically acceptable salts of a nitrogen atom or an amino group include for example salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, hydrobromic, sulfuric, phosphoric and sulfamic acids. Pharmaceutically acceptable salts of a compound of a hydroxy group include the anion of said compound in combination with a suitable cation such as $Na^+$ and $NX_4^+$ (wherein X is independently selected from H or a $C_1$-$C_4$ alkyl group).

For therapeutic use, salts of active ingredients of the compounds disclosed herein will typically be pharmaceutically acceptable, i.e. they will be salts derived from a physiologically acceptable acid or base. However, salts of acids or bases which are not pharmaceutically acceptable may also find use, for example, in the preparation or purification of a compound of formula I or another compound of the invention. All salts, whether or not derived from a physiologically acceptable acid or base, are within the scope of the present invention.

Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, $H_3PO_4$ or organic sulfonic acids, to basic centers, typically amines. Finally, it is to be understood that the compositions herein comprise compounds disclosed herein in their un-ionized, as well as zwitterionic form, and combinations with water as in hydrates.

Isotopes

It is understood by one skilled in the art that this invention also includes any compound claimed that may be enriched at any or all atoms above naturally occurring isotopic ratios with one or more isotopes such as, but not limited to, deuterium ($^2$H or D). As a non-limiting example, a —$CH_3$ group may be substituted with —$CD_3$.

Compounds

In one embodiment compounds are selected from:

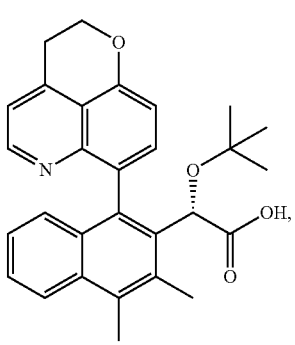

51
-continued
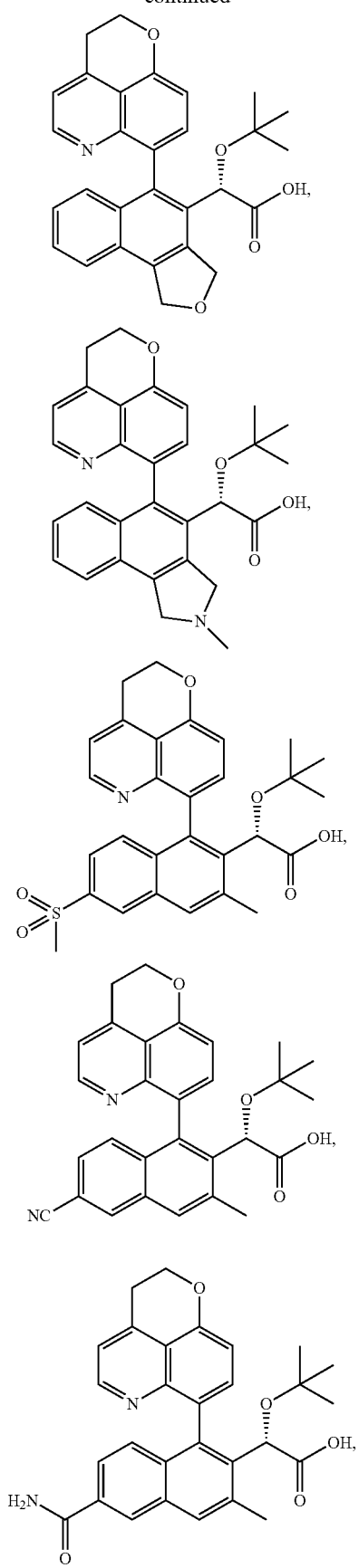
52
-continued
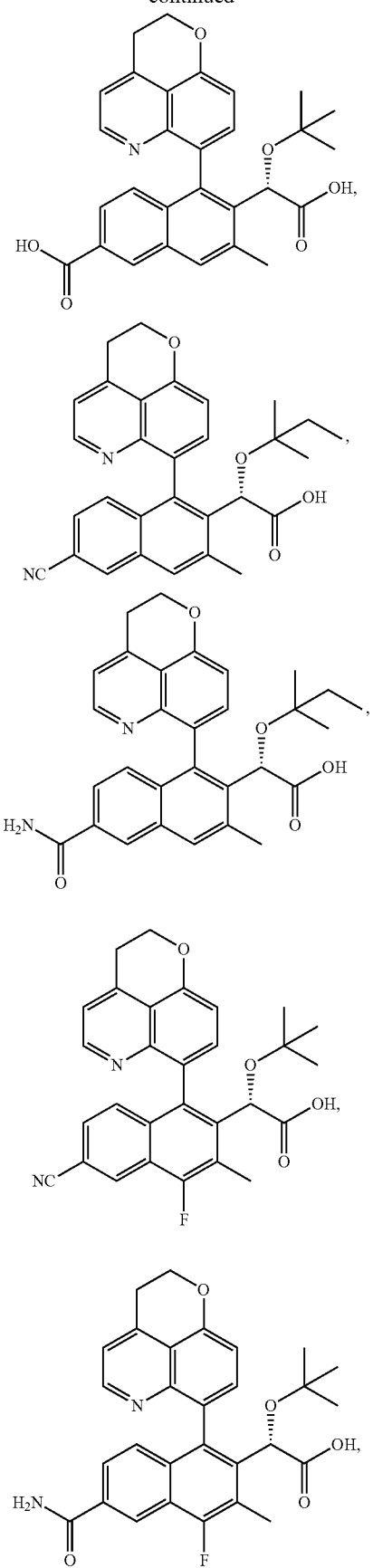

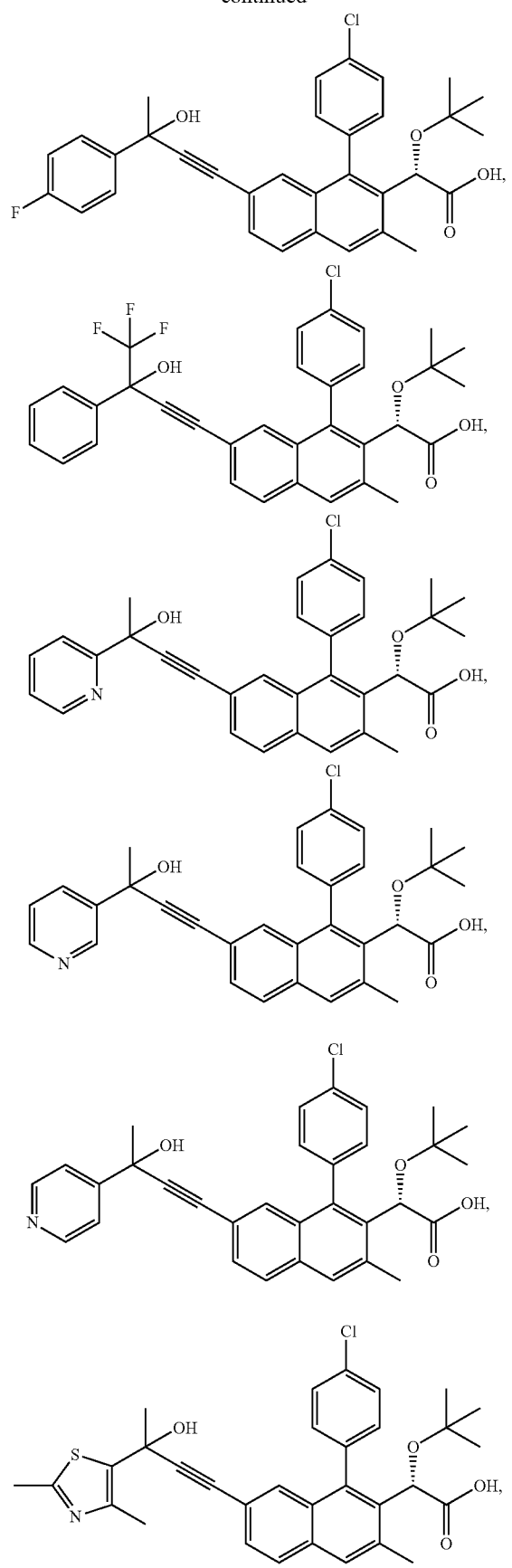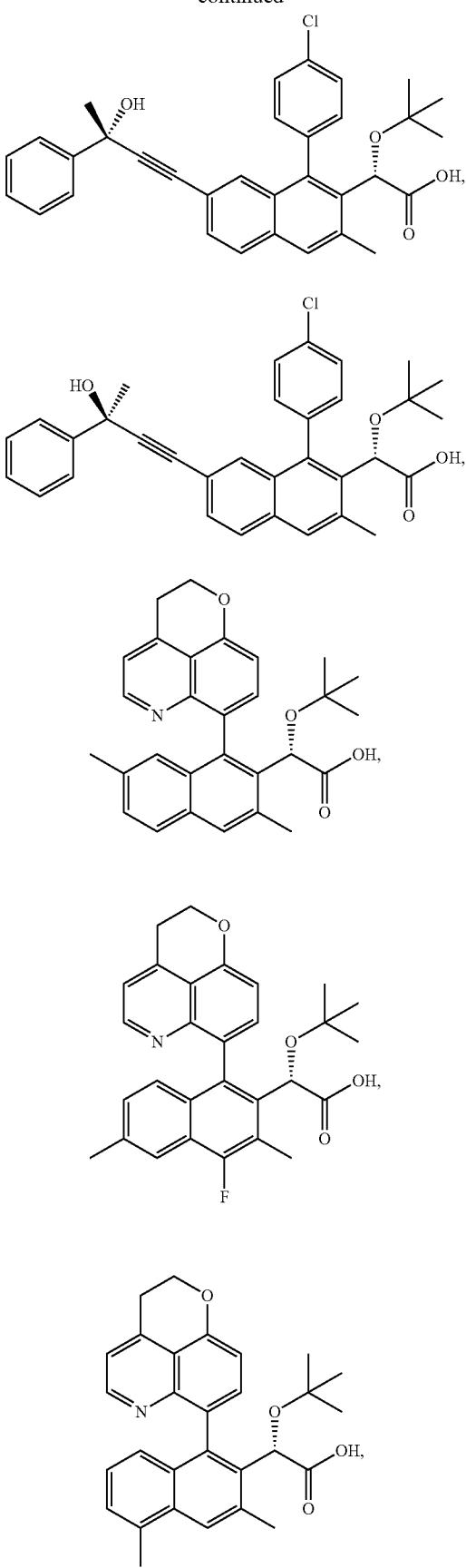

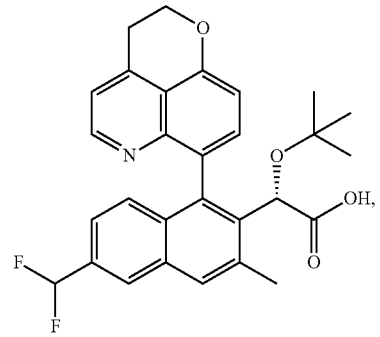
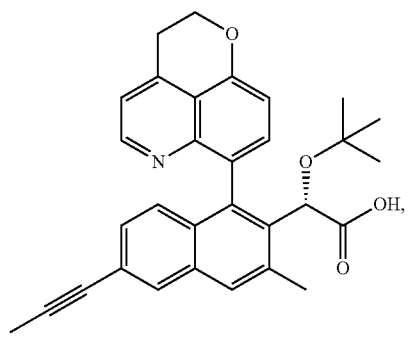
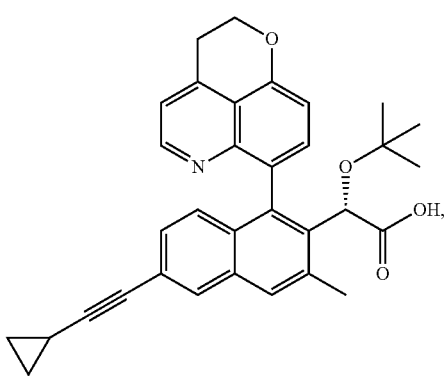
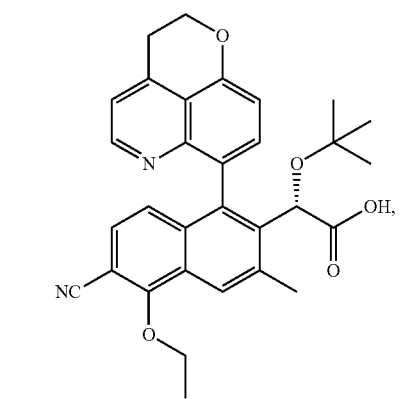
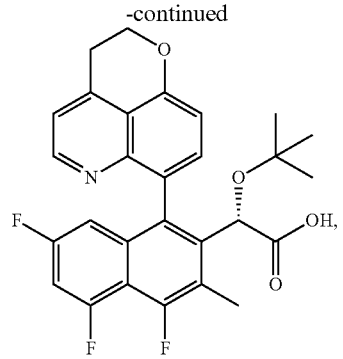
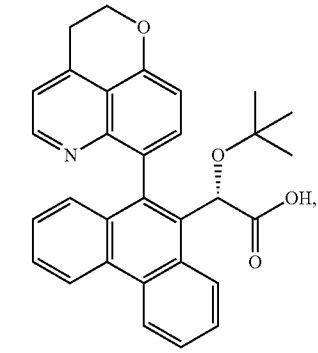
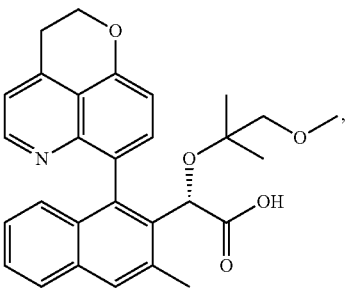
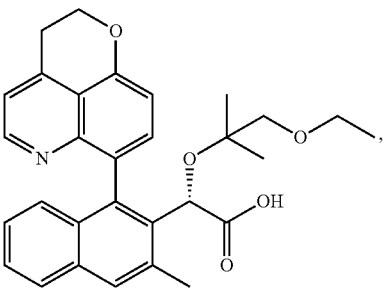
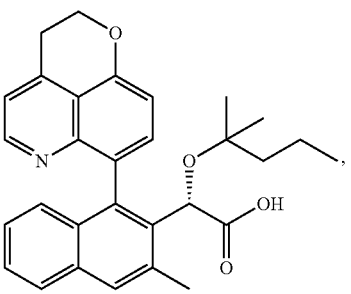

-continued
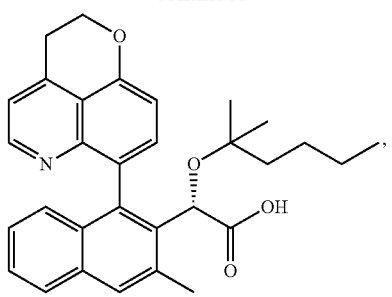
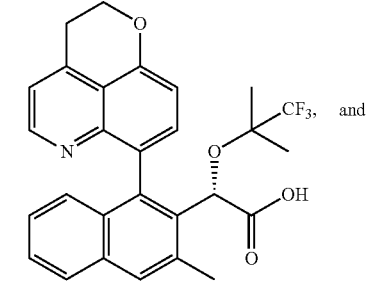
and
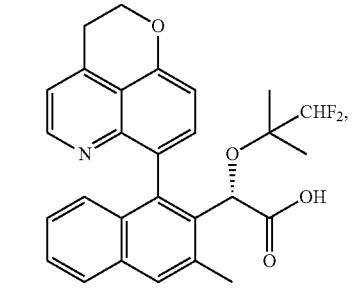
sand salts thereof
In one embodiment compounds are selected from:
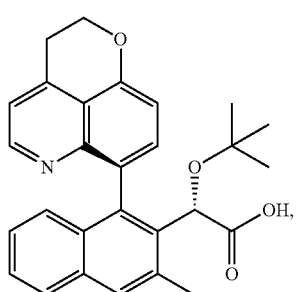
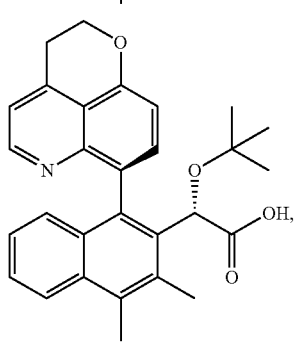
-continued
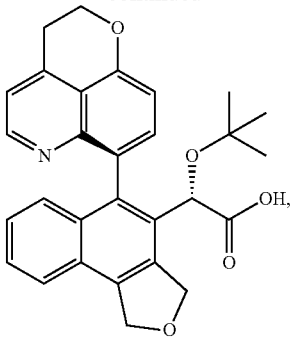
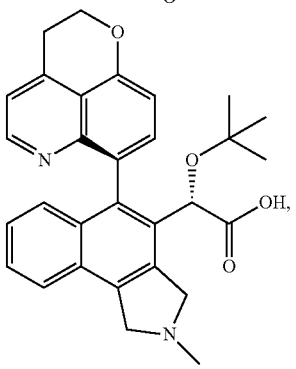
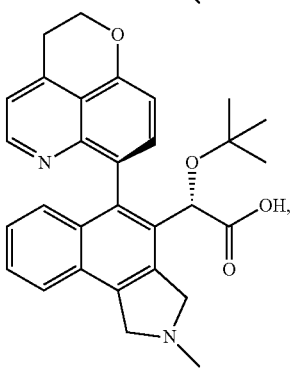
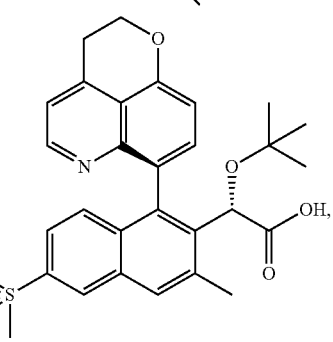
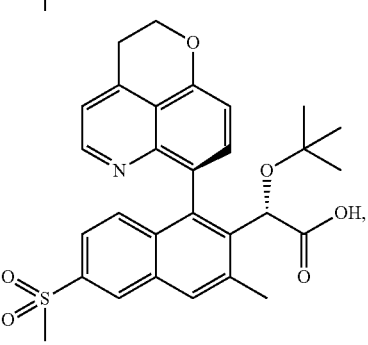

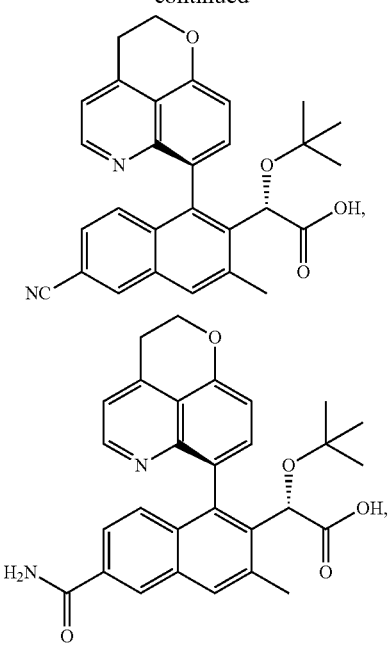
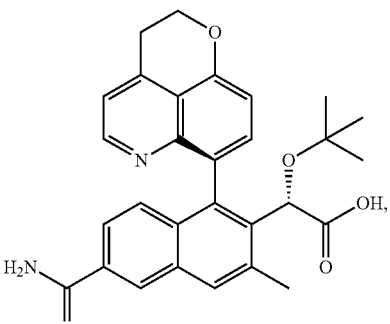
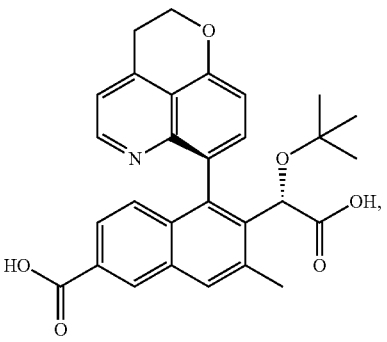
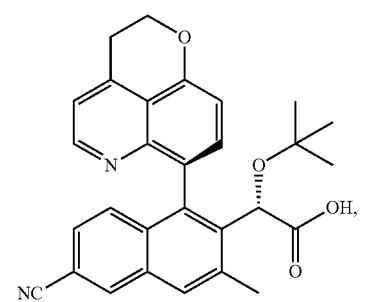
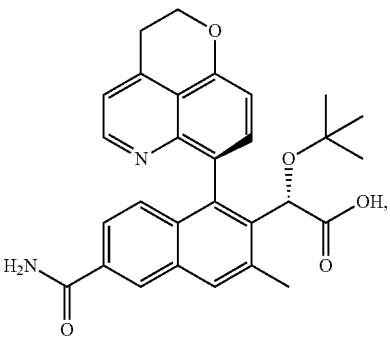
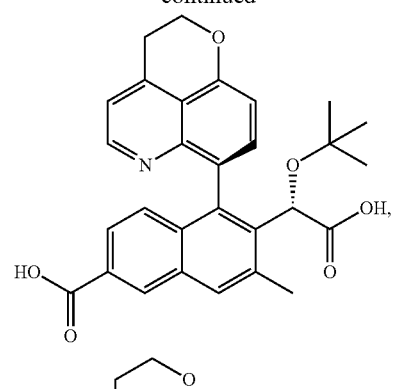
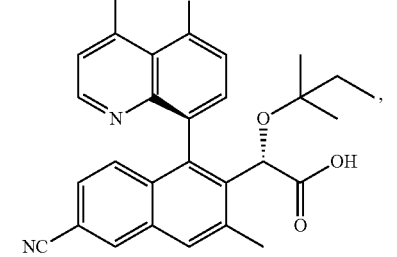
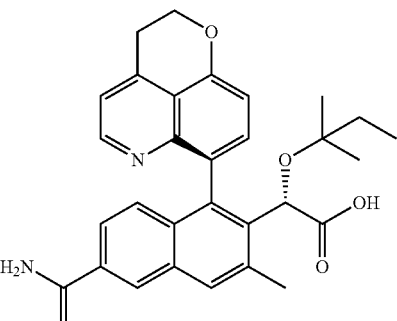
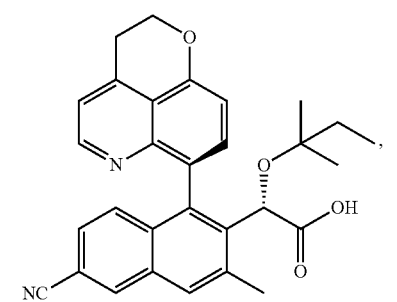
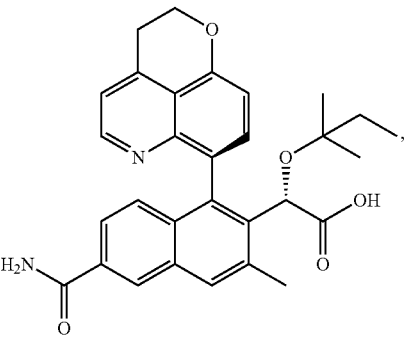

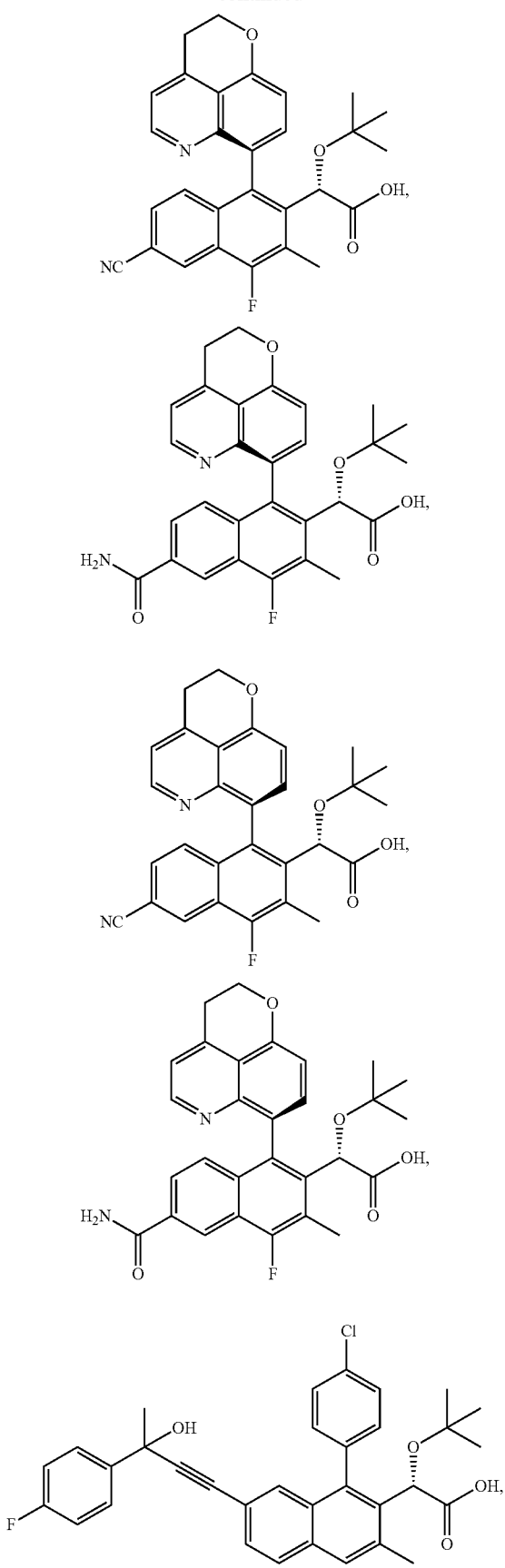
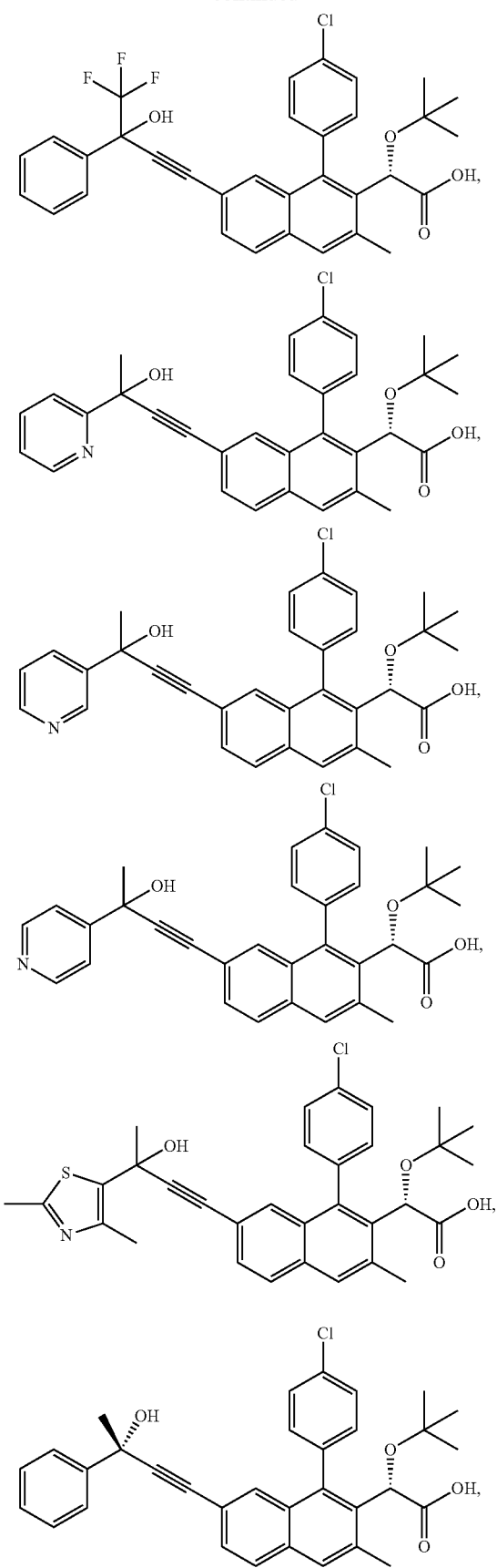
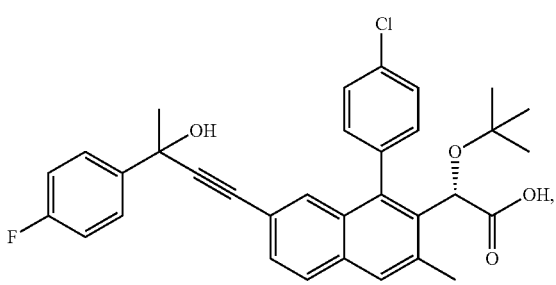

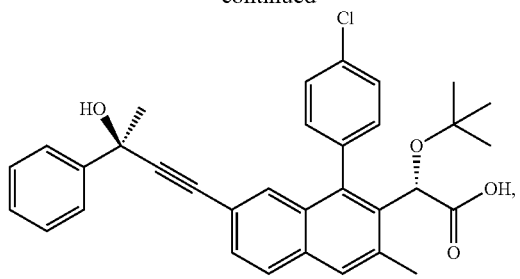
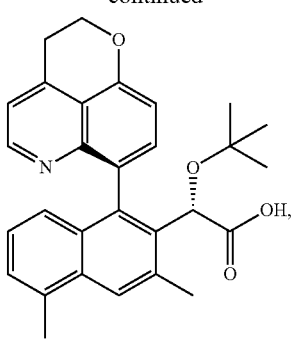
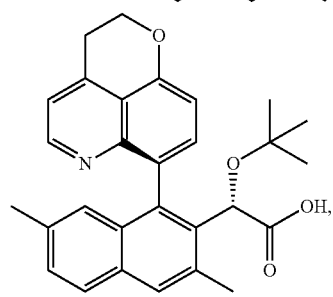
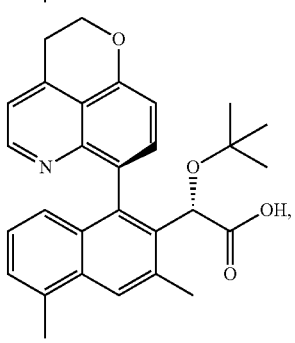
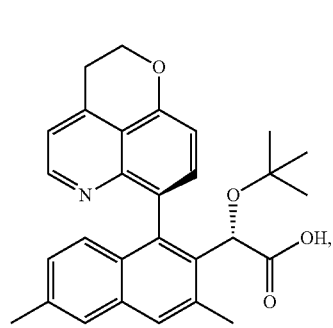
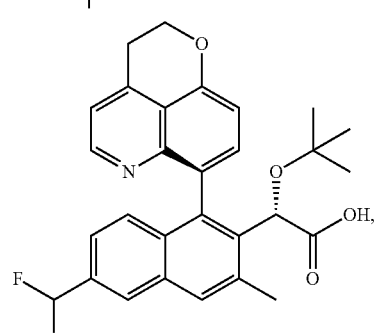
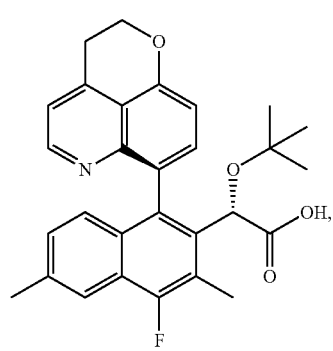
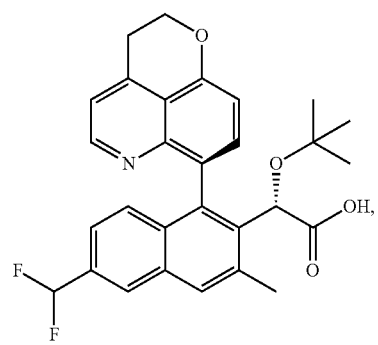
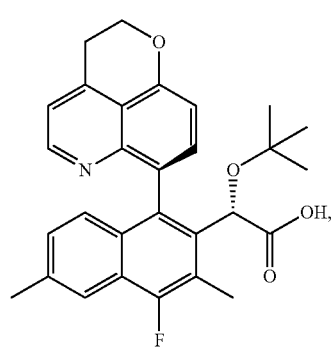
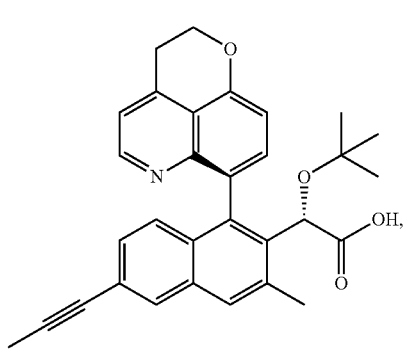

65
-continued
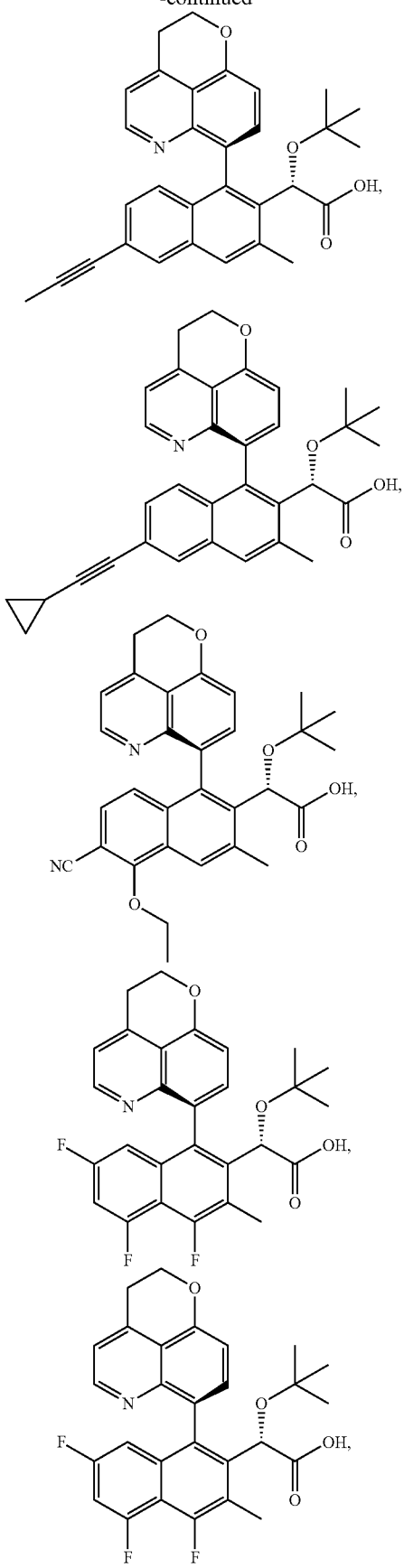
66
-continued
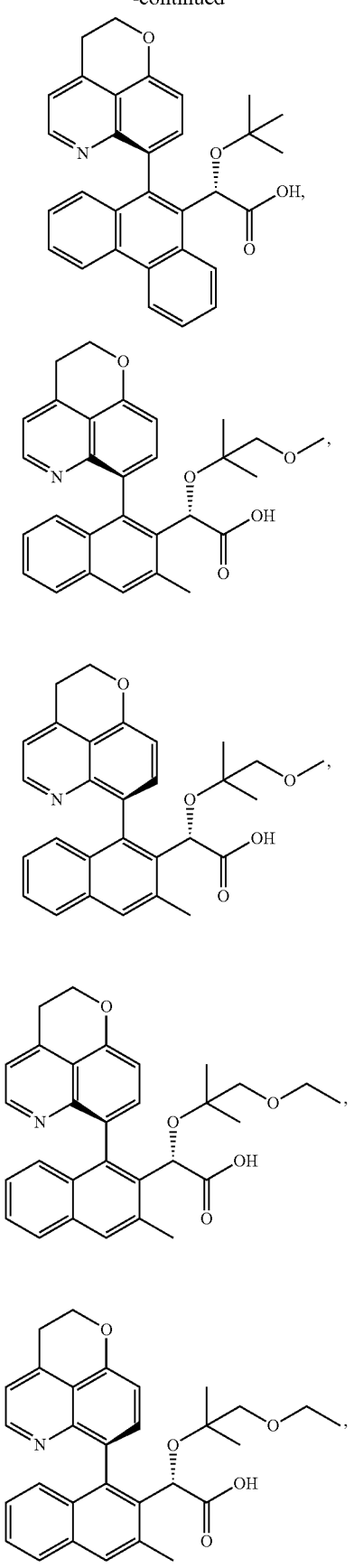

-continued
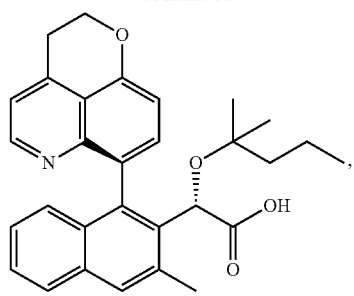
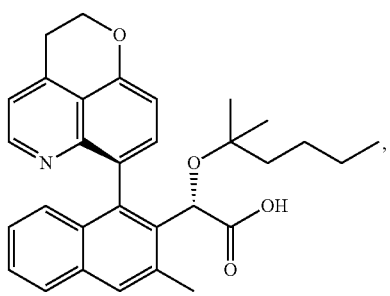
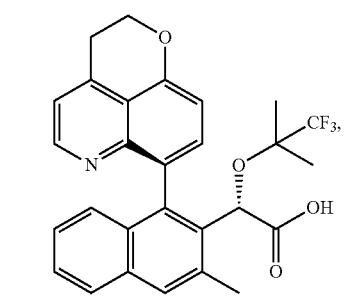
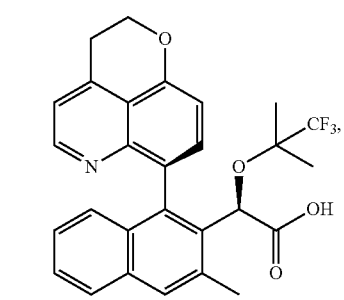
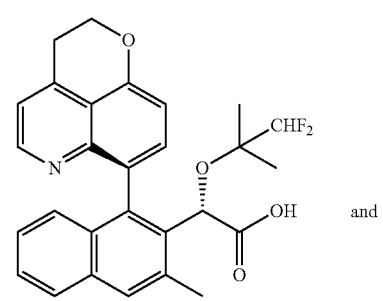
and
-continued
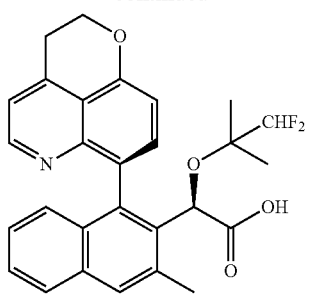
and salts thereof.
In one embodiment compounds are selected from:
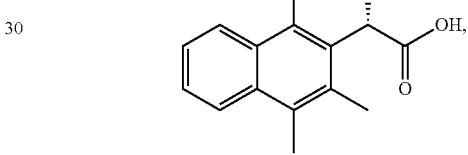
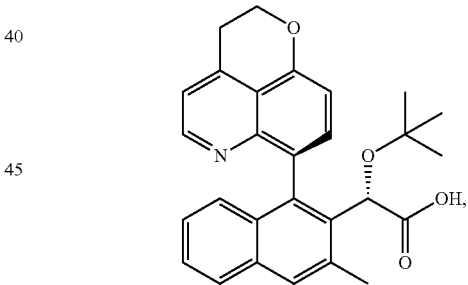
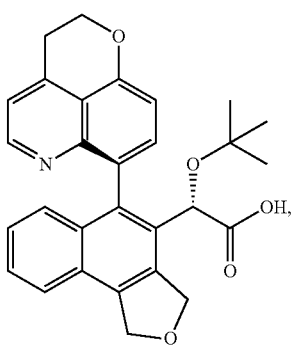

69
-continued
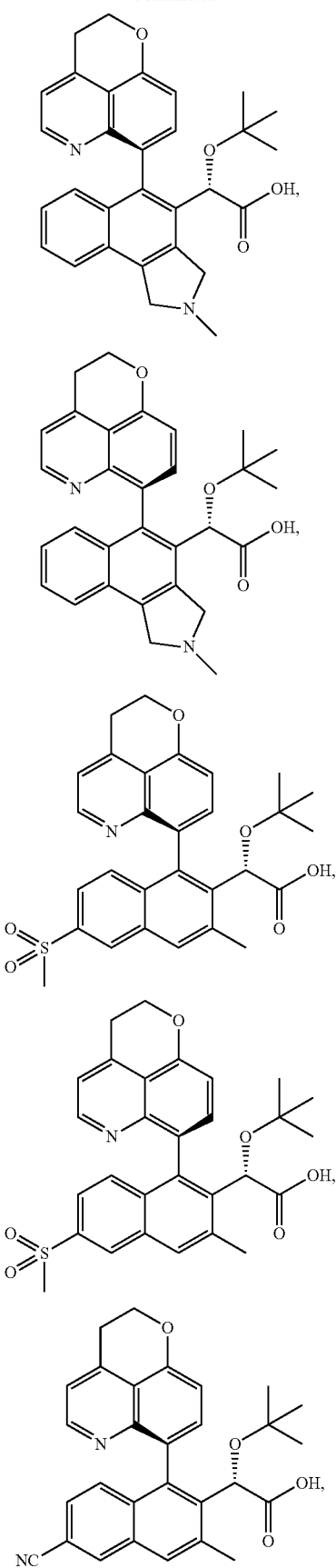
70
-continued
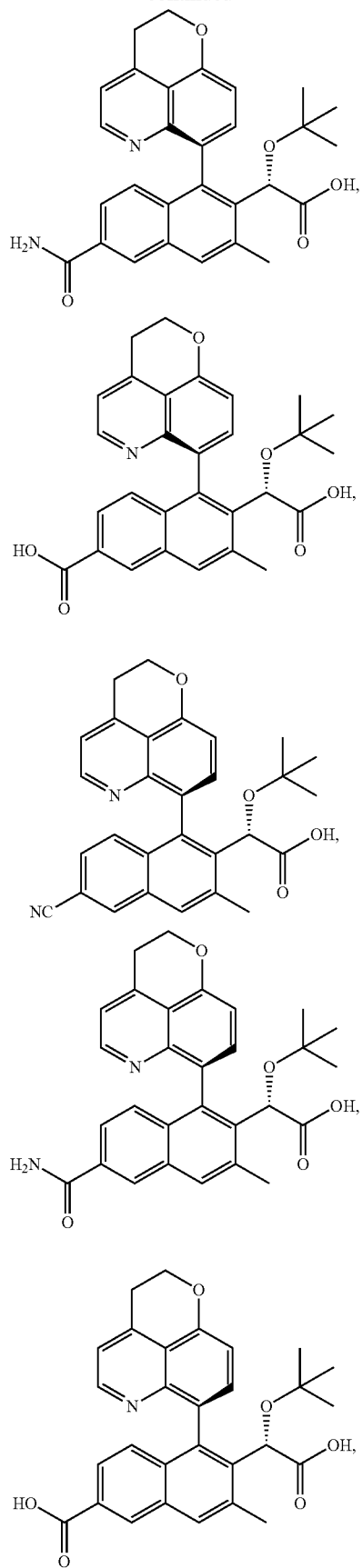

-continued
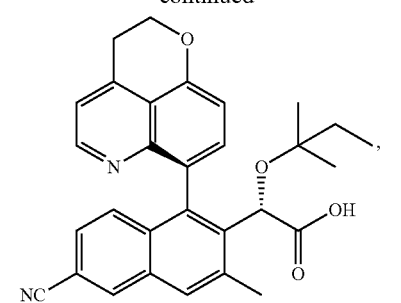
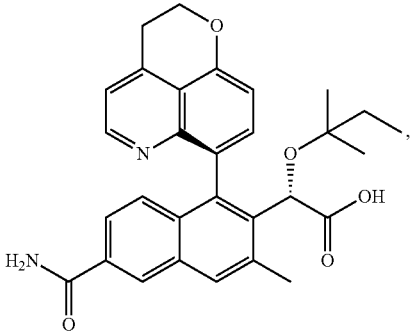
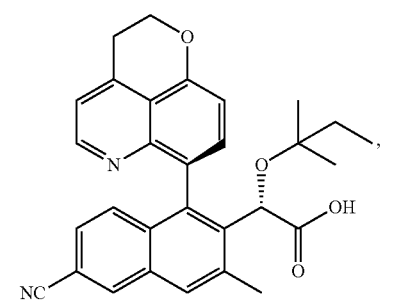
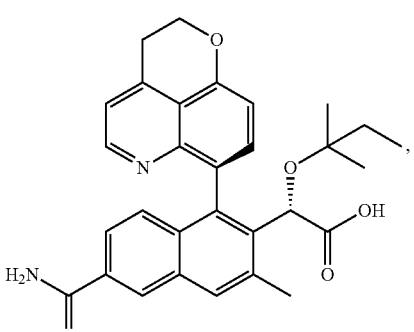
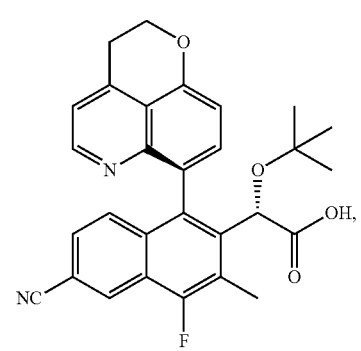
-continued
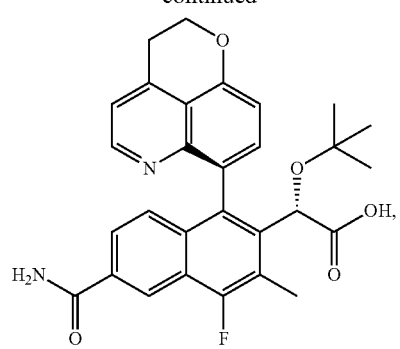
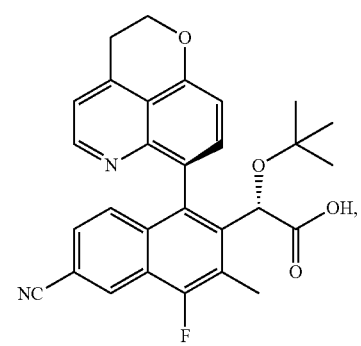
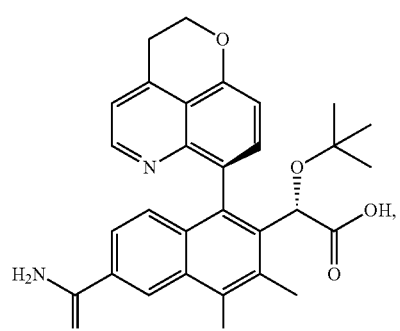
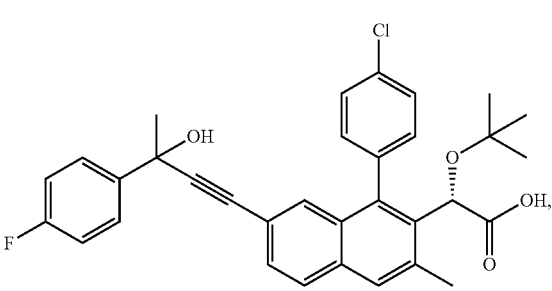
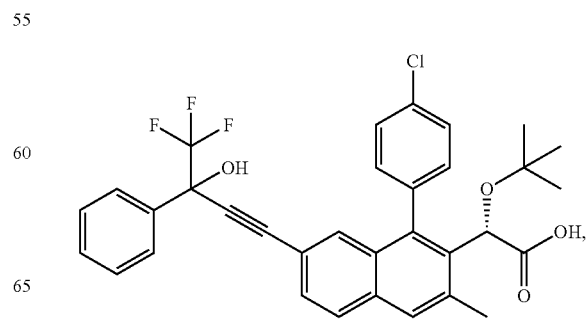

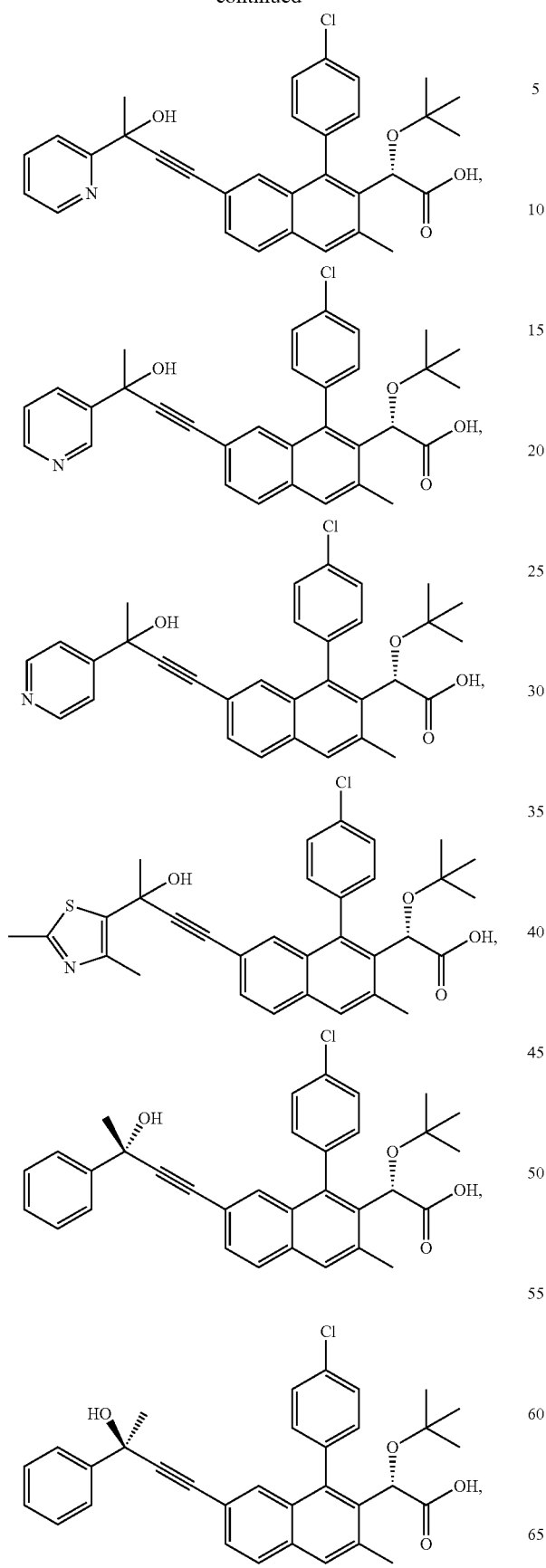
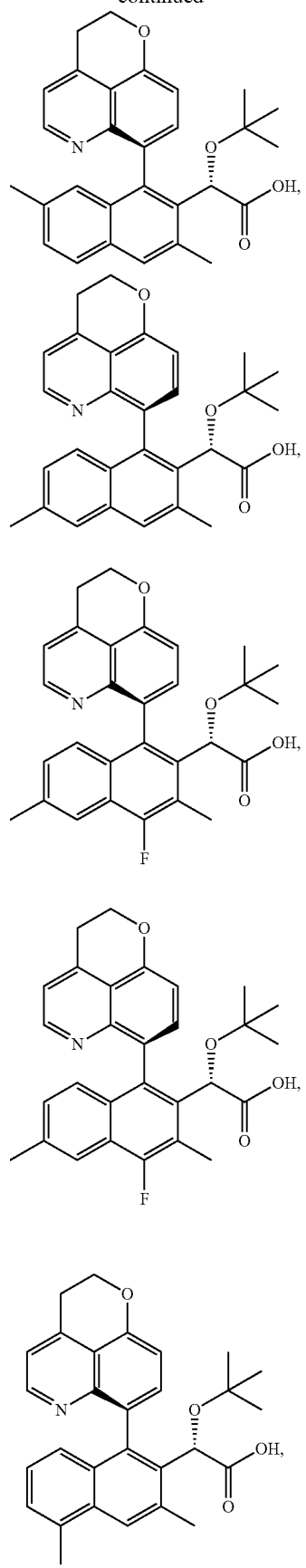

75
-continued
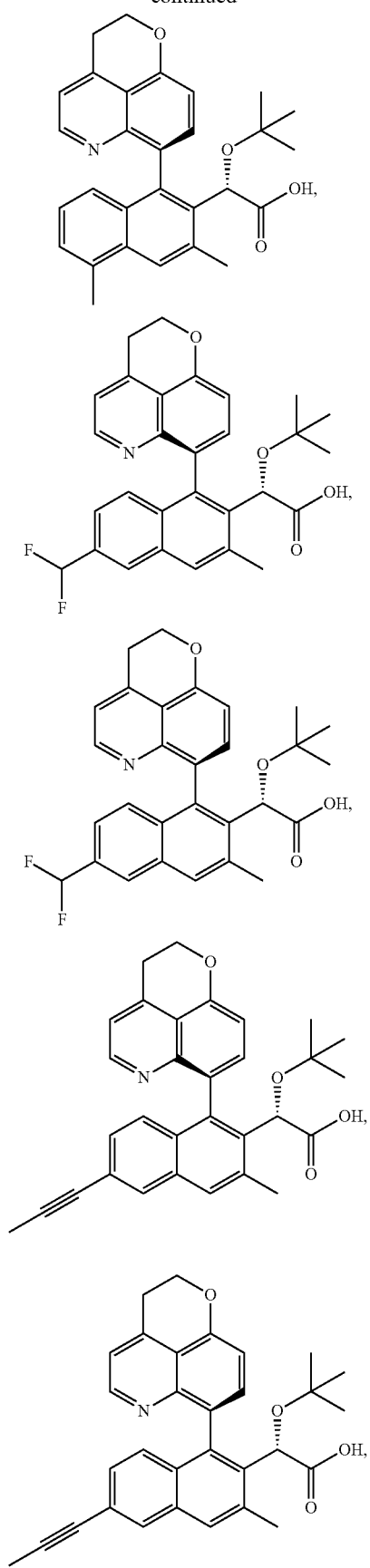
76
-continued
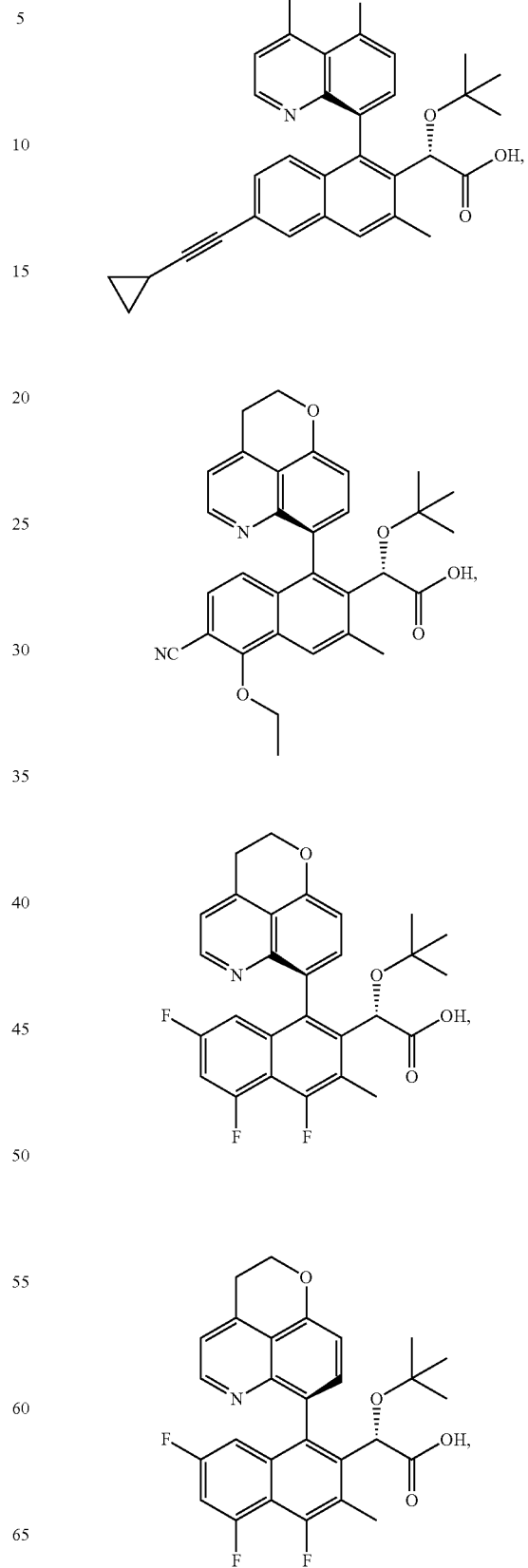

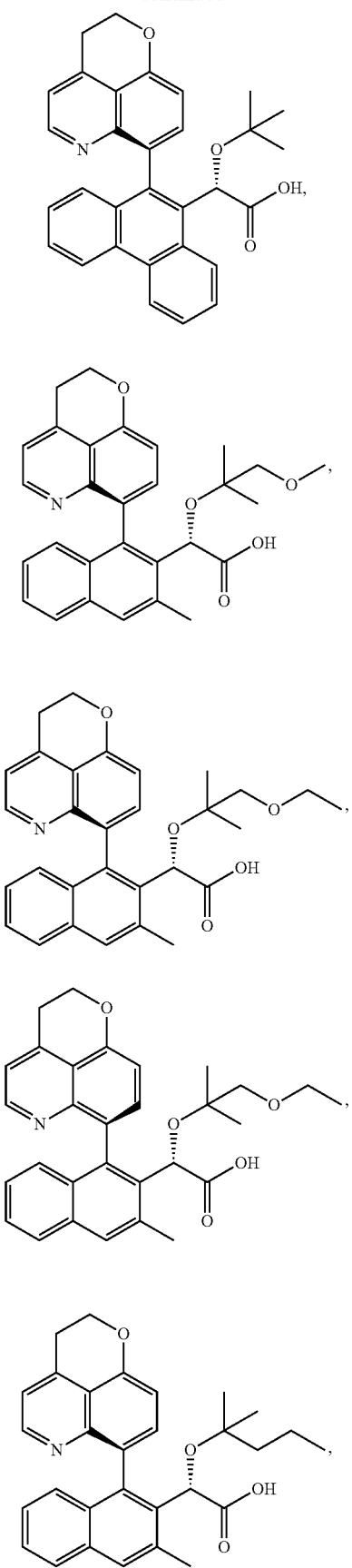
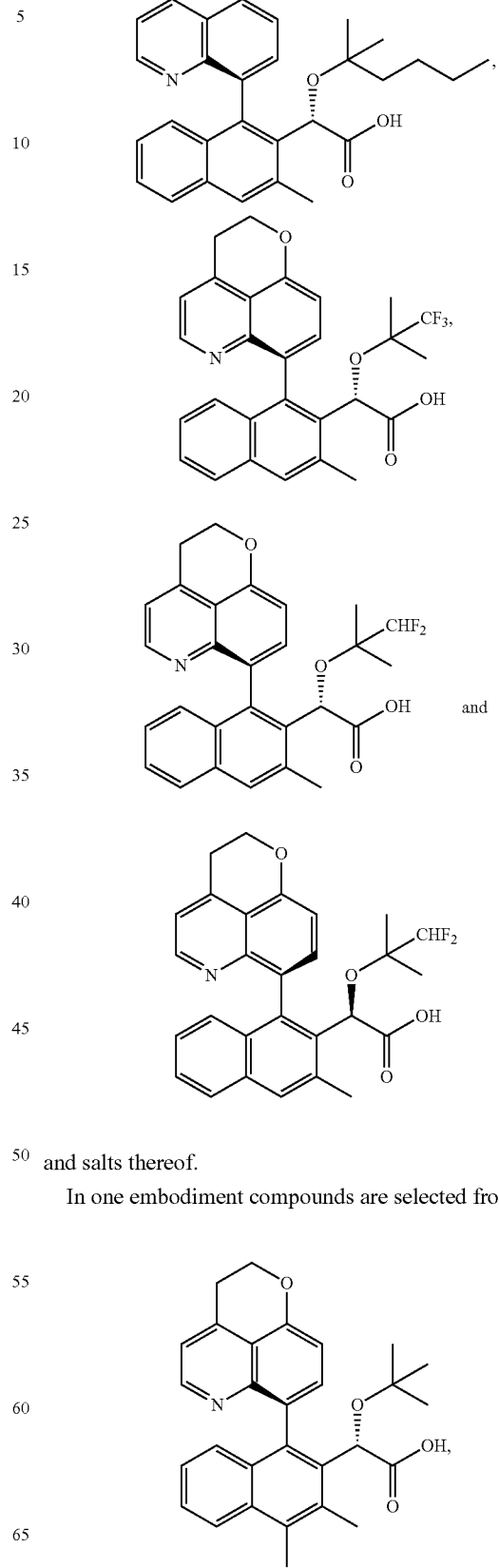
and salts thereof.
In one embodiment compounds are selected from:
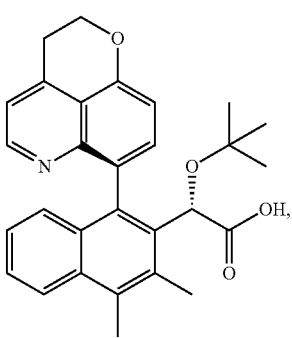

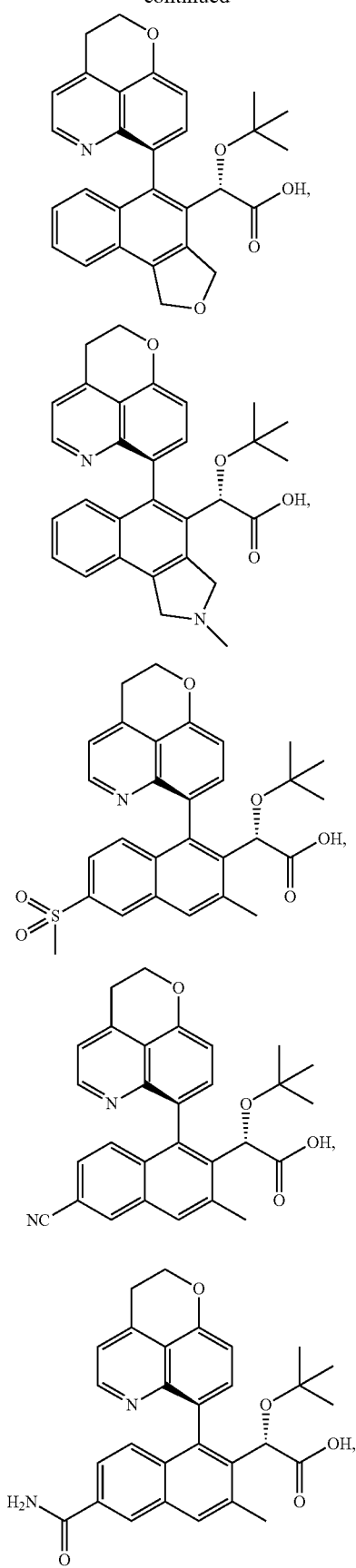
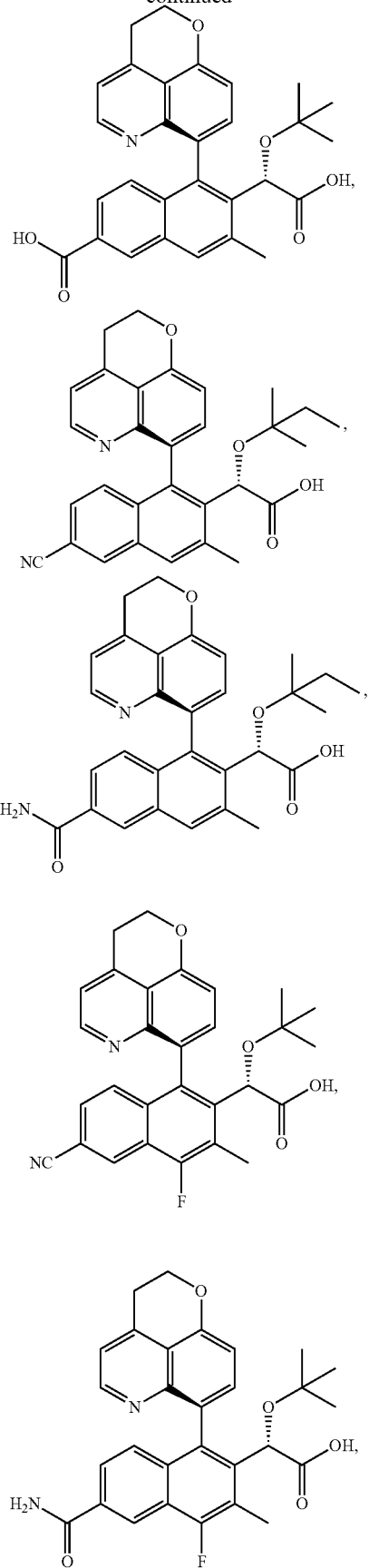

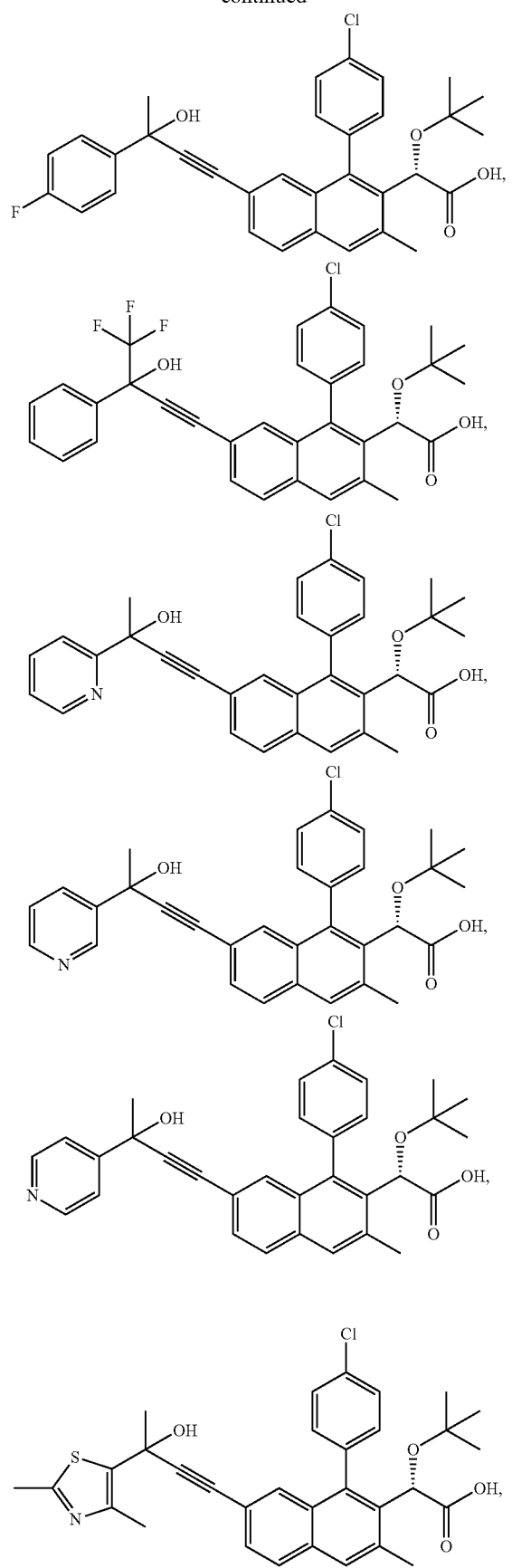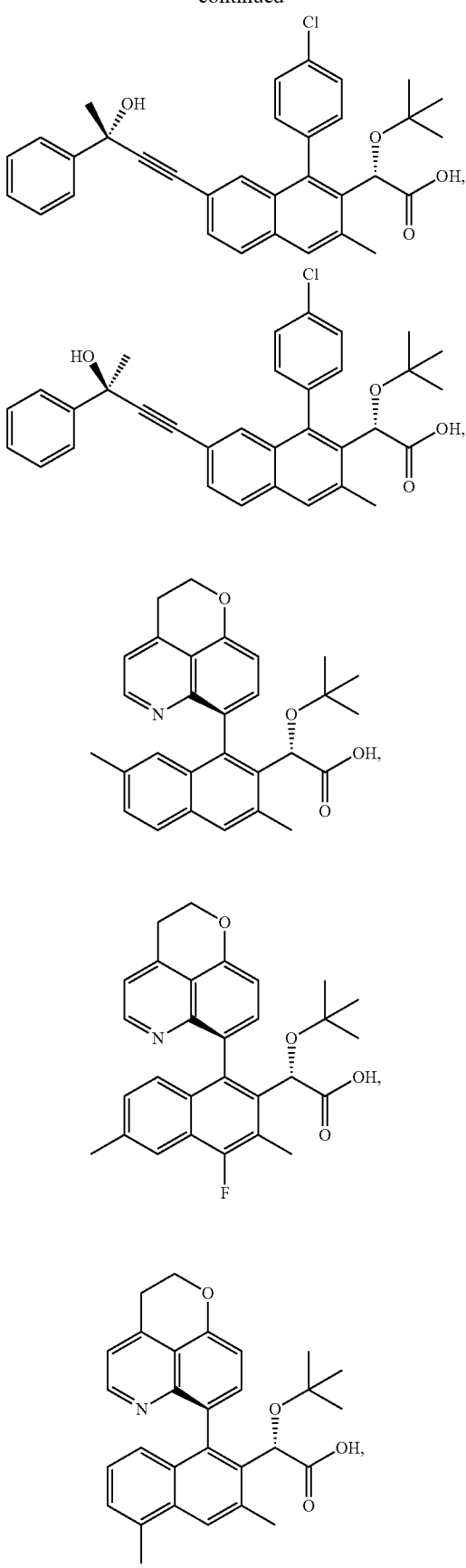

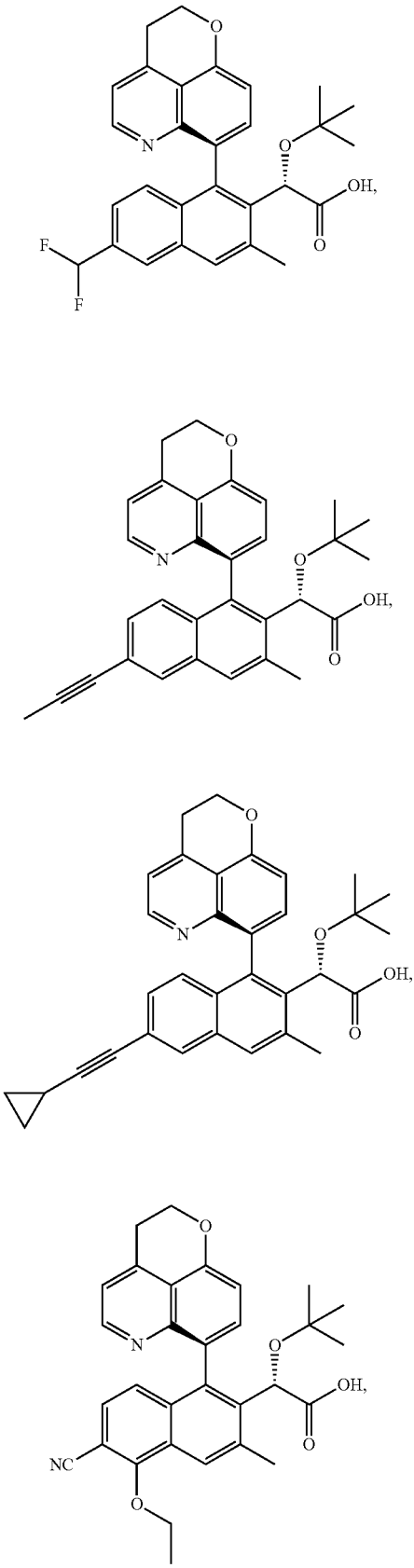
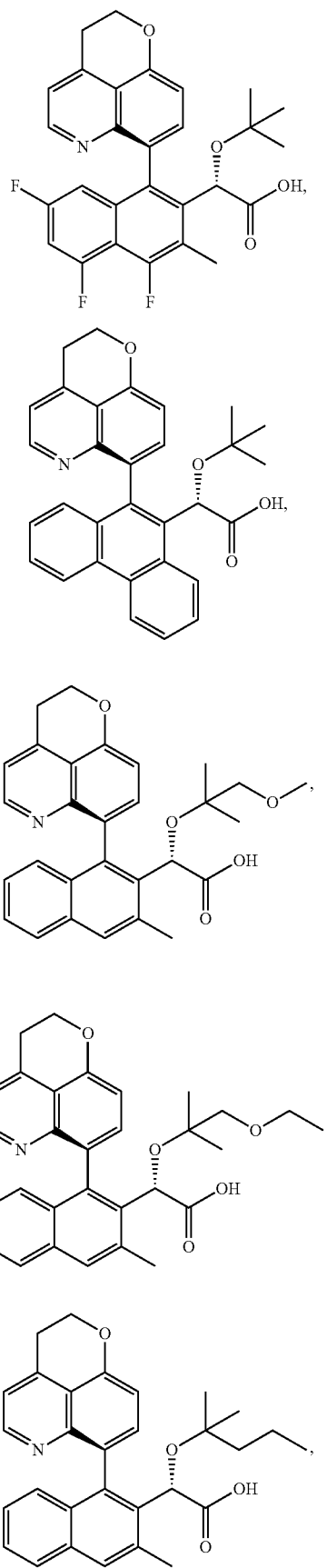

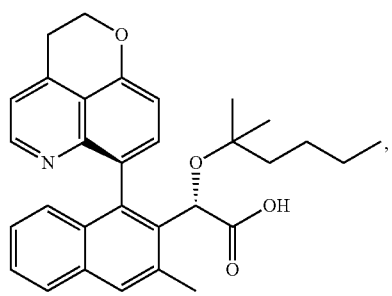
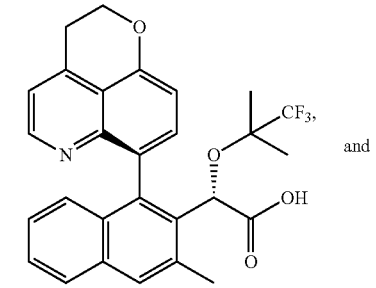
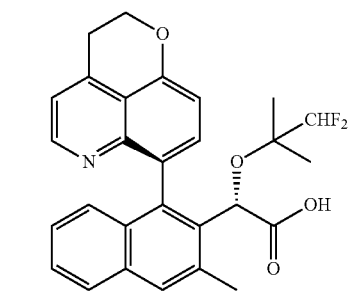
and salts thereof
In one embodiment compounds are selected from:
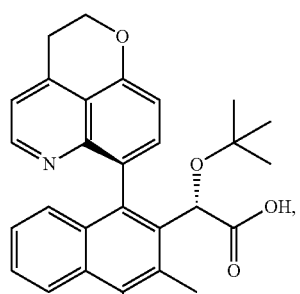
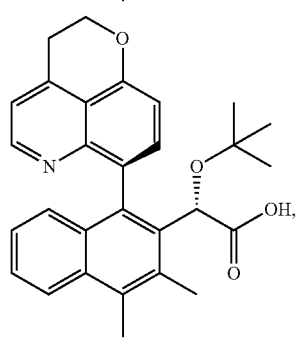
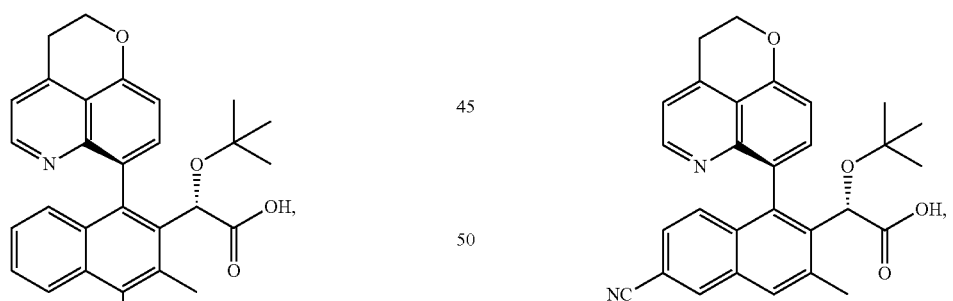
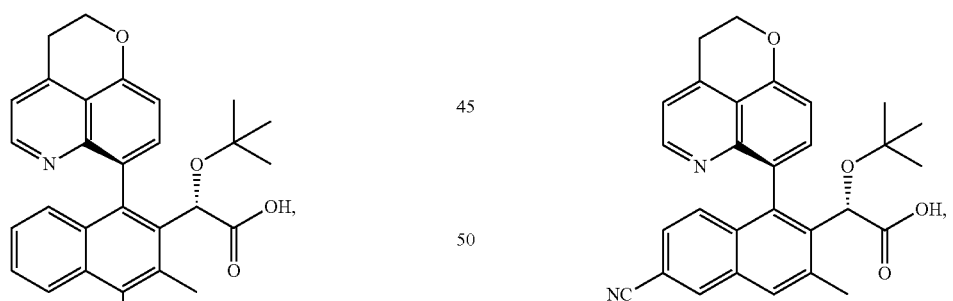
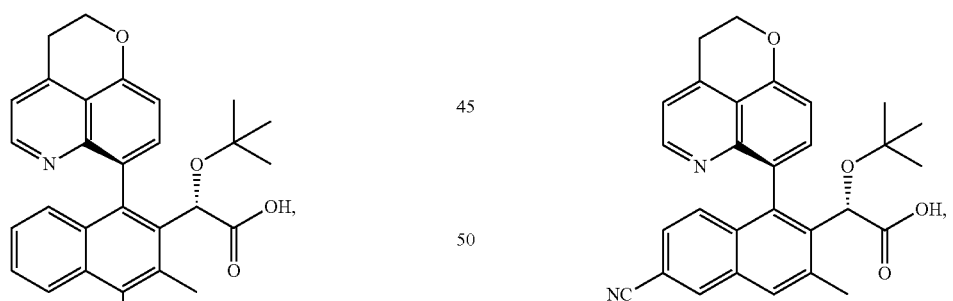
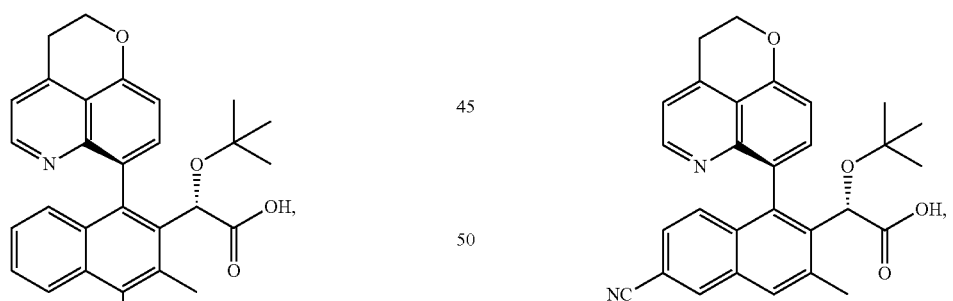
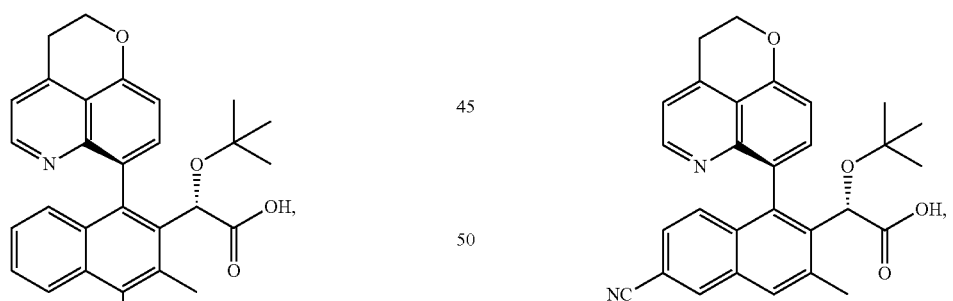
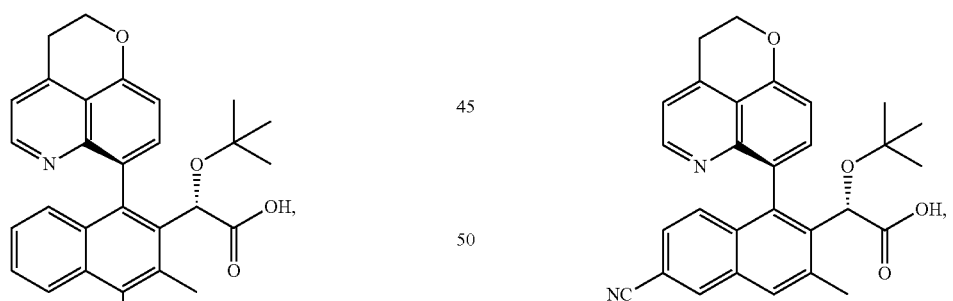

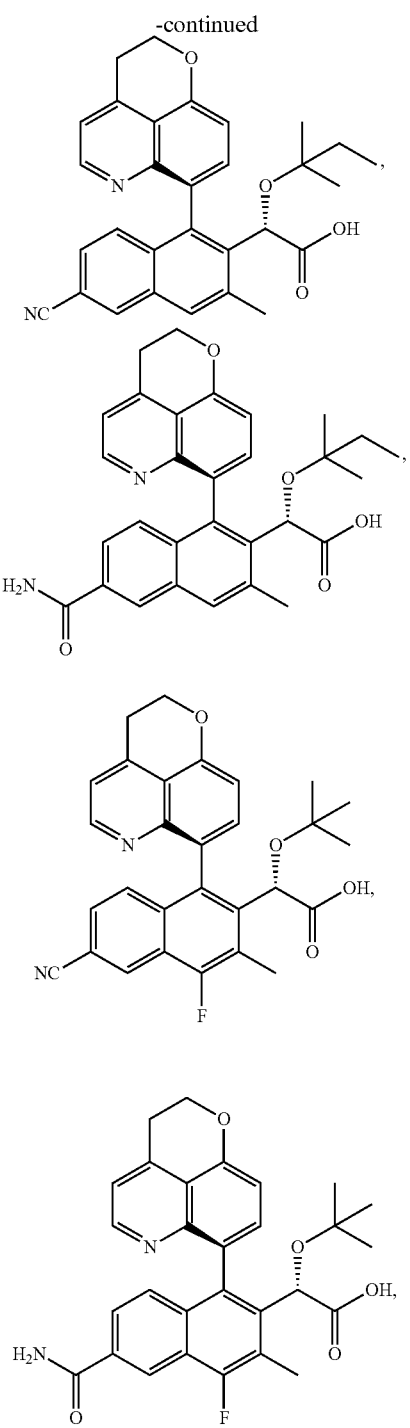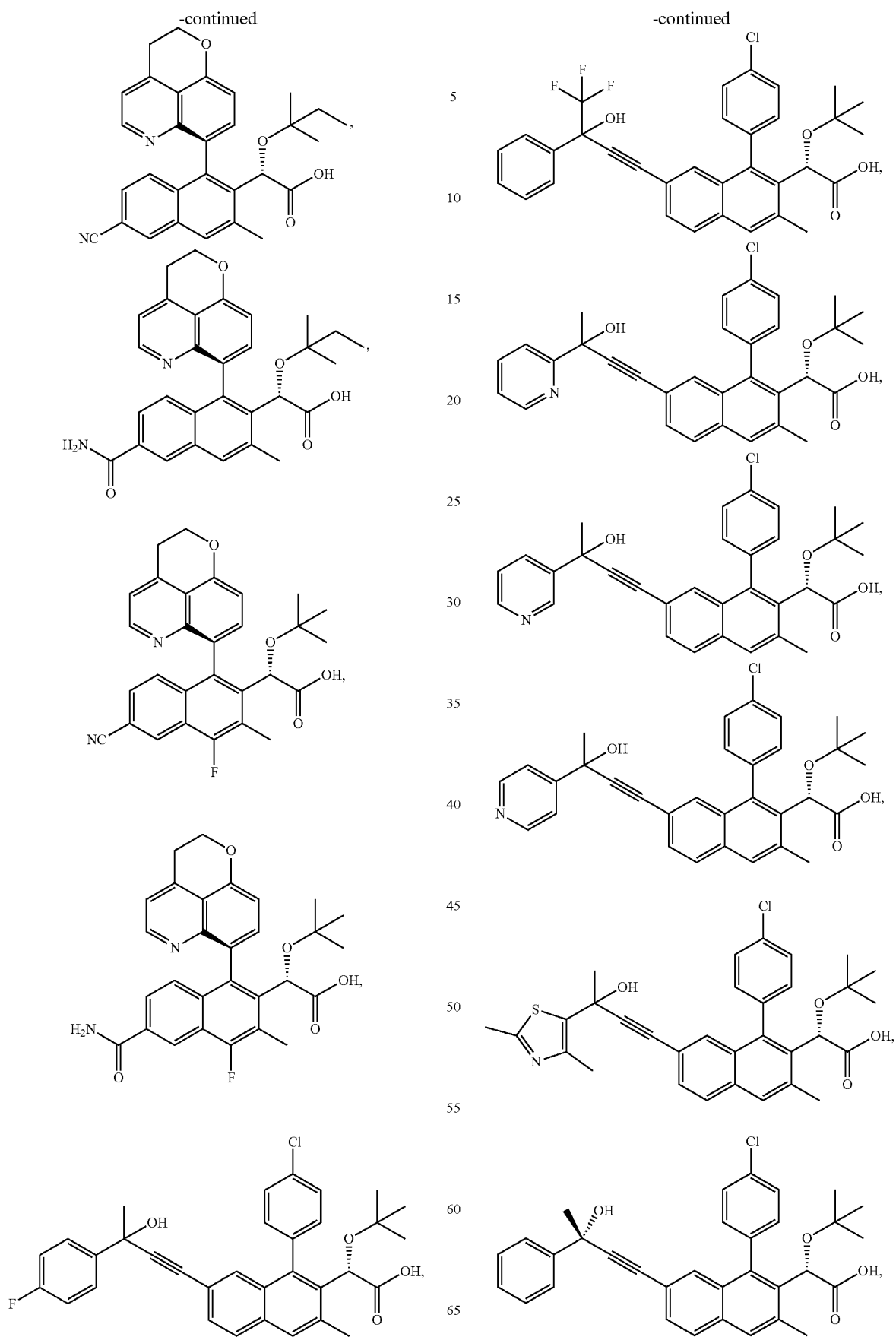

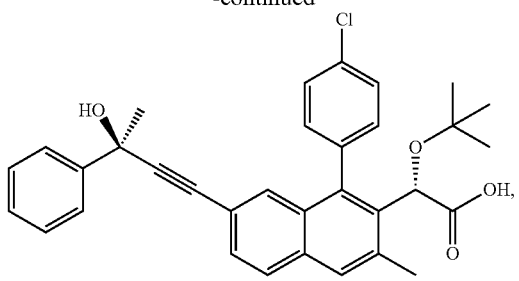
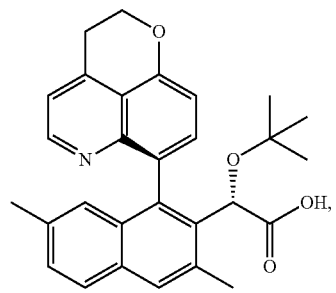
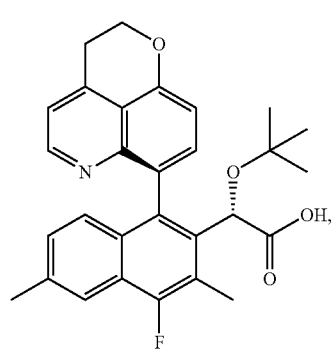
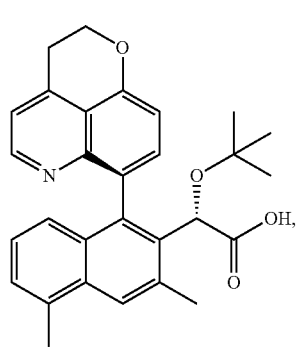
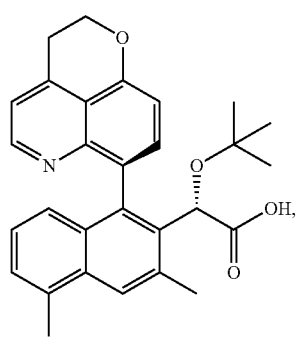
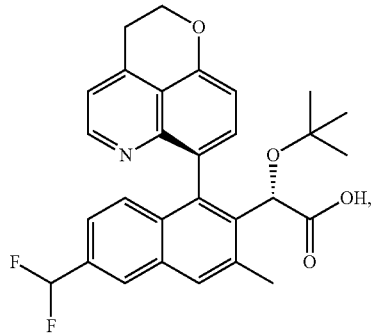
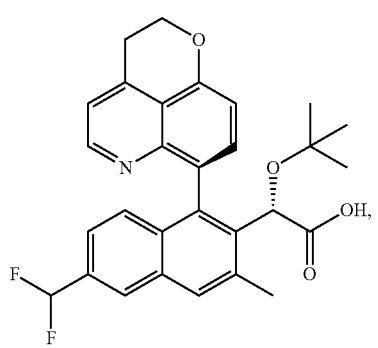
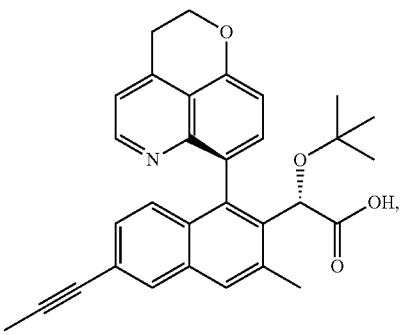
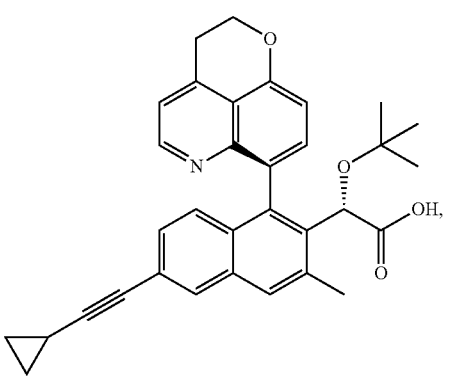

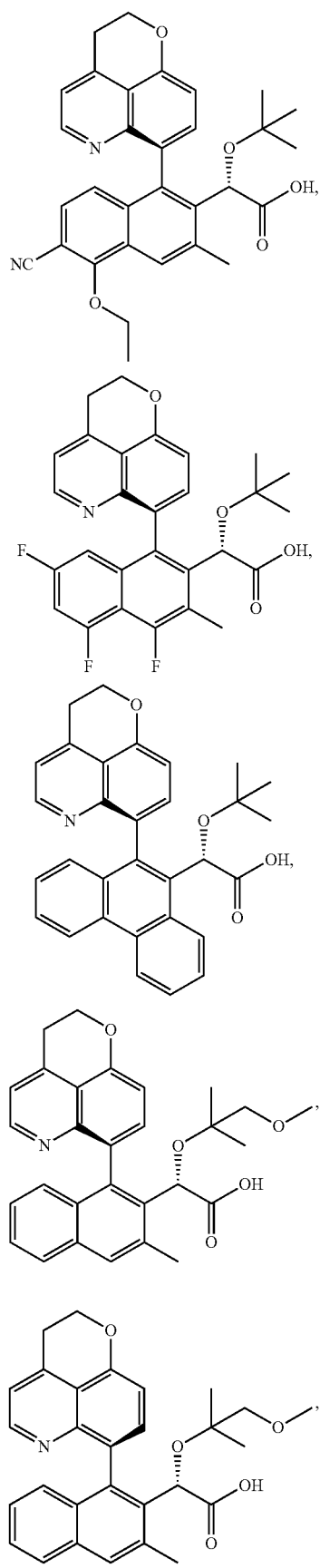
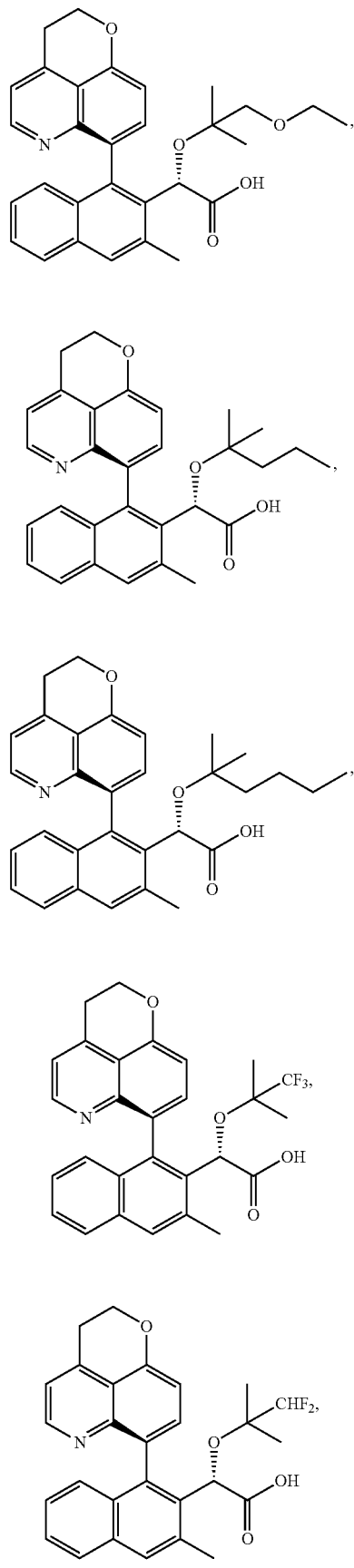

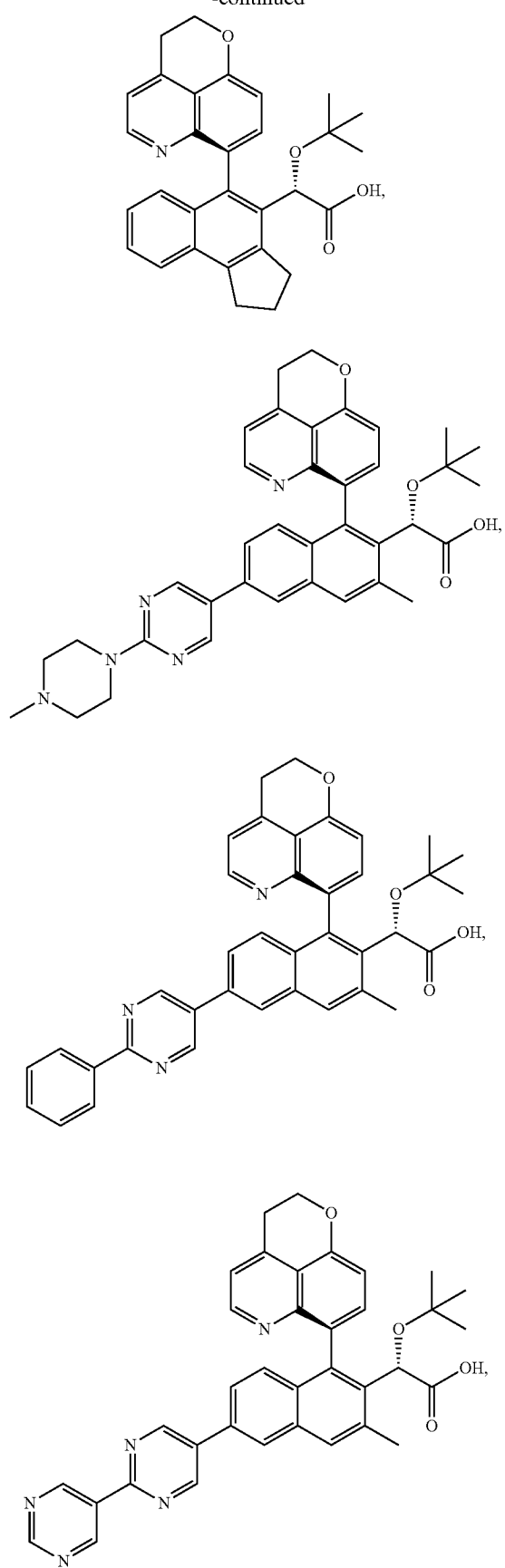

-continued
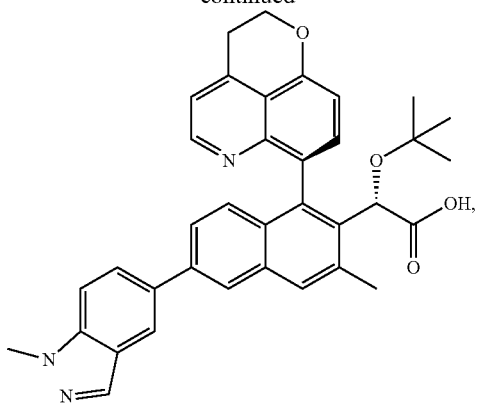
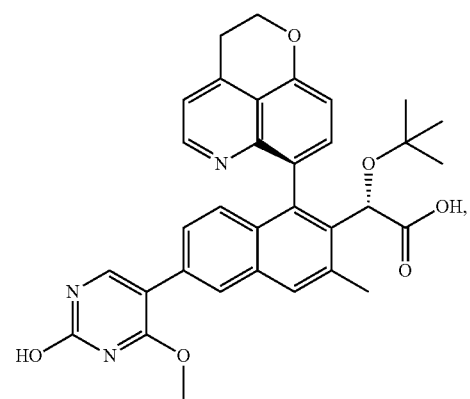
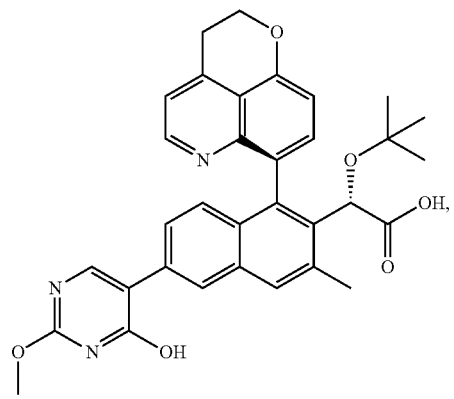
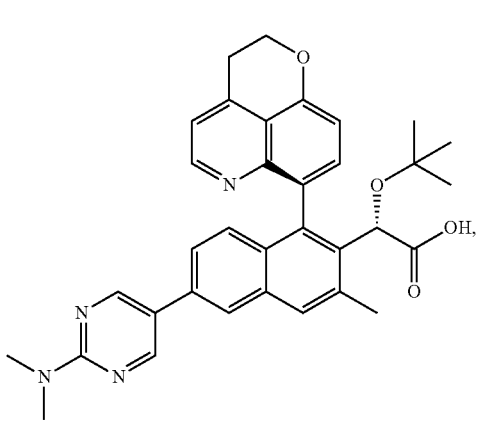
-continued
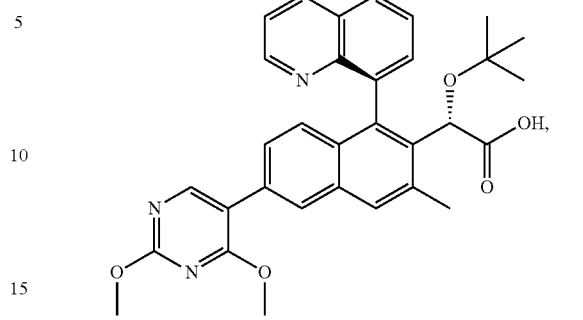
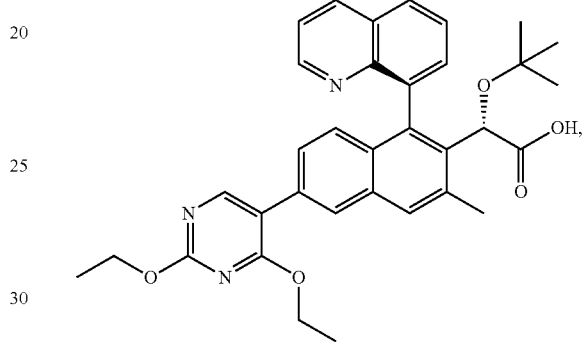
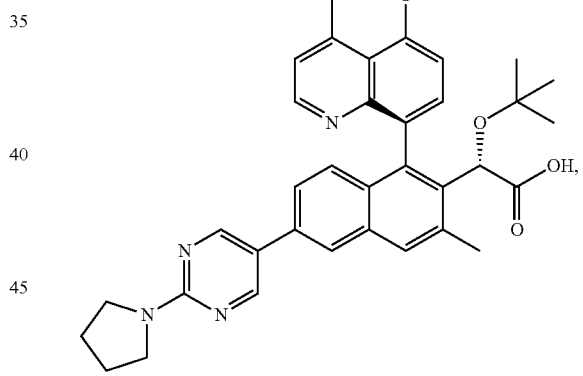
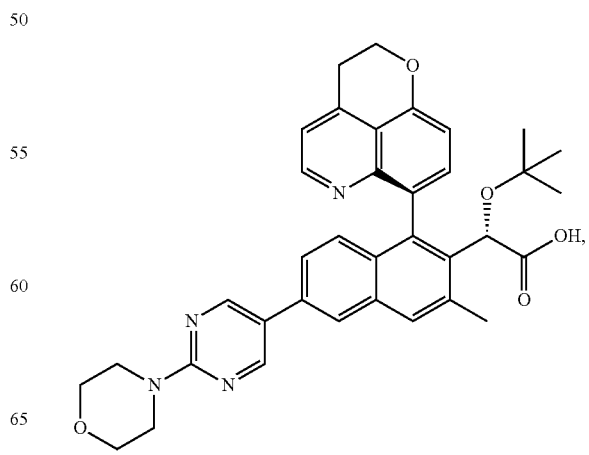

97
-continued
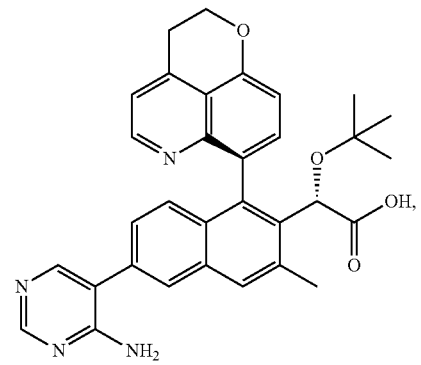
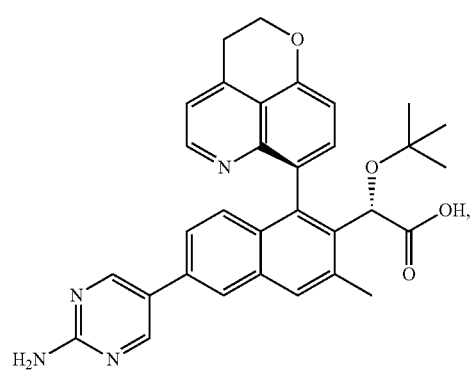
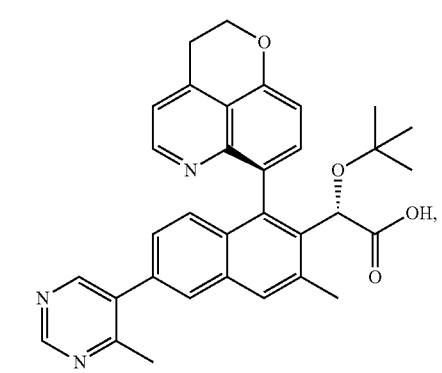
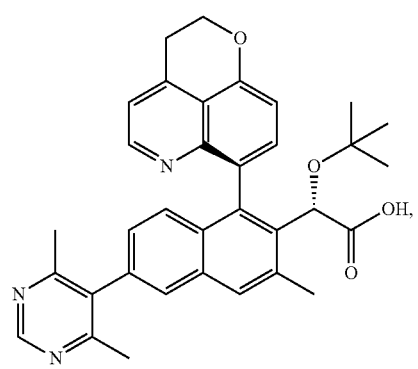
98
-continued
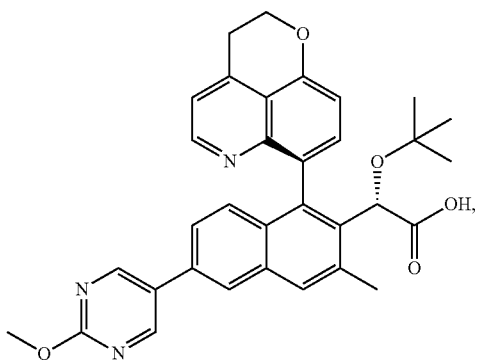
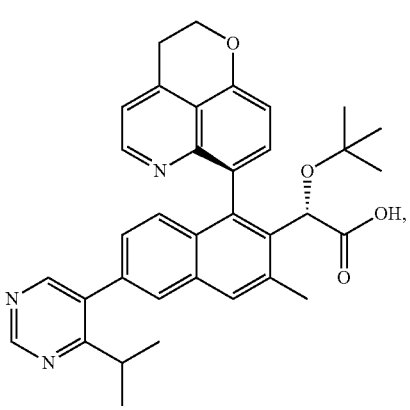
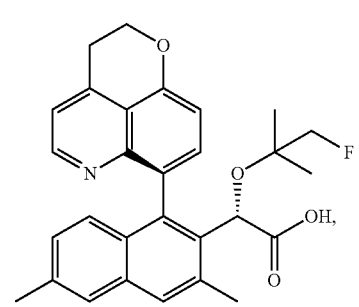
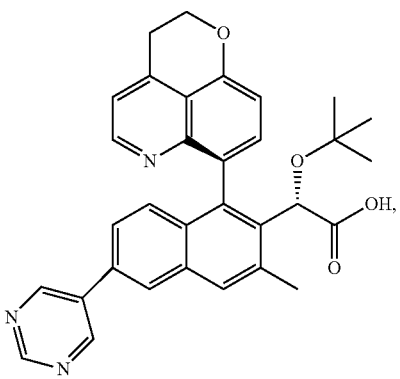

99
-continued
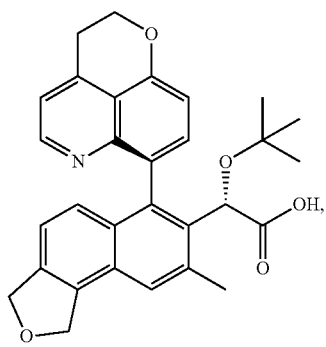
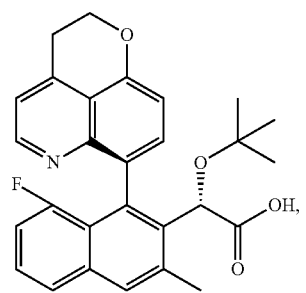
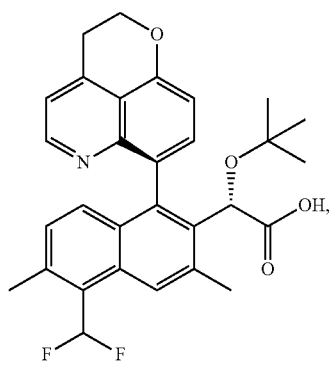
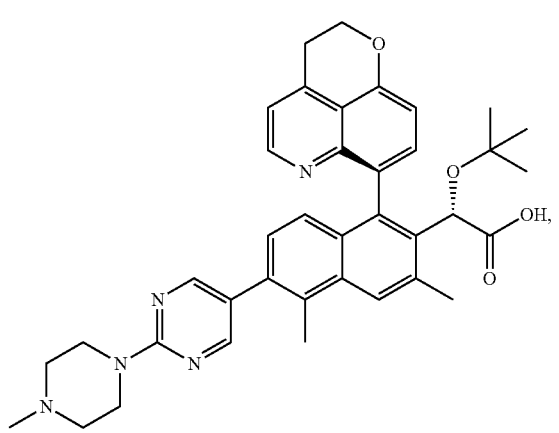
100
-continued
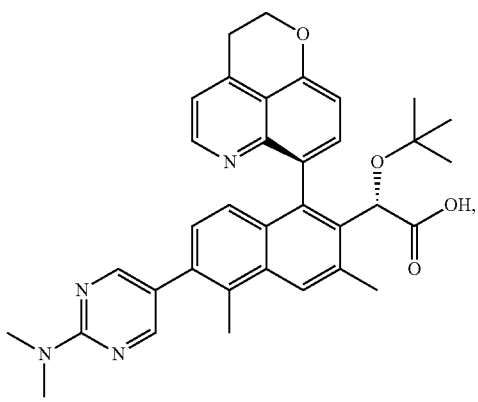
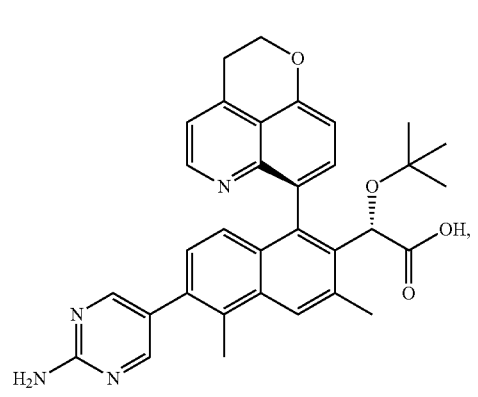
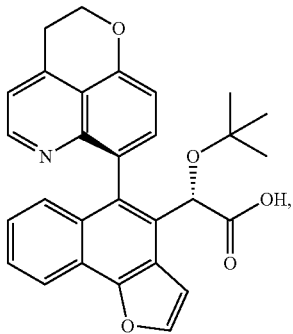
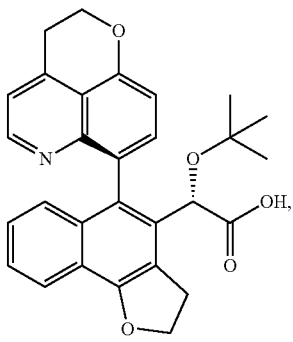

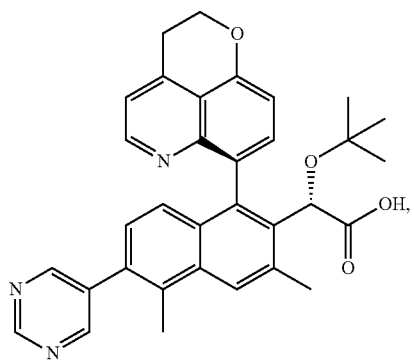
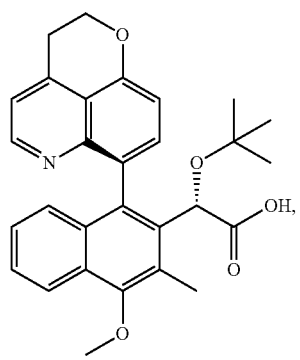
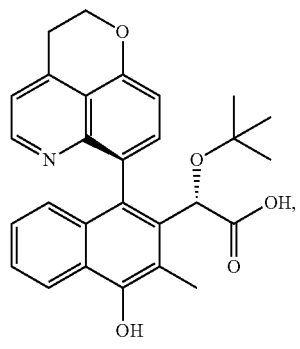
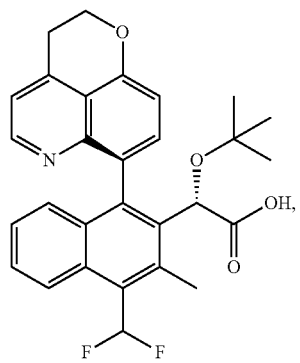
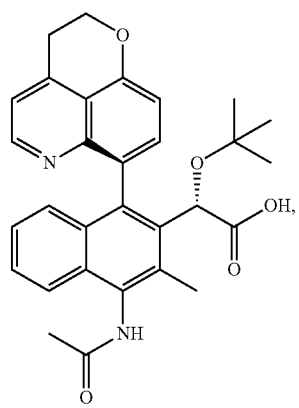
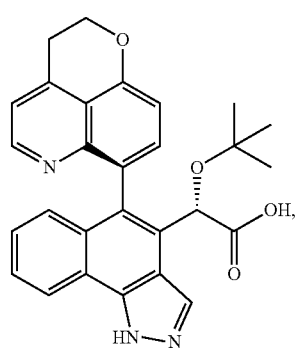
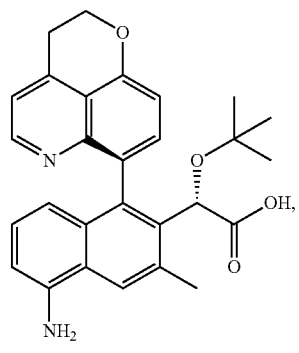
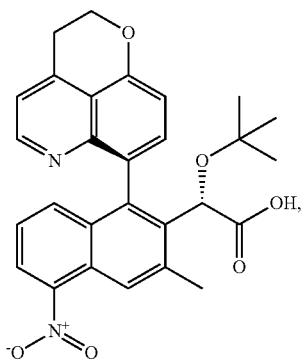

-continued
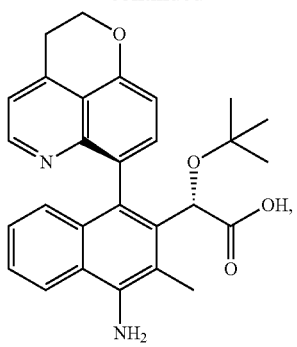
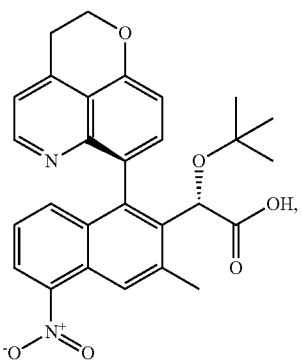
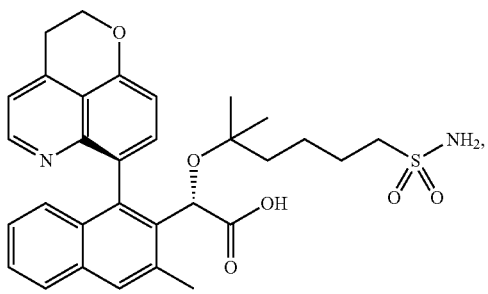
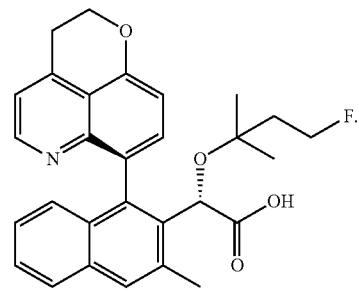
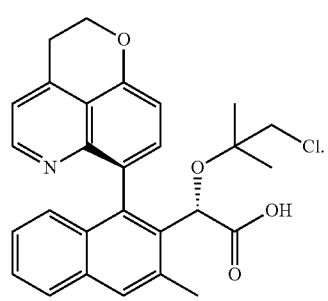
-continued
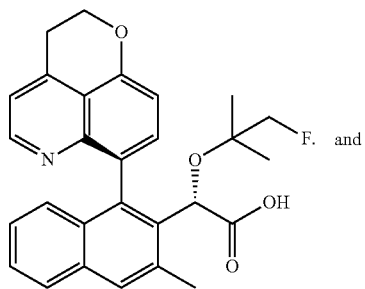
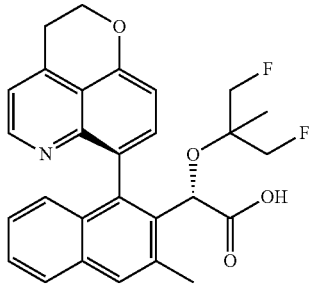
and salts thereof.
One embodiment provides compounds selected from:
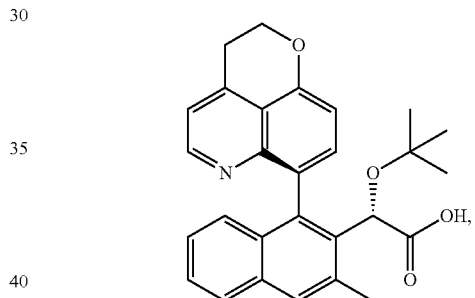
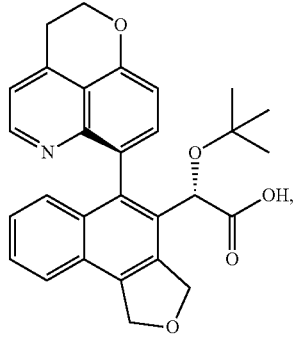
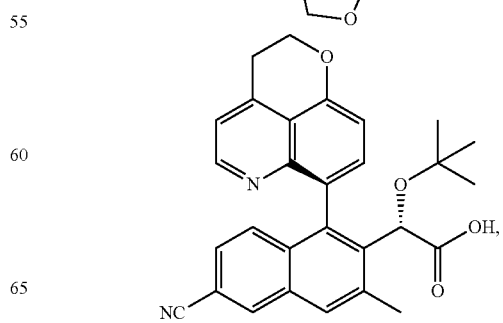

105
-continued
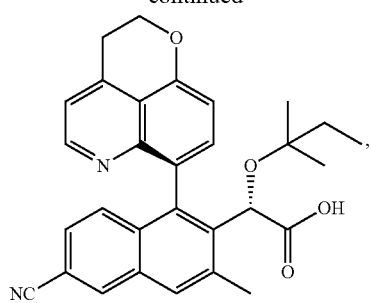
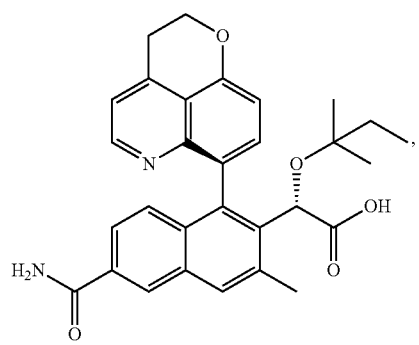
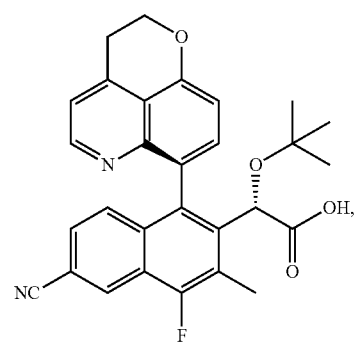
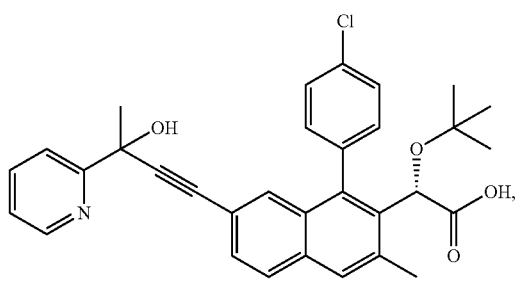
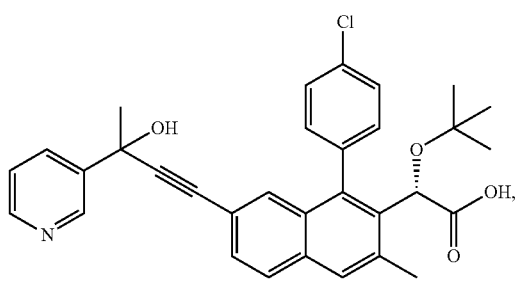
106
-continued
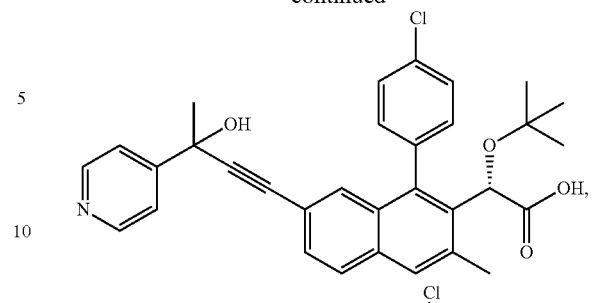
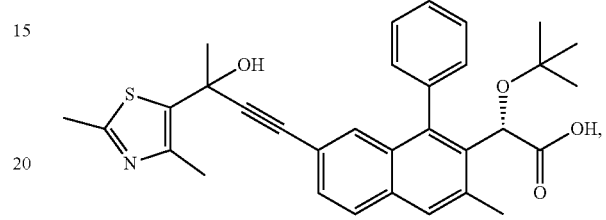
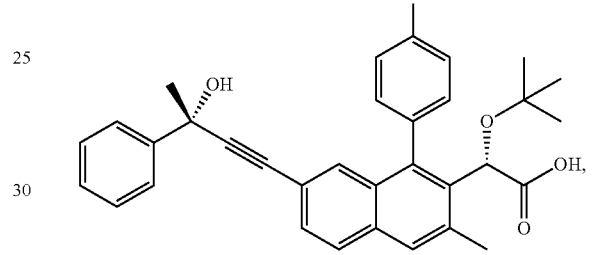
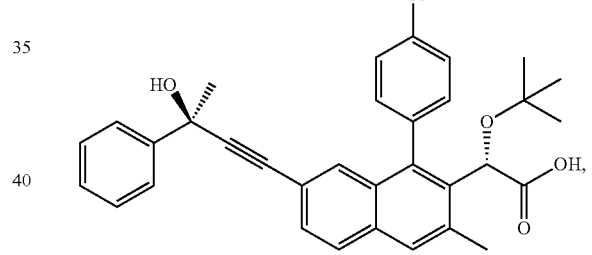
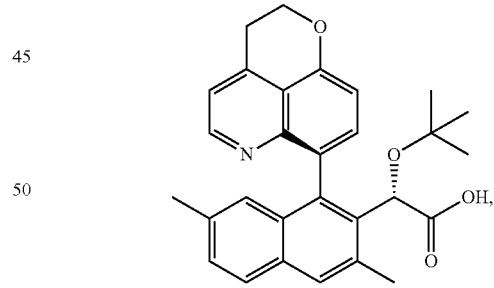
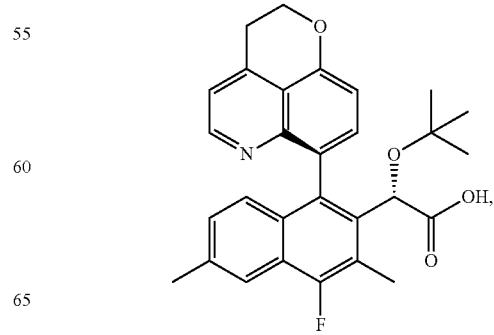

107
-continued
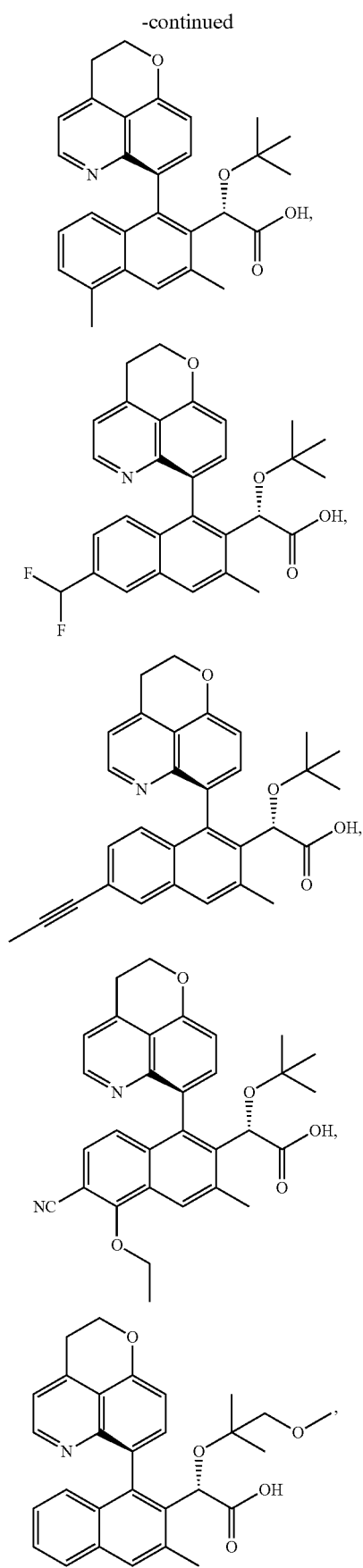
108
-continued
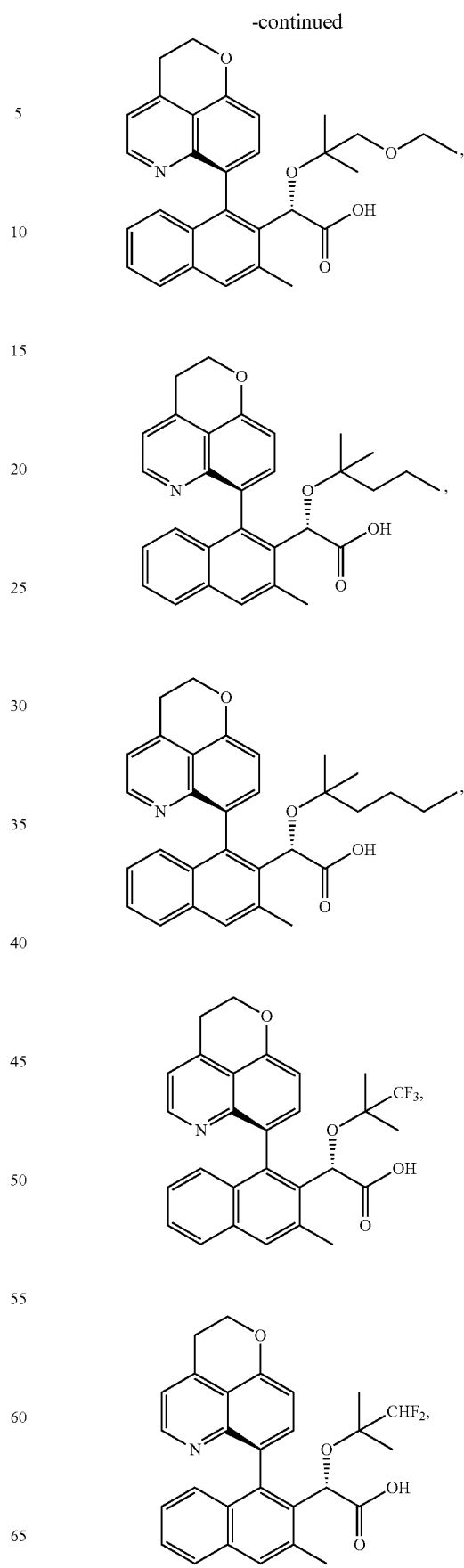

109
-continued
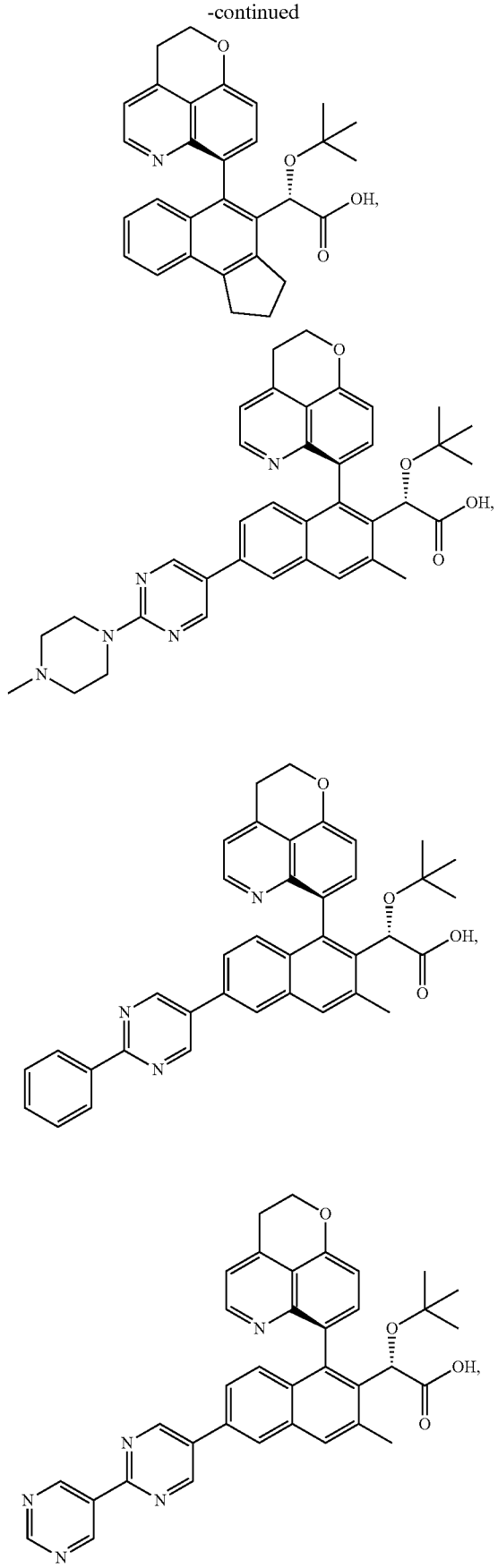
110
-continued
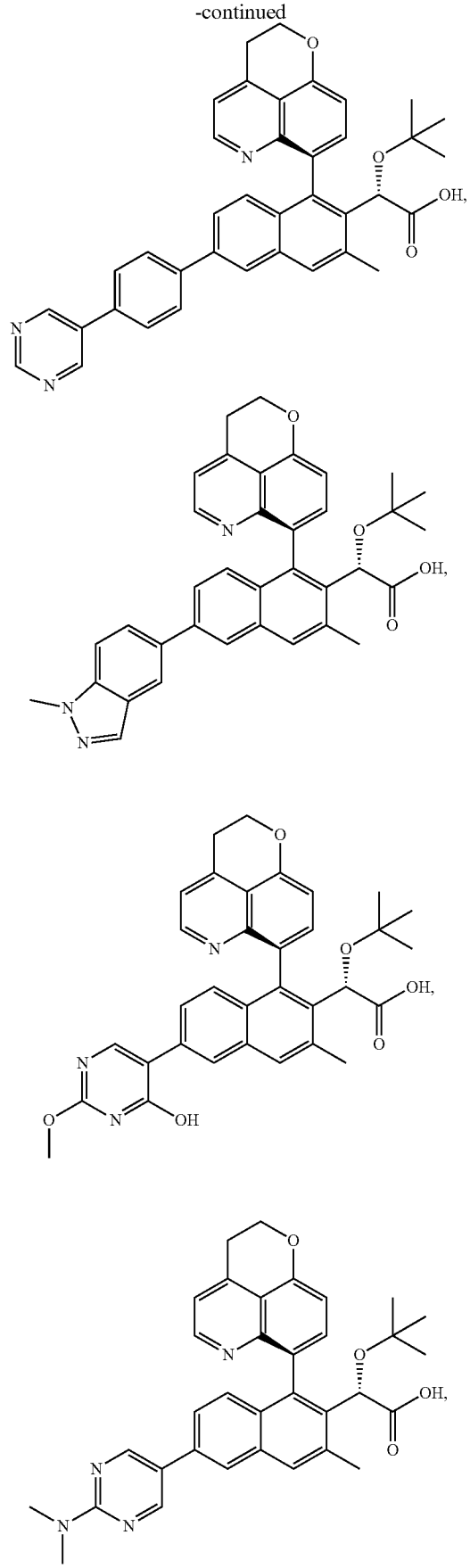

111
-continued
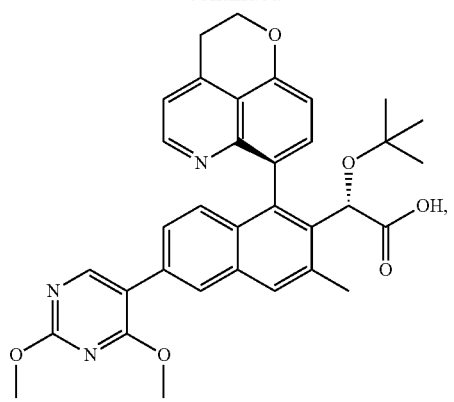
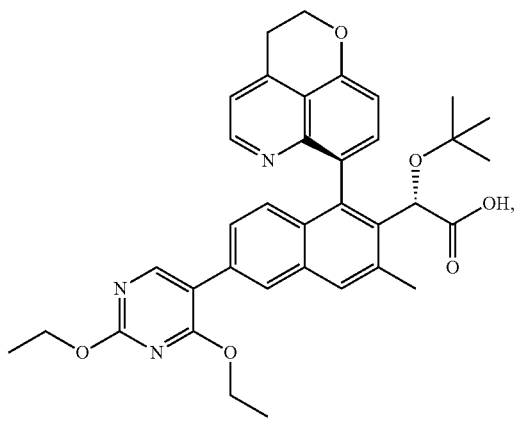
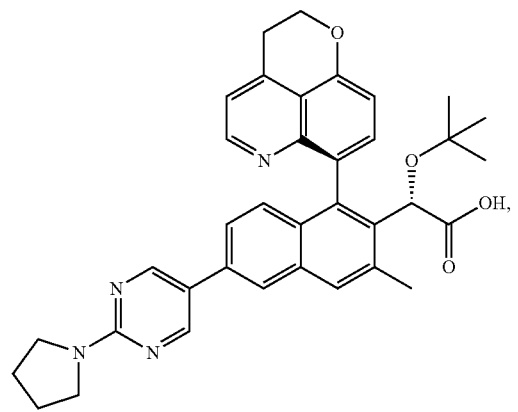
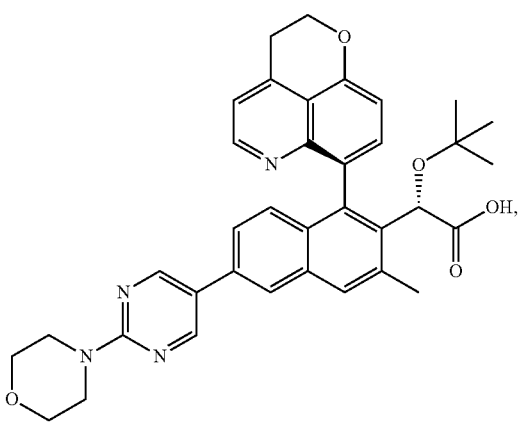
112
-continued
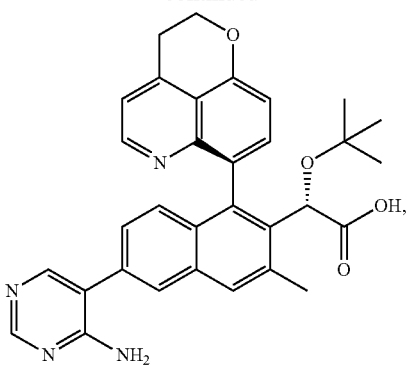
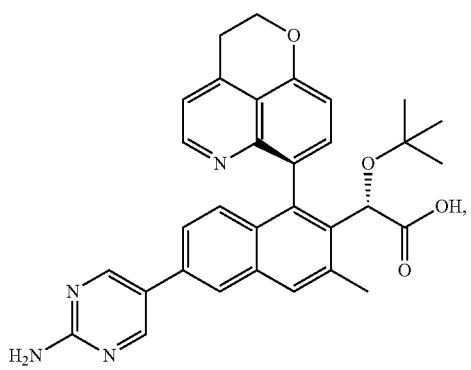
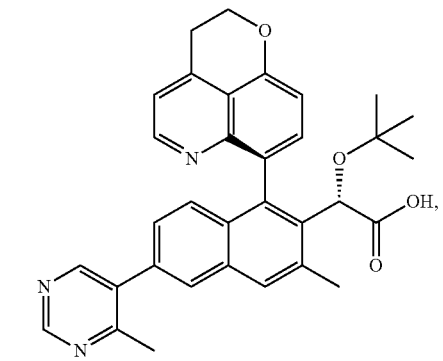
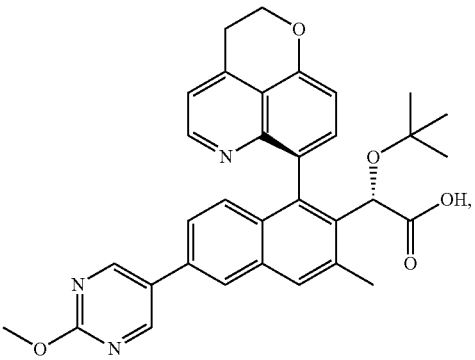

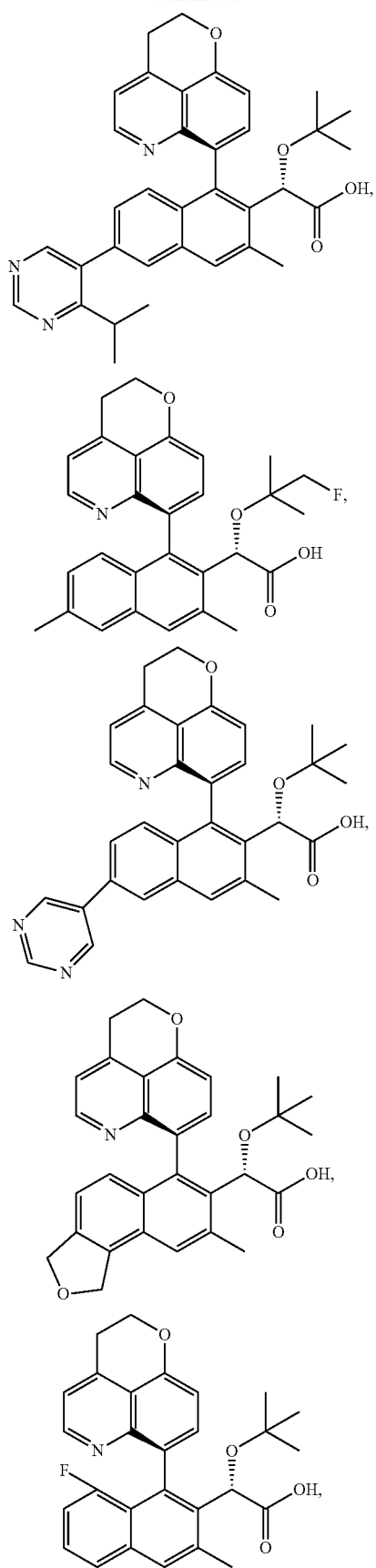
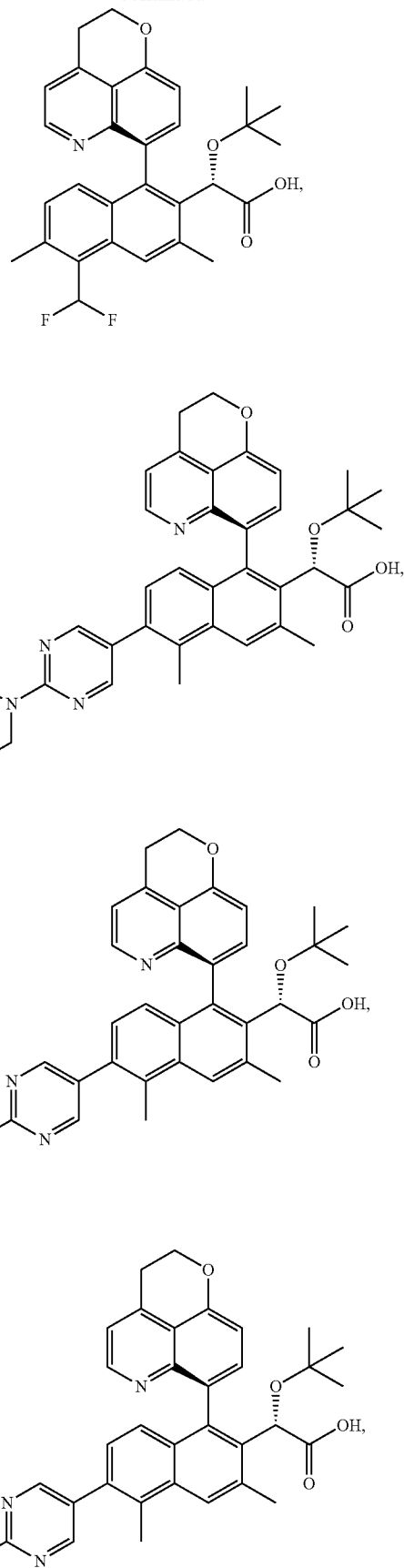

115
-continued
116
-continued
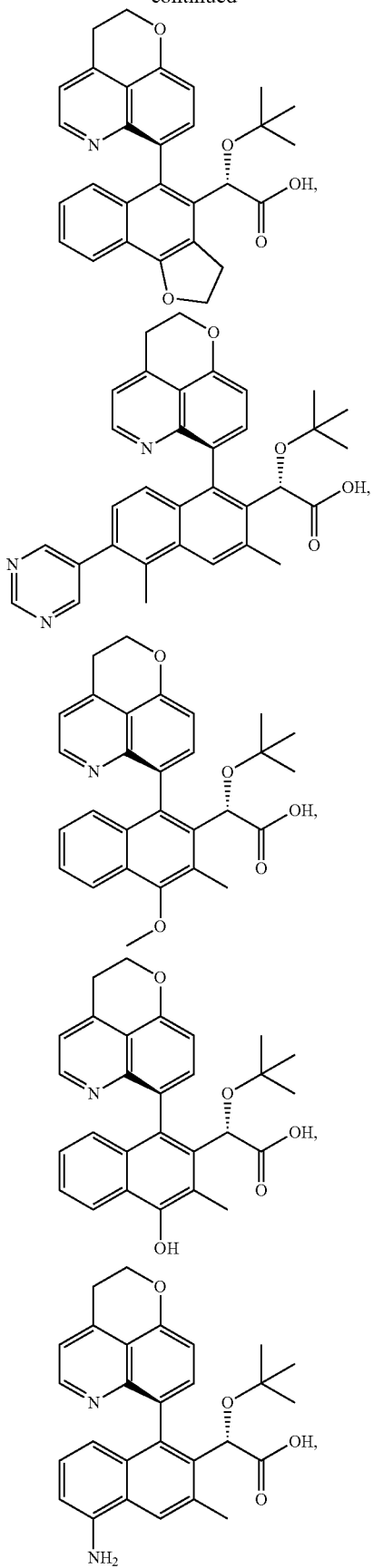
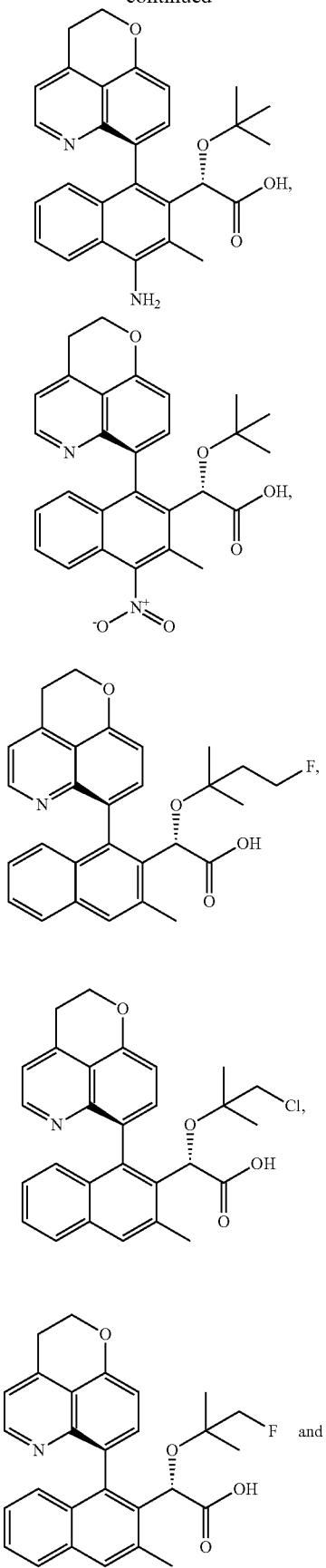

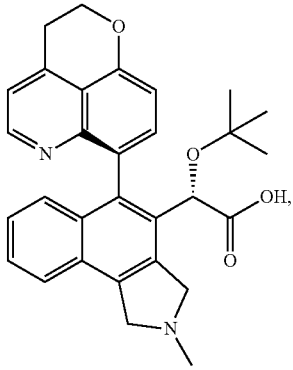
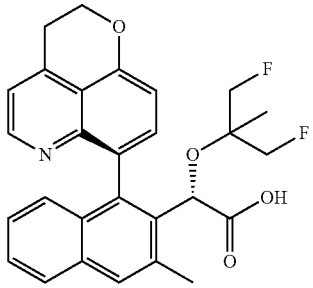
and salts thereof
One embodiment provides compounds selected from:
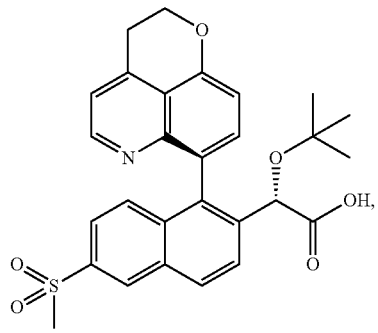
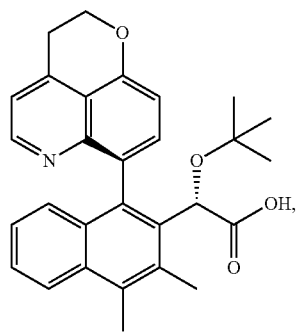
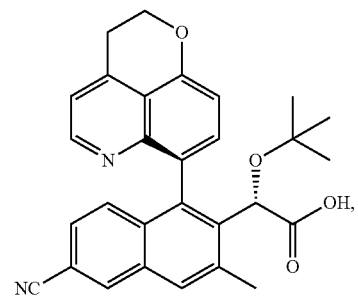
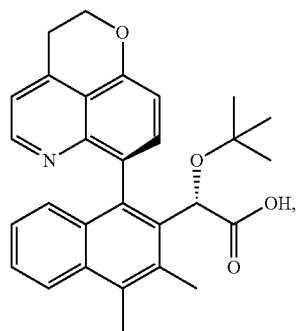
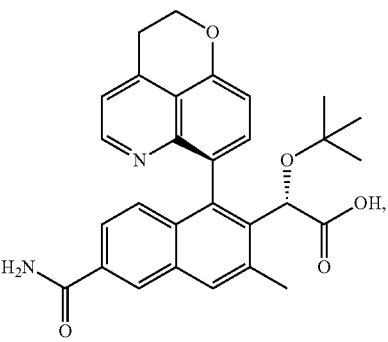
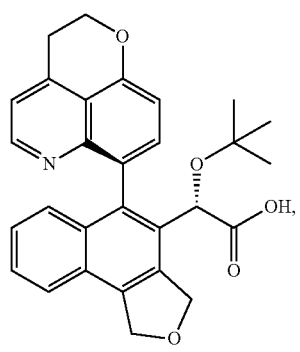
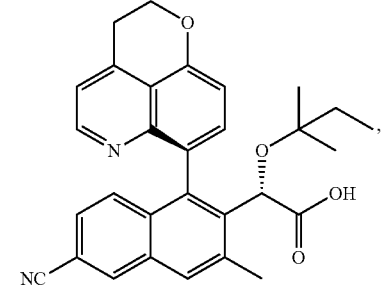

119
-continued
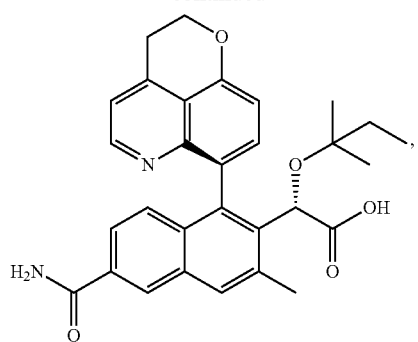
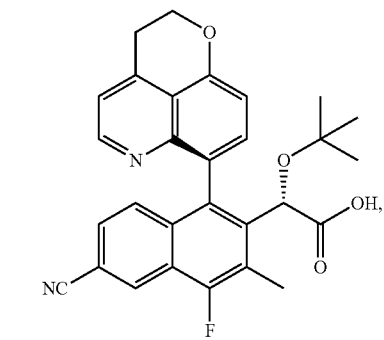
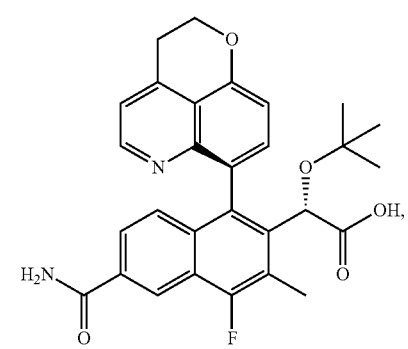
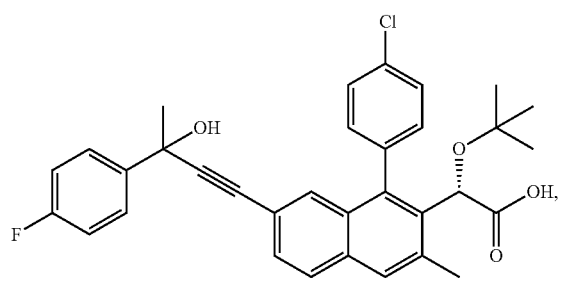
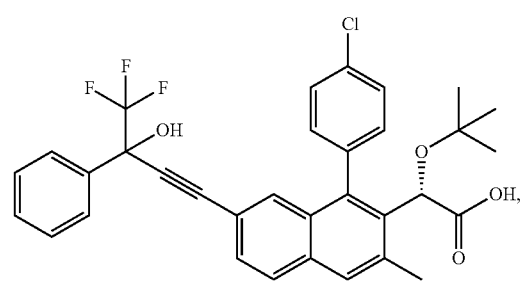
120
-continued
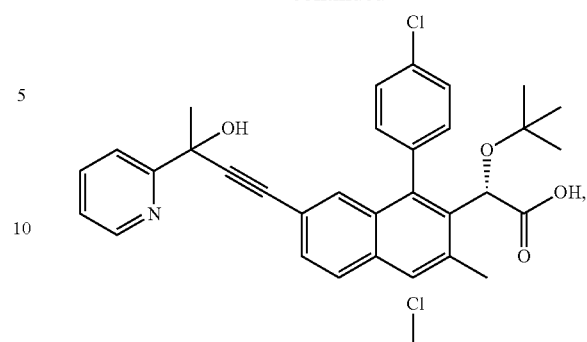
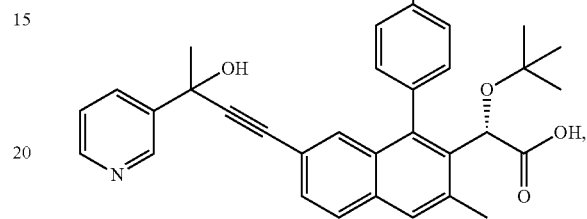
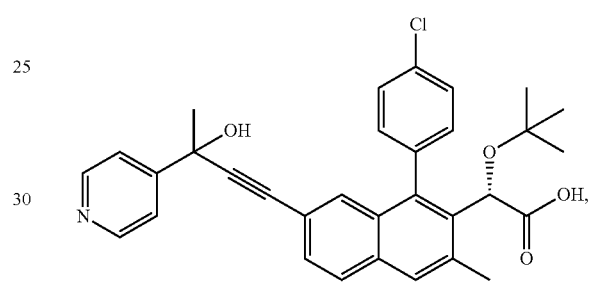
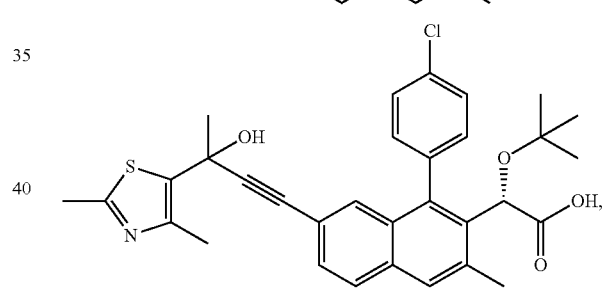
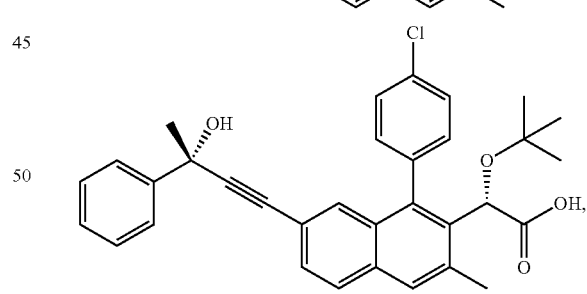
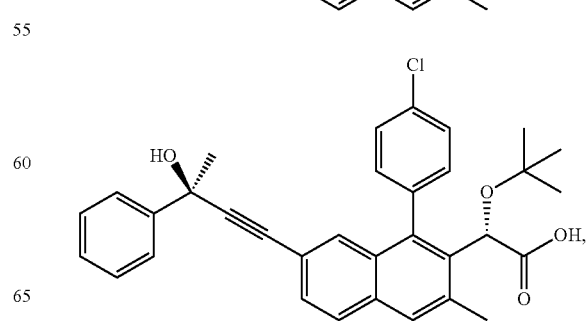

121
-continued
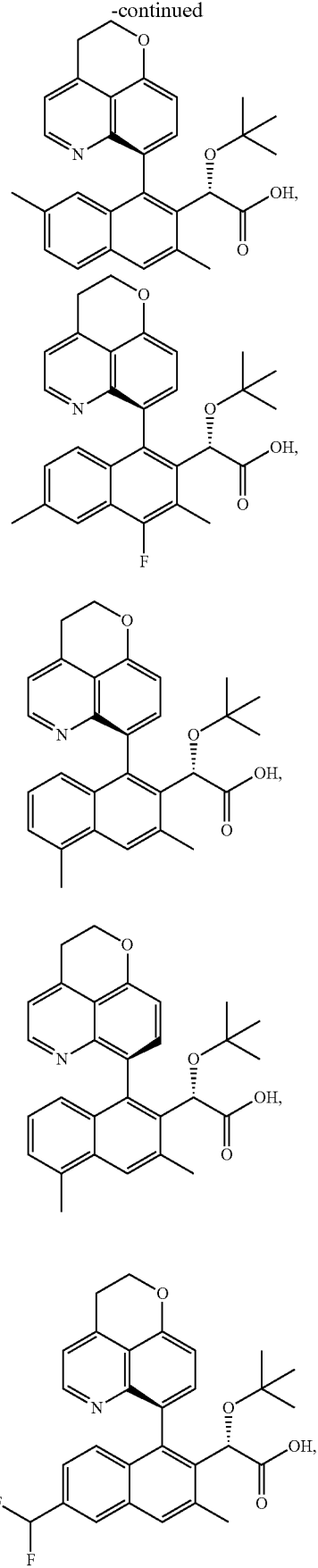
122
-continued
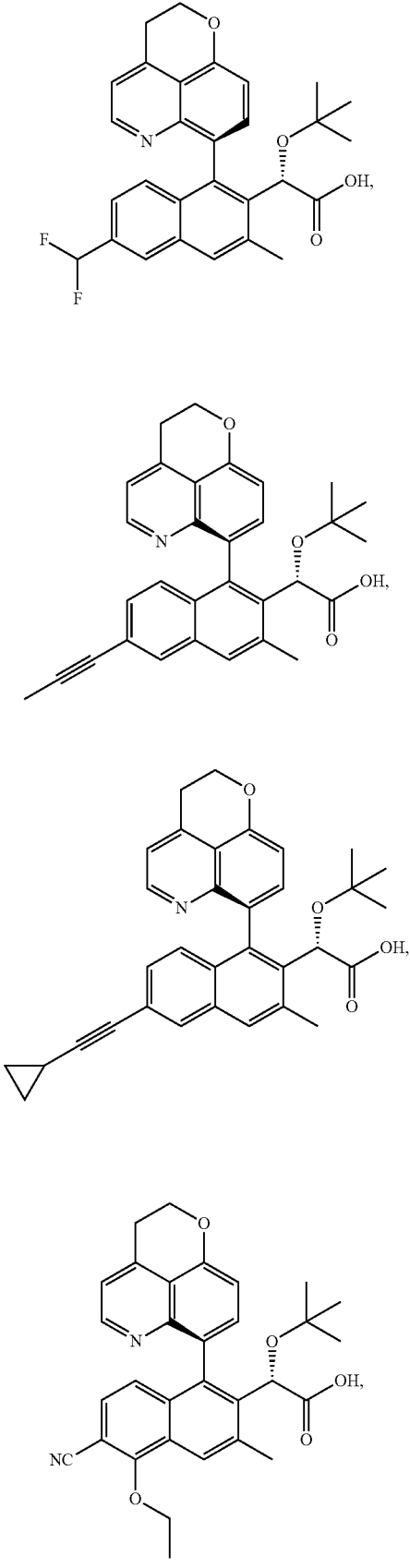

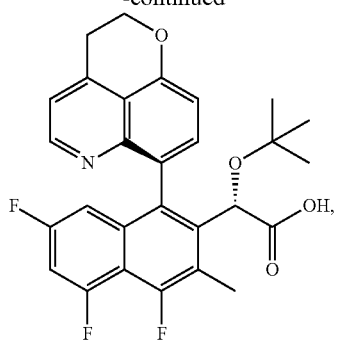
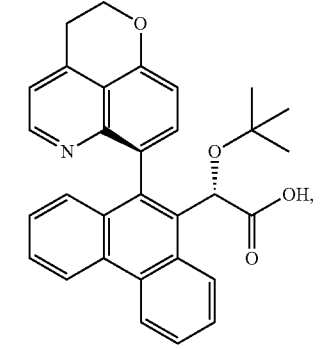
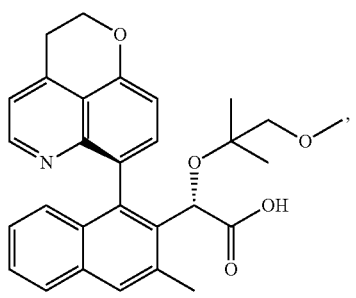
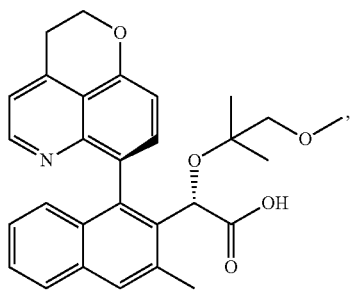
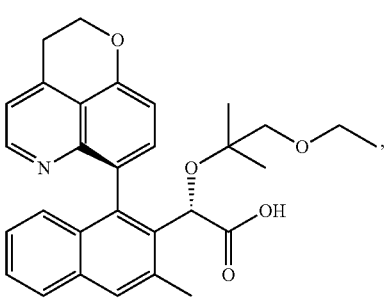
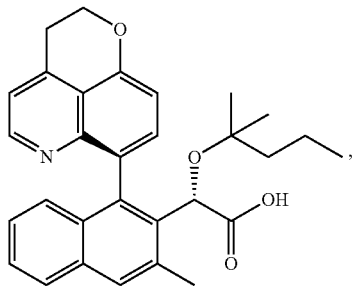
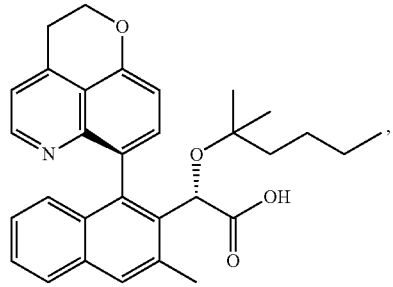
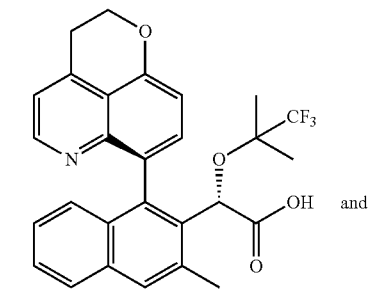
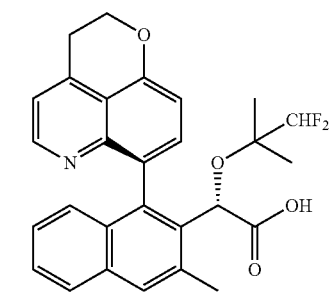
and salts thereof.
One embodiment provides compounds selected from:
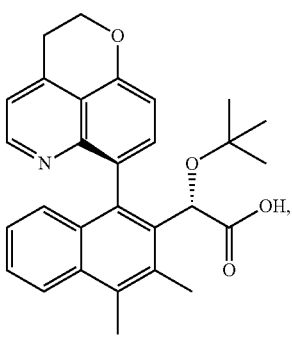

125
-continued
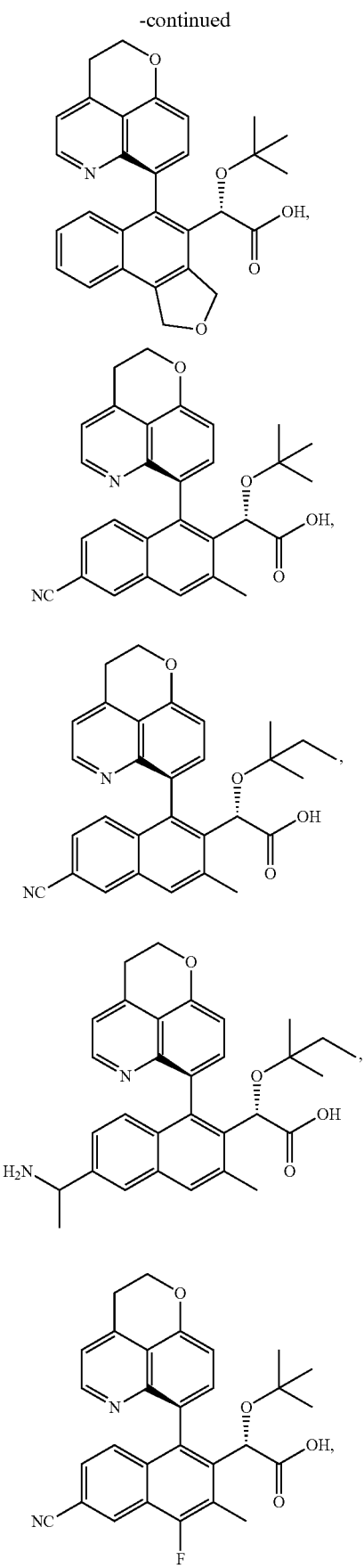
126
-continued
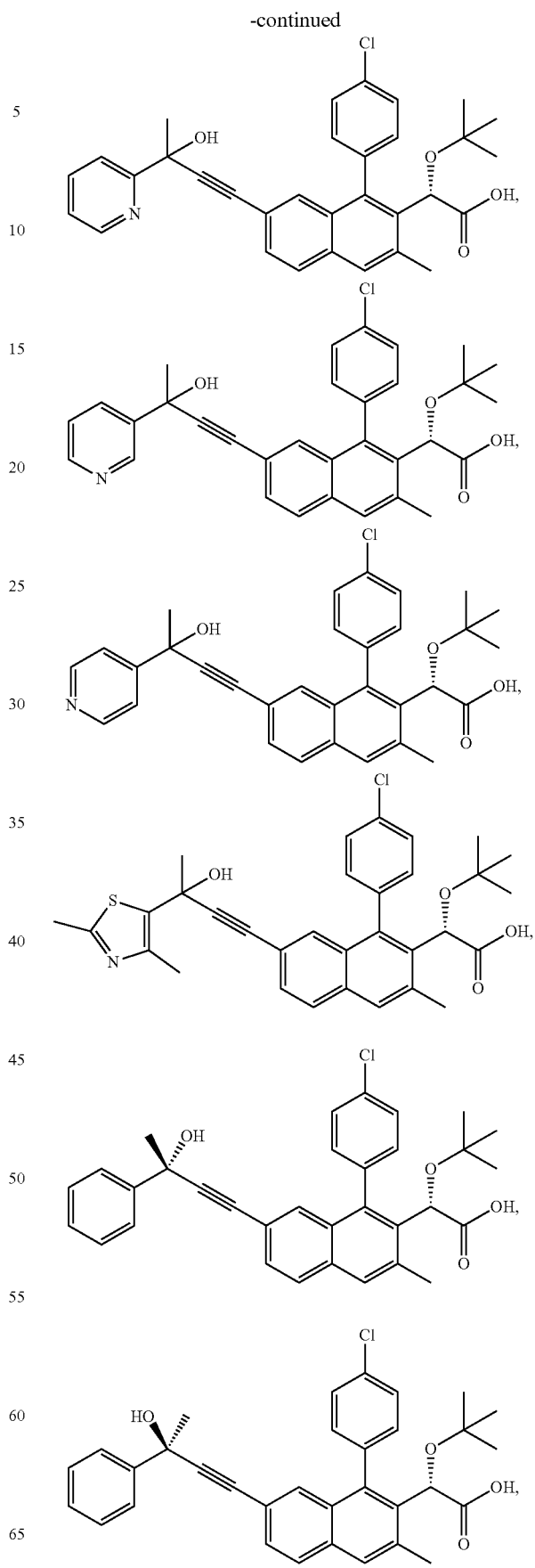

127
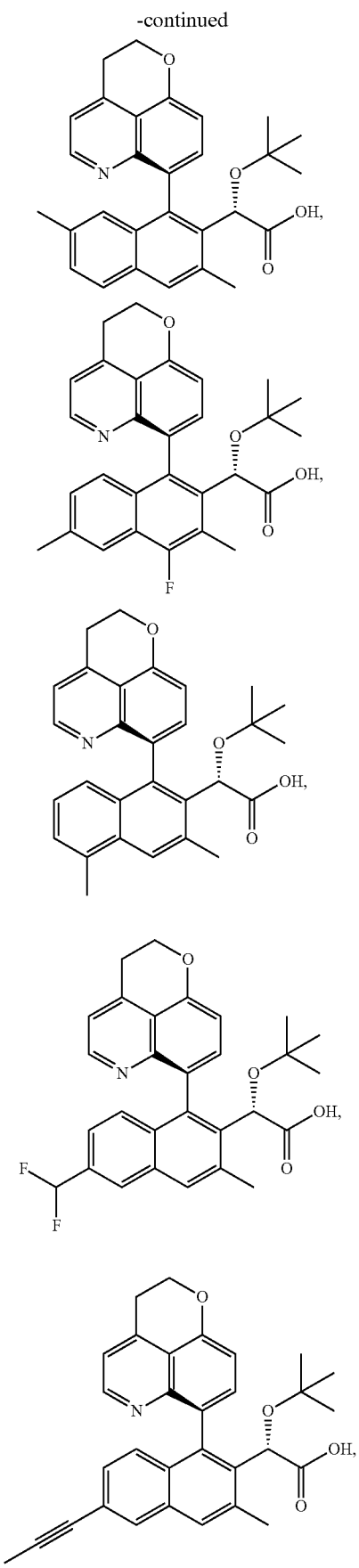
128
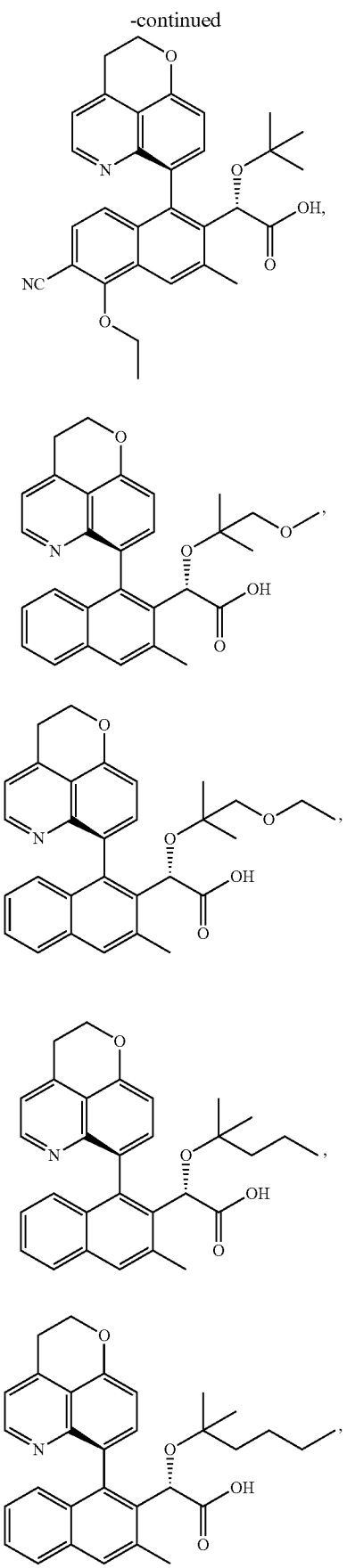

129
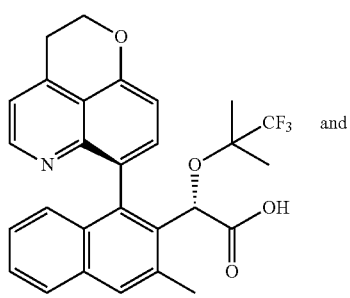
and
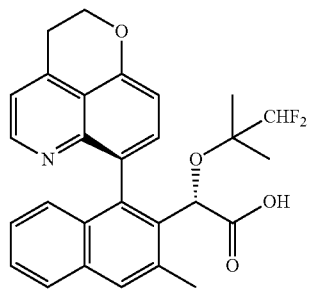
and salts thereof.
One embodiment provides compounds selected from:
130
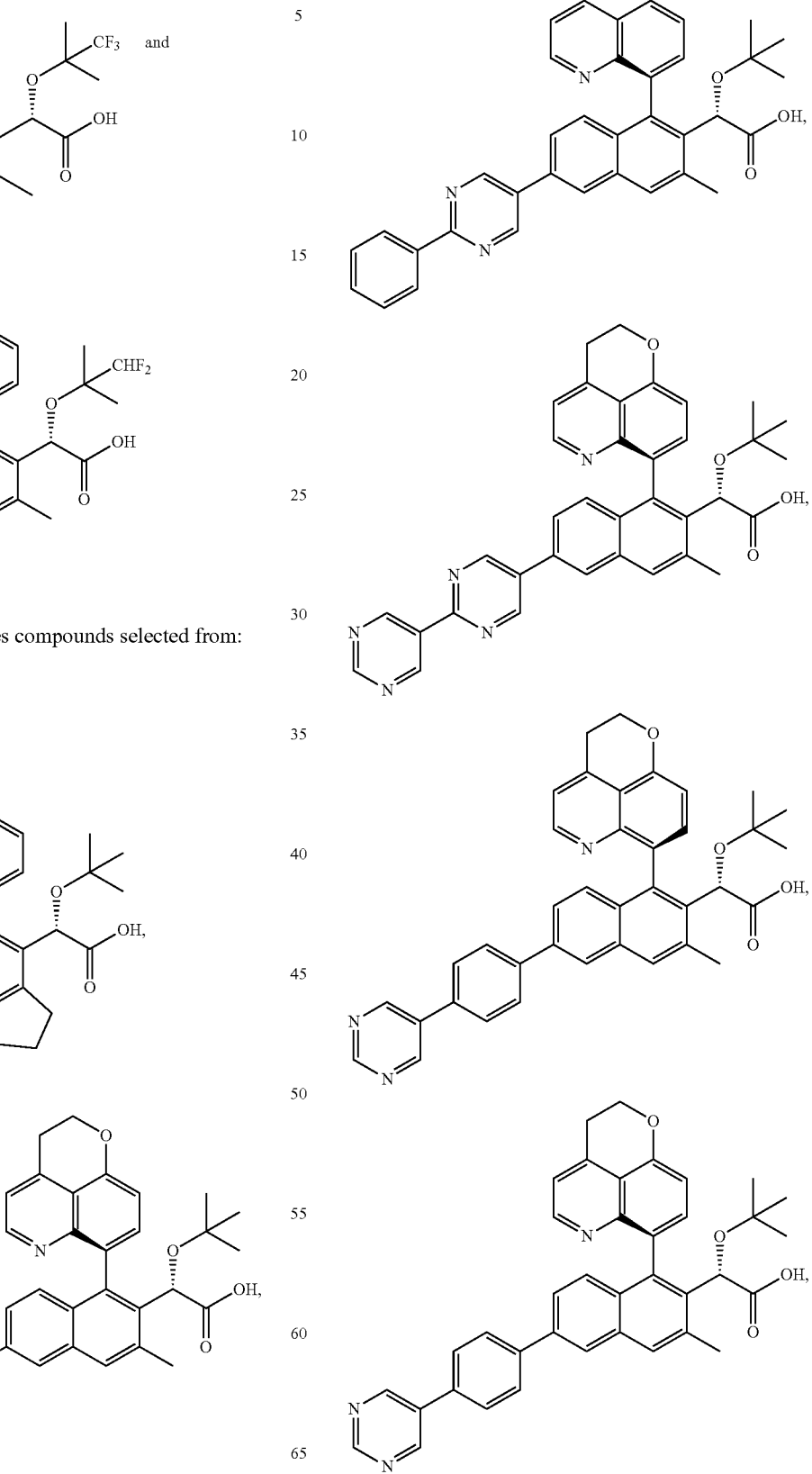

131
-continued
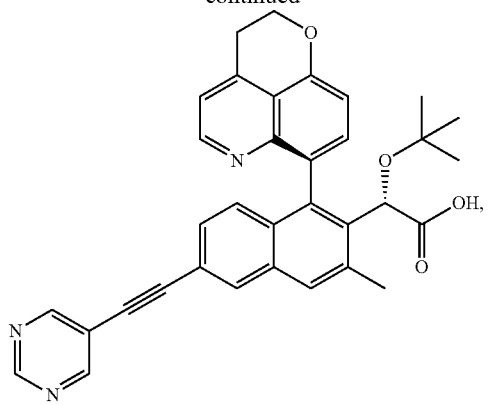
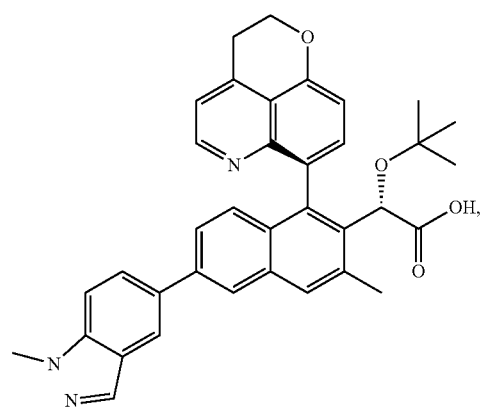
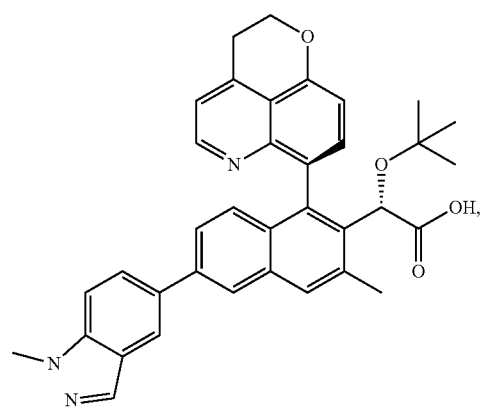
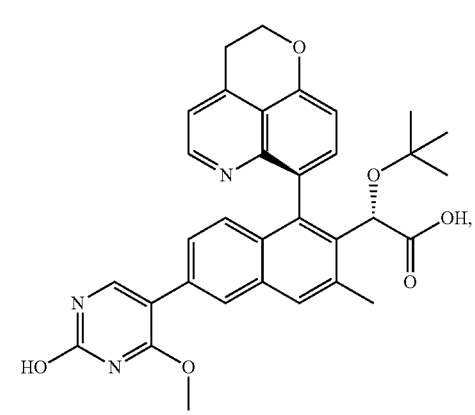
132
-continued
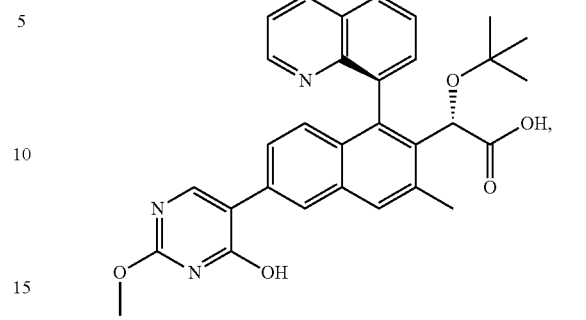
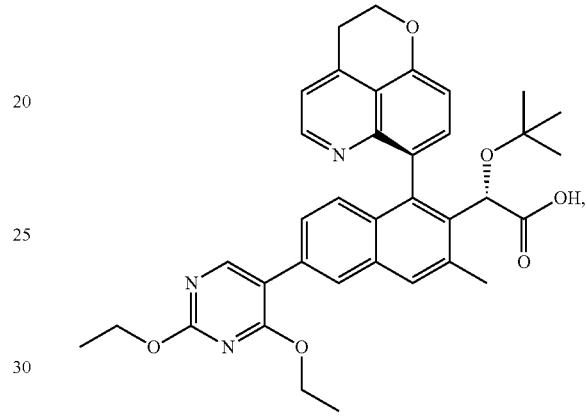
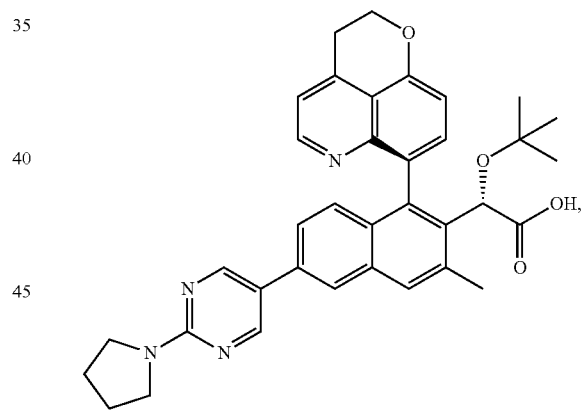
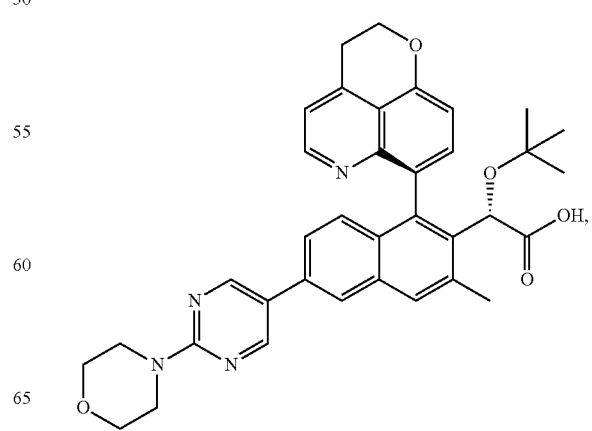

133
-continued
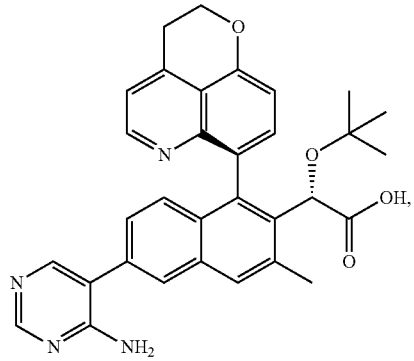
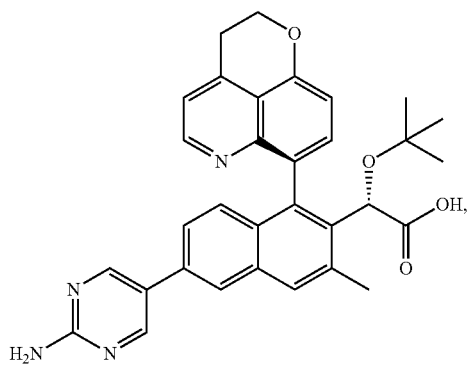
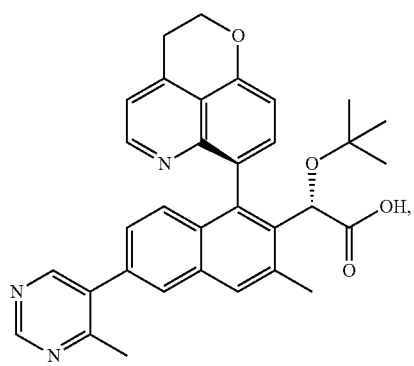
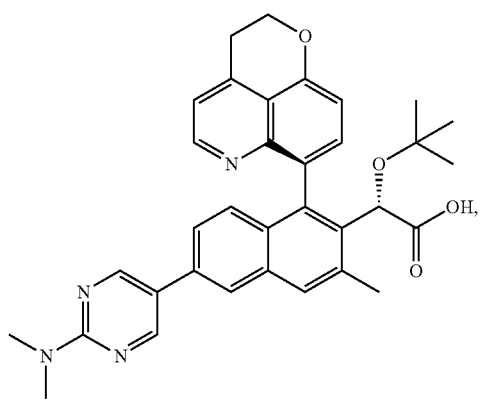
134
-continued
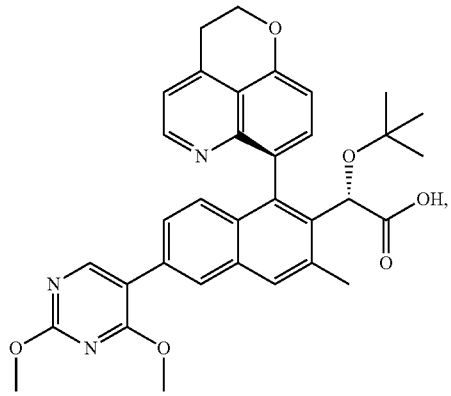
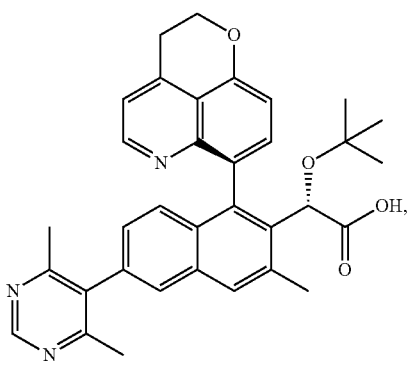
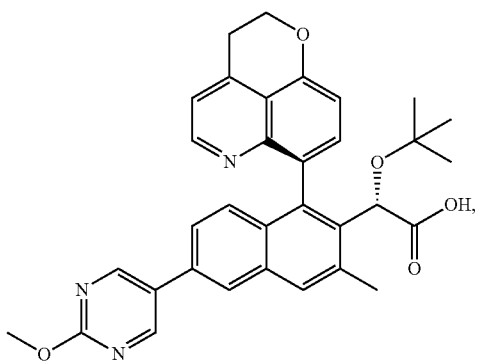
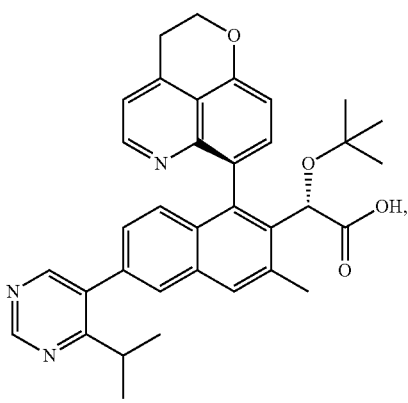

135
-continued
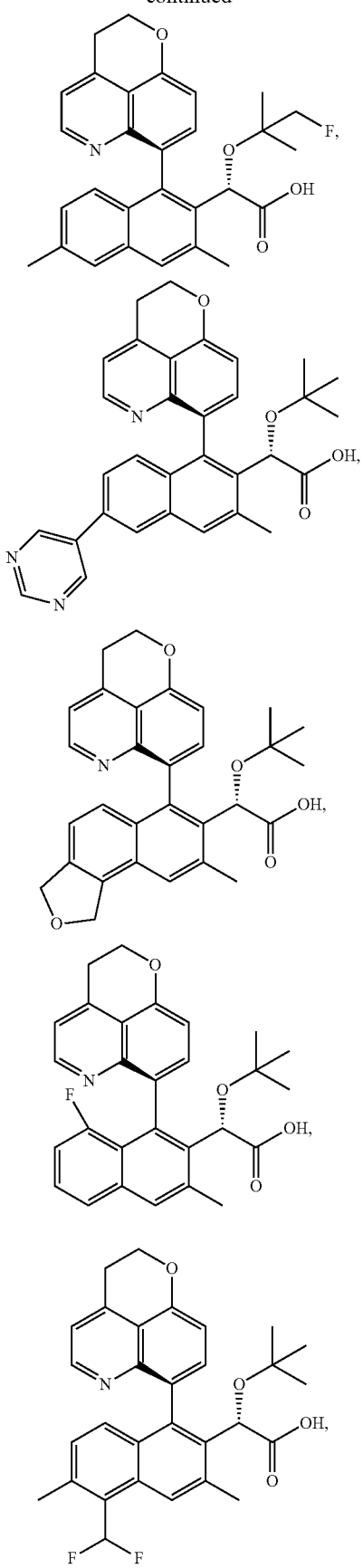
136
-continued
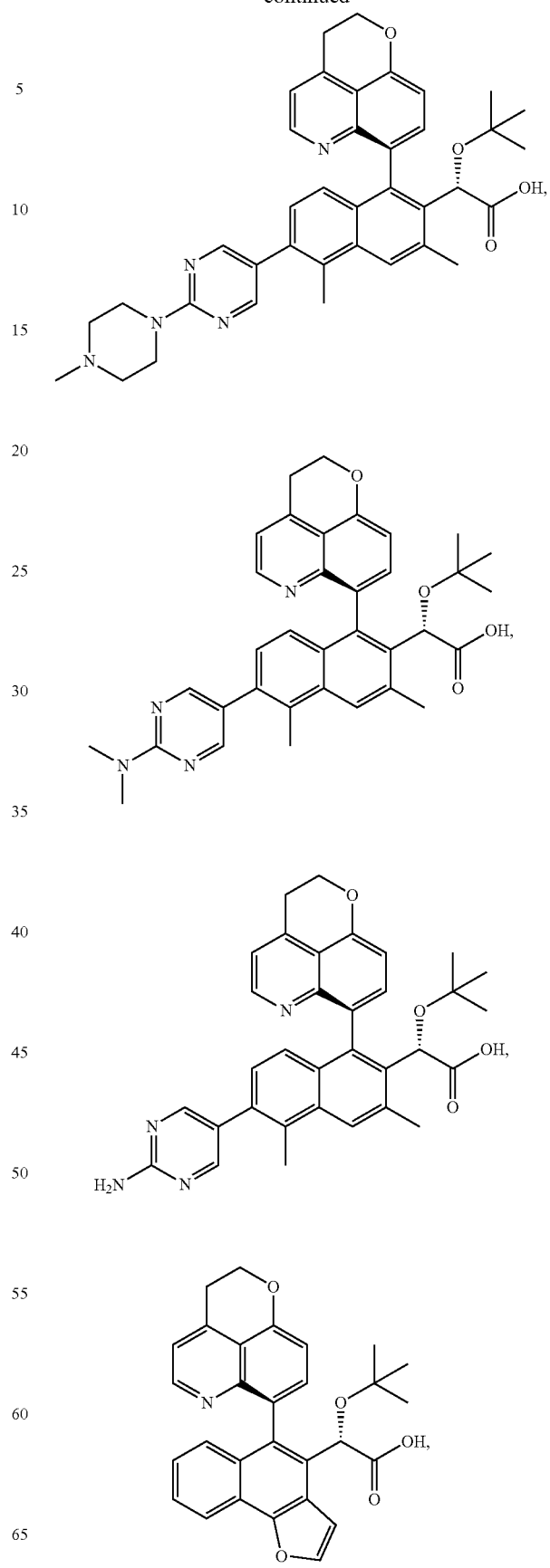

137
-continued
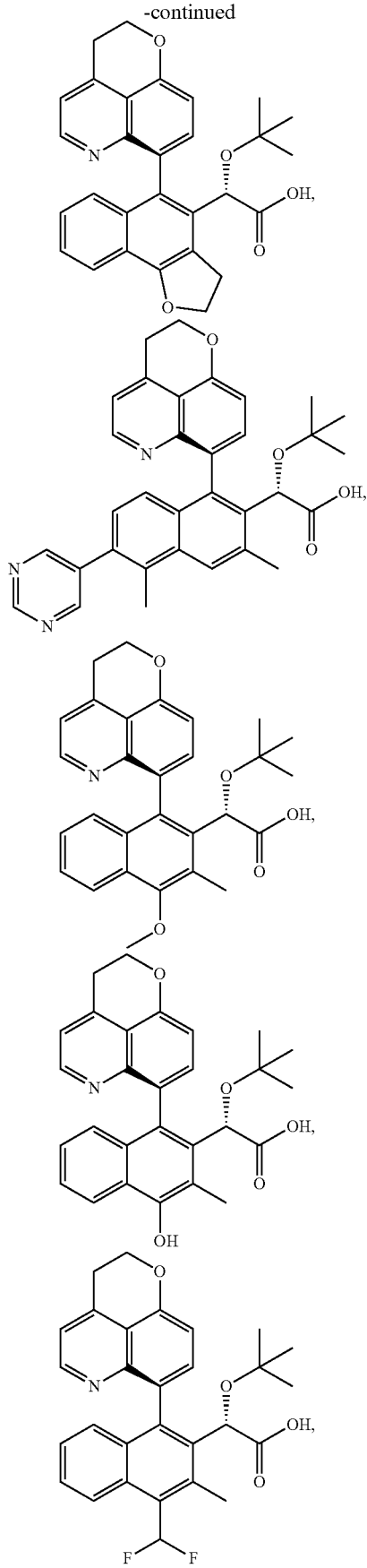
138
-continued
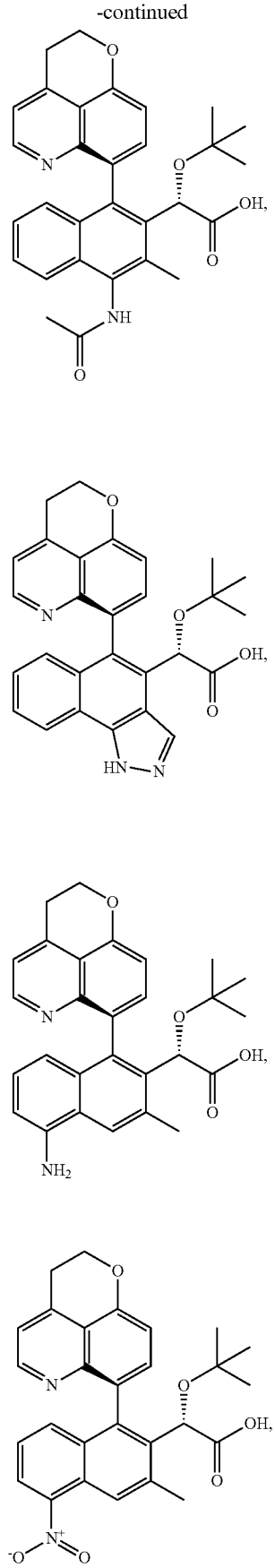

139
-continued
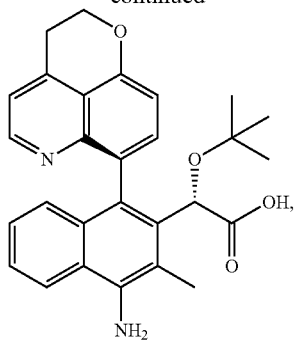
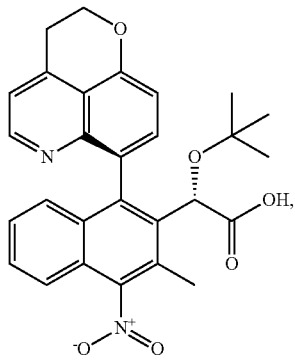
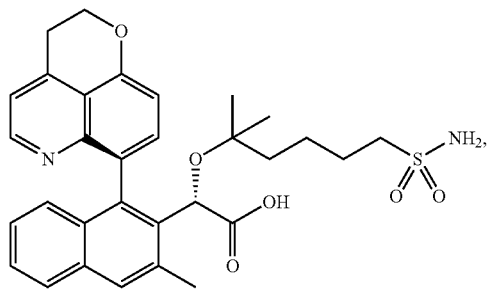
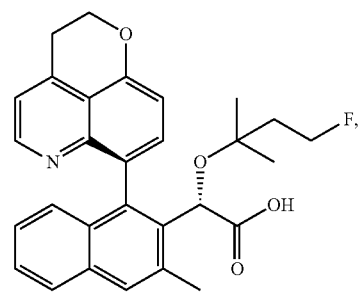
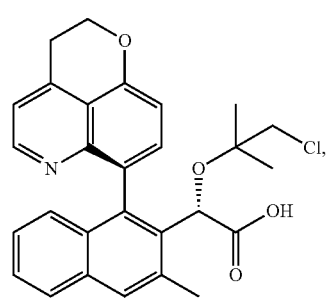
140
-continued
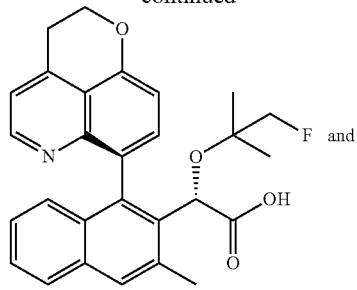
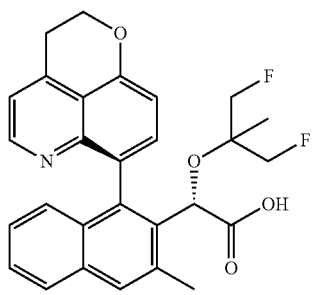
and salts thereof.
One embodiment provides compounds selected from:
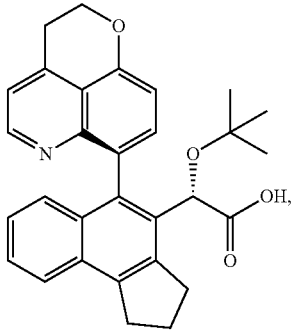
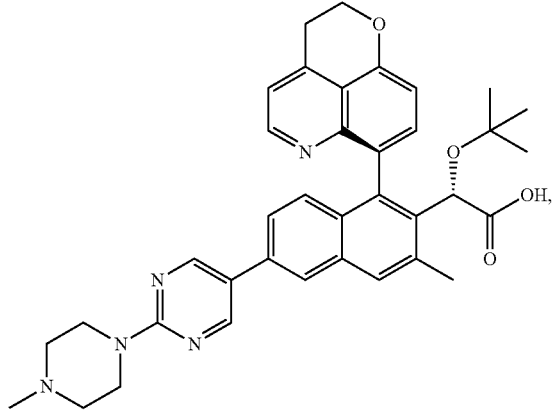

141
-continued
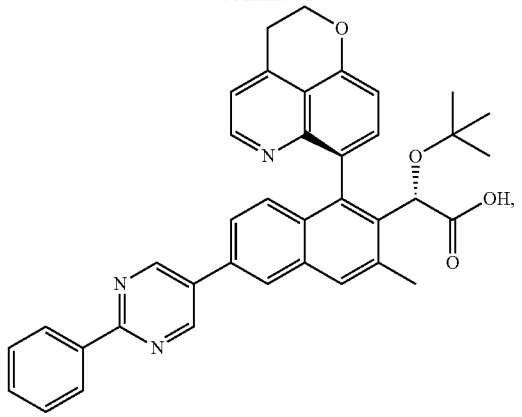
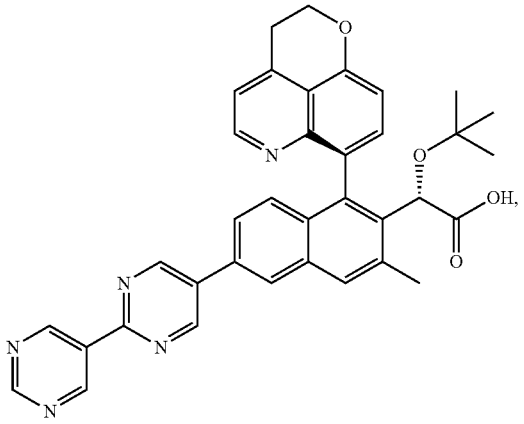
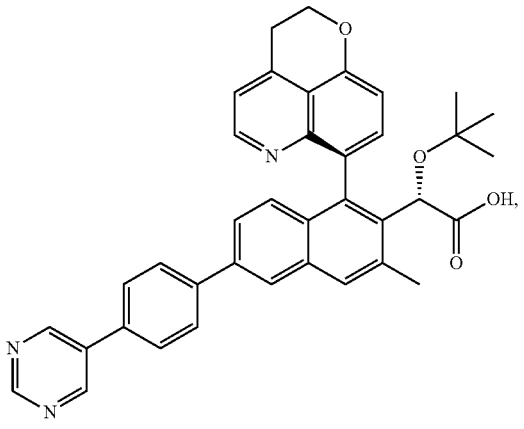
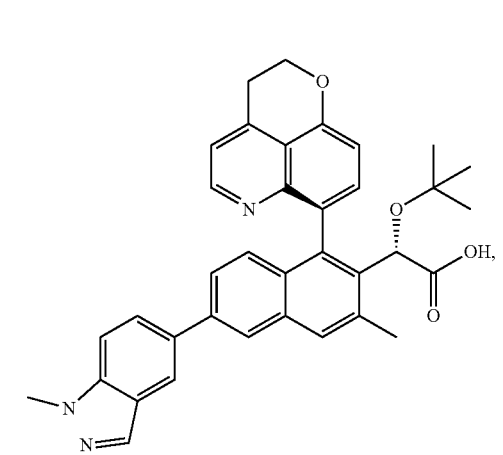
142
-continued
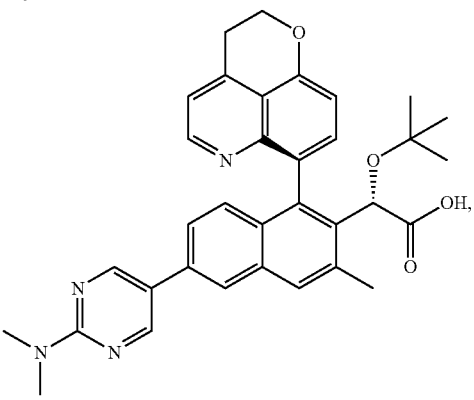
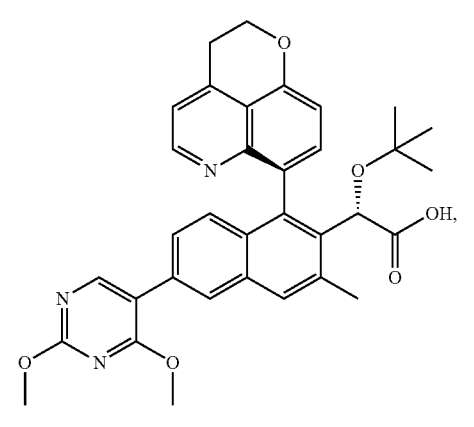
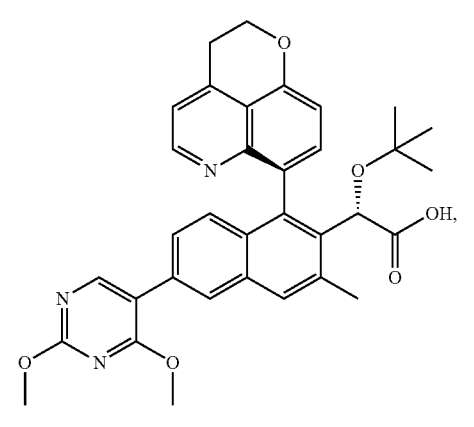
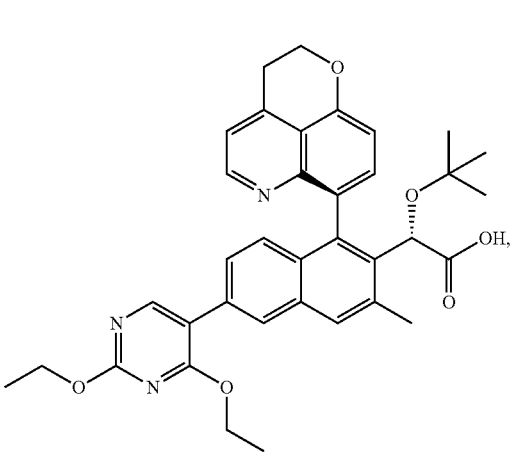

143
-continued
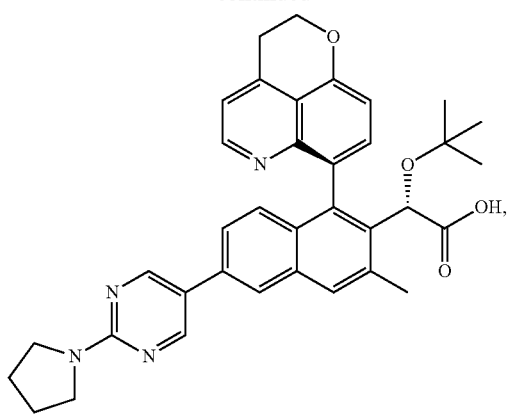
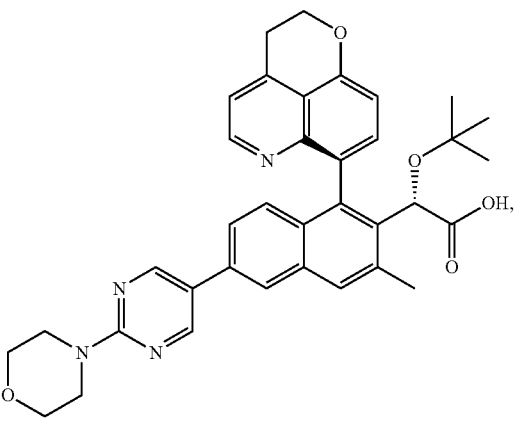
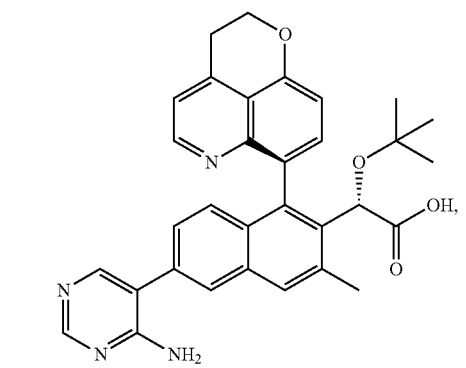
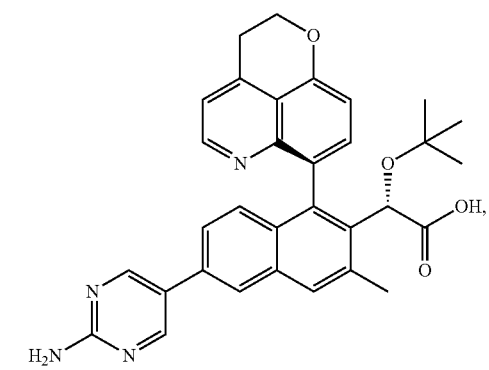
144
-continued
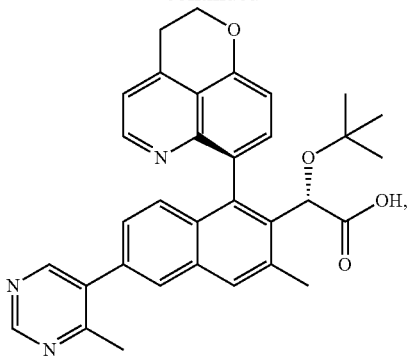
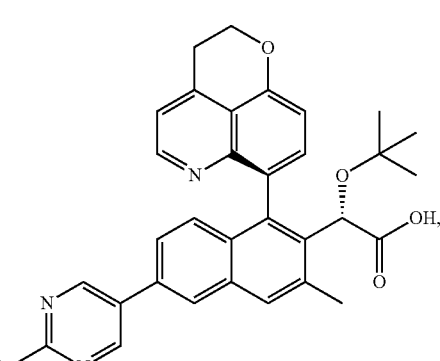
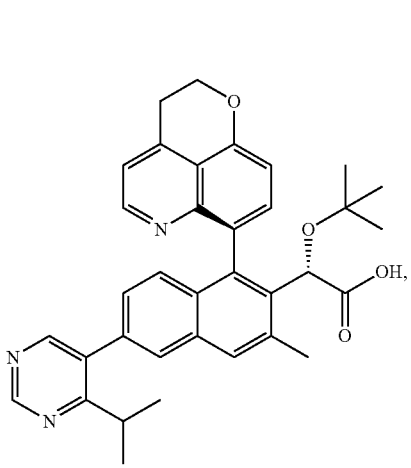
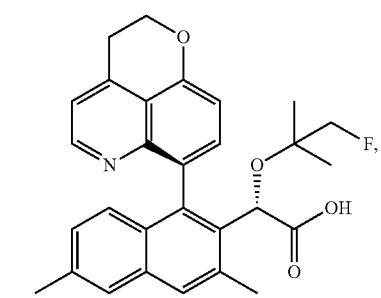

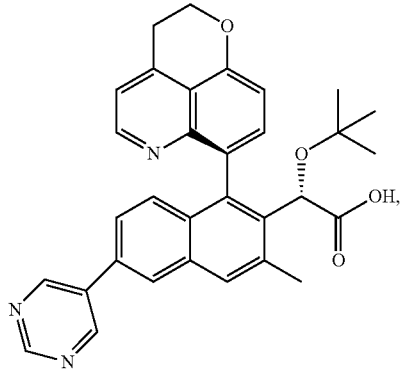
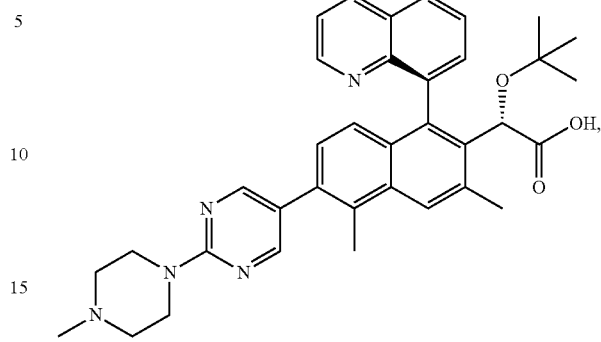
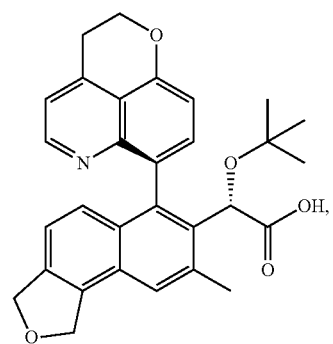
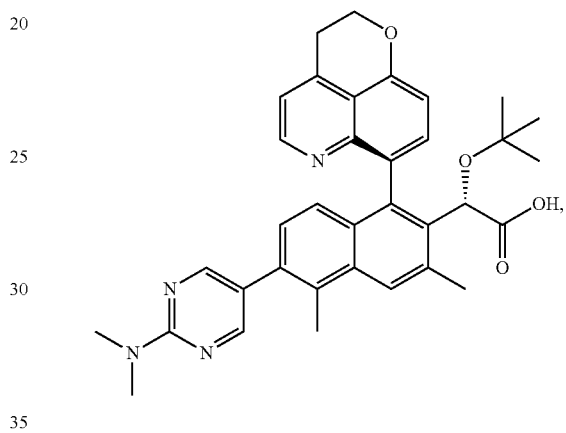
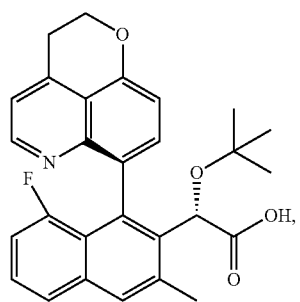
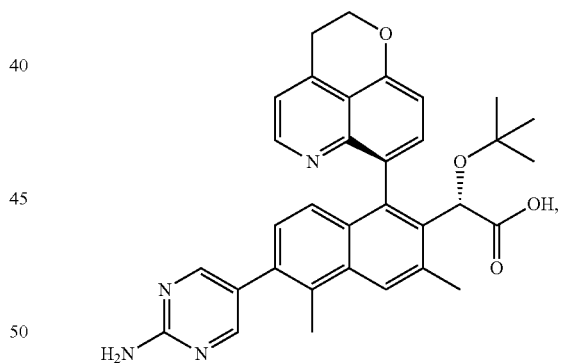
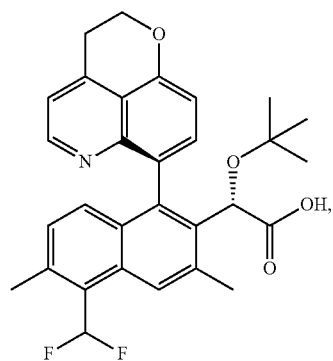
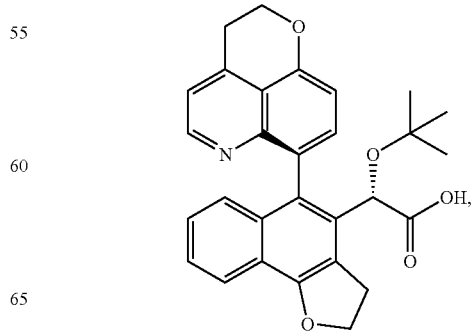

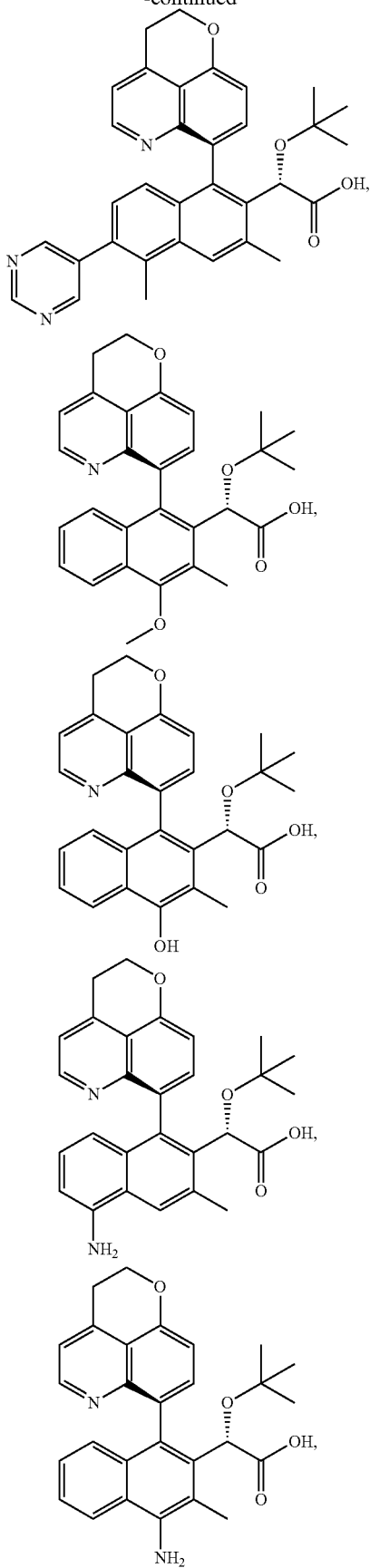
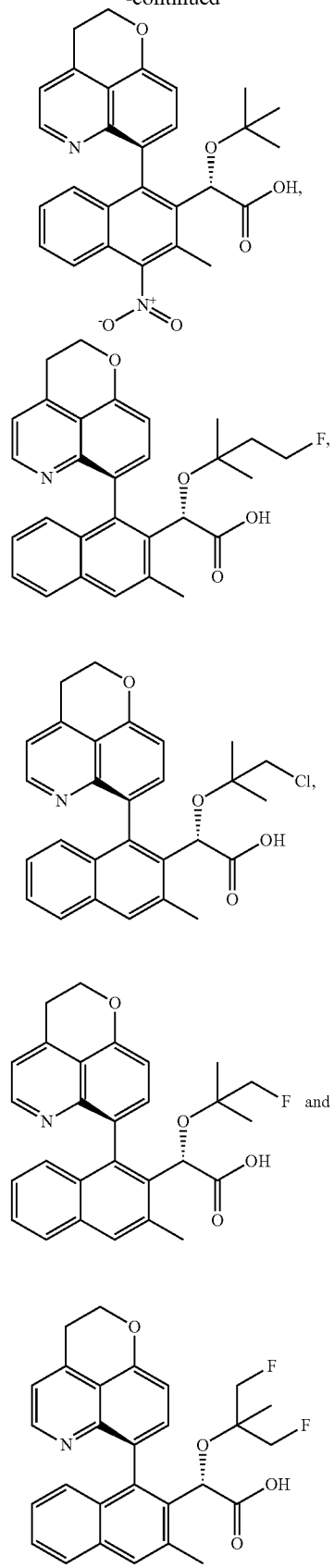
and salts thereof.

In one embodiment compounds are selected from:
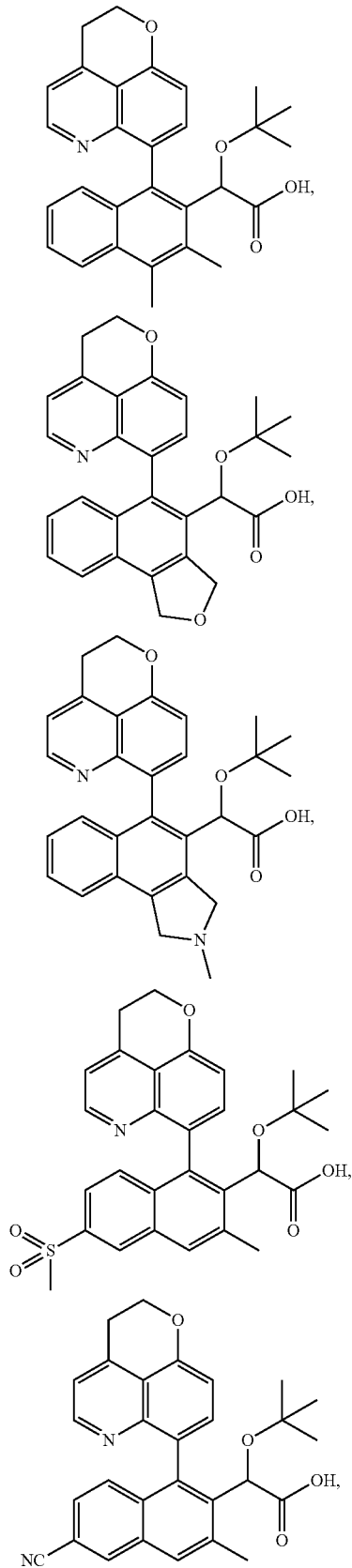
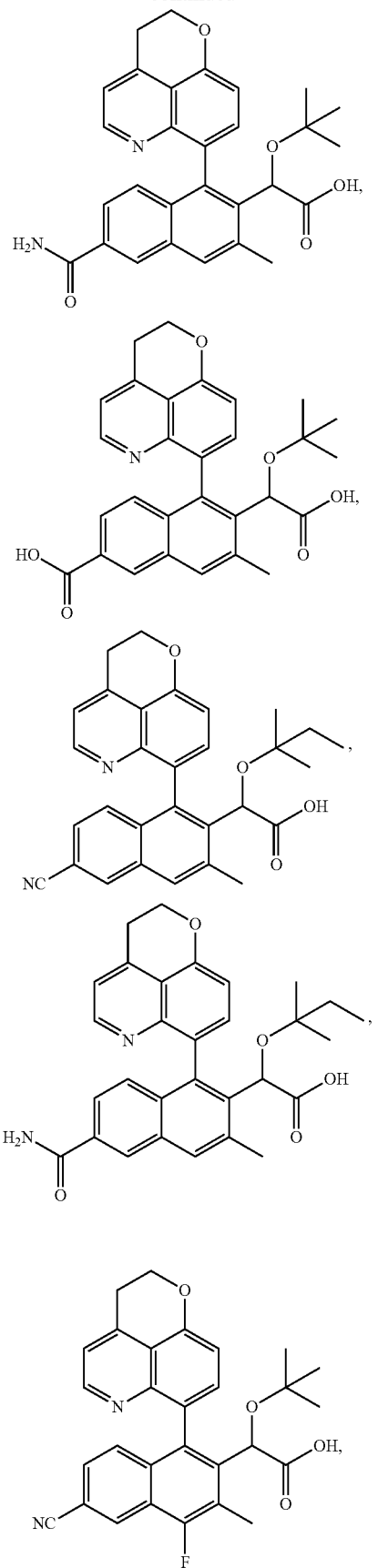

151
-continued
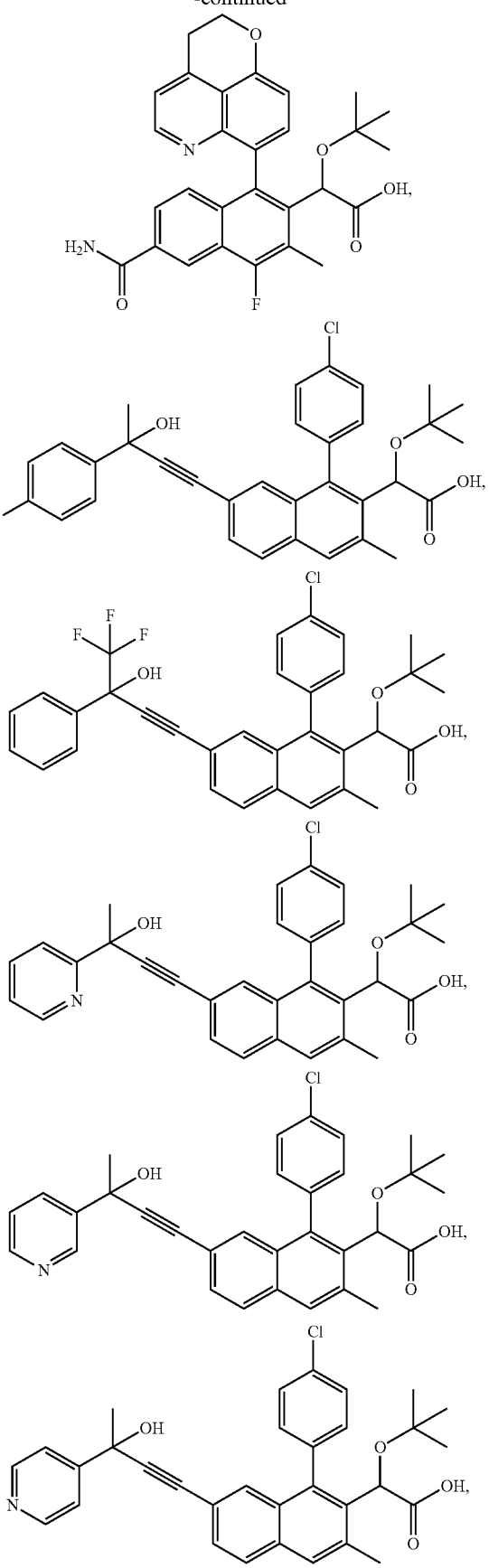
152
-continued
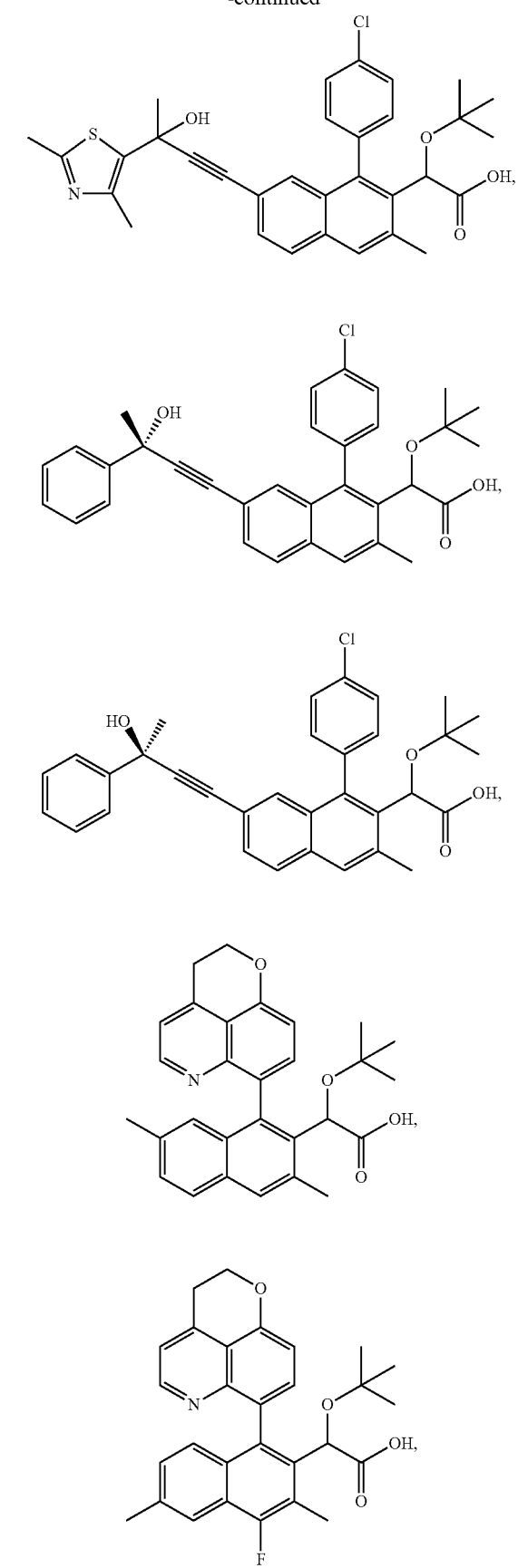

153
-continued
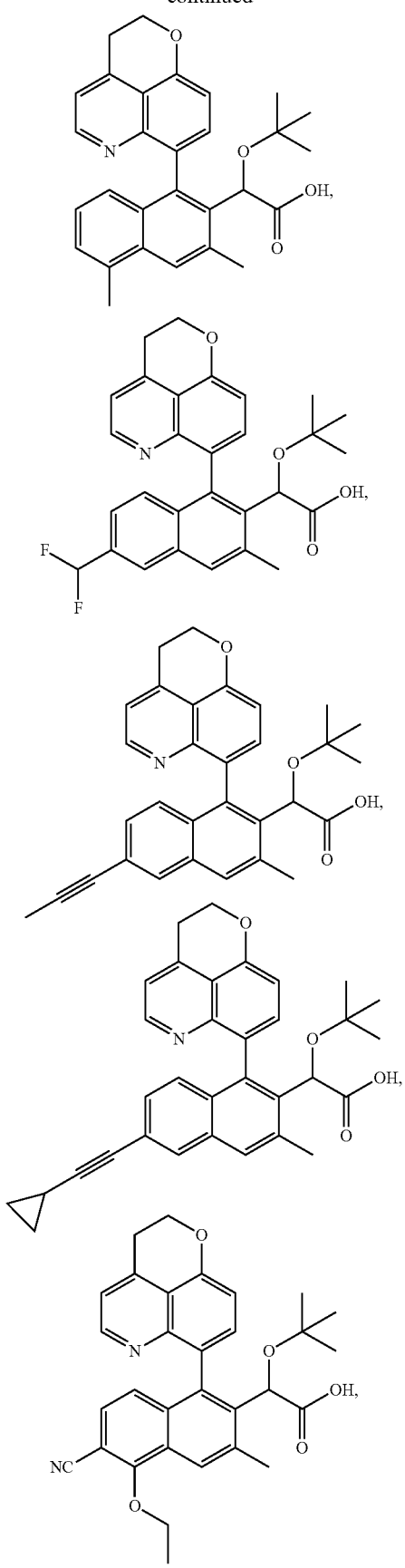
154
-continued
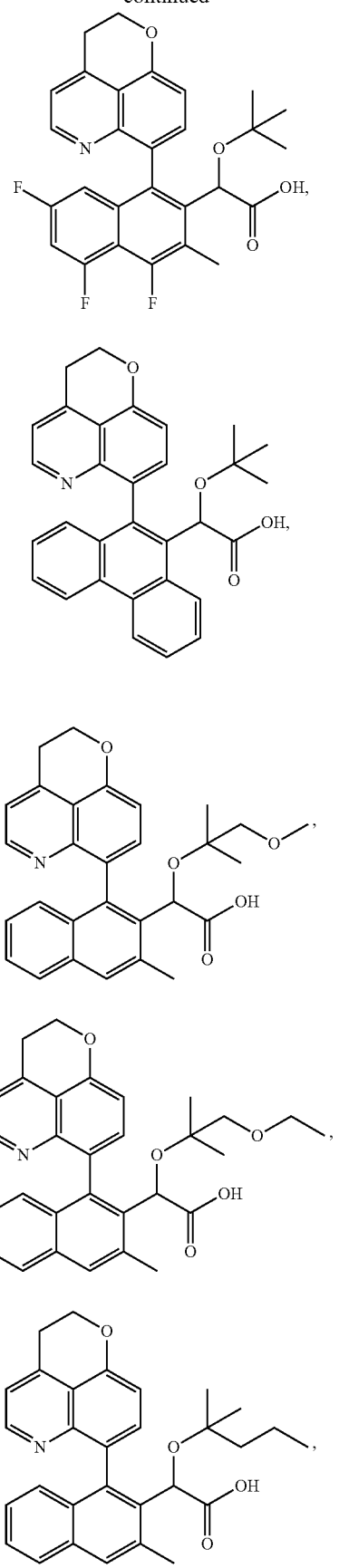

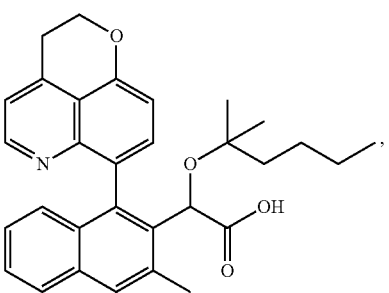
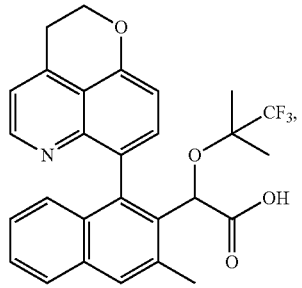
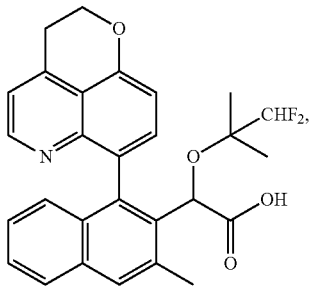
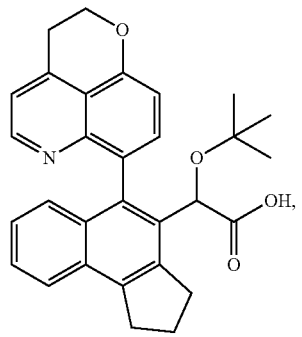
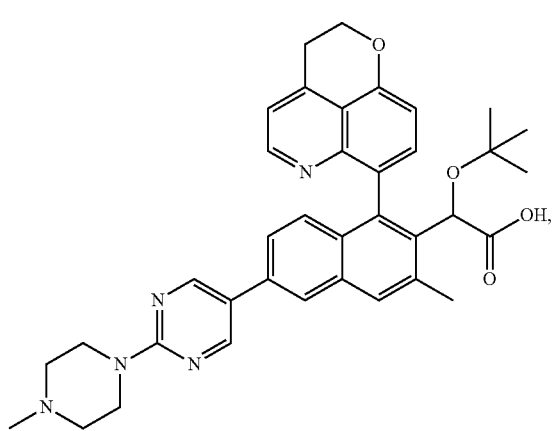
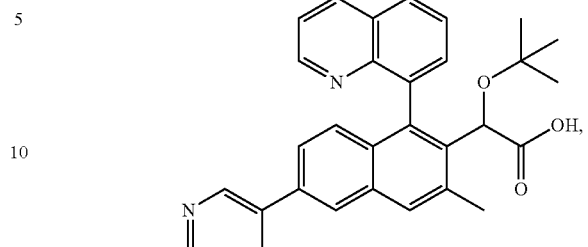
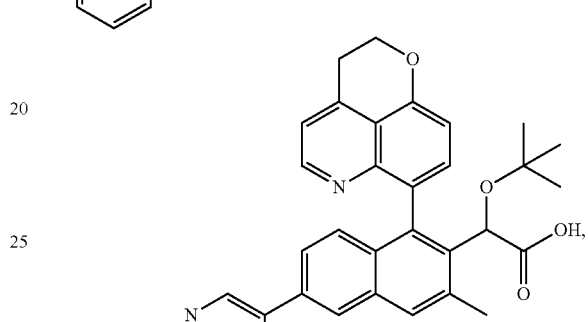
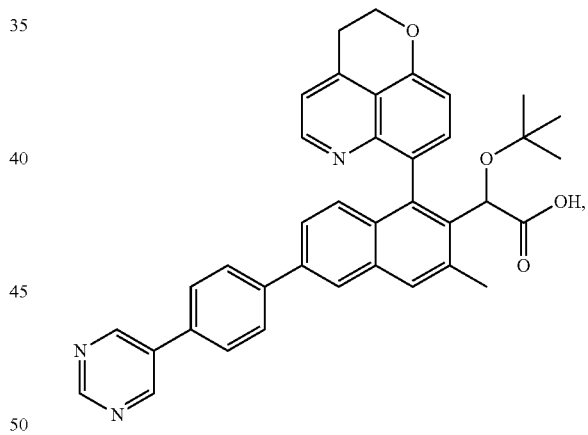
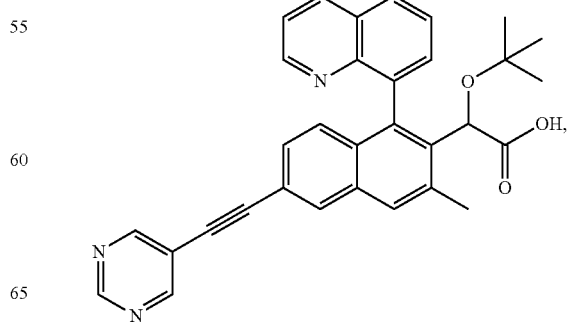

157
-continued
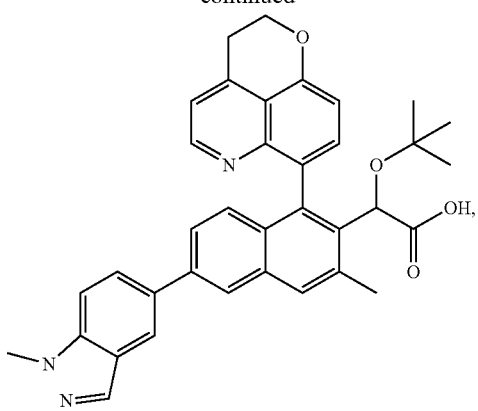
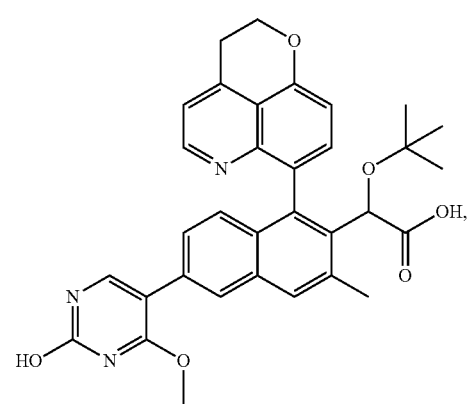
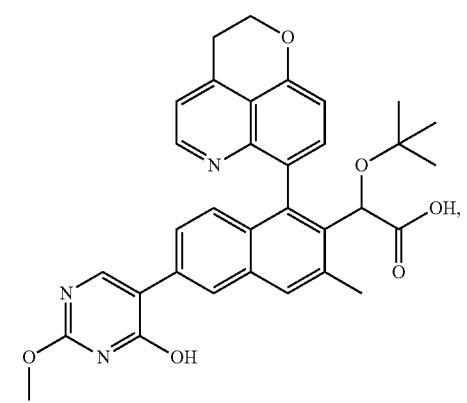
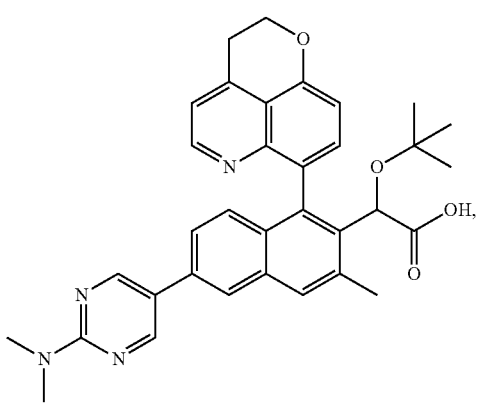
158
-continued
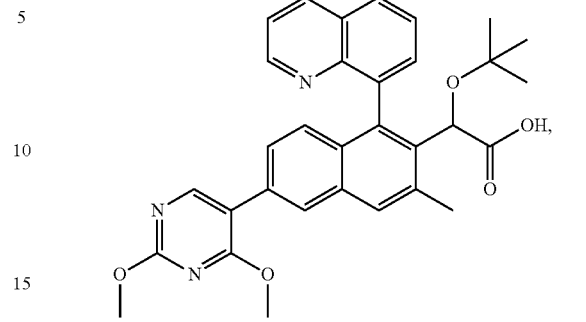
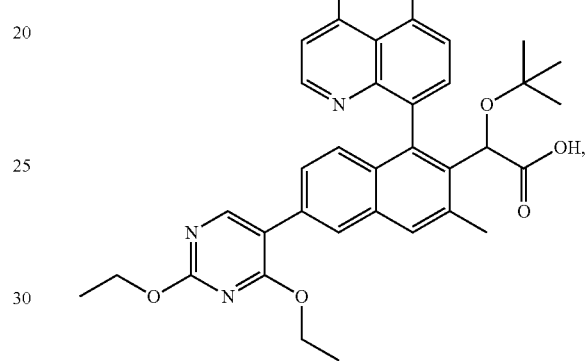
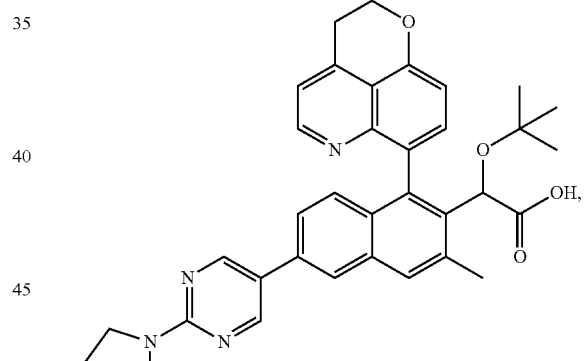
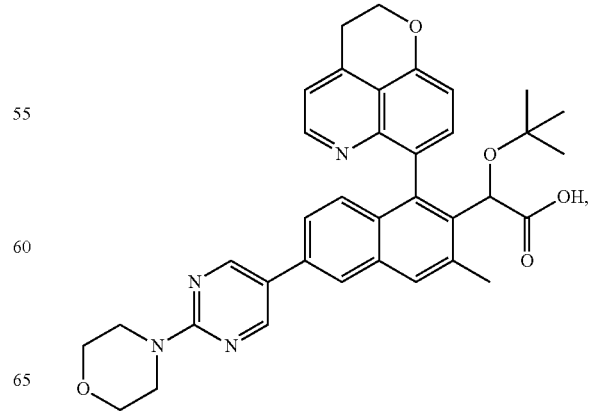

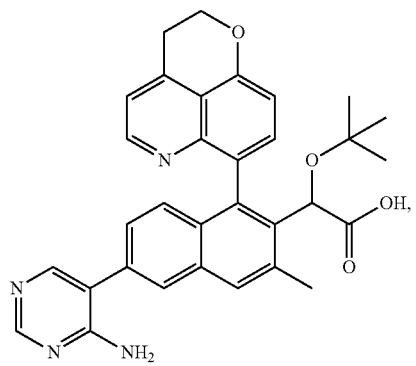
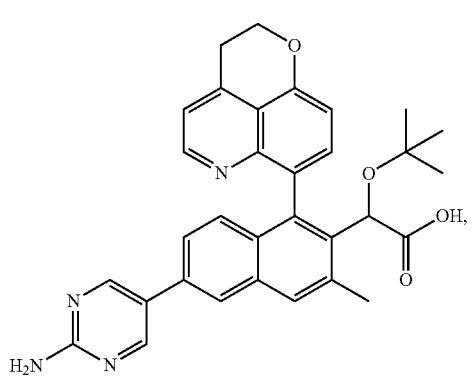
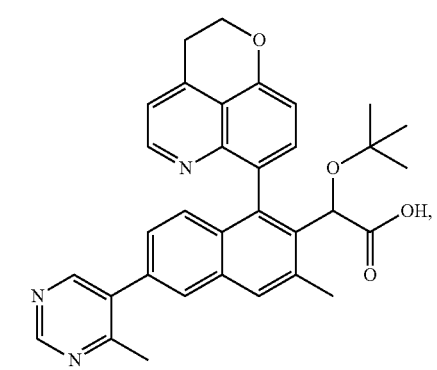
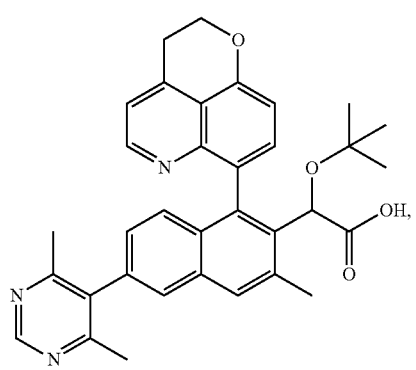
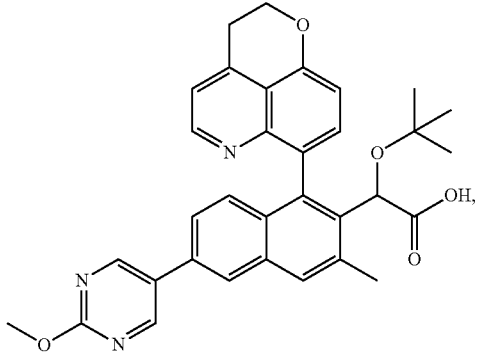
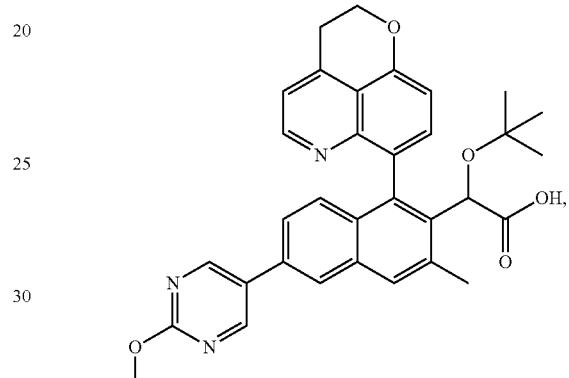
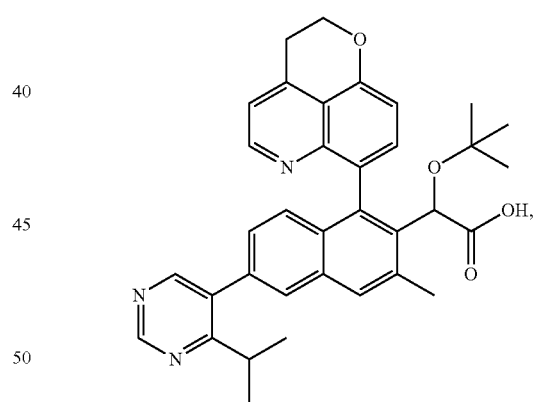
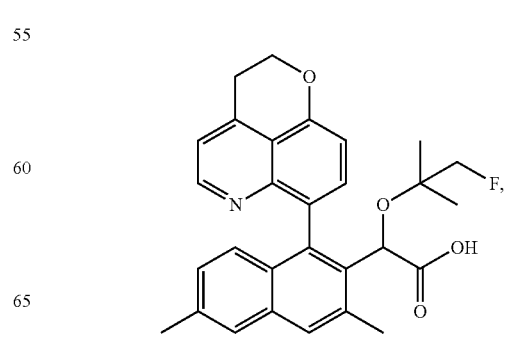

161
-continued
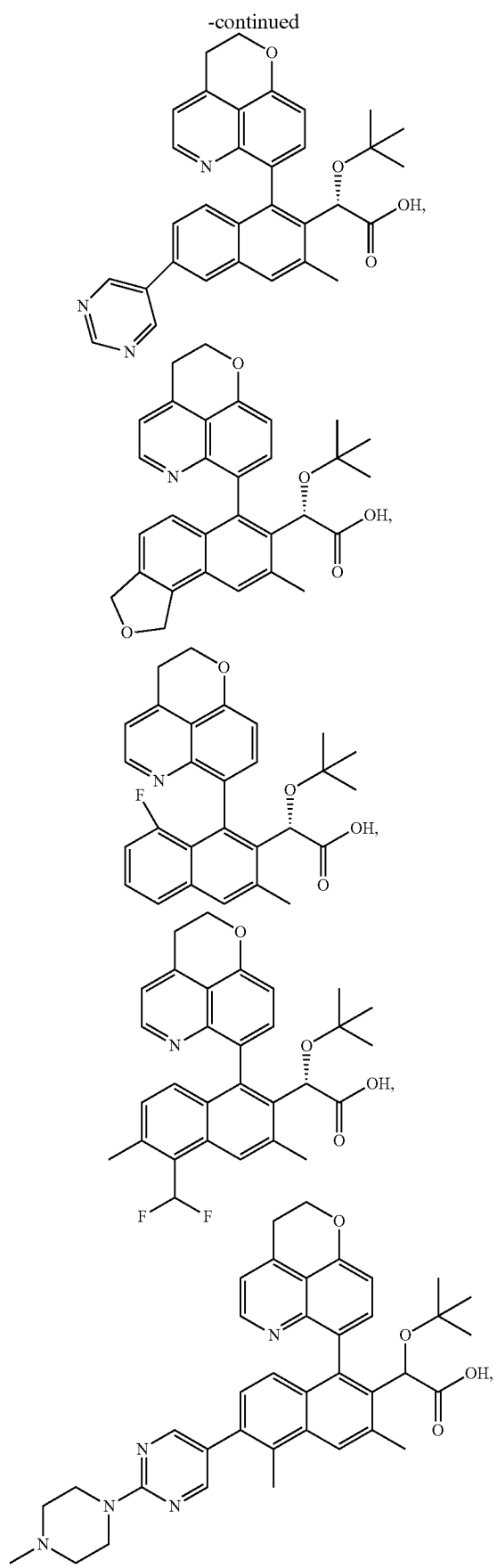
162
-continued
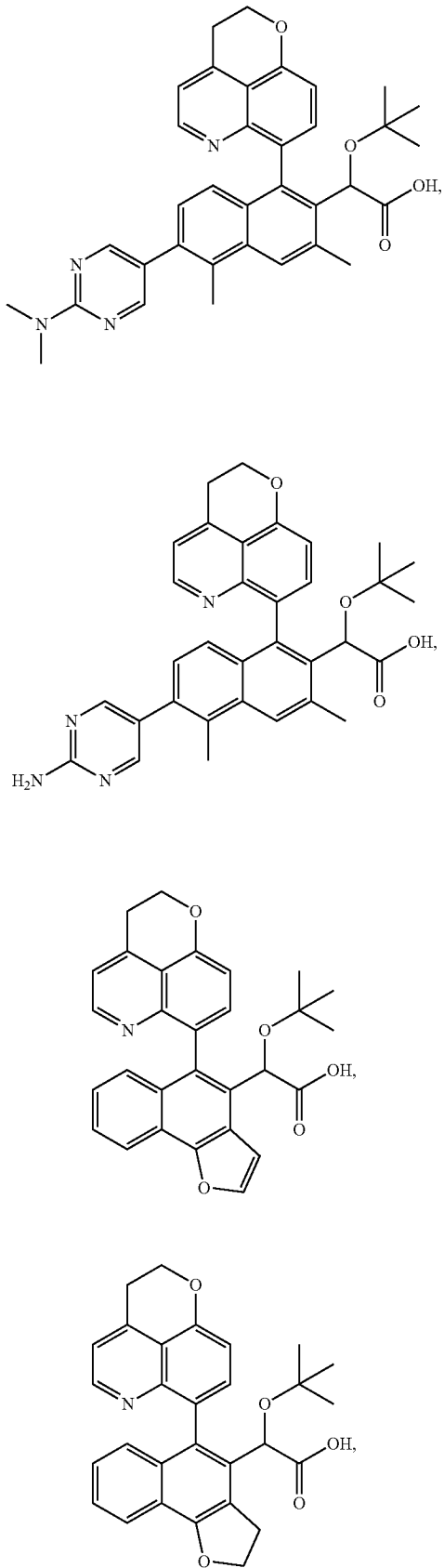

163
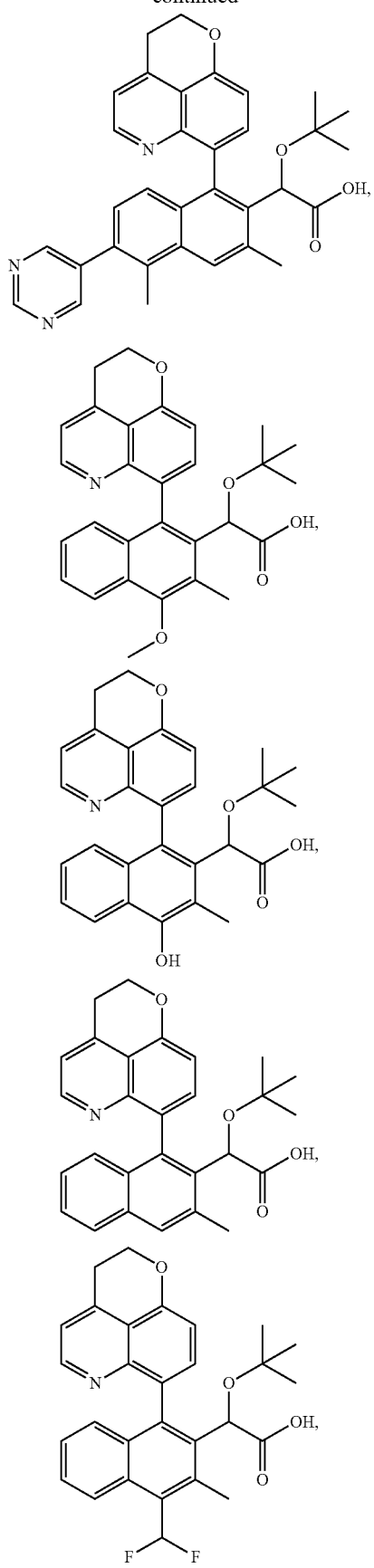
164
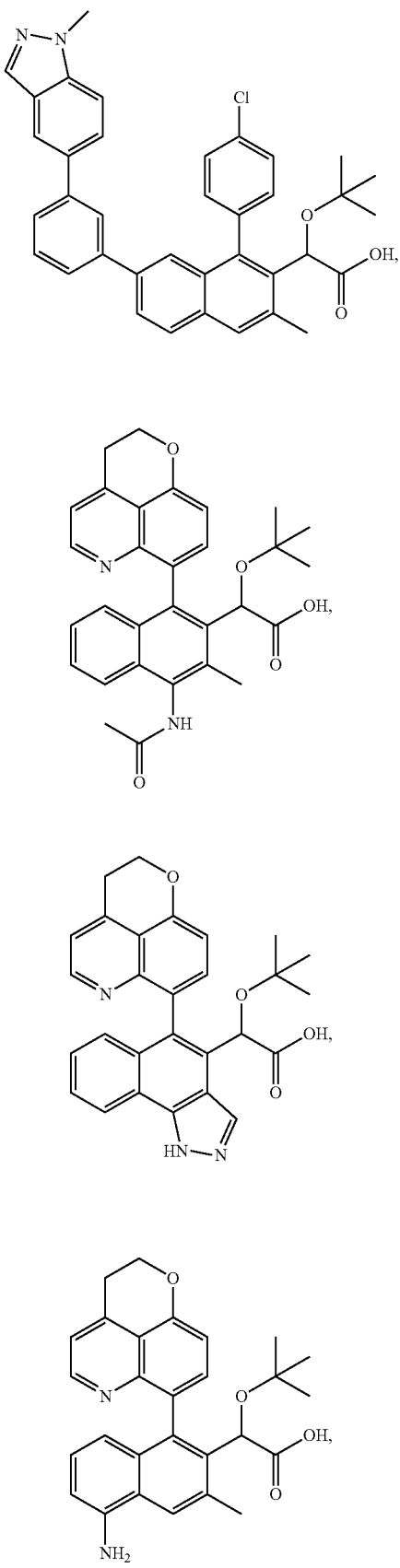

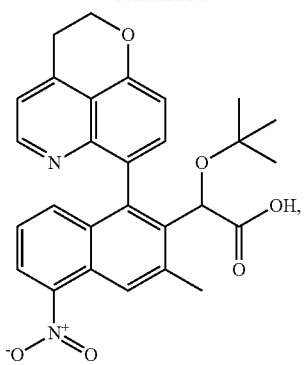

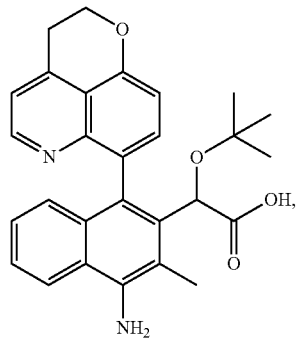

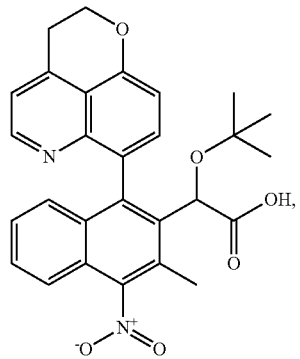

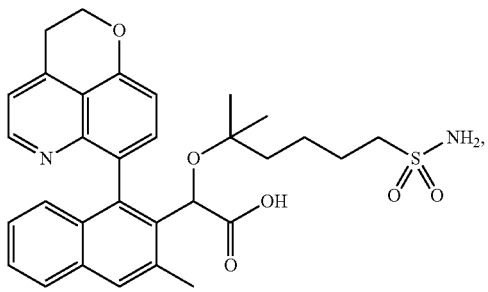

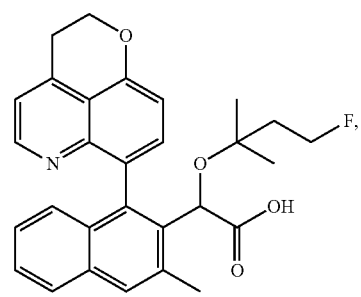

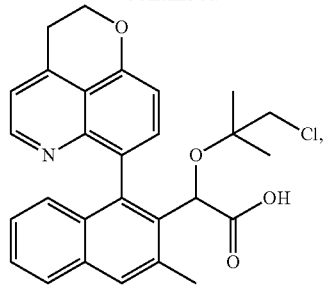

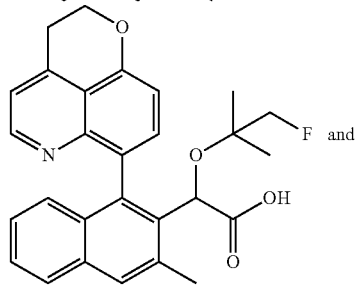

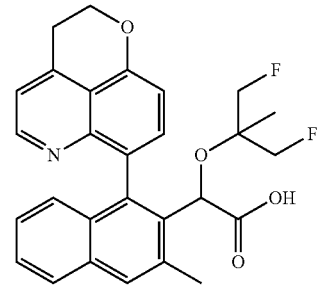

and salts thereof.

Combination Therapy

In one embodiment, the invention provides for a method for treating an HIV infection, comprising administering to a patient in need thereof a therapeutically effective amount of a compound of the invention, or a pharmaceutically acceptable salt, thereof, in combination with a therapeutically effective amount of one or more additional therapeutic agents which are suitable for treating an HIV infection.

In one embodiment, the invention provides pharmaceutical compositions comprising a compound of the present invention, or a pharmaceutically acceptable salt thereof, in combination with at least one additional therapeutic agent, and a pharmaceutically acceptable carrier. For example, the therapeutic agent used in combination with the compound of the present invention can be any anti-HIV agent.

In one embodiment, the invention provides pharmaceutical compositions comprising a compound of the present invention, or a pharmaceutically acceptable salt thereof, in combination with at least one additional therapeutic agent selected from the group consisting of HIV protease inhibiting compounds, HIV non-nucleoside inhibitors of reverse transcriptase, HIV nucleoside inhibitors of reverse transcriptase, HIV nucleotide inhibitors of reverse transcriptase, HIV integrase inhibitors, gp41 inhibitors, CXCR4 inhibitors, gp120 inhibitors, CCR5 inhibitors, capsid polymerization inhibitors, and other drugs for treating HIV, and combinations thereof, and a pharmaceutically acceptable carrier.

In another embodiment, the invention provides pharmaceutical compositions comprising a compound of the present invention, or a pharmaceutically acceptable salt thereof, in combination with at least one additional therapeutic agent selected from the group consisting of:

(1) HIV protease inhibiting compounds selected from the group consisting of amprenavir, atazanavir, fosamprenavir, indinavir, lopinavir, ritonavir, nelfinavir, saquinavir, tipranavir, brecanavir, darunavir, TMC-126, TMC-114, mozenavir (DMP-450), JE-2147 (AG1776), L-756423, R00334649, KNI-272, DPC-681, DPC-684, GW640385X, DG17, PPL-100, DG35, and AG 1859;

(2) HIV non-nucleoside inhibitors of reverse transcriptase selected from the group consisting of capravirine, emivirine, delaviridine, efavirenz, nevirapine, (+) calanolide A, etravirine, GW5634, DPC-083, DPC-961, DPC-963, MIV-150, and TMC-120, rilpivirene, BILR 355 BS, VRX 840773, UK-453061, RDEA806 and KMO23;

(3) HIV nucleoside inhibitors of reverse transcriptase selected from the group consisting of zidovudine, emtricitabine, didanosine, stavudine, zalcitabine, lamivudine, abacavir, amdoxovir, elvucitabine, alovudine, MIV-210, ±-FTC, D-d4FC, emtricitabine, phosphazide, fozivudine tidoxil, apricitibine (AVX754), amdoxovir, KP-1461, and fosalvudine tidoxil (formerly HDP 99.0003);

(4) HIV nucleotide inhibitors of reverse transcriptase selected from the group consisting of tenofovir, tenofovir disoproxil fumarate, tenofovir alafenamide fumarate (Gilead Sciences), adefovir, adefovir dipivoxil, CMX-001 (Chimerix) or CMX-157 (Chimerix)

(5) HIV integrase inhibitors selected from the group consisting of curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, S-1360, AR-177, L-870812, and L-870810, raltegravir, BMS-538158, GSK364735C, BMS-707035, MK-2048, BA 011, GS-5696, elvitegravir and dolutegravir;

(6) gp41 inhibitors selected from the group consisting of enfuvirtide, sifuvirtide, FB006M, and TRI-1144;

(7) the CXCR4 inhibitor AMD-070;

(8) the entry inhibitor SP01A;

(9) the gp120 inhibitor BMS-488043;

(10) the G6PD and NADH-oxidase inhibitor immunitin;

(11) CCR5 inhibitors selected from the group consisting of aplaviroc, vicriviroc, maraviroc, PRO-140, INCB15050, PF-232798 (Pfizer), and CCR5mAb004;

(12) other drugs for treating HIV selected from the group consisting of BAS-100, SPI-452, REP 9, SP-01A, TNX-355, DES6, ODN-93, ODN-112, VGV-1, PA-457 (bevirimat), HRG214, VGX-410, KD-247, AMZ 0026, CYT 99007A-221 HIV, DEBIO-025, BAY 50-4798, MDX010 (ipilimumab), PBS 119, ALG 889, and PA-1050040 (PA-040).

In some embodiments, one or more of the compounds disclosed herein are combined with one or more other active therapeutic agents in a unitary dosage form for simultaneous or sequential administration to a patient. The combination therapy may be administered as a simultaneous or sequential regimen. When administered sequentially, the combination may be administered in two or more administrations.

In some embodiments, one or more of the compounds disclosed herein are co-administered with one or more other active therapeutic agents. Co-administration of a compound of the invention with one or more other active therapeutic agents generally refers to simultaneous or sequential administration of a compound of the invention and one or more other active therapeutic agents, such that therapeutically effective amounts of the compound of the invention and one or more other active therapeutic agents are both present in the body of the patient.

In yet another embodiment, the present application provides a method for treating an HIV infection comprising administering to a patient in need thereof a therapeutically effective amount of a compound of the present invention, or a pharmaceutically acceptable salt thereof, in combination with a therapeutically effective amount of one or more additional therapeutic agents such as those disclosed above.

Pharmaceutical Formulations

The compounds disclosed herein are formulated with conventional carriers (e.g., inactive ingredient or excipient material) which will be selected in accord with ordinary practice. Tablets will contain excipients including glidants, fillers, binders and the like. Aqueous formulations are prepared in sterile form, and when intended for delivery by other than oral administration generally will be isotonic. All formulations will optionally contain excipients such as those set forth in the *Handbook of Pharmaceutical Excipients* (1986). Excipients include ascorbic acid and other antioxidants, chelating agents such as EDTA, carbohydrates such as dextrin, hydroxyalkylcellulose, hydroxyalkylmethylcellulose, stearic acid and the like. One embodiment provides the formulation as a solid dosage form including a solid oral dosage form. The pH of the formulations ranges from about 3 to about 11, but is ordinarily about 7 to 10.

While it is possible for the active ingredients to be administered alone it may be preferable to present them as pharmaceutical formulations (compositions). The formulations, both for veterinary and for human use, of the invention comprise at least one active ingredient, as above defined, together with one or more acceptable carriers and optionally other therapeutic ingredients. The carrier(s) must be "acceptable" in the sense of being compatible with the other ingredients of the formulation and physiologically innocuous to the recipient thereof The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with inactive ingredients (e.g., a carrier, pharmaceutical excipients, etc.) which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units including but not limited to capsules, cachets or tablets each containing a predetermined amount of the active ingredient.

Pharmaceutical formulations according to the present invention comprise one or more compounds disclosed herein together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredient that is combined with the inactive ingredients to produce a dosage form will vary depending upon the host treated and the particular mode of administration. For example, in some embodiments, a dosage form for oral administration to humans contains approximately 1 to 1000 mg of active material formulated with an appropriate and convenient amount of carrier material (i.e., inactive ingredient or excipient material). In certain embodiments, the carrier material varies from about 5 to about 95% of the total compositions (weight:weight).

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies.

Routes of Administration

One or more compounds disclosed herein (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

The antiviral properties of a compound disclosed herein may be determined using Test A described below.

Test A: Antiviral Assays in MT4 Cells

For the antiviral assay utilizing MT-4 cells, 0.4 µL of 189X test concentration of 3-fold serially diluted compound in DMSO was added to 40 µL of cell growth medium (RPMI 1640, 10% FBS, 1% penicillin/Streptomycin, 1% L-Glutamine, 1% HEPES) in each well of 384-well assay plates (10 concentrations) in quadruplicate.

1 mL aliquots of 2×10e6 MT-4 cells are pre-infected for 1 and 3 hrs respectively, @ 37° C. with 25 µL (MT4) or of either cell growth medium (mock-infected) or a fresh 1:250 dilution of an HIV-IIIb concentrated ABI stock (0.004 m.o.i. for MT4 cells). Infected and uninfected cells are diluted in cell growth medium and 35 µL of 2000 (for MT4) cells is added to each well of the assay plates.

Assay plates were then incubated in a 37° C. incubator. After 5 days of incubation, 25 µl of 2× concentrated CellTiter-Glo™ Reagent (catalog # G7573, Promega Biosciences, Inc., Madison, Wis.) was added to each well of the assay plate. Cell lysis was carried out by incubating at room temperature for 2-3 min and then chemiluminescence was read using the Envision reader (PerkinElmer).

Compounds of the present invention demonstrate antiviral activity in this assay (Test A) as depicted in Table I and Table II below.

TABLE I

| Example number | Compound name | Compound Structure | EC$_{50}$ (nM) |
|---|---|---|---|
| 1 | (S)-2-tert-butoxy-2-(1-((R)-2,3-dihydropyrano[4,3,2-de]quinolin-7-yl)-3,4-dimethylnaphthalen-2-yl)acetic acid | 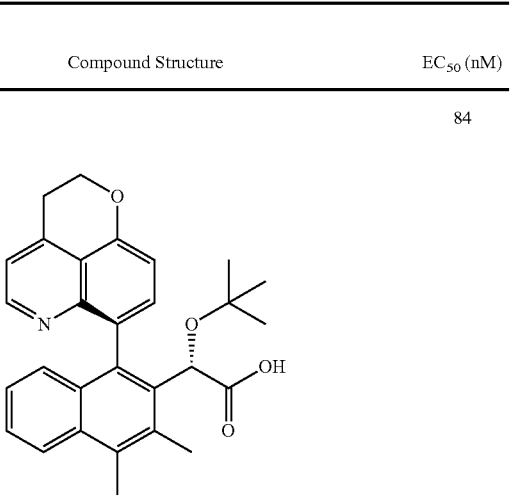 | 84 |

TABLE I-continued

| Example number | Compound name | Compound Structure | EC$_{50}$ (nM) |
|---|---|---|---|
| 1 | (S)-2-tert-butoxy-2-(1-((S)-2,3-dihydropyrano[4,3,2-de]quinolin-7-yl)-3,4-dimethylnaphthalen-2-yl)acetic acid | 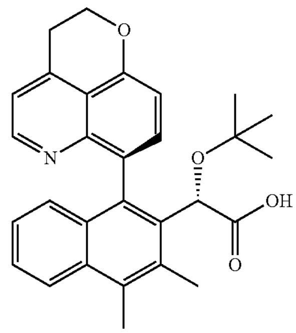 | 699 |
| 2 | S)-2-tert-butoxy-2-(5-((R)-2,3-dihydropyrano[4,3,2-de]quinolin-7-yl)-1,3-dihydronaphtho[1,2-c]furan-4-yl)acetic acid | | 44 |
| 2 | (S)-2-tert-butoxy-2-(5-((R)-2,3-dihydropyrano[4,3,2-de]quinolin-7-yl)-2-methyl-2,3-dihydro-1H-benzo[e]isoindol-4-yl)acetic acid | | 183 |
| 3 | (S)-2-tert-butoxy-2-(5-((S)-2,3-dihydropyrano[4,3,2-de]quinolin-7-yl)-2-methyl-2,3-dihydro-1H-benzo[e]isoindol-4-yl)acetic acid | 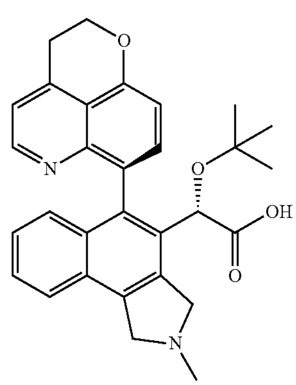 | 49000 |

TABLE I-continued

| Example number | Compound name | Compound Structure | EC$_{50}$ (nM) |
|---|---|---|---|
| 3 | (S)-2-tert-butoxy-2-(1-((R)-2,3-dihydropyrano[4,3,2-de]quinolin-7-yl)-3-methyl-6-(methylsulfonyl)naphthalen-2-yl)acetic acid | 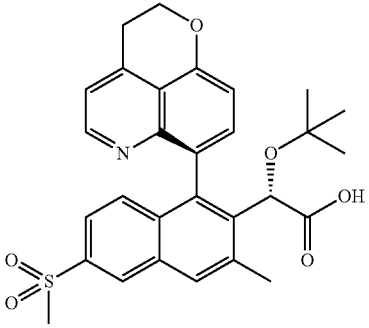 | 419 |
| 3 | (S)-2-tert-butoxy-2-(1-((s)-2,3-dihydropyrano[4,3,2-de]quinolin-7-yl)-3-methyl-6-(methylsulfonyl)-naphthalen-2-yl)acetic acid | 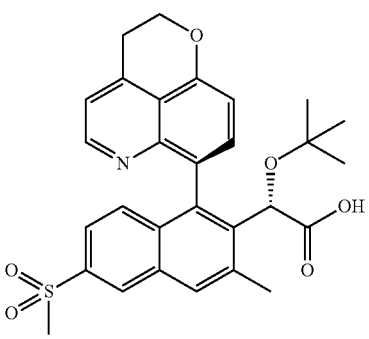 | 53200 |
| 5 | (S)-2-tert-butoxy-2-(6-cyano-1-((R)-2,3-dihydropyrano[4,3,2-de]quinolin-7-yl)-3-methylnaphthalen-2-yl)acetic acid | 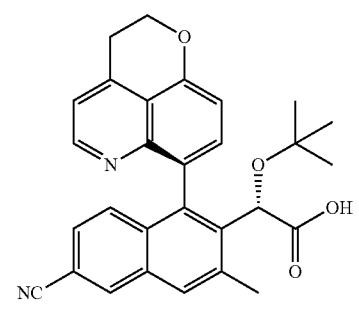 | 11 |
| 5 | (S)-2-tert-butoxy-2-(6-carbamoyl-1-((R)-2,3-dihydropyrano[4,3,2-de]quinolin-7-yl)-3-methylnaphthalen-2-yl)acetic acid | 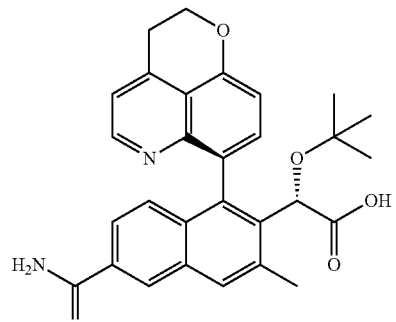 | 232 |

TABLE I-continued

| Example number | Compound name | Compound Structure | EC$_{50}$ (nM) |
|---|---|---|---|
| 5 | 6-((S)-tert-butoxy(carboxy)methyl)-5-((R)-2,3-dihydropyrano[4,3,2-de]quinolin-7-yl)-7-methyl-2-naphthoic acid | | 3620 |
| 5 | (S)-2-tert-butoxy-2-(6-cyano-1-((S)-2,3-dihydropyrano[4,3,2-de]quinolin-7-yl)-3-methylnaphthalen-2-yl)acetic acid | | 11030 |
| 5 | (S)-2-tert-butoxy-2-(6-carbamoyl-1-((S)-2,3-dihydropyrano[4,3,2-de]quinolin-7-yl)-3-methylnaphthalen-2-yl)acetic acid | | 53200 |
| 5 | 6-((S)-tert-butoxy(carboxy)methyl)-5-((S)-2,3-dihydropyrano[4,3,2-de]quinolin-7-yl)-7-methyl-2-naphthoic acid | | 53200 |

TABLE I-continued

| Example number | Compound name | Compound Structure | EC$_{50}$ (nM) |
|---|---|---|---|
| 6 | (S)-2-(6-cyano-1-((R)-2,3-dihydropyrano[4,3,2-de]quinolin-7-yl)-3-methylnaphthalen-2-yl)-2-(tert-pentyloxy)acetic acid | 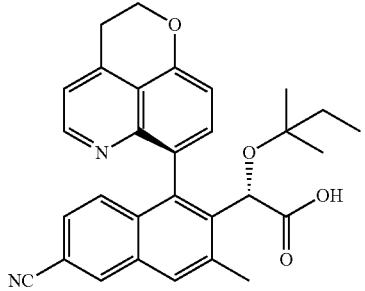 | 13 |
| 6 | (S)-2-(6-carbamoyl-1-((R)-2,3-dihydropyrano[4,3,2-de]quinolin-7-yl)-3-methylnaphthalen-2-yl)-2-(tert-pentyloxy)acetic acid | 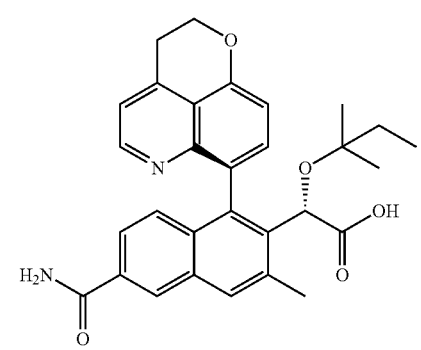 | 91 |
| 6 | (S)-2-(6-cyano-1-((S)-2,3-dihydropyrano[4,3,2-de]quinolin-7-yl)-3-methylnaphthalen-2-yl)-2-(tert-pentyloxy)acetic acid | 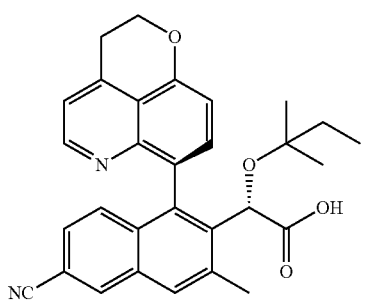 | 7642 |
| 6 | (S)-2-(6-carbamoyl-1-((S)-2,3-dihydropyrano[4,3,2-de]quinolin-7-yl)-3-methylnaphthalen-2-yl)-2-(tert-pentyloxy)acetic acid | 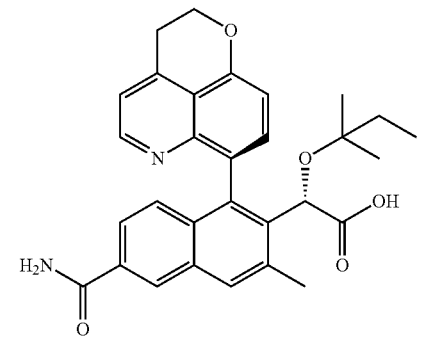 | 53200 |

TABLE I-continued

| Example number | Compound name | Compound Structure | EC$_{50}$ (nM) |
|---|---|---|---|
| 7 | (S)-2-tert-butoxy-2-(6-cyano-1-((R)-2,3-dihydropyrano[4,3,2-de]quinolin-7-yl)-4-fluoro-3-methylnaphthalen-2-yl)acetic acid | | 53 |
| 7 | (S)-2-tert-butoxy-2-(6-carbamoyl-1-((R)-2,3-dihydropyrano[4,3,2-de]quinolin-7-yl)-4-fluoro-3-methylnaphthalen-2-yl)acetic acid | | 292 |
| 7 | (S)-2-tert-butoxy-2-(6-cyano-1-((S)-2,3-dihydropyrano[4,3,2-de]quinolin-7-yl)-4-fluoro-3-methylnaphthalen-2-yl)acetic acid | | 33400 |
| 7 | S)-2-tert-butoxy-2-(6-carbamoyl-1-((R)-2,3-dihydropyrano[4,3,2-de]quinolin-7-yl)-4-fluoro-3-methylnaphthalen-2-yl)acetic acid | | 53200 |

TABLE I-continued

| Example number | Compound name | Compound Structure | EC$_{50}$ (nM) |
|---|---|---|---|
| 8 | (2S)-2-tert-butoxy-2-(1-(4-chlorophenyl)-7-(3-(4-fluorophenyl)-3-hydroxybut-1-ynyl)-3-methylnaphthalen-2-yl)acetic acid | 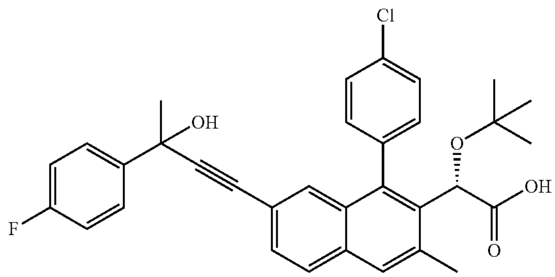 [SMILES: Cc1cc2ccc(C#CC(C)(O)c3ccc(F)cc3)cc2c(-c2ccc(Cl)cc2)c1[C@H](OC(C)(C)C)C(=O)O] | 120 |
| 9 | (2S)-2-tert-butoxy-2-(1-(4-chlorophenyl)-3-methyl-7-(4,4,4-trifluoro-3-hydroxy-3-phenylbut-1-ynyl)naphthalen-2-yl)acetic acid | 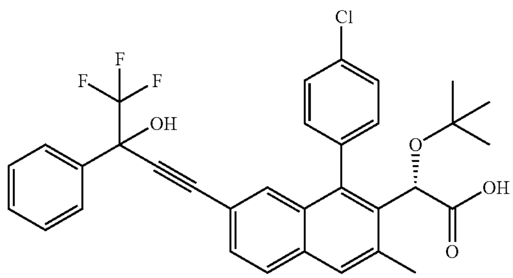 [SMILES: Cc1cc2ccc(C#CC(O)(c3ccccc3)C(F)(F)F)cc2c(-c2ccc(Cl)cc2)c1[C@H](OC(C)(C)C)C(=O)O] | 186 |
| 10 | (2S)-2-tert-butoxy-2-(1-(4-chlorophenyl)-7-(3-hydroxy-3-(pyridin-2-yl)but-1-ynyl)-3-methylnaphthalen-2-yl)acetic acid | 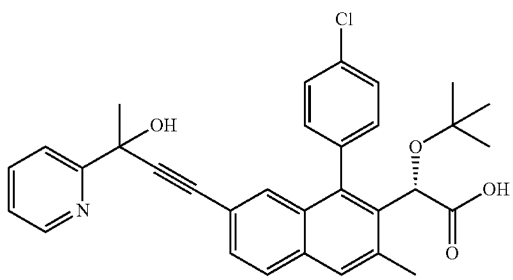 [SMILES: Cc1cc2ccc(C#CC(C)(O)c3ccccn3)cc2c(-c2ccc(Cl)cc2)c1[C@H](OC(C)(C)C)C(=O)O] | 62 |
| 11 | (2S)-2-tert-butoxy-2-(1-(4-chlorophenyl)-7-(3-hydroxy-3-(pyridin-3-yl)but-1-ynyl)-3-methylnaphthalen-2-yl)acetic acid | 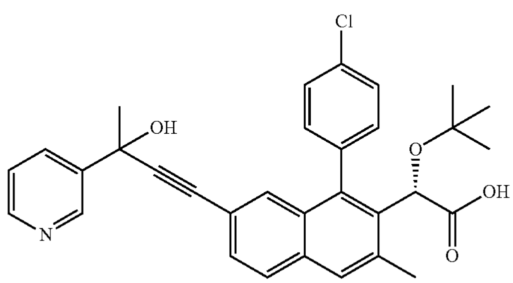 [SMILES: Cc1cc2ccc(C#CC(C)(O)c3cccnc3)cc2c(-c2ccc(Cl)cc2)c1[C@H](OC(C)(C)C)C(=O)O] | 24 |
| 12 | (2S)-2-tert-butoxy-2-(1-(4-chlorophenyl)-7-(3-hydroxy-3-(pyridin-4-yl)but-1-ynyl)-3-methylnaphthalen-2-yl)acetic acid | 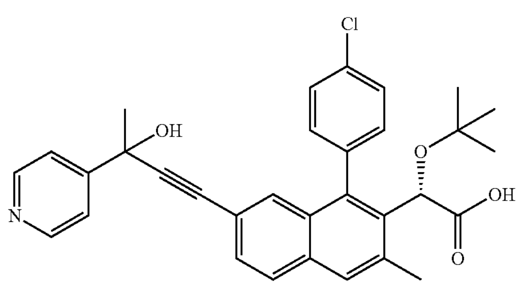 [SMILES: Cc1cc2ccc(C#CC(C)(O)c3ccncc3)cc2c(-c2ccc(Cl)cc2)c1[C@H](OC(C)(C)C)C(=O)O] | 32 |

TABLE I-continued

| Example number | Compound name | Compound Structure | EC$_{50}$ (nM) |
|---|---|---|---|
| 13 | (2S)-2-tert-butoxy-2-(1-(4-chlorophenyl)-7-(3-(2,4-dimethylthiazol-5-yl)-3-hydroxybut-1-ynyl)-3-methylnaphthalen-2-yl)acetic acid | 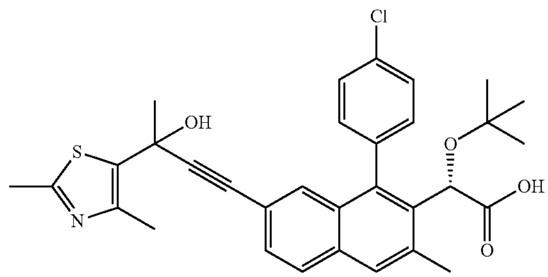 [SMILES: Cc1nc(C)c(C(C)(O)C#Cc2ccc3cc(C)c([C@H](OC(C)(C)C)C(=O)O)c(-c4ccc(Cl)cc4)c3c2)s1] | 65 |
| 14 | (S)-2-tert-butoxy-2-(1-(4-chlorophenyl)-7-((R)-3-hydroxy-3-phenylbut-1-ynyl)-3-methylnaphthalen-2-yl)acetic acid | | 56 |
| 14 | (S)-2-tert-butoxy-2-(1-(4-chlorophenyl)-7-((S)-3-hydroxy-3-phenylbut-1-ynyl)-3-methylnaphthalen-2-yl)acetic acid | | 85 |
| 15 | (S)-2-tert-butoxy-2-((R)-1-(2,3-dihydropyrano[4,3,2-de]quinolin-7-yl)-3,7-dimethylnaphthalen-2-yl)acetic acid | 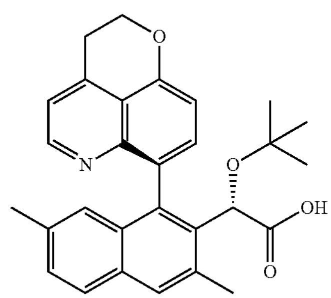 | 34 |
| 16 | (S)-2-tert-butoxy-2-((S)-1-(2,3-dihydropyrano[4,3,2-de]quinolin-7-yl)-3,6-dimethylnaphthalen-2-yl)acetic acid | 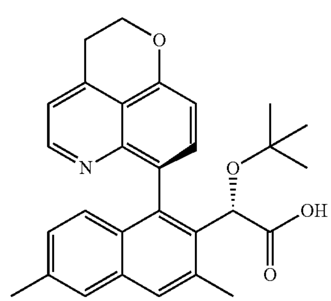 | 1740 |

TABLE I-continued

| Example number | Compound name | Compound Structure | EC$_{50}$ (nM) |
|---|---|---|---|
| 17 | (S)-2-tert-butoxy-2-((R)-1-(2,3-dihydropyrano[4,3,2-de]quinolin-7-yl)-4-fluoro-3,6-dimethylnaphthalen-2-yl)acetic acid | | 11 |
| 17 | (S)-2-tert-butoxy-2-((S)-1-(2,3-dihydropyrano[4,3,2-de]quinolin-7-yl)-4-fluoro-3,6-dimethyl-naphthalen-2-yl)acetic acid | | 9032 |
| 18 | (S)-2-tert-butoxy-2-((R)-1-(2,3-dihydropyrano[4,3,2-de]quinolin-7-yl)-3,5-dimethylnaphthalen-2-yl)acetic acid | | 82 |
| 18 | (S)-2-tert-butoxy-2-((S)-1-(2,3-dihydropyrano[4,3,2-de]quinolin-7-yl)-3,5-dimethylnaphthalen-2-yl)acetic acid | | 975 |

TABLE I-continued

| Example number | Compound name | Compound Structure | EC$_{50}$ (nM) |
|---|---|---|---|
| 19 | (S)-2-tert-butoxy-2-((R)-6-(difluoromethyl)-1-(2,3-dihydropyrano[4,3,2-de]quinolin-7-yl)-3-methylnaphthalen-2-yl)acetic acid | | 6 |
| 19 | (S)-2-tert-butoxy-2-((S)-6-(difluoromethyl)-1-(2,3-dihydropyrano[4,3,2-de]quinolin-7-yl)-3-methylnaphthalen-2-yl)acetic acid | | 203 |
| 20 | (S)-2-tert-butoxy-2-((R)-1-(2,3-dihydropyrano[4,3,2-de]quinolin-7-yl)-3-methyl-6-(prop-1-ynyl)naphthalen-2-yl)acetic acid | | 35 |
| 20 | (S)-2-tert-butoxy-2-((S)-1-(2,3-dihydropyrano[4,3,2-de]quinolin-7-yl)-3-methyl-6-(prop-1-ynyl)naphthalen-2-yl)acetic acid | | 12600 |

TABLE I-continued

| Example number | Compound name | Compound Structure | EC$_{50}$ (nM) |
|---|---|---|---|
| 21 | (S)-2-tert-butoxy-2-((R)-6-(cyclopropylethynyl)-1-(2,3-dihydropyrano[4,3,2-de]quinolin-7-yl)-3-methylnaphthalen-2-yl)acetic acid | 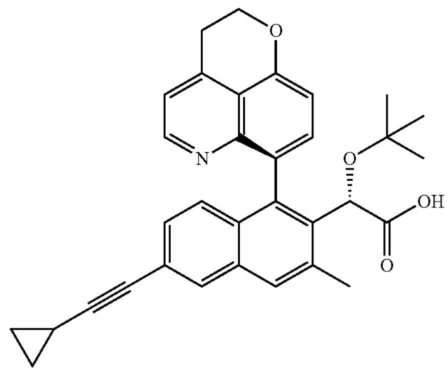 | 169 |
| 22 | (S)-2-tert-butoxy-2-((R)-6-cyano-1-(2,3-dihydropyrano[4,3,2-de]quinolin-7-yl)-5-ethoxy-3-methylnaphthalen-2-yl)acetic acid | 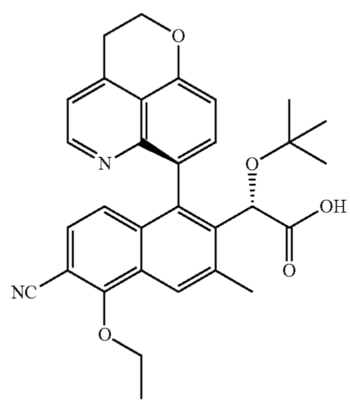 | 14 |
| 23 | (S)-2-tert-butoxy-2-((R)-1-(2,3-dihydropyrano[4,3,2-de]quinolin-7-yl)-3-methyl-6-(prop-1-ynyl)naphthalen-2-yl)acetic acid | | 296 |
| 23 | (S)-2-tert-butoxy-2-((S)-1-(2,3-dihydropyrano[4,3,2-de]quinolin-7-yl)-4,5,7-trifluoro-3-methylnaphthalen-2-yl)acetic acid | | 53300 |

TABLE I-continued

| Example number | Compound name | Compound Structure | EC$_{50}$ (nM) |
|---|---|---|---|
| 24 | (S)-2-tert-butoxy-2-((R)-10-(2,3-dihydropyrano[4,3,2-de]quinolin-7-yl)phenanthren-9-yl)acetic acid | 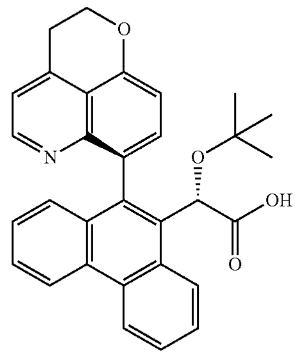 | 109 |
| 25 | (2S)-2-((R)-1-(2,3-dihydropyrano[4,3,2-de]quinolin-7-yl)-3-methylnaphthalen-2-yl)-2-(1-methoxy-2-methylpropan-2-yloxy)acetic acid | 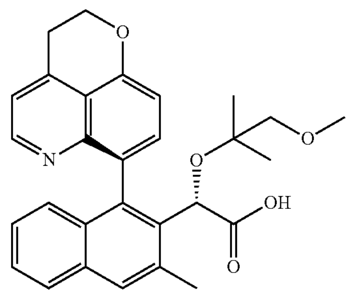 | 37 |
| 26 | (2S)-2-((S)-1-(2,3-dihydropyrano[4,3,2-de]quinolin-7-yl)-3-methylnaphthalen-2-yl)-2-(1-methoxy-2-methylpropan-2-yloxy)acetic acid | 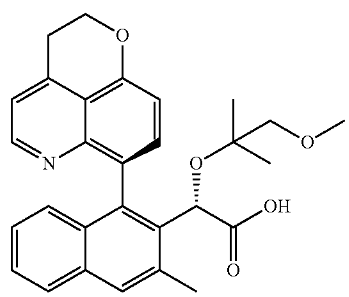 | 929 |
| 27 | (2S)-2-((R)-1-(2,3-dihydropyrano[4,3,2-de]quinolin-7-yl)-3-methylnaphthalen-2-yl)-2-(1-ethoxy-2-methylpropan-2-yloxy)acetic acid | 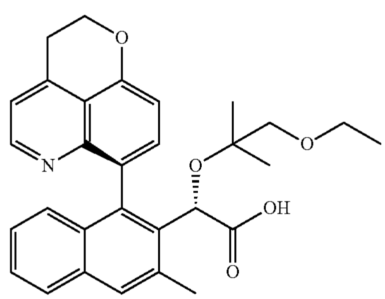 | 84 |
| 28 | (2S)-2-((S)-1-(2,3-dihydropyrano[4,3,2-de]quinolin-7-yl)-3-methylnaphthalen-2-yl)-2-(1-ethoxy-2-methylpropan-2-yloxy)acetic acid | 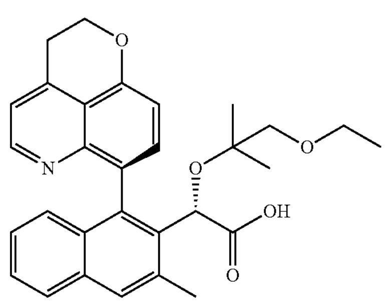 | 1230 |

TABLE I-continued

| Example number | Compound name | Compound Structure | EC$_{50}$ (nM) |
|---|---|---|---|
| 29 | (S)-2-((R)-1-(2,3-dihydropyrano[4,3,2-de]quinolin-7-yl)-3-methylnaphthalen-2-yl)-2-(2-methylpentan-2-yloxy)acetic acid | 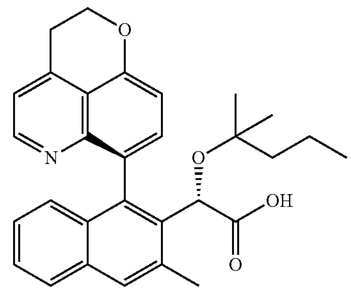 | 84 |
| 30 | (S)-2-((S)-1-(2,3-dihydropyrano[4,3,2-de]quinolin-7-yl)-3-methylnaphthalen-2-yl)-2-(2-methylhexan-2-yloxy)acetic acid | 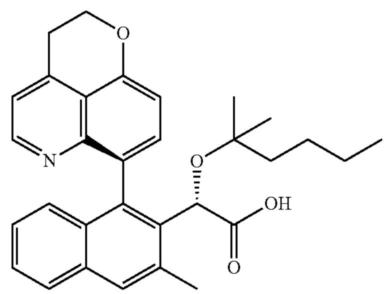 | 84 |
| 31 | (S)-2-((R)-1-(2,3-dihydropyrano[4,3,2-de]quinolin-7-yl)-3-methylnaphthalen-2-yl)-2-(1,1,1-trifluoro-2-methylpropan-2-yloxy)acetic acid. | | 36 |
| 31 | (R)-2-((S)-1-(2,3-dihydropyrano[4,3,2-de]quinolin-7-yl)-3-methylnaphthalen-2-yl)-2-(1,1,1-trifluoro-2-methylpropan-2-yloxy)acetic acid: | | 53200 |
| 32 | (S)-2-(1,1-difluoro-2-methylpropan-2-yloxy)-2-((R)-1-(2,3-dihydropyrano[4,3,2-de]quinolin-7-yl)-3-methylnaphthalen-2-yl)acetic acid | 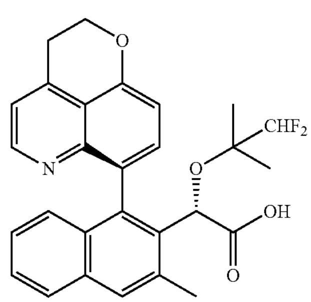 | 36 |

TABLE I-continued

| Example number | Compound name | Compound Structure | EC$_{50}$ (nM) |
|---|---|---|---|
| 32 | (R)-2-(1,1-difluoro-2-methylpropan-2-yloxy)-2-((S)-1-(2,3-dihydropyrano[4,3,2-de]quinolin-7-yl)-3-methylnaphthalen-2-yl)acetic acid | 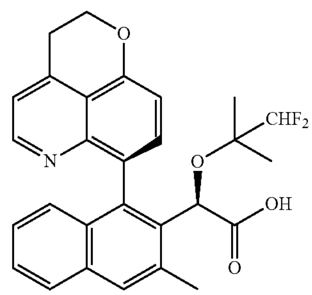 | 20205 |

TABLE II

| Example Number | Compound Structure | EC$_{50}$ (nM) |
|---|---|---|
| 33 | 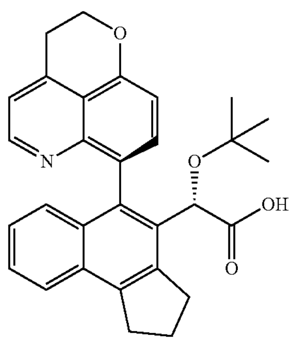 | 1661 |
| 34 | 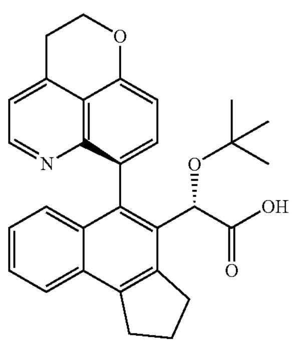 | 60 |
| 35 | 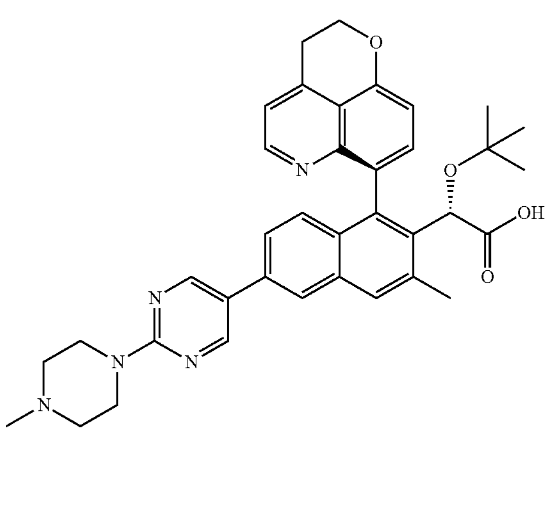 | 4.40 |

TABLE II-continued
| Example Number | Compound Structure | $EC_{50}$ (nM) |
|---|---|---|
| 36 | 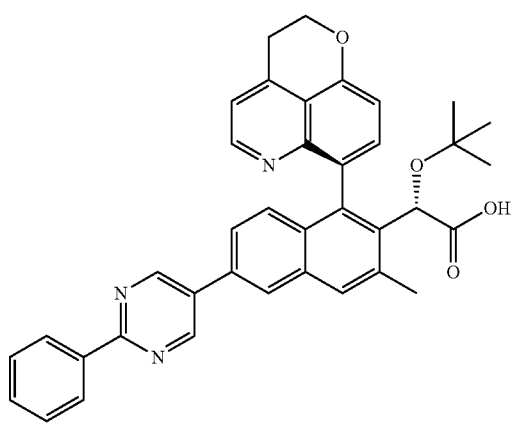 | 100 |
| 37 | 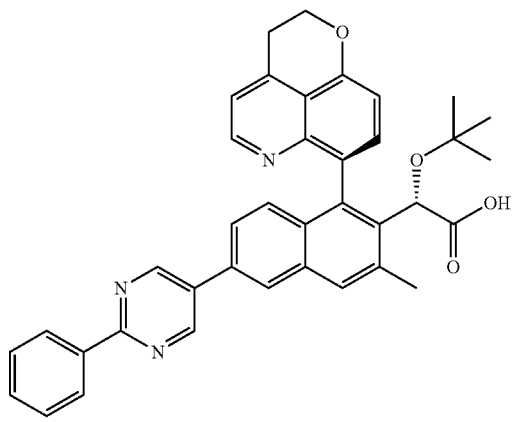 | 4450 |
| 38 | 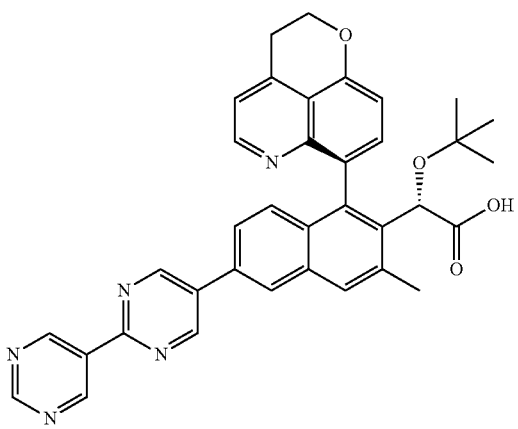 | 45.2 |

TABLE II-continued
| Example Number | Compound Structure | EC$_{50}$ (nM) |
|---|---|---|
| 39 | 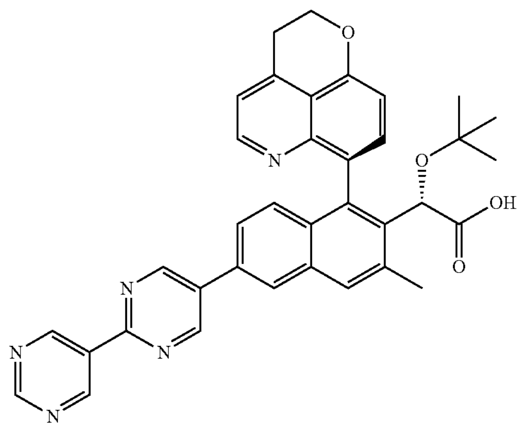 | 8680 |
| 40 | 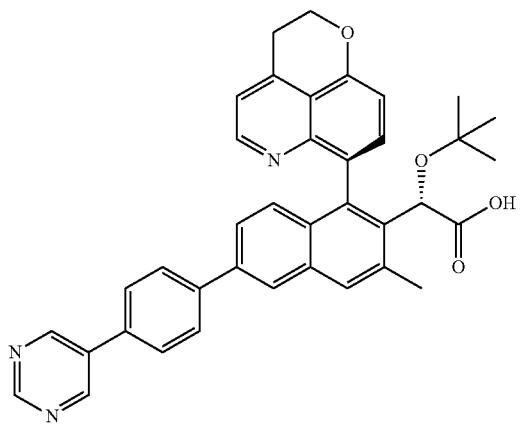 | 542 |
| 41 | 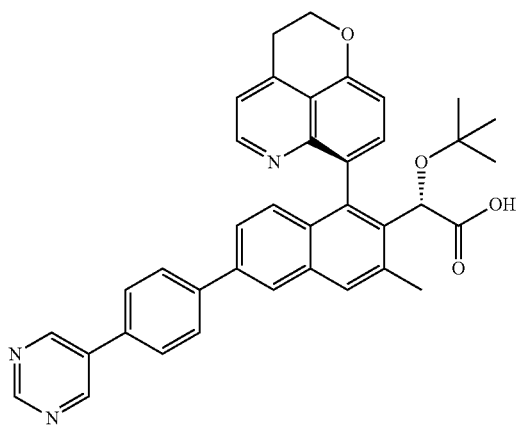 | 40.9 |

TABLE II-continued
| Example Number | Compound Structure | EC$_{50}$ (nM) |
| --- | --- | --- |
| 42 | 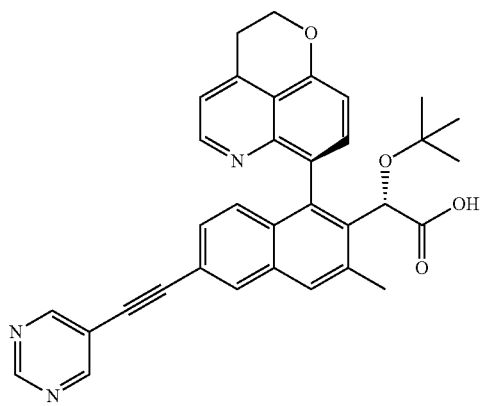 | 53200 |
| 43 | 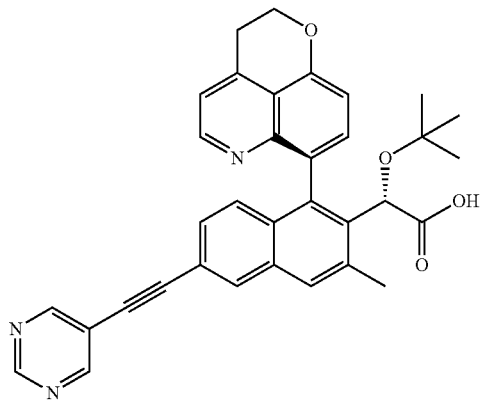 | 121 |
| 44 | 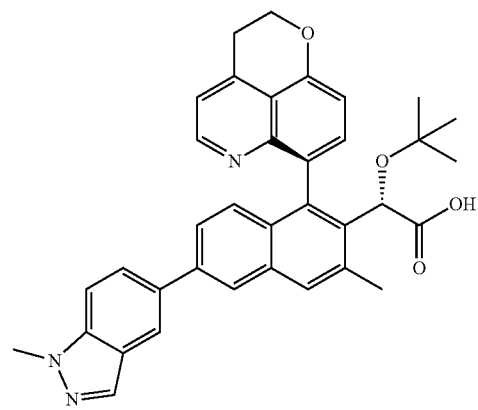 | 55.6 |

TABLE II-continued

| Example Number | Compound Structure | EC$_{50}$ (nM) |
|---|---|---|
| 45 | 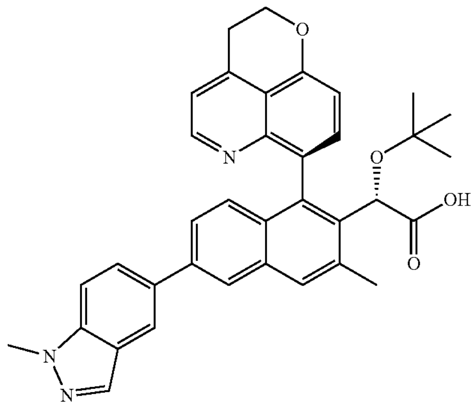 | 354 |
| 46 | 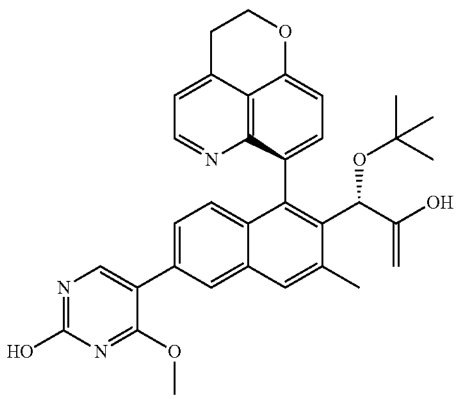 | 352 |
| 47 | 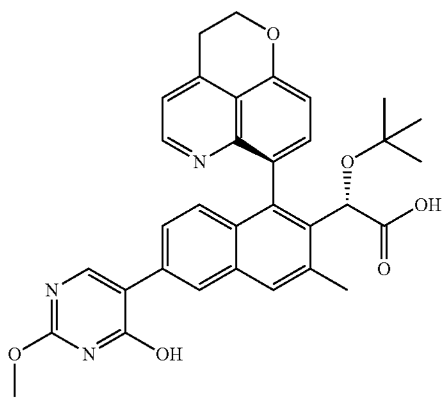 | 59.2 |
| 48 | 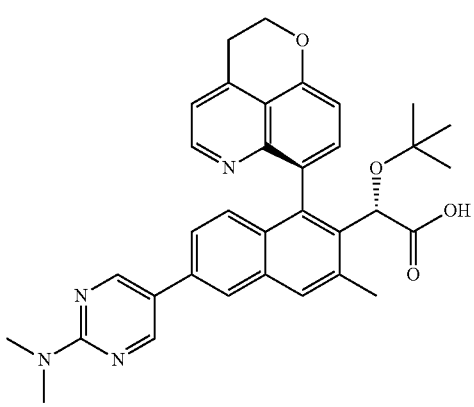 | 10.4 |

TABLE II-continued
| Example Number | Compound Structure | EC$_{50}$ (nM) |
|---|---|---|
| 49 | 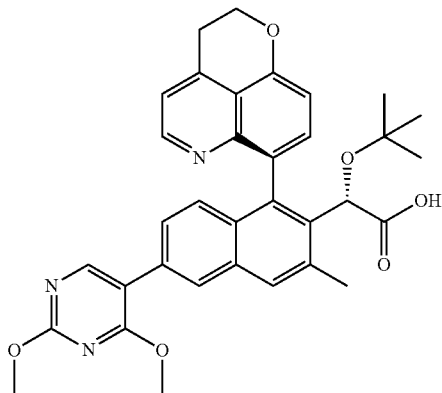 | 13.8 |
| 50 | 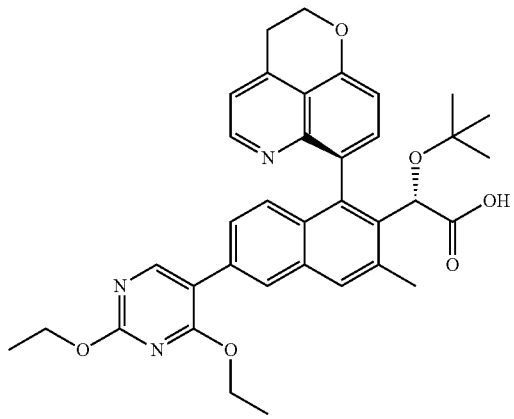 | 45.1 |
| 51 | 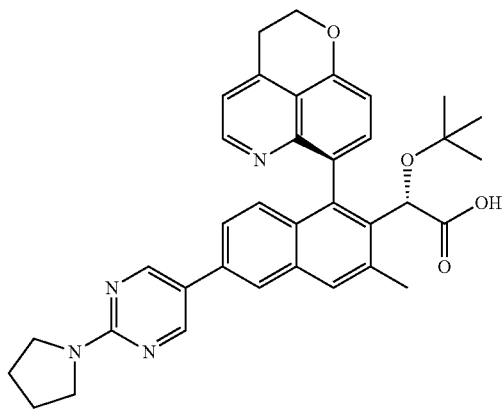 | 20.5 |

TABLE II-continued

| Example Number | Compound Structure | EC$_{50}$ (nM) |
|---|---|---|
| 52 | 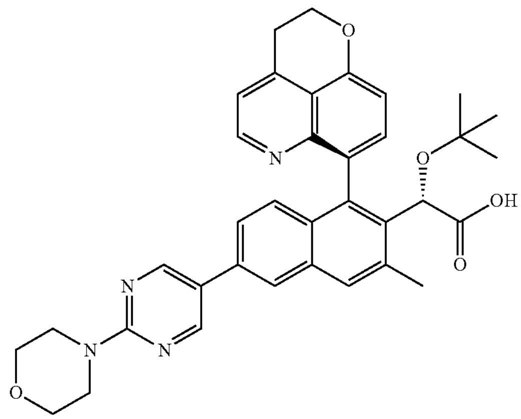 | 16.8 |
| 53 | 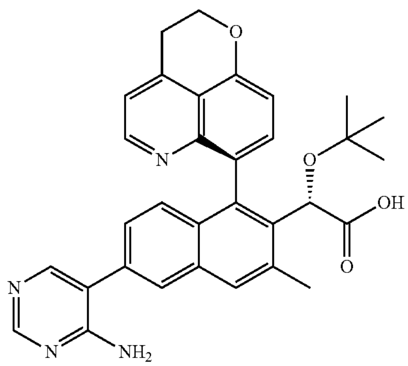 | 74.2 |
| 54 | 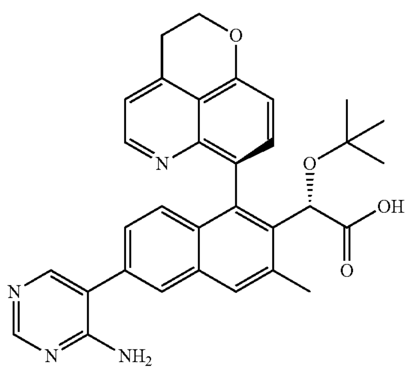 | 19400 |
| 55 | 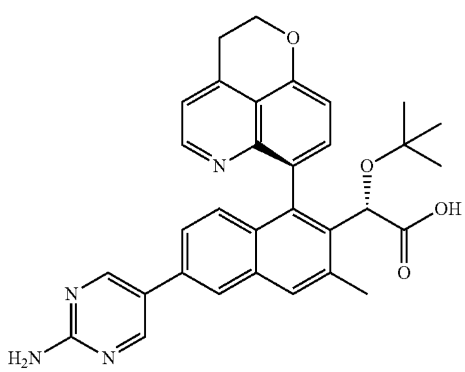 | 7.53 |

TABLE II-continued

| Example Number | Compound Structure | EC$_{50}$ (nM) |
| --- | --- | --- |
| 56 | 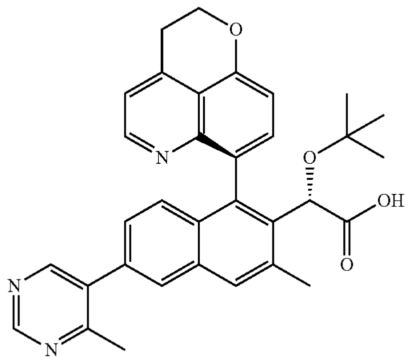 | 30.5 |
| 57 | 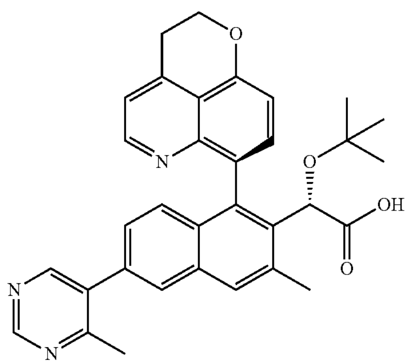 | 9997 |
| 58 | 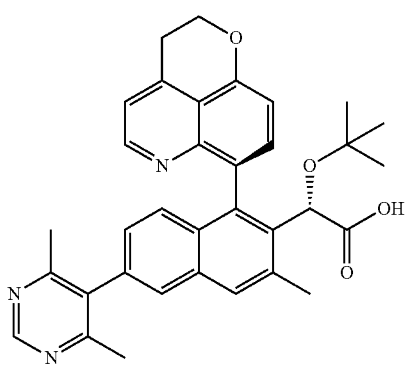 | 7761 |
| 59 | 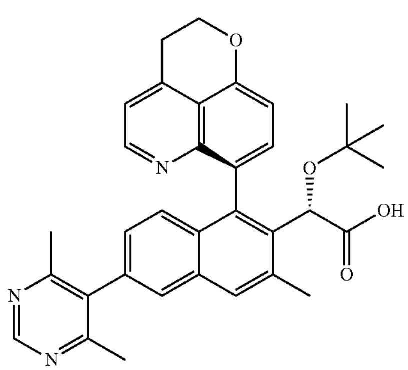 | 471 |

TABLE II-continued

| Example Number | Compound Structure | EC$_{50}$ (nM) |
|---|---|---|
| 60 | 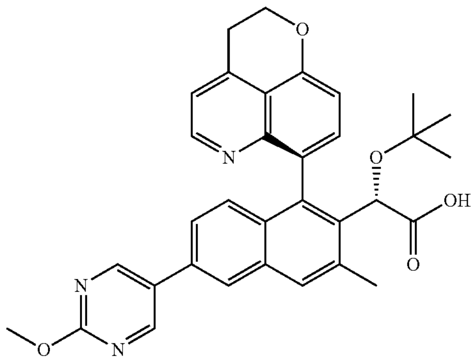 | 12.2 |
| 61 | 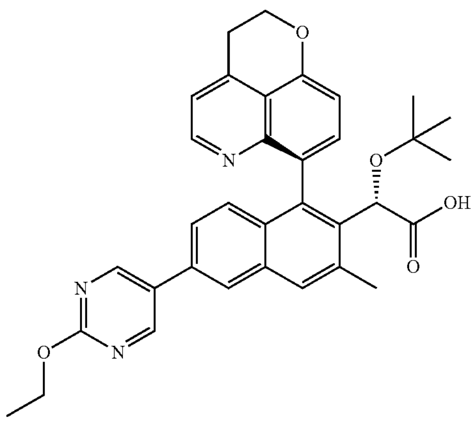 | n.d |
| 62 | 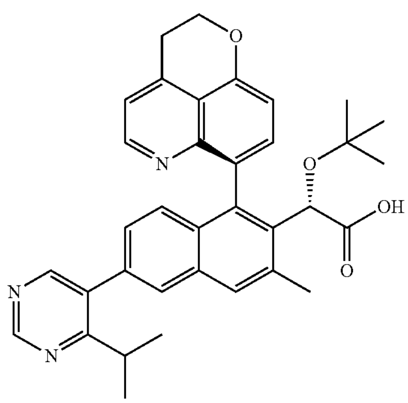 | 41.1 |
| 63 | 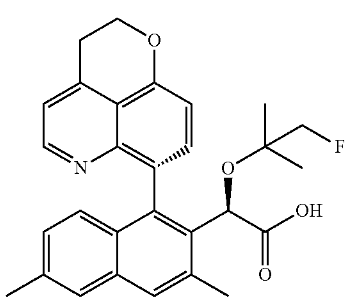 | 1683 |

TABLE II-continued

| Example Number | Compound Structure | EC$_{50}$ (nM) |
| --- | --- | --- |
| 64 | 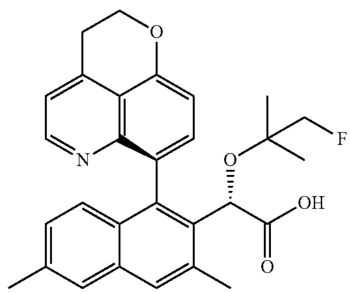 | 8.72 |
| 65 | 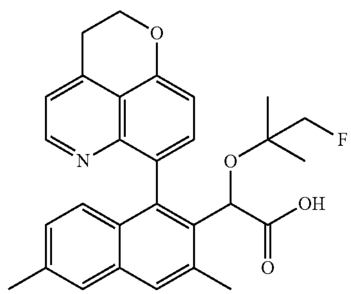 [SMILES: Cc1ccc2c(-c3ccc4c5c(ccnc35)CCO4)c(C(OC(C)(C)CF)C(=O)O)c(C)cc2c1] | 12.1 |
| 66 | 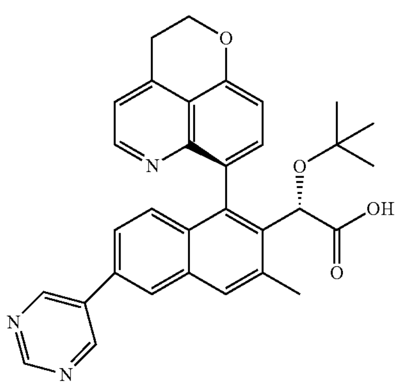 | 9.88 |
| 67 | 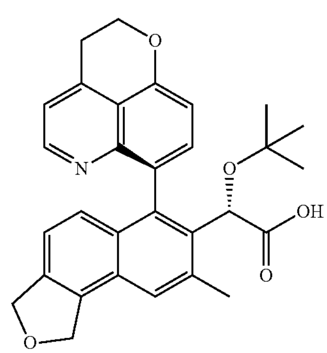 | 52.3 |

TABLE II-continued

| Example Number | Compound Structure | EC$_{50}$ (nM) |
|---|---|---|
| 68 | 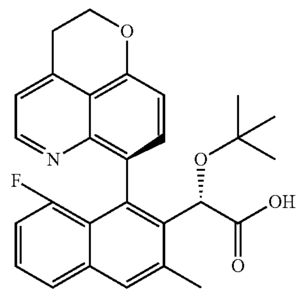 | 2936 |
| 69 | 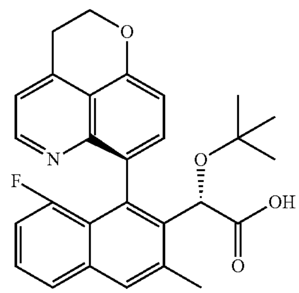 | 11.3 |
| 70 | 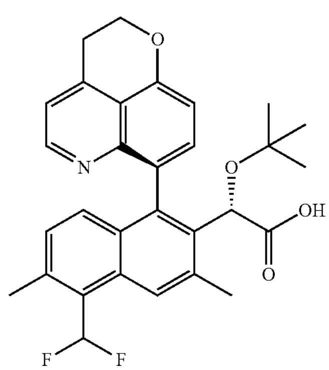 | 11.6 |
| 71 | 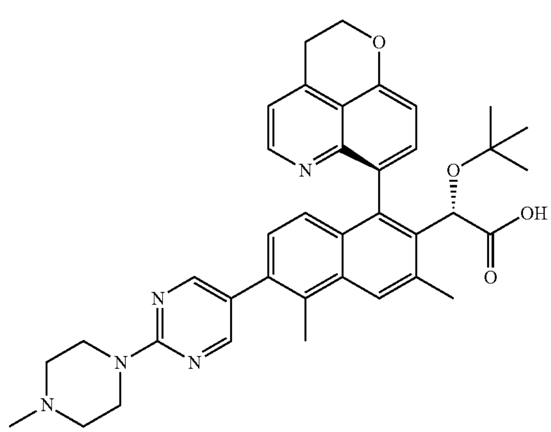 | 4.23 |

TABLE II-continued

| Example Number | Compound Structure | EC$_{50}$ (nM) |
|---|---|---|
| 72 | 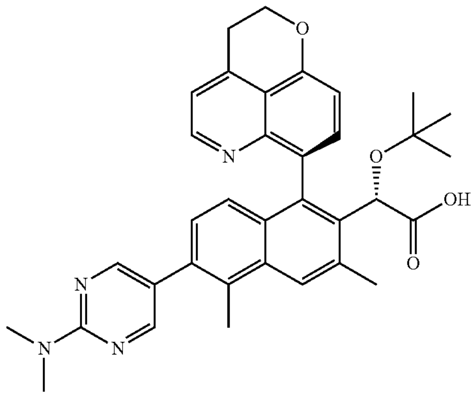 | 7024 |
| 73 | 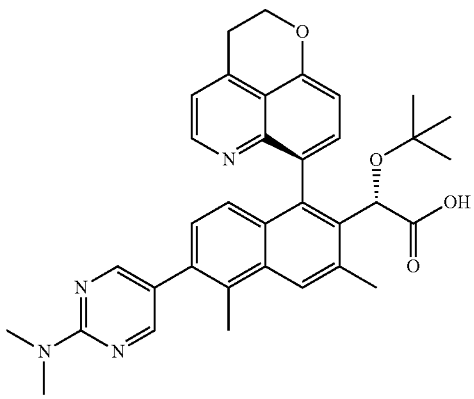 | 8.95 |
| 74 | 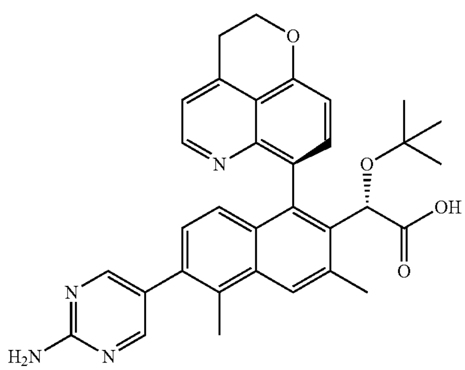 | 37800 |
| 75 | 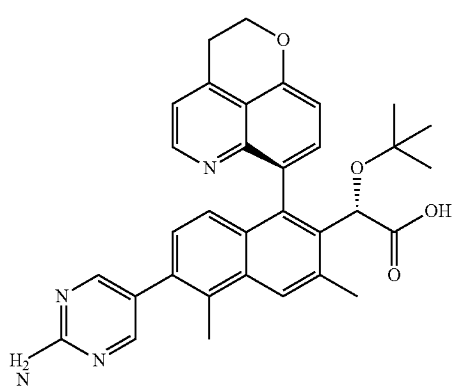 | 6.95 |

TABLE II-continued

| Example Number | Compound Structure | EC$_{50}$ (nM) |
|---|---|---|
| 76 | 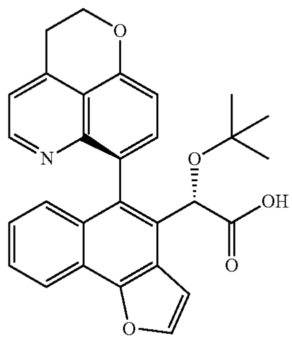 | 117 |
| 77 | 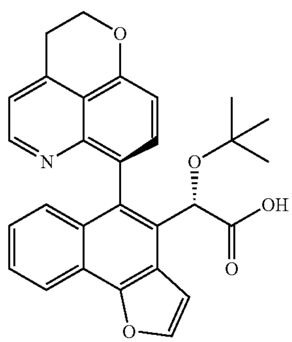 | 32400 |
| 78 | 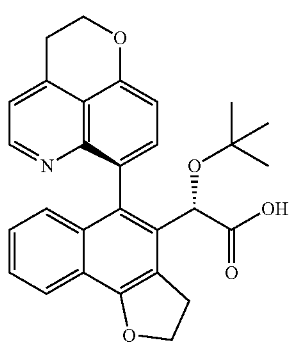 | 45.8 |
| 79 | 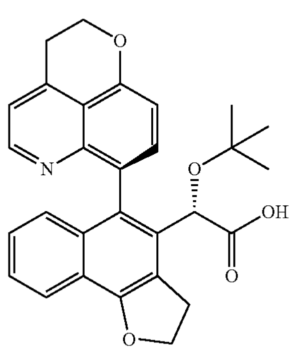 | 9906 |

TABLE II-continued

| Example Number | Compound Structure | EC$_{50}$ (nM) |
|---|---|---|
| 80 | 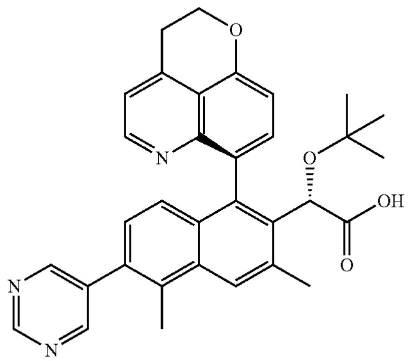 | 21.1 |
| 81 | 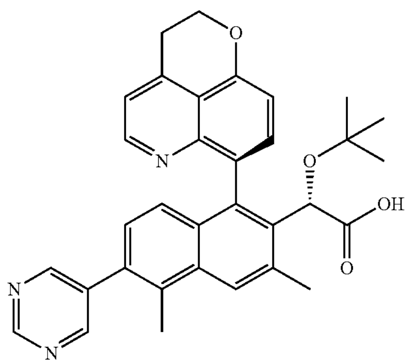 | 3369 |
| 82 | 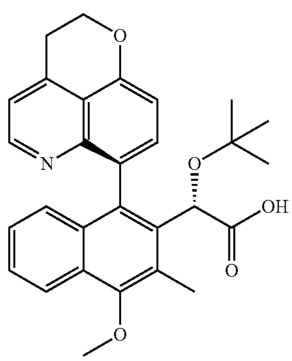 | 43.2 |
| 83 | 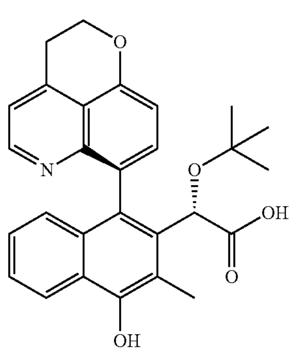 | 14.9 |

TABLE II-continued

| Example Number | Compound Structure | EC$_{50}$ (nM) |
|---|---|---|
| 84 | 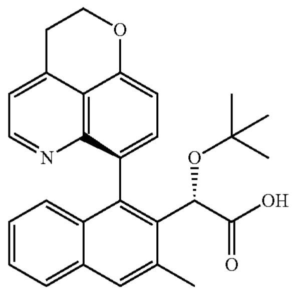 | 1055 |
| 85 | 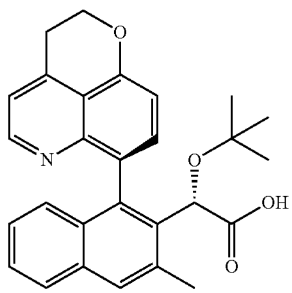 | 32200 |
| 86 | 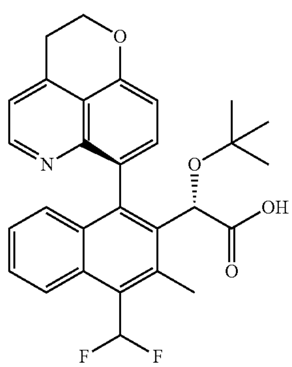 | 131 |
| 87 | 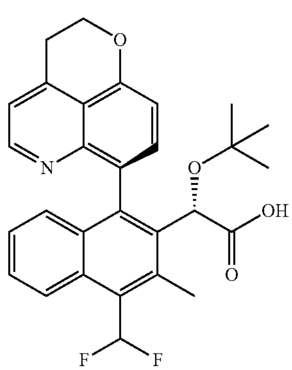 | 1311 |

TABLE II-continued
| Example Number | Compound Structure | $EC_{50}$ (nM) |
|---|---|---|
| 88 | 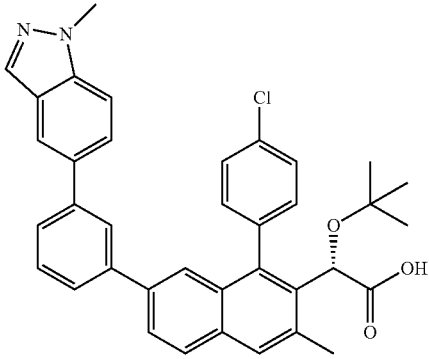 [SMILES: Cc1cc2ccc(-c3cccc(-c4ccc5c(cnn5C)c4)c3)cc2c(-c2ccc(Cl)cc2)c1[C@H](OC(C)(C)C)C(=O)O] | 3488 |
| 89 | 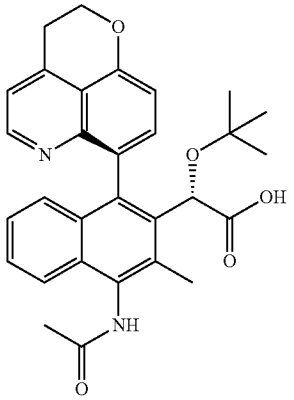 | 218 |
| 90 | 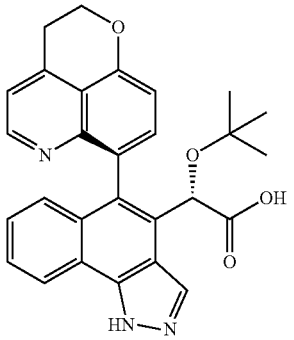 | 366 |
| 91 | 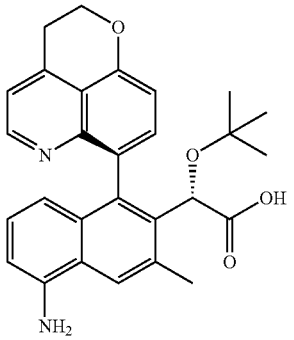 | 11.7 |

TABLE II-continued

| Example Number | Compound Structure | EC$_{50}$ (nM) |
| --- | --- | --- |
| 92 | 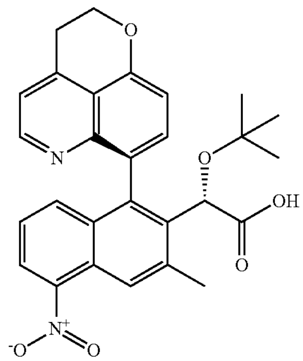 | 213 |
| 93 | 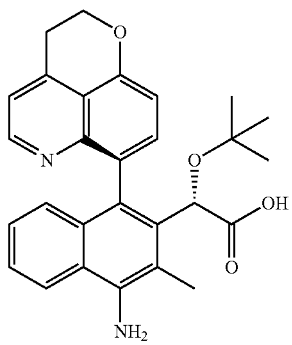 | 7.92 |
| 94 | 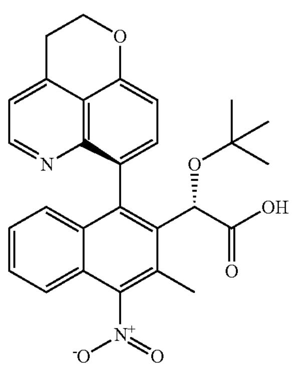 | 56.6 |
| 95 | 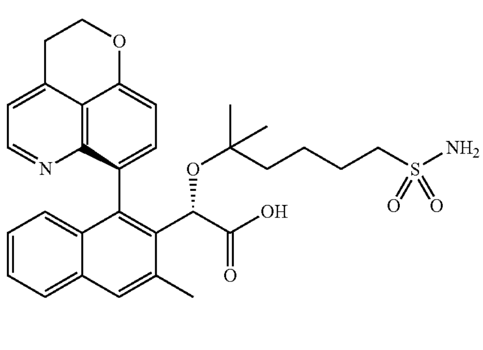 | 386 |

TABLE II-continued

| Example Number | Compound Structure | EC$_{50}$ (nM) |
|---|---|---|
| 96 | 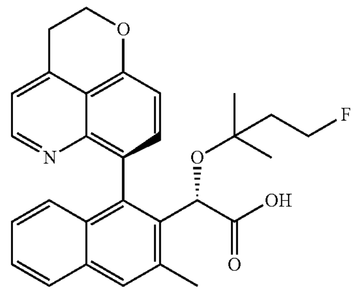 | 6420 |
| 97 | 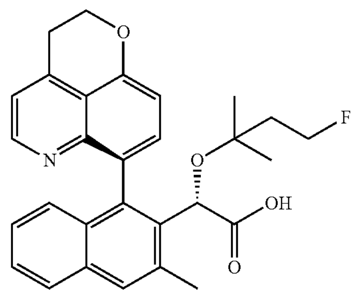 | 43.0 |
| 98 | 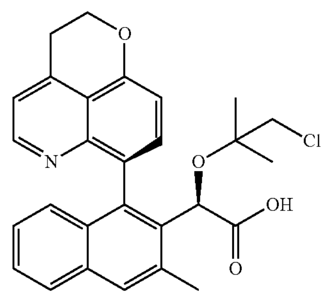 | 19350 |
| 99 | 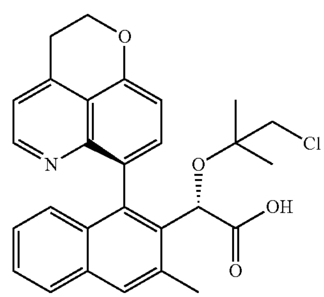 | 40.5 |
| 100 | 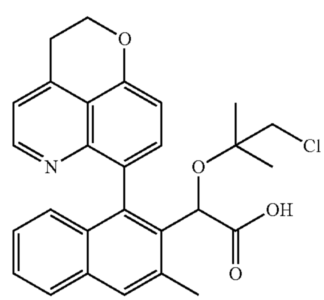 [SMILES: Cc1cc2ccccc2c(-c2ccc3c4c(ccnc24)CCO3)c1C(OC(C)(C)CCl)C(=O)O] | 161 |

TABLE II-continued
| Example Number | Compound Structure | EC$_{50}$ (nM) |
|---|---|---|
| 101 | 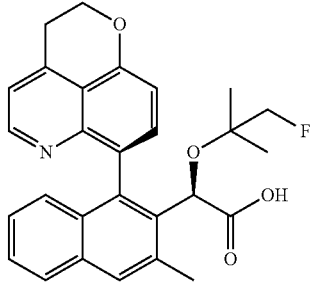 | 4740 |
| 102 | 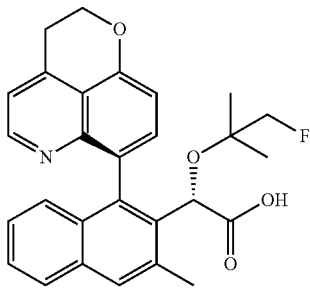 | 18.0 |
| 103 | 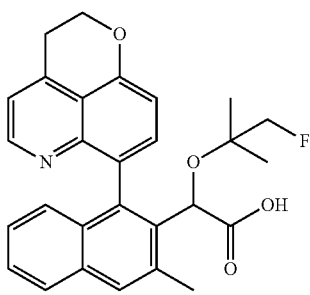 [SMILES: Cc1cc2ccccc2c(-c2ccc3c4c(ccnc24)CCO3)c1C(OC(C)(C)CF)C(=O)O] | 30.7 |
| 104 | 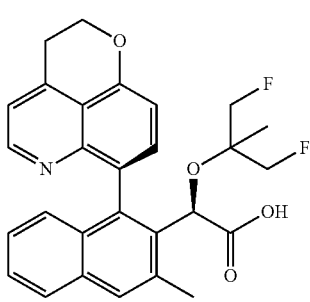 | 2954 |
| 105 | 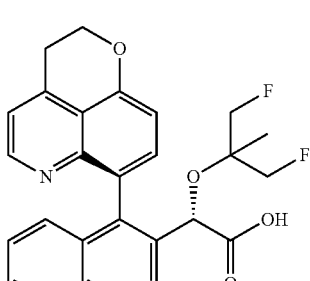 | 15.4 |

TABLE II-continued

| Example Number | Compound Structure | EC$_{50}$ (nM) |
|---|---|---|
| 106 | 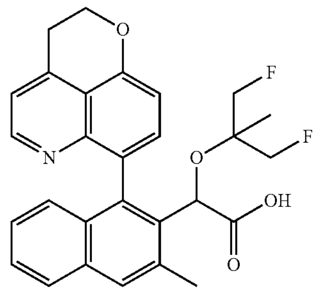 [SMILES: Cc1cc2ccccc2c(-c2ccc3c4c(ccnc24)CCO3)c1C(OC(C)(CF)CF)C(=O)O] | 40.7 |

In certain embodiments, the compounds demonstrate an EC50 of <50 μM. In certain embodiments, the compounds demonstrate an EC50 of <30 μM. In certain embodiments, the compounds demonstrate an EC50 of <10 μM. In certain embodiments, the compounds demonstrate an EC50 of <1 μM. In certain embodiments, the compounds demonstrate an EC50 of <0.5 μM. In certain embodiments, the compounds demonstrate an EC50 of <0.2 μM. In certain embodiments, the compounds demonstrate an EC50 of <0.1 μM. It is to be understood that the compounds disclosed herein can be grouped according to the EC50 activities described above.

The specific pharmacological responses observed may vary according to and depending on the particular active compound selected or whether there are present pharmaceutical carriers, as well as the type of formulation and mode of administration employed, and such expected variations or differences in the results are contemplated in accordance with practice of the present invention.

The Examples provided herein describe the synthesis of compounds disclosed herein as well as intermediates used to prepare the compounds. It is to be understood that individual steps described herein may be combined. It is also to be understood that separate batches of a compound may be combined and then carried forth in the next synthetic step.

EXAMPLE 1

(S)-2-tert-Butoxy-2-(1 AR)-2,3-dihydropyrano[4,3,2-de]quinolin-7-yl)-3,4-dimethylnaphthalen-2-yl) acetic acid and (S)-2-tert-butoxy-2-(1-((S)-2,3-dihydropyrano[4,3,2-de]quinolin-7-yl)-3,4-dimethylnaphthalen-2-yl)acetic acid

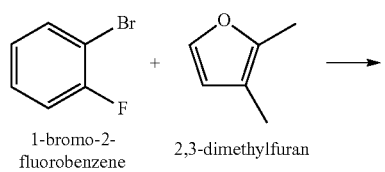

1-bromo-2-fluorobenzene + 2,3-dimethylfuran

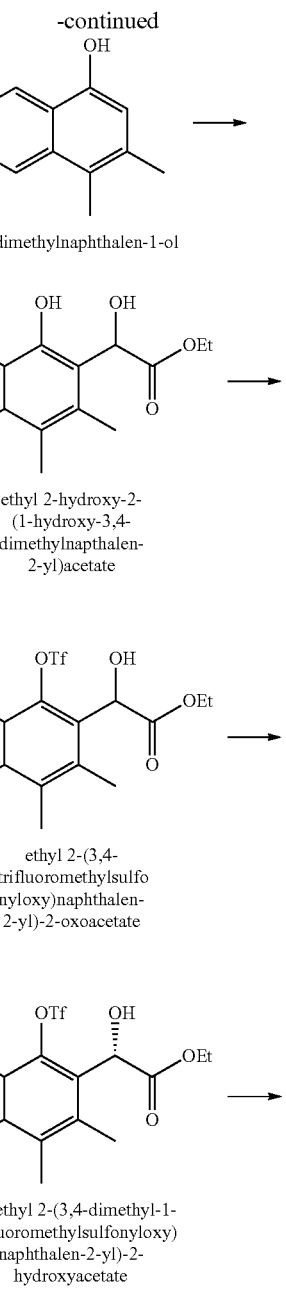

-continued 3,4-dimethylnaphthalen-1-ol ethyl 2-hydroxy-2-(1-hydroxy-3,4-dimethylnapthalen-2-yl)acetate ethyl 2-(3,4-(trifluoromethylsulfonyloxy)naphthalen-2-yl)-2-oxoacetate (S)-ethyl 2-(3,4-dimethyl-1-(trifluoromethylsulfonyloxy)naphthalen-2-yl)-2-hydroxyacetate

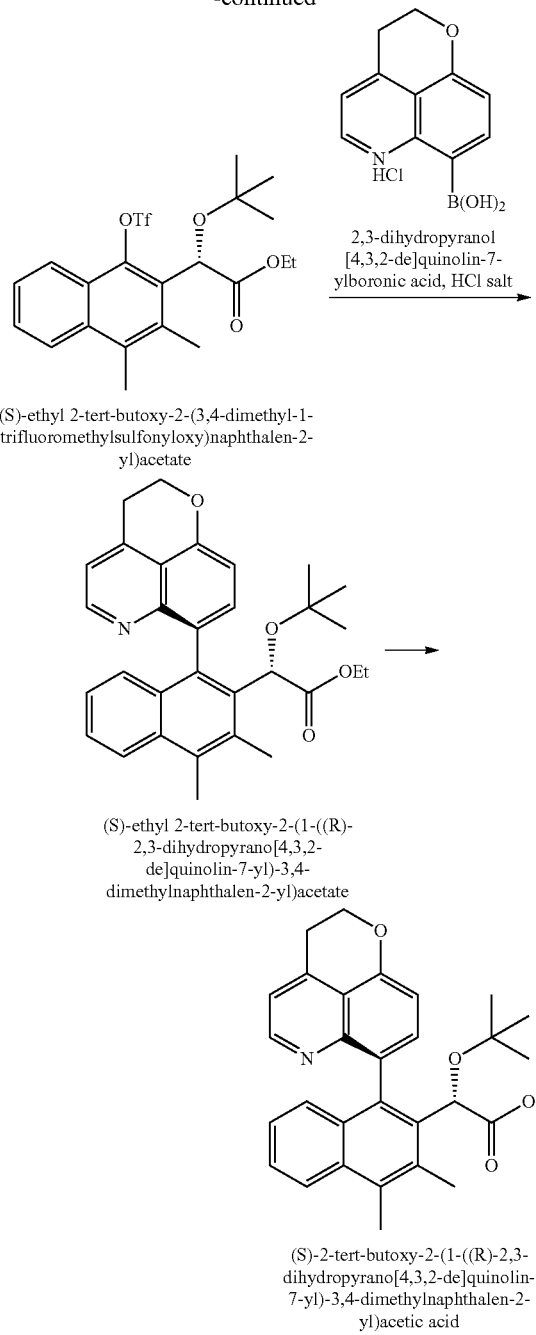

(S)-ethyl 2-tert-butoxy-2-(3,4-dimethyl-1-(trifluoromethylsulfonyloxy)naphthalen-2-yl)acetate 2,3-dihydropyranol[4,3,2-de]quinolin-7-ylboronic acid, HCl salt (S)-ethyl 2-tert-butoxy-2-(1-((R)-2,3-dihydropyrano[4,3,2-de]quinolin-7-yl)-3,4-dimethylnaphthalen-2-yl)acetate (S)-2-tert-butoxy-2-(1-((R)-2,3-dihydropyrano[4,3,2-de]quinolin-7-yl)-3,4-dimethylnaphthalen-2-yl)acetic acid Preparation of 3,4-dimethylnaphthalen-1-ol: To a solution of 2,3-dimethylfuran (1.06 mL, 10 mmol) in anhydrous THF (10 mL) was added magnesium powder (0.292 g, 12 mmol). The reaction mixture was heated to reflux for 5 minutes. The reaction flask was placed in a room temperature oil bath and a solution of 1-bromo-2-fluorobenzene (1.08 mL, 10 mmol) in anhydrous THF (10 mL) was added. The reaction mixture was heated to 35° C. for 1 hour, heated to reflux over 1 hour, and stirred at reflux for 1 hour. The reaction mixture was cooled and poured into saturated ammonium chloride solution and diluted with water. The product was extracted with ethyl acetate (2×) and the combined organic layer dried (MgSO$_4$), concentrated and purified by flash column chromatography (silica gel, 0 to 10% ethyl acetate/hexanes) to give the desired product.

To as solution of the above residue (1.088 g, 6.32 mmol) in dichloromethane (30 mL) was added p-toluenesulfonic acid (0.24 g, 1.26 mmol) and the reaction mixture was heated to 75° C. After 5 hours, the reaction was cooled to room temperature and concentrated to ~5 mL, filtered and purified by flash column chromatography (silica gel, 0 to 20% ethyl acetate/hexanes) to give 3,4-dimethylnaphthalen-1-ol. LCMS-ESI$^-$ (m/z): [M–H]$^-$ calcd for $C_{12}H_{11}O$: 171.2. Found: 171.0.

Preparation of ethyl 2-hydroxy-2-(1-hydroxy-3,4-dimethylnaphthalen-2-yl)acetate: To a solution of 3,4-dimethylnaphthalen-1-ol (3.18 g, 18.46 mmol) in dichloromethane (180 mL) at –40° C. was added a 1M solution of titanium tetrachloride in dichloromethane (18.46 mL, 18.46 mmol) over 10 minutes. In a separate flask, ethyl glyoxalate (2.26 g, 22.16 mmol) was heated at 100° C. for 45 minutes. The colorless oil was dissolved in dichloromethane (20 mL) and added to the reaction mixture over 10 minutes. The reaction mixture was stirred at –40° C. for 1.5 hours, then warmed to –25° C. over 30 minutes. The reaction mixture was quenched with acetic acid (5.8 mL). Acetonitrile (30 mL) was added and the reaction mixture was stirred for 5 minutes. The cold bath was removed and water (59 mL) was added and stirred for 15 minutes. The mixture was diluted with water and brine and extracted with dichloromethane (3×). The combined organic layer was dried (MgSO$_4$), filtered, concentrated and purified twice by flash column chromatography (silica gel, 0 to 25% ethyl acetate/hexanes) to give ethyl 2-hydroxy-2-(1-hydroxy-3,4-dimethylnaphthalen-2-yl)acetate. LCMS-ESI$^-$ (m/z): [M–H]$^-$ calcd for $C_{16}H_{17}O_4$: 273.31. Found: 272.8.

Preparation of ethyl 2-(3,4-dimethyl-1-(trifluoromethylsulfonyloxy)naphthalen-2-yl)-2-oxoacetate: To a solution of ethyl 2-hydroxy-2-(1-hydroxy-3,4-dimethylnaphthalen-2-yl)acetate (3.69 g, 13.45 mmol) in dichloromethane (100 mL) at 0° C. was added imidazole (1.19 g, 17.49 mmol), followed by chlorotriethylsilane (2.48 mL, 14.80 mmol). The reaction mixture was stirred for 1.5 hours at 0° C., quenched with water, and stirred for 5 minutes. The mixture was diluted with dichloromethane, washed with water, 1N HCl/brine, dried (MgSO$_4$), filtered and concentrated to give the desired product that was used in the next step without further purification.

The above residue was dissolved in dichloromethane (100 mL) and cooled to –78° C. Triethylamine (2.25 mL, 16.14 mmol) was added, followed by dropwise addition of trifluoromethanesulfonic anhydride (2.49 mL, 14.80 mmol) over 10 minutes. The resulting yellow solution was stirred for 1 hour at –78° C., quenched with brine and stirred for 10 minutes at room temperature. The mixture was washed with 1N HCl, saturated sodium bicarbonate solution/brine, dried (MgSO$_4$), filtered, concentrated and dried under vacuum to give the product that was used in the next step without further purification.

To a solution of the above residue in tetrahydrofuran (100 mL) at 0° C. was added 48% aqueous hydrofluoric acid. The reaction mixture was warmed to room temperature overnight. The reaction was incomplete, so the reaction was warmed to 45° C. After 1.5 hours, the reaction was complete and neutralized with the slow addition of solid sodium bicarbonate. Water was added and mixture was extracted with ethyl acetate (2×) and the combined organic layer was washed with saturated sodium bicarbonate solution/brine, dried (MgSO$_4$), filtered, concentrated and purified by flash column chromatography (silica gel, 0 to 20% ethyl acetate/hexanes) to give the desired product. LCMS-ESI$^+$ (m/z): [M+Na]$^+$ calcd for $C_{17}H_{17}F_3NaO_6S$: 429.37. Found: 428.8.

The above foam was dissolved in dichloromethane (100 mL), and cooled to 0° C. Dess-Martin periodinane (5.45 g, 12.85 mmol) was added in two portions over 5 minutes. The reaction mixture was stirred for 2 hours at 0° C., then quenched with sodium thiosulfate solution. The mixture was stirred for 10 minutes, diluted with dichloromethane and washed with sodium thiosulfate solution, water, saturated sodium bicarbonate solution, brine, dried (MgSO$_4$), filtered, concentrated and purified by flash column chromatography (silica gel, 0 to 20% ethyl acetate/hexanes) to give ethyl 2-(3,4-dimethyl-1-(trifluoromethylsulfonyloxy)naphthalen-2-yl)-2-oxoacetate. $^1$H NMR (400 MHz, CDCl$_3$) δ 8.11 (d, J=8.8 Hz, 2H), 7.73-7.59 (m, 2H), 4.39 (q, J=7.1 Hz, 2H), 2.64 (s, 3H), 2.37 (s, 3H), 1.37 (t, J=7.1 Hz, 3H).

Preparation of (S)-ethyl 2-(3,4-dimethyl-1-(trifluoromethylsulfonyloxy)naphthalen-2-yl)-2-hydroxyacetate: To a solution of ethyl 2-(3,4-dimethyl-1-(trifluoromethylsulfonyloxy)naphthalen-2-yl)-2-oxoacetate (3.93 g, 9.72 mmol) and (R)-2-methyl-CBS-oxazaoborolidine (0.539 g, 1.94 mmol) in anhydrous toluene (30 mL) at −40° C. was added dropwise a solution of catecholborane (1.40 mL, 13.22 mmol) in toluene (5 mL) over 20 minutes to give a pale yellow reaction mixture. The reaction mixture was stirred for another 20 minutes and quenched with saturated sodium carbonate solution and ethyl acetate was added. The mixture was stirred for 30 minutes, the aqueous layer removed and the organic layer washed with saturated sodium carbonate solution (3×), brine and dried (MgSO$_4$) and filtered. Concentration and purification by flash column chromatography (silica gel, 0 to 20% ethyl acetate/hexanes) gave the desired product. LCMS-ESI$^+$ (m/z): [M+Na]$^+$ calcd for C$_{17}$H$_{17}$F$_3$NaO$_6$S: 429.37. Found: 428.8.

Preparation of (S)-ethyl 2-tert-butoxy-2-(3,4-dimethyl-1-(trifluoromethylsulfonyloxy)naphthalen-2-yl)acetate: To a solution of (S)-ethyl 2-(3,4-dimethyl-1-(trifluoromethylsulfonyloxy)naphthalen-2-yl)-2-hydroxyacetate (3.80 g, 9.35 mmol) in tert-butyl acetate (94 mL) was added 70% perchloric acid (0.160 mL, 1.37 mmol). The reaction mixture was stirred for 5 h and quenched with solid sodium bicarbonate. The mixture was stirred for 5 minutes and saturated sodium bicarbonate solution was carefully added until pH 7, then diluted with water and extracted with ethyl acetate (2×). The combined organic layer was washed with saturated sodium bicarbonate solution and dried (MgSO$_4$), filtered, concentrated and purified by flash column chromatography (silica gel, 0 to 25% ethyl acetate/hexanes) to give the desired product. $^1$H NMR (400 MHz, CDCl$_3$) δ 8.08 (dd, J=8.7, 8.7 Hz, 2H), 7.63-7.55 (m, 2H), 5.75 (s, 1H), 4.3-4.1 (m, 2H), 2.63 (s, 3H), 2.47 (s, 3H), 1.20 (s, 3H), 1.17 (t, J=7.4 Hz, 3H).

Preparation of (S)-ethyl 2-tert-butoxy-2-(1-((R)-2,3-dihydropyrano[4,3,2-de]quinolin-7-yl)-3,4-dimethylnaphthalen-2-yl)acetate: Three separate Smith process vials were each charged with (S)-ethyl 2-tert-butoxy-2-(3,4-dimethyl-1-(trifluoromethylsulfonyloxy)naphthalen-2-yl)acetate (0.500 g, 1.08 mmol), 2,3-dihydropyrano[4,3,2-de]quinolin-7-ylboronic acid, HCl salt (0.326 g, 1.30 mmol) (prepared by the methods described in WO 2009/062289), SPhos Palladacycle (Strem, 0.109 g, 0.162 mmol) and cesium fluoride (0.722 g, 4.75 mmol) in distilled DME (10 mL) and was sparged with nitrogen for 5 minutes. The reaction mixture was heated in microwave at 120° C. for 1.5 hours. The three reaction mixtures were combined, diluted with ethyl acetate and washed with water/brine, dried (MgSO$_4$), filtered, and concentrated. Purification by flash column chromatography (silica gel, 0 to 35% ethyl acetate/hexanes) gave the desired atropisomer, (S)-ethyl 2-tert-butoxy-2-(1-((R)-2,3-dihydropyrano[4,3,2-de]quinolin-7-yl)-3,4-dimethylnaphthalen-2-yl)acetate. LCMS-ESI$^+$ (m/z): [M+H]$^+$ calcd for C$_{31}$H$_{34}$NO$_4$: 484.2. Found: 484.1.

The other atropisomer, (S)-ethyl 2-tert-butoxy-2-(1-((S)-2,3-dihydropyrano[4,3,2-de]quinolin-7-yl)-3,4-dimethylnaphthalen-2-yl)acetate was also isolated. LCMS-ESI$^+$ (m/z): [M+H]$^+$ calcd for C$_{31}$H$_{34}$NO$_4$: 484.2. Found: 484.1.

Preparation of (S)-2-tert-butoxy-2-(1-((R)-2,3-dihydropyrano[4,3,2-de]quinolin-7-yl)-3,4-dimethylnaphthalen-2-yl)acetic acid: To a mixture of (S)-ethyl 2-tert-butoxy-2-(1-((R)-2,3-dihydropyrano[4,3,2-de]quinolin-7-yl)-3,4-dimethylnaphthalen-2-yl)acetate (0.329 g, 0.680 mmol), 5M LiOH (2.72 mL, 13.61 mmol) in methanol (3.0 mL) and THF (10 mL) was added water and MeOH to give a clear yellow solution. The reaction mixture was heated at 45° C. for 36 hours, then at 55° C. for 24 hours. LC/MS indicated reaction was complete. The reaction mixture was concentrated to ~6 mL, acetic acid (0.82 mL, 14.3 mmol) was added, diluted with ethyl acetate and washed with brine. The aqueous layer was back-extracted with ethyl acetate and the combined organic layer was dried (MgSO$_4$), filtered and concentrated. The residue was dissolved in DMF and purified by reverse phase HPLC (Gemini, 5 to 100% ACN/H$_2$O+0.1% TFA). Product lyophilized to give the title compound as a TFA salt. $^1$H-NMR: 400 MHz, (CD$_3$OD) δ 8.64 (d, J=5.6 Hz, 1H), 8.26 (d, J=8.6 Hz, 1H), 7.89 (d, J=7.6 Hz, 1H), 7.80 (d, J=5.5 Hz, 1H), 7.59-7.42 (m, 2H), 7.25 (dd, J=7.6, 7.6 Hz, 1H), 6.92 (d, J=8.4 Hz, 1H), 5.22 (s, 1H), 4.78-4.67 (m, 2H), 3.66 (t, J=5.9 Hz, 2H), 2.79 (s, 3H), 2.71 (s, 3H), 0.97 (s, 9H). LCMS-ESI$^+$ (m/z): [M+H]$^+$ calcd for C$_{29}$H$_{30}$NO$_4$: 456.2. Found: 456.1.

The other atropisomer, (S)-2-tert-butoxy-2-(1-((S)-2,3-dihydropyrano[4,3,2-de]quinolin-7-yl)-3,4-dimethylnaphthalen-2-yl)acetic acid was prepared in a similar manner. LCMS-ESI$^+$ (m/z): [M+H]$^+$ calcd for C$_{29}$H$_{30}$NO$_4$: 456.2. Found: 456.1.

EXAMPLE 2

(S)-2-tert-Butoxy-2-(5-((R)-2,3-dihydropyrano[4,3,2-de]quinolin-7-yl)-1,3-dihydronaphtho[1,2-c]furan-4-yl)acetic acid

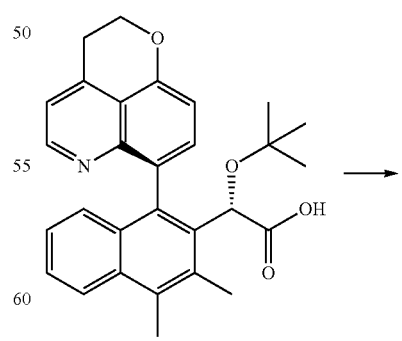

(S)-2-tert-butoxy-2-(1-((R)-2,3-dihydropyrano[4,3,2-de]quinolin-7-yl)-3,4-dimethylnaphthalen-2-yl)acetic acid -continued

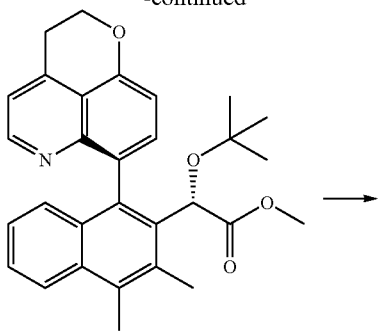

(S)-methyl 2-tert-butoxy-2-(1-
((R)-2,3-dihydropyrano[4,3,2-
de]quinolin-7-yl)-3,4-
dimethylnaphthalen-2-
yl)acetate

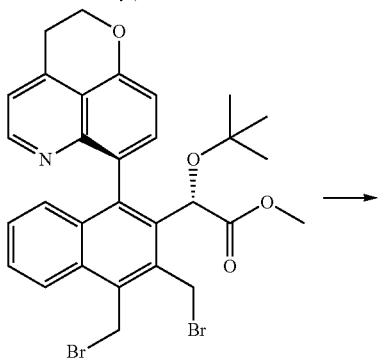

(S)-methyl 2-(3,4-
bis(bromomethyl)-1-((R)-2,3-
dihydropyrano[4,3,2-
de]quinolin-7-yl)naphthalen-2-
yl)-2-tert-butoxyacetate

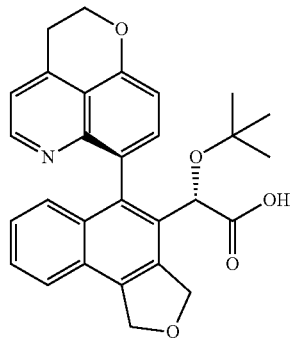

(S)-2-tert-butoxy-2-(5-((R)-
2,3-dihydropyrano[4,3,2-
de]quinolin-7-yl)-1,3-
dihydronaphtho[1,2-
c]furan-4-yl)acetic acid Preparation of (S)-methyl 2-tert-butoxy-2-(1-((R)-2,3-dihydropyrano[4,3,2-de]quinolin-7-yl)-3,4-dimethylnaphthalen-2-yl)acetate: To a solution of (S)-2-tert-butoxy-2-(1-((R)-2,3-dihydropyrano[4,3,2-de]quinolin-7-yl)-3,4-dimethylnaphthalen-2-yl)acetic acid (250 mg, 0.439 mmol) in MeOH (0.40 mL) and DMF (4.0 mL) was added a 2.0M solution of (trimethylsilyl)diazomethane in hexanes (0.48 mL, 0.966 mmol). The reaction mixture was stirred at room temperature for 45 minutes, then more 2.0M solution of (trimethylsilyl)diazomethane in hexanes (0.24 mL) was added and reaction mixture was stirred for 1 hour. A third portion of 2.0M solution of (trimethylsilyl)diazomethane in hexanes (0.24 mL) was added and reaction was complete after 1 hour. The reaction was quenched with acetic acid, diluted with ethyl acetate and washed with 5% lithium chloride solution/saturated sodium bicarbonate solution, 5% lithium chloride solution, brine and dried (MgSO$_4$) and filtered. The residue was concentrated and purified by flash column chromatography (silica gel, 15 to 50% ethyl acetate/hexanes) to give the desired product. LCMS-ESI$^+$ (m/z): [M+H]$^+$ calcd for C$_{30}$H$_{32}$NO$_4$: 470.2. Found: 470.1.

Preparation of (S)-methyl 2-(3,4-bis(bromomethyl)-1-((R)-2,3-dihydropyrano[4,3,2-de]quinolin-7-yl)naphthalen-2-yl)-2-tert-butoxyacetate: A mixture of (S)-methyl 2-tert-butoxy-2-(1-((R)-2,3-dihydropyrano[4,3,2-de]quinolin-7-yl)-3,4-dimethylnaphthalen-2-yl)acetate (105.3 mg, 0.224 mmol) and N-bromosuccinimide (80 g, 0.448 mmol) in carbon tetrachloride (2.5 mL) was heated to reflux. Azabiisobutyronitrile (5.5 mg, 0.0336 mmol) was added and the reaction mixture was refluxed for 1.5 hours. The reaction mixture was diluted with dichloromethane, adsorbed onto silica gel and purified by flash column chromatography (silica gel, 0 to 30% ethyl acetate/hexanes) to give the desired product. LCMS-ESI$^+$ (m/z): [M+H]$^+$ calcd for C$_{30}$H$_{30}$Br$_2$NO$_4$: 628.4. Found: 626.0, 627.9, 629.9.

Preparation of (S)-2-tert-butoxy-2-(5-((R)-2,3-dihydropyrano[4,3,2-de]quinolin-7-yl)-1,3-dihydronaphtho[1,2-c]furan-4-yl)acetic acid: A solution of (S)-methyl 2-(3,4-bis(bromomethyl)-1-((R)-2,3-dihydropyrano[4,3,2-de]quinolin-7-yl)naphthalen-2-yl)-2-tert-butoxyacetate (64 mg, 0.102 mmol) and 5M sodium hydroxide (0.816 mL, 4.08 mmol) in dioxane (5.0 mL) was stirred at 80° C. overnight. Acetic acid (0.234 mL, 4.08 mmol) was added and the mixture concentrated to ~1 mL, then diluted with DMF and acetic acid (0.2 mL). The crude solution was purified by reverse phase HPLC (Gemini, 5 to 100% ACN/H$_2$O+0.1% TFA). Product lyophilized to give the title compound as a TFA salt. $^1$H NMR (400 MHz, CD$_3$OD) δ 8.65 (d, J=5.7 Hz, 1H), 8.00 (d, J=8.1 Hz, 1H), 7.84 (d, J=8.0 Hz, 1H), 7.81 (d, J=5.6 Hz, 1H), 7.64-7.54 (m, 2H), 7.37 (ddd, J=8.1, 6.9, 1.1 Hz, 1H), 7.07 (d, J=8.6 Hz, 1H), 5.67-5.47 (m, 4H), 4.92 (s, 1H), 4.75 (t, J=6.1 Hz, 2H), 3.68 (t, J=6.0 Hz, 2H), 1.09 (s, 9H). LCMS-ESI$^+$ (m/z): [M+H]$^+$ calcd for C$_{30}$H$_{28}$NO$_5$: 470.2. Found: 470.1.

EXAMPLE 3

(S)-2-tert-Butoxy-2-(5-((R)-2,3-dihydropyrano[4,3,2-de]quinolin-7-yl)-2-methyl-2,3-dihydro-1H-benzo[e]isoindol-4-yl)acetic acid and (S)-2-tert-butoxy-2-(5-((S)-2,3-dihydropyrano[4,3,2-de]quinolin-7-yl)-2-methyl-2,3-dihydro-1H-benzo[e]isoindol-4-yl)acetic acid

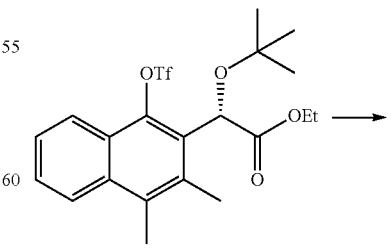

(S)-ethyl 2-tert-butoxy-2-
(3,4-dimethyl-1-
(trifluoromethylsulfonyloxy)
naphthalen-2-yl)acetate -continued

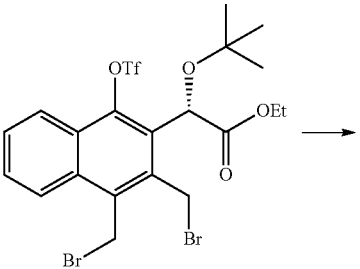

(S)-ethyl 2-(3,4-bis(bromomethyl)-1-(trifluoromethylsulfonyloxy)naphthalen-2-yl)-2-tert-butoxyacetate

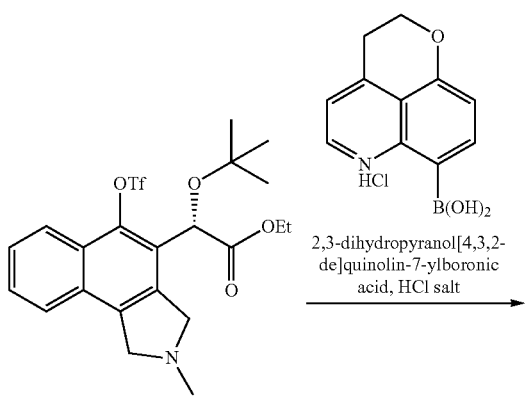

(S)-ethyl 2-tert-butoxy-2-(2-methyl-5-(trifluoromethylsulfonyloxy)-2,3-dihydro-1H-benzo[e]isoindol-4-yl)acetate 2,3-dihydropyrano[4,3,2-de]quinolin-7-ylboronic acid, HCl salt

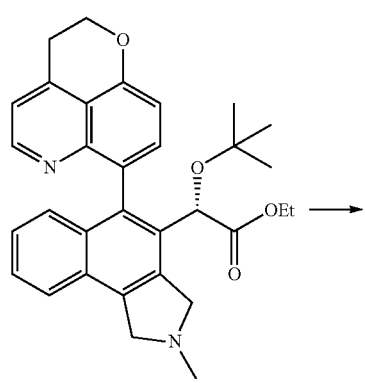

(2S)-ethyl 2-tert-butoxy-2-(5-(2,3-dihydropyrano[4,3,2-de]quinolin-7-yl)-2-methyl-2,3-dihydro-1H-benzo[e]isoindol-4-yl)acetate -continued

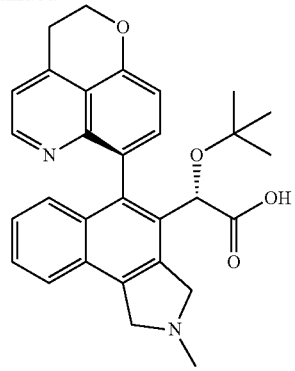

(S)-2-tert-butoxy-2-(5-((R)-2,3-dihydropyrano[4,3,2-de]quinolin-7-yl)-2-methyl-2,3-dihydro-1H-benzo[e]isoindol-4-yl)acetic acid Preparation of (S)-ethyl 2-(3,4-bis(bromomethyl)-1-(trifluoromethylsulfonyloxy)naphthalen-2-yl)-2-tert-butoxyacetate: To a solution of (S)-ethyl 2-tert-butoxy-2-(3,4-dimethyl-1-(trifluoromethylsulfonyloxy)naphthalen-2-yl) acetate (0.5145 g, 1.112 mmol) in carbon tetrachloride (4.0 mL) was added N-bromosuccinimide (0.435 g, 2.447 mmol), followed by azabiisobutyronitrile (10 mg, 0.061 mmol). The reaction mixture was refluxed for 1 hour. Additional azabiisobutyronitrile (10 mg) was added and stirred for 1 hour. The reaction mixture was cooled to room temperature, adsorbed onto silica gel and purified by flash column chromatography (silica gel, 0 to 10% ethyl acetate/hexanes) to give the desired product. $^1$H NMR (400 MHz, CDCl$_3$) δ 8.22 (d, J=8.6 Hz, 1H), 8.15 (d, J=8.2 Hz, 1H), 7.79-7.68 (m, 2H), 5.81 (s, 1H), 5.32-5.13 (m, 3H), 4.86 (d, J=15.0 Hz, 1H), 4.34-4.22 (m, 1H), 4.19-4.08 (m, 1H), 1.24 (s, 9H), 1.15 (t, J=7.2 Hz, 3H).

Preparation of (S)-ethyl 2-tert-butoxy-2-(2-methyl-5-(trifluoromethylsulfonyloxy)-2,3-dihydro-1H-benzo[e]isoindol-4-yl)acetate: To a solution of (S)-ethyl 2-(3,4-bis(bromomethyl)-1-(trifluoromethylsulfonyloxy)naphthalen-2-yl)-2-tert-butoxyacetate (0.1356 g, 0.219 mmol) and triethylamine (61 µL, 0.438 mmol) in anhydrous THF (10 mL) at 0° C. was added a 2M solution of methylamine in THF (109 µL, 0.219 mmol). The reaction mixture was stirred for 1 hour, then stirred overnight at room temperature. LC/MS shows some desired product. Reaction mixture was heated at 45° C. for 1.5 hours, then additional 2M solution of methylamine in THF (109 µL, 0.219 mmol) was added. After 1 hour, 2M solution of methylamine in THF (0.9 mL) was added and stirred for 45 minutes. LC/MS showed no starting material. The reaction mixture was concentrated and purified by flash column chromatography (silica gel, 30 to 100% ethyl acetate/hexanes) to give the desired product. LCMS-ESI$^+$ (m/z): [M+H]$^+$ calcd for $C_{22}H_{27}F_3NO_6S$: 490.2. Found: 490.1.

Preparation of (2S)-ethyl 2-tert-butoxy-2-(5-(2,3-dihydropyrano[4,3,2-de]quinolin-7-yl)-2-methyl-2,3-dihydro-1H-benzo[e]isoindol-4-yl)acetate: A mixture of (S)-ethyl 2-tert-butoxy-2-(2-methyl-5-(trifluoromethylsulfonyloxy)-2,3-dihydro-1H-benzo[e]isoindol-4-yl)acetate (72.8 mg, 0.149 mmol), 2,3-dihydropyrano[4,3,2-de]quinolin-7-ylboronic acid, HCl salt (45 mg, 0.178 mmol), SPhos Palladacycle (Strem, 15 mg g, 0.022 mmol) and cesium fluoride (100 mg, 0.656 mmol) in distilled DME (1.0 mL) and was sparged with nitrogen for 10 minutes. The reaction mixture was heated in a microwave at 120° C. for 1.5 hours. The reaction mixture was diluted with water/brine, extracted with ethyl acetate (2×), dried (MgSO₄), filtered, and concentrated. Purification by reverse phase HPLC (Gemini, 5 to 100% ACN/H₂O+0.1% TFA) and lyophilization gave the title compound as a 1:1 mixture of atropisomers. LCMS-ESI⁺ (m/z): [M+H]⁺ calcd for $C_{32}H_{35}N_2O_4$: 511.6. Found: 511.2.

Preparation of (S)-2-tert-butoxy-2-(5-((R)-2,3-dihydropyrano[4,3,2-de]quinolin-7-yl)-2-methyl-2,3-dihydro-1H-benzo[e]isoindol-4-yl)acetic acid: A solution of (2S)-ethyl 2-tert-butoxy-2-(5-(2,3-dihydropyrano[4,3,2-de]quinolin-7-yl)-2-methyl-2,3-dihydro-1H-benzo[e]isoindol-4-yl)acetate (14.9 mg, 0.021 mmol), 5M NaOH solution (83 µL, 0.415 mmol) in methanol (0.1 mL) and THF (1.0 mL) was stirred at 45° C. for 24 hours, then stored in freezer for 2 days. Acetic acid (25 µL, 21 eq) was added and mixture was concentrated to give a yellow paste that was dissolved in DMF/water, filtered and purified by reverse phase HPLC (Gemini, 5 to 100% ACN/H₂O+0.1% TFA). Product lyophilized to give the title compound as a TFA salt. ¹H NMR (400 MHz, CD₃OD) δ 8.60 (d, J=4.7 Hz, 1H), 7.92 (d, J=8.2 Hz, 1H), 7.83 (d, J=8.1 Hz, 1H), 7.71-7.56 (m, 2H), 7.53-7.40 (m, 2H), 7.17 (d, J=8.5 Hz, 1H), 5.61-5.30 (m, 2H), 5.10-4.91 (m, 1H), 4.90 (s, 1H), 4.69 (t, J=5.8 Hz, 2H), 3.59 (d, J=5.5 Hz, 2H), 3.30 (s, 3H), 1.11 (s, 9H). LCMS-ESI⁺ (m/z): [M+H]⁺ calcd for $C_{30}H_{31}N_2O_4$: 483.2. Found: 483.2.

The other atropisomer, (S)-2-tert-butoxy-2-(5-((S)-2,3-dihydropyrano[4,3,2-de]quinolin-7-yl)-2-methyl-2,3-dihydro-1H-benzo[e]isoindol-4-yl)acetic acid was also isolated. LCMS-ESI⁺ (m/z): [M+H]⁺ calcd for $C_{30}H_{31}N_2O_4$: 483.2. Found: 483.2.

EXAMPLE 4

(S)-2-tert-Butoxy-2-(1-((R)-2,3-dihydropyrano[4,3,2-de]quinolin-7-yl)-3-methyl-6-(methylsulfonyl)naphthalen-2-yl)acetic acid and ((S)-2-tert-butoxy-2-(1-((S)-2,3-dihydropyrano[4,3,2-de]quinolin-7-yl)-3-methyl-6-(methylsulfonyl)naphthalen-2-yl)acetic acid

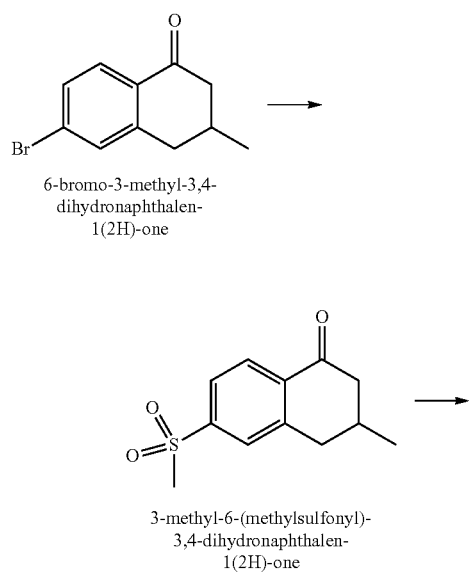

6-bromo-3-methyl-3,4-dihydronaphthalen-1(2H)-one 3-methyl-6-(methylsulfonyl)-3,4-dihydronaphthalen-1(2H)-one

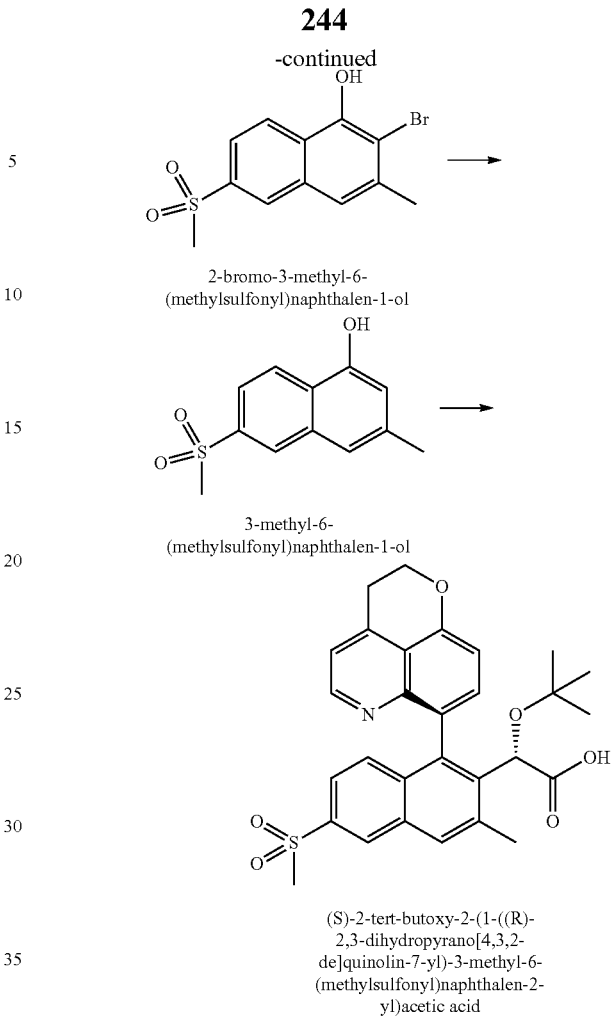

2-bromo-3-methyl-6-(methylsulfonyl)naphthalen-1-ol 3-methyl-6-(methylsulfonyl)naphthalen-1-ol (S)-2-tert-butoxy-2-(1-((R)-2,3-dihydropyrano[4,3,2-de]quinolin-7-yl)-3-methyl-6-(methylsulfonyl)naphthalen-2-yl)acetic acid Preparation of 3-methyl-6-(methylsulfonyl)-3,4-dihydronaphthalen-1(2H)-one: A mixture of 6-bromo-3-methyl-3,4-dihydronaphthalen-1(2H)-one (10 g, 41.8 mmol) methanesulfinic acid, sodium salt (16.7 g, 163.1 mmol), copper(I) iodide (3.18 g, 16.7 mmol), cesium carbonate (6.81 g, 20.9 mmol) and L-proline (3.85 g, 33.4 mmol) in DMSO (200 mL) was heated at 100° C., protected from light. After 3.5 hours, copper(I) iodide (1.59 g) and L-proline (1.9 g) were added and the reaction continued for 5 hours, and then stirred overnight at room temperature. The mixture was diluted with ice/water (200 mL) and extracted with ethyl ether (3×), ethyl acetate (3×). The combined organic layer was washed with brine, dried (MgSO₄), filtered, and purified by flash column chromatography (silica gel, 30 to 60% ethyl acetate/hexanes) to give the desired product. ¹H NMR (400 MHz, CDCl₃) δ 8.20 (d, J=8.1 Hz, 1H), 7.87 (s, 1H), 7.86 (d, J=7.7 Hz, 1H), 3.10-3.00 (m, 1H), 3.08 (s, 3H), 2.86-2.71 (m, 2H), 2.48-2.31 (m, 2H), 1.19 (d, J=6.0 Hz, 3H).

Preparation of 2-bromo-3-methyl-6-(methylsulfonyl)naphthalen-1-ol: To a solution of 3-methyl-6-(methylsulfonyl)-3,4-dihydronaphthalen-1(2H)-one (7.64 g, 32.06 mmol) in dichloromethane (200 mL) at room temperature was added a solution of bromine (3.38 mL, 65.72 mmol) in dichloromethane (5 mL) over 30 minutes to give an orange mixture. The reaction mixture was stirred at room temperature for 2 hours, then more bromine (0.3 mL) was added and stirring continued for 1 hour. The reaction mixture was concentrated and co-evaporated with dichloromethane and dried under house vacuum. The resulting off-white residue was suspended in acetonitrile and cooled to −40° C. 1,8-Diazabicyclo

[5.4.0]dunde-7-ene (7.19 mL, 48.09 mmol) was added over 5 minutes and the reaction mixture was warmed to room temperature overnight. The reaction mixture was concentrated, diluted with ethyl acetate, washed with dilute acetic acid solution, brine and dried (MgSO$_4$) and filtered. Concentration and purification by flash column chromatography (silica gel, 20-60% ethyl acetate/hexanes) gave an impure product. Repurification by flash column chromatography (silica gel, 40% ethyl acetate/hexanes) gave the desired product. LCMS-ESI$^+$ (m/z): [M–H]$^-$ calcd for $C_{12}H_{10}BrO_3S$: 314.2. Found: 313.2, 315.1.

Preparation of 3-methyl-6-(methylsulfonyl)naphthalen-1-ol: A mixture of 2-bromo-3-methyl-6-(methylsulfonyl)naphthalen-1-ol (0.500 g, 1.59 mmol), 10% palladium on carbon (0.050 g) and triethylamine (0.331 mL, 2.38 mmol) in ethanol was stirred under a hydrogen atmosphere for 1.5 hours. Celite was added and the mixture was stirred for 10 minutes, filtered through a pad of Celite and the filtrate concentrated. The residue was dissolved in ethyl acetate, washed with dilute HCl/brine, dried (MgSO$_4$), filtered, concentrated, and purified by flash column chromatography (silica gel, 20 to 50% ethyl acetate/hexanes) to give the desired product. LCMS-ESI$^+$ (m/z): [M–H]$^-$ calcd for $C_{12}H_{11}O_3S$: 235.3. Found: 235.2.

Preparation of (S)-2-tert-butoxy-2-(1-((R)-2,3-dihydropyrano[4,3,2-de]quinolin-7-yl)-3-methyl-6-(methylsulfonyl)naphthalen-2-yl)acetic acid: (S)-2-tert-butoxy-2-(1-((R)-2,3-dihydropyrano[4,3,2-de]quinolin-7-yl)-3-methyl-6-(methylsulfonyl)naphthalen-2-yl)acetic acid was prepared in a similar way as (S)-2-tert-butoxy-2-(1-((R)-2,3-dihydropyrano[4,3,2-de]quinolin-7-yl)-3,4-dimethylnaphthalen-2-yl)acetic acid in Example 1 expect using 3-methyl-6-(methylsulfonyl)naphthalen-1-ol instead of 3,4-dimethylnaphthalen-1-ol. $^1$H NMR (400 MHz, CD$_3$OD) δ 8.70 (d, J=5.6 Hz, 1H), 8.61 (s, 1H), 8.20 (s, 1H), 7.82 (t, J=8.1 Hz, 2H), 7.70 (d, J=8.9 Hz, 1H), 7.47 (d, J=8.1 Hz, 1H), 7.20 (d, J=9.1 Hz, 1H), 5.27 (s, 1H), 4.73 (dd, J=11.1, 5.9 Hz, 2H), 3.67 (t, J=6.0 Hz, 2H), 3.15 (s, 3H), 2.83 (s, 3H), 0.93 (s, 9H). LCMS-ESI$^+$ (m/z): [M+H]$^+$ calcd for $C_{29}H_{30}NO_6S$: 520.2. Found: 520.1.

The other atropisomer, ((S)-2-tert-butoxy-2-(1-((S)-2,3-dihydropyrano[4,3,2-de]quinolin-7-yl)-3-methyl-6-(methylsulfonyl)naphthalen-2-yl)acetic acid was also prepared in a similar way. LCMS-ESI$^+$ (m/z): [M+H]$^+$ calcd for $C_{29}H_{30}NO_6S$: 520.2. Found: 520.1.

EXAMPLE 5

(S)-2-tert-Butoxy-2-(6-cyano-1-((R)-2,3-dihydropyrano[4,3,2-de]quinolin-7-yl)-3-methylnaphthalen-2-yl)acetic acid, (S)-2-tert-butoxy-2-(6-carbamoyl-1-((R)-2,3-dihydropyrano[4,3,2-de]quinolin-7-yl)-3-methylnaphthalen-2-yl)acetic acid, 6-((S)-tert-butoxy(carboxy)methyl)-5-((R)-2,3-dihydropyrano[4,3,2-de]quinolin-7-yl)-7-methyl-2-naphthoic acid, (S)-2-tert-butoxy-2-(6-cyano-1-((S)-2,3-dihydropyrano[4,3,2-de]quinolin-7-yl)-3-methylnaphthalen-2-yl)acetic acid, (S)-2-tert-butoxy-2-(6-carbamoyl-1-((S)-2,3-dihydropyrano[4,3,2-de]quinolin-7-yl)-3-methylnaphthalen-2-yl)acetic acid and 6-((S)-tert-butoxy(carboxy)methyl)-5-((S)-2,3-dihydropyrano[4,3,2-de]quinolin-7-yl)-7-methyl-2-naphthoic acid

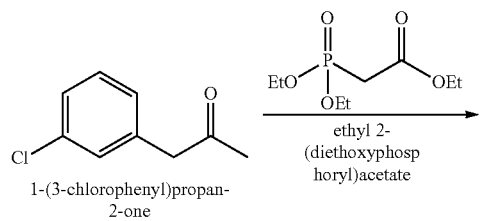

1-(3-chlorophenyl)propan-2-one ethyl 2-(diethoxyphosphoryl)acetate

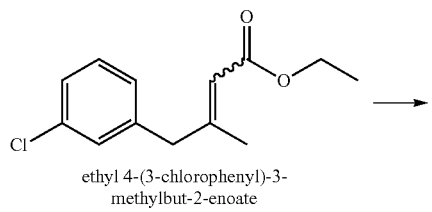

ethyl 4-(3-chlorophenyl)-3-methylbut-2-enoate

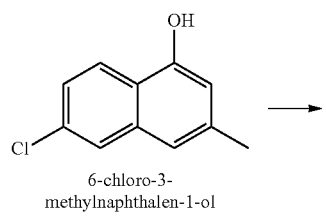

6-chloro-3-methylnaphthalen-1-ol

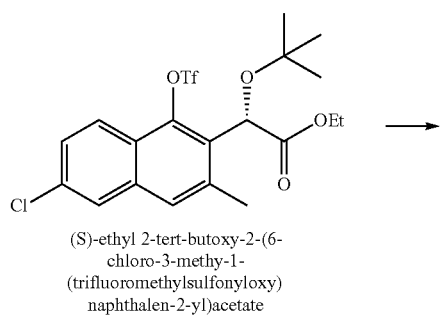

(S)-ethyl 2-tert-butoxy-2-(6-chloro-3-methy-1-(trifluoromethylsulfonyloxy)naphthalen-2-yl)acetate

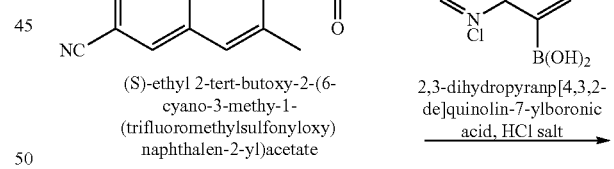

(S)-ethyl 2-tert-butoxy-2-(6-cyano-3-methy-1-(trifluoromethylsulfonyloxy)naphthalen-2-yl)acetate 2,3-dihydropyranp[4,3,2-de]quinolin-7-ylboronic acid, HCl salt

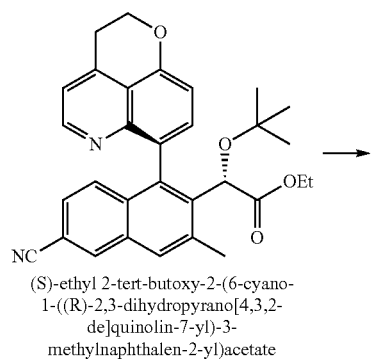

(S)-ethyl 2-tert-butoxy-2-(6-cyano-1-((R)-2,3-dihydropyrano[4,3,2-de]quinolin-7-yl)-3-methylnaphthalen-2-yl)acetate

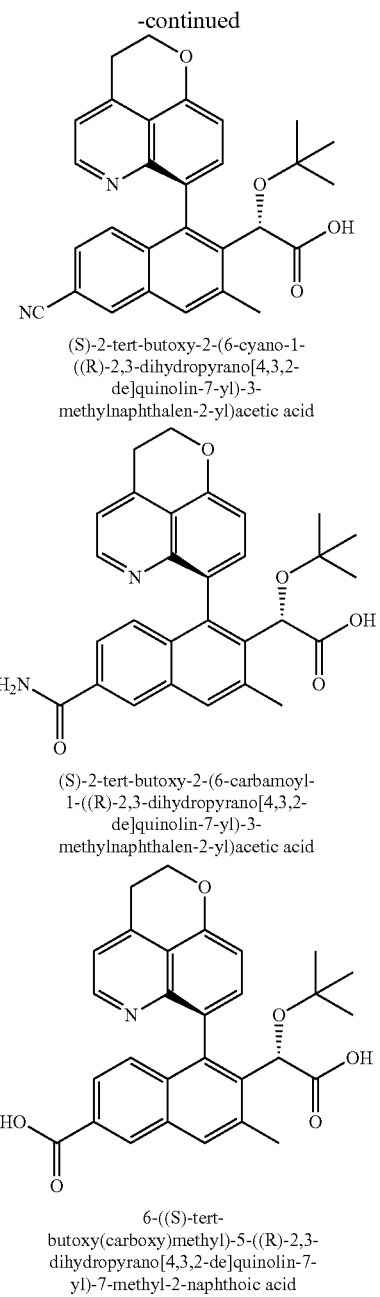

(S)-2-tert-butoxy-2-(6-cyano-1-
((R)-2,3-dihydropyrano[4,3,2-
de]quinolin-7-yl)-3-
methylnaphthalen-2-yl)acetic acid (S)-2-tert-butoxy-2-(6-carbamoyl-
1-((R)-2,3-dihydropyrano[4,3,2-
de]quinolin-7-yl)-3-
methylnaphthalen-2-yl)acetic acid 6-((S)-tert-
butoxy(carboxy)methyl)-5-((R)-2,3-
dihydropyrano[4,3,2-de]quinolin-7-
yl)-7-methyl-2-naphthoic acid Preparation of ethyl 4-(3-chlorophenyl)-3-methylbut-2-enoate: At 0° C., a suspension of 60% w/w NaH/mineral oil (7.13 g, 0.176 mol) in THF (250 mL) was treated dropwise with a solution of ethyl 2-(diethoxyphosphoryl)acetate (39.5 g, 0.176 mol) in THF (72 mL) over a 30 min period. The reaction was stirred for another 30 minutes, and a solution of 1-(3-chlorophenyl)propan-2-one (19.7 g, 0.117 mol) in THF (108 mL) was added dropwise over 1 h (reaction was kept at 0° C. during addition). The reaction was allowed to warm to 23° C. overnight and quenched with saturated aqueous NH$_4$Cl (250 mL). After 2 h, the mixture was diluted with water (250 mL) and hexane (100 mL). The organic phase was collected. The aqueous layer was extracted with EtOAc (2×150 mL). Combined organic phases were dried (MgSO$_4$), filtered, and concentrated, giving crude ethyl 4-(3-chlorophenyl)-3-methylbut-2-enoate as a mixture of E and Z isomers.

The residue was carried onward without further purification. (~25 grams). The $^1$H NMR reported below is from a crude mixture containing both the E and Z isomer. $^1$H NMR (400 MHz, CDCl$_3$) δ 7.24-7.22 (m, 2H), 7.16 (s, 1H), 7.06-7.04 (m, 1H); 5.67 (s, 1H); 4.18-4.13 (dd, 2H); 3.40 (s, 2H), 2.11 (s, 3H), 1.30-1.26 (t, 3H).

Preparation of 6-chloro-3-methylnaphthalen-1-ol: A flask containing the crude ethyl 4-(3-chlorophenyl)-3-methylbut-2-enoate (~25 grams) was treated with concentrated H$_2$SO$_4$ (120 mL) and warmed to 50° C. for 2.5 h. The reaction was poured onto ~500 mL of crushed ice. Once the ice had melted, the brown suspension was extracted with two portions of EtOAc (500 mL and 100 mL, respectively). The two extracts were combined, washed with saturated aq. NaHCO$_3$, dried (MgSO$_4$), filtered, and concentrated to ~55 mL. The residue was treated with DCM and loaded onto a silica gel column and purified by flash chromatography (ethyl acetate/hexanes) giving the desired product. $^1$H NMR (400 MHz, CDCl$_3$) δ 8.07-8.05 (d, J=8.8 Hz, 1H), 7.69-7.68 (d, J=2.0 Hz, 1H), 7.35-7.32 (dd, J=2.0, 8.8 Hz, 1H); 7.12 (s, 1H); 6.65 (s, 1H); 5.21 (bs, 1H); 4.21-4.17 (dd, 2H); 2.41 (s, 3H).

Preparation of (S)-ethyl 2-tert-butoxy-2-(6-chloro-3-methyl-1-(trifluoromethylsulfonyloxy)naphthalen-2-yl)acetate: (S)-ethyl 2-tert-butoxy-2-(6-chloro-3-methyl-1-(trifluoromethylsulfonyloxy)naphthalen-2-yl)acetate was prepared in a similar way as (S)-ethyl 2-tert-butoxy-2-(3,4-dimethyl-1-(trifluoromethylsulfonyloxy)naphthalen-2-yl)acetate in Example 1 except using 6-chloro-3-methylnaphthalen-1-ol instead of 3,4-dimethylnaphthalen-1-ol. $^1$H NMR (400 MHz, CDCl$_3$) δ 7.98 (d, J=9.1 Hz, 1H), 7.78 (s, 1H), 7.58 (s, 1H), 7.51 (dd, J=9.0, 1.8 Hz, 1H), 5.70 (s, 1H), 4.17 (dqd, J=14.2, 7.1, 3.2 Hz, 2H), 2.55 (s, 3H), 1.20 (s, J=6.5 Hz, 9H), 1.17 (t, J=7.1 Hz, 3H).

Preparation of (S)-ethyl 2-tert-butoxy-2-(6-cyano-3-methyl-1-(trifluoromethylsulfonyloxy)naphthalen-2-yl)acetate: A mixture of (S)-ethyl 2-tert-butoxy-2-(6-chloro-3-methyl-1-(trifluoromethylsulfonyloxy)naphthalen-2-yl)acetate (0.546 g, 1.13 mmol), zinc(II) cyanide (0.080 g, 0.678 mmol), XPhos Palladacycle (Strem, 0.083 g, 0.113 mmol) and sodium bicarbonate (0.009 g, 0.113 mmol) in DMF (3.0 mL) was sparged with nitrogen for 5 minutes. The reaction mixture was heated in microwave at 110° C. for 1 hour. The reaction mixture was diluted with ethyl acetate and washed with 5% lithium chloride solution (2×), brine and dried (MgSO$_4$) and filtered. Concentration and purification by flash column chromatography (silica gel, 0 to 10% ethyl acetate/hexanes) gave the title compound. NMR (400 MHz, CDCl$_3$) δ 8.19 (s, H), 8.13 (d, J=8.8 Hz, H), 7.74 (s, H), 7.71 (d, J=8.8 Hz, H), 5.73 (s, H), 4.27-4.09 (m, 2H), 2.59 (s, 3H), 1.21 (s, 9H), 1.17 (t, J=7.1 Hz, 2H).

Preparation of (S)-ethyl 2-tert-butoxy-2-(6-cyano-1-((R)-2,3-dihydropyrano[4,3,2-de]quinolin-7-yl)-3-methylnaphthalen-2-yl)acetate: (S)-ethyl 2-tert-butoxy-2-(6-cyano-1-((R)-2,3-dihydropyrano[4,3,2-de]quinolin-7-yl)-3-methylnaphthalen-2-yl)acetate was prepared in a similar way as (S)-ethyl 2-tert-butoxy-2-(1-((R)-2,3-dihydropyrano[4,3,2-de]quinolin-7-yl)-3,4-dimethylnaphthalen-2-yl)acetate in Example 1 except (S)-ethyl 2-tert-butoxy-2-(6-cyano-3-methyl-1-(trifluoromethylsulfonyloxy)naphthalen-2-yl)acetate was used instead of (S)-ethyl 2-tert-butoxy-2-(3,4-dimethyl-1-(trifluoromethylsulfonyloxy)naphthalen-2-yl)acetate.
LCMS-ESI$^+$ (m/z): [M+H]$^+$ calcd for C$_{31}$H$_{31}$N$_2$O$_4$: 495.2. Found: 495.1.

The other atropisomer, (S)-ethyl 2-tert-butoxy-2-(6-cyano-1-((S)-2,3-dihydropyrano[4,3,2-de]quinolin-7-yl)-3- methylnaphthalen-2-yl)acetate was also isolated. LCMS-ESI$^+$ (m/z): [M+H]$^+$ calcd for $C_{31}H_{31}N_2O_4$: 495.2. Found: 495.1.

Preparation of (S)-2-tert-butoxy-2-(6-cyano-1-((R)-2,3-dihydropyrano[4,3,2-de]quinolin-7-yl)-3-methylnaphthalen-2-yl)acetic acid: A solution of (S)-ethyl 2-tert-butoxy-2-(6-cyano-1-((R)-2,3-dihydropyrano[4,3,2-de]quinolin-7-yl)-3-methylnaphthalen-2-yl)acetate (113 mg, 0.228 mmol), 5M NaOH solution (0.91 mL, 5.57 mmol) in methanol (0.91 mL) and THF (3.0 mL) was stirred at 55° C. for 40 hours. Acetic acid (21 eq) was added and the mixture was concentrated to ~1 mL, diluted with DMF, filtered and purified by reverse phase HPLC (Gemini, 5 to 100% ACN/H$_2$O+0.1% TFA). The product was lyophilized to give the title compound as a TFA salt. $^1$H NMR (400 MHz, CD$_3$OD) δ 8.70 (d, J=5.7 Hz, 1H), 8.45 (s, 1H), 8.11 (s, 1H), 7.89-7.78 (m, 2H), 7.46 (dd, J=8.4, 5.2 Hz, 2H), 7.12 (d, J=8.8 Hz, 1H), 5.26 (s, 1H), 4.77-4.68 (m, 2H), 3.67 (t, J=5.9 Hz, 2H), 2.81 (s, 3H), 0.93 (s, 9H). LCMS-ESI$^+$ (m/z): [M+H]$^+$ calcd for $C_{29}H_{27}N_2O_4$: 467.2. Found: 467.1.

(S)-2-tert-butoxy-2-(6-carbamoyl-1-((R)-2,3-dihydropyrano[4,3,2-de]quinolin-7-yl)-3-methylnaphthalen-2-yl)acetic acid was also isolated (30.8 mg, %). $^1$H NMR (400 MHz, CD$_3$OD) δ 8.68 (d, J=5.7 Hz, 1H), 8.49 (s, 1H), 8.09 (s, 1H), 7.89-7.78 (m, 2H), 7.71 (d, J=8.8 Hz, 1H), 7.47 (d, J=8.1 Hz, 1H), 7.02 (d, J=8.8 Hz, 1H), 5.26 (s, 1H), 4.79-4.68 (m, 2H), 3.67 (t, J=5.9 Hz, 2H), 2.81 (s, 3H), 0.93 (s, 9H). LCMS-ESI$^+$ (m/z): [M+H]$^+$ calcd for $C_{29}H_{29}N_2O_5$: 485.5. Found: 485.1.

6-((S)-tert-butoxy(carboxy)methyl)-5-((R)-2,3-dihydropyrano[4,3,2-de]quinolin-7-yl)-7-methyl-2-naphthoic acid was also isolated (5.7 mg, %). $^1$H NMR (400 MHz, CD$_3$OD) δ 8.68 (d, J=5.9 Hz, 1H), 8.66 (s, 1H), 8.12 (s, 1H), 7.85-7.75 (m, 2H), 7.46 (d, J=8.1 Hz, 1H), 7.02 (d, J=8.9 Hz, 1H), 5.26 (s, 1H), 4.75-4.68 (m, 2H), 3.67 (t, J=5.9 Hz, 2H), 2.81 (s, 3H), 0.93 (s, 9H). LCMS-ESI$^+$ (m/z): [M+H]$^+$ calcd for $C_{29}H_{28}N_2O_6$: 486.2. Found: 486.1.

The other atropisomers were also prepared in a similar way.

(S)-2-tert-butoxy-2-(6-cyano-1-((S)-2,3-dihydropyrano[4,3,2-de]quinolin-7-yl)-3-methylnaphthalen-2-yl)acetic acid: LCMS-ESI$^+$ (m/z): [M+H]$^+$ calcd for $C_{29}H_{27}N_2O_4$: 467.2. Found: 467.1.

(S)-2-tert-butoxy-2-(6-carbamoyl-1-((S)-2,3-dihydropyrano[4,3,2-de]quinolin-7-yl)-3-methylnaphthalen-2-yl)acetic acid: LCMS-ESI$^+$ (m/z): [M+H]$^+$ calcd for $C_{29}H_{29}N_2O_5$: 485.5; Found: 485.1.

6-((S)-tert-butoxy(carboxy)methyl)-5-((S)-2,3-dihydropyrano[4,3,2-de]quinolin-7-yl)-7-methyl-2-naphthoic acid: LCMS-ESI$^+$ (m/z): [M+H]$^+$ calcd for $C_{29}H_{28}N_2O_6$: 486.2. Found: 486.1.

EXAMPLE 6

(S)-2-(6-Cyano-1-((R)-2,3-dihydropyrano[4,3,2-de]quinolin-7-yl)-3-methylnaphthalen-2-yl)-2-(tert-pentyloxy)acetic acid, (S)-2-(6-carbamoyl-1-((R)-2,3-dihydropyrano[4,3,2-de]quinolin-7-yl)-3-methylnaphthalen-2-yl)-2-(tert-pentyloxy)acetic acid, (S)-2-(6-cyano-1-((S)-2,3-dihydropyrano[4,3,2-de]quinolin-7-yl)-3-methylnaphthalen-2-yl)-2-(tert-pentyloxy)acetic acid, (S)-2-(6-carbamoyl-1-((S)-2,3-dihydropyrano[4,3,2-de]quinolin-7-yl)-3-methylnaphthalen-2-yl)-2-(tert-pentyloxy)acetic acid

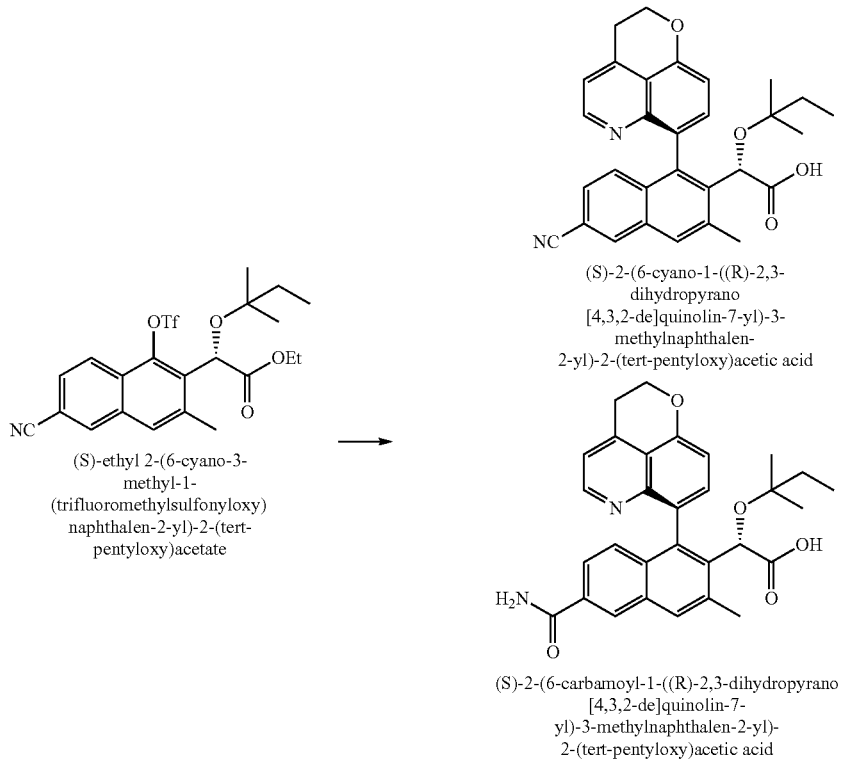

(S)-ethyl 2-(6-cyano-3-methyl-1-(trifluoromethylsulfonyloxy)naphthalen-2-yl)-2-(tert-pentyloxy)acetate

→

(S)-2-(6-cyano-1-((R)-2,3-dihydropyrano[4,3,2-de]quinolin-7-yl)-3-methylnaphthalen-2-yl)-2-(tert-pentyloxy)acetic acid (S)-2-(6-carbamoyl-1-((R)-2,3-dihydropyrano[4,3,2-de]quinolin-7-yl)-3-methylnaphthalen-2-yl)-2-(tert-pentyloxy)acetic acid Preparation of (S)-ethyl 2-(6-cyano-3-methyl-1-(trifluoromethylsulfonyloxy)naphthalen-2-yl)-2-(tert-pentyloxy) acetate: (S)-ethyl 2-(6-cyano-3-methyl-1(trifluoromethylsulfonyloxy)-naphthalen-2-yl)-2-(tert-pentyloxy)acetate was prepared in a similar way to (S)-ethyl 2-tert-butoxy-2-(6-cyano-3-methyl-1-(trifluoromethylsulfonyloxy)naphthalen-2-yl)acetate in Example 5 except tert-amyl acetate was used instead of tert-butyl acetate. $^1$H NMR (400 MHz, CDCl$_3$) 8.18 (s, 1H), 8.13 (d, J=8.7 Hz, 1H), 7.73 (s, 1H), 7.71 (d, J=8.9 Hz, 1H), 5.73 (s, 1H), 4.27-4.08 (m, 2H), 2.59 (s, 3H), 1.62-1.43 (m, 2H), 1.20 (s, 3H), 1.17 (t, J=7.2 Hz, 3H), 1.08 (s, 3H), 0.77 (t, J=7.4 Hz, 3H).

Preparation of (S)-2-(6-cyano-1-((R)-2,3-dihydropyrano[4,3,2-de]quinolin-7-yl)-3-methylnaphthalen-2-yl)-2-(tert-pentyloxy)acetic acid: (S)-2-(6-cyano-1-((R)-2,3-dihydropyrano[4,3,2-de]quinolin-7-yl)-3-methylnaphthalen-2-yl)-2-(tert-pentyloxy)acetic acid was prepared in a similar way to (S)-2-tert-butoxy-2-(6-cyano-1-((R)-2,3-dihydropyrano[4,3,2-de]quinolin-7-yl)-3-methylnaphthalen-2-yl)acetic acid in Example 5 except (S)-ethyl 2-(6-cyano-1-((R)-2,3-dihydropyrano[4,3,2-de]quinolin-7-yl)-3-methylnaphthalen-2-yl)-2-(tert-pentyloxy)acetate was used instead of (S)-ethyl 2-tert-butoxy-2-(6-cyano-1-((R)-2,3-dihydropyrano[4,3,2-de]quinolin-7-yl)-3-methylnaphthalen-2-yl)acetate. $^1$H NMR (400 MHz, CD$_3$OD) δ 8.68 (d, J=5.5 Hz, 2H), 8.44 (s, 1H), 8.09 (s, 1H), 7.84 (d, J=7.4 Hz, 1H), 7.79 (d, J=5.4 Hz, 1H), 7.47 (d, J=9.3 Hz, 1H), 7.43 (s, 1H), 7.11 (d, J=8.7 Hz, 1H), 5.20 (s, 1H), 4.78-4.63 (m, 2H), 3.66 (t, J=5.9 Hz, 2H), 2.81 (s, 3H), 1.31-1.02 (m, 2H), 0.92 (s, 6H), 0.62 (t, J=7.4 Hz, 3H). LCMS-ESI$^+$ (m/z): [M+H]$^+$ calcd for C$_{30}$H$_{29}$N$_2$O$_4$: 480.2. Found: 480.0.

(S)-2-(6-carbamoyl-1-((R)-2,3-dihydropyrano[4,3,2-de]quinolin-7-yl)-3-methylnaphthalen-2-yl)-2-(tert-pentyloxy)acetic acid was also isolated. $^1$H NMR (400 MHz, CD$_3$OD) δ 8.67 (d, J=5.6 Hz, 1H), 8.48 (s, 1H), 8.08 (s, 1H), 7.86 (d, J=8.6 Hz, 1H), 7.80 (d, J=5.7 Hz, 1H), 7.70 (d, J=9.0 Hz, 1H), 7.48 (d, J=7.8 Hz, 1H), 7.01 (d, J=8.7 Hz, 1H), 5.21 (s, 1H), 4.80-4.62 (m, 2H), 3.67 (t, J=5.9 Hz, 2H), 2.80 (s, 3H), 1.31-1.04 (m, 2H), 0.92 (d, J=6.0 Hz, 6H), 0.62 (t, J=7.8 Hz, 3H). LCMS-ESI$^+$ (m/z): [M+H]$^+$ calcd for C$_{30}$H$_{31}$N$_2$O$_5$: 499.2. Found: 499.1.

The other atropisomers were also prepared in a similar way.

(S)-2-(6-cyano-1-((S)-2,3-dihydropyrano[4,3,2-de]quinolin-7-yl)-3-methylnaphthalen-2-yl)-2-(tert-pentyloxy)acetic acid: LCMS-ESI$^+$ (m/z): [M+H]$^+$ calcd for C$_{30}$H$_{29}$N$_2$O$_4$: 480.2. Found: 480.0.

(S)-2-(6-carbamoyl-1-((S)-2,3-dihydropyrano[4,3,2-de]quinolin-7-yl)-3-methylnaphthalen-2-yl)-2-(tert-pentyloxy) acetic acid: LCMS-ESI$^+$ (m/z): [M+H]$^+$ calcd for C$_{30}$H$_{31}$N$_2$O$_5$: 499.2. Found: 499.1.

EXAMPLE 7

(S)-2-tert-Butoxy-2-(6-cyano-1-((R)-2,3-dihydropyrano[4,3,2-de]quinolin-7-yl)-4-fluoro-3-methylnaphthalen-2-yl)acetic acid, (S)-2-tert-butoxy-2-(6-carbamoyl-1-((R)-2,3-dihydropyrano[4,3,2-de]quinolin-7-yl)-4-fluoro-3-methylnaphthalen-2-yl)acetic acid, (S)-2-tert-butoxy-2-(6-cyano-1-((S)-2,3-dihydropyrano[4,3,2-de]quinolin-7-yl)-4-fluoro-3-methylnaphthalen-2-yl)acetic acid, (S)-2-tert-butoxy-2-(6-carbamoyl-1-((S)-2,3-dihydropyrano[4,3,2-de]quinolin-7-yl)-4-fluoro-3-methylnaphthalen-2-yl)acetic acid

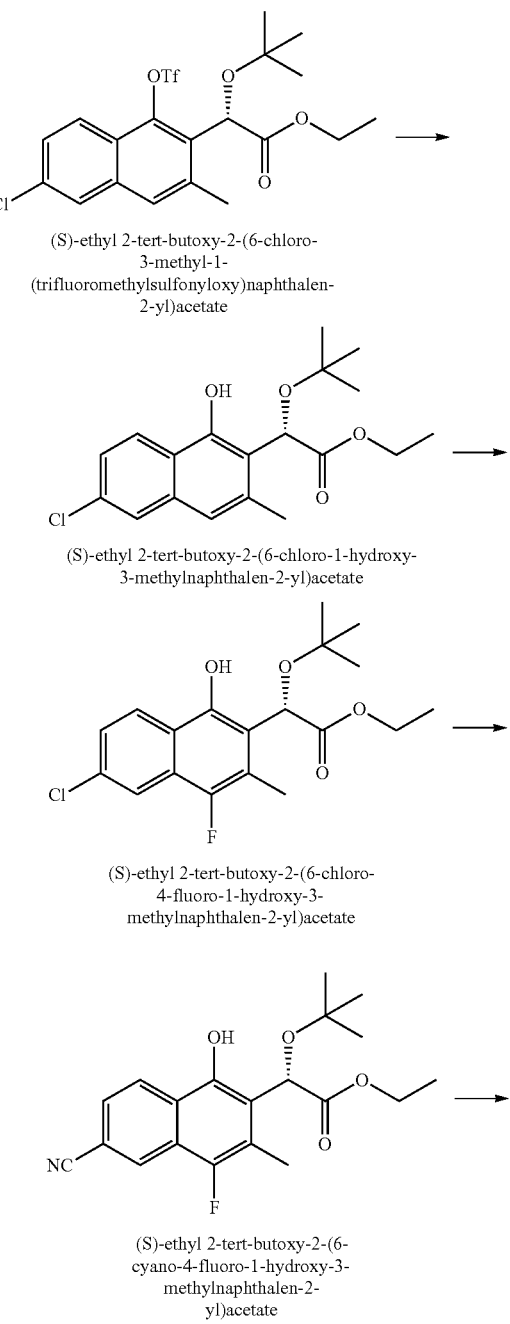

(S)-ethyl 2-tert-butoxy-2-(6-chloro-3-methyl-1-(trifluoromethylsulfonyloxy)naphthalen-2-yl)acetate (S)-ethyl 2-tert-butoxy-2-(6-chloro-1-hydroxy-3-methylnaphthalen-2-yl)acetate (S)-ethyl 2-tert-butoxy-2-(6-chloro-4-fluoro-1-hydroxy-3-methylnaphthalen-2-yl)acetate (S)-ethyl 2-tert-butoxy-2-(6-cyano-4-fluoro-1-hydroxy-3-methylnaphthalen-2-yl)acetate

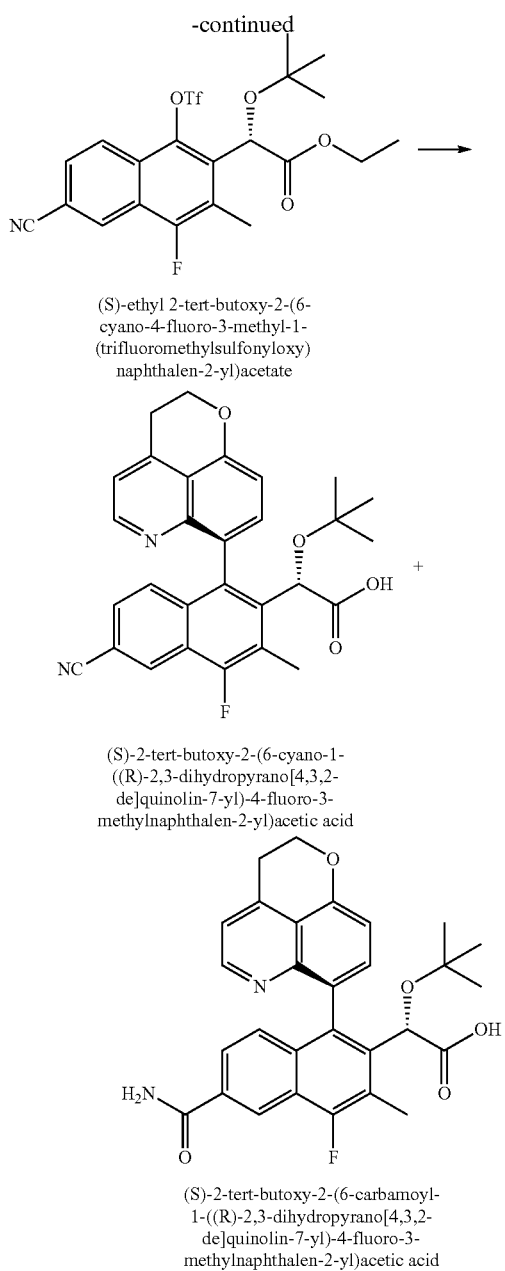

(S)-ethyl 2-tert-butoxy-2-(6-cyano-4-fluoro-3-methyl-1-(trifluoromethylsulfonyloxy)naphthalen-2-yl)acetate (S)-2-tert-butoxy-2-(6-cyano-1-((R)-2,3-dihydropyrano[4,3,2-de]quinolin-7-yl)-4-fluoro-3-methylnaphthalen-2-yl)acetic acid (S)-2-tert-butoxy-2-(6-carbamoyl-1-((R)-2,3-dihydropyrano[4,3,2-de]quinolin-7-yl)-4-fluoro-3-methylnaphthalen-2-yl)acetic acid Preparation of (S)-ethyl 2-tert-butoxy-2-(6-chloro-1-hydroxy-3-methylnaphthalen-2-yl)acetate: To a solution of (S)-ethyl 2-tert-butoxy-2-(6-chloro-3-methyl-1-(trifluoromethylsulfonyloxy)naphthalen-2-yl)acetate (1.521 g, 3.15 mmol) in anhydrous THF (30 mL) at 0° C. was added a 1M solution of tetrabutylammonium fluoride in THF (6.30 mL, 6.30 mmol) to give a bright yellow solution. The reaction mixture was stirred for 45 minutes and quenched with saturated ammonium chloride solution and stirred for 5 minutes. The product was extracted with ethyl acetate/hexane (1:1, 2×). The combined organic layer was dried (MgSO$_4$), filtered, concentrated and purified by flash column chromatography (silica gel, 0 to 10% ethyl acetate/hexanes) to give the desired product. LCMS-ESI$^+$ (m/z): [M+H]$^+$ calcd for C$_{19}$H$_{24}$ClO$_4$: 349.1. Found: 349.1.

Preparation of (S)-ethyl 2-tert-butoxy-2-(6-chloro-4-fluoro-1-hydroxy-3-methylnaphthalen-2-yl)acetate: To a solution of (S)-ethyl 2-tert-butoxy-2-(6-chloro-1-hydroxy-3-methylnaphthalen-2-yl)acetate (0.9705 g, 2.77 mmol) in anhydrous acetonitrile (20 mL) at 0° C. was added Select-Fluor (1.078 g, 3.04 mmol) in one portion. The reaction mixture was stirred for 4 hours at 0° C., then 1 hour at room temperature. The reaction mixture was quenched with saturated Na$_2$HPO$_4$ solution and stirred for 20 minutes. The mixture was extracted with ethyl acetate (2×), dried (MgSO$_4$), filtered, concentrated and stored overnight in a freezer. The residue was purified by flash column chromatography (silica gel, 0 to 15% ethyl acetate/hexanes) to give the desired product. LCMS-ESI$^+$ (m/z): [M+H]$^+$ calcd for C$_{19}$H$_{21}$ClFO$_4$: 367.8. Found: 366.9, 368.9.

Preparation of (S)-ethyl 2-tert-butoxy-2-(6-cyano-4-fluoro-1-hydroxy-3-methylnaphthalen-2-yl)acetate: A mixture of (S)-ethyl 2-tert-butoxy-2-(6-chloro-4-fluoro-1-hydroxy-3-methylnaphthalen-2-yl)acetate (0.2186 g, 0.593 mmol), zinc(II) cyanide (0.0695 g, 0.593 mmol), XPhos Palladacycle (0.044 g, 0.0593 mmol) and sodium bicarbonate (0.005 g, 0.0593 mmol) in anhydrous DMF (3.0 mL) was heated in a microwave at 100° C. for 1 hour. The reaction mixture was diluted with water and extracted with ethyl acetate (2×). The Combined organic layer was washed with 5% lithium chloride solution, brine, dried (MgSO$_4$), filtered, concentrated and purified by flash column chromatography (silica gel, 0 to 15% ethyl acetate/hexanes) to give the desired product. LCMS-ESI$^+$ (m/z): [M+H]$^+$ calcd for C$_{20}$H$_{21}$FNO$_4$: 358.2. Found: 357.9.

Preparation of (S)-ethyl 2-tert-butoxy-2-(6-cyano-4-fluoro-3-methyl-1-(trifluoromethylsulfonyloxy)naphthalen-2-yl)acetate: To a solution of (S)-ethyl 2-tert-butoxy-2-(6-cyano-4-fluoro-1-hydroxy-3-methylnaphthalen-2-yl)acetate (42.5 mg, 0.118 mmol) in anhydrous THF (1.2 mL) at 0° C. was added N-phenyltrifluoromethylsulfonimide (84.5 mg, 0.237 mmol), followed by cesium carbonate (77.2 mg, 0.237 mmol) to give a yellow mixture that was warmed to room temperature overnight. The reaction mixture was diluted with water and extracted with ethyl acetate (2×). The combined organic layer was washed with brine, dried (MgSO$_4$), filtered, concentrated and purified by flash column chromatography (silica gel, 0 to 20% ethyl acetate/hexanes) to give the desired product. $^1$H NMR (400 MHz, CDCl$_3$) δ 8.47 (s, 1H), 8.13 (d, J=8.8 Hz, 1H), 7.77 (d, J=8.9 Hz, 1H), 5.71 (s, 1H), 4.29-4.05 (m, 2H), 2.48 (d, J=2.8 Hz, 3H), 1.20 (s, 9H), 1.18 (t, J=7.2 Hz, 3H).

Preparation of (S)-2-tert-butoxy-2-(6-cyano-1-((R)-2,3-dihydropyrano[4,3,2-de]quinolin-7-yl)-4-fluoro-3-methylnaphthalen-2-yl)acetic acid: (S)-2-tert-butoxy-2-(6-cyano-1-((R)-2,3-dihydropyrano[4,3,2-de]quinolin-7-yl)-4-fluoro-3-methylnaphthalen-2-yl)acetic acid was prepared in a similar way as (S)-2-tert-butoxy-2-(6-cyano-1-((R)-2,3-dihydropyrano[4,3,2-de]quinolin-7-yl)-3-methylnaphthalen-2-yl)acetic acid in Example 5 except (S)-ethyl 2-tert-butoxy-2-(6-cyano-4-fluoro-3-methyl-1-(trifluoromethylsulfonyloxy)naphthalen-2-yl)acetate was used instead of (S)-ethyl 2-tert-butoxy-2-(6-cyano-1-((R)-2,3-dihydropyrano[4,3,2-de]quinolin-7-yl)-3-methylnaphthalen-2-yl)acetate. $^1$H NMR (400 MHz, CD$_3$OD) δ 8.70 (d, J=5.6 Hz, 1H), 8.65 (s, 1H), 7.88 (d, J=7.8 Hz, 1H), 7.80 (d, J=5.7 Hz, 1H), 7.54 (d, J=8.6 Hz, 1H), 7.47 (d, J=8.0 Hz, 1H), 7.18 (d, J=8.8 Hz, 1H), 5.20 (s, 1H), 4.79-4.67 (m, 2H), 3.66 (t, J=5.9 Hz, 2H), 2.70 (d, J=2.6 Hz, 3H), 0.96 (s, 9H). LCMS-ESI$^+$ (m/z): [M+H]$^+$ calcd for C$_{29}$H$_{26}$FN$_2$O$_4$: 485.2. Found: 485.1.

(S)-2-tert-butoxy-2-(6-carbamoyl-1-((R)-2,3-dihydropyrano[4,3,2-de]quinolin-7-yl)-4-fluoro-3-methylnaphthalen-2-yl)acetic acid was also isolated. $^1$H NMR (400 MHz, CD$_3$OD) δ 8.76 (s, 1H), 8.68 (d, J=5.7 Hz, 1H), 7.87 (d, J=8.8

Hz, 1H), 7.79 (d, J=7.0 Hz, 1H), 7.47 (d, J=8.5 Hz, 1H), 7.08 (d, J=8.9 Hz, 1H), 5.20 (s, 1H), 4.78-4.67 (m, 25H), 3.66 (t, J=5.6 Hz, 2H), 2.69 (d, J=2.2 Hz, 3H), 0.96 (s, 9H). LCMS-ESI+ (m/z): [M+H]+ calcd for $C_{29}H_{28}FN_2O_5$: 503.2. Found: 503.1.

The other atropisomers were also prepared in a similar way.

(S)-2-tert-butoxy-2-(6-cyano-1-((S)-2,3-dihydropyrano[4,3,2-de]quinolin-7-yl)-4-fluoro-3-methylnaphthalen-2-yl)acetic acid: LCMS-ESI+ (m/z): [M+H]+ calcd for $C_{29}H_{26}FN_2O_4$: 485.2. Found: 485.1.

(S)-2-tert-butoxy-2-(6-carbamoyl-1-((S)-2,3-dihydropyrano[4,3,2-de]quinolin-7-yl)-4-fluoro-3-methylnaphthalen-2-yl)acetic acid: LCMS-ESI+ (m/z): [M+H]+ calcd for $C_{29}H_{28}FN_2O_5$: 503.2. Found: 503.1.

EXAMPLE 8

(2S)-2-tert-Butoxy-2-(1-(4-chlorophenyl)-7-(3-(4-fluorophenyl)-3-hydroxybut-1-ynyl)-3-methylnaphthalen-2-yl)acetic acid

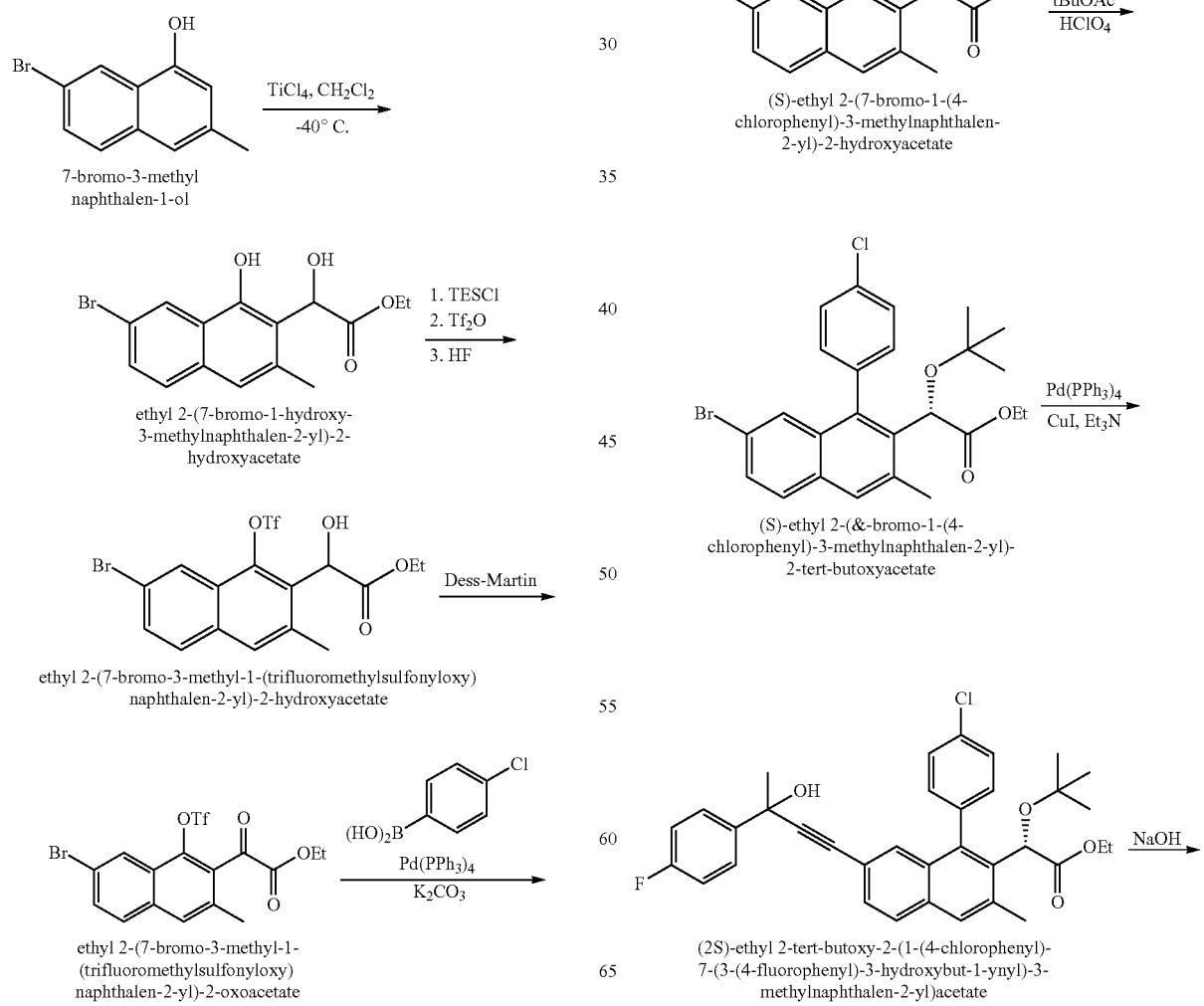
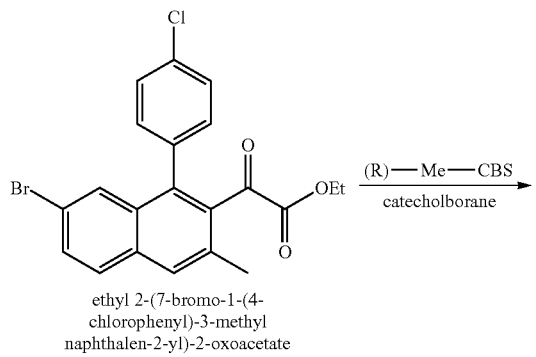
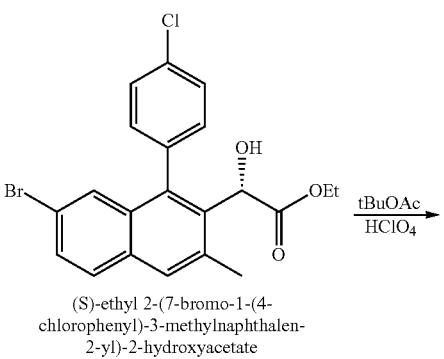
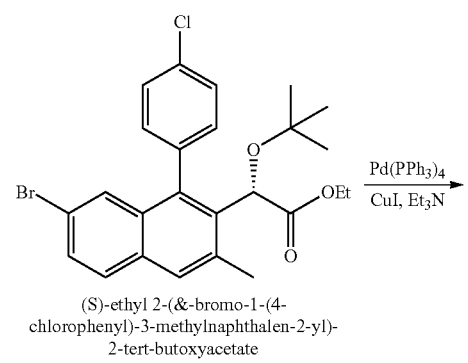
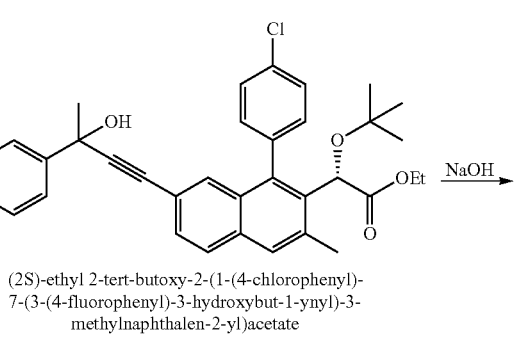

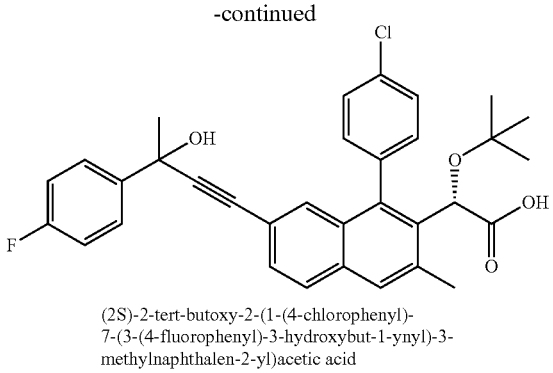

(2S)-2-tert-butoxy-2-(1-(4-chlorophenyl)-
7-(3-(4-fluorophenyl)-3-hydroxybut-1-ynyl)-3-
methylnaphthalen-2-yl)acetic acid Preparation of ethyl 2-(7-bromo-1-hydroxy-3-methyl-naphthalen-2-yl)-2-hydroxyacetate: 7-Bromo-3-methyl-naphthalen-1-ol was prepared in a similar manner as 6-chloro-3-methylnaphthalen-1-ol in Example 5 except using 1-(4-bromophenyl)propan-2-one instead of 1-(3-chlorophenyl)propan-2-one. To a solution of 7-bromo-3-methylnaphthalen-1-ol (11.5 g, 48.5 mmol) in dichloromethane (145 mL) at 0° C. was added a 1 M titanium(IV) chloride solution in dichloromethane (48.5 mL, 48.5 mmol) and stirred for 20 min. Ethyl glyoxylate (50% solution in $PhCH_3$, 10.6 mL, 53.3 mmol) was added over 15 minutes and stirred for 1 hour at 0° C. The reaction was quenched by the addition of Rochelle's salt solution and stirred at room temperature for 14 hours. The layers were separated, and the aqueous layer was extracted with $CH_2Cl_2$. The combined organic layers were dried, filtered, concentrated and purified by flash column chromatography (EtOAc/Hexanes) to provide the desired product. $^1$H-NMR: 400 MHz, (CDCl$_3$) δ: 8.52 (s, 1H), 8.34 (s, 1H), 7.49 (m, 2H), 7.13 (s, 1H), 5.67 (s, 1H), 4.24 (m, 1H), 4.16 (m, 1H), 2.29 (s, 3H), 1.23 (m, 3H).

Preparation of ethyl 2-(7-bromo-3-methyl-1-(trifluoromethylsulfonyloxy)-naphthalen-2-yl)-2-hydroxyacetate: To a solution of ethyl 2-(7-bromo-1-hydroxy-3-methylnaphthalen-2-yl)-2-hydroxyacetate (7.67 g, 22.6 mmol) in $CH_2Cl_2$ (50 mL) was added imidazole (3.08 g, 45.2 mmol) and chlorotriethylsilane (4.55 mL, 27.1 mmol). After 16 h, a saturated solution of NH$_4$Cl was added. The layers were separated, and the aqueous layer was extracted with $CH_2Cl_2$. The combined organic layers were dried, filtered, concentrated to ~50 mL of solution. The solution was cooled to −78° C., and triethylamine (1.7 eq) and trifluoromethanesulfonic anhydride (1.5 eq) were added. After 30 min, a saturated solution of NH$_4$Cl was added. The layers were separated, and the aqueous layer was extracted with $CH_2Cl_2$. The combined organic layers were dried, filtered, concentrated. THF was added (100 mL) followed by 48% aqueous HF solution (10 mL). The reaction was stirred in a plastic vessel overnight at rt. Solid NaHCO$_3$ was added in small portions then H$_2$O was added to reach pH of ~7-8. The layers were separated, and the aqueous layer was extracted with EtOAc. The combined organic layers were dried, filtered, concentrated in vacuo. The product was used without further purification. $^1$H-NMR: 400 MHz, (CDCl$_3$) δ: 8.20 (s, 1H), 7.65 (m, 3H), 5.79 (s, 1H), 4.24 (m, 2H), 3.46 (br s, 1H), 2.48 (s, 3H), 1.20 (m, 3H).

Preparation of ethyl 2-(7-bromo-3-methyl-1-(trifluoromethylsulfonyloxy)naphthalen-2-yl)-2-oxoacetate: To a solution of ethyl 2-(7-bromo-3-methyl-1-(trifluoromethylsulfonyloxy)naphthalen-2-yl)-2-hydroxyacetate (~8.7 mmol) in $CH_2Cl_2$ (40 mL) was added Dess-Martin periodinane (4.07 g, 9.6 mmol). After 1.5 h, a saturated solution of Na$_2$S$_2$O$_4$ (20 mL) and water (20 mL) was added. The mixture was stirred vigorously for 30 min. The layers were separated, and the organic layer was dried, filtered, and concentrated in vacuo. The crude material was purified by column chromatography (EtOAc/hexanes) to give 3 the titled compound. $^1$H-NMR: 400 MHz, (CDCl$_3$) δ: 8.22 (s, 1H), 7.70 (m, 3H), 4.41 (q, J=7 Hz, 2H), 2.47 (s, 3H), 1.39 (t, J=7 Hz, 3H). $^{19}$F-NMR: 377 MHz, (CDCl$_3$) δ: −73.2.

Preparation of ethyl 2-(7-bromo-1-(4-chlorophenyl)-3-methylnaphthalen-2-yl)-2-oxoacetate: To a solution of ethyl 2-(7-bromo-3-methyl-1-(trifluoromethylsulfonyloxy)naphthalen-2-yl)-2-oxoacetate (235 mg, 0.50 mmol) in $PhCH_3$ (1.2 mL), EtOH (0.6 mL), H$_2$O (0.6 mL) was added 4-chlorophenylboronic acid (86 mg, 0.55 mmol), K$_2$CO$_3$ (207 mg, 1.5 mmol), and PdCl$_2$dppf (11 mg, 0.015 mmol). The reaction mixture was stirred at room temperature for 2 h and was then diluted with H$_2$O and EtOAc. The layers were separated, and the organic layer was dried, filtered, and concentrated in vacuo. The crude material was purified by column chromatography (EtOAc/hexanes) to give the titled compound and 37 mg of the bis-coupled product (ethyl 2-(1,7-bis(4-chlorophenyl)-3-methylnaphthalen-2-yl)-2-oxoacetate). $^1$H-NMR: 400 MHz, (CDCl$_3$) δ: 7.60-7.72 (m, 4H), 7.45 (m, 2H), 7.23 (m, 2H), 3.93 (q, J=7 Hz, 2H), 2.48 (s, 3H), 1.13 (t, J=7 Hz, 3H).

Preparation of ethyl 2-(7-bromo-1-(4-chlorophenyl)-3-methylnaphthalen-2-yl)-2-hydroxyacetate: To a solution of ethyl 2-(7-bromo-1-(4-chlorophenyl)-3-methylnaphthalen-2-yl)-2-oxoacetate (1.6 g, 2.78 mmol) and (R)-2-methyl-CBS-oxazaborolidine (116 mg, 0.42 mmol) in anhydrous toluene at −40° C. was added a solution of catecholborane (355 µL, 3.34 mmol) in toluene (1.6 mL) over 15 minutes. The reaction mixture was stirred for 1 hour and quenched with sodium carbonate solution, diluted with ethyl acetate and stirred vigorously for 20 minutes at room temperature. The aqueous layer was removed and the organic layer was washed with sodium carbonate solution (4×), saturated ammonium chloride solution, dried, filtered, concentrated in vacuo and purified by flash column chromatography to give the desired product.
$^1$H-NMR: 400 MHz, (CDCl$_3$) δ: 7.64 (m, 2H), 7.45 (m, 3H), 7.39 (s, 1H), 7.28 (m, 2H), 5.18 (s, 1H), 4.17 (m, 2H), 2.48 (s, 3H), 1.20 (t, J=7 Hz, 3H).

Preparation of ethyl 2-(7-bromo-1-(4-chlorophenyl)-3-methylnaphthalen-2-yl)-2-tert-butoxyacetate: To a solution of ethyl 2-(7-bromo-1-(4-chlorophenyl)-3-methylnaphthalen-2-yl)-2-hydroxyacetate (~2.78 mmol) in t-BuOAc (14 mL) was added 70% perchloric acid (HClO$_4$) (334 µL, 5.56 mmol). After 3 h, water was added. The layers were separated, and the organic layer was dried, filtered, and concentrated in vacuo. The crude material was purified by column chromatography (EtOAc/hexanes) to give the titled compound. $^1$H-NMR: 400 MHz, (CDCl$_3$) δ: 7.62 (m, 2H), 7.51 (m, 4H), 7.27 (m, 2H), 5.09 (s, 1H), 4.15 (m, 2H), 2.59 (s, 3H), 1.19 (t, J=7 Hz, 3H), 1.00 (s, 9H).

Preparation of (2S)-ethyl 2-tert-butoxy-2-(1-(4-chlorophenyl)-7-(3-(4-fluorophenyl)-3-hydroxybut-1-ynyl)-3-methylnaphthalen-2-yl)acetate: To a solution of ethyl 2-(7- bromo-1-(4-chlorophenyl)-3-methylnaphthalen-2-yl)-2-tert-butoxyacetate (70 mg, 0.14 mmol) in THF (2 mL) was added 2-(4-fluorophenyl)but-3-yn-2-ol (46 mg, 0.28 mmol), CuI (5 mg, 0.028 mmol), Pd(PPh$_3$)$_4$ (17 mg, 0.014 mmol), and Et$_3$N (80 µL, 0.57 mmol). The reaction mixture was stirred at 70° C. for 1 h. A saturated solution of NH$_4$Cl was added. The layers were separated, and the organic layer was dried, filtered, and concentrated in vacuo. The crude material was purified by column chromatography (EtOAc/hexanes) to give the titled compound. $^1$H-NMR: 400 MHz, (CDCl$_3$) δ: 7.56-7.66 (m, 4H), 7.29 (m, 6H), 6.97 (m, 2H), 5.02 (s, 1H), 4.06 (q, J=7 Hz, 2H). 2.54 (s, 3H), 1.76 (s, 3H), 1.10 (s, 9H), 0.80 (t, J=7 Hz, 3H).

Preparation of (2S)-2-tert-butoxy-2-(1-(4-chlorophenyl)-7-(3-(4-fluorophenyl)-3-hydroxybut-1-ynyl)-3-methylnaphthalen-2-yl)acetic acid: To a solution of (2S)-ethyl 2-tert-butoxy-2-(1-(4-chlorophenyl)-7-(3-(4-fluorophenyl)-3-hydroxybut-1-ynyl)-3-methylnaphthalen-2-yl)acetate (22 mg, 0.045 mmol) in 2:2:1 THF/MeOH/H$_2$O (1 mL total) was added a NaOH solution (4 M, 0.2 mL). The reaction mixture was stirred at 60° C. for 2 h. The mixture was partially concentrated and diluted with MeCN and H$_2$O and purified by reverse phase HPLC (MeCN/H$_2$O) to give the titled compound. $^1$H-NMR: 400 MHz, (CD$_3$OD) δ: 7.75 (d, J=8 Hz, 1H), 7.67 (m, 4H), 7.56 (m, 2H), 7.43 (m, 1H), 7.35 (s, 1H), 7.31 (d, J=8 Hz, 1H), 7.05 (m, 2H), 5.12 (s, 1H), 2.62 (s, 3H), 1.74 (s, 1H), 0.96 (s, 9H). LCMS-ESI$^+$ (m/z): [M-OH]$^+$ calcd for C$_{33}$H$_{29}$ClFO$_3$: 527.2. Found: 527.2.

EXAMPLE 9

(2S)-2-tert-Butoxy-2-(1-(4-chlorophenyl)-3-methyl-7-(4,4,4-trifluoro-3-hydroxy-3-phenylbut-1-ynyl) naphthalen-2-yl)acetic acid

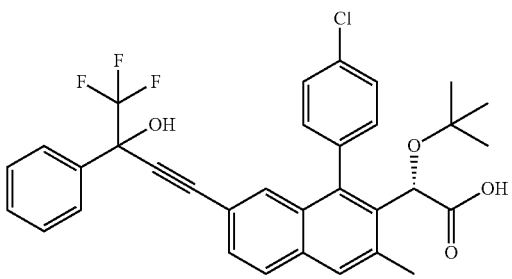

(2S)-2-tert-butoxy-2-(1-(4-chlorophenyl)-3-methyl-7-(4,4,4-trifluoro-3-hydroxy-3-phenylbut-1-ynyl)naphthalen-2-yl)acetic acid Preparation of (2S)-2-tert-butoxy-2-(1-(4-chlorophenyl)-3-methyl-7-(4,4,4-trifluoro-3-hydroxy-3-phenylbut-1-ynyl) naphthalen-2-yl)acetic acid: (2S)-2-tert-butoxy-2-(1-(4-chlorophenyl)-3-methyl-7-(4,4,4-trifluoro-3-hydroxy-3-phenylbut-1-ynyl)naphthalen-2-yl)acetic acid was prepared by the method in Example 8 from ethyl 2-(7-bromo-1-(4-chlorophenyl)-3-methylnaphthalen-2-yl)-2-tert-butoxyacetate and 1,1,1-trifluoro-2-phenylbut-3-yn-2-ol. $^1$H-NMR: 400 MHz, (CD$_3$OD) δ: 7.74 (m, 3H), 7.67 (s, 1H), 7.55 (m, 4H), 7.46 (m, 2H), 7.39 (m, 2H), 7.33 (m, 1H), 5.07 (s, 1H), 2.66 (s, 3H), 0.94 (s, 9H). LCMS-ESI$^+$ (m/z): [M-OH]$^+$ calcd for C$_{31}$H$_{32}$ClF$_3$O$_3$: 563.2. found: 563.1.

EXAMPLE 10

(2S)-2-tert-Butoxy-2-(1-(4-chlorophenyl)-7-(3-hydroxy-3-(pyridin-2-yl)but-1-ynyl)-3-methylnaphthalen-2-yl)acetic acid

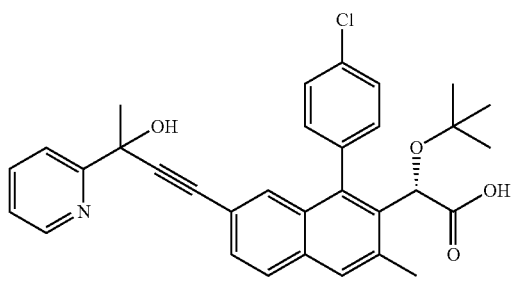

(2S)-2-tert-butoxy-2-(1-(4-chlorophenyl)-7-(3-hydroxy-3-(pyridin-2-yl)but-1-ynyl)-3-methylnaphthalen-2-yl)acetic acid Preparation of (2S)-2-tert-butoxy-2-(1-(4-chlorophenyl)-7-(3-hydroxy-3-(pyridin-2-yl)but-1-ynyl)-3-methylnaphthalen-2-yl)acetic acid: (2S)-2-tert-butoxy-2-(1-(4-chlorophenyl)-7-(3-hydroxy-3-(pyridin-2-yl)but-1-ynyl)-3-methylnaphthalen-2-yl)acetic acid was prepared by the method in Example 8 from ethyl 2-(7-bromo-1-(4-chlorophenyl)-3-methylnaphthalen-2-yl)-2-tert-butoxyacetate and 2-(pyridin-2-yl)but-3-yn-2-ol. $^1$H-NMR: 400 MHz, (CD$_3$OD) δ: 8.61 (d, J=6 Hz, 1H), 8.22 (t, J=8 Hz, 1H), 8.05 (d, J=8 Hz, 1H), 7.78 (d, J=8 Hz, 1H), 7.66 (m, 2H), 7.57 (m, 3H), 7.47 (d, J=8 Hz, 1H), 7.35 (s, 1H), 7.30 (d, J=8 Hz, 1H), 5.16 (s, 1H), 2.61 (s, 3H), 1.87 (s, 3H), 0.98 (s, 9H). LCMS-ESI$^+$ (m/z): [M+H]$^+$ calcd for C$_{32}$H$_{30}$ClNO$_4$: 528.2. found: 528.1.

EXAMPLE 11

(2S)-2-tert-Butoxy-2-(1-(4-chlorophenyl)-7-(3-hydroxy-3-(pyridin-3-yl)but-1-ynyl)-3-methylnaphthalen-2-yl)acetic acid

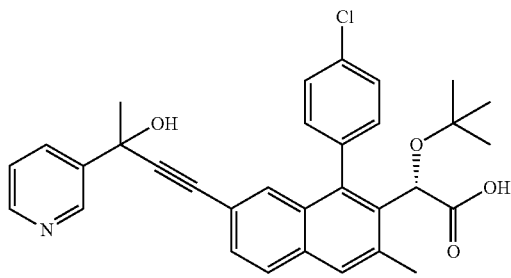

(2S)-2-tert-butoxy-2-(1-(4-chlorophenyl)-7-(3-hydroxy-3-(pyridin-3-yl)but-1-ynyl)-3-methylnaphthalen-2-yl)acetic acid Preparation of (2S)-2-tert-butoxy-2-(1-(4-chlorophenyl)-7-(3-hydroxy-3-(pyridin-3-yl)but-1-ynyl)-3-methylnaphthalen-2-yl)acetic acid: (2S)-2-tert-butoxy-2-(1-(4-chlorophenyl)-7-(3-hydroxy-3-(pyridin-3-yl)but-1-ynyl)-3-methylnaphthalen-2-yl)acetic acid was prepared by the method in Example 8 from ethyl 2-(7-bromo-1-(4-chlorophenyl)-3-methylnaphthalen-2-yl)-2-tert-butoxyacetate and 2-(pyridin-3-yl)but-3-yn-2-ol. $^1$H-NMR: 400 MHz, (CD$_3$OD) δ: 9.05 (s, 1H), 8.86 (d, J=8 Hz, 1H), 8.80 (s, 1H), 8.08 (m, 1H), 7.80 (d, J=8 Hz, 1H), 7.72 (s, 1H), 7.56 (m, 3H), 7.49 (d, J=8 Hz, 1H), 7.36 (s, 1H), 7.30 (d, J=8 Hz, 1H), 5.16 (s, 1H), 2.61 (s, 3H), 1.87 (s, 3H), 0.98 (s, 9H). LCMS-ESI$^+$ (m/z): [M+H]$^+$ calcd for C$_{32}$H$_{30}$ClNO$_4$: 528.2. found: 528.1.

EXAMPLE 12

(2S)-2-tert-Butoxy-2-(1-(4-chlorophenyl)-7-(3-hydroxy-3-(pyridin-4-yl)but-1-ynyl)-3-methylnaphthalen-2-yl)acetic acid

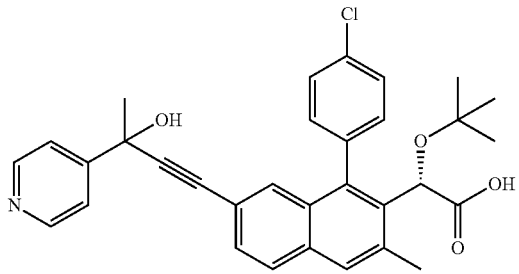

(2S)-2-tert-butoxy-2-(1-(4-chlorophenyl)-7-(3-hydroxy-3-(pyridin-4-yl)but-1-ynyl)-3-methylnaphthalen-2-yl)acetic acid Preparation of (2S)-2-tert-butoxy-2-(1-(4-chlorophenyl)-7-(3-hydroxy-3-(pyridin-4-yl)but-1-ynyl)-3-methylnaphthalen-2-yl)acetic acid: (2S)-2-tert-butoxy-2-(1-(4-chlorophenyl)-7-(3-hydroxy-3-(pyridin-4-yl)but-1-ynyl)-3-methylnaphthalen-2-yl)acetic acid was prepared by the method Example 8 from ethyl 2-(7-bromo-1-(4-chlorophenyl)-3-methylnaphthalen-2-yl)-2-tert-butoxyacetate and 2-(pyridin-4-yl)but-3-yn-2-ol. $^1$H-NMR: 400 MHz, (CD$_3$OD) δ: 8.80 (d, J=5 Hz, 2H), 8.27 (d, J=5H, 2H), 7.80 (d, J=8 Hz, 1H), 7.71 (s, 1H), 7.56 (m, 3H), 7.48 (d, J=8 Hz, 1H), 7.34 (s, 1H), 7.30 (d, J=8 Hz, 1H), 5.16 (s, 1H), 2.61 (s, 3H), 1.83 (s, 3H), 0.98 (s, 9H). LCMS-ESI$^+$ (m/z): [M+H]$^+$ calcd for C$_{32}$H$_{30}$ClNO$_4$: 528.2. found: 528.1.

EXAMPLE 13

(2S)-2-tert-Butoxy-2-(1-(4-chlorophenyl)-7-(3-(2,4-dimethylthiazol-5-yl)-3-hydroxybut-1-ynyl)-3-methylnaphthalen-2-yl)acetic acid

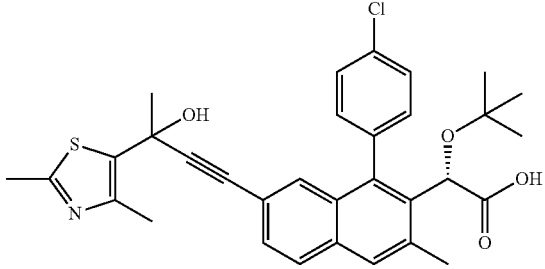

(2S)-2-tert-butoxy-2-(1-(4-chlorophenyl)-7-(3-(2,4-dimethylthiazol-5-yl)-3-hydroxybut-1-ynyl)-3-methylnaphthalen-2-yl)acetic acid Preparation of (2S)-2-tert-butoxy-2-(1-(4-chlorophenyl)-7-(3-(2,4-dimethylthiazol-5-yl)-3-hydroxybut-1-ynyl)-3-methylnaphthalen-2-yl)acetic acid: (2S)-2-tert-butoxy-2-(1-(4-chlorophenyl)-7-(3-(2,4-dimethylthiazol-5-yl)-3-hydroxybut-1-ynyl)-3-methylnaphthalen-2-yl)acetic acid was prepared by the method in Example 8 from ethyl 2-(7-bromo-1-(4-chlorophenyl)-3-methylnaphthalen-2-yl)-2-tert-butoxyacetate and 2-(2,4-dimethylthiazol-5-yl)but-3-yn-2-ol. $^1$H-NMR: 400 MHz, (CD$_3$OD) δ: 7.78 (d, J=8 Hz, 1H), 7.70 (s, 1H), 7.58 (m, 3H), 7.43 (d, J=8 Hz, 1H), 7.32 (m, 2H), 5.18 (s, 1H), 2.64 (s, 3H), 2.61 (s, 3H), 2.47 (s, 3H), 1.82 (s, 3H), 0.98 (s, 9H). LCMS-ESI$^+$ (m/z): [M+H]$^+$ calcd for C$_{32}$H$_{32}$ClNSO$_4$: 562.2. found: 562.1.

EXAMPLE 14

(S)-2-tert-Butoxy-2-(1-(4-chlorophenyl)-7-((R)-3-hydroxy-3-phenylbut-1-ynyl)-3-methylnaphthalen-2-yl)acetic acid and (S)-2-tert-butoxy-2-(1-(4-chlorophenyl)-7-((S)-3-hydroxy-3-phenylbut-1-ynyl)-3-methylnaphthalen-2-yl)acetic acid

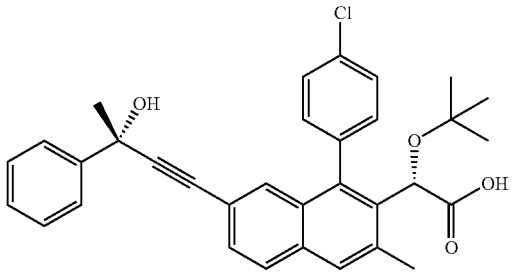

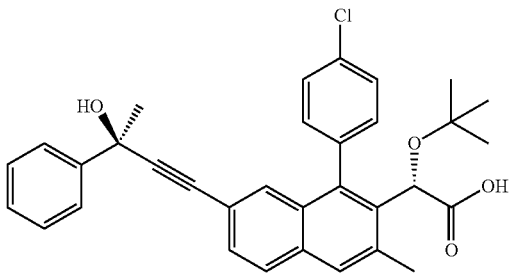

(S)-2-tert-butoxy-2-(1-(4-chlorophenyl)-7-((R)-3-hydroxy-3-phenylbut-1-ynyl)-3-methylnaphthalen-2-yl)acetic acid and (S)-2-tert-butoxy-2-(1-(4-chlorophenyl)-7-((S)-3-hydroxy-3-phenylbut-1-ynyl)-3-methylnaphthalen-2-yl)acetic acid were prepared by the method Example 8 from ethyl 2-(7-bromo-1-(4-chlorophenyl)-3-methylnaphthalen-2-yl)-2-tert-butoxyacetate and 2-phenylbut-3-yn-2-ol. The diastereomers were separated as their ethyl esters using Chiralcel OJ-H with heptane/ethanol (80:20), and then they were saponified independently. Their $^1$H-NMR spectra were identical. $^1$H-NMR: 400 MHz, (CD$_3$OD) δ: 7.76 (d, J=8 Hz, 1H), 7.69 (s, 1H), 7.64 (d, J=8 Hz, 2H), 7.57 (m, 3H), 7.46 (d, J=8 Hz, 1H), 7.33 (m, 5H), 5.18 (s, 1H), 2.61 (s, 3H), 1.75 (s, 3H), 0.98 (s, 9H). LCMS-ESI⁺ (m/z): [M-OH]⁺ calcd for $C_{33}H_{31}ClO_4$: 509.1. found: 508.8.
EXAMPLE 15
(S)-2-tert-Butoxy-2-((R)-1-(2,3-dihydropyrano[4,3,2-de]quinolin-7-yl)-3,7-dimethylnaphthalen-2-yl)acetic acid
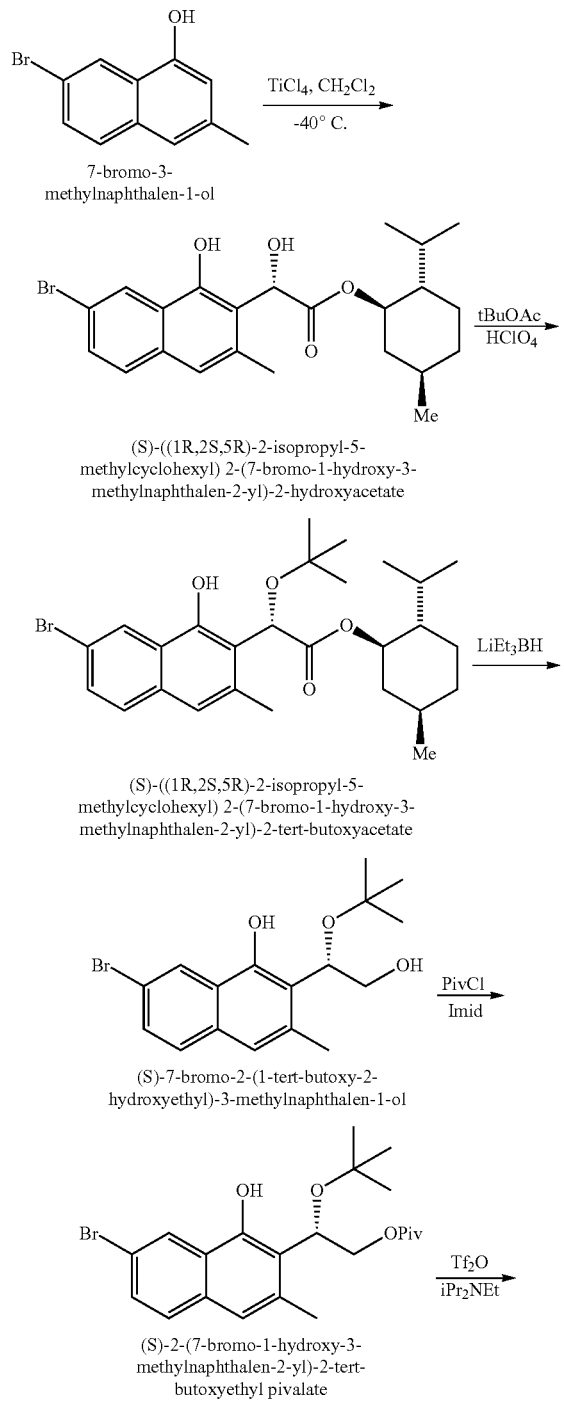
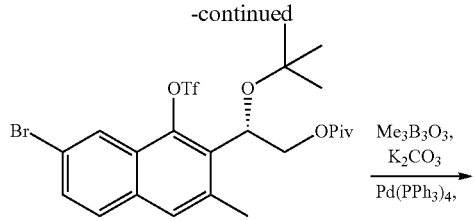
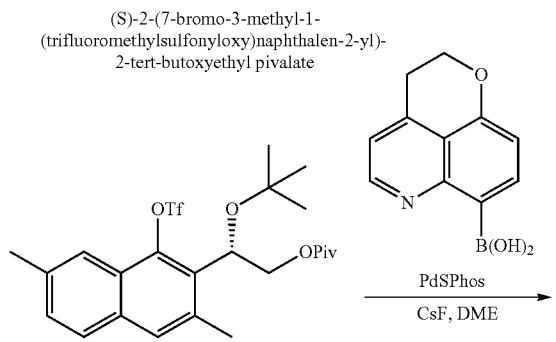
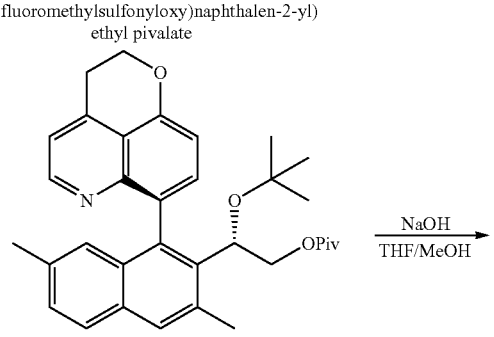
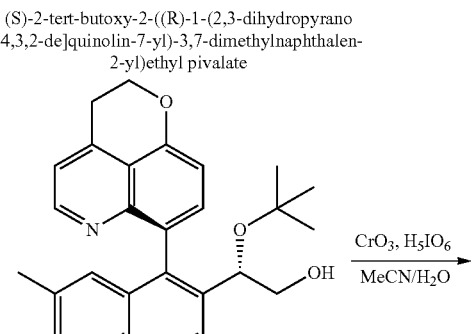
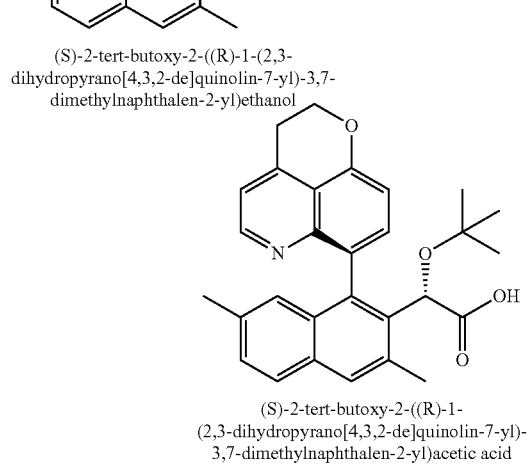

Preparation of (S)-((1R,2S,5R)-2-isopropyl-5-methylcyclohexyl) 2-(7-bromo-1-hydroxy-3-methylnaphthalen-2-yl)-2-hydroxyacetate: To a solution of 7-bromo-3-methylnaphthalen-1-ol (11.8 g, 50.0 mmol) in dichloromethane (25 mL) at −40° C. was added a 1 M titanium(IV) chloride solution in dichloromethane (50.0 mL, 50.0 mmol) and stirred for 20 min. (1R)-(−)-Menthyl glyoxylate hydrate (12.1 g, 52.5 mmol) was added over 15 minutes in small portions as a solid and stirred for 1 hour at 40° C. Then acetic acid (20 mL) and acetonitrile (60 mL) were added while cold. Water (200 mL) was added and the resulting solution was stirred at room temperature for 30 min. The layers were separated, and the aqueous layer was extracted with $CH_2Cl_2$. The combined organic layer was dried, filtered, concentrated. The crude material, which was about 8:1 d.r., was taken on without further purification.

Preparation of (S)-((1R,2S,5R)-2-isopropyl-5-methylcyclohexyl) 2-(7-bromo-1-hydroxy-3-methylnaphthalen-2-yl)-2-tert-butoxyacetate: To a solution of (S)-((1R,2S,5R)-2-isopropyl-5-methylcyclohexyl) 2-(7-bromo-1-hydroxy-3-methylnaphthalen-2-yl)-2-hydroxyacetate in t-BuOAc (150 mL) was added 70% perchloric acid ($HClO_4$) (3.0 mL). After 3 h, water was added. The layers were separated, and the organic layer was dried, filtered, and concentrated in vacuo. The crude material was purified by column chromatography (EtOAc/hexanes). Upon sitting, crystals formed in the resulting oil that were the desired diastereomer. $^1$H-NMR: 400 MHz, ($CDCl_3$) δ: 9.11 (s, 1H), 8.39 (s, 1H), 7.48 (m, 2H), 7.10 (s, 1H), 5.46 (s, 1H), 4.66 (m, 2H), 2.53 (s, 3H), 1.71 (m, 2H), 1.62 (m, 2H), 1.36 (m, 2H), 1.32 (s, 9H), 0.80 (m, 7H), 0.60 (d, J=6 Hz, 3H).

Preparation of (S)-7-bromo-2-(1-tert-butoxy-2-hydroxyethyl)-3-methylnaphthalen-1-ol: To a solution of (S)-((1R,2S,5R)-2-isopropyl-5-methylcyclohexyl) 2-(7-bromo-1-hydroxy-3-methylnaphthalen-2-yl)-2-tert-butoxyacetate (4.56 g, 9.02 mmol) in THF (45 mL) was added lithium triethylborohydride solution (Super Hydride, 1.0 M in THF, 36 mL, 36 mmol). The reaction was stirred at 55° C. for 2.5 h. A saturated solution of $NH_4Cl$ was added. The layers were separated, and the organic layer was dried, filtered, and concentrated in vacuo. The crude material was purified by column chromatography (EtOAc/hexanes) to give 2.84 g. $^1$H-NMR: 400 MHz, ($CDCl_3$) δ: 9.77 (s, 1H), 8.37 (s, 1H), 7.50 (m, 2H), 7.10 (s, 1H), 5.26 (dd, J=9, 4 Hz, 1H), 4.20 (m, 2H), 2.48 (s, 3H), 1.25 (s, 9H) 1.21 (s, 9H).

Preparation of (S)-2-(7-bromo-1-hydroxy-3-methylnaphthalen-2-yl)-2-tert-butoxyethyl pivalate: To a solution of (S)-7-bromo-2-(1-tert-butoxy-2-hydroxyethyl)-3-methylnaphthalen-1-ol (1.84 g, 5.20 mmol) in $CH_2Cl_2$ (15 mL) added imidazole (426 mg, 6.25 mmol) and pivalyl chloride (705 μL, 5.7 mmol). The reaction was stirred at room temperature for 36 h. A saturated solution of $NH_4Cl$ was added. The layers were separated, and the organic layer was dried, filtered, and concentrated in vacuo. The crude material was purified by column chromatography (EtOAc/hexanes) to give the product. $^1$H-NMR: 400 MHz, ($CDCl_3$) δ: 8.21 (s, 1H), 7.63 (m, 2H), 7.26 (s, 1H), 5.47 (dd, J=10, 3 Hz, 1H), 4.62 (dd, J=12, 10 Hz, 1H), 4.14 (dd, J=12, 3 Hz, 1H), 2.75 (s, 3H), 1.22 (s, 9H) 1.11 (s, 9H).

Preparation of (S)-2-(7-bromo-3-methyl-1-(trifluoromethylsulfonyloxy)naphthalen-2-yl)-2-tert-butoxyethyl pivalate: To a solution of (S)-2-(7-bromo-1-hydroxy-3-methylnaphthalen-2-yl)-2-tert-butoxyethyl pivalate (1.70 g, 3.89 mmol) in $CH_2Cl_2$ (20 mL) at −78° C. was added $iPr_2NEt$ (7.8 mmol) and trifluoromethanesulfonic anhydride (5 mmol). After 30 min, a saturated solution of $NH_4Cl$ was added. The layers were separated, and the organic layer was dried, filtered, and concentrated in vacuo. The crude material was purified by column chromatography (EtOAc/hexanes) to give the desired product. $^1$H-NMR: 400 MHz, ($CDCl_3$) δ: 8.21 (s, 1H), 7.63 (m, 2H), 7.26 (s, 1H), 5.47 (dd, J=10, 3 Hz, 1H), 4.62 (dd, J=12, 10 Hz, 1H), 4.14 (dd, J=12, 3 Hz, 1H), 2.75 (s, 3H), 1.22 (s, 9H) 1.11 (s, 9H).

Preparation of (S)-2-tert-butoxy-2-(3,7-dimethyl-1-(trifluoromethylsulfonyloxy)naphthalen-2-yl)ethyl pivalate: To a solution of (S)-2-(7-bromo-3-methyl-1-(trifluoromethylsulfonyloxy)naphthalen-2-yl)-2-tert-butoxyethyl pivalate (825 mg, 1.45 mmol) in 1,4-dioxane (7 mL) was added potassium carbonate (601 mg, 4.35 mmol), trimethylboroxine (220 mg, 1.74 mmol), and PdXPhos catalyst (107 mg, 0.145 mmol). The mixture was heated in a sealed vial in the microwave at 125° C. for 1 h. The mixture was filtered and concentrated in vacuo. The crude material was purified by column chromatography (EtOAc/hexanes) to give the desired product. $^1$H-NMR: 400 MHz, ($CDCl_3$) δ: 7.84 (s, 1H), 7.66 (d, J=8 Hz, 1H), 7.62 (s, 1H), 7.36 (d, J=8 Hz, 1H), 5.48 (dd, J=9, 3 Hz, 1H), 4.65 (dd, J=12, 9 Hz, 1H), 4.16 (dd, J=12, 3 Hz, 1H), 2.75 (s, 3H), 2.54 (s, 3H), 1.23 (s, 9H) 1.12 (s, 9H).

Preparation of (S)-2-tert-butoxy-2-((R)-1-(2,3-dihydropyrano[4,3,2-de]quinolin-7-yl)-3,7-dimethylnaphthalen-2-yl)ethyl pivalate: To a solution of (S)-2-tert-butoxy-2-(3,7-dimethyl-1-(trifluoromethylsulfonyloxy)naphthalen-2-yl)ethyl pivalate (610 mg, 1.2 mmol) in distilled dimethoxyethane (12 mL) was added 2,3-dihydropyrano[4,3,2-de]quinolin-7-yl-boronic acid (HCl salt, 456 mg (1.8 mmol) and cesium fluoride (881 mg, 5.8 mmol). The mixture was stirred in a sealed tube at 115° C. for 4 h. The mixture was diluted with $H_2O$ and EtOAc. The layers were separated, and the organic layer was dried, filtered, and concentrated in vacuo. The crude material was purified by column chromatography (EtOAc with 5% MeOH/hexanes) to give the desired product. $^1$H-NMR: 400 MHz, ($CD_3OD$) δ: 8.46 (d, J=4 Hz, 1H), 7.68 (m, 2H), 7.58 (d, J=8 Hz, 1H), 7.21 (m, 3H), 6.82 (s, 1H), 4.58 (m, 3H), 4.24 (dd, J=12, 9 Hz, 1H), 4.11 (m, 1H), 3.34 (m, 2H), 2.77 (s, 3H), 2.19 (s, 3H), 0.99 (s, 9H), 0.87 (s, 9H).

Preparation of (S)-2-tert-butoxy-2-((R)-1-(2,3-dihydropyrano[4,3,2-de]quinolin-7-yl)-3,7-dimethylnaphthalen-2-yl)ethanol: To a solution of (S)-2-tert-butoxy-2-((R)-1-(2,3-dihydropyrano[4,3,2-de]quinolin-7-yl)-3,7-dimethylnaphthalen-2-yl)ethyl pivalate (352 mg) in THF/MeOH (1:1, 5 mL) was added 2 M NaOH (200 μL). The reaction mixture was stirred at 50° C. for 16 h. A saturated solution of $NH_4Cl$ was added. The layers were separated, and the organic layer was dried, filtered, and concentrated in vacuo. The crude material was purified by column chromatography (EtOAc/hexanes) to give the desired product. $^1$H-NMR: 400 MHz, ($CD_3OD$) δ: 8.50 (d, J=4 Hz, 1H), 7.66 (m, 2H), 7.58 (d, J=8 Hz, 1H), 7.25 (d, J=4 Hz, 1H), 7.20 (m, 2H), 6.83 (s, 1H), 4.56 (m, 3H), 3.69 (dd, J=12, 10 Hz, 1H), 3.43 (dd, J=12, 4 Hz, 1H), 3.36 (m, 2H), 2.78 (s, 3H), 2.15 (s, 3H), 1.04 (s, 9H).

Preparation of (S)-2-tert-butoxy-2-((R)-1-(2,3-dihydropyrano[4,3,2-de]quinolin-7-yl)-3,7-dimethylnaphthalen-2-yl)acetic acid: A stock solution of periodic acid/chromium trioxide was prepared according to WO 99/52850 by dissolving periodic acid (11.4 g, 50.0 mmol) and chromium trioxide (23 mg, 1.2 mol %) in wet acetonitrile (0.75% $H_2O$) to a volume of 114 mL. To a solution of (S)-2-tert-butoxy-2-((R)-1-(2,3-dihydropyrano[4,3,2-de]quinolin-7-yl)-3,7-dimethylnaphthalen-2-yl)ethanol (211 mg) in MeCN (3 mL) was added the above stock solution (200 μL). After 2 h, the mixture was filtered and purified by reverse phase HPLC (MeCN w/0.1% TFA/$H_2O$) to give the desired product. $^1$H-NMR: 400 MHz, ($CD_3OD$) δ: 8.55 (d, J=5 Hz, 1H), 7.69 (m, 2H), 7.53 (d, J=8

Hz, 1H), 7.35 (d, J=5 Hz, 1H), 7.24 (d, J=8 Hz, 1H), 7.18 (d, J=8 Hz, 1H), 6.63 (s, 1H), 5.18 (s, 1H), 4.58 (m, 2H), 3.42 (m, 2H), 2.66 (s, 3H), 2.17 (s, 3H), 0.90 (s, 9H). LCMS-ESI$^+$ (m/z): [M+H]$^+$ calcd for C$_{29}$H$_{29}$NO$_4$: 456.2. Found: 456.1.
EXAMPLE 16
(S)-2-tert-Butoxy-2-((S)-1-(2,3-dihydropyrano[4,3,2-de]quinolin-7-yl)-3,6-dimethylnaphthalen-2-yl)acetic acid
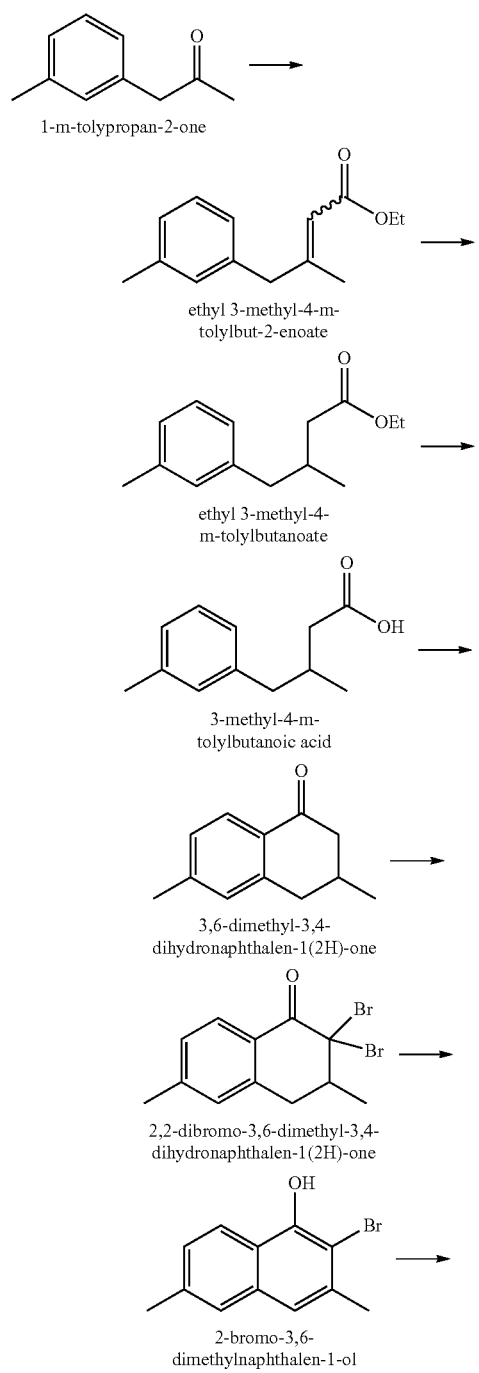
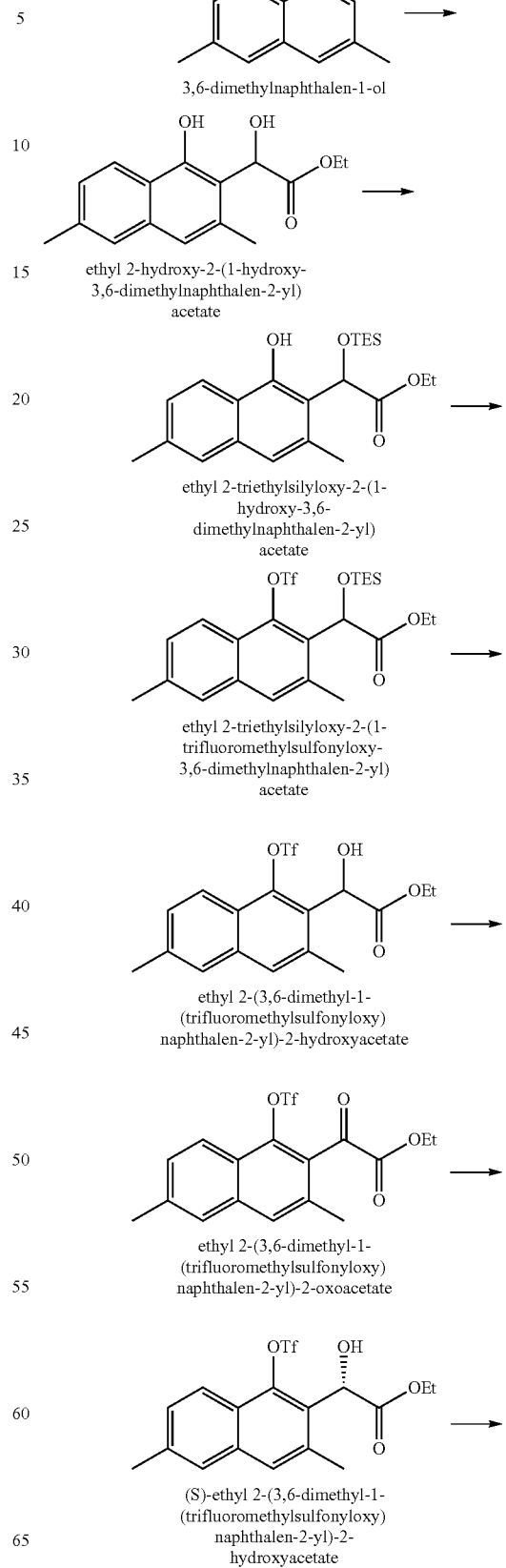

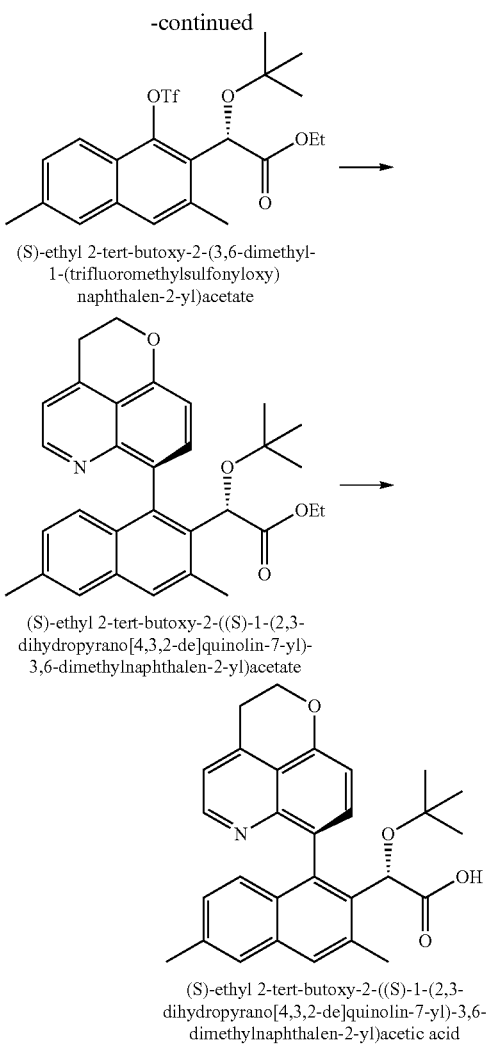

(S)-ethyl 2-tert-butoxy-2-(3,6-dimethyl-1-(trifluoromethylsulfonyloxy)naphthalen-2-yl)acetate (S)-ethyl 2-tert-butoxy-2-((S)-1-(2,3-dihydropyrano[4,3,2-de]quinolin-7-yl)-3,6-dimethylnaphthalen-2-yl)acetate (S)-ethyl 2-tert-butoxy-2-((S)-1-(2,3-dihydropyrano[4,3,2-de]quinolin-7-yl)-3,6-dimethylnaphthalen-2-yl)acetic acid Preparation of ethyl 3-methyl-4-m-tolylbut-2-enoate. A three neck flask was charged with NaHMDS (1M in THF, 59 mL, 59 mmol) under an atmosphere of Ar and cooled to an internal temperature of 0° C. Triethyl phosphonoacetate (10.1 mL, 50.6 mmol) was diluted in THF (41 mL) and added via additional funnel at a rate to maintain a temperature ≤5° C. The resulting yellow-orange solution was allowed to stir for 15 minutes at 0° C. following completion of addition. Following addition of 1-m-tolylpropan-2-one (5 g, 33.7 mmol, diluted in 50 mL THF) via addition funnel, the resulting mixture was allowed to stir at 0° C. for 60 minutes before removing cooling and allowing the reaction to warm to room temperature over 1.5 hours. The reaction was slowly quenched with water, and the resulting aqueous phase extracted thoroughly with EtOAc. The combined organics were washed with brine, dried over anhydrous $MgSO_4$, and concentrated in vacuo. The resulting oil was eluted on Yamazen silica gel chromatography (0-15% EtOAc/hex) to afford 3-methyl-4-m-tolylbut-2-enoate as an approximately 85:15 E:Z mixture. LCMS-ESI$^+$ (m/z): [M+H]$^+$ calcd for $C_{14}H_{19}O_2$: 219.3. found: 219.3.

Preparation of ethyl 3-methyl-4-m-tolylbutanoate. Ethyl 3-methyl-4-m-tolylbutanoate (50 g, 229 mmol) was taken up in EtOAc (1 L) and treated with Rh (5% on alumina, 24 g catalyst). The atmosphere was replaced with $H_2$ and the reaction left under balloon pressure of $H_2$ overnight with vigorous stirring. The next morning, the $H_2$ atmosphere was replaced with air and Celite (25 g) was added with stirring. After 10 min, the reaction slurry was filtered through a pad of Celite and the filtrate concentrated to produce the desired product that was used in the next step without further purification. LCMS-ESI$^+$ (m/z): [M+H]$^+$ calcd for $C_{14}H_{21}O_2$: 221.3. found: 221.2.

Preparation of 3-methyl-4-m-tolylbutanoic acid. The material from the previous preparation was taken up in a 1/1 mixture of THF/EtOH (250 mL each), treated with a solution of LiOH.H$_2$O (46.5 g, 1.1 mol) in water (250 mL) and heated to 50° C. After 2.5 hours, the solution was cooled to 0° C., diluted with EtOAc (300 mL) and treated with 2M HCl (300 mL). The solution was further adjusted to pH~3 using aliquots of concentrated HCl. The resulting aqueous layer was extracted with EtOAc. The combined organics were washed with brine and allowed to stand over anhydrous $Na_2SO_4$ for 72 hours. The EtOAc was removed in vacuo and the resulting oil taken up in hexanes and allowed to stand over anhydrous $Na_2SO_4$ overnight. Following concentration, the material was taken up in $CHCl_3$ and concentrated again to afford 3-methyl-4-m-tolylbutanoic acid. $^1$H-NMR: 400 MHz, (CDCl$_3$) δ: 7.18 (t, J=8 Hz, 1H); 7.02 (d, J=8 Hz, 1H); 6.99 (s, 1H); 6.97 (d, J=8 Hz, 1H); 2.61 (dd, J=13.6, 6.8 Hz, 1H); 2.50 (dd, J=14, 7 Hz, 1H); 2.40 (dd, J=14.8, 5.6 Hz, (1H); 2.34 (s, 3H); 2.28 (m, 1H); 2.18 (dd, J=16, 8 Hz, 1H); 0.99 (d, J=6.4 Hz, 3H).

Preparation of 3,6-dimethyl-3,4-dihydronaphthalen-1(2H)-one. 3-Methyl-4-m-tolylbutanoic acid (20.6 g, 107 mmol, dissolved in 125 mL DCM) was added slowly to triflic acid (250 g, 1.7 mol) that was pre-cooled to 0° C. under an Ar atmosphere. After 30 minutes, the volume of the reaction is doubled with DCM and poured slowly onto 1.5 L crushed ice. The resulting icy slurry is allowed to stir and come to room temperature over 1 hour. The resulting aqueous layer was extracted with DCM and the combined organics dried over anhydrous $MgSO_4$ and concentrated in vacuo. The procedure was repeated once and the two lots of crude product were combined and purified via elution on Isco silica gel column chromatography (0-15% EtOAc/hex) to afford 3,6-dimethyl-3,4-dihydronaphthalen-1(2H)-one. LCMS-ESI$^+$ (m/z): [M+H]$^+$ calcd for $C_{12}H_{15}O$: 175.3. found: 175.4.

Preparation of 2,2-dibromo-3,6-dimethyl-3,4-dihydronaphthalen-1(2H)-one. 3,6-Dimethyl-3,4-dihydronaphthalen-1(2H)-one (32.4 g, 186 mmol) was taken up in DCM (1.5 L and treated with a solution of Br$_2$ (19.1 mL, 372 mmol) in DCM (300 mL) that was added via an addition funnel at room temperature over 2 hours. An additional 1.5 mL of Br$_2$ was added and the reaction allowed to age another 1.5 hours. The reaction was concentrated in vacuo to produce 2,2-dibromo-3,6-dimethyl-3,4-dihydronaphthalen-1(2H)-one that was used directly in the next procedure without further purification. LCMS-ESI$^+$ (m/z): [M+H]$^+$ calcd for $C_{12}H_{13}Br_2O$: 333.1. found: 333.2.

Preparation of 2-bromo-3,6-dimethylnaphthalen-1-ol. A solution of 2,2-dibromo-3,6-dimethyl-3,4-dihydronaphthalen-1(2H)-one (61.2 g, 184 mmol) in MeCN (1.5 L) was cooled to −40° C. internal temperature using a dry ice/acetone bath. 1,8-Diazabicycloundec-7-ene (41.6 mL, 279 mmol) was added as a solution in MeCN (150 mL) and the reaction was allowed to warm to room temperature overnight. The majority of the reaction solvent was removed in vacuo and the residue taken up in EtOAc (1 L) and washed with 0.5 M HCl (1 L). The resulting aqueous layer was extracted with several portions of EtOAc and the combined organics were washed with brine. Following drying over anhydrous $MgSO_4$ and concentration in vacuo, the resulting residue was absorbed directly onto 200 g silica gel and eluted on Isco silica gel column chromatography (0-20% EtOAc/hex) to afford 2-bromo-3,6-dimethylnaphthalen-1-ol. LCMS-ESI$^+$ (m/z): [M]$^+$ calcd for $C_{12}H_{11}BrO$: 251.1. found: 251.4.

Preparation of 3,6-dimethylnaphthalen-1-ol. A solution of 2-bromo-3,6-dimethylnaphthalen-1-ol (31.9 g, 127 mmol) in EtOH (1.3 L) was treated with Et$_3$N (26.6 mL, 191 mmol) at room temperature. Pd/C (13.5 g, 12.7 mmol, 10% wt on C) was added in one portion and the atmosphere replaced with H$_2$. The reaction was left under balloon pressure of H$_2$ for 6 hours. After replacing the atmosphere with air, Celite (20 g) was added and the slurry stirred for 15 minutes before filtering the solution through a pad of Celite. The volatiles were removed in vacuo, and the residue was taken up in EtOAc/water (250 mL each). The organics were washed with brine, dried over anhydrous MgSO$_4$, filtered and concentrated in vacuo. The resulting residue was purified on Isco silica gel column chromatography (0-35% EtOAc/hex) to afford 3,6-dimethylnaphthalen-1-ol. LCMS-ESI$^+$ (m/z): [M+H]$^+$ calcd for $C_{12}H_{13}O$: 173.1. found: 173.4.

Preparation of ethyl 2-hydroxy-2-(1-hydroxy-3,6-dimethylnaphthalen-2-yl)acetate. A solution of 3,6-dimethylnaphthalen-1-ol (4.76 g, 27.6 mmol) in DCM (345 mL) was cooled to 0° C. internal temperature. TiCl$_4$ (1M in DCM, 36 mL, 36 mmol) was added at a rate to maintain the internal temperature at 0° C. to produce a dark purple solution that was allowed to stir at 0° C. for 20 min. Freshly distilled ethyl glyoxylate (3.66 g, 35.9 mmol) was gently warmed with a heat gun for 3 minutes prior to dilution in DCM (250 mL). The reagent solution was then added via addition funnel slowly. After 90 minutes, the reaction was poured onto 800 mL ice/500 mL saturated Rochelle's salt solution. The opaque orange slurry was allowed to come to room temperature over 2.5 hours and filtered through a Celite pad. The aqueous phase was extracted with DCM and the combined organics were washed with water, brine, and dried over anhydrous MgSO$_4$, and filtered. Following concentration in vacuo, the resulting residue was purified via Yamazen silica gel column chromatography (3-35% EtOAc/hex) to provide 2-hydroxy-2-(1-hydroxy-3,6-dimethylnaphthalen-2-yl)acetate. LCMS-ESI$^+$ (m/z): [M-OH]$^+$ calcd for $C_{16}H_{17}O_3$: 257.3. found: 257.5.

Preparation of ethyl 2-triethylsilyloxy-2-(1-hydroxy-3,6-dimethylnaphthalen-2-yl)acetate. A solution of 2-hydroxy-2-(1-hydroxy-3,6-dimethylnaphthalen-2-yl)acetate (4.55 g, 16.6 mmol) in DCM (165 mL) at 0° C. was subsequently treated with imidazole (1.53 g, 22.4 mmol) and triethylsilyl chloride (3.2 mL, 19.1 mmol). The cooling bath was removed and the reaction allowed to warm to room temperature over 1.5 hours. Water was added, and the resulting aqueous layer was extracted with DCM. The combined organics were washed with 1M HCl and brine. Following drying over anhydrous MgSO$_4$, concentration in vacuo afforded the desired product that was used without further purification.

Preparation of ethyl 2-triethylsilyloxy-2-(1-trifluoromethylsulfonyloxy-3,6-dimethylnaphthalen-2-yl)acetate. A solution of ethyl 2-triethylsilyloxy-2-(1-hydroxy-3,6-dimethylnaphthalen-2-yl)acetate (5.62 g of crude product from above, 14.5 mmol) in THF (58 mL) was treated with phenyl triflimide (7.75 g, 21.7 mmol) and Cs$_2$CO$_3$ (11.8 g, 36.3 mmol) at room temperature. After 3 hours, the reaction was diluted with EtOAc and water. The resulting organics were washed with 1M NaOH and brine. Following drying over MgSO$_4$ and concentration in vacuo, the resulting residue was purified via Yamazen silica gel column chromatography (0-10% EtOAc/hex) to afford ethyl 2-triethylsilyloxy-2-(1-trifluoromethylsulfonyloxy-3,6-dimethylnaphthalen-2-yl)acetate. LCMS-ESI$^+$ (m/z): [M+Na]$^+$ calcd for $C_{23}H_{31}F_3O_6SSiNa$: 543.6. found: 543.0.

Preparation of ethyl 2-(3,6-dimethyl-1-(trifluoromethylsulfonyloxy)naphthalen-2-yl)-2-hydroxyacetate. A solution of ethyl 2-triethylsilyloxy-2-(1-trifluoromethylsulfonyl-oxy-3,6-dimethylnaphthalen-2-yl)acetate (~29 g) in THF (375 mL) was treated with 48% HF (71 mL, 1.96 mol) at room temperature and allowed to stir overnight. Solid NaHCO$_3$ was added in small portions until pH~8 by test strip. Water and EtOAc were added, and the layers separated. The aqueous layer was slurried with Celite, filtered through a Celite pad and further extracted with EtOAc. The combined organics were washed with brine, dried over anhydrous MgSO$_4$, filtered and concentrated in vacuo. The resulting ethyl 2-(3,6-dimethyl-1-(trifluoromethylsulfonyloxy)naphthalen-2-yl)-2-hydroxyacetate was used without further purification. LCMS-ESI$^+$ (m/z): [M-OH]$^+$ calcd for $C_{17}H_{16}F_3O_5S$: 389.4. found: 389.4.

Preparation of ethyl 2-(3,6-dimethyl-1-(trifluoromethylsulfonyloxy)naphthalen-2-yl)-2-oxoacetate. A solution of ethyl 2-(3,6-dimethyl-1-(trifluoromethylsulfonyloxy) naphthalen-2-yl)-2-hydroxyacetate (~22.8 g, 56 mmol) in DCM (560 mL) was treated with solid Dess-Martin periodinane (35.7 g, 84.2 mmol) at room temperature. After 60 minutes, isopropyl alcohol (25 mL) was added and allowed to stir for 30 minutes. A mixture of saturated NaHCO$_3$ and saturated Na$_2$S$_2$O$_3$ (100 mL each, diluted to 400 mL with water) was added and the resulting aqueous layer extracted with DCM. The combined organics were washed with water, brine and dried over anhydrous MgSO$_4$ and filtered. Following concentration in vacuo, the residue was purified via Isco silica gel column chromatography (0-35% EtOAc/hex) to afford ethyl 2-(3,6-dimethyl-1-(trifluoromethylsulfonyloxy)naphthalen-2-yl)-2-oxoacetate. $^1$H-NMR: 400 MHz, (CDCl$_3$) δ: 7.98 (d, J=8.4 Hz, 1H); 7.66 (s, 1H); 7.61 (s, 1H); 7.47 (d, J=8.4 Hz, 1H); 4.41 (q, J=7.2 Hz, 2H); 2.55 (s, 3H); 2.49 (s, 3H); 1.40 (t, J=8.4 Hz, 3H).

Preparation of (S)-ethyl 2-(3,6-dimethyl-1-(trifluoromethylsulfonyloxy) naphthalen-2-yl)-2-hydroxyacetate. A solution of ethyl 2-(3,6-dimethyl-1-(trifluoromethylsulfonyloxy) naphthalen-2-yl)-2-oxoacetate (16.3 g, 40 mmol) in toluene (250 mL) cooled to an internal temperature of −40° C. was treated with (R)-(+)-2-methyl-CBS-oxazaborolidine (5.6 g, 20.1 mmol). Freshly distilled catecholborane (4.7 mL, 44.2 mmol) was diluted with toluene (20 mL) and the solution added dropwise to the reaction over 30 minutes to produce a clear yellow solution. After an additional 15 minutes, saturated Na$_2$CO$_3$ (300 mL) was added and the reaction allowed to warm to room temperature over 2.5 hours. The aqueous layer is extracted with EtOAc and the combined organics are washed with saturated Na$_2$CO$_3$ (3×300 mL), saturated NH$_4$Cl (300 mL) and brine. Following drying over anhydrous MgSO$_4$ and concentration in vacuo, the residue was purified using Isco silica gel column chromatography (10-75% EtOAc/hex) to produce 15.1 g of (S)-ethyl 2-(3,6-dimethyl-1-(trifluoromethylsulfonyloxy)naphthalen-2-yl)-2-hydroxyacetate that was determined to be 66% enantiomeric excess by HPLC analysis on a Chiralpak AS-H column with a 80:20 heptane/EtOH isocratic method. LCMS-ESI+ (m/z): [M+Na]+ calcd for $C_{17}H_{17}F_3O_6SNa$: 429.3. found: 429.3.

Preparation of (S)-ethyl 2-tert-butoxy-2-(3,6-dimethyl-1-(trifluoromethylsulfonyl-oxy)naphthalen-2-yl)acetate. A solution of (S)-ethyl 2-(3,6-dimethyl-1-(trifluoromethyl-sulfonyloxy)naphthalen-2-yl)-2-hydroxyacetate (7.5 g, 18.5 mmol) in tBuOAc (100 mL) at room temperature was treated with perchloric acid (70%, 0.16 mL, 1.8 mmol) and allowed to stir at room temperature overnight. The reaction was slowly poured into ice-cold saturated NaHCO₃ (150 mL). The aqueous layer was extracted with EtOAc and the combined organics washed with brine and dried over anhydrous MgSO₄ and filtered. Following concentration in vacuo, purification of the residue by Yamazen silica gel column chromatography (2-20-50% EtOAc/hex) afforded (S)-ethyl 2-tert-butoxy-2-(3,6-dimethyl-1-(trifluoromethylsulfonyloxy)naphthalen-2-yl)acetate. LCMS-ESI+ (m/z): [M+Na]+ calcd for $C_{21}H_{25}F_3O_6SNa$: 485.5. found: 485.8.

Preparation of (S)-ethyl 2-tert-butoxy-2-((R)-1-(2,3-dihydropyrano[4,3,2-de]quinolin-7-yl)-3,6-dimethylnaphthalen-2-yl)acetate and (S)-ethyl 2-tert-butoxy-2-((S)-1-(2,3-dihydropyrano[4,3,2-de]quinolin-7-yl)-3,6-dimethylnaphthalen-2-yl)acetate. A solution of (S)-ethyl 2-tert-butoxy-2-(3,6-dimethyl-1-(trifluoromethylsulfonyl-oxy)naphthalen-2-yl)acetate (~0.5 g, 1.1 mmol) in 10.8 mL DME (freshly distilled from Na/benzophenone) was treated with 2,3-dihydropyrano[4,3,2-de]quinolin-7-ylboronic acid hydrochloride (0.33 g, 1.3 mmol), SPhos precatalyst (Strem, 0.073 g, 0.11 mmol), and CsF (0.722 g, 4.8 mmol). The reaction tube was sealed and the reaction mixture sparged with Ar for 30 minutes prior to heating at 120° C. for 90 minutes in a microwave reactor. The reaction mixture was absorbed directly onto silica gel and purified via Yamazen silica gel column chromatography (3-50% EtOAc/hex) to afford (S)-ethyl 2-tert-butoxy-2-((R)-1-(2,3-dihydropyrano[4,3,2-de]quinolin-7-yl)-3,6-dimethylnaphthalen-2-yl)acetate (¹H-NMR: 400 MHz, (CDCl₃) δ: 8.68 (br s, 1H); 7.64 (s, 1H); 7.54 (s, 1H); 7.49 (d, J=8 Hz, 1H); 7.11 (d, J=8 Hz, 1H); 7.08 (br s, 1H); 6.99-6.84 (m, 2H); 5.08 (s, 1H); 4.58 (t, J=6 Hz, 2H); 3.98 (m, 1H); 3.82 (m, 1H); 3.34 (m, 2H); 2.78 (s, 3H); 2.42 (s, 3H); 0.97 (s, 9H); 0.97 (obscured t, 3H)) and (S)-ethyl 2-tert-butoxy-2-((S)-1-(2,3-dihydropyrano[4,3,2-de]quinolin-7-yl)-3,6-dimethylnaphthalen-2-yl)acetate (¹H-NMR: 400 MHz, (CDCl₃) δ: 8.64 (d, J=4 Hz, 1H); 7.73 (d, J=8 Hz, 1H); 7.60 (s, 1H); 7.53 (s, 1H); 7.11 (d, J=8 Hz, 1H); 7.04 (d, J=4 Hz, 1H); 6.93 (dd, J=8, 1.2 Hz, 1H); 6.82 (d, J=8 Hz, 1H); 5.12 (s, 1H); 4.57 (t, J=5.6 Hz, 2H); 4.20-4.04 (m, 2H); 3.33 (m, 2H); 2.65 (s, 3H); 2.42 (s, 3H); 1.22 (t, J=7.2 Hz, 3H); 0.76 (s, 9H)).

Preparation of (S)-2-tert-butoxy-2-((S)-1-(2,3-dihydropyrano[4,3,2-de]quinolin-7-yl)-3,6-dimethylnaphthalen-2-yl)acetic acid. A solution of (S)-ethyl 2-tert-butoxy-2-((S)-1-(2,3-dihydropyrano[4,3,2-de]quinolin-7-yl)-3,6-dimethylnaphthalen-2-yl)acetate (1.06 g, 2.2 mmol) in THF (32 mL)/MeOH (16 mL)/water (18 mL) was treated with LiOH.H₂O (0.92 g, 22 mmol) and heated to 60° C. for 24 hours. The reaction mixture was filtered through glass wool, concentrated in vacuo and purified via preparatory HPLC to produce (S)-2-tert-butoxy-2-((S)-1-(2,3-dihydropyrano[4,3,2-de]quinolin-7-yl)-3,6-dimethylnaphthalen-2-yl)acetic acid (TFA salt). LCMS-ESI+ (m/z): [M+H]+ calcd for $C_{29}H_{30}NO_4$: 456.5. found: 456.8.

EXAMPLE 17

(S)-2-tert-Butoxy-2-((R)-1-(2,3-dihydropyrano[4,3,2-de]quinolin-7-yl)-4-fluoro-3,6-dimethylnaphthalen-2-yl)acetic acid and (S)-2-tert-butoxy-2-((S)-1-(2,3-dihydropyrano[4,3,2-de]quinolin-7-yl)-4-fluoro-3,6-dimethyl-naphthalen-2-yl)acetic acid

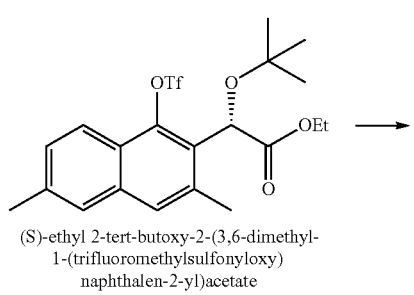

(S)-ethyl 2-tert-butoxy-2-(3,6-dimethyl-1-(trifluoromethylsulfonyloxy) naphthalen-2-yl)acetate

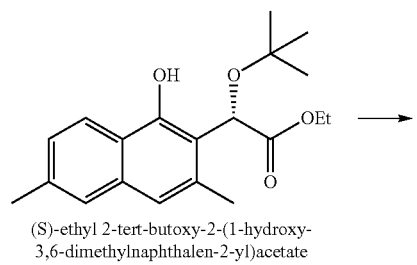

(S)-ethyl 2-tert-butoxy-2-(1-hydroxy-3,6-dimethylnaphthalen-2-yl)acetate

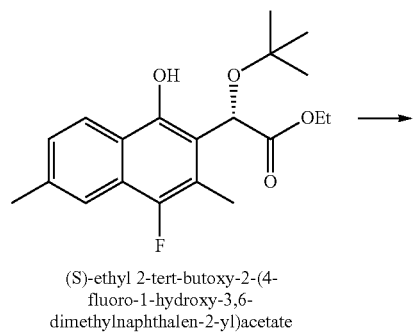

(S)-ethyl 2-tert-butoxy-2-(4-fluoro-1-hydroxy-3,6-dimethylnaphthalen-2-yl)acetate

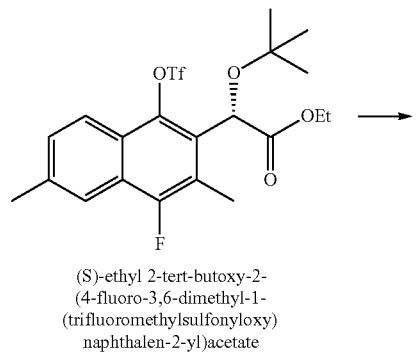

(S)-ethyl 2-tert-butoxy-2-(4-fluoro-3,6-dimethyl-1-(trifluoromethylsulfonyloxy) naphthalen-2-yl)acetate

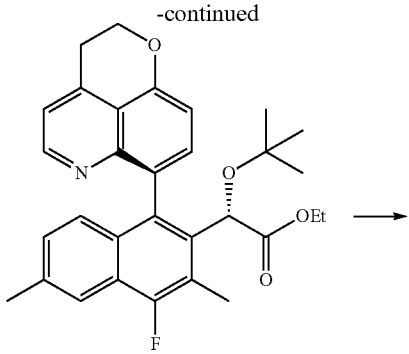

(S)-ethyl 2-tert-butoxy-2-((R)-1-(2,3-dihydropyrano[4,3,2-de]quinolin-7-yl)-4-fluoro-3,6-dimethylnaphthalen-2-yl)acetate

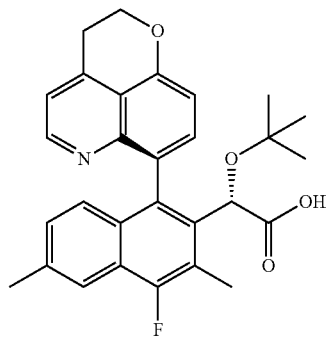

(S)-2-tert-butoxy-2-((R)-1-(2,3-dihydropyrano[4,3,2-de]quinolin-7-yl)-4-fluoro-3,6-dimethylnaphthalen-2-yl)acetic acid

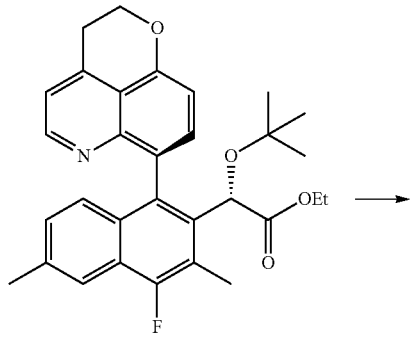

(S)-ethyl 2-tert-butoxy-2-((S)-1-(2,3-dihydropyrano[4,3,2-de]quinolin-7-yl)-4-fluoro-3,6-dimethylnaphthalen-2-yl)acetate

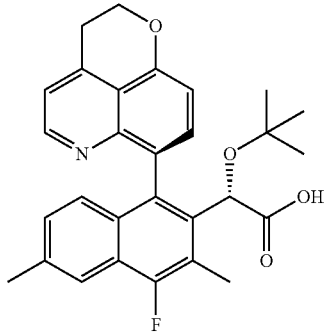

(S)-2-tert-butoxy-2-((S)-1-(2,3-dihydropyrano[4,3,2-de]quinolin-7-yl)-4-fluoro-3,6-dimethylnaphthalen-2-yl)acetic acid Preparation of (S)-ethyl 2-tert-butoxy-2-(1-hydroxy-3,6-dimethylnaphthalen-2-yl)acetate. A solution of (S)-ethyl 2-tert-butoxy-2-(3,6-dimethyl-1-(trifluoromethyl-sulfonyloxy) naphthalen-2-yl)acetate (1.8 g, 3.9 mmol) in THF (18.2 mL) pre-cooled to −10° C. was treated dropwise with tetrabutylammonium fluoride (1M in THF, 7.8 mL, 7.8 mmol). After 1 hour, saturated NaHCO$_3$ was added and the mixture stirred for 20 minutes. Following extraction of the aqueous layer with EtOAc, the combined organics were washed with brine, dried over anhydrous MgSO$_4$, filtered and concentrated in vacuo. Purification via Yamazen silica gel column chromatography afforded (S)-ethyl 2-tert-butoxy-2-(1-hydroxy-3,6-dimethylnaphthalen-2-yl)acetate. LCMS-ESI⁻ (m/z): [M−H]⁻ calcd for C$_{20}$H$_{25}$O$_4$: 329.4. found: 329.1.

Preparation of (S)-ethyl 2-tert-butoxy-2-(4-fluoro-1-hydroxy-3,6-dimethylnaphthalen-2-yl)acetate. A solution of (S)-ethyl 2-tert-butoxy-2-(1-hydroxy-3,6-dimethylnaphthalen-2-yl)acetate (0.62 g, 1.9 mmol) in MeCN (14 mL) cooled to 0° C. was treated with SelectFluor® fluorinating reagent (0.66 g, 1.9 mmol). The cold bath was removed and after 90 minutes the reaction was quenched with pH 7 buffer solution. The aqueous layer was extracted with EtOAc and the combined organics washed with brine and dried over anhydrous MgSO$_4$ and filtered. Following concentration in vacuo, the desired product was obtained via silica gel chromatography followed by preparatory HPLC to afford (S)-ethyl 2-tert-butoxy-2-(4-fluoro-1-hydroxy-3,6-dimethylnaphthalen-2-yl)acetate. LCMS-ESI⁻ (m/z): [M−H]⁻ calcd for C$_{20}$H$_{24}$O$_4$F: 347.4. found: 347.2.

Preparation of (S)-ethyl 2-tert-butoxy-2-(4-fluoro-3,6-dimethyl-1-(trifluoromethyl-sulfonyloxy)naphthalen-2-yl) acetate. A solution of (S)-ethyl 2-tert-butoxy-2-(4-fluoro-1-hydroxy-3,6-dimethylnaphthalen-2-yl)acetate (0.225 g, 0.65 g) in THF (5 mL) was treated with phenyl triflimide (0.26 g, 0.72 mmol) and allowed to stir at room temperature overnight. The reaction mixture was absorbed directly onto silica gel and purified via Yamazen silica gel column chromatography to afford (S)-ethyl 2-tert-butoxy-2-(4-fluoro-3,6-dimethyl-1-(trifluoromethylsulfonyloxy)naphthalen-2-yl)acetate. ¹H-NMR: 400 MHz, (CDCl$_3$) δ: 7.93 (d, J=8.4 Hz, 1H); 7.86 (s, 1H); 7.47 (d, J=8.4 Hz, 1H); 5.70 (s, 1H); 4.28-4.09 (m, 2H); 2.56 (s, 3H); 2.44 (d, J$_{HF}$=2.8 Hz, 3H); 1.21 (s, 9H); 1.19 (t, J=6.8 Hz, 3H).

Preparation of (S)-ethyl 2-tert-butoxy-2-((R)-1-(2,3-dihydropyrano[4,3,2-de]quinolin-7-yl)-4-fluoro-3,6-dimethylnaphthalen-2-yl)acetate and (S)-ethyl 2-tert-butoxy-2-((S)-1-(2,3-dihydropyrano[4,3,2-de]quinolin-7-yl)-4-fluoro-3,6-dimethylnaphthalen-2-yl)acetate. (S)-ethyl 2-tert-butoxy-2-((R)-1-(2,3-dihydropyrano[4,3,2-de]quinolin-7-yl)-4-fluoro-3,6-dimethylnaphthalen-2-yl)acetate and (S)-ethyl 2-tert-butoxy-2-((S)-1-(2,3-dihydropyrano[4,3,2-de]quinolin-7-yl)-4-fluoro-3,6-dimethylnaphthalen-2-yl)acetate were prepared in a similar fashion to (S)-ethyl 2-tert-butoxy-2-((R)-1-(2,3-dihydropyrano[4,3,2-de]quinolin-7-yl)-3,6-dimethylnaphthalen-2-yl)acetate and (S)-ethyl 2-tert-butoxy-2-((S)-1-(2,3-dihydropyrano[4,3,2-de]quinolin-7-yl)-3,6-dimethylnaphthalen-2-yl)acetate beginning with (S)-ethyl 2-tert-butoxy-2-(4-fluoro-3,6-dimethyl-1-(trifluoromethyl-sulfonyloxy)naphthalen-2-yl)acetate. Purification via Yamazen silica gel column chromatography afforded (S)-ethyl 2-tert-butoxy-2-((R)-1-(2,3-dihydropyrano[4,3,2-de]quinolin-7-yl)-4-fluoro-3,6-dimethylnaphthalen-2-yl)acetate. (LCMS-ESI⁺ (m/z): [M+H]⁺ calcd for C$_{31}$H$_{33}$FNO$_4$: 502.6. found: 502.6) and (S)-ethyl 2-tert-butoxy-2-((S)-1-(2,3-dihydropyrano[4,3,2-de]quinolin-7-yl)-4-fluoro-3,6-dimethylnaphthalen-2-yl)acetate. LCMS-ESI⁺ (m/z): [M+H] calcd for $C_{31}H_{33}FNO_4$: 502.6. found: 502.6.

Preparation of (S)-2-tert-butoxy-2-((R)-1-(2,3-dihydropyrano[4,3,2-de]quinolin-7-yl)-4-fluoro-3,6-dimethylnaphthalen-2-yl)acetic acid. A solution of (S)-ethyl 2-tert-butoxy-2-((R)-1-(2,3-dihydropyrano[4,3,2-de]quinolin-7-yl)-4-fluoro-3,6-dimethylnaphthalen-2-yl)acetate in THF/MeOH/water (1 mL each) was treated with LiOH.H₂O (0.055 g, 1.3 mmol), sealed and heated to 60° C. overnight for 2 days. The reaction is purified by preparatory HPLC to afford (S)-2-tert-butoxy-2-((R)-1-(2,3-dihydropyrano[4,3,2-de]quinolin-7-yl)-4-fluoro-3,6-dimethylnaphthalen-2-yl)acetic acid (TFA salt). LCMS-ESI⁺ (m/z): [M+H]⁺ calcd for $C_{29}H_{29}FNO_4$: 474.5. found: 474.5. ¹H-NMR: 400 MHz, (CD₃OD) δ: 8.65 (d, J=5.6 Hz, 1H); 7.95 (s, 1H); 7.81 (d, J=8.4 Hz, 1H); 7.73 (d, J=5.2 Hz, 1H); 7.42 (d, J=8.4 Hz, 1H); 7.19 (dd, J=8.8, 1.2 Hz, 1H); 6.85 (br d, J=8.8 Hz, 1H); 5.17 (s, 1H); 4.70-4.65 (m, 2H); 3.63 (t, J=6 Hz, 2H); 2.64 (d, $J_{HF}$=2.8 Hz, 3H); 2.50 (s, 3H); 0.96 (9H).

Preparation of (S)-2-tert-butoxy-2-((S)-1-(2,3-dihydropyrano[4,3,2-de]quinolin-7-yl)-4-fluoro-3,6-dimethylnaphthalen-2-yl)acetic acid. (S)-2-tert-Butoxy-2-((S)-1-(2,3-dihydropyrano[4,3,2-de]quinolin-7-yl)-4-fluoro-3,6-dimethylnaphthalen-2-yl)acetic acid was prepared in a similar fashion to (S)-2-tert-butoxy-2-((R)-1-(2,3-dihydropyrano[4,3,2-de]quinolin-7-yl)-4-fluoro-3,6-dimethylnaphthalen-2-yl)acetic acid beginning with (S)-ethyl 2-tert-butoxy-2-((S)-1-(2,3-dihydropyrano[4,3,2-de]quinolin-7-yl)-4-fluoro-3,6-dimethylnaphthalen-2-yl)acetate to afford (S)-2-tert-butoxy-2-((S)-1-(2,3-dihydropyrano[4,3,2-de]quinolin-7-yl)-4-fluoro-3,6-dimethylnaphthalen-2-yl)acetic acid. LCMS-ESI⁺ (m/z): [M+H]⁺ calcd for $C_{29}H_{29}FNO_4$: 474.5. found: 474.5.

EXAMPLE 18

(S)-2-tert-Butoxy-2-((R)-1-(2,3-dihydropyrano[4,3,2-de]quinolin-7-yl)-3,5-dimethylnaphthalen-2-yl)acetic acid and (S)-2-tert-butoxy-2-((S)-1-(2,3-dihydropyrano[4,3,2-de]quinolin-7-yl)-3,5-dimethylnaphthalen-2-yl)acetic acid

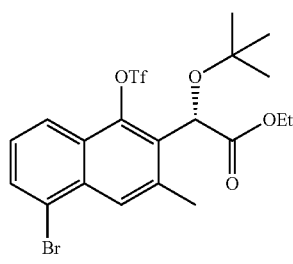

(S)-ethyl 2-(5-bromo-3-methyl-1-(trifluoromethylsulfonyloxy)naphthalen-2-yl)-2-tert-butoxyacetate

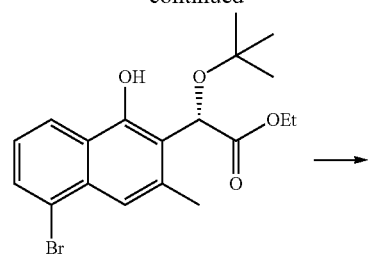

(S)-ethyl 2-(5-bromo-1-hydroxy-3-methylnaphthalen-2-yl)-2-tert-butoxyacetate

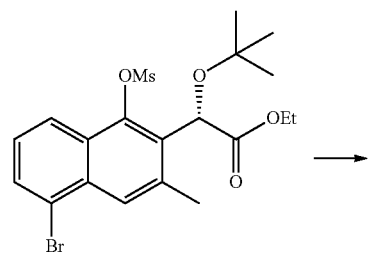

(S)-ethyl 2-(5-bromo-3-methyl-1-(methylsulfonyloxy)naphthalen-2-yl)-2-tert-butoxyacetate

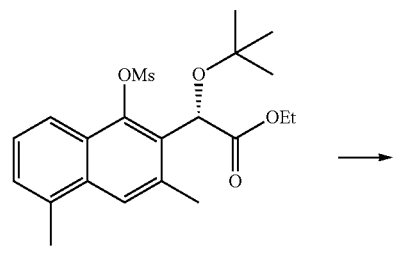

(S)-ethyl 2-tert-butoxy-2-(3,5-dimethyl-1-(methylsulfonyloxy)naphthalen-2-yl)acetate

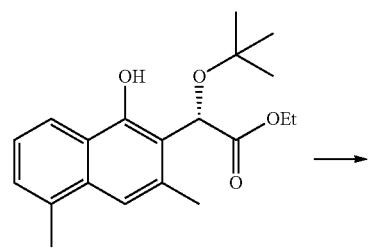

(S)-ethyl 2-tert-butoxy-2-(1-hydroxy-3,5-dimethylnaphthalen-2-yl)acetate

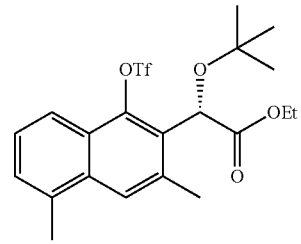

(S)-ethyl 2-tert-butoxy-2-(3,5-dimethyl-1-(trifluoromethylsulfonyloxy)naphthalen-2-yl)acetate 279
-continued


(S)-ethyl 2-tert-butoxy-2-((R)-1-
(2,3-dihydropyrano[4,3,2-de]
quinolin-7-yl)-3,5-
dimethylnaphthalen-2-yl)acetate

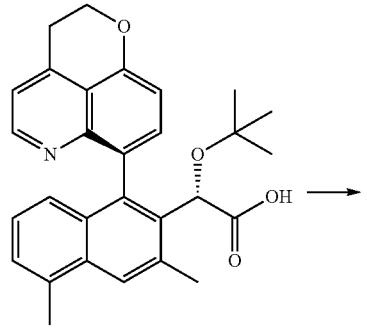

(S)-2-tert-butoxy-2-((R)-1-
(2,3-dihydropyrano[4,3,2-de]
quinolin-7-yl)-3,5-
dimethylnaphthalen-2-yl)acetic acid

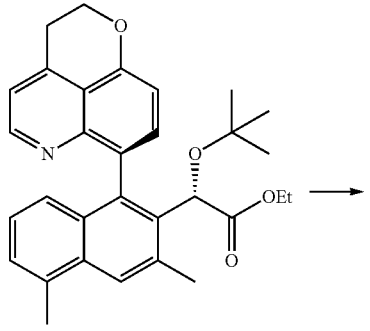

(S)-ethyl 2-tert-butoxy-2-((S)-1-
(2,3-dihydropyrano[4,3,2-de]
quinolin-7-yl)-3,5-
dimethylnaphthalen-2-yl)acetate

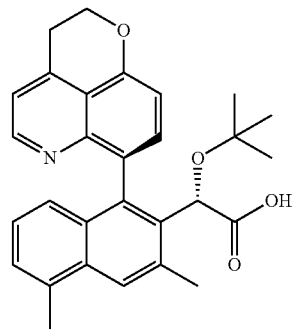

(S)-2-tert-butoxy-2-((S)-1-
(2,3-dihydropyrano[4,3,2-de]
quinolin-7-yl)-3,5-
dimethylnaphthalen-2-yl)acetic acid

280

Preparation of (S)-ethyl 2-(5-bromo-1-hydroxy-3-methyl-naphthalen-2-yl)-2-tert-butoxyacetate. A solution of (S)-ethyl 2-(5-bromo-3-methyl-1-(trifluoromethylsulfonyloxy)naphthalen-2-yl)-2-tert-butoxyacetate (0.90 g, 1.7 mmol; prepared in a similar fashion to (S)-ethyl 2-tert-butoxy-2-(3,6-dimethyl-1-(trifluoromethylsulfonyloxy)naphthalen-2-yl)acetate beginning with 1-(2-bromophenyl)propan-2-one) in THF (7 mL) cooled to 0° C. was treated with tetrabutylammonium fluoride (1M in THF, 1.7 mL, 1.7 mmol) dropwise. After 1 hour, saturated NaHCO$_3$ and EtOAc were added and the aqueous layer extracted with EtOAc. The combined organics were washed with brine, dried over anhydrous MgSO$_4$, filtered, and concentrated in vacuo. Purification via Yamazen column chromatography (0-15% EtOAc/hex) afforded (S)-ethyl 2-(5-bromo-1-hydroxy-3-methylnaphthalen-2-yl)-2-tert-butoxyacetate. LCMS-ESI$^-$ (m/z): [M−H]$^-$ calcd for $C_{19}H_{22}O_4Br$: 395.07. found: 395.04.

Preparation of (S)-ethyl 2-(5-bromo-3-methyl-1-(methylsulfonyloxy)naphthalen-2-yl)-2-tert-butoxyacetate. A solution of (S)-ethyl 2-(5-bromo-1-hydroxy-3-methylnaphthalen-2-yl)-2-tert-butoxyacetate (0.215 g, 0.54 mmol) in DCM (5 mL) cooled to 0° C. was treated with methanesulfonic anhydride (0.142 g, 0.82 mmol) and diisopropylethylamine (0.28 mL, 1.6 mmol). After 1 hour, the reaction mixture was loaded directly onto silica gel and eluted via Yamazen column chromatography (0-40% EtOAc/hex) to afford (S)-ethyl 2-(5-bromo-3-methyl-1-(methylsulfonyloxy)naphthalen-2-yl)-2-tert-butoxyacetate. $^1$H-NMR: 400 MHz, (CDCl$_3$) δ: 8.25 (br d, J=8 Hz, 1H); 8.04 (s, 1H); 7.81 (d, J=7.2 Hz, 1H); 7.38 (dd, J=8, 7.2 Hz, 1H); 5.72 (s, 1H); 4.28-4.10 (m, 2H); 3.49 (s, 3H); 2.67 (s, 3H); 1.24 (s, 9H); 1.19 (t, J=7.2 Hz, 3H).

Preparation of (S)-ethyl 2-tert-butoxy-2-(3,5-dimethyl-1-(methylsulfonyloxy) naphthalen-2-yl)acetate. A solution of (S)-ethyl 2-(5-bromo-3-methyl-1-(methylsulfonyloxy)naphthalen-2-yl)-2-tert-butoxyacetate (0.47 g, 0.99 mmol) in toluene/EtOH (6 mL/2.5 mL) was treated with trimethylboroxine (0.42 mL, 3 mmol), PdCl$_2$dppf (0.036 g, 0.05 mmol) and K$_2$CO$_3$ (2M, 1.5 mL, 3 mmol). The vessel was sealed and sparged with Ar for 20 minutes prior to heating in a microwave reactor at 125° C. for 90 minutes. The reaction mixture was loaded directly onto silica gel and purified via Yamazen column chromatography to afford (S)-ethyl 2-tert-butoxy-2-(3,5-dimethyl-1-(methylsulfonyloxy)naphthalen-2-yl)acetate that was approximately an 85:15 mixture with an inseparable, uncharacterized side product. $^1$H-NMR: 400 MHz, (CDCl$_3$) δ: 8.09 (br d, J=8.4 Hz, 1H); 7.77 (s, 1H); 7.44 (dd, J=8.4, 7.2 Hz, 1H); 7.35 (d, J=7.2 Hz, 1H); 5.77 (s, 1H); 4.27-4.09 (m, 2H); 3.43 (s, 3H); 2.68 (s, 3H); 2.63 (s, 3H); 1.24 (s, 9H); 1.20 (t, J=7.2 Hz, 3H).

Preparation of (S)-ethyl 2-tert-butoxy-2-(1-hydroxy-3,5-dimethylnaphthalen-2-yl)acetate. A solution of (S)-ethyl 2-tert-butoxy-2-(3,5-dimethyl-1-(methylsulfonyloxy)naphthalen-2-yl)acetate (0.19 g, 0.48 mmol) in THF (3 mL) cooled to 0° C. was treated with tetrabutylammonium fluoride (1M in THF, 1.4 mL, 1.4 mmol). After 1 hour, saturated NaHCO$_3$ was added and the aqueous layer extracted with EtOAc. The combined organics are washed with brine, dried over anhydrous MgSO$_4$, filtered, and concentrated in vacuo. Purification via Yamazen column chromatography afforded (S)-ethyl 2-tert-butoxy-2-(1-hydroxy-3,5-dimethylnaphthalen-2-yl)acetate that is contaminated with a small percentage of an inseparable, uncharacterized side product. $^1$H-NMR: 400 MHz, (CDCl$_3$) δ: 8.96 (s, 1H); 8.13 (obs m, 1H); 7.30 (obs m, 2H); 5.51 (s, 1H); 4.23-4.05 (m, 2H); 2.62 (br s, 6H); 1.31 (s, 9H); 1.19 (t, J=7.2 Hz, 3H).

Preparation of (S)-ethyl 2-tert-butoxy-2-(3,5-dimethyl-1-(trifluoromethylsulfonyloxy)naphthalen-2-yl)acetate. A solution of (S)-ethyl 2-tert-butoxy-2-(1-hydroxy-3,5-dimethylnaphthalen-2-yl)acetate (0.103 g, 0.312 mmol) in DCM (3 mL) cooled to 0° C. was treated with diisopropylethylamine (0.16 mL, 0.94 mmol) and trifluoromethanesulfonic anhydride (0.08 mL, 0.47 mmol) to produce a dark red-orange solution. After 1 hour, the reaction mixture is loaded directly onto silica gel and purified via Yamazen column chromatography to afford (S)-ethyl 2-tert-butoxy-2-(3,5-dimethyl-1-(trifluoromethylsulfonyloxy)naphthalen-2-yl)acetate that is contaminated with a small amount of an inseparable, uncharacterized side product. $^1$H-NMR: 400 MHz, (CDCl$_3$) δ: 7.94 (d, J=8.8 Hz, 1H); 7.84 (s, 1H); 7.47 (dd, J=8.8, 7.2 Hz, 1H); 7.39 (d, J=7.2 Hz, 1H); 5.75 (s, 1H); 4.26-4.08 (m, 2H); 2.70 (s, 3H); 2.60 (s, 3H); 1.22 (s, 9H); 1.18 (t, J=7.2 Hz, 3H).

Preparation of (S)-2-tert-butoxy-2-((R)-1-(2,3-dihydropyrano[4,3,2-de]quinolin-7-yl)-3,5-dimethylnaphthalen-2-yl)acetic acid and (S)-2-tert-butoxy-2-((S)-1-(2,3-dihydropyrano[4,3,2-de]quinolin-7-yl)-3,5-dimethylnaphthalen-2-yl)acetic acid. A solution of (S)-ethyl 2-tert-butoxy-2-(3,5-dimethyl-1-(trifluoromethylsulfonyloxy) naphthalen-2-yl)acetate (0.035 g, 0.076 mmol) in DME (1 mL, freshly distilled from Na/benzophenone) was treated with 2,3-dihydropyrano[4,3,2-de]quinolin-7-ylboronic acid hydrochloride (0.025 g, 0.098 mmol), SPhos precatalyst (0.009 g, 0.011 mmol) and CsF (0.051 g, 0.334 mmol). The reaction vessel was sealed and sparged with Ar for 30 minutes prior to heating in a microwave reactor at 125° C. for 90 minutes. The reaction mixture was loaded directly onto silica gel and purified via Yamazen column chromatography to afford of (S)-ethyl 2-tert-butoxy-2-((R)-1-(2,3-dihydropyrano[4,3,2-de]quinolin-7-yl)-3,5-dimethylnaphthalen-2-yl)acetate and of (S)-ethyl 2-tert-butoxy-2-((S)-1-(2,3-dihydropyrano[4,3,2-de]quinolin-7-yl)-3,5-dimethylnaphthalen-2-yl)acetate. Both compounds were taken up separately in THF/MeOH/water (0.30 mL each) and treated with LiOH.H$_2$O (0.003 g, 0.072 mmol). The reaction vessels were sealed and heated to 65° C. in a microwave reactor for 2 hours. Each sample was purified separately via preparatory HPLC to produce (S)-2-tert-butoxy-2-((R)-1-(2,3-dihydropyrano[4,3,2-de]quinolin-7-yl)-3,5-dimethylnaphthalen-2-yl)acetic acid (TFA salt, LCMS-ESI$^+$ (m/z): [M+H]$^+$ calcd for C$_{29}$H$_{30}$NO$_4$: 456.6. found: 456.3. $^1$H-NMR: 400 MHz, (CD$_3$CN) δ: 8.56 (d, J=5.2 Hz, 1H); 8.07 (s, 1H); 7.68 (d, J=8 Hz, 1H); 7.51 (d, J=5.2, 1H); 7.32 (d, J=6.8 Hz, 1H); 7.28 (d, J=8 Hz, 1H); 7.11 (dd, J=8, 6.8 Hz, 1H); 6.71 (d, J=8 Hz, 1H); 5.18 (s, 1H); 4.65-4.58 (m, 2H); 3.28 (t, J=5.6 Hz, 2H); 2.73 (s, 3H); 2.71 (s, 3H); 0.92 (s, 9H)) and (S)-2-tert-butoxy-2-((S)-1-(2,3-dihydropyrano[4,3, 2-de]quinolin-7-yl)-3,5-dimethylnaphthalen-2-yl)acetic acid (TFA salt, LCMS-ESI$^+$ (m/z): [M+H]$^+$ calcd for C$_{29}$H$_{30}$NO$_4$: 456.6. found: 456.3).

EXAMPLE 19

(S)-2-tert-Butoxy-2-((R)-6-(difluoromethyl)-1-(2,3-dihydropyrano[4,3,2-de]quinolin-7-yl)-3-methylnaphthalen-2-yl)acetic acid and (S)-2-tert-butoxy-2-((S)-6-(difluoromethyl)-1-(2,3-dihydropyrano[4,3,2-de]quinolin-7-yl)-3-methylnaphthalen-2-yl)acetic acid

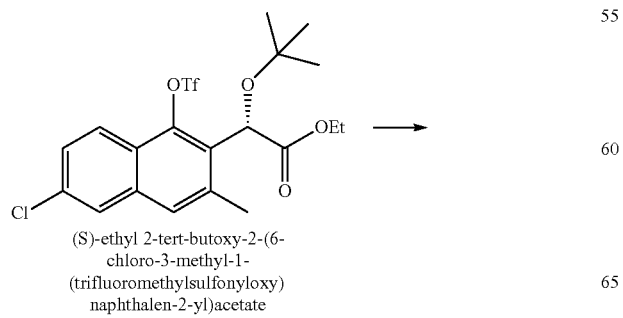

(S)-ethyl 2-tert-butoxy-2-(6-chloro-3-methyl-1-(trifluoromethylsulfonyloxy)naphthalen-2-yl)acetate

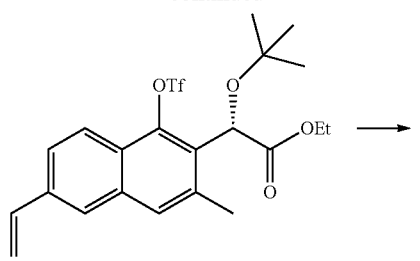

(S)-ethyl 2-tert-butoxy-2-(3-methyl-1-(trifluoromethylsulfonyloxy)-6-vinylnaphthalen-2-yl)acetate

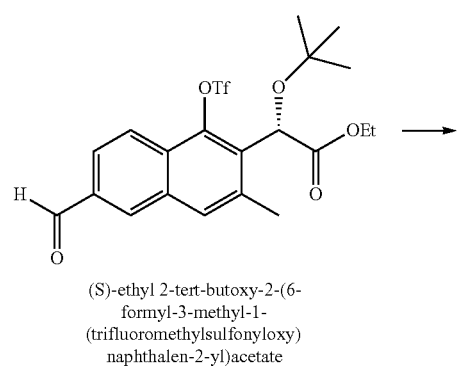

(S)-ethyl 2-tert-butoxy-2-(6-formyl-3-methyl-1-(trifluoromethylsulfonyloxy)naphthalen-2-yl)acetate

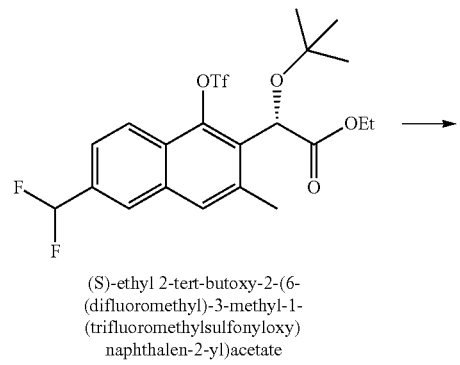

(S)-ethyl 2-tert-butoxy-2-(6-(difluoromethyl)-3-methyl-1-(trifluoromethylsulfonyloxy)naphthalen-2-yl)acetate

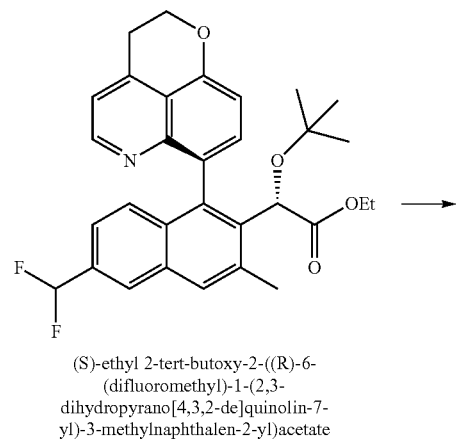

(S)-ethyl 2-tert-butoxy-2-((R)-6-(difluoromethyl)-1-(2,3-dihydropyrano[4,3,2-de]quinolin-7-yl)-3-methylnaphthalen-2-yl)acetate

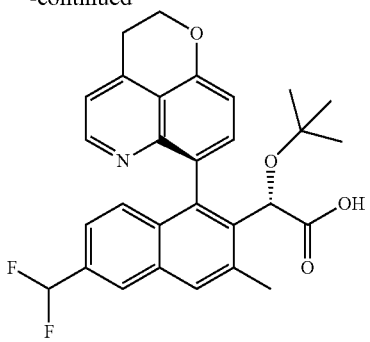

(S)-2-tert-butoxy-2-((R)-6-(difluoromethyl)-1-(2,3-dihydropyrano[4,3,2-de]quinolin-7-yl)-3-methylnaphthalen-2-yl)acetic acid

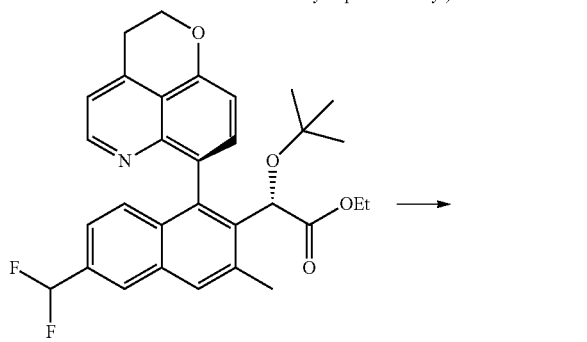

(S)-ethyl 2-tert-butoxy-2-((S)-6-(difluoromethyl)-1-(2,3-dihydropyrano[4,3,2-de]quinolin-7-yl)-3-methylnaphthalen-2-yl)acetate

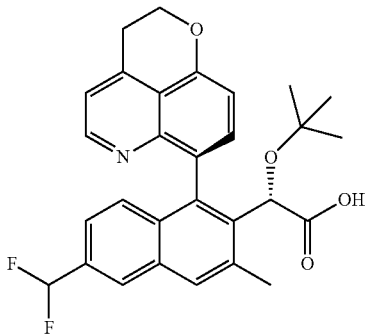

(S)-2-tert-butoxy-2-((S)-6-(difluoromethyl)-1-(2,3-dihydropyrano[4,3,2-de]quinolin-7-yl)-3-methylnaphthalen-2-yl)acetic acid Preparation of (S)-ethyl 2-tert-butoxy-2-(3-methyl-1-(trifluoromethylsulfonyloxy)-6-vinylnaphthalen-2-yl)acetate. A solution of (S)-ethyl 2-tert-butoxy-2-(6-chloro-3-methyl-1-(trifluoromethylsulfonyloxy)naphthalen-2-yl)acetate (1.0 g, 2.1 mmol) in DMF (10 mL) at room temperature is treated with BrettPhos precatalyst (Strem, 0.23 g, 0.31 mmol), vinyl tributyltin (0.68 mL, 2.3 mmol) and solid NaHCO$_3$ (0.026 g, 0.31 mmol). The reaction mixture is sealed and sparged with Ar for 10 minutes prior to heating at 120° C. for 90 minutes. The reaction mixture is allowed to cool to room temperature, loaded directly onto silica gel and purified via Yamazen column chromatography to afford (S)-ethyl 2-tert-butoxy-2-(3-methyl-1-(trifluoromethylsulfonyloxy)-6-vinylnaphthalen-2-yl)acetate. $^1$H-NMR: 400 MHz, (CDCl$_3$) δ: 8.00 (d, J=8.8 Hz, 1H); 7.72 (d, J=8.8 Hz, 1H); 7.70 (s, 1H); 7.64 (s, 1H); 6.87 (dd, J=17.2, 11.2 Hz, 1H); 5.92 (d, J=17.2 Hz, 1H); 5.41 (d, J=11.2 Hz, 1H); 4.27-4.08 (m, 2H); 2.55 (s, 3H); 1.22 (s, 9H); 1.18 (t, J=7.2 Hz, 3H).

Preparation of (S)-ethyl 2-tert-butoxy-2-(6-formyl-3-methyl-1-(trifluoromethyl-sulfonyloxy)naphthalen-2-yl)acetate: A solution of (S)-ethyl 2-tert-butoxy-2-(3-methyl-1-(trifluoromethylsulfonyloxy)-6-vinylnaphthalen-2-yl) acetate (0.60 g, 1.3 mmol) in THF (7 mL) at room temperature was treated with a previously prepared mixture of K$_2$OsO$_4$.2H$_2$O (0.023 g, 0.063 mmol) and NaIO$_4$ (0.81 g, 3.8 mmol) in water (5 mL). The resulting suspension becomes thick and opaque. After vigorous stirring for 20 min, the suspension is filtered through a pad of Celite, and the filtrate is washed with batches of EtOAc until white in color. The collected mother liquor is further diluted with water and EtOAc. Following separation, the aqueous layer is extracted with EtOAc until colorless. The combined organics are washed with brine, dried over anhydrous MgSO$_4$, filtered and concentrated in vacuo. The residue is purified by Yamazen column chromatography (15-35% EtOAc/hex) to afford the desired material. $^1$H-NMR: 400 MHz, (CDCl$_3$) δ: 10.19 (s, 1H); 8.31 (br s, 1H); 8.16 (d, J=8.8 Hz, 1H); 8.05 (dd, J=8.8, 1.6 Hz, 1H); 7.85 (s, 1H); 5.76 (s, 1H); 4.28-4.10 (m, 2H); 2.61 (s, 3H); 1.22 (s, 9H); 1.18 (t, J=7.2 Hz, 3H).

Preparation of (S)-ethyl 2-tert-butoxy-2-(6-(difluoromethyl)-3-methyl-1-(trifluoromethylsulfonyloxy)naphthalen-2-yl)acetate. A solution of (S)-ethyl 2-tert-butoxy-2-(6-formyl-3-methyl-1-(trifluoromethyl-sulfonyloxy) naphthalen-2-yl)acetate (0.100 g, 0.21 mmol) in DCM (1 mL) cooled to 0° C. was treated with Deoxo-Fluor® (0.097 mL, 0.53 mmol) and allowed to stir. A second lot was prepared identically beginning with 0.225 g of the starting material. After 3 hours, the reactions were combined and loaded directly onto silica gel (exothermic!) and purified via Yamazen column chromatography to afford (S)-ethyl 2-tert-butoxy-2-(6-(difluoromethyl)-3-methyl-1-(trifluoromethylsulfonyloxy)naphthalen-2-yl)acetate. $^1$H-NMR: 400 MHz, (CDCl$_3$) δ: 8.14 (d, J=8.8 Hz, 1H); 7.95 (s, 1H); 7.75 (s, 1H); 7.69 (d, J=8.8 Hz, 1H); 6.81 (t, J$_{HF}$=56.4 Hz, 1H); 5.75 (s, 1H); 4.28-4.10 (m, 2H); 2.58 (s, 3H); 1.22 (s, 9H); 1.18 (t, J=7.2 Hz, 3H).

Preparation of (S)-2-tert-butoxy-2-((R)-6-(difluoromethyl)-1-(2,3-dihydropyrano[4,3,2-de]quinolin-7-yl)-3-methylnaphthalen-2-yl)acetic acid and (S)-2-tert-butoxy-2-((S)-6-(difluoromethyl)-1-(2,3-dihydropyrano[4,3,2-de]quinolin-7-yl)-3-methylnaphthalen-2-yl)acetic acid. (S)-ethyl 2-tert-butoxy-2-(6-(difluoromethyl)-3-methyl-1-(trifluoromethylsulfonyloxy)naphthalen-2-yl)acetate was converted to (S)-2-tert-butoxy-2-((R)-6-(difluoromethyl)-1-(2,3-dihydropyrano[4,3,2-de]quinolin-7-yl)-3-methylnaphthalen-2-yl)acetic acid (TFA salt, LCMS-ESI$^+$ (m/z): [M+H]$^+$ calcd for C$_{29}$H$_{28}$F$_2$NO$_4$: 492.2. found: 492.1. $^1$H-NMR: 400 MHz, (CD$_3$OD) δ: 8.67 (d, J=4.4 Hz, 1H); 8.13 (s, 1H); 8.08 (s, 1H); 7.85-7.99 (m, 2H); 7.46 (d, J=8.8 Hz, 1H); 7.40 (d, J=8.8 Hz, 1H); 7.07 (d, 8.8 Hz, 1H); 6.90 (t, J=56 Hz, 1H); 5.26 (s, 1H); 4.77-4.69 (m, 2H); 3.67 (t, J=6 Hz, 2H); 2.80 (s, 3H); 0.93 (s, 9H)) and (S)-2-tert-butoxy-2-((S)-6-(difluoromethyl)-1-(2,3-dihydropyrano[4,3,2-de]quinolin-7-yl)-3-methylnaphthalen-2-yl)acetic acid (TFA salt, LCMS-ESI$^+$ (m/z): [M+H]$^+$ calcd for C$_{29}$H$_{28}$F$_2$NO$_4$: 492.2) via a sequence of steps similar to those described in Example 16 for the conversion of (S)-ethyl 2-tert-butoxy-2-(3,6-dimethyl-1-(trifluoromethylsulfonyloxy) naphthalen-2-yl)acetate to (S)-

2-tert-butoxy-2-((S)-1-(2,3-dihydropyrano[4,3,2-de]quinolin-7-yl)-3,6-dimethylnaphthalen-2-yl)acetic acid.
EXAMPLE 20
(S)-2-tert-Butoxy-2-((R)-1-(2,3-dihydropyrano[4,3,2-de]quinolin-7-yl)-3-methyl-6-(prop-1-ynyl)naphthalen-2-yl)acetic acid and (S)-2-tert-butoxy-2-((S)-1-(2,3-dihydropyrano[4,3,2-de]quinolin-7-yl)-3-methyl-6-(prop-1-ynyl)naphthalen-2-yl)acetic acid
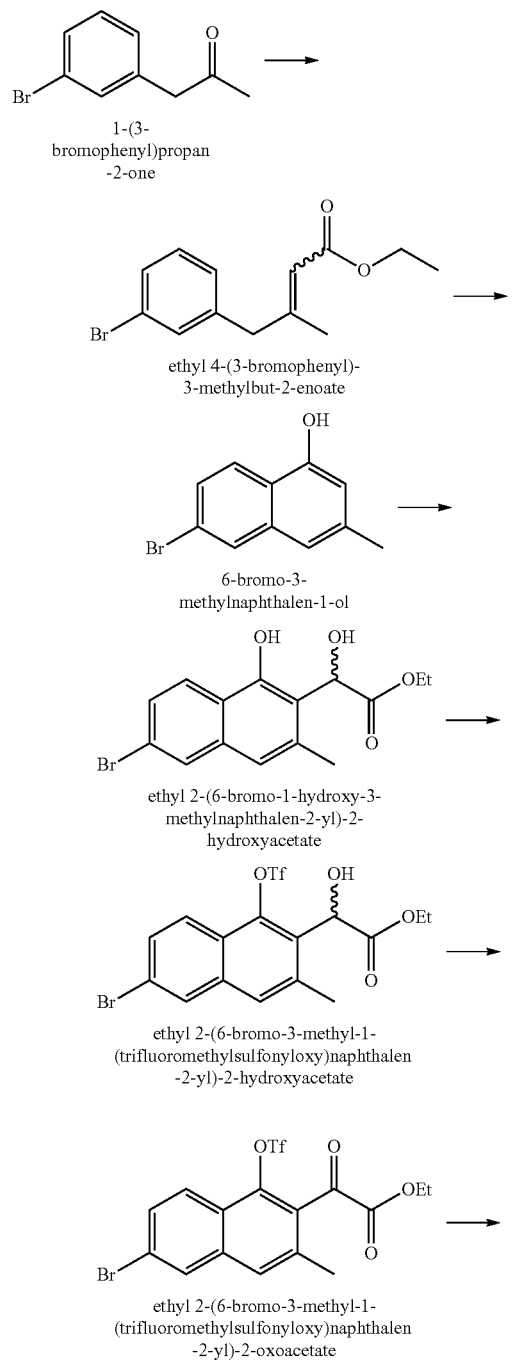
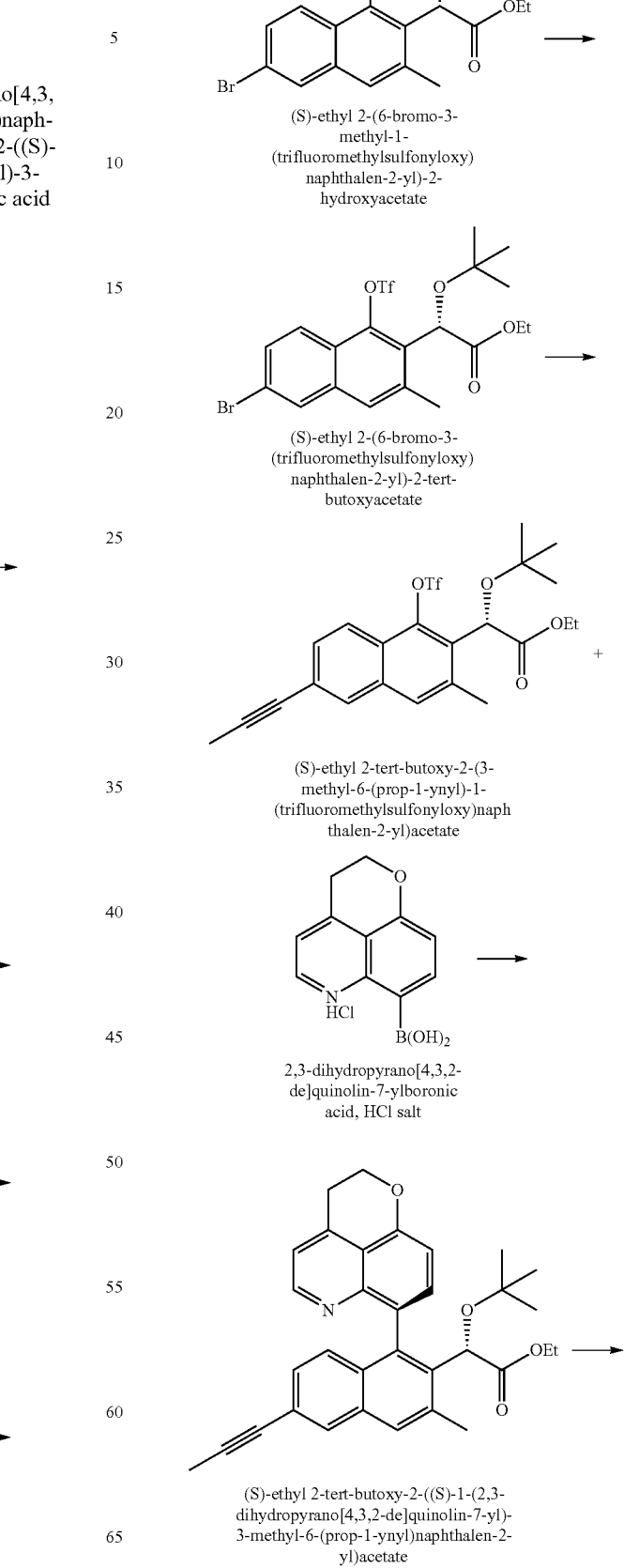

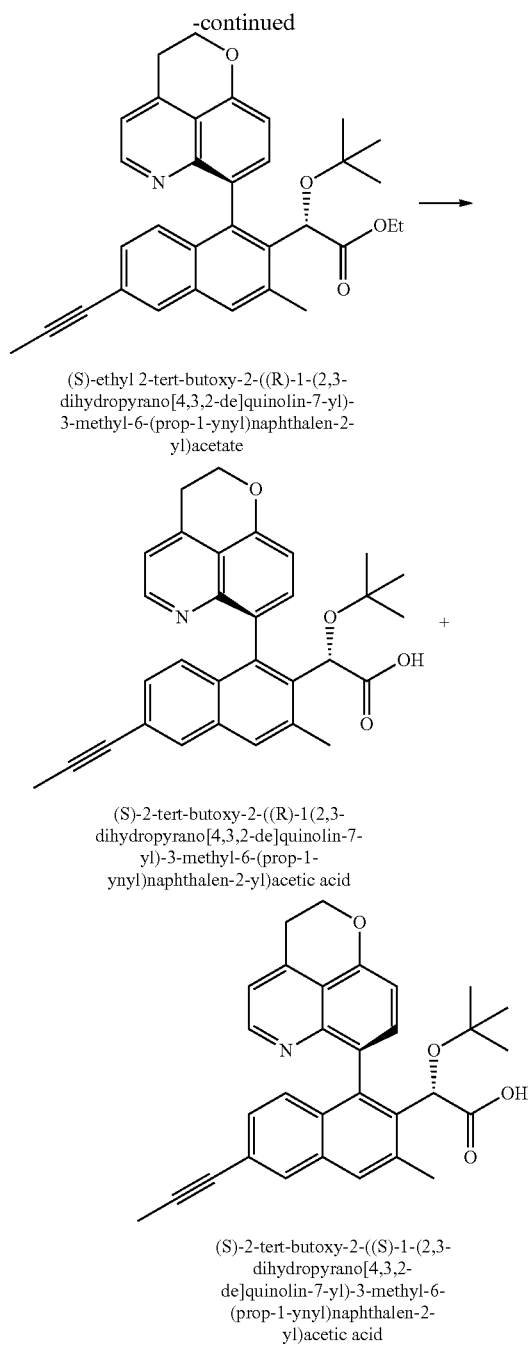

(S)-ethyl 2-tert-butoxy-2-((R)-1-(2,3-dihydropyrano[4,3,2-de]quinolin-7-yl)-3-methyl-6-(prop-1-ynyl)naphthalen-2-yl)acetate (S)-2-tert-butoxy-2-((R)-1-(2,3-dihydropyrano[4,3,2-de]quinolin-7-yl)-3-methyl-6-(prop-1-ynyl)naphthalen-2-yl)acetic acid (S)-2-tert-butoxy-2-((S)-1-(2,3-dihydropyrano[4,3,2-de]quinolin-7-yl)-3-methyl-6-(prop-1-ynyl)naphthalen-2-yl)acetic acid Preparation of ethyl 4-(3-bromophenyl)-3-methylbut-2-enoate: To a solution of triethylphosphonoacetate (28.18 mL, 140.79 mmol) in anhydrous tetrahydrofuran (300 mL) at 0° C. was added 60% sodium hydride (5.63 g, 140.79 mmol) and the resulting mixture stirred for 30 minutes. 1-(3-Bromophenyl)propan-2-one (20 g, 93.86 mmol) in tetrahydrofuran (10 mL) was added and reaction mixture was stirred for 2 hours and quenched with saturated sodium bicarbonate solution. The mixture was extracted with ethyl acetate and organic layer was concentrated and purified by flash column chromatography (silica gel, ethyl acetate/hexanes) to give mixture of E/Z isomers. $^1$H NMR (400 MHz, CDCl$_3$): δ 7.38 (m, 1H), 7.32 (m, 1H), 7.18 (m, 1H), 7.06 (m, 1H), 5.79, 5.64 (s, s, 1H), 4.13 (m, 2H), 3.36 (s, 2H), 2.03 (s, 3H), 1.26 (m, 3H).

Preparation of 6-bromo-3-methylnaphthalen-1-ol: A solution of ethyl 4-(3-bromophenyl)-3-methylbut-2-enoate (8.07 g, 28.5 mmol) in concentrated sulfuric acid (20 mL) was stirred at 60° C. for 90 minutes. The reaction mixture was poured onto ice and diluted with water and extracted with ethyl acetate. The organic layer was concentrated and purified by flash column chromatography (silica gel, ethyl acetate/hexanes) to give the desired compound. $^1$H-NMR: 400 MHz, (CDCl$_3$) δ: 7.98 (d, J=10.4 Hz, 1H), 7.83 (s, 1H), 7.43 (d, J=7.2 Hz, 1H), 7.08 (s, 1H), 6.67 (s, 1H), 2.42 (s, 3H). LCMS-ESI$^-$ (m/z): [M–H]$^-$ calcd for C$_{11}$H$_9$BrO: 236.09. Found: 236.9.

Preparation of ethyl 2-(6-bromo-1-hydroxy-3-methylnaphthalen-2-yl)-2-hydroxyacetate: To a mixture of 6-bromo-3-methylnaphthalen-1-ol (3.79 g, 15.98 mmol) in anhydrous dichloromethane (150 mL) at –40° C. was added a 1M titanium(IV) chloride solution in dichloromethane (20.78 mL, 13.78 mmol) and stirred for 45 min. Ethyl glyoxalate (2.45 g, 23.97 mmol) dissolved in dichloromethane (10 mL) was added over 15 minutes and stirred for 1 hour at –40° C. The reaction was quenched by the addition of Rochelle's salt solution and stirred at room temperature for 2.5 hours. The resulting mixture was washed with water and aqueous layer back-extracted with dichloromethane (2×). The combined organic layer was dried (MgSO$_4$), filtered, concentrated and purified by flash column chromatography (silica gel, 5 to 30% ethyl acetate/hexanes) to give the desired compound. LCMS-ESI$^-$ (m/z): [M–H]$^-$ calcd for C$_{15}$H$_{15}$BrO$_4$: 338.18. Found: 338.8.

Preparation of ethyl 2-(6-bromo-3-methyl-1-(trifluoromethylsulfonyloxy)-naphthalen-2-yl)-2-hydroxyacetate: To a solution of ethyl 2-(6-bromo-1-hydroxy-3-methylnaphthalen-2-yl)-2-hydroxyacetate (2.03 g, 6 mmol) in anhydrous dichloromethane (120 mL) at 0° C. was added imidazole (531 mg, 7.8 mmol), followed by chlorotriethylsilane (1.21 mL, 7.2 mmol). The cloudy reaction mixture was stirred for 1 hour, quenched with water and diluted with dichloromethane. The mixture was washed with 1N HCl solution/brine and organic layer dried (MgSO$_4$), filtered, concentrated and used in next step without further purification.

The above residue was dissolved in anhydrous dichloromethane (130 mL) containing triethylamine (1 mL, 7.2 mmol) and cooled in a dry ice/acetone bath. Trifluoromethanesulfonic anhydride (1.11 mL, 6.6 mmol) was added dropwise over 20 minutes and stirred for 1 hour. The reaction was quenched with brine and stirred for 15 minutes at room temperature. The mixture was diluted with dichloromethane, washed with 1N HCl solution, saturated sodium bicarbonate solution/brine and dried (MgSO$_4$), filtered, concentrated to give an orange oil that used in next step without further purification.

The above residue was dissolved in tetrahydrofuran (100 mL) and 48% hydrofluoric acid (4.31 mL, 120 mmol) was added. The reaction mixture was stirred overnight at room temperature and quenched with solid sodium bicarbonate and stirred for 30 minutes. Water and then saturated sodium bicarbonate solution were added and the mixture was extracted with ethyl acetate (2×). The combined organic layer was dried (MgSO$_4$), filtered, concentrated and purified by flash column chromatography (silica gel, 5 to 30% ethyl acetate/hexanes) to the desired compound. LCMS-ESI$^-$ (m/z): [M–H]$^-$ calcd for C$_{16}$H$_{14}$BrF$_3$O$_4$S: 470.24. Found: 470.14.

Preparation of ethyl 2-(6-bromo-3-methyl-1-(trifluoromethylsulfonyloxy)-naphthalen-2-yl)-2-oxoacetate: To a solution of ethyl 2-(6-bromo-3-methyl-1-(trifluoromethylsulfonyloxy)naphthalen-2-yl)-2-hydroxyacetate (2.19 g, 4.65 mmol) in anhydrous dichloromethane (50 mL) at 0° C. was added Dess-Martin Periodinane (2.76 g, 6.51 mmol) portionwise over 5 minutes. The reaction mixture was stirred at 0° C. for 1 hour and quenched with sodium thiosulfate solution and saturated sodium bicarbonate solution and stirred for 30 minutes. The mixture was diluted with ethyl ether and washed with saturated sodium bicarbonate solution (3×), brine and dried ($MgSO_4$), filtered, concentrated to give a yellow oil with a white precipitate. The mixture was suspended in diethyl ether, washed with brine, dried ($MgSO_4$), filtered, concentrated and purified by flash column chromatography (silica gel, 0 to 10% ethyl acetate/hexanes) to give the desired compound.

Preparation of (S)-ethyl 2-(6-bromo-3-methyl-1-(trifluoromethylsulfonyloxy)naphthalen-2-yl)-2-hydroxyacetate: To a solution of ethyl 2-(6-bromo-3-methyl-1-(trifluoromethylsulfonyloxy)naphthalen-2-yl)-2-oxoacetate (2 g, 4.26 mmol) and (R)-2-methyl-CBS-oxazaborolidine (0.236 g, 0.85 mmol) in anhydrous toluene at −40° C. was added a solution of catecholborane (0.615 mL, 5.79 mmol) in toluene (10 mL) over 40 minutes. The reaction mixture was stirred for 1 hour and quenched with sodium carbonate solution, diluted with ethyl acetate and stirred vigorously for 20 minutes at −20° C., then at room temperature for 45 minutes. The aqueous layer was removed and the organic layer was washed with sodium carbonate solution (4×), saturated ammonium chloride solution, dried ($MgSO_4$), filtered, concentrated and purified by flash column chromatography (silica gel, 0 to 20% ethyl acetate/hexanes) to give the desired compound.

Preparation of (S)-ethyl 2-(6-bromo-3-methyl-1-(trifluoromethylsulfonyloxy)naphthalen-2-yl)-2-tert-butoxyacetate: To a solution of (S)-ethyl 2-(6-bromo-3-methyl-1-(trifluoromethylsulfonyloxy)naphthalen-2-yl)-2-hydroxyacetate (2 g, 4.26 mmol) in tert-butylacetate (30 mL) was added 70% perchloric acid (1.10 mL, 4.69 mmol). The reaction mixture was stirred for 2.5 hours and quenched with solid sodium bicarbonate and stirred for 45 minutes. Water and solid sodium bicarbonate were carefully added and stirred for another 15 minutes. The mixture was diluted with ethyl acetate, washed with saturated bicarbonate solution (2×), brine, dried ($MgSO_4$), filtered, concentrated and purified by flash column chromatography (silica gel, 0 to 20% ethyl acetate/hexanes) to give the desired compound. $^1$H NMR (400 MHz, $CDCl_3$) δ: 7.96 (s, 1H), 7.90 (d, J=10.2 Hz, 1H), 7.62 (d, J=9.2 Hz, 1H), 7.58 (s, 1H), 5.90 (s, 1H), 4.26-4.08 (m, 2H), 2.53 (s, 3H), 1.20 (s, 9H), 1.17 (t, J=7.1 Hz, 3H).

Preparation of (S)-ethyl 2-tert-butoxy-2-(3-methyl-6-(prop-1-ynyl)-1-(trifluoromethylsulfonyloxy)naphthalen-2-yl)acetate: A Smith process vial was charged (S)-ethyl 2-(6-bromo-3-methyl-1-(trifluoromethylsulfonyloxy)naphthalen-2-yl)-2-tert-butoxyacetate (55 mg, 0.104 mmol), (1-Propynyl)tributylstannane (35 μL, 0.115 mmol), Chloro(2-dicyclohexylphosphino-2',4',6'-triisopropyl-1,1'-biphenyl)[2-(2-aminoethyl)phenyl]palladium(II) (8 mg, 0.01 mmol), $NaHCO_3$ (4 mg, 0.05 mmol), triethylamine (44 μL, 0.3 mmol) and flushed with nitrogen. DMF (2.0 mL) was added and mixture sparged with nitrogen for 10 minutes and then heated in microwave at 120° C. for 1 hour. The reaction mixture was diluted with ethyl acetate and washed with brine, dried ($MgSO_4$), filtered, concentrated and purified by flash column chromatography (silica gel, 0 to 20% ethyl acetate/hexanes) to give (S)-ethyl 2-tert-butoxy-2-(3-methyl-6-(prop-1-ynyl)-1-(trifluoromethylsulfonyloxy)naphthalen-2-yl)acetate. $^1$H NMR (400 MHz, $CDCl_3$): δ 7.94 (d, J=4.4 Hz, 1H), 7.80 (s, 1H), 7.56 (s, 1H), 7.50 (d, J=4.6 Hz, 1H), 5.63 (s, 1H), 4.08 (m, 2H), 2.52 (s, 3H), 2.08 (s, 3H), 1.21 (s, 9H), 1.18 (t, 3H).

Preparation of (S)-ethyl 2-tert-butoxy-2-((S)-1-(2,3-dihydropyrano[4,3,2-de]quinolin-7-yl)-3-methyl-6-(prop-1-ynyl)naphthalen-2-yl)acetate: A Smith process vial was charged with (S)-ethyl 2-tert-butoxy-2-(3-methyl-6-(prop-1-ynyl)-1-(trifluoromethylsulfonyloxy)naphthalen-2-yl)acetate (66 mg, 0.136 mmol), 2,3-dihydropyrano[4,3,2-de]quinolin-7-ylboronic acid, HCl salt (41 mg, 0.163 mmol), Chloro(2-dicyclohexylphosphino-2',6'-dimethoxy-1,1'-biphenyl)[2-(2-aminoethylphenyl)]palladium(II)-methyl-t-butyl ether adduct (9.4 mg, 0.014 mmol), cesium fluoride (91 mg, 0.60 mmol) and flushed with nitrogen. Dimethoxyethane (1.5 mL, distilled from Na/benzophenone) was added and mixture sparged with nitrogen for 10 minutes and then heated in microwave at 120° C. for 40 minutes. The reaction mixture was diluted with ethyl acetate and washed with brine, dried ($MgSO_4$), filtered, concentrated and purified by flash column chromatography (silica gel, 0 to 100% ethyl acetate/hexanes) to give (S)-ethyl 2-tert-butoxy-2-((R)-1-(2,3-dihydropyrano[4,3,2-de]quinolin-7-yl)-3-methyl-6-(prop-1-ynyl)naphthalen-2-yl)acetate. LCMS-ESI$^+$ (m/z): [M+H]$^+$ calcd for $C_{33}H_{34}NO_4$: 508.62. Found: 508.20.

The other atropisomer, (S)-ethyl 2-tert-butoxy-2-((S)-1-(2,3-dihydropyrano[4,3,2-de]quinolin-7-yl)-3-methyl-6-(prop-1-ynyl)naphthalen-2-yl)acetate, was also isolated. LCMS-ESI$^+$ (m/z): [M+H]$^+$ calcd for $C_{33}H_{34}NO_4$: 508.62. Found: 508.20.

Preparation of (S)-2-tert-butoxy-2-((R)-1-(2,3-dihydropyrano[4,3,2-de]quinolin-7-yl)-3-methyl-6-(prop-1-ynyl)naphthalen-2-yl)acetic acid: A solution of (S)-ethyl 2-tert-butoxy-2-((R)-1-(2,3-dihydropyrano[4,3,2-de]quinolin-7-yl)-3-methyl-6-(prop-1-ynyl)naphthalen-2-yl)acetate (14 mg, 0.0275 mmol) and 1M sodium hydroxide (1 mL) in tetrahydrofuran (0.5 mL) and ethanol (1.0 mL) was heated at 50° C. overnight. The reaction mixture was diluted with ethyl acetate and washed with brine. The aqueous layer was back-extracted with ethyl acetate and the combined organic layer was dried ($MgSO_4$), filtered, concentrated and purified by reverse phase HPLC (Gemini, 5 to 100% ACN/$H_2O$+0.1% TFA). Product lyophilized to give the desired compound. $^1$H-NMR: 400 MHz, ($CD_3OD$) δ: 8.67 (d, J=5.4 Hz, 1H), 7.93 (d, J=12.9 Hz, 2H), 7.81 (m, 2H), 7.43 (d, J=7.8 Hz, 1H), 7.20 (d, J=8.6 Hz, 1H), 6.85 (d, J=8.6 Hz, 1H), 5.21 (s, 1H), 4.71 (m, 2H), 3.66 (t, J=6.2 Hz, 2H), 2.76 (s, 3H), 2.04 (s, 3H), 0.92 (s, 9H). LCMS-ESI$^+$ (m/z): [M+H]$^+$ calcd for $C_{31}H_{30}NO_4$: 480.57. Found: 480.16.

Preparation of (S)-2-tert-butoxy-2-((S)-1-(2,3-dihydropyrano[4,3,2-de]quinolin-7-yl)-3-methyl-6-(prop-1-ynyl)naphthalen-2-yl)acetic acid: A solution of (S)-ethyl 2-tert-butoxy-2-((S)-1-(2,3-dihydropyrano[4,3,2-de]quinolin-7-yl)-3-methyl-6-(prop-1-ynyl)naphthalen-2-yl)acetate (14 mg, 0.0275 mmol) and 1M sodium hydroxide (1 mL) in tetrahydrofuran (0.5 mL) and ethanol (1.0 mL) was heated at 50° C. overnight. The reaction mixture was diluted with ethyl acetate and washed with brine. The aqueous layer was back-extracted with ethyl acetate and the combined organic layer was dried ($MgSO_4$), filtered, concentrated and purified by reverse phase HPLC (Gemini, 5 to 100% ACN/$H_2O$+0.1% TFA). Product lyophilized to give the desired compound. $^1$H-NMR: 400 MHz, ($CD_3OD$) δ: 8.58 (d, J=5.2 Hz, 1H), 8.15 (d, J=8.21 Hz, 1H), 7.91 (s, 1H), 7.85 (s, 1H), 7.68 (d, J=5.48 Hz, 1H), 7.48 (d, J=8.21 Hz, 1H), 7.16 (d, J=8.6 Hz, 1H), 6.81 (d, J=8.6 Hz, 1H), 5.20 (s, 1H), 4.68 (m, 2H), 3.66 (t, J=6.2

Hz, 2H), 2.71 (s, 3H), 2.04 (s, 3H), 0.87 (s, 9H). LCMS-ESI⁺ (m/z): [M+H]⁺ calcd for $C_{31}H_{30}NO_4$: 480.57. Found: 480.16.

EXAMPLE 21

(S)-2-tert-Butoxy-2-((R)-6-(cyclopropylethynyl)-1-(2,3-dihydropyrano[4,3,2-de]quinolin-7-yl)-3-methylnaphthalen-2-yl)acetic acid

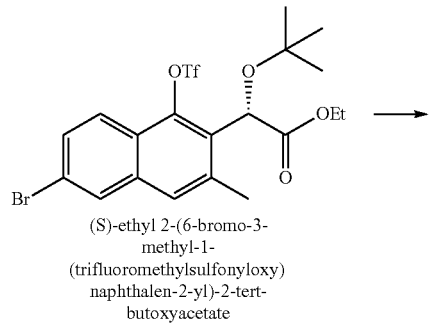

(S)-ethyl 2-(6-bromo-3-methyl-1-(trifluoromethylsulfonyloxy)naphthalen-2-yl)-2-tert-butoxyacetate

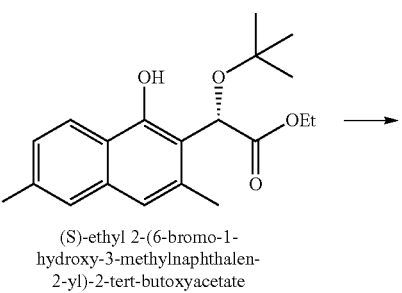

(S)-ethyl 2-(6-bromo-1-hydroxy-3-methylnaphthalen-2-yl)-2-tert-butoxyacetate

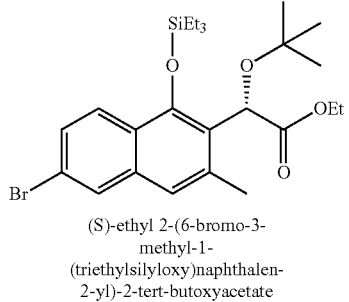

(S)-ethyl 2-(6-bromo-3-methyl-1-(triethylsilyloxy)naphthalen-2-yl)-2-tert-butoxyacetate

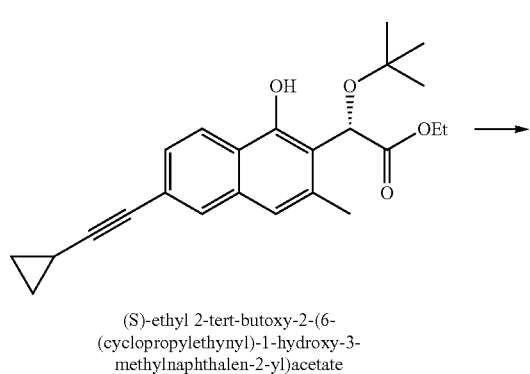

(S)-ethyl 2-tert-butoxy-2-(6-(cyclopropylethynyl)-1-hydroxy-3-methylnaphthalen-2-yl)acetate

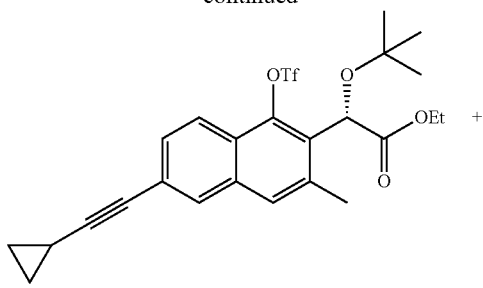

(S)-ethyl 2-tert-butoxy-2-(6-(cyclopropylethynyl)-3-methyl-1-(trifluoromethylsulfonyloxy)naphthalen-2-yl)acetate

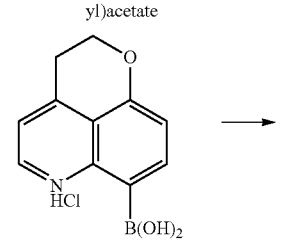

2,3-dihydropyrano[4,3,2-de]quinolin-7-ylboronic acid, HCl salt

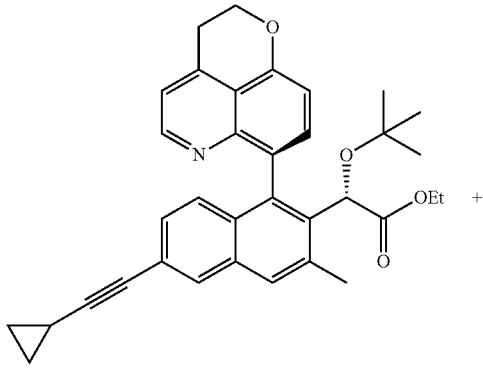

(S)-ethyl 2-tert-butoxy-2-((S)-6-(cyclopropylethynyl)-1-(2,3-dihydropyrano[4,3,2-de]quinolin-7-yl)-3-methylnaphthalen-2-yl)acetate

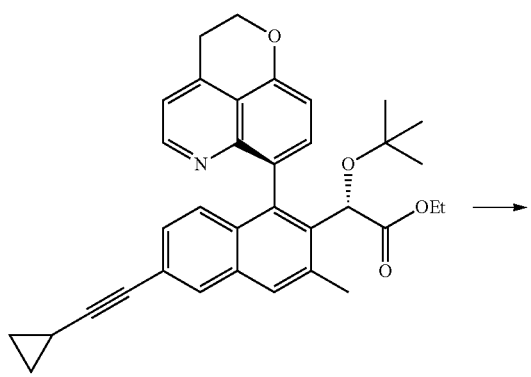

(S)-ethyl 2-tert-butoxy-2-((R)-6-(cyclopropylethynyl)-1-(2,3-dihydropyrano[4,3,2-de]quinolin-7-yl)-3-methylnaphthalen-2-yl)acetate -continued

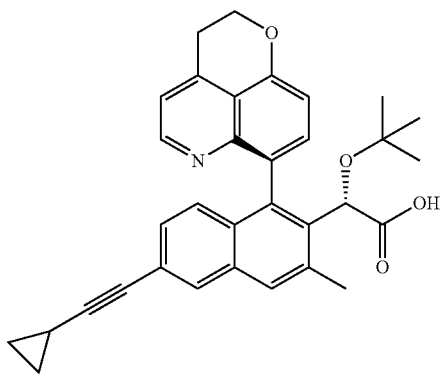

(S)-2-tert-butoxy-2-((R)-6-(cyclopropylethynyl)-1-(2,3-dihydropyrano[4,3,2-de]quinolin-7-yl)-3-methylnaphthalen-2-yl)acetic acid Preparation of (S)-ethyl 2-(6-bromo-1-hydroxy-3-methylnaphthalen-2-yl)-2-tert-butoxyacetate: To a solution of (S)-ethyl 2-(6-bromo-3-methyl-1-(trifluoromethylsulfonyloxy)naphthalen-2-yl)-2-tert-butoxyacetate (260 mg, 0.5 mmol) in anhydrous THF (4 mL) at 0° C. was added a 1N tetrabutylammonium fluoride in THF (0.6 mL, 0.6 mmol) and stirred for 1 hour. The reaction was quenched by the addition saturated NaHCO$_3$ solution and extracted using EtOAc. The organic layer was dried (MgSO$_4$), filtered, concentrated and purified by flash column chromatography (silica gel, 5 to 30% ethyl acetate/hexanes) to give the desired compound. LCMS-ESI$^-$ (m/z): [M−H]$^-$ calcd for C$_{19}$H$_{22}$BrO$_4$: 394.29. Found: 394.0.

Preparation of (S)-ethyl 2-(6-bromo-3-methyl-1-(triethylsilyloxy)naphthalen-2-yl)-2-tert-butoxyacetate: To a solution of (S)-ethyl 2-(6-bromo-1-hydroxy-3-methylnaphthalen-2-yl)-2-tert-butoxyacetate (238 mg, 0.6 mmol) in anhydrous DCM (20 mL) at 0° C. was added diisopropylethylamine (0.21 mL, 1.2 mmol), followed by chlorotriethylsilane (0.12 mL, 0.72 mmol) and the resulting mixture stirred for 1 hour. The reaction was quenched with saturated sodium bicarbonate solution. The mixture was extracted with DCM and organic layer was concentrated and purified by flash column chromatography (silica gel, ethyl acetate/hexanes) to give the desired compound. $^1$H NMR (400 MHz, CDCl$_3$): δ 7.82 (m, 2H), 7.42 (m, 1H), 7.08 (s, 1H), 5.98 (s, 1H), 4.19 (m, 2H), 2.43 (s, 3H), 1.21 (s, 9H), 0.98 (t, 9H), 0.83 (m, 6H).

Preparation of (S)-ethyl 2-tert-butoxy-2-(6-(cyclopropylethynyl)-1-hydroxy-3-methylnaphthalen-2-yl)acetate: A Smith process vial was charged (S)-ethyl 2-(6-bromo-3-methyl-1-(triethylsilyloxy)naphthalen-2-yl)-2-tert-butoxyacetate (151 mg, 0.287 mmol), (cyclopropylethynyl)trimethylsilane (195 mg, 0.316 mmol), Pd(PPh$_3$)$_4$ (33 mg, 0.03 mmol), CuI (55 mg, 0.28 mmol), triethylamine (0.12 mL, 0.86 mmol), cesium fluoride (144 mg, 0.95 mmol) and flushed with nitrogen. THF (3 mL) was added and mixture sparged with nitrogen for 10 minutes and then heated in microwave at 110° C. for 1 hour. Reaction mixture was diluted with ethyl acetate and washed with brine, dried (MgSO$_4$), filtered, concentrated and purified by flash column chromatography (silica gel, 0 to 100% ethyl acetate/hexanes) to give (S)-ethyl 2-tert-butoxy-2-(6-(cyclopropylethynyl)-1-hydroxy-3-methylnaphthalen-2-yl)acetate. LCMS-ESI$^-$ (m/z): [M−H]$^-$ calcd for C$_{24}$H$_{27}$O$_4$: 379.48. Found: 379.20.

Preparation of (S)-ethyl 2-tert-butoxy-2-(6-(cyclopropylethynyl)-3-methyl-1-(trifluoromethylsulfonyloxy)naphthalen-2-yl)acetate: (S)-ethyl 2-tert-butoxy-2-(6-(cyclopropylethynyl)-1-hydroxy-3-methylnaphthalen-2-yl)acetate (36 mg) was dissolved in anhydrous dichloromethane (2 mL) containing triethylamine (0.1 mL, excess) and cooled in a dry ice/acetone bath. Trifluoromethanesulfonic anhydride (0.1 mL, excess) was added dropwise over 20 minutes and stirred for 1 hour. Reaction was quenched with brine and stirred for 15 minutes at room temperature. The mixture was diluted with dichloromethane, washed with 1N HCl solution, saturated sodium bicarbonate solution/brine and dried (MgSO$_4$), filtered, concentrated to give the desired compound. $^1$H-NMR: 400 MHz, (CDCl$_3$) δ: 8.18 (d, J=5.4 Hz, 1H), 8.03 (s, 1H), 7.80 (s, 1H), 7.78 (d, J=7.8 Hz, 1H), 7.50 (s, 1H), 5.95 (s, 1H), 4.40 (m, 2H), 3.73 (s, 3H), 1.78 (m, 1H), 1.42 (s, 9H), 1.40 (m, 3H), 1.14 (m, 4H). $^{19}$F-NMR: 377 MHz, (CDCl$_3$) δ: −73.39.

Preparation of (S)-ethyl 2-tert-butoxy-2-((R)-6-(cyclopropylethynyl)-1-(2,3-dihydropyrano[4,3,2-de]quinolin-7-yl)-3-methylnaphthalen-2-yl)acetate: A Smith process vial was charged with (S)-ethyl 2-tert-butoxy-2-(6-(cyclopropylethynyl)-3-methyl-1-(trifluoromethylsulfonyloxy)naphthalen-2-yl)acetate (45 mg, 0.088 mmol), 2,3-dihydropyrano[4,3,2-de]quinolin-7-ylboronic acid, HCl salt (27 mg, 0.11 mmol), Chloro(2-dicyclohexylphosphino-2',6'-dimethoxy-1,1'-biphenyl)[2-(2-aminoethylphenyl)]palladium(II)-methyl-t-butyl ether adduct (7 mg, 0.009 mmol), cesium fluoride (59 mg, 0.39 mmol) and flushed with nitrogen. Dimethoxyethane (1.5 mL, distilled from Na/benzophenone) was added and mixture sparged with nitrogen for 10 minutes and then heated in microwave at 120° C. for 40 minutes. Reaction mixture was diluted with ethyl acetate and washed with brine, dried (MgSO$_4$), filtered, concentrated and purified by flash column chromatography (silica gel, 0 to 100% ethyl acetate/hexanes) to give (S)-ethyl 2-tert-butoxy-2-((R)-6-(cyclopropylethynyl)-1-(2,3-dihydropyrano[4,3,2-de]quinolin-7-yl)-3-methylnaphthalen-2-yl)acetate. LCMS-ESI$^+$ (m/z): [M+H]$^+$ calcd for C$_{35}$H$_{36}$NO$_4$: 534.66. Found: 534.1.

The other atropisomer, (S)-ethyl 2-tert-butoxy-2-((S)-6-(cyclopropylethynyl)-1-(2,3-dihydropyrano[4,3,2-de]quinolin-7-yl)-3-methylnaphthalen-2-yl)acetate, was also isolated. LCMS-ESI$^+$ (m/z): [M+H]$^+$ calcd for C$_{35}$H$_{36}$NO$_4$: 534.66. Found: 534.1.

Preparation of (S)-2-tert-butoxy-2-((R)-6-(cyclopropylethynyl)-1-(2,3-dihydropyrano[4,3,2-de]quinolin-7-yl)-3-methylnaphthalen-2-yl)acetic acid: A solution of (S)-ethyl 2-tert-butoxy-2-((R)-6-(cyclopropylethynyl)-1-(2,3-dihydropyrano[4,3,2-de]quinolin-7-yl)-3-methylnaphthalen-2-yl)acetate (5 mg) and 1M sodium hydroxide (1 mL) in tetrahydrofuran (0.5 mL) and ethanol (1.0 mL) was heated at 50° C. overnight. Reaction mixture was diluted with ethyl acetate and washed with brine. The aqueous layer was back-extracted with ethyl acetate and the combined organic layer was dried (MgSO$_4$), filtered, concentrated and purified by reverse phase HPLC (Gemini, 5 to 100% ACN/H$_2$O+0.1% TFA). Product lyophilized to give the desired compound.
$^1$H-NMR: 400 MHz, (CD$_3$OD) δ: 8.57 (d, J=5.8 Hz, 1H), 7.81 (d, J=9.78 Hz, 2H), 7.68 (m, 2H), 7.34 (d, J=8.21 Hz, 1H), 7.07 (d, J=8.6 Hz, 1H), 6.74 (d, J=8.9 Hz, 1H), 5.11 (s, 1H), 4.61 (m, 2H), 3.56 (t, J=5.86 Hz, 2H), 2.65 (s, 3H), 1.38

(m, 1H), 0.82 (s+m, 11H), 0.64 (m, 2H). LCMS-ESI⁺ (m/z): [M+H]⁺ calcd for $C_{33}H_{32}NO_4$: 506.6. Found: 506.25.

EXAMPLE 22

(S)-2-tert-Butoxy-2-((R)-6-cyano-1-(2,3-dihydropyrano[4,3,2-de]quinolin-7-yl)-5-ethoxy-3-methylnaphthalen-2-yl)acetic acid

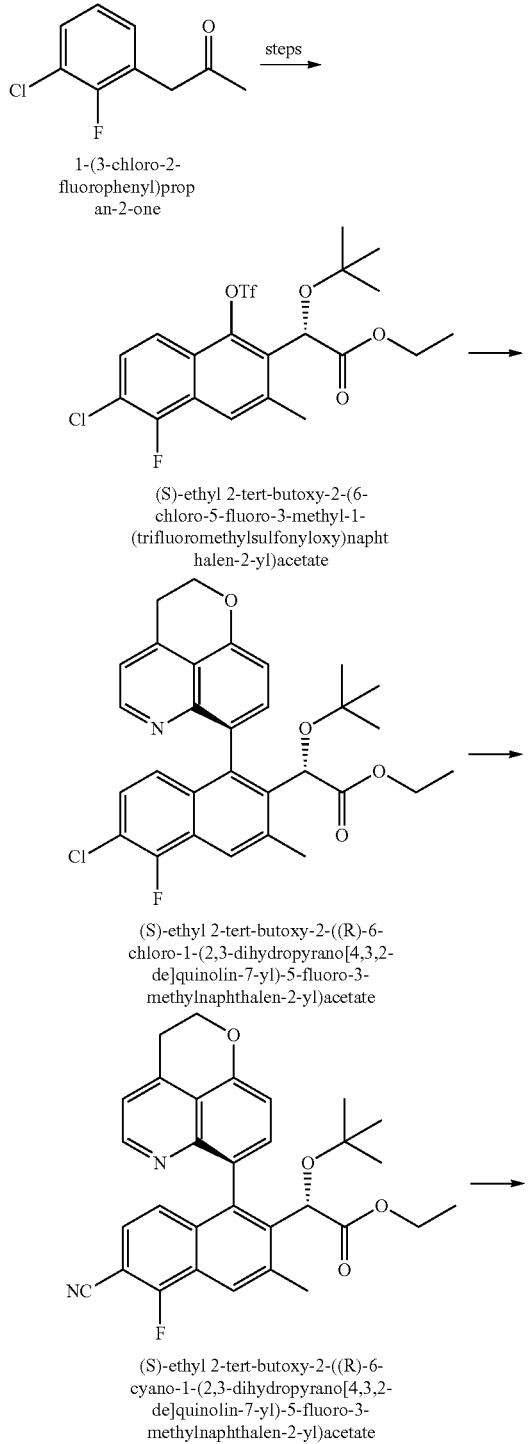

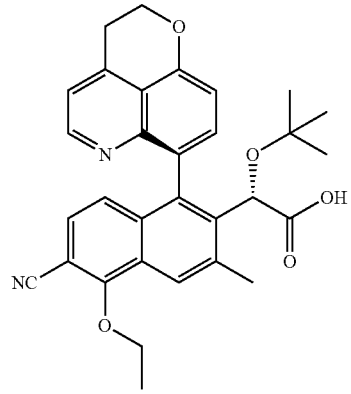

(S)-2-tert-butoxy-2-((R)-6-cyano-1-(2,3-dihydropyrano[4,3,2-de]quinolin-7-yl)-5-ethoxy-3-methylnaphthalen-2-yl)acetic acid Preparation of (S)-ethyl 2-tert-butoxy-2-((R)-6-chloro-1-(2,3-dihydropyrano[4,3,2-de]quinolin-7-yl)-5-fluoro-3-methylnaphthalen-2-yl)acetate: (S)-ethyl 2-tert-butoxy-2-((R)-6-chloro-1-(2,3-dihydropyrano[4,3,2-de]quinolin-7-yl)-5-fluoro-3-methylnaphthalen-2-yl)acetate was prepared in a similar way as (S)-ethyl 2-tert-butoxy-2-((R)-1-(2,3-dihydropyrano[4,3,2-de]quinolin-7-yl)-3-methyl-6-(prop-1-ynyl)naphthalen-2-yl)acetate in Example 20, except used 1-(3-chloro-2-fluorophenyl)propan-2-one instead of 1-(3-bromophenyl)propan-2-one. LCMS-ESI⁺ (m/z): [M+H]⁺ calcd for $C_{30}H_{30}ClFNO_4$: 522.01. Found: 522.08.

Preparation of (S)-ethyl 2-tert-butoxy-2-((R)-6-cyano-1-(2,3-dihydropyrano[4,3,2-de]quinolin-7-yl)-5-fluoro-3-methylnaphthalen-2-yl)acetate: A Smith process vial was charged with (S)-ethyl 2-tert-butoxy-2-((R)-6-chloro-1-(2,3-dihydropyrano[4,3,2-de]quinolin-7-yl)-5-fluoro-3-methylnaphthalen-2-yl)acetate (21 mg, 0.04 mmol), Zn(CN)₂ (5 mg, 0.04 mmol), NaHCO₃ (5 mg, 0.04 mmol), chloro(2-dicyclohexylphosphino-2',4',6'-triisopropyl-1,1'-biphenyl)[2-(2-aminoethyl)phenyl]palladium(II) (7 mg, 0.009 mmol). Dimethoxyethane (1.5 mL, distilled from Na/benzophenone) was added and mixture sparged with nitrogen for 10 minutes and then heated in microwave at 130° C. for one hour. Reaction mixture was diluted with ethyl acetate and washed with brine, dried (MgSO₄), filtered, concentrated and purified by flash column chromatography (silica gel, 0 to 100% ethyl acetate/hexanes) to give (S)-ethyl 2-tert-butoxy-2-((R)-6-cyano-1-(2,3-dihydropyrano[4,3,2-de]quinolin-7-yl)-5-fluoro-3-methylnaphthalen-2-yl)acetate. LCMS-ESI⁺ (m/z): [M+H]⁺ calcd for $C_{31}H_{30}FN_2O_4$: 513.57. Found: 513.1.

Preparation of (S)-2-tert-butoxy-2-((R)-6-cyano-1-(2,3-dihydropyrano[4,3,2-de]quinolin-7-yl)-5-ethoxy-3-methylnaphthalen-2-yl)acetic acid: A solution of (S)-ethyl 2-tert-butoxy-2-((R)-6-cyano-1-(2,3-dihydropyrano[4,3,2-de]quinolin-7-yl)-5-fluoro-3-methylnaphthalen-2-yl)acetate (12 mg) and 5M lithium hydroxide (0.5 mL) in tetrahydrofuran (0.5 mL) and ethanol (1.0 mL) was heated at 50° C. overnight. Reaction mixture was diluted with ethyl acetate and washed with brine. The aqueous layer was back-extracted with ethyl acetate and the combined organic layer was dried (MgSO₄), filtered, concentrated and purified by reverse phase HPLC (Gemini, 5 to 100% ACN/H₂O+0.1% TFA). Product lyophilized to give the desired compound. ¹H-NMR: 400 MHz, (CD₃OD) δ: 8.69 (d, J=5.47 Hz, 1H), 8.33 (s, 1H), 7.81 (m, 2H), 7.44 (d, J=7.82 Hz, 1H), 7.31 (d, J=8.6 Hz, 1H), 6.78 (d, J=8.9 Hz, 1H), 5.23 (s, 1H), 4.69 (m, 2H), 4.54 (m, 2H), 3.64 (t, J=5.86 Hz, 2H), 2.81 (s, 3H), 1.61 (t, J=7.03 Hz, 3H), 0.92 (s, 9H). LCMS-ESI+ (m/z): [M+H]+ calcd for $C_{31}H_{31}N_2O_5$: 511.58. Found: 511.1.
EXAMPLE 23
(S)-2-tert-Butoxy-2-((R)-1-(2,3-dihydropyrano[4,3,2-de]quinolin-7-yl)-3-methyl-6-(prop-1-ynyl)naphthalen-2-yl)acetic acid and (S)-2-tert-butoxy-2-((S)-1-(2,3-dihydropyrano[4,3,2-de]quinolin-7-yl)-4,5,7-trifluoro-3-methylnaphthalen-2-yl)acetic acid
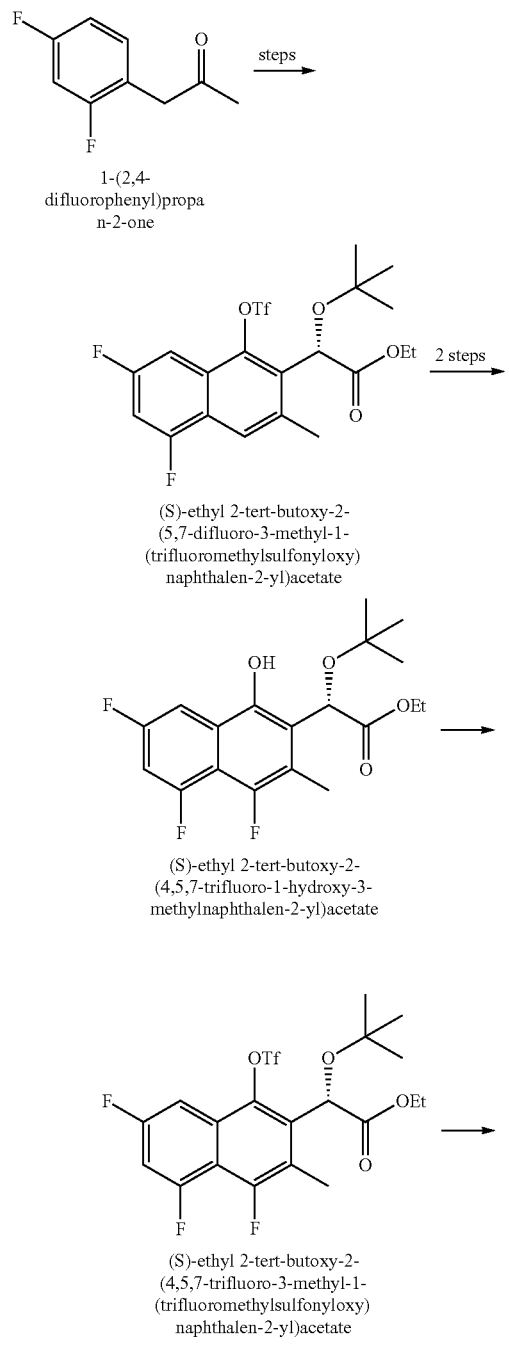
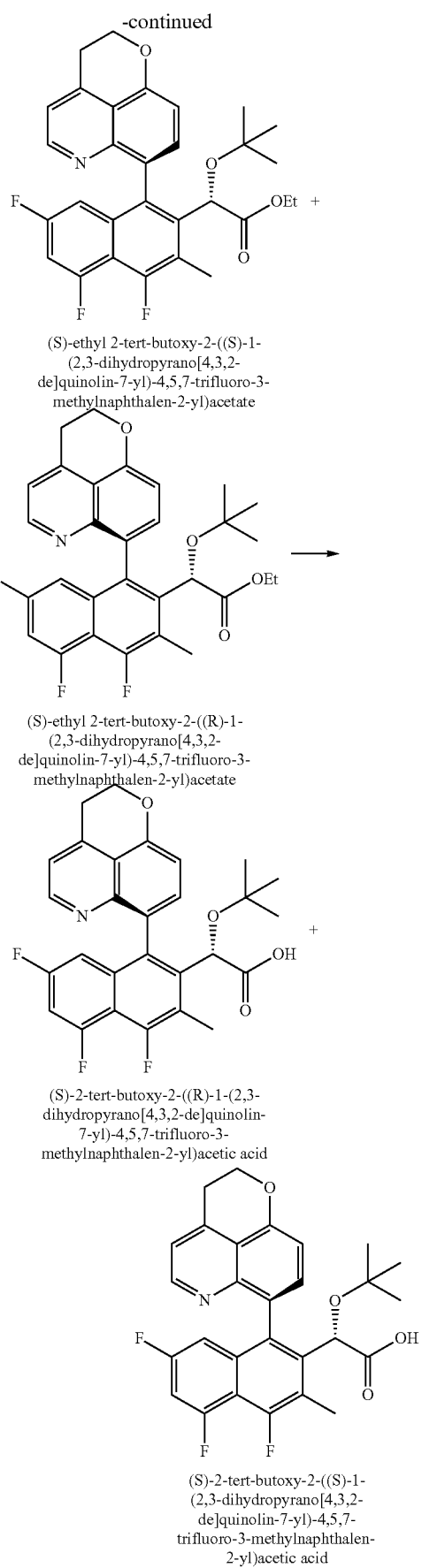

Preparation of (S)-ethyl 2-tert-butoxy-2-(5,7-difluoro-3-methyl-1-(trifluoromethylsulfonyloxy)naphthalen-2-yl)acetate: (S)-ethyl 2-tert-butoxy-2-(5,7-difluoro-3-methyl-1-(trifluoromethylsulfonyloxy)naphthalen-2-yl)acetate was prepared in a similar was as (S)-ethyl 2-(6-bromo-3-methyl-1-(trifluoromethylsulfonyloxy)naphthalen-2-yl)-2-tert-butoxyacetate in Example 20, except using 1-(2,4-difluorophenyl)propan-2-one instead of 1-(3-bromophenyl)propan-2-one. $^1$H-NMR: 400 MHz, (CDCl$_3$) δ: 7.82 (s, 1H), 7.39 (d, J=5.47 Hz, 1H), 6.99 (m, 1H), 5.63 (s, 1H), 4.18 (m, 2H), 2.49 (s, 3H), 1.11 (s+t, 12H). $^{19}$F-NMR: 377 MHz, (CDCl$_3$) δ: −73.27 (s, 3F), −109.1 (m, 1F), −117.5 (m, 1F).

Preparation of (S)-ethyl 2-tert-butoxy-2-(4,5,7-trifluoro-1-hydroxy-3-methylnaphthalen-2-yl)acetate: (S)-ethyl 2-tert-butoxy-2-(4,5,7-trifluoro-1-hydroxy-3-methylnaphthalen-2-yl)acetate was prepared in a similar way as (S)-ethyl 2-tert-butoxy-2-(6-chloro-4-fluoro-1-hydroxy-3-methylnaphthalen-2-yl)acetate in Example 7 except (S)-ethyl 2-tert-butoxy-2-(5,7-difluoro-3-methyl-1-(trifluoromethylsulfonyloxy)naphthalen-2-yl)acetate was used instead of (S)-ethyl 2-tert-butoxy-2-(6-chloro-1-hydroxy-3-methylnaphthalen-2-yl)acetate.

Preparation of (S)-ethyl 2-tert-butoxy-2-(4,5,7-trifluoro-3-methyl-1-(trifluoromethylsulfonyloxy)naphthalen-2-yl)acetate: (S)-ethyl 2-tert-butoxy-2-(4,5,7-trifluoro-3-methyl-1-(trifluoromethylsulfonyloxy)naphthalen-2-yl)acetate was prepared in a similar manner as (S)-ethyl 2-tert-butoxy-2-(6-cyano-4-fluoro-3-methyl-1-(trifluoromethylsulfonyloxy)naphthalen-2-yl)acetate in Example 7.

$^1$H-NMR: 400 MHz, (CDCl$_3$) δ: 7.44 (d, J=5.47 Hz, 1H), 7.08 (m, 1H), 5.63 (s, 1H), 4.20 (m, 2H), 2.41 (s, 3H), 1.22 (s+t, 12H). $^{19}$F-NMR: 377 MHz, (CDCl$_3$) δ: −73.19 (s, 3F), −107.6 (m, 1F), −110.07 (m, 1F), −114.72 (d, 1F).

Preparation of (S)-ethyl 2-tert-butoxy-2-((R)-1-(2,3-dihydropyrano[4,3,2-de]quinolin-7-yl)-4,5,7-trifluoro-3-methylnaphthalen-2-yl)acetate: A Smith process vial was charged with (S)-ethyl 2-tert-butoxy-2-(4,5,7-trifluoro-3-methyl-1-(trifluoromethylsulfonyloxy)naphthalen-2-yl)acetate (65 mg, 0.129 mmol), 2,3-dihydropyrano[4,3,2-de]quinolin-7-ylboronic acid, HCl salt (65 mg, 0.258 mmol), chloro(2-dicyclohexylphosphino-2',6'-dimethoxy-1,1'-biphenyl)[2-(2-aminoethylphenyl)]palladium(II)-methyl-t-butyl ether adduct (Strem, 9 mg, 0.013 mmol), cesium fluoride (98 mg, 0.645 mmol) and flushed with nitrogen. Dimethoxyethane (2 mL, distilled from Na/benzophenone) was added and mixture sparged with nitrogen for 10 minutes and then heated in microwave at 120° C. for 40 minutes. The reaction mixture was diluted with ethyl acetate and washed with brine, dried (MgSO$_4$), filtered, concentrated and purified by flash column chromatography (silica gel, 0 to 100% ethyl acetate/hexanes) to give (S)-ethyl 2-tert-butoxy-2-((R)-1-(2,3-dihydropyrano[4,3,2-de]quinolin-7-yl)-4,5,7-trifluoro-3-methylnaphthalen-2-yl)acetate. LCMS-ESI$^+$ (m/z): [M+H]$^+$ calcd for C$_{30}$H$_{29}$F$_3$NO$_4$: 524.54. Found: 524.1.

The other atropisomer, (S)-ethyl 2-tert-butoxy-2-((S)-1-(2,3-dihydropyrano[4,3,2-de]quinolin-7-yl)-4,5,7-trifluoro-3-methylnaphthalen-2-yl)acetate, was also isolated. LCMS-ESI$^+$ (m/z): [M+H]$^+$ calcd for C$_{30}$H$_{29}$F$_3$NO$_4$: 524.54. Found: 524.1.

Preparation of (S)-2-tert-butoxy-2-((R)-1-(2,3-dihydropyrano[4,3,2-de]quinolin-7-yl)-3-methyl-6-(prop-1-ynyl)naphthalen-2-yl)acetic acid: A solution of (S)-ethyl 2-tert-butoxy-2-((R)-1-(2,3-dihydropyrano[4,3,2-de]quinolin-7-yl)-4,5,7-trifluoro-3-methylnaphthalen-2-yl)acetate (10 mg) and 1M sodium hydroxide (0.5 mL) in tetrahydrofuran (0.5 mL) and ethanol (1.0 mL) was heated at 40° C. overnight. The reaction mixture was diluted with ethyl acetate and washed with brine. The aqueous layer was back-extracted with ethyl acetate and the combined organic layer was dried (MgSO$_4$), filtered, concentrated and purified by reverse phase HPLC (Gemini, 5 to 100% ACN/H$_2$O+0.1% TFA). Product lyophilized to give the desired compound. $^1$H-NMR: 400 MHz, (CD$_3$OD) δ: 8.64 (d, J=5.47 Hz, 1H), 8.12 (d, J=8.21 Hz, 1H), 7.68 (d, J=5.47 Hz, 1H), 7.45 (d, J=8.21 Hz, 1H), 7.17 (m, 1H), 6.43 (m, 1H), 5.14 (s, 1H), 4.69 (m, 2H), 3.61 (t, J=6.2 Hz, 2H), 2.59 (d, J=3.12 Hz 3H), 0.84 (s, 9H). LCMS-ESI$^+$ (m/z): [M+H]$^+$ calcd for C$_{28}$H$_{25}$F$_3$NO$_4$: 496.49. Found: 496.1.

Preparation of (S)-2-tert-butoxy-2-((S)-1-(2,3-dihydropyrano[4,3,2-de]quinolin-7-yl)-4,5,7-trifluoro-3-methylnaphthalen-2-yl)acetic acid: A solution of (S)-ethyl 2-tert-butoxy-2-((S)-1-(2,3-dihydropyrano[4,3,2-de]quinolin-7-yl)-4,5,7-trifluoro-3-methylnaphthalen-2-yl)acetate (16 mg) and 1M sodium hydroxide (0.5 mL) in tetrahydrofuran (0.5 mL) and ethanol (1.0 mL) was heated at 40° C. overnight. The reaction mixture was diluted with ethyl acetate and washed with brine. The aqueous layer was back-extracted with ethyl acetate and the combined organic layer was dried (MgSO$_4$), filtered, concentrated and purified by reverse phase HPLC (Gemini, 5 to 100% ACN/H$_2$O+0.1% TFA). Product lyophilized to give the desired compound. $^1$H-NMR: 400 MHz, (CD$_3$OD) δ: 8.64 (d, J=5.47 Hz, 1H), 7.84 (d, J=8.21 Hz, 1H), 7.78 (d, J=5.48 Hz, 1H), 7.45 (d, J=8.21 Hz, 1H), 7.22 (m, 1H), 6.43 (m, 1H), 5.17 (s, 1H), 4.69 (m, 2H), 3.63 (t, J=6.2 Hz, 2H), 2.62 (d, J=3.12 Hz 3H), 0.94 (s, 9H). LCMS-ESI$^+$ (m/z): [M+H]$^+$ calcd for C$_{28}$H$_{25}$F$_3$NO$_4$: 496.49. Found: 496.1.

EXAMPLE 24

(S)-2-tert-Butoxy-2-((R)-10-(2,3-dihydropyrano[4,3,2-de]quinolin-7-yl)phenanthren-9-yl)acetic acid

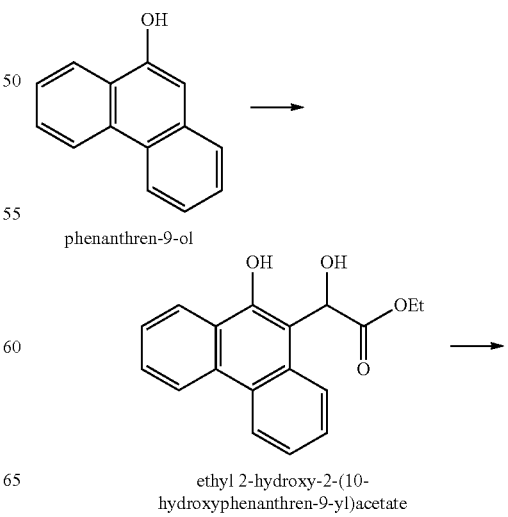

phenanthren-9-ol ethyl 2-hydroxy-2-(10-hydroxyphenanthren-9-yl)acetate

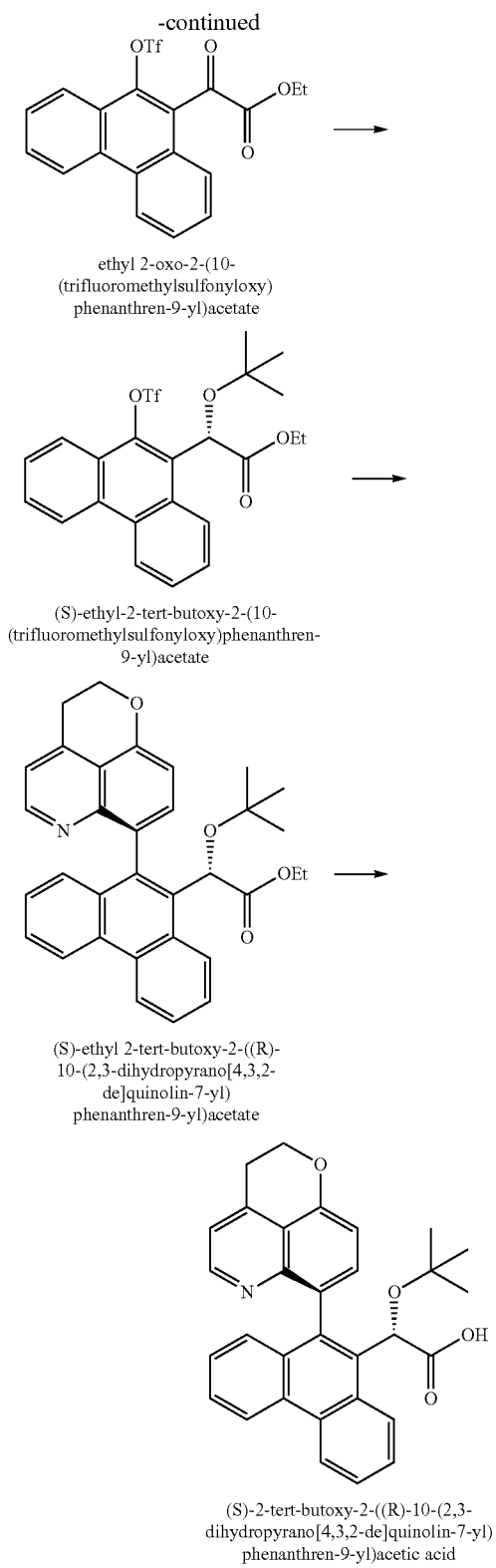

ethyl 2-oxo-2-(10-(trifluoromethylsulfonyloxy)phenanthren-9-yl)acetate (S)-ethyl-2-tert-butoxy-2-(10-(trifluoromethylsulfonyloxy)phenanthren-9-yl)acetate (S)-ethyl 2-tert-butoxy-2-((R)-10-(2,3-dihydropyrano[4,3,2-de]quinolin-7-yl)phenanthren-9-yl)acetate (S)-2-tert-butoxy-2-((R)-10-(2,3-dihydropyrano[4,3,2-de]quinolin-7-yl)phenanthren-9-yl)acetic acid Preparation of ethyl 2-hydroxy-2-(10-hydroxyphenanthren-9-yl)acetate: Prepared by the similar method to make ethyl 2-(6-bromo-1-hydroxy-3-methylnaphthalen-2-yl)-2-hydroxyacetate in Example 20, using phenanthren-9-ol instead of 6-bromo-3-methylnaphthalen-1-ol. $^1$H-NMR: 400 MHz, (CDCl$_3$) δ: 8.90 (s, 1H), 8.66-8.62 (m, 2H), 8.40 (d, J=4.2 Hz, 1H), 7.97-7.94 (m, 1H), 7.71-7.49 (m, 4H), 6.23 (s, 1H), 4.14-4.08 (m, 2H), 3.81 (bs, 1H), 1.11 (t, J=7.4 Hz, 3H).

Preparation of ethyl 2-oxo-2-(10-(trifluoromethylsulfonyloxy)phenanthren-9-yl)acetate: Prepared by the similar method to make ethyl 2-(6-bromo-3-methyl-1-(trifluoromethylsulfonyloxy)naphthalen-2-yl)-2-oxoacetate in Example 20, using ethyl 2-hydroxy-2-(10-hydroxyphenanthren-9-yl)acetate instead of ethyl 2-(6-bromo-1-hydroxy-3-methylnaphthalen-2-yl)-2-hydroxyacetate. $^1$H-NMR: 400 MHz, (CDCl$_3$) δ: 8.77-8.74 (m, 2H), 8.25 (d, J=4.0 Hz, 1H), 7.87-7.84 (m, 2H), 7.81-7.77 (m, 2H), 7.70-7.67 (m, 2H), 4.44-4.38 (m, 2H), 1.37 (t, J=7.2 Hz, 3H). 17F-NMR: 400 MHz, (CDCl$_3$) δ: −73.18 (s).

Preparation of (S)-ethyl 2-tert-butoxy-2-(10 (trifluoromethylsulfonyloxy)phenanthren-9-yl)acetate: Prepared by the similar method to make (S)-ethyl 2-(6-bromo-3-methyl-1-(trifluoromethylsulfonyloxy)naphthalen-2-yl)-2-tert-butoxyacetate in Example 20, using ethyl 2-oxo-2-(10-(trifluoromethylsulfonyloxy)phenanthren-9-yl)acetate instead of ethyl 2-(6-bromo-3-methyl-1-(trifluoromethylsulfonyloxy)naphthalen-2-yl)-2-oxoacetate. $^1$H-NMR: 400 MHz, (CDCl$_3$) δ: 8.74-8.69 (m, 2H), 8.41 (d, J=4.4 Hz, 1H), 8.19 (d, J=4.2 Hz, 1H), 7.79-7.61 (m, 4H), 6.00 (s, 1H), 4.189-4.14 (m, 1H), 4.05-4.00 (m, 1H), 1.25 (s, 9H), 1.03 (t, J=7 Hz, 3H).

Preparation of (S)-ethyl 2-tert-butoxy-2-((R)-10-(2,3-dihydropyrano[4,3,2-de]quinolin-7-yl)phenanthren-9-yl)acetate: Prepared the similar method to make (S)-ethyl 2-(6-bromo-3-methyl-1-(trifluoromethylsulfonyloxy)naphthalen-2-yl)-2-tert-butoxyacetate (S)-ethyl 2-(6-bromo-3-methyl-1-(trifluoromethylsulfonyloxy)naphthalen-2-yl)-2-tert-butoxyacetate, using ethyl 2-oxo-2-(10-(trifluoromethylsulfonyloxy)phenanthren-9-yl)acetate instead of ethyl 2-(6-bromo-3-methyl-1-(trifluoromethylsulfonyloxy)naphthalen-2-yl)-2-oxoacetate. LCMS-ESI$^+$ (m/z): [M+H]$^+$ calcd for $C_{33}H_{31}NO_4$: 506.6. Found: 506.1.

Preparation of (S)-2-tert-butoxy-2-((R)-10-(2,3-dihydropyrano[4,3,2-de]quinolin-7-yl)phenanthren-9-yl)acetic acid: Prepared by the similar method to make (S)-2-tert-butoxy-2-((R)-1-(2,3-dihydropyrano[4,3,2-de]quinolin-7-yl)-3-methyl-6-(prop-1-ynyl)naphthalen-2-yl)acetic acid, using (S)-ethyl 2-tert-butoxy-2-((R)-10-(2,3-dihydropyrano[4,3,2-de]quinolin-7-yl)phenanthren-9-yl)acetate instead of (S)-ethyl 2-tert-butoxy-2-((R)-1-(2,3-dihydropyrano[4,3,2-de]quinolin-7-yl)-3-methyl-6-(prop-1-ynyl)naphthalen-2-yl)acetate. $^1$H-NMR: 400 MHz, (CDCl$_3$) δ: 8.80 (d, J=4.4 Hz, 1H), 8.68 (d, J=3.8 Hz, 2H), 8.54 (d, J=2.2 Hz, 1H), 7.64-7.60 (m, 3H), 7.54-7.50 (m, 1H), 7.23-7.16 (m, 3H), 6.78 (d, J=4.2 Hz, 1H), 5.30 (s, 1H), 4.58 (t, J=5.8 Hz, 2H), 3.36 (t, J=5.6 Hz, 2H), 0.938 (s, 9H). LCMS-ESI$^+$ (m/z): [M+H]$^+$ calcd for $C_{31}H_{27}NO_4$: 478.5. Found: 478.1.

EXAMPLE 25

(2S)-2-((R)-1-(2,3-Dihydropyrano[4,3,2-de]quinolin-7-yl)-3-methylnaphthalen-2-yl)-2-(1-methoxy-2-methylpropan-2-yloxy)acetic acid Preparation of (S)-2-(1-(1-chloro-3-methylnaphthalen-2-yl)-2-(trityloxy)ethoxy)-2-methylpropyl acetate.

3-methylnaphthalen-2-ol

-continued

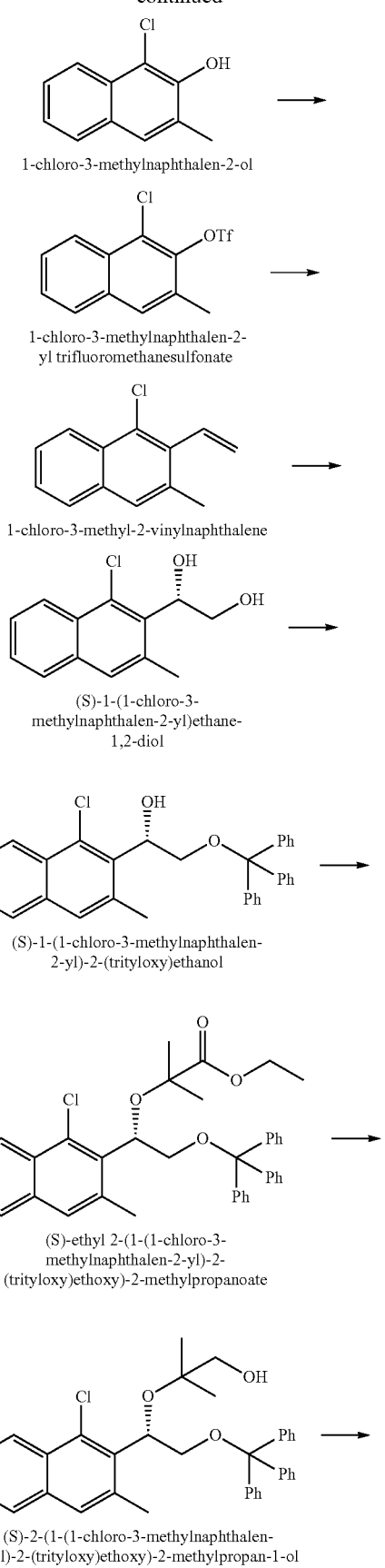

1-chloro-3-methylnaphthalen-2-ol 1-chloro-3-methylnaphthalen-2-yl trifluoromethanesulfonate 1-chloro-3-methyl-2-vinylnaphthalene (S)-1-(1-chloro-3-methylnaphthalen-2-yl)ethane-1,2-diol (S)-1-(1-chloro-3-methylnaphthalen-2-yl)-2-(trityloxy)ethanol (S)-ethyl 2-(1-(1-chloro-3-methylnaphthalen-2-yl)-2-(trityloxy)ethoxy)-2-methylpropanoate (S)-2-(1-(1-chloro-3-methylnaphthalen-2-yl)-2-(trityloxy)ethoxy)-2-methylpropan-1-ol -continued

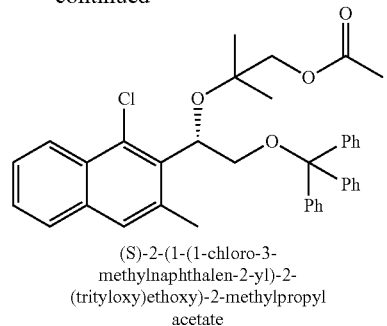

(S)-2-(1-(1-chloro-3-methylnaphthalen-2-yl)-2-(trityloxy)ethoxy)-2-methylpropyl acetate Preparation of 1-chloro-3-methyl-naphthalen-2-ol: To a solution of N-chlorosuccinimide (8.02 g, 60.05 mmol) in dichloromethane (475 mL) at −78° C. was added zirconium (IV) chloride (2.80 g, 12.01 mmol), followed by 3-methyl-naphthalen-2-ol (CombiBlocks, 9.5 g, 60.05 mmol) under argon. The reaction mixture was stirred at −78° C. for 5 minutes, the cooling bath was removed and the reaction was stirred at room temperature for 5 h. The reaction was quenched with saturated sodium bicarbonate solution and stirred for 5 minutes. The mixture was diluted with $H_2O$, extracted with dichloromethane (3×) and the combined organic layer was dried ($MgSO_4$), filtered, concentrated and purified by flash column chromatography (silica gel, 0 to 10% ethyl acetate/hexanes) to give 1-chloro-3-methyl-naphthalen-2-ol. $^1$H NMR (400 MHz, $CDCl_3$) δ 8.01 (d, J=8.2 Hz, 1H), 7.72 (d, J=8.2 Hz, 1H), 7.54 (s, 1H), 7.52 (dd, J=8.2, 8.2 Hz, 1H), 7.36 (dd, J=8.2, 8.2 Hz, 1H), 5.99 (s, 1H), 2.47 (s, 3H).

Preparation of trifluoro-methanesulfonic acid 1-chloro-3-methyl-naphthalen-2-yl ester: To a solution of 1-chloro-3-methyl-naphthalen-2-ol (9.05 g, 46.98 mmol) in dichloromethane (235 mL) at −78° C. was added trifluoromethanesulfonic anhydride (11.9 mL, 70.47 mmol), followed by 2,6-lutidine (8.2 mL, 70.47 mmol). The reaction mixture was stirred for 3 h to give a yellow solution, which was diluted with dichloromethane and washed with $H_2O$/brine. The organic layer was dried ($MgSO_4$), filtered, concentrated and purified by flash column chromatography (silica gel, 0 to 10% ethyl acetate/hexanes) to give trifluoro-methanesulfonic acid 1-chloro-3-methyl-naphthalen-2-yl ester. $^1$H NMR (400 MHz, $CDCl_3$) δ 8.26 (d, J=8.2 Hz, 1H), 7.79 (d, J=7.9 Hz, 1H), 7.69 (s, 1H), 7.64-7.58 (m, 2H), 2.59 (s, 3H). $^{19}$F NMR (377 MHz, $CDCl_3$) δ −72.9.

Preparation of 1-chloro-3-methyl-2-vinyl-naphthalene: To a solution of trifluoro-methanesulfonic acid 1-chloro-3-methyl-naphthalen-2-yl ester (14.75 g, 45.43 mmol), tributyl(vinyl)tin (14.59 mL, 49.97 mmol) and lithium chloride (5.78 g, 136.29 mmol) was added dichlorobis(triphenylphosphine)palladium(II) under argon. The reaction mixture was heated at 50° C. for 20 h, then heated at 90° C. for 8 h. The reaction mixture was than cooled to room temperature, diluted with ethyl acetate, washed with 5% lithium chloride solution (3×), brine and dried ($MgSO_4$), filtered and then concentrated and purified by flash column chromatography (silica gel, 0 to 10% ethyl acetate/hexanes) to give 1-chloro-3-methyl-2-vinyl-naphthalene contaminated by organotin. The residue was dissolved in dichloromethane and stirred with 10% KF solution overnight. The resulting white mixture was filtered through a pad of Celite and extracted with dichloromethane (2×). The organic layer was concentrated and purified by flash column chromatography (silica gel, 0 to 10% ethyl acetate/hexanes) to give 1-chloro-3-methyl-2-vinyl-naphthalene. $^1$H NMR (400 MHz, CDCl$_3$) δ 8.28 (d, J=8.2 Hz, 1H), 7.73 (d, J=8.2 Hz, 1H), 7.59 (s, 1H), 7.59-7.48 (m, 2H), 6.90 (dd, J=18.0, 11.8 Hz, 1H), 5.73 (d, J=11.8 Hz, 1H), 5.53 (d, J=18.0 Hz, 1H), 2.50 (s, 3H).

Preparation of 1-(1-chloro-3-methyl-naphthalen-2-yl)-ethane-1,2-diol: A biphasic mixture of AD mix-α (6.907 g) in tert-butanol (24.5 mL)/H$_2$O (24.5 mL) was cooled to 0° C. and 1-chloro-3-methyl-2-vinyl-naphthalene (1.00 g, 4.93 mmol) was added. The reaction mixture was stirred for 8 h at 0° C. Sodium sulfite (7.4 g) was added at 0° C. and the reaction was stirred for 40 minutes to give a white mixture. The mixture was diluted with dichloromethane and H$_2$O. The mixture was extracted with dichloromethane (3×) and the combined organic layer was dried (MgSO$_4$), filtered, concentrated and purified by flash column chromatography (silica gel, 0 to 100% ethyl acetate/hexanes) to give 1-(1-chloro-3-methyl-naphthalen-2-yl)-ethane-1,2-diol. $^1$H NMR (400 MHz, CDCl$_3$) δ 8.27 (d, J=8.2 Hz, 1H), 7.72 (d, J=7.8 Hz, 1H), 7.57 (s, 1H), 7.56-7.47 (m, 2H), 5.70 (dd, J=9.4, 3.9 Hz, 1H), 4.11 (dd, J=10.5, 10.5 Hz, 1H), 3.80 (dd, J=11.6, 3.9 Hz, 1H), 2.66 (s, 3H).

Preparation of (S)-1-(1-chloro-3-methylnaphthalen-2-yl)-2-(trityloxy)ethanol: A suspension of (S)-1-(1-chloro-3-methylnaphthalen-2-yl)ethane-1,2-diol (6.70 grams, 28.2 mmol) and CH$_2$Cl$_2$ (67 mL) was treated with pyridine (4.78 mL, 59.2 mmol) at 23° C. Trityl chloride (8.28 g, 29.6 mmol) was added and the reaction was stirred for 24 h. The reaction was washed with 1.0 M aq CuSO$_4$ monohydrate (3×50 mL), H$_2$O (2×50 mL), and brine (50 mL). The final organic layer was dried over Na$_2$SO$_4$, filtered, and concentrated. The residue was treated with benzene and purified by flash column chromatography (silica gel, 0 to 20% ethyl acetate/hexanes) to give (S)-1-(1-chloro-3-methylnaphthalen-2-yl)-2-(trityloxy)ethanol. $^1$H NMR (400 MHz, CDCl$_3$) δ 8.22 (d, J=8.2 Hz, 1H), 7.69 (d, J=8.2 Hz, 1H), 7.53-7.44 (m, 2H), 7.51 (s, 1H), 7.43-7.40 (m, 6H), 7.30-7.20 (m, 9H), 5.93-5.77 (m, broad, 1H), 3.59 (dd, J=9.4, 9.0 Hz, 1H), 3.52 (dd, J=9.4, 5.0 Hz, 1H), 2.85 (d, broad, J=4.3 Hz, 1H), 2.52 (s, 3H).

Preparation of (S)-ethyl 2-(1-(1-chloro-3-methylnaphthalen-2-yl)-2-(trityloxy)ethoxy)-2-methylpropanoate: A slurry of (S)-1-(1-chloro-3-methylnaphthalen-2-yl)-2-(trityloxy)ethanol (10.8 grams, 22.5 mmol) and DMF (40 mL) was treated with NaH (60% w/w in mineral oil, 11.3 mmol) at 23° C. After 5 min, ethyl-(2-bromovalerate) (1.65 mL, 11.3 mmol) was added. After 30 min had passed, more NaH (60% w/w in mineral oil, 11.3 mmol) was added. After stirring for 5 min, additional ethyl-(2-bromovalerate) (1.65 mL, 11.3 mmol) was added. Again, after 30 min had passed, more NaH (60% w/w in mineral oil, 11.3 mmol) was added. After stirring for 5 min, additional ethyl-(2-bromovalerate) (1.65 mL, 11.3 mmol) was added. Once more, after 30 min had passed, more NaH (60% w/w in mineral oil, 11.3 mmol) was added. After stirring for 5 min, additional ethyl-(2-bromovalerate) (1.65 mL, 11.3 mmol) was added. The reaction was stirred for another hour. Saturated aq. NH$_4$Cl (100 mL) was added, followed by H$_2$O (100 mL). After stirring for 10 min, the reaction was extracted with EtOAc (200 mL). The organic extract was washed with 5% w/v aq. LiCl (3×100 mL). The final organic phase was dried over Na$_2$SO$_4$, filtered, and concentrated. The residue was treated with benzene and purified by flash column chromatography (silica gel, 0 to 20% ethyl acetate/hexanes) to give (S)-ethyl 2-(1-(1-chloro-3-methyl-naphthalen-2-yl)-2-(trityloxy)ethoxy)-2-methylpropanoate. $^1$H NMR (400 MHz, CDCl$_3$) δ 8.30 (d, J=8.6 Hz, 1H), 7.70 (d, J=8.2 Hz, 1H), 7.57-7.38 (m, 2H), 7.49 (s, 1H), 7.36-7.32 (m, 6H), 7.21-7.14 (m, 9H), 5.94 (dd, J=6.7, 6.7 Hz, 1H), 3.93-3.74 (m, 2H), 3.61 (dd, J=9.0, 7.0 Hz, 1H), 3.33 (dd, J=9.0, 5.3 Hz, 1H), 2.52 (s, 3H), 1.46 (s, 3H), 1.37 (s, 3H), 0.99 (dd, J=7.0, 7.0 Hz, 3H). Additionally, starting material ((S)-1-(1-chloro-3-methylnaphthalen-2-yl)-2-(trityloxy)ethanol) was recovered. Yield was not determined.

Preparation of (S)-2-(1-(1-chloro-3-methylnaphthalen-2-yl)-2-(trityloxy)ethoxy)-2-methylpropan-1-ol: A solution of (S)-ethyl 2-(1-(1-chloro-3-methylnaphthalen-2-yl)-2-(trityloxy)ethoxy)-2-methylpropanoate (1.58 g, 2.66 mmol) in diethyl ether (62 mL) was treated with DIBAL-H (1.0 M in hexanes, 13.3 mL, 13.3 mmol) at 23° C. After 5 min, aq. Rochelle's salt (excess) was added dropwise over 5 min until bubbling ceased. The quenched reaction was agitated manually for 1 min to ensure full quenching. The system transitioned from a slurry to a gel. 50% w/v aw KOH (10 mL) was added, followed by H$_2$O (40 mL), and the reaction was manually agitated until magnetic stirring was achievable (the reaction transitioned from a gel to a biphasic solution). After 15 min of stirring the reaction was extracted with diethyl ether (3×30 mL). Combined organic layers were dried quickly over MgSO$_4$ for 1 min and promptly filtered and concentrated. The residue was treated with benzene and purified by flash column chromatography (silica gel, 0 to 100% ethyl acetate/hexanes) to give (S)-2-(1-(1-chloro-3-methylnaphthalen-2-yl)-2-(trityloxy)ethoxy)-2-methylpropan-1-ol. $^1$H NMR (400 MHz, CDCl$_3$) δ 8.23 (d, J=8.2 Hz, 1H), 7.67 (d, J=7.8 Hz, 1H), 7.52-7.38 (m, 9H), 7.31-7.18 (m, 9H), 5.87 (dd, J=9.5, 3.9 Hz, 1H), 3.76 (d, AB-spin system, J=11.8 Hz, 1H), 3.60 (dd, J=9.6, 9.6 Hz, 1H), 3.32 (d, AB-spin system, J=11.8 Hz, 1H), 3.26 (dd, J=9.8, 3.9 Hz, 1H), 2.49 (s, 3H), 1.16 (s, 3H), 1.02 (s, 3H).

Preparation of (S)-2-(1-(1-chloro-3-methylnaphthalen-2-yl)-2-(trityloxy)ethoxy)-2-methylpropyl acetate: At 23° C., a flask containing (S)-2-(1-(1-chloro-3-methylnaphthalen-2-yl)-2-(trityloxy)ethoxy)-2-methylpropan-1-ol (1.31 g, 2.21 mmol) was charged with Ac$_2$O (5.00 mL) immediately followed by pyridine (5.00 mL). 4-(N,N-dimethylamino)-pyridine (20 mg, 0.164 mmol) was added. After 1.5 h, the reaction was poured onto 50 mL of crushed ice and H$_2$O. A white precipitate developed. EtOAc (50 mL) was added after several hours had passed. Solid NaHCO$_3$ was added portionwise (bubbling) until the aq. layer had a pH of 9. The slurry was extracted with EtOAc (2×25 mL). The combined organic layers were washed with 1.0 M aq. CuSO$_4$ monohydrate (3×25 mL) and H$_2$O (25 mL). The final organic phase was dried over Na$_2$SO$_4$, filtered, and concentrated. The residue was treated with benzene and purified by flash column chromatography (silica gel, 0 to 100% ethyl acetate/hexanes) to give (S)-2-(1-(1-chloro-3-methylnaphthalen-2-yl)-2-(trityloxy)ethoxy)-2-methylpropyl acetate. $^1$H NMR (400 MHz, CDCl$_3$) δ 8.25 (d, J=8.6 Hz, 1H), 7.68 (d, J=7.8 Hz, 1H), 7.52-7.41 (m, 9H), 7.26-7.16 (m, 9H), 5.99 (dd, J=8.2, 4.7 Hz, 1H), 4.02 (app. s, 2H), 3.55 (dd, J=8.6, 8.4 Hz, 1H), 3.12 (dd, J=9.8 Hz, 4.7 Hz, 1H), 2.52 (s, 3H), 1.86 (s, 3H), 1.32 (s, 3H), 1.15 (s, 3H).

Preparation of 2-((S)-1-((R)-1-(2,3-dihydropyrano[4,3,2-de]quinolin-7-yl)-3-methylnaphthalen-2-yl)-2-(trityloxy)ethoxy)-2-methylpropyl acetate and 2-((S)-1-((S)-1-(2,3-dihydropyrano[4,3,2-de]quinolin-7-yl)-3-methylnaphthalen-2-yl)-2-(trityloxy)ethoxy)-2-methylpropyl acetate.

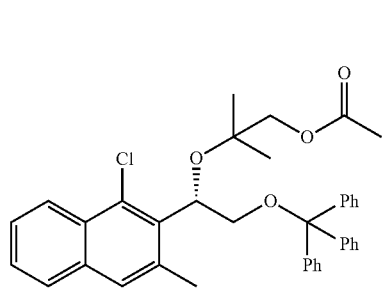

(S)-2-(1-(1-chloro-3-methylnaphthalen-2-yl)-2-(trityloxy)ethoxy)-2-methylpropyl acetate

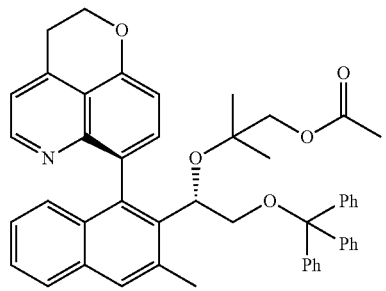

2-((S)-1-((R)-1-(2,3-dihydropyrano[4,3,2-de]quinolin-7-yl)-3-methylnaphthalen-2-yl)-2-(trityloxy)ethoxy)-2-methylpropyl acetate

+

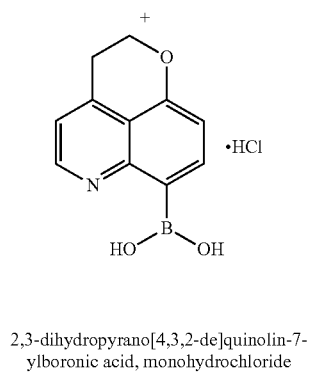

2,3-dihydropyrano[4,3,2-de]quinolin-7-ylboronic acid, monohydrochloride

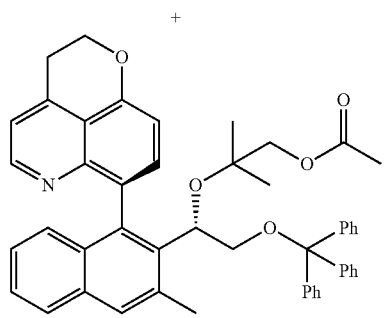

2-((S)-1-((S)-1-(2,3-dihydropyrano[4,3,2-de]quinolin-7-yl)-3-methylnaphthalen-2-yl)-2-(trityloxy)ethoxy)-2-methylpropyl acetate Preparation of 2-((S)-1-((R)-1-(2,3-dihydropyrano[4,3,2-de]quinolin-7-yl)-3-methylnaphthalen-2-yl)-2-(trityloxy)ethoxy)-2-methylpropyl acetate: A 100 mL round-bottom flash was charged with (S)-2-(1-(1-chloro-3-methylnaphthalen-2-yl)-2-(trityloxy)ethoxy)-2-methylpropyl acetate (1.32 g, 2.23 mmol), 2,3-dihydropyrano[4,3,2-de]quinolin-7-ylboronic acid, monohydrochloride (673 mg, 2.68 mmol), CsF (1.49 g, 9.81 mmol), and Buchwald's S-Phos Palladacycle precatalyst (Strem, 225 mg, 0.331 mmol). The vessel was evacuated under vacuum and backfilled with dry argon. Freshly distilled 1,2-dimethoxyethane (distilled from sodium/benzophenone, 20 mL) was introduced. With vigorous stirring, the flask was wrapped in foil and heated to 120° C. for 3 h. The reaction was cooled to 23° C. and added to brine (20 mL) and H$_2$O (20 mL). EtOAc (30 mL) was introduced, followed by hexane (10 mL). The slurry was filtered over a pad of Celite. The filtrate now separated into two layers. The organic phase was collected. The aq. layer was extracted with EtOAc (3×30 mL). Combined organic layers were dried over Na$_2$SO$_4$, filtered, and concentrated. The residue was treated with benzene and purified by flash column chromatography (silica gel, 0 to 100% ethyl acetate/hexanes) to give two products: The first was 2-((S)-1-((R)-1-(2,3-dihydropyrano[4,3,2-de]quinolin-7-yl)-3-methylnaphthalen-2-yl)-2-(trityloxy)ethoxy)-2-methylpropyl acetate. LCMS-ESI$^+$: calc'd for C$_{49}$H$_{45}$NO$_5$: 728.3 (M+H$^+$). Found: 728.3 (M+H$^+$), 750.3 (M+Na)$^+$. The second was 2-((S)-1-((S)-1-(2,3-dihydropyrano[4,3,2-de]quinolin-7-yl)-3-methylnaphthalen-2-yl)-2-(trityloxy)ethoxy)-2-methylpropyl acetate. LCMS-ESI$^+$ (m/z): [M+H]$^+$ calcd for C$_{49}$H$_{45}$NO$_5$: 728.3. Found: 728.1.

Preparation of (2S)-2-((R)-1-(2,3-dihydropyrano[4,3,2-de]quinolin-7-yl)-3-methylnaphthalen-2-yl)-2-(1-methoxy-2-methylpropan-2-yloxy)acetic acid.

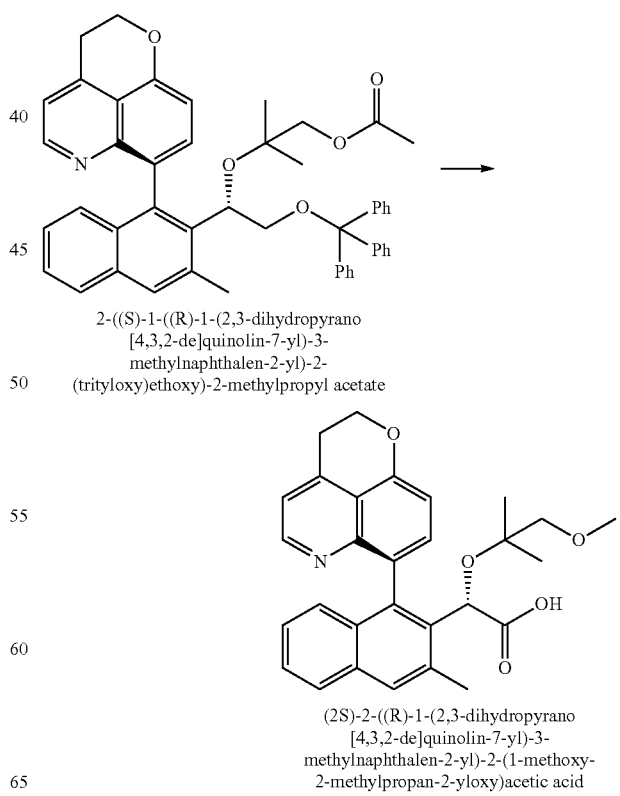

2-((S)-1-((R)-1-(2,3-dihydropyrano[4,3,2-de]quinolin-7-yl)-3-methylnaphthalen-2-yl)-2-(trityloxy)ethoxy)-2-methylpropyl acetate (2S)-2-((R)-1-(2,3-dihydropyrano[4,3,2-de]quinolin-7-yl)-3-methylnaphthalen-2-yl)-2-(1-methoxy-2-methylpropan-2-yloxy)acetic acid Preparation of (2S)-2-((R)-1-(2,3-dihydropyrano[4,3,2-de]quinolin-7-yl)-3-methylnaphthalen-2-yl)-2-(1-methoxy-2-methylpropan-2-yloxy)acetic acid: A slurry of 2-((S)-1-((R)-1-(2,3-dihydropyrano[4,3,2-de]quinolin-7-yl)-3-methylnaphthalen-2-yl)-2-(trityloxy)ethoxy)-2-methylpropyl acetate (15 mg, 21 µmol), THF (1.5 mL), EtOH (absolute, 750 µL), and H₂O (750 µL) was treated with LiOH monohydrate (75 mg, excess) at 23° C. After 1 h, the reaction was diluted with H₂O (15 mL) and extracted with EtOAc (2×15 mL). Combined organic layers were dried over Na₂SO₄, filtered, concentrated, treated with THF, and concentrated again to remove residual EtOAc.

DMF (750 µL) was introduced, followed by iodomethane (150 µL). The solution was treated with NaH (60% w/v in mineral oil, 30 mg, excess) at 23° C. After 1.5 h, the reaction was quenched with saturated aq. NH₄Cl. After dilution with H₂O (15 mL), the reaction was extracted with EtOAc (2×15 mL). The combined organic layers were washed with 5% w/v aq. LiCl (3×10 mL), dried (Na₂SO₄), filtered, and concentrated.

MeOH (1.5 mL) was introduced followed by MsOH monohydrate (15 µL, excess) at 23° C. After 30 min, saturated aq. NaHCO₃ (3 mL) was added in one portion (bubbling). After 10 min, H₂O (10 mL) was added and the reaction was extracted with EtOAc (3×15 mL) Combined organic layers were dried (Na₂SO₄), filtered, and concentrated. EtOAc was added, and again the solution was concentrated to remove residual methanol.

CH₃CN (800 µL) and H₂O (200 µL) were added, followed by H₅IO₆ (30 mg, excess). CrO₃ (7 mg, excess) was added at 23° C. with vigorous stirring. After 15 min, the reaction was directly purified on a C18 Gemini column (Eluent: H₂O/CH₃CN 95:5→0:100+0.1% v/v TFA), giving (2S)-2-((R)-1-(2,3-dihydropyrano[4,3,2-de]quinolin-7-yl)-3-methylnaphthalen-2-yl)-2-(1-methoxy-2-methylpropan-2-yloxy)acetic acid as its mono-trifluoroacetic acid salt. ¹H NMR (400 MHz, CD₃OD) δ 8.65 (d, J=5.2 Hz, 1H), 7.91 (s, 1H), 7.90 (d, J=8.6 Hz, 1H), 7.76-7.64 (m, 2H), 7.46 (dd, J=8.4, 8.0 Hz, 1H), 7.38 (d, J=7.6 Hz, 1H), 7.23 (dd, J=7.4, 7.0 Hz, 1H), 6.89 (d, J=8.2 Hz, 1H), 5.53 (s, broad, 1H), 4.73-4.66 (m, 2H), 3.63-3.58 (m, 2H), 3.40-2.99 (m, 2H), 3.08 (s, 3H), 2.74 (s, 3H), 0.91 (s, broad, 3H), 0.88 (s, broad, 3H). ¹⁹F NMR (377 MHz, CD₃OD) δ −105.6 (s, 1F), −77.5. LCMS-ESI⁺ (m/z): [M+H]⁺ calcd for C₂₉H₂₉NO₅: 472.2. Found: 472.2.

EXAMPLE 26

(2S)-2-((S)-1-(2,3-Dihydropyrano[4,3,2-de]quinolin-7-yl)-3-methylnaphthalen-2-yl)-2-(1-methoxy-2-methylpropan-2-yloxy)acetic acid

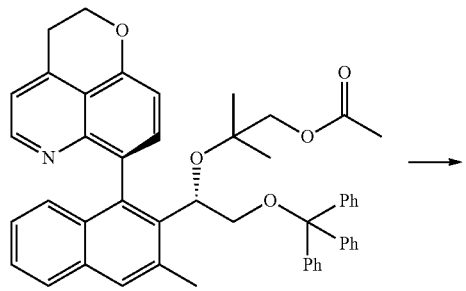

2-((S)-1-((S)-1-(2,3-dihydropyrano
[4,3,2-de]quinolin-7-yl)-3-
methylnaphthalen-2-yl)-2-
(trityloxy)ethoxy)-2-methylpropyl acetate

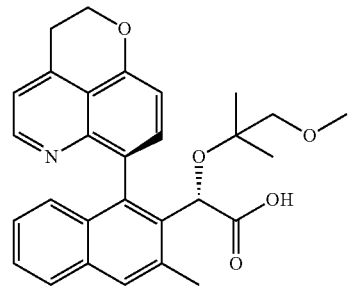

(2S)-2-((S)-1-(2,3-dihydropyrano
[4,3,2-de]quinolin-7-yl)-3-
methylnaphthalen-2-yl)-2-(1-methoxy-
2-methylpropan-2-yloxy)acetic acid Preparation of (2S)-2-((S)-1-(2,3-dihydropyrano[4,3,2-de]quinolin-7-yl)-3-methylnaphthalen-2-yl)-2-(1-methoxy-2-methylpropan-2-yloxy)acetic acid: Prepared in a manner similar to (2S)-2-((R)-1-(2,3-dihydropyrano[4,3,2-de]quinolin-7-yl)-3-methylnaphthalen-2-yl)-2-(1-methoxy-2-methylpropan-2-yloxy)acetic acid in Example 25, except using 2-((S)-1-((S)-1-(2,3-dihydropyrano[4,3,2-de]quinolin-7-yl)-3-methylnaphthalen-2-yl)-2-(trityloxy)ethoxy)-2-methylpropyl acetate (Example 25) as the starting material. ¹H NMR (400 MHz, CD₃OD) δ 8.59 (d, J=5.5 Hz, 1H), 8.17 (d, J=8.2, 1H), 7.93 (s, 1H), 7.92 (d, J=8.2 Hz, 1H), 7.70 (d, J=5.1 Hz, 1H), 7.50-7.44 (m, 2H), 7.24 (dd, J=7.8, 7.4 Hz, 1H), 6.90 (d, J=7.8 Hz, 1H), 5.55 (s, broad, 1H), 4.71 (dd, J=5.9, 5.9 Hz, 2H), 3.64 (dd, J=5.9, 5.9 Hz, 2H), 3.38-3.00 (m, 2H), 3.07 (s, 3H), 2.73 (s, 3H), 0.95 (s, broad, 3H), 0.75 (s, broad, 3H). ¹⁹F NMR (377 MHz, CD₃OD) δ −77.7. LCMS-ESI⁺ (m/z): [M+H]⁺ calcd for C₂₉H₂₉NO₅: 472.2. Found: 472.1.

EXAMPLE 27

(2S)-2-((R)-1-(2,3-Dihydropyrano[4,3,2-de]quinolin-7-yl)-3-methylnaphthalen-2-yl)-2-(1-ethoxy-2-methylpropan-2-yloxy)acetic acid

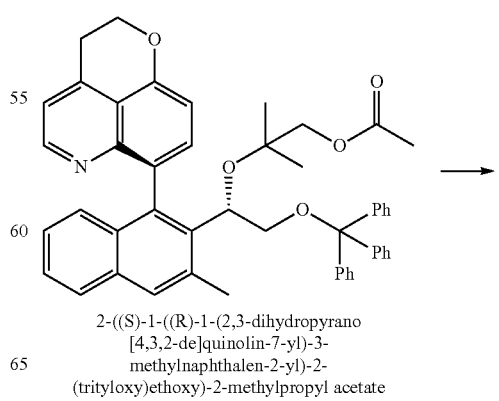

2-((S)-1-((R)-1-(2,3-dihydropyrano
[4,3,2-de]quinolin-7-yl)-3-
methylnaphthalen-2-yl)-2-
(trityloxy)ethoxy)-2-methylpropyl acetate

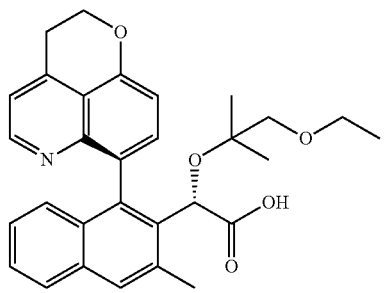

(2S)-2-((R)-1-(2,3-dihydropyrano
[4,3,2-de]quinolin-7-yl)-3-
methylnaphthalen-2-yl)-2-(1-ethoxy-
2-methylpropan-2-yloxy)acetic acid Preparation of (2S)-2-((R)-1-(2,3-dihydropyrano[4,3,2-de]quinolin-7-yl)-3-methylnaphthalen-2-yl)-2-(1-ethoxy-2-methylpropan-2-yloxy)acetic acid: Prepared in a manner similar to (2S)-2-((R)-1-(2,3-dihydropyrano[4,3,2-de]quinolin-7-yl)-3-methylnaphthalen-2-yl)-2-(1-methoxy-2-methylpropan-2-yloxy)acetic acid in Example 25, using 2-((S)-1-((R)-1-(2,3-dihydropyrano[4,3,2-de]quinolin-7-yl)-3-methylnaphthalen-2-yl)-2-(trityloxy)ethoxy)-2-methylpropyl acetate as the starting material. $^1$H NMR (400 MHz, CD$_3$OD) δ 8.68 (d, J=5.5 Hz, 1H), 7.92 (s, 1H), 7.91 (d, J=8.6 Hz, 1H), 7.80-7.68 (m, 2H), 7.50-7.38 (m, 2H), 7.25 (dd, J=8.2, 8.2 Hz, 1H), 6.90 (d, J=8.2 Hz, 1H), 5.70 (s, broad, 1H), 4.75-4.68 (m, 2H), 3.68-3.59 (m, 2H), 3.48-3.45 (m, 1H), 3.48-3.08 (m, 2H), 3.16-3.13 (m, 1H), 2.74 (s, 3H), 0.97 (s, broad, 3H), 0.94-0.84 (m, 6H). $^{19}$F NMR (377 MHz, CD$_3$OD) δ −77.5. LCMS-ESI$^+$ (m/z): [M+H]$^+$ calcd for C$_{30}$H$_{31}$NO$_5$: 486.2. Found: 486.2.

EXAMPLE 28

(2S)-2-((S)-1-(2,3-Dihydropyrano[4,3,2-de]quinolin-7-yl)-3-methylnaphthalen-2-yl)-2-(1-ethoxy-2-methylpropan-2-yloxy)acetic acid

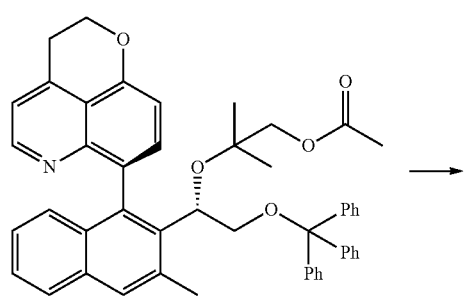

2-((S)-1-((S)-1-(2,3-dihydropyrano
[4,3,2-de]quinolin-7-yl)-3-
methylnaphthalen-2-yl)-2-
(trityloxy)ethoxy)-2-methylpropyl acetate

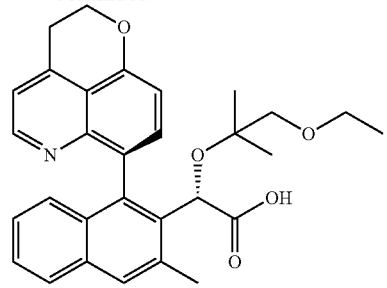

(2S)-2-((S)-1-(2,3-dihydropyrano
[4,3,2-de]quinolin-7-yl)-3-
methylnaphthalen-2-yl)-2-(1-ethoxy-
2-methylpropan-2-yloxy)acetic acid Preparation of (2S)-2-((S)-1-(2,3-dihydropyrano[4,3,2-de]quinolin-7-yl)-3-methylnaphthalen-2-yl)-2-(1-ethoxy-2-methylpropan-2-yloxy)acetic acid: Prepared in a manner similar to (2S)-2-((S)-1-(2,3-dihydropyrano[4,3,2-de]quinolin-7-yl)-3-methylnaphthalen-2-yl)-2-(1-methoxy-2-methylpropan-2-yloxy)acetic acid using 2-((S)-1-((S)-1-(2,3-dihydropyrano[4,3,2-de]quinolin-7-yl)-3-methylnaphthalen-2-yl)-2-(trityloxy)ethoxy)-2-methylpropyl acetate as the starting material). $^1$H NMR (400 MHz, CD$_3$OD) δ 8.57 (d, J=5.5 Hz, 1H), 8.12 (d, J=8.8 Hz, 1H), 7.89 (d, J=8.6 Hz, 1H), 7.88 (s, 1H), 7.63-7.59 (m, 1H), 7.49-7.37 (m, 2H), 7.21 (dd, J=8.8, 8.0 Hz, 1H), 6.90 (d, J=8.6 Hz, 1H), 5.58 (s, broad, 1H), 4.70-4.65 (m, 2H), 3.62-3.55 (m, 2H), 3.49-3.47 (m, 1H), 3.47-3.00 (m, 2H), 3.15-3.13 (m, 1H), 2.70 (s, 3H), 1.02-0.94 (m, 6H), 0.88 (s, broad, 3H). $^{19}$F NMR (377 MHz, CD$_3$OD) δ −77.6. LCMS-ESI$^+$ (m/z): [M+H]$^+$ calcd for C$_{30}$H$_{31}$NO$_5$: 486.2. Found: 486.1.

EXAMPLE 29

(S)-2-((R)-1-(2,3-Dihydropyrano[4,3,2-de]quinolin-7-yl)-3-methylnaphthalen-2-yl)-2-(2-methylpentan-2-yloxy)acetic acid Preparation of (S)-ethyl 2-hydroxy-2-(3-methyl-1-(trifluoromethylsulfonyloxy)-naphthalen-2-yl)acetate.

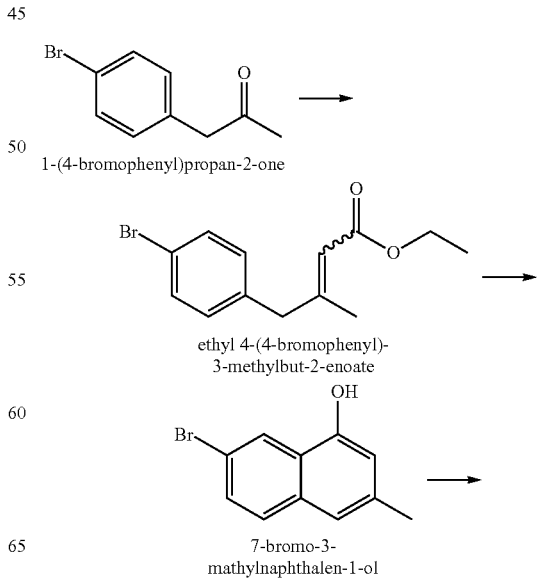

1-(4-bromophenyl)propan-2-one ethyl 4-(4-bromophenyl)-
3-methylbut-2-enoate 7-bromo-3-
mathylnaphthalen-1-ol

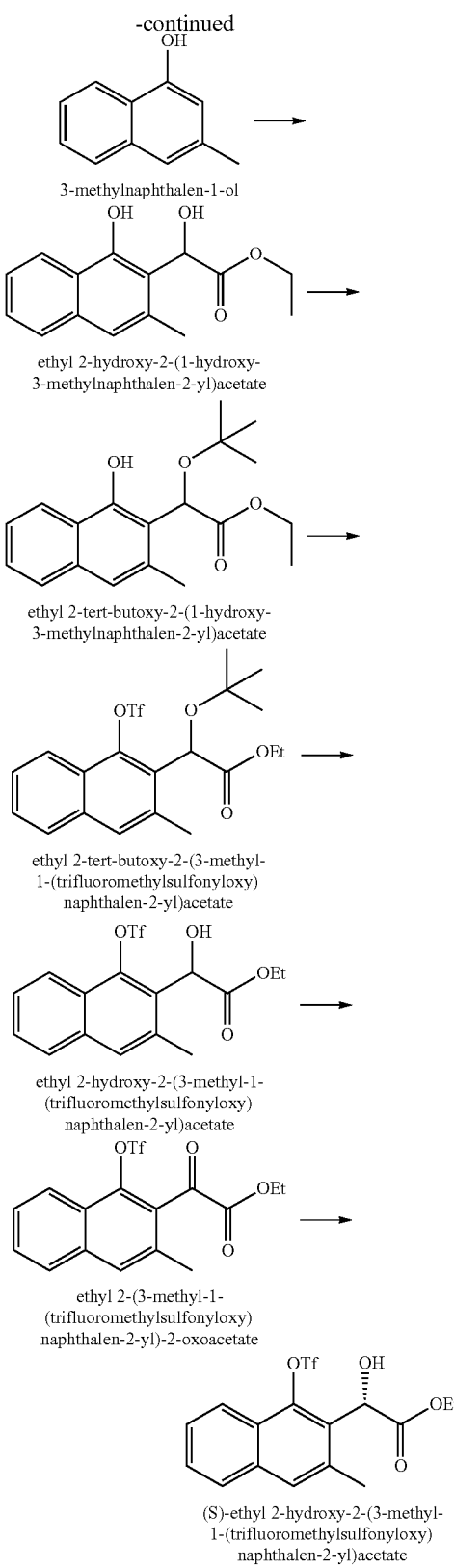

3-methylnaphthalen-1-ol ethyl 2-hydroxy-2-(1-hydroxy-3-methylnaphthalen-2-yl)acetate ethyl 2-tert-butoxy-2-(1-hydroxy-3-methylnaphthalen-2-yl)acetate ethyl 2-tert-butoxy-2-(3-methyl-1-(trifluoromethylsulfonyloxy)naphthalen-2-yl)acetate ethyl 2-hydroxy-2-(3-methyl-1-(trifluoromethylsulfonyloxy)naphthalen-2-yl)acetate ethyl 2-(3-methyl-1-(trifluoromethylsulfonyloxy)naphthalen-2-yl)-2-oxoacetate (S)-ethyl 2-hydroxy-2-(3-methyl-1-(trifluoromethylsulfonyloxy)naphthalen-2-yl)acetate Preparation of ethyl 4-(4-bromophenyl)-3-methylbut-2-enoate: At 0° C., a suspension of 60% w/w NaH/mineral oil (7.13 g, 0.176 mol) in THF (250 mL) was treated dropwise with a solution of triethylphosphonoacetate (39.5 g, 0.176 mol) in THF (72 mL) over a 30 min period. The reaction was stirred for another 30 min, and a solution of 1-(4-bromophenyl)propan-2-one (25.0 g, 0.117 mol) in THF (108 mL) was added dropwise over 1 h (reaction was kept at 0° C. during addition. The reaction was allowed to warm to 23° C. as it was stirred overnight. The next day, saturated NH₄Cl (250 mL) was added. After 2 h, the reaction was diluted with H₂O (250 mL) and hexane (100 mL). The organic phase was collected. The aqueous layer was extracted with EtOAc (2×150 mL). Combined organic phases were dried (MgSO₄), filtered, and concentrated, giving crude 4-(4-bromophenyl)-3-methylbut-2-enoate as a mixture of E and Z geometric isomers. The residue was carried onward without further purification. The $^1$H NMR reported below was from a crude mixture containing both the E and Z isomer. $^1$H NMR (400 MHz, CDCl$_3$) δ 7.43 (d, J=8.6 Hz, 1.6H), 7.39 (d, J=8.6 Hz, 0.4H), 7.12 (d, J=8.2 Hz, 0.4H), 7.04 (d, J=8.2 Hz, 1.6H), 4.42-4.21 (m, 2H), 3.96 (s, 0.4H), 3.38 (s, 1.6H), 2.10 (s, 2.4H), 1.77 (s, 0.6H), 1.37-1.23 (m, 3H).

Preparation of 7-bromo-3-methylnaphthalen-1-ol: A flask containing the crude ethyl 4-(4-bromophenyl)-3-methylbut-2-enoate from above (~30 grams) was treated with concentrated H₂SO₄ (120 mL) and warmed to 50° C. for 2.5 h. The reaction was poured onto ~500 mL of crushed ice. Once the ice had thawed, the brown suspension was extracted with two portions of EtOAc (500 mL and 100 mL, respectively). The two extracts were combined, washed with saturated NaHCO₃, dried (MgSO₄), filtered, and concentrated to ~55 mL. The residue was treated with DCM and loaded onto a silica gel column and purified by flash chromatography (ethyl acetate/hexanes) giving the desired product. $^1$H NMR (400 MHz, CDCl$_3$) δ 8.29 (d, J=1.9 Hz, 1H), 7.57 (d, J=8.6 Hz, 1H), 7.50 (dd, J=8.6, 2.0 Hz, 1H), 7.17 (s, 1H), 6.67 (s, 1H), 2.42 (s, 3H).

Preparation of 3-methylnaphthalen-1-ol: A slurry of 7-bromo-3-methylnaphthalen-1-ol (100 mg, 0.421 mmol), 10% w/w Pd/C (45 mg, 42.1 μmol Pd), and absolute EtOH (2.0 mL) was purged under vacuum and backfilled with H₂ from a balloon several times. The suspension was stirred under a balloon of H₂ at 23° C. overnight. The reaction was filtered over Celite, the cake was washed with EtOAc. The filtrate was concentrated and dissolved in DCM. The solution was loaded onto a 12 g "gold" ISCO silica gel column and purified by flash chromatography (ethyl acetate/hexanes) giving the desired product. $^1$H NMR (400 MHz, CDCl$_3$) δ 8.10 (d, J=7.8 Hz, 1H), 7.72 (d, J=7.8 Hz, 1H), 7.47-7.39 (m, 2H), 7.22 (s, 1H), 6.67 (s, 1H), 2.45 (s, 3H).

Preparation of ethyl 2-hydroxy-2-(1-hydroxy-3-methylnaphthalen-2-yl)acetate: A flask containing DCM (5.0 mL) was charged with TiCl₄ (1.0 M in DCM, 3.16 mL, 3.16 mmol). After cooling to −40° C. (dry ice/CH₃CN bath), a solution of 3-methylnaphthalen-1-ol (500 mg, 3.16 mmol) in DCM (5.0 mL) was added dropwise over a 5 min period. The reaction turned deep violet. After 30 min, a solution of ethyl glyoxylate (323 mg, 3.16 mmol, distilled freshly from P₂O₅ under N₂ from the 50% w/w toluene solution of ethyl glyoxylate) in DCM (2.0 mL) was added quickly. The reaction was warmed to 0° C. After 1 h, glacial AcOH (1.0 mL) was added. 5 min later, CH₃CN (5.0 mL) was introduced, followed by H₂O (10 mL). The reaction transitioned from violet to yellow-orange. The reaction was warmed to 23° C. and stirred for 30 min. The reaction was diluted with H₂O (15 mL) and extracted with DCM (3×20 mL). The combined extracts were washed with saturated NaHCO₃ (20 mL) (this decolorized the organic phase from orange to yellow), dried (Na₂SO₄), filtered, concentrated, treated with DCM (10 mL), and concentrated again. The residue was dissolved in DCM and loaded onto a 24 g "gold" ISCO silica gel column and purified by flash chromatography (ethyl acetate/hexanes) giving the desired product. $^1$H NMR (400 MHz, CDCl$_3$) δ 8.41 (s, 1H), 8.20 (d, J=8.2 Hz, 1H), 7.67 (d, J=8.8 Hz, 1H), 7.46 (dd, J=8.8, 8.0 Hz, 1H), 7.40 (dd, J=8.2, 8.0 Hz, 1H), 7.20 (s, 1H), 5.68 (s, 1H), 4.31-4.08 (m, 2H), 3.94 (s, broad, 1H), 2.52 (s, 3H), 1.18 (t, J=7.0 Hz, 3H).

Preparation of ethyl 2-tert-butoxy-2-(1-hydroxy-3-methylnaphthalen-2-yl)acetate: A solution of ethyl 2-hydroxy-2-(1-hydroxy-3-methylnaphthalen-2-yl)acetate (622 mg, 2.39 mmol) in tert-butyl acetate (12 mL) was treated with 70% HClO$_4$ (20 µL) at 23° C.). After 3 h, the reaction was added slowly over 5 min to saturated NaHCO$_3$ (25 mL). The resulting system was extracted with DCM (3×15 mL). The combined organic layers were dried (Na$_2$SO$_4$), filtered, and concentrated. Hexane (10 mL) was added, and the mixture was concentrated again. The residue was dissolved in benzene. The solution was loaded onto a 24 g "gold" ISCO silica gel column and purified by flash chromatography (hexane→ethyl acetate) giving the desired product. $^1$H NMR (400 MHz, CDCl$_3$) δ 9.00 (s, 1H), 8.26 (d, J=8.2 Hz, 1H), 7.65 (d, J=8.8 Hz, 1H), 7.44 (dd, J=8.2, 8.0 Hz, 1H), 7/39 (dd, J=8.8, 8.0 Hz, 1H), 7.17 (s, 1H), 5.52 (s, 1H), 4.25-4.06 (m, 2H), 2.59 (s, 3H), 1.33 (s, 9H), 1.20 (t, J=7.0 Hz, 3H).

Preparation of ethyl 2-tert-butoxy-2-(3-methyl-1-(trifluoromethylsulfonyloxy) naphthalen-2-yl)acetate: A solution of ethyl 2-tert-butoxy-2-(1-hydroxy-3-methylnaphthalen-2-yl)acetate (9.37 g, 29.7 mmol) in THF (250 mL) was treated with N-phenyltriflimide (12.7 g, 35.6 mmol) followed by Cs$_2$CO$_3$ (19.3 g, 59.3 mmol). More THF (50 mL) was added to aide fluidity, and the reaction was stirred at 23° C. for 2 h. The reaction was added slowly to a premade mixture of saturated aq. Na$_2$HPO$_4$ (400 mL) and 2 M aq. NaHSO$_4$ (120 mL). System was then stirred for 10 min, reaching a final pH of 8. It was extracted with 9:1 EtOAc/hexanes (3×200 mL). Combined organic layers were dried (Na$_2$SO$_4$), filtered, and concentrated. Hexane was added and the slurry was concentrated again to remove residual THF. The mix was treated with benzene and purified by silica gel chromatography (hexane→ethyl acetate) to give product that was contaminated with a small amount of PhNH(Tf). LCMS-ESI$^+$ (m/z): [M-C$_4$H$_9$+H]$^+$ calcd for C$_{16}$H$_{15}$F$_3$O$_6$S: 392.4. found: 392.6.

Preparation of ethyl 2-hydroxy-2-(3-methyl-1-(trifluoromethylsulfonyl-oxy)naphthalen-2-yl)acetate: A solution of ethyl 2-tert-butoxy-2-(3-methyl-1-(trifluoromethylsulfonyloxy)naphthalen-2-yl)acetate (6.0 grams, ~13 mmol, semi pure) in DCM (60 mL) was treated with TFA (6.0 mL) at 23° C. The reaction was diluted with H$_2$O (60 mL) and the organic phase collected. The aqueous layer was extracted with DCM (2×30 mL). The combined organic layers were dried (Na$_2$SO$_4$), filtered, and concentrated. The residue (5.5 grams) was used in the next reaction without further purification. $^1$H NMR (400 MHz, CDCl$_3$): 8.08-8.06 (m, 1H), 7.81-7.78 (m, 1H), 7.69 (s, 1H), 7.62-7.55 (m, 2H), 5.81 (app. s, 1H), 4.35-4.21 (m, 2H), 3.26 (app. s, broad, 1H), 2.50 (s, 3H), 1.21 (t, J=7.0 Hz, 3H).

Preparation of ethyl 2-(3-methyl-1-(trifluoromethylsulfonyloxy)naphthalen-2-yl)-2-oxoacetate: A solution of ethyl 2-hydroxy-2-(3-methyl-1-(trifluoromethylsulfonyloxy) naphthalen-2-yl)acetate (5.5 g, crude) in DCM (160 mL) was treated with Dess-Martin periodinane (7.18 g, 16.9 mmol) at 23° C. After 1 h, the reaction was added slowly over 5 min to 10% Na$_2$S$_2$O$_3$ (100 mL). After 30 min, the reaction was extracted with DCM (3×50 mL). The combined organic layers were dried (Na$_2$SO$_4$), filtered, and concentrated. The residue was treated with benzene, filtered, and loaded onto a silica gel column and purified by flash chromatography (ethyl acetate/hexanes) giving the desired product in semi pure form. $^1$H NMR (400 MHz, CDCl$_3$): δ 8.11-8.08 (m, 1H), 7.86-7.83 (m, 1H), 7.76 (s, 1H), 7.66-7.60 (m, 2H), 4.41 (q, J=7.4 Hz, 2H), 2.50 (s, 3H), 1.40 (t, J=7.4 Hz, 3H). $^{19}$F NMR (377 MHz, CDCl$_3$) δ -73.3 (s).

Preparation of (S)-ethyl 2-hydroxy-2-(3-methyl-1-(trifluoromethylsulfonyloxy) naphthalen-2-yl)acetate: Ethyl 2-(3-methyl-1-(trifluoromethylsulfonyloxy)naphthalen-2-yl)-2-oxoacetate (1.31 g, 3.3 mmol) was dissolved in toluene (20 mL) and cooled to −40° C. After stirring for 20 minutes, (R)-(+)-2-Methyl-CBS-oxazaborolidine (219 mg, 7.5 mmol) and catecholborane (750 µL, 7.04 mmol) were added and the mixture stirred at −40° C. After 2 hrs at −40° C. the reaction was quenched by the addition of 15% Na$_2$CO$_3$ (12 mL) and the mixture was allowed to warm to room temperature. The mixture was washed with 15% Na$_2$CO$_3$ (8×12 mL) and saturated NH$_4$Cl (24 mL), organic layer was dried with sodium sulfate, filtered and concentrated in vacuo. Chromatography using silica gel using EtOAc in hexanes produced the desired (S)-ethyl 2-hydroxy-2-(3-methyl-1-(trifluoromethylsulfonyloxy)naphthalen-2-yl)acetate. $^1$H-NMR: 400 MHz, (CDCl$_3$): δ 8.08-8.06 (m, 1H); 7.81-7.79 (m, 1H); 7.69 (s, 1H); 7.60-7.57 (m, 2H); 5.81-5.80 (m, 1H); 4.35-4.19 (m, 2H); 3.42 (d, J=2.4 Hz, 1H); 2.50 (s, 3H); 1.21 (t, J=7.0 Hz, 3H).

Preparation of (S)-2-((R)-1-(2,3-dihydropyrano[4,3,2-de]quinolin-7-yl)-3-methylnaphthalen-2-yl)-2-(2-methylpentan-2-yloxy)acetic acid.

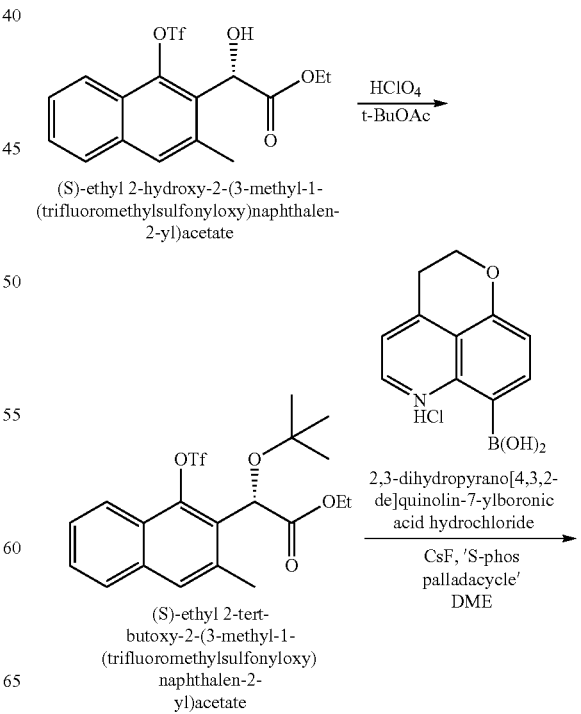

(S)-ethyl 2-hydroxy-2-(3-methyl-1-(trifluoromethylsulfonyloxy)naphthalen-2-yl)acetate (S)-ethyl 2-tert-butoxy-2-(3-methyl-1-(trifluoromethylsulfonyloxy)naphthalen-2-yl)acetate 2,3-dihydropyrano[4,3,2-de]quinolin-7-ylboronic acid hydrochloride CsF, 'S-phos palladacycle' DME

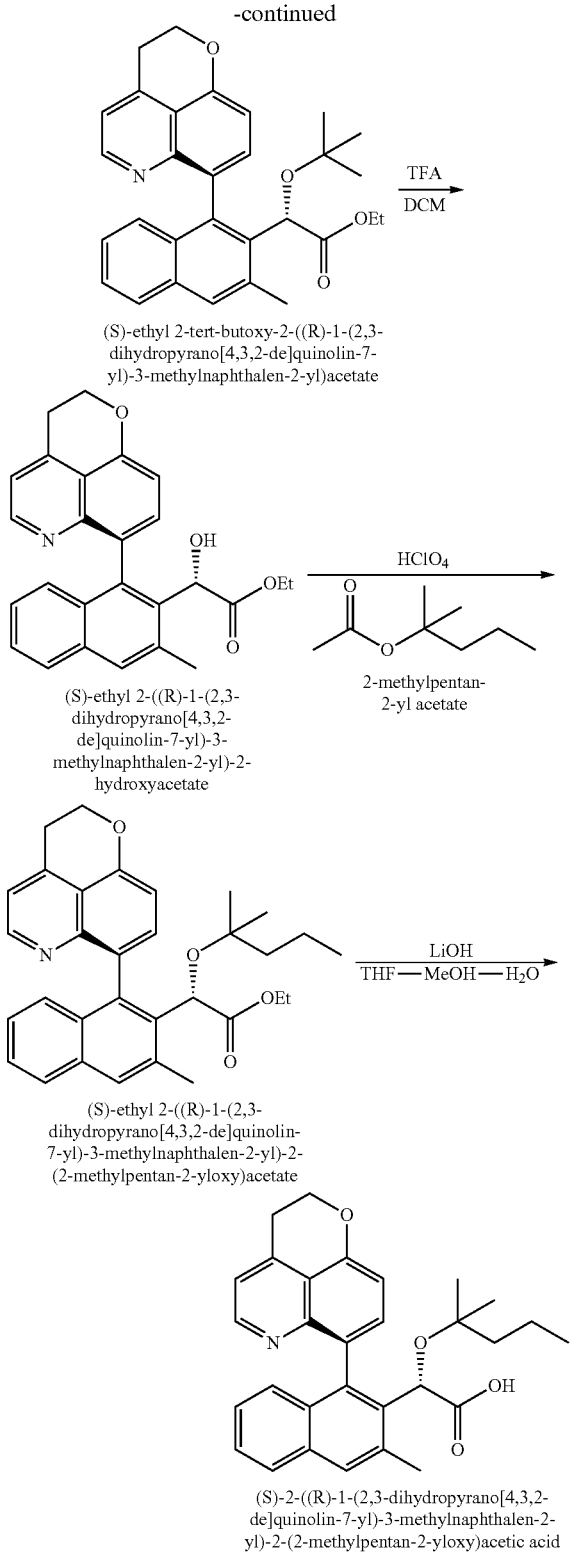

(S)-ethyl 2-tert-butoxy-2-((R)-1-(2,3-dihydropyrano[4,3,2-de]quinolin-7-yl)-3-methylnaphthalen-2-yl)acetate (S)-ethyl 2-((R)-1-(2,3-dihydropyrano[4,3,2-de]quinolin-7-yl)-3-methylnaphthalen-2-yl)-2-hydroxyacetate 2-methylpentan-2-yl acetate (S)-ethyl 2-((R)-1-(2,3-dihydropyrano[4,3,2-de]quinolin-7-yl)-3-methylnaphthalen-2-yl)-2-(2-methylpentan-2-yloxy)acetate (S)-2-((R)-1-(2,3-dihydropyrano[4,3,2-de]quinolin-7-yl)-3-methylnaphthalen-2-yl)-2-(2-methylpentan-2-yloxy)acetic acid Preparation of (S)-ethyl 2-tert-butoxy-2-(3-methyl-1-(trifluoromethylsulfonyloxy)naphthalen-2-yl)acetate: To a stirring solution of (S)-ethyl 2-hydroxy-2-(3-methyl-1-(trifluoromethylsulfonyloxy)naphthalen-2-yl)acetate (560 mg, 1.42 mmol) in t-BuOAc (32.0 mL, 381 mmol) was added 4 drops (catalytic) of 70% HClO$_4$ and the mixture allowed to stir at room temperature for 2 hrs. The mixture was quenched by dumping it into an icy solution of saturated NaHCO$_3$. Extraction with EtOAc (3×20 mL), drying with sodium sulfate and subsequent chromatography on silica gel using EtOAc in Hexanes gave (S)-ethyl 2-tert-butoxy-2-(3-methyl-1-(trifluoromethylsulfonyloxy)naphthalen-2-yl)acetate. $^1$H-NMR: 400 MHz, (CDCl$_3$): δ 8.06-8.03 (m, 1H); 7.81-7.78 (m, 1H); 7.67 (s, 1H); 7.59-7.53 (m, 2H); 5.73 (s, 1H); 4.25-4.10 (m, 2H); 2.55 (s, 3H); 1.21 (s, 9H); 1.17 (t, 3H).

Preparation of (S)-ethyl 2-tert-butoxy-2-((R)-1-(2,3-dihydropyrano[4,3,2-de]quinolin-7-yl)-3-methylnaphthalen-2-yl)acetate: (S)-ethyl 2-tert-butoxy-2-(3-methyl-1-(trifluoromethylsulfonyloxy)naphthalen-2-yl)acetate (555 mg, 1.23 mmol) in freshly distilled DME (5.0 mL) was added to a 5-10 mL microwave vial charged with a mixture of 2,3-dihydropyrano[4,3,2-de]quinolin-7-ylboronic acid, HCl salt (368 mg, 1.46 mmol); S-Phos Palladacycle (Strem, 155 mg, 0.23 mmol), and cesium fluoride (743 mg, 4.89 mmol). This heterogeneous mixture was then microwaved at 125° C. for 60 minutes. The mixture was then diluted 400% with EtOAc, extracted with saturated NH$_4$Cl, brine, and dried with sodium sulfate, filtered and concentrated. Chromatography via ISCO using a 15 µm particle size silica gel column eluting with ethyl acetate/hexanes gave the desired atropisomer. $^1$H-NMR: 400 MHz, (CDCl$_3$): δ 8.67 (d, J=4.4 Hz, 1H); 7.76 (d, J=8.0 Hz, 1H); 7.72 (s, 1H); 7.49 (d, J=8.0 Hz, 1H); 7.36-7.33 (m, 1H); 7.13-7.01 (m, 4H); 5.09 (s, 1H); 4.58-4.52 (m, 2H); 4.03-3.78 (m, 2H); 3.38-3.23 (m, 2H); 2.79 (s, 3H); 0.97-0.94 (m, 12H). LCMS-ESI$^+$ (m/z): [M+H]$^+$ calcd for C$_{30}$H$_{32}$NO$_4$: 470.23. Found: 470.39. The undesired atropisomer was also isolated. LCMS-ESI$^+$ (m/z): [M+H]$^+$ calcd for C$_{30}$H$_{32}$NO$_4$: 470.23. Found: 470.39.

Preparation of (S)-ethyl 2-((R)-1-(2,3-dihydropyrano[4,3,2-de]quinolin-7-yl)-3-methylnaphthalen-2-yl)-2-hydroxyacetate: To a solution of (S)-ethyl 2-tert-butoxy-2-((R)-1-(2,3-dihydropyrano[4,3,2-de]quinolin-7-yl)-3-methylnaphthalen-2-yl)acetate (49.0 mg, 0.104 mmol) in DCM (10 mL) was added TFA (650 µL, 0.0084 mmol) and reaction mixture was stirred at room temperature overnight. Mixture was quenched by pouring into an icy solution of saturated NaHCO$_3$ and extracted with EtOAc to give crude (S)-ethyl 2-((R)-1-(2,3-dihydropyrano[4,3,2-de]quinolin-7-yl)-3-methylnaphthalen-2-yl)-2-hydroxyacetate. $^1$H-NMR: δ 400 MHz, (CDCl$_3$): 8.67 (d, J=4.0 Hz, 1H); 7.79-7.76 (m, 2H); 7.47 (d, J=7.6 Hz, 1H), 7.38 (t, 1H); 7.16-7.10 (m, 3H); 6.96 (d, J=8.4 Hz, 1H); 5.36 (s, 1H); 4.58-4.55 (m, 2H); 3.89-3.72 (m, 2H); 3.38-3.31 (m, 2H); 2.69 (s, 3H); 1.04 (t, 3H). LCMS-ESI$^+$ (m/z): [M+H]$^+$ calcd for C$_{26}$H$_{23}$NO$_4$: 414.16. Found: 414.1.

Preparation of (S)-ethyl 2-((R)-1-(2,3-dihydropyrano[4,3,2-de]quinolin-7-yl)-3-methylnaphthalen-2-yl)-2-(2-methylpentan-2-yloxy)acetate: (S)-ethyl 2-((R)-1-(2,3-dihydropyrano[4,3,2-de]quinolin-7-yl)-3-methylnaphthalen-2-yl)-2-hydroxyacetate (21.2 mg, 0.415 mmol) was slurried in 2.5 mL of 2-methylpentan-2-yl acetate (preparation described in Example 30) and 2.5 mL of DCM and 70% perchloric acid (5 µL) was added. The mixture was allowed to stir overnight at rt. The reaction was quenched by dumping it into icy saturated NaHCO$_3$. This mixture was extracted with EtOAc (3×15 mL), dried with sodium sulfate, filtered and concentrated in vacuo. Silica gel chromatography using EtOAc in hexanes gave rise to desired (S)-ethyl 2-((R)-1-(2,3-dihydropyrano[4,3,2-de]quinolin-7-yl)-3-methylnaphthalen-2-yl)-2-(2-methylpentan-2-yloxy)acetate. $^1$H-NMR: S 400 MHz, (CDCl$_3$): 8.69 (s, 1H); 7.78-7.74 (m, 3H); 7.52-7.49 (m, 2H); 7.37-7.33 (m, 2H), 7.13-7.10 (m, 2H); 5.10 (s, 1H); 4.59 (t, 2H); 4.07-3.83 (m, 2H); 3.35 (s, 2H); 2.79 (s, 3H); 1.62-1.48 (m, 4H);

1.34-1.18 (m, 9H); 0.90 (t, 3H). LCMS-ESI⁺ (m/z): [M+H]⁺ calcd for $C_{32}H_{36}NO_4$: 498.26. Found: 498.11.

Preparation of (S)-2-((R)-1-(2,3-dihydropyrano[4,3,2-de]quinolin-7-yl)-3-methylnaphthalen-2-yl)-2-(2-methylpentan-2-yloxy)acetic acid: (S)-ethyl 2-((R)-1-(2,3-dihydropyrano[4,3,2-de]quinolin-7-yl)-3-methylnaphthalen-2-yl)-2-(2-methylpentan-2-yloxy)acetate (30 mg, 0.06 mmol) was dissolved in THF (9.0 mL), MeOH (3 mL) and water (3.0 mL). Lithium hydroxide monohydrate (192 mg, 4.58 mmol) and was microwaved at 100° C. for 90 minutes. Mixture was then diluted 400% with EtOAc, washed with water, brine, dried, filtered and concentrated in vacuo. Crude product was dissolved in MeOH and purified via PREP HPLC (5 µM Gemini $C_{18}$ column (100×30 mm), (5 to 100% MeCN/$H_2O$+ 0.05% TFA) to give rise to the TFA salt of (S)-2-((R)-1-(2,3-dihydropyrano[4,3,2-de]quinolin-7-yl)-3-methylnaphthalen-2-yl)-2-(2-methylpentan-2-yloxy)acetic acid. 1H-NMR: 400 MHz, ($CD_3OD$): 8.68-8.67 (d, J=5.6 Hz, 1H); 7.98-7.94 (m, 2H); 7.88-7.81 (m, 2H); 7.56-7.49 (m, 2H); 7.19-7.26 (m, 1H); 6.946.92 (d, J=8.0 Hz, 1H); 5.22 (s, 1H); 4.78-4.69 (m, 2H); 3.70-3.67 (t, 2H); 2.79 (s, 3H); 1.37-1.26 (m, 2H); 1.21-1.09 (m, 2H), 0.94 (s, 6H); 0.75 (t, 3H). ¹⁹F-NMR: 400 MHz, ($CD_3OD$): –77.665. LCMS-ESI⁺ (m/z): [M+H]⁺ calcd for $C_{30}H_{32}NO_4$: 469.57. Found: 470.12.

EXAMPLE 30

(S)-2-((S)-1-(2,3-Dihydropyrano[4,3,2-de]quinolin-7-yl)-3-methylnaphthalen-2-yl)-2-(2-methylhexan-2-yloxy)acetic acid

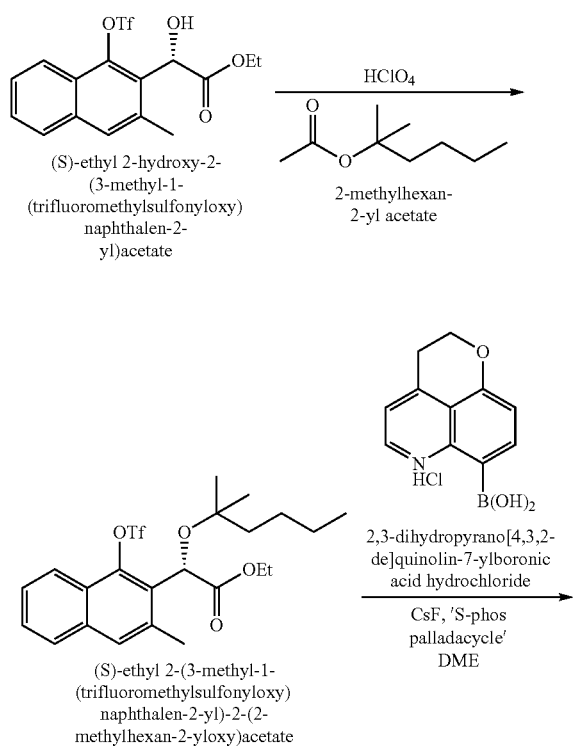

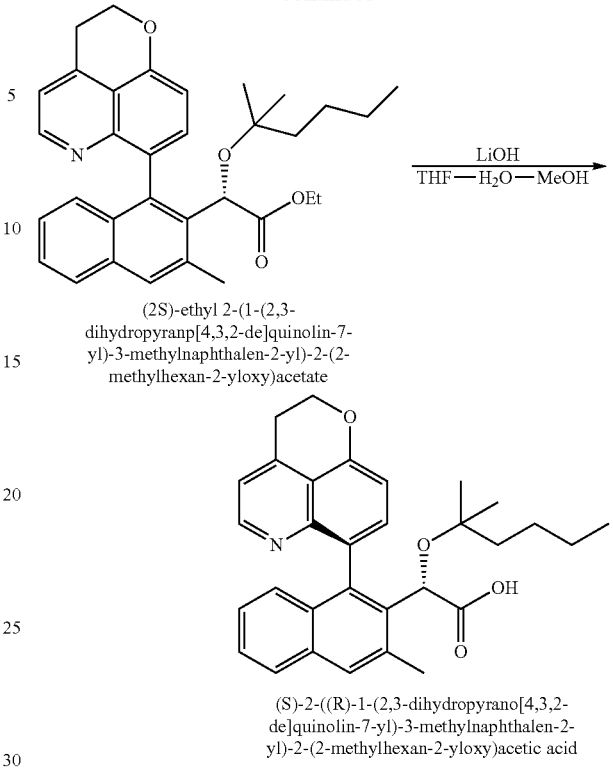

Preparation of (S)-ethyl 2-(3-methyl-1-(trifluoromethylsulfonyloxy)naphthalen-2-yl)-2-(2-methylhexan-2-yloxy)acetate: (S)-ethyl 2-hydroxy-2-(3-methyl-1-(trifluoromethylsulfonyloxy)naphthalen-2-yl)acetate: To a stirring solution of (512 mg, 1.30 mmol) in 2-methylhexan-2-yl acetate (5.0 mL) was added 3 drops (catalytic) of $HClO_4$ and the mixture allowed to stir at room temp for 2.5 hrs. The mixture was quenched by pouring it into an icy solution of saturated $NaHCO_3$. Extraction with EtOAc (3×20 mL), drying with sodium sulfate and subsequent chromatography on silica gel using EtOAc in hexanes gave (S)-ethyl 2-(3-methyl-1-(trifluoromethylsulfonyloxy)naphthalen-2-yl)-2-(2-methylhexan-2-yloxy)acetate. ¹H-NMR: δ 400 MHz, ($CDCl_3$): 8.05-8.03 (m, 1H); 7.81-7.79 (m, 1H); 7.68 (s, 1H); 7.59-7.53 (m, 2H); 5.73 (s, 1H); 4.26-4.11 (m, 2H); 2.55 (s, 3H); 1.54-1.39 (2H); 1.33-1.00 (m, 13H), 0.71 (t, 3H).

Preparation of (2S)-ethyl 2-(1-(2,3-dihydropyrano[4,3,2-de]quinolin-7-yl)-3-methylnaphthalen-2-yl)-2-(2-methylhexan-2-yloxy)acetate: (S)-ethyl 2-(3-methyl-1-(trifluoromethylsulfonyloxy)naphthalen-2-yl)-2-(2-methylhexan-2-yloxy)acetate (416 mg, 0.848 mmol) in freshly distilled DME (5.0 mL) was added to a 25 mL flask charged with a mixture of 2,3-dihydropyrano[4,3,2-de]quinolin-7-ylboronic acid, HCl salt (236 mg, 0.938 mmol), S-Phos Palladacycle (Strem, 87 mg, 0.129 mmol), and cesium fluoride (386 mg, 2.54 mmol). This heterogeneous mixture was heated thermally at 120° C. for 60 minutes. The mixture was then diluted 400% with EtOAc, extracted with saturated $NH_4Cl$, brine, and dried with sodium sulfate, filtered and concentrated. Purification via ethyl acetate-hexane chromatography using an Isco 12 gram Gold silica gel column failed to completely separate the two atropisomers. Two atropisomer mixtures were obtained. The first eluting mixture, mixture A, was further purified via PRP HPLC (5 µM Gemini $C_{18}$ column (100×30 mm), (5 to 100% MeCN/$H_2O$+0.05% TFA) and resulting in enriched (S)-2-((S)-1-(2,3-dihydropyrano[4,3,2-de]quinolin-7-yl)-3-methylnaphthalen-2-yl)-2-(2-methylhexan-2-yloxy)acetic acid. LCMS-ESI⁺ (m/z): [M+H]⁺ calcd for $C_{33}H_{38}NO_4$: 512.65. Found: 512.17.

The later eluting mixture, mixture B, was carried forward without additional purification and was (S)-2-((R)-1-(2,3-dihydropyrano[4,3,2-de]quinolin-7-yl)-3-methylnaphthalen-2-yl)-2-(2-methylhexan-2-yloxy)acetic acid. LCMS-ESI⁺ (m/z): [M+H]⁺ calcd for $C_{33}H_{38}NO_4$: 512.65. Found: 512.17.

Preparation of (S)-2-((R)-1-(2,3-dihydropyrano[4,3,2-de]quinolin-7-yl)-3-methylnaphthalen-2-yl)-2-(2-methylhexan-2-yloxy)acetic acid: (S)-ethyl 2-((R)-1-(2,3-dihydropyrano[4,3,2-de]quinolin-7-yl)-3-methylnaphthalen-2-yl)-2-(2-methylhexan-2-yloxy)acetate (15.6 mg, 0.0305 mmol) was dissolved in THF (3.0 mL), MeOH (1.0 mL) and water 1.0 mL. Lithium hydroxide monohydrate (102.1 mg, 2.43 mmol) was added and the mixture was and stirred at room temperature overnight. The mixture was then diluted 400% with EtOAc, washed with water, brine, dried, filtered and concentrated in vacuo. Crude product was dissolved in MeOH and purified via PREP HPLC (5 µM Gemini $C_{18}$ column (100×30 mm), (5 to 100% MeCN/$H_2O$+0.05% TFA) to give (S)-2-((R)-1-(2,3-dihydropyrano[4,3,2-de]quinolin-7-yl)-3-methylnaphthalen-2-yl)-2-(2-methylhexan-2-yloxy) acetic acid as a TFA salt.

¹H-NMR: 400 MHz, (CD₃OD): δ 8.66-8.65 (d, J=8.0 Hz, 1H); 7.96-7.92 (m, 2H), 7.86-7.84 (d, J=8.0 Hz, 1H); 7.79-7.77 (d, J=8.0 Hz, 1H); 7.50-7.46 (m, 2H); 7.27-7.24 (t, 1H); 6.91-6.89 (d, J=8.4 Hz, 1H); 5.20 (s, 1H); 4.76-4.69 (m, 2H); 3.67-3.64 (t, 2H); 2.77 (s, 3H); 1.21-1.10 (m, 2H); 0.93-0.87 (m, 6H), 0.81-0.77 (m, 3H).

¹⁹F-NMR: 400 MHz, (CD₃OD): 8-77.595. LCMS-ESI⁺ (m/z): [M+H]⁺ calcd for $C_{31}H_{34}NO_4$: 484.2. Found: 484.12.

Preparation of (S)-2-((S)-1-(2,3-dihydropyrano[4,3,2-de]quinolin-7-yl)-3-methylnaphthalen-2-yl)-2-(2-methylhexan-2-yloxy)acetic acid: (S)-ethyl 2-((S)-1-(2,3-dihydropyrano[4,3,2-de]quinolin-7-yl)-3-methylnaphthalen-2-yl)-2-(2-methylhexan-2-yloxy)acetate (27.3 mg, 0.0534 mmol) was dissolved in THF (3.0 mL), MeOH (1.0 mL) and water 1.0 mL. Lithium hydroxide monohydrate (98.7 mg, 2.35 mmol) was added and the mixture was and stirred at room temperature overnight. The mixture was then diluted 400% with EtOAc, washed with water, brine, dried, filtered and concentrated in vacuo. The crude product was dissolved in MeOH and purified via PREP HPLC (5 µM Gemini $C_{18}$ column (100×30 mm), (5 to 100% MeCN/$H_2O$+0.05% TFA) to give (S)-2-((S)-1-(2,3-dihydropyrano[4,3,2-de]quinolin-7-yl)-3-methylnaphthalen-2-yl)-2-(2-methylhexan-2-yloxy) acetic acid as a TFA salt. ¹H-NMR: 400 MHz, (CD₃OD): δ 8.57-8.55 (d, J=5.6 Hz, 1H); 8.15-8.13 (d, J=7.2 Hz, 1H); 7.96-7.90 (m, 2H), 7.67 (m, 1H); 7.48-7.44 (m, 2H); 7.24-7.20 (m, 1H), 6.91-6.88 (d, J=8.8 Hz, 1H); 5.27 (s, 1H); 4.71-4.68 (m, 2H); 3.61 (bs, 2H); 2.74 (s, 3H); 1.29-1.13 (m, 6H); 0.89 (s, 3H); 0.81-0.73 (m, 6H) ppm. ¹⁹F-NMR: δ 400 MHz, (CD₃OD): −77.687. LCMS-ESI⁺ (m/z): [M+H]⁺ calcd for $C_{31}H_{34}NO_4$: 484.2. Found: 484.13.

Preparation of 2-methylpentan-2-yl acetate and 2-methylhexan-2-yl acetate

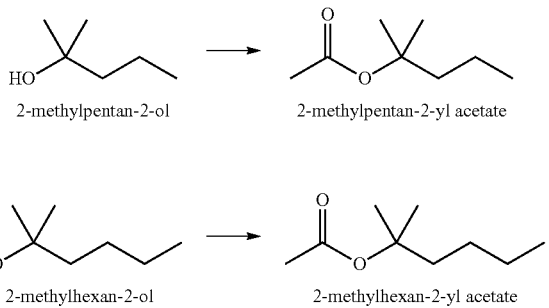

Preparation of 2-methylhexan-2-yl acetate: 2-Methylhexan-2-ol (30.0 g, 0.258 mol) was treated with acetic anhydride (36.6 mL, 0.387 mol). Pyridine (30.0 mL, excess) was added dropwise over a 3 min period at 23° C. Then 4-(N,N-dimethylamino)-pyridine (1.27 g, 10.0 mmol) was added. The reaction was heated to 70° C. for 16 h. The reaction was cooled to 23° C. and poured onto 300 mL of crushed ice. After 15 min of stirring, most of the ice had melted. Solid NaHCO₃ was added in portions (bubbling) until the pH was 9. The system was extracted with two portions of diethyl ether (100 mL, then 50 mL). The combined extracts were washed with 1.0 M aq. CuSO₄ monohydrate (4×50 mL), dried over MgSO₄, and filtered. The filtrate was distilled at ambient pressure at a bath temperature of 80-100° C. to remove most of the diethyl ether. The resulting oil left in the pot was fractionally distilled through a Snyder column with 3 chambers under reduced pressure (6-8 mmHg). A small-volume forerun was collected and discarded (bp<45° C.). The main fraction contained 2-methylhexan-2-yl acetate (bp 45-48° C.). ¹H NMR (400 MHz, CDCl₃) δ 1.94 (s, 3H), 1.74-1.68 (m, 2H), 1.40 (s, 6H), 1.33-1.22 (m, 4H), 0.88 (t, J=6.8 Hz, 3H).

Preparation of 2-methylpentan-2-yl acetate: Prepared in a manner similar to 2-methylhexan-2-yl acetate, except using 2-methylpentan-2-ol. A 500 mL round bottom flask was charged with pyridine (30 mL), 2-methylpentanol (30 mL, 208 mmol) and was added followed by DMAP (1.213 g, 9.93 mmol). Acetic anhydride (46 mL, 417 mmol) was added slowly and the mixture heated at 70° C. for 20 hours. The reaction was quenched by pouring into a 10° C. Et₂O bath on ice. 200 mL of water was added and the mixture was extracted with saturated CuSO₄ (4×50 mL). The mixture was then washed with water (2×200 mL), saturated NaHCO₃ (1×50 mL) and brine (1×50 mL). Mixture was dried with sodium sulfate, filtered and concentrated in vacuo. Distillation of the concentrate at 90° C. at reduced pressure (100 mtorr) resulted in 95% pure 2-methylpentan-2-yl acetate. ¹H-NMR: 400 MHz, (CDCl₃): 1.91 (s, 3H); 1.69-1.5 (m, 2H); 1.37 (s, 6H); 1.31-1.25 (m, 2H); 0.87 (t J=7.2 Hz, 3H).

EXAMPLE 31
(S)-2-((R)-1-(2,3-Dihydropyrano[4,3,2-de]quinolin-7-yl)-3-methylnaphthalen-2-yl)-2-(1,1,1-trifluoro-2-methylpropan-2-yloxy)acetic acid and (R)-2-((S)-1-(2,3-dihydropyrano[4,3,2-de]quinolin-7-yl)-3-methylnaphthalen-2-yl)-2-(1,1,1-trifluoro-2-methylpropan-2-yloxy)acetic acid
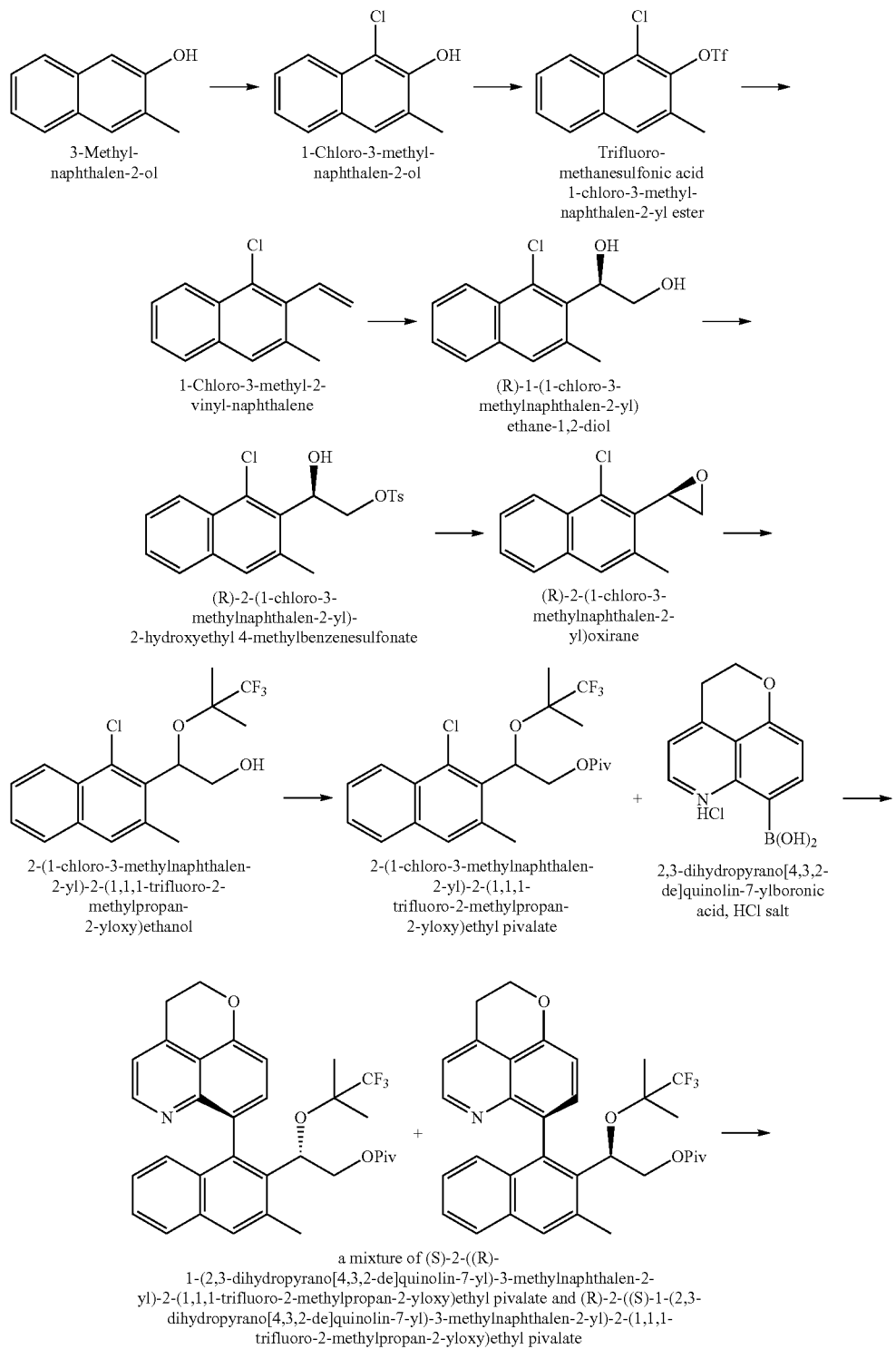

-continued

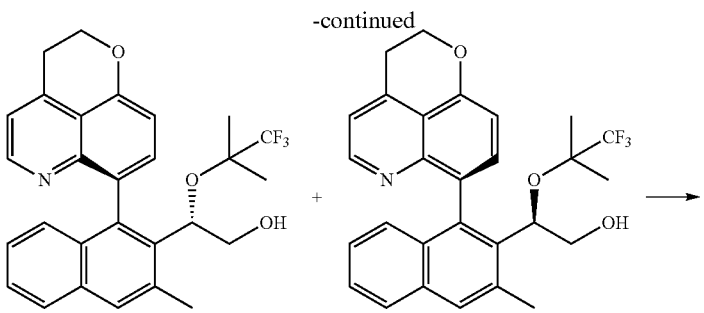

a mixture of (S)-2-((R)-1-(2,3-dihydropyrano[4,3,2-de]quinolin-7-yl)-3-methylnaphthalen-2-yl)-2-(1,1,1-trifluoro-2-methylpropan-2-yloxy)ethanol and (R)-2-((S)-1-(2,3-dihydropyrano[4,3,2-de]quinolin-7-yl)-3-methylnaphthalen-2-yl)-2-(1,1,1-trifluoro-2-methylpropan-2-yloxy)ethanol

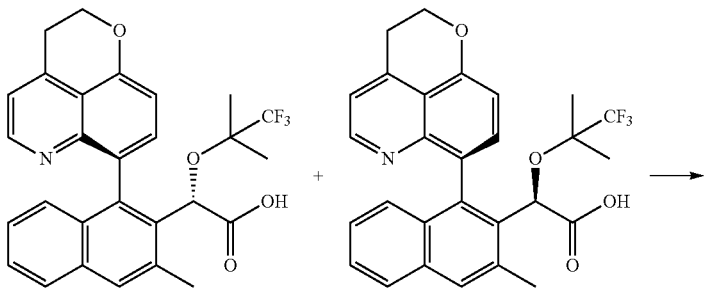

a mixture of (S)-2-((R)-1-(2,3-dihydropyrano[4,3,2-de]quinolin-7-yl)-3-methylnaphthalen-2-yl)-2-(1,1,1-trifluoro-2-methylpropan-2-yloxy)acetic acid and (R)-2-((S)-1-(2,3-dihydropyrano[4,3,2-de]quinolin-7-yl)-3-methylnaphthalen-2-yl)-2-(1,1,1-trifluoro-2-methylpropan-2-yloxy)acetic acid

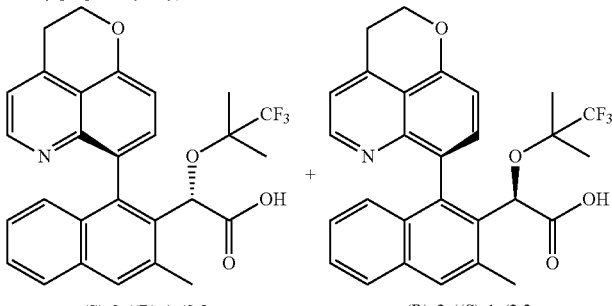

(S)-2-((R)-1-(2,3-dihydropyrano[4,3,2-de]quinolin-7-yl)-3-methylnaphthalen-2-yl)-2-(1,1,1-trifluoro-2-methylpropan-2-yloxy)acetic acid (R)-2-((S)-1-(2,3-dihydropyrano[4,3,2-de]quinolin-7-yl)-3-methylnaphthalen-2-yl)-2-(1,1,1-trifluoro-2-methylpropan-2-yloxy)acetic acid Preparation of 1-chloro-3-methyl-naphthalen-2-ol: To a solution of N-chlorosuccinimide (8.02 g, 60.05 mmol) in dichloromethane (475 mL) at −78° C. was added zirconium (IV) chloride (2.80 g, 12.01 mmol), followed by 3-methyl-naphthalen-2-ol (CombiBlocks, 9.5 g, 60.05 mmol) under argon. The reaction mixture was stirred at −78° C. for 5 minutes, the cooling bath was removed and the reaction was stirred at room temperature for 5 h. The reaction was quenched with saturated sodium bicarbonate solution and stirred for 5 minutes. The mixture was diluted with $H_2O$, extracted with dichloromethane (3×) and the combined organic layer was dried ($MgSO_4$), filtered, concentrated and purified by flash column chromatography (silica gel, 0 to 10% ethyl acetate/hexanes) to give 1-chloro-3-methyl-naphthalen-2-ol.

Preparation of trifluoro-methanesulfonic acid 1-chloro-3-methyl-naphthalen-2-yl ester: To a solution of 1-chloro-3-methyl-naphthalen-2-ol (9.05 g, 46.98 mmol) in dichloromethane (235 mL) at −78° C. was added trifluoromethanesulfonic anhydride (11.9 mL, 70.47 mmol), followed by 2,6-lutidine (8.2 mL, 70.47 mmol). The reaction mixture was stirred for 3 h to give a yellow solution, which was diluted with dichloromethane and washed with $H_2O$/brine. The organic layer was dried ($MgSO_4$), filtered, concentrated and purified by flash column chromatography (silica gel, 0 to 10% ethyl acetate/hexanes) to give trifluoro-methanesulfonic acid 1-chloro-3-methyl-naphthalen-2-yl ester.

Preparation of 1-chloro-3-methyl-2-vinyl-naphthalene: To a solution of trifluoro-methanesulfonic acid 1-chloro-3-methyl-naphthalen-2-yl ester (14.75 g, 45.43 mmol), tributyl(vinyl)tin (14.59 mL, 49.97 mmol) and lithium chloride (5.78 g, 136.29 mmol) was added dichlorobis(triphenylphosphine)palladium(II) under argon. The reaction mixture was heated at 50° C. for 20 h, then heated at 90° C. for 8 h. The reaction mixture was than cooled to room temperature, diluted with ethyl acetate, washed with 5% lithium chloride solution (3×), brine and dried (MgSO₄), filtered and then concentrated and purified by flash column chromatography (silica gel, 0 to 10% ethyl acetate/hexanes) to give 1-chloro-3-methyl-2-vinyl-naphthalene contaminated by organotin. The residue was dissolved in dichloromethane and stirred with 10% KF solution overnight. The resulting white mixture was filtered through a pad of Celite and extracted with dichloromethane (2×). The organic layer was concentrated and purified by flash column chromatography (silica gel, 0 to 10% ethyl acetate/hexanes) to give 1-chloro-3-methyl-2-vinyl-naphthalene.

Preparation of (R)-1-(1-chloro-3-methylnaphthalen-2-yl)ethane-1,2-diol: A biphasic mixture of AD-mix-β (45.7 g, excess) in tert-butanol (147 mL)/H₂O (147 mL) was cooled to 0° C. and 1-chloro-3-methyl-2-vinyl-naphthalene (4.46 g, 22.0 mmol) was added. The reaction mixture was stirred for 7 days at 0° C. The mixture was diluted with ethyl acetate, washed with water and brine, dried over Na₂SO₄, filtered and concentrated and purified by flash column chromatography (silica gel, 0 to 100% ethyl acetate/hexanes) to give (R)-1-(1-chloro-3-methylnaphthalen-2-yl)ethane-1,2-diol. ¹H-NMR: 400 MHz, (CDCl₃) δ 8.27 (d, J=8.4 Hz, 1H), 7.73 (d, J=7.6 Hz, 1H), 7.57-7.50 (m, 3H), 5.70 (dd, J=10.0, 4.0 Hz, 1H), 4.11 (t, J=10.4 Hz, 1H), 3.79 (dd, J=11.6, 4.0 Hz, 1H), 2.66 (s, 3H).

Preparation of (R)-2-(1-chloro-3-methylnaphthalen-2-yl)-2-hydroxyethyl 4-methylbenzenesulfonate: To a stirred solution of (R)-1-(1-chloro-3-methylnaphthalen-2-yl)ethane-1,2-diol (2.30 g, 9.74 mmol) in CH₂Cl₂ (97 mL), dibutyltinoxide (48.5 mg, 0.19 mmol), p-toluenesulfonyl chloride (2.08 g, 10.90 mmol), and Et₃N (1.60 mL, 11.58 mmol) were added at room temperature). After stirring for 15 h, the reaction mixture was quenched with saturated aqueous NH₄Cl, and then diluted with CH₂Cl₂. The organic phase was washed with brine, dried over Na₂SO₄, filtered and concentrated and purified by flash column chromatography (silica gel, 0 to 100% ethyl acetate/hexanes) to give (R)-2-(1-chloro-3-methylnaphthalen-2-yl)-2-hydroxyethyl 4-methylbenzenesulfonate. ¹H-NMR: 400 MHz, (CDCl₃) δ 8.18 (d, J=8.8 Hz, 1H), 7.79 (d, J=8.4 Hz, 1H), 7.57-7.54 (m, 5H), 5.82 (t, J=5.6 Hz, 1H), 4.44 (dd, J=10.0, 6.8 Hz, 1H), 4.35 (dd, J=10.4, 5.6 Hz, 1H), 2.59 (s, 3H), 2.29 (s, 3H).

Preparation of (R)-2-(1-chloro-3-methylnaphthalen-2-yl)oxirane: To a solution of (R)-2-(1-chloro-3-methylnaphthalen-2-yl)-2-hydroxyethyl 4-methylbenzenesulfonate (1.38 g, 3.54 mmol) in THF (39 mL) at 0° C. was added potassium tert-butoxide (3.90 mL of 1.0 M solution in THF, 3.90 mmol). After stirring for 1 h, the reaction mixture was quenched with saturated aqueous NH₄Cl, and then diluted with EtOAc. The organic phase was washed with water and brine, dried over Na₂SO₄, filtered and concentrated and purified by flash column chromatography (silica gel, 0 to 20% ethyl acetate/hexanes) to give (R)-2-(1-chloro-3-methylnaphthalen-2-yl)oxirane. ¹H-NMR: 400 MHz, (CDCl₃) δ 8.26 (d, J=8.4 Hz, 1H), 7.74 (d, J=7.6 Hz, 1H), 7.57-7.48 (m, 3H), 4.13 (t, J=3.6 Hz, 1H), 3.34 (t, J=5.6 Hz, 1H), 2.97 (dd, J=5.2, 2.8 Hz, 1H), 2.64 (s, 3H).

Preparation of 2-(1-chloro-3-methylnaphthalen-2-yl)-2-(1,1,1-trifluoro-2-methylpropan-2-yloxy)ethanol: To a stirred solution of (R)-2-(1-chloro-3-methylnaphthalen-2-yl)oxirane (340 mg, 1.56 mmol) and 2-trifluoromethyl-2-propanol (4.3 mL, 38.97 mmol) in CH₂Cl₂ (4.3 mL), boron trifluoride diethyl etherate (1.9 mL, 15.60 mmol) was added at 0° C. The reaction mixture was stirred for 16 h at 0° C. and allowed to warm to room temperature overnight. The mixture was quenched with saturated aqueous NaHCO₃, and then diluted with CH₂Cl₂. The organic phase was washed with brine, dried over Na₂SO₄, filtered and concentrated and purified by flash column chromatography (silica gel, 0 to 20% ethyl acetate/hexanes) to give 2-(1-chloro-3-methylnaphthalen-2-yl)-2-(1,1,1-trifluoro-2-methylpropan-2-yloxy)ethanol. ¹H-NMR: 400 MHz, (CDCl₃) δ 8.27 (d, J=8.4 Hz, 1H), 7.73 (d, J=7.6 Hz, 1H), 7.57-7.49 (m, 3H), 5.90 (dd, J=9.6, 4.4 Hz, 1H), 3.98 (t, J=11.2 Hz, 1H), 3.66 (dd, J=12.0, 4.0 Hz, 1H), 2.69 (s, 3H), 2.18 (br s, 1H), 1.45 (s, 3H), 1.19 (s, 3H).

Preparation of 2-(1-chloro-3-methylnaphthalen-2-yl)-2-(1,1,1-trifluoro-2-methylpropan-2-yloxy)ethyl pivalate: To a stirred solution of trimethylacetyl chloride (0.17 mL, 1.36 mmol) and 4-(Dimethylamino)pyridine (55 mg, 0.45 mmol) in pyridine (2.4 mL, 29.48 mmol), 2-(1-chloro-3-methylnaphthalen-2-yl)-2-(1,1,1-trifluoro-2-methylpropan-2-yloxy)ethanol (157 mg, 0.45 mmol) in CH₂Cl₂ (2.4 mL) was added at 0° C. The reaction mixture was allowed to warm to room temperature overnight. The mixture was quenched with water and concentrated and purified by flash column chromatography (silica gel, 0 to 20% ethyl acetate/hexanes) to give 2-(1-chloro-3-methylnaphthalen-2-yl)-2-(1,1,1-trifluoro-2-methylpropan-2-yloxy)ethyl pivalate. ¹H-NMR: 400 MHz, (CDCl₃) δ 8.26 (d, J=8.4 Hz, 1H), 7.73 (d, J=8.0 Hz, 1H), 7.58-7.48 (m, 3H), 6.05 (dd, J=8.4, 5.2 Hz, 1H), 4.50 (dd, J=11.2, 8.4 Hz, 1H), 4.21 (dd, J=11.2, 4.8 Hz, 1H), 2.73 (s, 3H), 1.43 (s, 3H), 1.19 (s, 3H), 1.16 (s, 9H).

Preparation of a mixture of (S)-2-((R)-1-(2,3-dihydropyrano[4,3,2-de]quinolin-7-yl)-3-methylnaphthalen-2-yl)-2-(1,1,1-trifluoro-2-methylpropan-2-yloxy)ethyl pivalate and (R)-2-((S)-1-(2,3-dihydropyrano[4,3,2-de]quinolin-7-yl)-3-methylnaphthalen-2-yl)-2-(1,1,1-trifluoro-2-methylpropan-2-yloxy)ethyl pivalate: 2-(1-chloro-3-methylnaphthalen-2-yl)-2-(1,1,1-trifluoro-2-methylpropan-2-yloxy)ethyl pivalate (82 mg, 0.19 mmol) in freshly distilled DME (7.0 mL) was added to a microwave vial charged with a mixture of 2,3-dihydropyrano[4,3,2-de]quinolin-7-ylboronic acid, HCl salt (77 mg, 0.31 mmol), SPhos precatalyst (Strem, 14 mg, 0.02 mmol), and CsF (155 mg, 1.02 mmol). This heterogeneous mixture was then microwaved at 120° C. for 90 minutes. The mixture was then diluted with EtOAc, extracted with saturated NaHCO₃, brine, and dried over Na₂SO₄, filtered and concentrated and purified by flash column chromatography (silica gel, 0 to 50% ethyl acetate/hexanes) to give a mixture of (S)-2-((R)-1-(2,3-dihydropyrano[4,3,2-de]quinolin-7-yl)-3-methylnaphthalen-2-yl)-2-(1,1,1-trifluoro-2-methylpropan-2-yloxy)ethyl pivalate and (R)-2-((S)-1-(2,3-dihydropyrano[4,3,2-de]quinolin-7-yl)-3-methylnaphthalen-2-yl)-2-(1,1,1-trifluoro-2-methylpropan-2-yloxy)ethyl pivalate. ¹H-NMR: 400 MHz, (CDCl₃) δ 8.63 (d, J=4.0 Hz, 1H), 7.78 (d, J=8.0 Hz, 1H), 7.75 (s, 1H), 7.55 (d, J=8.0 Hz, 1H), 7.39 (t, J=6.8 Hz, 1H), 7.20-7.12 (m, 3H), 7.07 (d, J=4.0 Hz, 1H), 4.69 (d, J=5.2 Hz, 1H), 4.58-4.52 (m, 2H), 4.42 (d, J=5.2 Hz, 2H), 3.31 (t, J=5.2 Hz, 2H), 2.79 (s, 3H), 1.07 (s, 3H), 1.04 (s, 3H), 0.89 (s, 9H); LCMS-ESI⁺ (m/z): [M+H]⁺ calcd for C₃₃H₃₅F₃NO₄: 566.25. Found: 566.2.

Preparation of a mixture of (S)-2-((R)-1-(2,3-dihydropyrano[4,3,2-de]quinolin-7-yl)-3-methylnaphthalen-2-yl)-2-(1,1,1-trifluoro-2-methylpropan-2-yloxy)ethanol and (R)-2-((S)-1-(2,3-dihydropyrano[4,3,2-de]quinolin-7-yl)-3-methylnaphthalen-2-yl)-2-(1,1,1-trifluoro-2-methylpropan-2-yloxy)ethanol: To a stirred solution of (S)-2-((R)-1-(2,3-dihydropyrano[4,3,2-de]quinolin-7-yl)-3-methylnaphthalen-2-yl)-2-(1,1,1-trifluoro-2-methylpropan-2-yloxy)ethyl pivalate and (R)-2-((S)-1-(2,3-dihydropyrano[4,3,2-de]quinolin-7-yl)-3-methylnaphthalen-2-yl)-2-(1,1,1-trifluoro-2-methylpropan-2-yloxy)ethyl pivalate (45 mg, 0.08 mmol) in THF (3.5 mL) and methanol (3.5 mL) was added 1 M NaOH solution (3.5 mL, excess). The reaction mixture was stirred at 50° C. overnight. The mixture was diluted with ethyl acetate, washed with water and brine, dried over $Na_2SO_4$, filtered and concentrated and purified by flash column chromatography (silica gel, 0 to 100% ethyl acetate/hexanes) to give a mixture of (S)-2-((R)-1-(2,3-dihydropyrano[4,3,2-de]quinolin-7-yl)-3-methylnaphthalen-2-yl)-2-(1,1,1-trifluoro-2-methylpropan-2-yloxy)ethanol and (R)-2-((S)-1-(2,3-dihydropyrano[4,3,2-de]quinolin-7-yl)-3-methylnaphthalen-2-yl)-2-(1,1,1-trifluoro-2-methylpropan-2-yloxy)ethanol as a yellow oil. $^1$H-NMR: 400 MHz, ($CDCl_3$) δ 8.67 (d, J=4.4 Hz, 1H), 7.78 (s, 1H), 7.75 (s, 1H), 7.55 (d, J=7.6 Hz, 1H), 7.36 (t, J=7.2 Hz, 1H), 7.18-7.11 (m, 3H), 6.86 (d, J=8.4 Hz, 1H), 4.82 (t, J=7.6 Hz, 1H), 4.60 (t, J=5.6 Hz, 2H), 3.80 (m, 2H), 3.36 (t, J=5.6 Hz, 2H), 2.80 (s, 3H), 1.15 (s, 3H), 1.10 (s, 3H); LCMS-ESI$^+$ (m/z): [M+H]$^+$ calcd for $C_{28}H_{27}F_3NO_3$: 482.20. Found: 482.1.

Preparation of a mixture of (S)-2-((R)-1-(2,3-dihydropyrano[4,3,2-de]quinolin-7-yl)-3-methylnaphthalen-2-yl)-2-(1,1,1-trifluoro-2-methylpropan-2-yloxy)acetic acid and (R)-2-((S)-1-(2,3-dihydropyrano[4,3,2-de]quinolin-7-yl)-3-methylnaphthalen-2-yl)-2-(1,1,1-trifluoro-2-methylpropan-2-yloxy)acetic acid: To a solution of (S)-2-((R)-1-(2,3-dihydropyrano[4,3,2-de]quinolin-7-yl)-3-methylnaphthalen-2-yl)-2-(1,1,1-trifluoro-2-methylpropan-2-yloxy)ethanol and (R)-2-((S)-1-(2,3-dihydropyrano[4,3,2-de]quinolin-7-yl)-3-methylnaphthalen-2-yl)-2-(1,1,1-trifluoro-2-methylpropan-2-yloxy)ethanol (26 mg, 0.05 mmol) in wet acetonitrile (0.75% wt $H_2O$) was added $H_5IO_6$/$CrO_3$ (0.439 M stock solution in wet acetonitrile, 0.5 mL) at 0° C. The reaction mixture was stirred at 0° C. for 45 min. The reaction mixture was filtered and purified by reverse phase HPLC (Gemini, 5 to 100% ACN/$H_2O$+0.1% TFA) to give a mixture of (S)-2-((R)-1-(2,3-dihydropyrano[4,3,2-de]quinolin-7-yl)-3-methylnaphthalen-2-yl)-2-(1,1,1-trifluoro-2-methylpropan-2-yloxy)acetic acid and (R)-2-((S)-1-(2,3-dihydropyrano[4,3,2-de]quinolin-7-yl)-3-methylnaphthalen-2-yl)-2-(1,1,1-trifluoro-2-methylpropan-2-yloxy)acetic acid as TFA salt. $^1$H-NMR: 400 MHz, ($CD_3OD$) δ 8.65 (d, J=5.6 Hz, 1H), 8.01 (s, 1H), 7.95 (d, J=8.0 Hz, 1H), 7.84-7.81 (m, 2H), 7.54-7.50 (m, 1H), 7.46 (d, J=8.4 Hz, 1H), 7.31-7.27 (m, 1H), 6.95 (d, J=8.4 Hz, 1H), 5.47 (s, 1H), 4.79-4.65 (m, 2H), 3.68 (t, J=6.0 Hz, 2H), 2.76 (s, 3H), 1.25 (s, 3H), 1.00 (s, 3H). LCMS-ESI$^+$ (m/z): [M+H]$^+$ calcd for $C_{28}H_{25}F_3NO_4$: 496.18. Found: 496.1.

Preparation of (S)-2-((R)-1-(2,3-dihydropyrano[4,3,2-de]quinolin-7-yl)-3-methylnaphthalen-2-yl)-2-(1,1,1-trifluoro-2-methylpropan-2-yloxy)acetic acid: Separation by chiral HPLC, using a Chiralpak AZ-H column (4.6×250 mm) and an isocratic solvent system of 70% heptane and 30% isopropyl alcohol provides (S)-2-((R)-1-(2,3-dihydropyrano[4,3,2-de]quinolin-7-yl)-3-methylnaphthalen-2-yl)-2-(1,1,1-trifluoro-2-methylpropan-2-yloxy)acetic acid. $^1$H-NMR: 400 MHz, ($CD_3OD$) δ 8.54 (d, J=4.4 Hz, 1H), 7.81 (d, J=8.0 Hz, 1H), 7.79 (s, 1H), 7.57 (d, J=8.0 Hz, 1H), 7.41 (t, J=6.8 Hz, 1H), 7.35 (d, J=4.8 Hz, 1H), 7.21 (d, J=8.0 Hz, 1H), 7.15 (t, J=8.0 Hz, 1H), 6.87 (d, J=8.0 Hz, 1H), 5.35 (s, 1H), 4.58-4.61 (m, 2H), 3.43 (t, J=6.0 Hz, 2H), 2.68 (s, 3H), 1.17 (s, 3H), 1.04 (s, 3H). LCMS-ESI$^+$ (m/z): [M+H]$^+$ calcd for $C_{28}H_{25}F_3NO_4$: 496.18. Found: 496.1.

Preparation of (R)-2-((S)-1-(2,3-dihydropyrano[4,3,2-de]quinolin-7-yl)-3-methylnaphthalen-2-yl)-2-(1,1,1-trifluoro-2-methylpropan-2-yloxy)acetic acid: Separation by chiral HPLC, using a Chiralpak AZ-H column (4.6×250 mm) and an isocratic solvent system of 70% heptane and 30% isopropyl alcohol (R)-2-((S)-1-(2,3-dihydropyrano[4,3,2-de]quinolin-7-yl)-3-methylnaphthalen-2-yl)-2-(1,1,1-trifluoro-2-methylpropan-2-yloxy)acetic acid. $^1$H-NMR: 400 MHz, ($CD_3OD$) δ 8.54 (d, J=4.4 Hz, 1H), 7.81 (d, J=8.0 Hz, 1H), 7.79 (s, 1H), 7.57 (d, J=8.0 Hz, 1H), 7.41 (t, J=6.8 Hz, 1H), 7.35 (d, J=4.8 Hz, 1H), 7.21 (d, J=8.0 Hz, 1H), 7.15 (t, J=8.0 Hz, 1H), 6.87 (d, J=8.0 Hz, 1H), 5.35 (s, 1H), 4.58-4.61 (m, 2H), 3.43 (t, J=6.0 Hz, 2H), 2.68 (s, 3H), 1.17 (s, 3H), 1.04 (s, 3H). LCMS-ESI$^+$ (m/z): [M+H]$^+$ calcd for $C_{28}H_{25}F_3NO_4$: 496.18. Found: 496.1.

EXAMPLE 32

(S)-2-(1,1-Difluoro-2-methylpropan-2-yloxy)-2-((R)-1-(2,3-dihydropyrano[4,3,2-de]quinolin-7-yl)-3-methylnaphthalen-2-yl)acetic acid and (R)-2-(1,1-difluoro-2-methylpropan-2-yloxy)-2-((S)-1-(2,3-dihydropyrano[4,3,2-de]quinolin-7-yl)-3-methylnaphthalen-2-yl)acetic acid

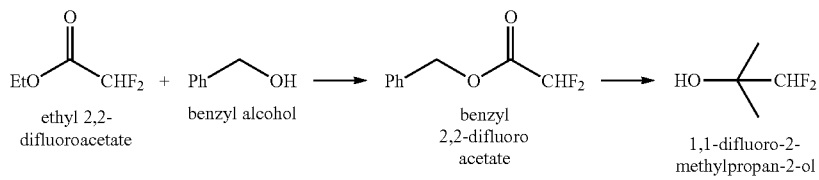

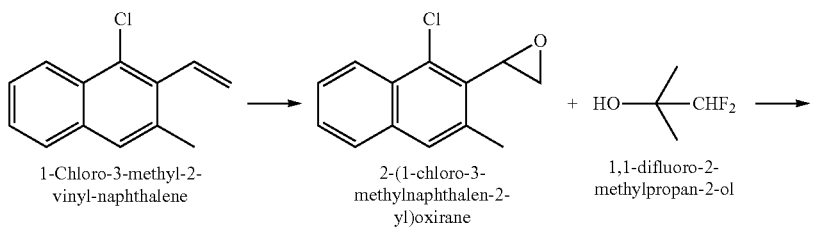

-continued

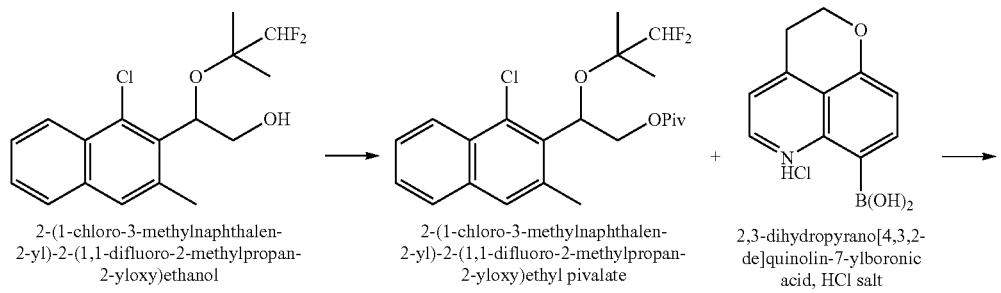

2-(1-chloro-3-methylnaphthalen-2-yl)-2-(1,1-difluoro-2-methylpropan-2-yloxy)ethanol 2-(1-chloro-3-methylnaphthalen-2-yl)-2-(1,1-difluoro-2-methylpropan-2-yloxy)ethyl pivalate 2,3-dihydropyrano[4,3,2-de]quinolin-7-ylboronic acid, HCl salt

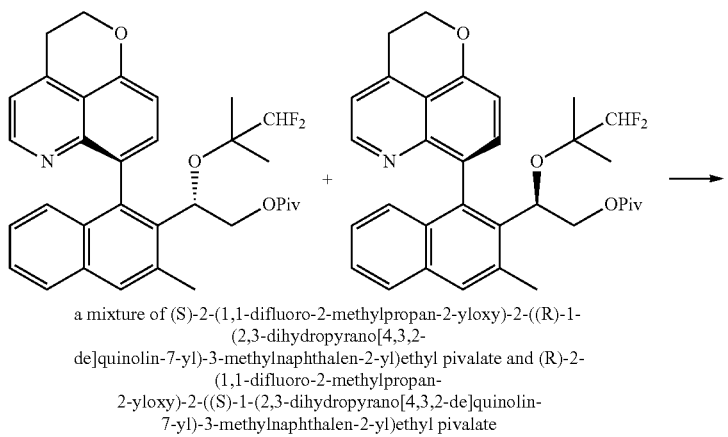

a mixture of (S)-2-(1,1-difluoro-2-methylpropan-2-yloxy)-2-((R)-1-(2,3-dihydropyrano[4,3,2-de]quinolin-7-yl)-3-methylnaphthalen-2-yl)ethyl pivalate and (R)-2-(1,1-difluoro-2-methylpropan-2-yloxy)-2-((S)-1-(2,3-dihydropyrano[4,3,2-de]quinolin-7-yl)-3-methylnaphthalen-2-yl)ethyl pivalate

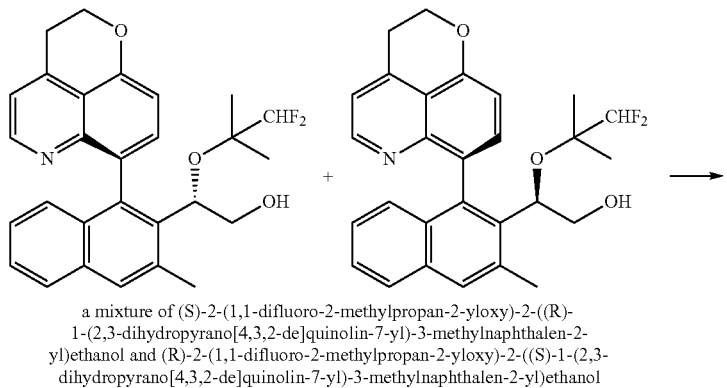

a mixture of (S)-2-(1,1-difluoro-2-methylpropan-2-yloxy)-2-((R)-1-(2,3-dihydropyrano[4,3,2-de]quinolin-7-yl)-3-methylnaphthalen-2-yl)ethanol and (R)-2-(1,1-difluoro-2-methylpropan-2-yloxy)-2-((S)-1-(2,3-dihydropyrano[4,3,2-de]quinolin-7-yl)-3-methylnaphthalen-2-yl)ethanol

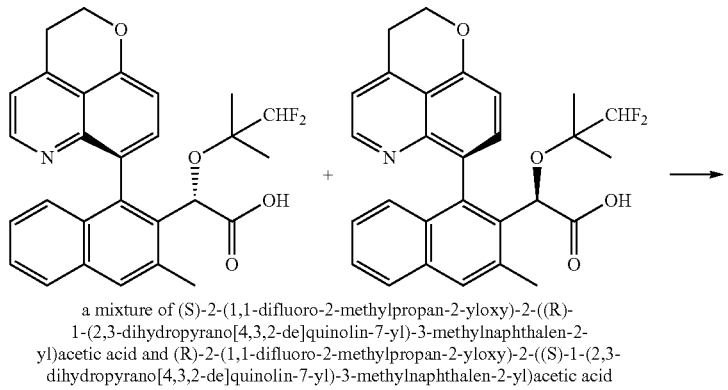

a mixture of (S)-2-(1,1-difluoro-2-methylpropan-2-yloxy)-2-((R)-1-(2,3-dihydropyrano[4,3,2-de]quinolin-7-yl)-3-methylnaphthalen-2-yl)acetic acid and (R)-2-(1,1-difluoro-2-methylpropan-2-yloxy)-2-((S)-1-(2,3-dihydropyrano[4,3,2-de]quinolin-7-yl)-3-methylnaphthalen-2-yl)acetic acid

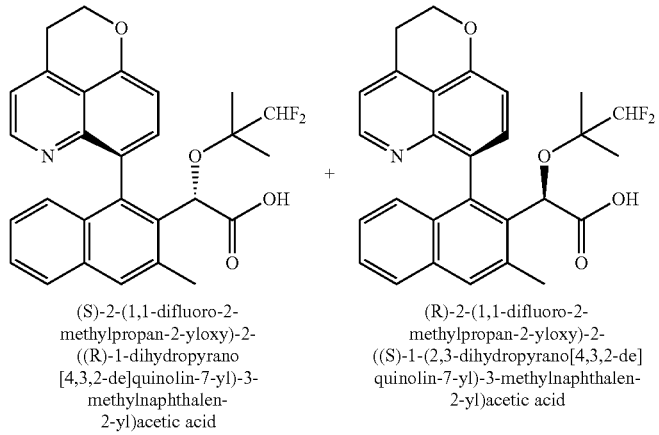

(S)-2-(1,1-difluoro-2-
methylpropan-2-yloxy)-2-
((R)-1-dihydropyrano
[4,3,2-de]quinolin-7-yl)-3-
methylnaphthalen-
2-yl)acetic acid (R)-2-(1,1-difluoro-2-
methylpropan-2-yloxy)-2-
((S)-1-(2,3-dihydropyrano[4,3,2-de]
quinolin-7-yl)-3-methylnaphthalen-
2-yl)acetic acid Preparation of benzyl 2,2-difluoroacetate: To a dried round bottom flask was added ethyl 2,2-difluoroacetate (25 g, 0.20 mol), benzyl alcohol (62.6 mL, 0.60 mol) and boron trifluoride etherate (2.5 mL, 0.02 mmol) under nitrogen atmosphere. The reaction mixture was stirred at 75° C. overnight. The mixture was quenched with saturated aqueous $NaHCO_3$, and then diluted with EtOAc. The organic phase was washed with brine, dried over $Na_2SO_4$, filtered and concentrated and purified by flash column chromatography (silica gel, 0 to 10% ethyl acetate/hexanes) to give benzyl 2,2-difluoroacetate. $^1$H-NMR: 400 MHz, ($CDCl_3$) δ 7.39-7.29 (m, 4H), 5.93 (t, J=52.8 Hz, 1H), 5.31 (s, 2H).

Preparation of 1,1-difluoro-2-methylpropan-2-ol: To a stirred solution of methylmagnesium bromide (70.2 mL of 3.0 M solution in $Et_2O$, 0.21 mol) was added benzyl 2,2-difluoroacetate (13.7 g, 0.07 mol) in $Et_2O$ (40.2 mL) at 0° C. The reaction mixture was stirred for 30 min at 0° C. and quenched with ice water and hydrochloric acid. The ethereal layer was separated, washed with saturated $NaHCO_3$ and brine, dried over $Na_2SO_4$, filtered and distilled to give 1,1-difluoro-2-methylpropan-2-ol. $^1$H-NMR: 400 MHz, ($CDCl_3$) δ 5.52 (t, J=56.4 Hz, 1H), 1.28 (t, J=1.6 Hz, 6H).

Preparation of 2-(1-chloro-3-methylnaphthalen-2-yl)oxirane: To a stirred solution of 1-chloro-3-methyl-2-vinylnaphthalene (3.0 g, 14.8 mmol) in $CH_2Cl_2$ (120 mL) was added 3-chloroperoxybenzoic acid (3.8 g, 22.0 mmol) at 0° C. and allowed to warm to room temperature overnight. The reaction mixture was washed with $NaHCO_3$, brine, dried over $Na_2SO_4$, filtered and concentrated and purified by flash column chromatography (silica gel, 0 to 20% ethyl acetate/hexanes) to give 2-(1-chloro-3-methylnaphthalen-2-yl)oxirane. $^1$H-NMR: 400 MHz, ($CDCl_3$) δ 8.26 (d, J=7.2 Hz, 1H), 7.74 (dd, J=7.2, 2.0 Hz, 1H), 7.57-7.48 (m, 3H), 4.13 (t, J=3.6 Hz, 1H), 3.34 (t, J=5.6 Hz, 1H), 2.97 (dd, J=5.2, 2.8 Hz, 1H), 2.64 (s, 3H).

Preparation of 2-(1-chloro-3-methylnaphthalen-2-yl)-2-(1,1-difluoro-2-methylpropan-2-yloxy)ethanol: Compound 2-(1-chloro-3-methylnaphthalen-2-yl)-2-(1,1-difluoro-2-methylpropan-2-yloxy)ethanol was prepared following the procedure used to prepare 2-(1-chloro-3-methylnaphthalen-2-yl)-2-(1,1,1-trifluoro-2-methylpropan-2-yloxy)ethanol of Example 31, except that 1,1-difluoro-2-methylpropan-2-ol (10 eq) was used instead of 2-trifluoromethyl-2-propanol (25 eq). $^1$H-NMR: 400 MHz, ($CDCl_3$) δ 8.27 (d, J=8.4 Hz, 1H), 7.73 (d, J=7.6 Hz, 1H), 7.57-7.49 (m, 3H), 5.85 (dd, J=9.2, 3.6 Hz, 1H), 5.61 (t, J=56.4 Hz, 1H), 3.94 (dd, J=11.6, 9.6 Hz, 1H), 3.65 (dd, J=11.6, 4.4 Hz, 1H), 2.69 (s, 3H), 2.18 (br s, 1H), 1.32 (s, 3H), 1.10 (s, 3H).

Preparation of 2-(1-chloro-3-methylnaphthalen-2-yl)-2-(1,1-difluoro-2-methylpropan-2-yloxy)ethyl pivalate: Compound 2-(1-chloro-3-methylnaphthalen-2-yl)-2-(1,1-difluoro-2-methylpropan-2-yloxy)ethyl pivalate was prepared following the procedure used to prepare 2-(1-chloro-3-methylnaphthalen-2-yl)-2-(1,1,1-trifluoro-2-methylpropan-2-yloxy)ethyl pivalate of Example 31, except that 2-(1-chloro-3-methylnaphthalen-2-yl)-2-(1,1-difluoro-2-methylpropan-2-yloxy)ethanol was used instead of 2-(1-chloro-3-methylnaphthalen-2-yl)-2-(1,1,1-trifluoro-2-methylpropan-2-yloxy)ethanol. $^1$H-NMR: 400 MHz, ($CDCl_3$) δ 8.27 (d, J=8.0 Hz, 1H), 7.73 (d, J=8.8 Hz, 1H), 7.57 (s, 1H), 7.56-7.50 (m, 2H), 6.01 (dd, J=8.4, 4.8 Hz, 1H), 5.53 (t, J=56.4 Hz, 1H), 4.47 (dd, J=11.6, 8.4 Hz, 1H), 4.19 (dd, J=11.6, 5.6 Hz, 1H), 2.72 (s, 3H), 1.27 (s, 6H), 1.16 (s, 9H).

Preparation of a mixture of (S)-2-(1,1-difluoro-2-methylpropan-2-yloxy)-2-((R)-1-(2,3-dihydropyrano[4,3,2-de]quinolin-7-yl)-3-methylnaphthalen-2-yl)ethyl pivalate and (R)-2-(1,1-difluoro-2-methylpropan-2-yloxy)-2-((S)-1-(2,3-dihydropyrano[4,3,2-de]quinolin-7-yl)-3-methylnaphthalen-2-yl)ethyl pivalate: Mixture of (S)-2-(1,1-difluoro-2-methylpropan-2-yloxy)-2-((R)-1-(2,3-dihydropyrano[4,3,2-de]quinolin-7-yl)-3-methylnaphthalen-2-yl)ethyl pivalate and (R)-2-(1,1-difluoro-2-methylpropan-2-yloxy)-2-((S)-1-(2,3-dihydropyrano[4,3,2-de]quinolin-7-yl)-3-methylnaphthalen-2-yl)ethyl pivalate was prepared following the procedure used to prepare the mixture of (S)-2-((R)-1-(2,3-dihydropyrano[4,3,2-de]quinolin-7-yl)-3-methylnaphthalen-2-yl)-2-(1,1,1-trifluoro-2-methylpropan-2-yloxy)ethyl pivalate and (R)-2-((S)-1-(2,3-dihydropyrano[4,3,2-de]quinolin-7-yl)-3-methylnaphthalen-2-yl)-2-(1,1,1-trifluoro-2-methylpropan-2-yloxy)ethyl pivalate of Example 31, except that 2-(1- chloro-3-methylnaphthalen-2-yl)-2-(1,1-difluoro-2-methylpropan-2-yloxy)ethyl pivalate was used instead of 2-(1-chloro-3-methylnaphthalen-2-yl)-2-(1,1,1-trifluoro-2-methylpropan-2-yloxy)ethyl pivalate. $^1$H-NMR: 400 MHz, (CDCl$_3$) δ 8.64 (d, J=3.6 Hz, 1H), 7.78 (d, J=8.4 Hz, 1H), 7.75 (s, 1H), 7.57 (d, J=8.4 Hz, 1H), 7.41-7.36 (m, 1H), 7.26-7.08 (m, 4H), 5.37 (t, J=56.8 Hz, 1H), 4.66 (t, J=5.6 Hz, 1H), 4.58-4.52 (m, 2H), 4.39 (d, J=5.6 Hz, 2H), 3.32 (t, J=5.2 Hz, 2H), 2.78 (s, 3H), 0.94 (s, 6H), 0.89 (s, 9H); LCMS-ESI$^+$ (m/z):

Preparation of a mixture of (S)-2-(1,1-difluoro-2-methylpropan-2-yloxy)-2-((R)-1-(2,3-dihydropyrano[4,3,2-de]quinolin-7-yl)-3-methylnaphthalen-2-yl)ethanol and (R)-2-(1,1-difluoro-2-methylpropan-2-yloxy)-2-((S)-1-(2,3-dihydropyrano[4,3,2-de]quinolin-7-yl)-3-methylnaphthalen-2-yl)ethanol: Mixture of (S)-2-(1,1-difluoro-2-methylpropan-2-yloxy)-2-((R)-1-(2,3-dihydropyrano[4,3,2-de]quinolin-7-yl)-3-methylnaphthalen-2-yl)ethanol and (R)-2-(1,1-difluoro-2-methylpropan-2-yloxy)-2-((S)-1-(2,3-dihydropyrano[4,3,2-de]quinolin-7-yl)-3-methylnaphthalen-2-yl)ethanol was prepared following the procedure used to prepare the mixture of (S)-2-((R)-1-(2,3-dihydropyrano[4,3,2-de]quinolin-7-yl)-3-methylnaphthalen-2-yl)-2-(1,1,1-trifluoro-2-methylpropan-2-yloxy)ethanol and (R)-2-((S)-1-(2,3-dihydropyrano[4,3,2-de]quinolin-7-yl)-3-methylnaphthalen-2-yl)-2-(1,1,1-trifluoro-2-methylpropan-2-yloxy)ethanol of Example 31, except that the mixture of (S)-2-(1,1-difluoro-2-methylpropan-2-yloxy)-2-((R)-1-(2,3-dihydropyrano[4,3,2-de]quinolin-7-yl)-3-methylnaphthalen-2-yl)ethyl pivalate and (R)-2-(1,1-difluoro-2-methylpropan-2-yloxy)-2-((S)-1-(2,3-dihydropyrano[4,3,2-de]quinolin-7-yl)-3-methylnaphthalen-2-yl)ethyl pivalate was used instead of the mixture of (S)-2-((R)-1-(2,3-dihydropyrano[4,3,2-de]quinolin-7-yl)-3-methylnaphthalen-2-yl)-2-(1,1,1-trifluoro-2-methylpropan-2-yloxy)ethyl pivalate and (R)-2-((S)-1-(2,3-dihydropyrano[4,3,2-de]quinolin-7-yl)-3-methylnaphthalen-2-yl)-2-(1,1,1-trifluoro-2-methylpropan-2-yloxy)ethyl pivalate. $^1$H-NMR: 400 MHz, (CDCl$_3$) δ 8.71 (d, J=4.8 Hz, 1H), 7.79-7.75 (m, 2H), 7.61 (d, J=8.4 Hz, 1H), 7.39-7.34 (m, 1H), 7.22-7.10 (m, 3H), 6.80 (d, J=8.4 Hz, 1H), 5.43 (t, J=56.0 Hz, 1H), 4.77 (t, J=8.0 Hz, 1H), 4.61 (t, J=5.6 Hz, 2H), 3.84 (dd, J=11.6, 6.8 Hz, 1H), 3.72 (dd, J=11.6, 8.4 Hz, 1H), 3.37 (t, J=6.0 Hz, 2H), 2.78 (s, 3H), 1.04 (s, 3H), 1.02 (s, 3H); LCMS-ESI$^+$ (m/z):

Preparation of a mixture of (S)-2-(1,1-difluoro-2-methylpropan-2-yloxy)-2-((R)-1-(2,3-dihydropyrano[4,3,2-de]quinolin-7-yl)-3-methylnaphthalen-2-yl)acetic acid and (R)-2-(1,1-difluoro-2-methylpropan-2-yloxy)-2-((S)-1-(2,3-dihydropyrano[4,3,2-de]quinolin-7-yl)-3-methylnaphthalen-2-yl)acetic acid: Mixture of (S)-2-(1,1-difluoro-2-methylpropan-2-yloxy)-2-((R)-1-(2,3-dihydropyrano[4,3,2-de]quinolin-7-yl)-3-methylnaphthalen-2-yl)acetic acid and (R)-2-(1,1-difluoro-2-methylpropan-2-yloxy)-2-((S)-1-(2,3-dihydropyrano[4,3,2-de]quinolin-7-yl)-3-methylnaphthalen-2-yl)acetic acid was prepared following the procedure used to prepare the mixture of (S)-2-((R)-1-(2,3-dihydropyrano[4,3,2-de]quinolin-7-yl)-3-methylnaphthalen-2-yl)-2-(1,1,1-trifluoro-2-methylpropan-2-yloxy)acetic acid and (R)-2-((S)-1-(2,3-dihydropyrano[4,3,2-de]quinolin-7-yl)-3-methylnaphthalen-2-yl)-2-(1,1,1-trifluoro-2-methylpropan-2-yloxy)acetic acid of Example 31, except that (S)-2-(1,1-difluoro-2-methylpropan-2-yloxy)-2-((R)-1-(2,3-dihydropyrano[4,3,2-de]quinolin-7-yl)-3-methylnaphthalen-2-yl)ethanol and (R)-2-(1,1-difluoro-2-methylpropan-2-yloxy)-2-((S)-1-(2,3-dihydropyrano[4,3,2-de]quinolin-7-yl)-3-methylnaphthalen-2-yl)ethanol was used instead of the mixture of (S)-2-((R)-1-(2,3-dihydropyrano[4,3,2-de]quinolin-7-yl)-3-methylnaphthalen-2-yl)-2-(1,1,1-trifluoro-2-methylpropan-2-yloxy)ethanol and (R)-2-((S)-1-(2,3-dihydropyrano[4,3,2-de]quinolin-7-yl)-3-methylnaphthalen-2-yl)-2-(1,1,1-trifluoro-2-methylpropan-2-yloxy)ethanol. LCMS-ESI$^+$ (m/z): [M+H]$^+$ calcd for C$_{28}$H$_{26}$F$_2$NO$_4$: 478.19. Found: 478.1.

Preparation of (S)-2-(1,1-difluoro-2-methylpropan-2-yloxy)-2-((R)-1-(2,3-dihydropyrano[4,3,2-de]quinolin-7-yl)-3-methylnaphthalen-2-yl)acetic acid: Compound (S)-2-(1,1-difluoro-2-methylpropan-2-yloxy)-2-((R)-1-(2,3-dihydropyrano[4,3,2-de]quinolin-7-yl)-3-methylnaphthalen-2-yl)acetic acid was prepared following the procedure used to prepare (S)-2-((R)-1-(2,3-dihydropyrano[4,3,2-de]quinolin-7-yl)-3-methylnaphthalen-2-yl)-2-(1,1,1-trifluoro-2-methylpropan-2-yloxy)acetic acid of Example 31. $^1$H-NMR: 400 MHz, (CD$_3$OD) δ 8.65 (d, J=5.6 Hz, 1H), 7.99 (s, 1H), 7.85 (d, J=8.0 Hz, 1H), 7.84-7.80 (m, 2H), 7.53-7.45 (m, 2H), 7.27 (t, J=7.2 Hz, 1H), 6.92 (d, J=8.0 Hz, 1H), 5.41 (s, 1H), 5.40 (t, J=56.8 Hz, 1H), 4.77-4.60 (m, 2H), 3.67 (t, J=5.6 Hz, 2H), 2.76 (s, 3H), 1.04 (s, 3H), 0.97 (s, 3H); LCMS-ESI$^+$ (m/z): [M+H]$^+$ calcd for C$_{28}$H$_{26}$F$_2$NO$_4$: 478.19. Found: 478.1.

Preparation of (R)-2-(1,1-difluoro-2-methylpropan-2-yloxy)-2-((S)-1-(2,3-dihydropyrano[4,3,2-de]quinolin-7-yl)-3-methylnaphthalen-2-yl)acetic acid: Compound (R)-2-(1,1-difluoro-2-methylpropan-2-yloxy)-2-((S)-1-(2,3-dihydropyrano[4,3,2-de]quinolin-7-yl)-3-methylnaphthalen-2-yl)acetic acid was prepared following the procedure used to prepare (R)-2-((S)-1-(2,3-dihydropyrano[4,3,2-de]quinolin-7-yl)-3-methylnaphthalen-2-yl)-2-(1,1,1-trifluoro-2-methylpropan-2-yloxy)acetic acid of Example 31. $^1$H-NMR: 400 MHz, (CD$_3$OD) δ 8.65 (d, J=5.6 Hz, 1H), 7.99 (s, 1H), 7.85 (d, J=8.0 Hz, 1H), 7.84-7.80 (m, 2H), 7.53-7.45 (m, 2H), 7.27 (t, J=7.2 Hz, 1H), 6.92 (d, J=8.0 Hz, 1H), 5.41 (s, 1H), 5.40 (t, J=56.8 Hz, 1H), 4.77-4.60 (m, 2H), 3.67 (t, J=5.6 Hz, 2H), 2.76 (s, 3H), 1.04 (s, 3H), 0.97 (s, 3H); LCMS-ESI$^+$ (m/z): [M+H]$^+$ calcd for C$_{28}$H$_{26}$F$_2$NO$_4$: 478.19. Found: 478.1.

EXAMPLES 33-106

The compounds of Examples 33-106 where prepared following similar synthetic procedures as those procedures described in Examples 1-32 and Example 107.

| HPLC Method | |
|---|---|
| Column | Phenomenex Kinetex C18 (2.6 um 100 Å, 4.6 × 100 mm) |
| Flow Rate | 2.5 mL/min |
| Solvent A | MilliQ H20 + 0.1% TFA |
| Solvent B | ACN + 0.1% TFA |
| Gradient | % B 2-98 |
| Gradient time | 8.5 min |
| Wavelength | 214 nm |

| Example Number | Compound | Parent MW | LC/MS (M + H)+ | HPLC t (min) |
|---|---|---|---|---|
| 33 | | 467.56 | 468.1 | 6.11 |
| 34 | | 467.56 | 468.1 | 6.27 |
| 35 | | 617.75 | 618.2 | 5.00 |
| 36 | | 595.7 | 596.2 | 6.95 |

| Example Number | Compound | Parent MW | LC/MS (M + H)+ | HPLC t (min) |
|---|---|---|---|---|
| 37 | 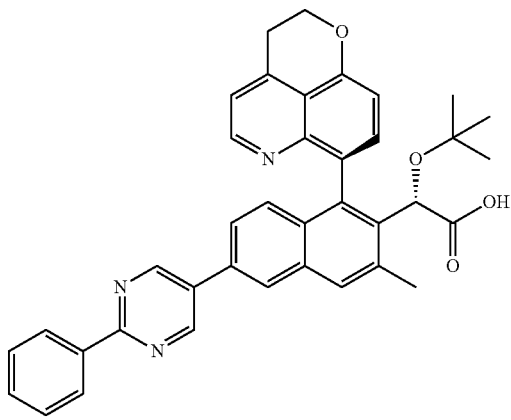 | 595.7 | 596.2 | 6.90 |
| 38 | 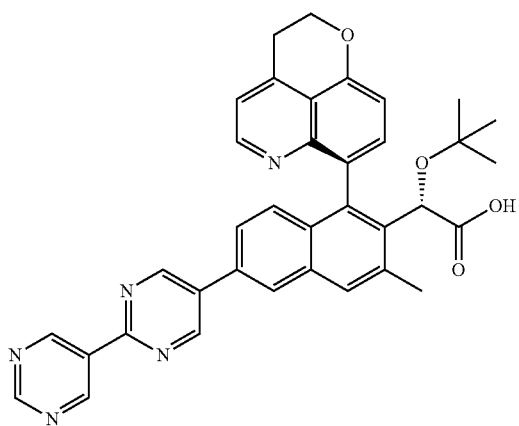 | 597.68 | 598.2 | 5.94 |
| 39 | 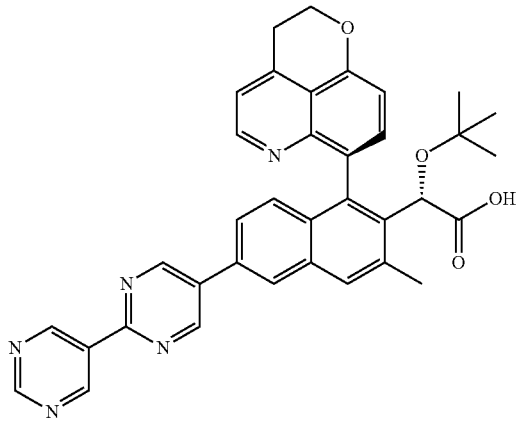 | 597.68 | 598.2 | 5.92 |

-continued
| Example Number | Compound | Parent MW | LC/MS (M + H)+ | HPLC t (min) |
|---|---|---|---|---|
| 40 | | 595.7 | 596.2 | 6.26 |
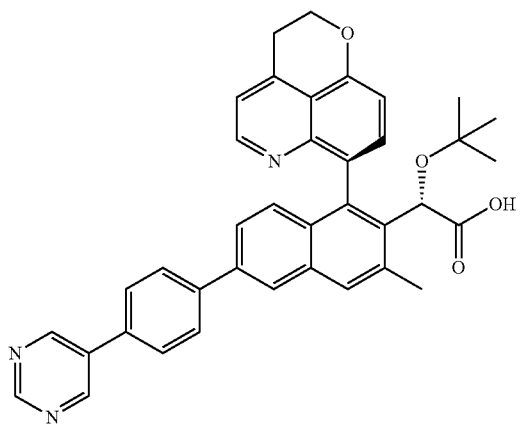
| 41 | | 595.7 | 596.2 | 6.31 |
|---|---|---|---|---|
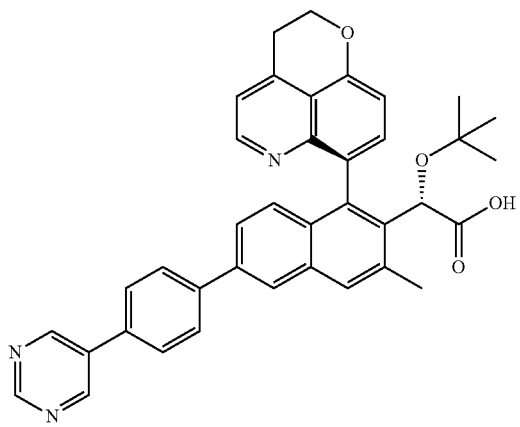
| 42 | | 543.62 | 544.1 | 5.97 |
|---|---|---|---|---|
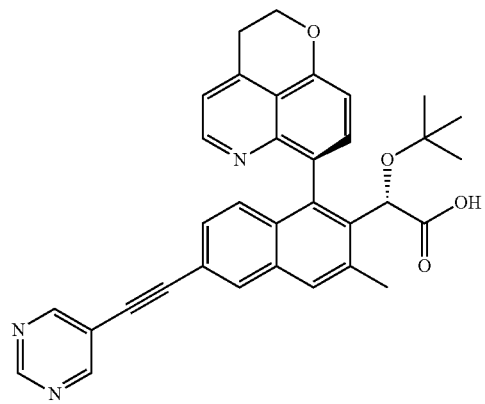

-continued
| Example Number | Compound | Parent MW | LC/MS (M + H)+ | HPLC t (min) |
|---|---|---|---|---|
| 43 | 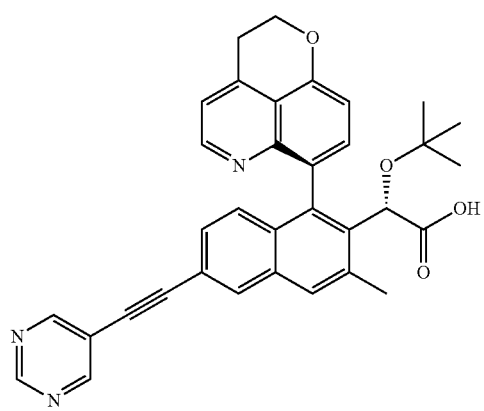 | 543.62 | 544.1 | 5.98 |
| 44 | 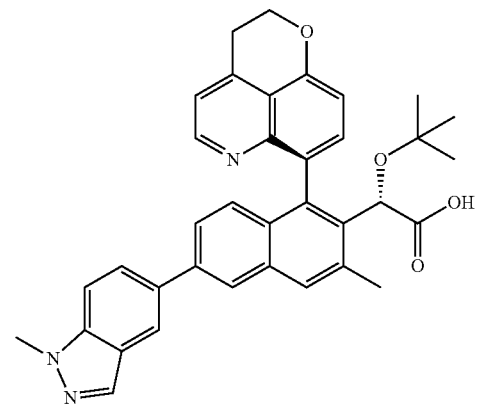 | 571.68 | 572.2 | 6.40 |
| 45 | 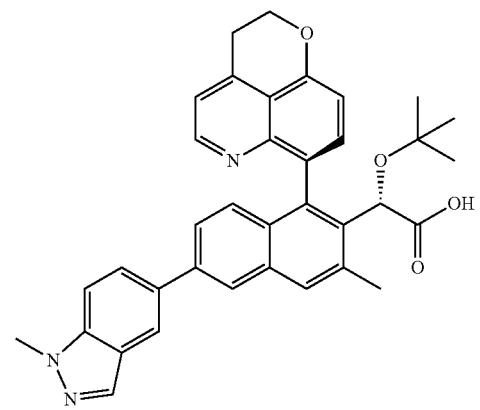 | 571.68 | 572.2 | 5.34 |

-continued

| Example Number | Compound | Parent MW | LC/MS (M + H)+ | HPLC t (min) |
|---|---|---|---|---|
| 46 | | 565.63 | 566.1 | 5.09 |
| 47 | | 565.63 | 566.1 | 5.33 |
| 48 | | 562.67 | 563.1 | 5.59 |
| 49 | | 579.65 | 580.1 | 5.96 |

| Example Number | Compound | Parent MW | LC/MS (M + H)+ | HPLC t (min) |
|---|---|---|---|---|
| 50 | 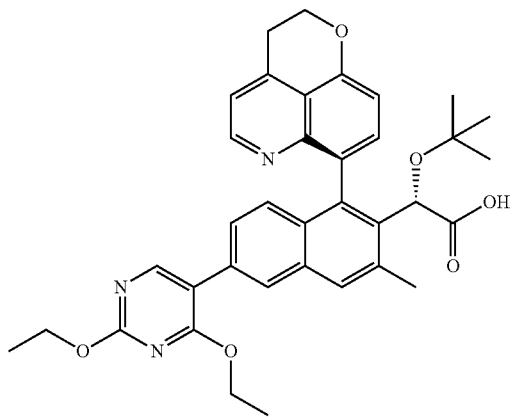 | 607.71 | 608.1 | 6.35 |
| 51 | 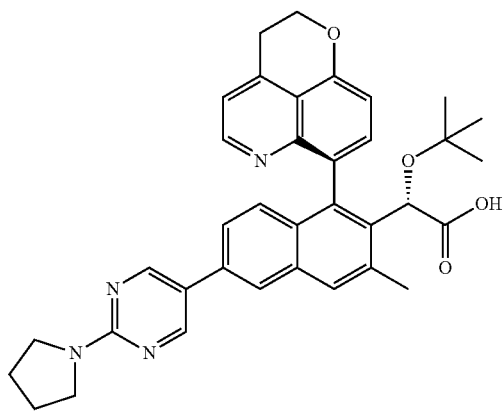 | 588.71 | 589.2 | 5.55 |
| 52 | 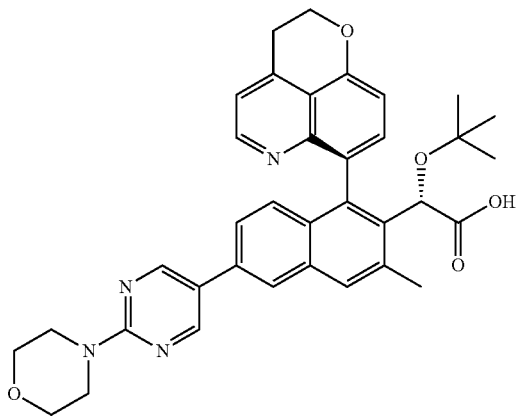 | 604.71 | 605.2 | 6.06 |

-continued

| Example Number | Compound | Parent MW | LC/MS (M + H)+ | HPLC t (min) |
|---|---|---|---|---|
| 53 | | 534.62 | 535.2 | 4.48 |
| 54 | | 534.62 | 535.2 | 4.50 |
| 55 | | 534.62 | 535.1 | 4.96 |
| 56 | | 533.63 | 534.1 | 5.48 |

-continued

| Example Number | Compound | Parent MW | LC/MS (M + H)+ | HPLC t (min) |
|---|---|---|---|---|
| 57 | | 533.63 | 534.1 | 5.45 |
| 58 | | 547.66 | 548.2 | 5.29 |
| 59 | | 547.66 | 548.2 | 5.39 |
| 60 | | 549.63 | 550.1 | 5.95 |

-continued
| Example Number | Compound | Parent MW | LC/MS (M + H)+ | HPLC t (min) |
|---|---|---|---|---|
| 61 | 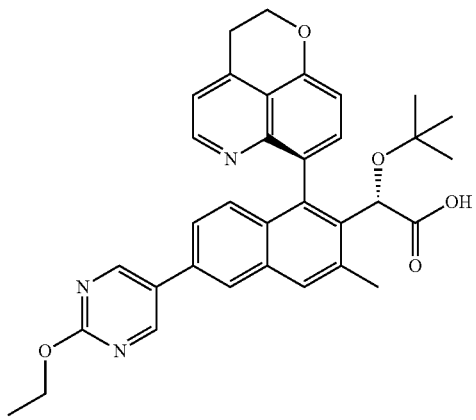 | 563.65 | 564.1 | 6.21 |
| 62 | 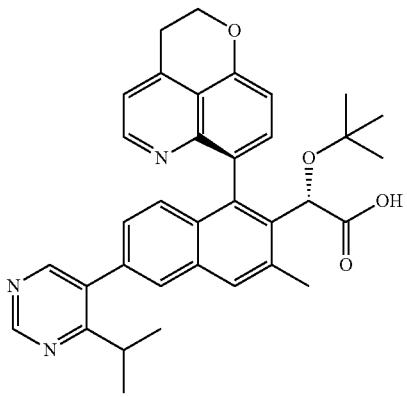 | 561.68 | 562.2 | 6.24 |
| 63 | 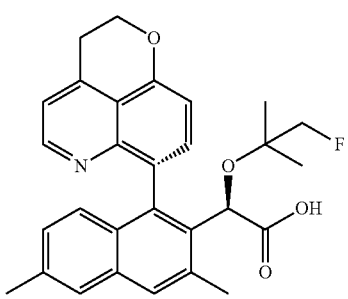 | 473.54 | 474.1 | 6.08 |
| 64 | 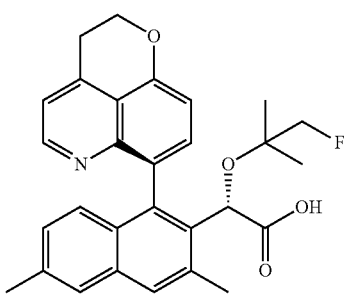 | 473.54 | 474.1 | 6.07 |

-continued
| Example Number | Compound | Parent MW | LC/MS (M + H)+ | HPLC t (min) |
|---|---|---|---|---|
| 65 | 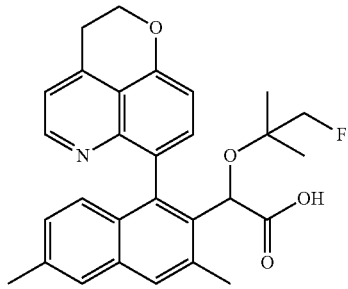 | 473.54 | 474.1 | |
| 66 | 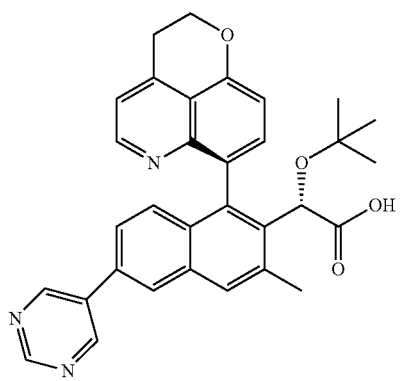 | 519.6 | 520.1 | 5.55 |
| 67 | 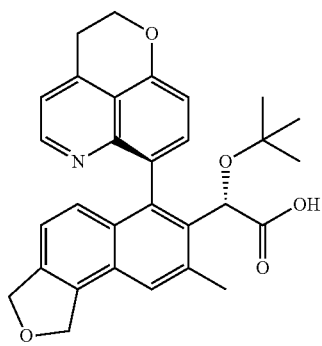 | 483.56 | 484.1 | 5.67 |
| 68 | 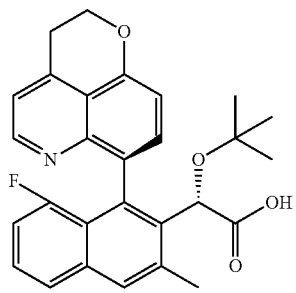 | 459.52 | 460.1 | 5.86 |

-continued

| Example Number | Compound | Parent MW | LC/MS (M + H)+ | HPLC t (min) |
|---|---|---|---|---|
| 69 | | 459.52 | 460.1 | 5.91 |
| 70 | | 505.56 | 506.1 | 6.27 |
| 71 | | 631.78 | 632.3 | 4.99 |
| 72 | | 576.7 | 577.2 | 5.69 |

-continued

| Example Number | Compound | Parent MW | LC/MS (M + H)+ | HPLC t (min) |
|---|---|---|---|---|
| 73 | | 576.7 | 577.2 | 5.66 |
| 74 | | 548.64 | 550.2 | 5.02 |
| 75 | | 548.64 | 549.2 | 5.01 |
| 76 | | 467.52 | 468.1 | 6.14 |

-continued

| Example Number | Compound | Parent MW | LC/MS (M + H)+ | HPLC t (min) |
|---|---|---|---|---|
| 77 | | 467.52 | 468.1 | 5.70 |
| 78 | | 469.54 | 470.2 | 6.03 |
| 79 | | 469.54 | 470.1 | 5.62 |
| 80 | | 533.63 | 534.2 | 5.54 |

-continued
| Example Number | Compound | Parent MW | LC/MS (M + H)+ | HPLC t (min) |
|---|---|---|---|---|
| 81 | 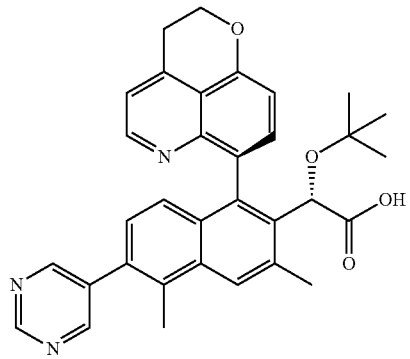 | 533.63 | 534.2 | 5.51 |
| 82 | 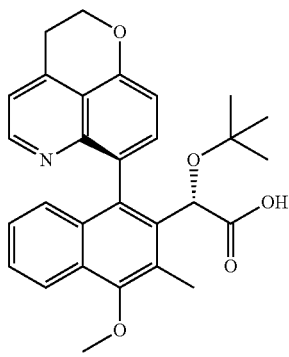 | 471.55 | 472.1 | 5.96 |
| 83 | 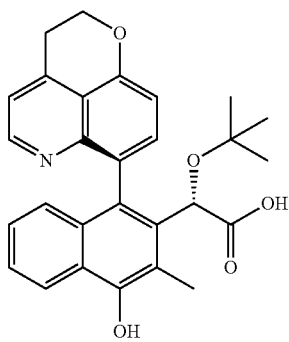 | 457.53 | 458.1 | 5.58 |
| 84 | 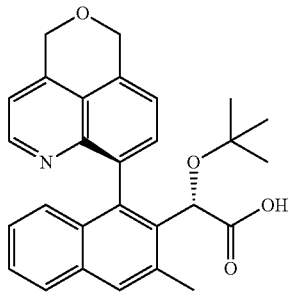 | 441.53 | 442.1 | 5.64 |

-continued

| Example Number | Compound | Parent MW | LC/MS (M + H)+ | HPLC t (min) |
|---|---|---|---|---|
| 85 | | 441.53 | 442.1 | 5.70 |
| 86 | | 491.53 | 492.1 | 6.21 |
| 87 | | 491.53 | 492.1 | 6.03 |
| 88 | | 589.14 | 590.1 | 9.34 |

-continued

| Example Number | Compound | Parent MW | LC/MS (M + H)+ | HPLC t (min) |
|---|---|---|---|---|
| 89 | | 498.58 | 499.3 | 5.18 |
| 90 | | 467.52 | 468.3 | 5.40 |
| 91 | | 456.54 | 457.3 | 5.63 |
| 92 | | 486.52 | 487.2 | 5.99 |

| Example Number | Compound | Parent MW | LC/MS (M + H)+ | HPLC t (min) |
|---|---|---|---|---|
| 93 | | 456.54 | 457.3 | 5.43 |
| 94 | | 486.52 | 487.1 | 6.20 |
| 95 | | 562.68 | 563.1 | 5.47 |
| 96 | | 473.54 | 474.2 | 5.96 |
| 97 | | 473.54 | 474.1 | 5.86 |

| Example Number | Compound | Parent MW | LC/MS (M + H)+ | HPLC t (min) |
|---|---|---|---|---|
| 98 | | 475.97 | 476.2 | 6.11 |
| 99 | | 475.97 | 476.1 | 6.11 |
| 100 | | 475.97 | 476.1 | 6.06 |
| 101 | | 459.52 | 460.1 | 5.78 |
| 102 | | 459.52 | 460.1 | 5.78 |

| Example Number | Compound | Parent MW | LC/MS (M + H)+ | HPLC t (min) |
|---|---|---|---|---|
| 103 | | 459.52 | 460.1 | 5.76 |
| 104 | | 477.51 | 478.1 | 5.77 |
| 105 | | 477.51 | 478.2 | 5.77 |
| 106 | | 477.51 | 478.1 | 5.77 |
EXAMPLE 107
Synthetic method for the preparation of (S)-2-tert-butoxy-2-((R)-1-(2,3-dihydropyrano[4,3,2-de]quinolin-7-yl)-3,6-dimethylnaphthalen-2-yl)acetic acid
One embodiment provides methods and intermediates to prepare (S)-2-tert-butoxy-2-((R)-1-(2,3-dihydropyrano[4,3,2-de]quinolin-7-yl)-3,6-dimethylnaphthalen-2-yl)acetic acid as described hereinbelow.
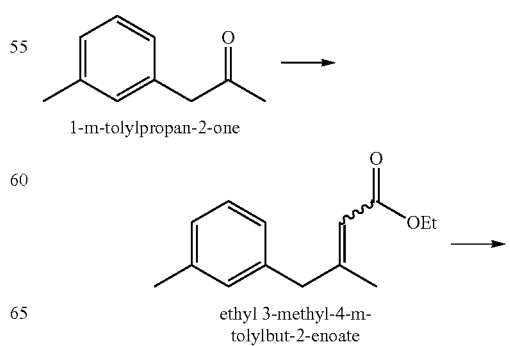

375
-continued

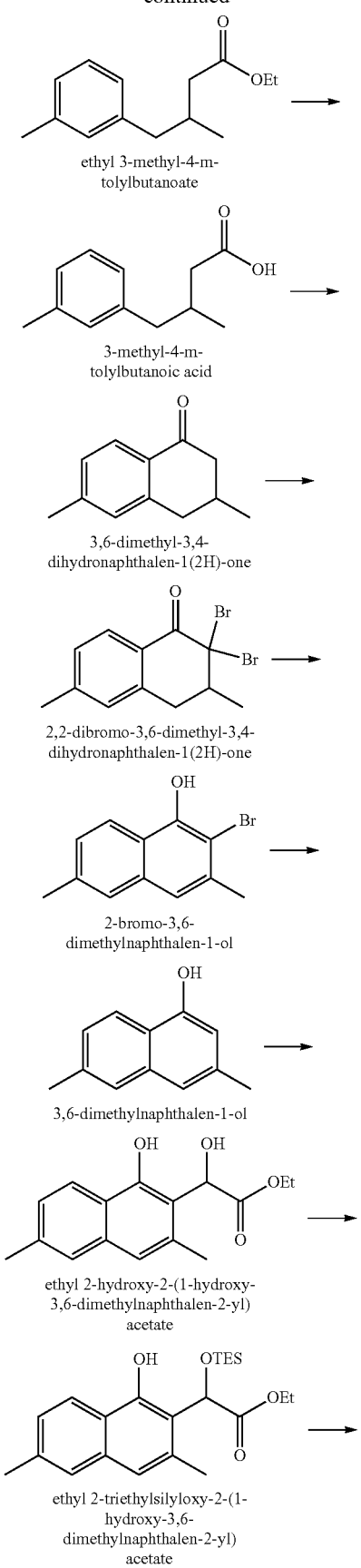

ethyl 3-methyl-4-m-tolylbutanoate 3-methyl-4-m-tolylbutanoic acid 3,6-dimethyl-3,4-dihydronaphthalen-1(2H)-one 2,2-dibromo-3,6-dimethyl-3,4-dihydronaphthalen-1(2H)-one 2-bromo-3,6-dimethylnaphthalen-1-ol 3,6-dimethylnaphthalen-1-ol ethyl 2-hydroxy-2-(1-hydroxy-3,6-dimethylnaphthalen-2-yl)acetate ethyl 2-triethylsilyloxy-2-(1-hydroxy-3,6-dimethylnaphthalen-2-yl)acetate 376
-continued

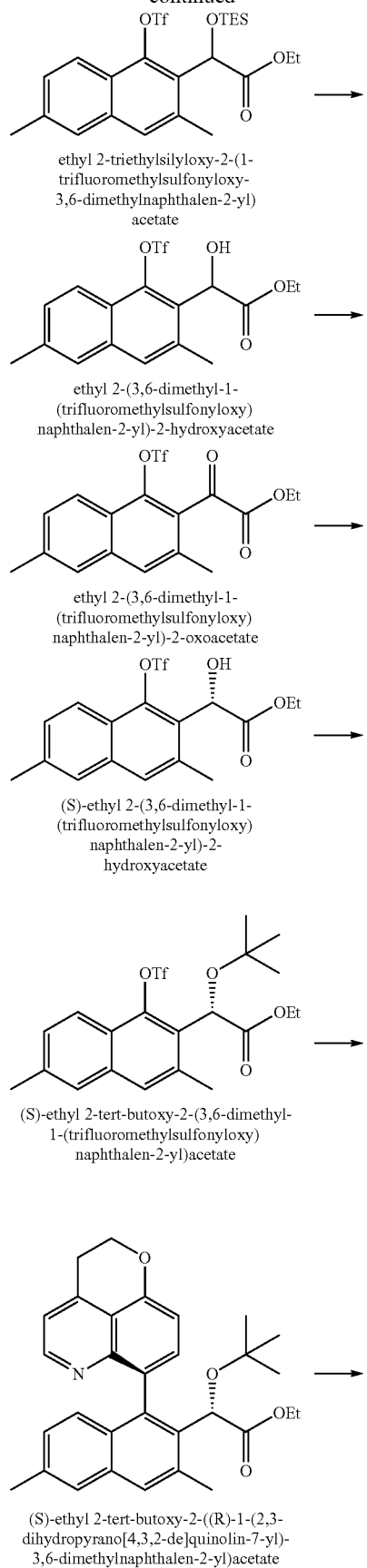

ethyl 2-triethylsilyloxy-2-(1-trifluoromethylsulfonyloxy-3,6-dimethylnaphthalen-2-yl)acetate ethyl 2-(3,6-dimethyl-1-(trifluoromethylsulfonyloxy)naphthalen-2-yl)-2-hydroxyacetate ethyl 2-(3,6-dimethyl-1-(trifluoromethylsulfonyloxy)naphthalen-2-yl)-2-oxoacetate (S)-ethyl 2-(3,6-dimethyl-1-(trifluoromethylsulfonyloxy)naphthalen-2-yl)-2-hydroxyacetate (S)-ethyl 2-tert-butoxy-2-(3,6-dimethyl-1-(trifluoromethylsulfonyloxy)naphthalen-2-yl)acetate (S)-ethyl 2-tert-butoxy-2-((R)-1-(2,3-dihydropyrano[4,3,2-de]quinolin-7-yl)-3,6-dimethylnaphthalen-2-yl)acetate -continued

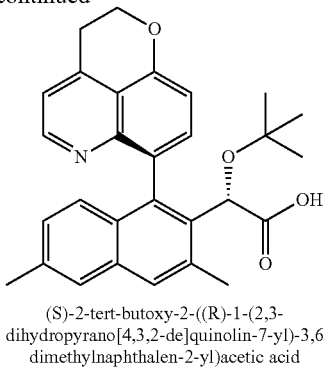

(S)-2-tert-butoxy-2-((R)-1-(2,3-dihydropyrano[4,3,2-de]quinolin-7-yl)-3,6-dimethylnaphthalen-2-yl)acetic acid Preparation of ethyl 3-methyl-4-m-tolylbut-2-enoate. A three neck flask was charged with NaHMDS (1M in THF, 59 mL, 59 mmol) under an atmosphere of Ar and cooled to an internal temperature of 0° C. Triethyl phosphonoacetate (10.1 mL, 50.6 mmol) was diluted in THF (41 mL) and added via additional funnel at a rate to maintain a temperature ≤5° C. The resulting yellow-orange solution was allowed to stir for 15 minutes at 0° C. following completion of addition. Following addition of 1-m-tolylpropan-2-one (5 g, 33.7 mmol, diluted in 50 mL THF) via addition funnel, the resulting mixture was allowed to stir at 0° C. for 60 minutes before removing cooling and allowing the reaction to warm to room temperature over 1.5 hours. The reaction was slowly quenched with water, and the resulting aqueous phase extracted thoroughly with EtOAc. The combined organics were washed with brine, dried over anhydrous $MgSO_4$, filtered and concentrated in vacuo. The resulting oil was eluted on Yamazen silica gel chromatography (0-15% EtOAc/hex) to afford an approximately 85:15 E:Z mixture. LCMS-ESI⁺ (m/z): [M+H]⁺ calcd for $C_{14}H_{19}O_2$: 219.3. found: 219.3.

Preparation of ethyl 3-methyl-4-m-tolylbutanoate. Ethyl 3-methyl-4-m-tolylbutanoate (50 g, 229 mmol) was taken up in EtOAc (1 L) and treated with Rh (5% on alumina, 24 g catalyst). The atmosphere was replaced with $H_2$ and the reaction left under balloon pressure of $H_2$ overnight with vigorous stirring. The next morning, the $H_2$ atmosphere was replaced with air and Celite (25 g) was added with stirring. After 10 min, the reaction slurry was filtered through a pad of Celite and the filtrate concentrated to the desired compound that was used in the next step without further purification. LCMS-ESI⁺ (m/z): [M+H]⁺ calcd for $C_{14}H_{21}O_2$: 221.3. found: 221.2.

Preparation of 3-methyl-4-m-tolylbutanoic acid. The material from the previous preparation was taken up in a 1/1 mixture of THF/EtOH (250 mL each), treated with a solution of $LiOH \cdot H_2O$ (46.5 g, 1.1 mol) in water (250 mL) and heated to 50° C. After 2.5 hours, the solution was cooled to 0° C., diluted with EtOAc (300 mL) and treated with 2M HCl (300 mL). The solution was further adjusted to pH~3 using aliquots of concentrated HCl. The resulting aqueous layer was extracted with EtOAc. The combined organics were washed with brine and allowed to stand over anhydrous $Na_2SO_4$ for 72 hours. The EtOAc was removed in vacuo and the resulting oil taken up in hexanes and allowed to stand over anhydrous $Na_2SO_4$ overnight. Following concentration, the material was taken up in $CHCl_3$ and concentrated again to afford 3-methyl-4-m-tolylbutanoic acid. ¹H-NMR: 400 MHz, ($CDCl_3$) δ: 7.18 (t, J=8 Hz, 1H); 7.02 (d, J=8 Hz, 1H); 6.99 (s, 1H); 6.97 (d, J=8 Hz, 1H); 2.61 (dd, J=13.6, 6.8 Hz, 1H); 2.50 (dd, J=14, 7 Hz, 1H); 2.40 (dd, J=14.8, 5.6 Hz, (1H); 2.34 (s, 3H); 2.28 (m, 1H); 2.18 (dd, J=16, 8 Hz, 1H); 0.99 (d, J=6.4 Hz, 3H).

Preparation of 3,6-dimethyl-3,4-dihydronaphthalen-1 (2H)-one. 3-Methyl-4-m-tolylbutanoic acid (20.6 g, 107 mmol) was added slowly to triflic acid (250 g, 1.7 mol) that was pre-cooled to 0° C. under an Ar atmosphere. After 30 minutes, the volume of the reaction is doubled with DCM and poured slowly onto 1.5 L crushed ice. The resulting icy slurry is allowed to stir and come to room temperature over 1 hour. The resulting aqueous layer was extracted with DCM and the combined organics dried over anhydrous $MgSO_4$, filtered and concentrated in vacuo. The procedure was repeated once and the two lots of crude product were combined and purified via elution on Isco silica gel column chromatography (0-15% EtOAc/hex) to afford 3,6-dimethyl-3,4-dihydronaphthalen-1(2H)-one. LCMS-ESI⁺ (m/z): [M+H]⁺ calcd for $C_{12}H_{15}O$: 175.3. found: 175.4.

Preparation of 2,2-dibromo-3,6-dimethyl-3,4-dihydronaphthalen-1(2H)-one. 3,6-Dimethyl-3,4-dihydronaphthalen-1(2H)-one (32.4 g, 186 mmol) was taken up in DCM (1.5 L and treated with a solution of $Br_2$ (19.1 mL, 372 mmol) in DCM (300 mL) that was added via an addition funnel at room temperature over 2 hours. An additional 1.5 mL of $Br_2$ was added and the reaction allowed to age another 1.5 hours. The reaction was concentrated in vacuo to produce 2,2-dibromo-3,6-dimethyl-3,4-dihydronaphthalen-1(2H)- that was used directly in the next procedure without further purification. LCMS-ESI⁺ (m/z): [M+H]⁺ calcd for $C_{12}H_{13}Br_2O$: 333.1. found: 333.2.

Preparation of 2-bromo-3,6-dimethylnaphthalen-1-ol. A solution of 2,2-dibromo-3,6-dimethyl-3,4-dihydronaphthalen-1(2H)-one (61.2 g, 184 mmol) in MeCN (1.5 L) was cooled to –40° C. internal temperature using a dry ice/acetone bath. 1,8-Diazabicycloundec-7-ene (41.6 mL, 279 mmol) was added as a solution in MeCN (150 mL) and the reaction was allowed to warm to room temperature overnight. The majority of the reaction solvent was removed in vacuo and the residue taken up in EtOAc (1 L) and washed with 0.5 M HCl (1 L). The resulting aqueous layer was extracted with several portions of EtOAc and the combined organics were washed with brine. Following drying over anhydrous $MgSO_4$ and concentration in vacuo, the resulting residue was absorbed directly onto 200 g silica gel and eluted on Isco silica gel column chromatography (0-20% EtOAc/hex) to afford 2-bromo-3,6-dimethylnaphthalen-1-ol. LCMS-ESI⁺ (m/z): [M]⁺ calcd for $C_{12}H_{11}BrO$: 251.1. found: 251.4.

Preparation of 3,6-dimethylnaphthalen-1-ol. A solution of 2-bromo-3,6-dimethylnaphthalen-1-ol (31.9 g, 127 mmol) in EtOH (1.3 L) was treated with $Et_3N$ (26.6 mL, 191 mmol) at room temperature. Pd/C (13.5 g, 12.7 mmol, 10% wt on C) was added in one portion and the atmosphere replaced with $H_2$. The reaction was left under balloon pressure of $H_2$ for 6 hours. After replacing the atmosphere with air, Celite (20 g) was added and the slurry stirred for 15 minutes before filtering the solution through a pad of Celite. The volatiles were removed in vacuo, and the residue was taken up in EtOAc/water (250 mL each). The organics were washed with brine, dried over anhydrous $MgSO_4$, filtered and concentrated in vacuo. The resulting residue was purified on Isco silica gel column chromatography (0-35% EtOAc/hex) to afford 3,6-dimethylnaphthalen-1-ol. LCMS-ESI⁺ (m/z): [M+H]⁺ calcd for $C_{12}H_{13}O$: 173.1. found: 173.4.

Preparation of ethyl 2-hydroxy-2-(1-hydroxy-3,6-dimethylnaphthalen-2-yl)acetate. A solution of 3,6-dimethylnaphthalen-1-ol (4.76 g, 27.6 mmol) in DCM (345 mL) was cooled to 0° C. internal temperature. $TiCl_4$ (1M in DCM, 36 mL, 36 mmol) was added at a rate to maintain the internal temperature at 0° C. to produce a dark purple solution that was allowed to stir at 0° C. for 20 min. Freshly distilled ethyl glyoxylate (3.66 g, 35.9 mmol) was gently warmed with a heat gun for 3 minutes prior to dilution in DCM (250 mL). The reagent solution was then added via addition funnel slowly. After 90 minutes, the reaction was poured onto 800 mL ice/500 mL saturated Rochelle's salt solution. The opaque orange slurry was allowed to come to room temperature over 2.5 hours and filtered through a Celite pad. The aqueous phase was extracted with DCM and the combined organics were washed with water, brine, and dried over anhydrous $MgSO_4$ and filtered. Following concentration in vacuo, the resulting residue was purified via Yamazen silica gel column chromatography (3-35% EtOAc/hex) to provide 2-hydroxy-2-(1-hydroxy-3,6-dimethylnaphthalen-2-yl)acetate. LCMS-ESI$^+$ (m/z): [M-OH]$^+$ calcd for $C_{16}H_{17}O_3$: 257.3. found: 257.5.

Preparation of ethyl 2-triethylsilyloxy-2-(1-hydroxy-3,6-dimethylnaphthalen-2-yl)acetate. A solution of 2-hydroxy-2-(1-hydroxy-3,6-dimethylnaphthalen-2-yl)acetate (4.55 g, 16.6 mmol) in DCM (165 mL) at 0° C. was subsequently treated with imidazole (1.53 g, 22.4 mmol) and triethylsilyl chloride (3.2 mL, 19.1 mmol). The cooling bath was removed and the reaction allowed to warm to room temperature over 1.5 hours. Water was added, and the resulting aqueous layer was extracted with DCM. The combined organics were washed with 1M HCl and brine. Following drying over anhydrous $MgSO_4$, concentration in vacuo afforded the desired compound that was used without further purification.

Preparation of ethyl 2-triethylsilyloxy-2-(1-trifluoromethylsulfonyloxy-3,6-dimethylnaphthalen-2-yl)acetate. A solution of ethyl 2-triethylsilyloxy-2-(1-hydroxy-3,6-dimethyl-naphthalen-2-yl)acetate (5.62 g of crude product from above, 14.5 mmol) in THF (58 mL) was treated with phenyl triflimide (7.75 g, 21.7 mmol) and $Cs_2CO_3$ (11.8 g, 36.3 mmol) at room temperature. After 3 hours, the reaction was diluted with EtOAc and water. The resulting organics were washed with 1M NaOH and brine. Following drying over $MgSO_4$ and concentration in vacuo, the resulting residue was purified via Yamazen silica gel column chromatography (0-10% EtOAc/hex) to afford ethyl 2-triethylsilyloxy-2-(1-trifluoromethylsulfonyloxy-3,6-dimethylnaphthalen-2-yl)acetate. LCMS-ESI$^+$ (m/z): [M+Na]$^+$ calcd for $C_{23}H_{31}F_3O_6SSiNa$: 543.6. found: 543.0.

Preparation of ethyl 2-(3,6-dimethyl-1-(trifluoromethylsulfonyloxy)naphthalen-2-yl)-2-hydroxyacetate. A solution of ethyl 2-triethylsilyloxy-2-(1-trifluoromethylsulfonyl-oxy-3,6-dimethylnaphthalen-2-yl)acetate (~29 g) in THF (375 mL) was treated with 48% HF (71 mL, 1.96 mol) at room temperature and allowed to stir overnight. Solid $NaHCO_3$ was added in small portions until pH~8 by test strip. Water and EtOAc were added, and the layers separated. The aqueous layer was slurried with Celite, filtered through a Celite pad and further extracted with EtOAc. The combined organics were washed with brine, dried over anhydrous $MgSO_4$, filtered and concentrated in vacuo. The resulting ethyl 2-(3,6-dimethyl-1-(trifluoromethylsulfonyloxy)naphthalen-2-yl)-2-hydroxyacetate was used without further purification. LCMS-ESI$^+$ (m/z): [M-OH]$^+$ calcd for $C_{17}H_{16}F_3O_5S$: 389.4. found: 389.4.

Preparation of ethyl 2-(3,6-dimethyl-1-(trifluoromethylsulfonyloxy)naphthalen-2-yl)-2-oxoacetate. A solution of ethyl 2-(3,6-dimethyl-1-(trifluoromethylsulfonyloxy) naphthalen-2-yl)-2-hydroxyacetate (~22.8 g, 56 mmol) in DCM (560 mL) was treated with solid Dess-Martin periodinane (35.7 g, 84.2 mmol) at room temperature. After 60 minutes, isopropyl alcohol (25 mL) was added and allowed to stir for 30 minutes. A mixture of saturated $NaHCO_3$ and saturated $Na_2S_2O_3$ (100 mL each, diluted to 400 mL with water) was added and the resulting aqueous layer extracted with DCM. The combined organics were washed with water, brine and dried over anhydrous $MgSO_4$ and filtered. Following concentration in vacuo, the residue was purified via Isco silica gel column chromatography (0-35% EtOAc/hex) to afford ethyl 2-(3,6-dimethyl-1-(trifluoromethylsulfonyloxy)naphthalen-2-yl)-2-oxoacetate. $^1$H-NMR: 400 MHz, (CDCl$_3$) δ: 7.98 (d, J=8.4 Hz, 1H); 7.66 (s, 1H); 7.61 (s, 1H); 7.47 (d, J=8.4 Hz, 1H); 4.41 (q, J=7.2 Hz, 2H); 2.55 (s, 3H); 2.49 (s, 3H); 1.40 (t, J=8.4 Hz, 3H).

Preparation of (S)-ethyl 2-(3,6-dimethyl-1-(trifluoromethylsulfonyloxy) naphthalen-2-yl)-2-hydroxyacetate. A solution of ethyl 2-(3,6-dimethyl-1-(trifluoromethylsulfonyloxy) naphthalen-2-yl)-2-oxoacetate (16.3 g, 40 mmol) in toluene (250 mL) cooled to an internal temperature of −40° C. was treated with (R)-(+)-2-methyl-CBS-oxazaborolidine (5.6 g, 20.1 mmol). Freshly distilled catecholborane (4.7 mL, 44.2 mmol) was diluted with toluene (20 mL) and the solution added dropwise to the reaction over 30 minutes to produce a clear yellow solution. After an additional 15 minutes, saturated $Na_2CO_3$ (300 mL) was added and the reaction allowed to warm to room temperature over 2.5 hours. The aqueous layer is extracted with EtOAc and the combined organics are washed with saturated $Na_2CO_3$ (3×300 mL), saturated $NH_4Cl$ (300 mL) and brine. Following drying over anhydrous $MgSO_4$ and concentration in vacuo, the residue was purified using Isco silica gel column chromatography (10-75% EtOAc/hex) to produce (S)-ethyl 2-(3,6-dimethyl-1-(trifluoromethylsulfonyloxy)naphthalen-2-yl)-2-hydroxyacetate that was determined to be 66% enantiomeric excess by HPLC analysis on a Chiralpak AS-H column with a 80:20 heptane/EtOH isocratic method. LCMS-ESI$^+$ (m/z): [M+Na]$^+$ calcd for $C_{17}H_{17}F_3O_6SNa$: 429.3. found: 429.3.

Preparation of (S)-ethyl 2-tert-butoxy-2-(3,6-dimethyl-1-(trifluoromethylsulfonyl-oxy)naphthalen-2-yl)acetate. A solution of (S)-ethyl 2-(3,6-dimethyl-1-(trifluoromethyl-sulfonyloxy)naphthalen-2-yl)-2-hydroxyacetate (7.5 g, 18.5 mmol) in tBuOAc (100 mL) at room temperature was treated with perchloric acid (70%, 0.16 mL, 1.8 mmol) and allowed to stir at room temperature overnight. The reaction was slowly poured into ice-cold saturated $NaHCO_3$ (150 mL). The aqueous layer was extracted with EtOAc and the combined organics washed with brine and dried over anhydrous $MgSO_4$ and filtered. Following concentration in vacuo, purification of the residue by Yamazen silica gel column chromatography (2-20-50% EtOAc/hex) afforded (S)-ethyl 2-tert-butoxy-2-(3,6-dimethyl-1-(trifluoromethylsulfonyloxy)naphthalen-2-yl)acetate. LCMS-ESI$^+$ (m/z): [M+Na]$^+$ calcd for $C_{21}H_{25}F_3O_6SNa$: 485.5. found: 485.8.

Preparation of (S)-ethyl 2-tert-butoxy-2-((R)-1-(2,3-dihydropyrano[4,3,2-de]quinolin-7-yl)-3,6-dimethylnaphthalen-2-yl)acetate and (S)-ethyl 2-tert-butoxy-2-((S)-1-(2,3-dihydropyrano[4,3,2-de]quinolin-7-yl)-3,6-dimethylnaphthalen-2-yl)acetate. A solution of (S)-ethyl 2-tert-butoxy-2-(3,6-dimethyl-1-(trifluoromethylsulfonyl-oxy)naphthalen-2-yl) acetate (~0.5 g, 1.1 mmol) in 10.8 mL DME (freshly distilled from Na/benzophenone) was treated with 2,3-dihydropyrano[4,3,2-de]quinolin-7-ylboronic acid hydrochloride (0.33 g, 1.3 mmol), SPhos precatalyst (Strem, 0.073 g, 0.11 mmol), and CsF (0.722 g, 4.8 mmol). The reaction tube was sealed and the reaction mixture sparged with Ar for 30 minutes prior to heating at 120° C. for 90 minutes in a microwave reactor. The reaction mixture was absorbed directly onto silica gel and purified via Yamazen silica gel column chromatography (3-50% EtOAc/hex) to afford (S)-ethyl 2-tert-butoxy-2-((R)-1-(2,3-dihydropyrano[4,3,2-de]quinolin-7-yl)-3,6-dimethyl-naphthalen-2-yl)acetate ($^1$H-NMR: 400 MHz, (CDCl$_3$) δ: 8.68 (br s, 1H); 7.64 (s, 1H); 7.54 (s, 1H); 7.49 (d, J=8 Hz, 1H); 7.11 (d, J=8 Hz, 1H); 7.08 (br s, 1H); 6.99-6.84 (m, 2H); 5.08 (s, 1H); 4.58 (t, J=6 Hz, 2H); 3.98 (m, 1H); 3.82 (m, 1H); 3.34 (m, 2H); 2.78 (s, 3H); 2.42 (s, 3H); 0.97 (s, 9H); 0.97 (obscured t, 3H)) and (S)-ethyl 2-tert-butoxy-2-((S)-1-(2,3-dihydropyrano[4,3,2-de]quinolin-7-yl)-3,6-dimethylnaphthalen-2-yl)acetate ($^1$H-NMR: 400 MHz, (CDCl$_3$) δ: 8.64 (d, J=4 Hz, 1H); 7.73 (d, J=8 Hz, 1H); 7.60 (s, 1H); 7.53 (s, 1H);

7.11 (d, J=8 Hz, 1H); 7.04 (d, J=4 Hz, 1H); 6.93 (dd, J=8, 1.2 Hz, 1H); 6.82 (d, J=8 Hz, 1H); 5.12 (s, 1H); 4.57 (t, J=5.6 Hz, 2H); 4.20-4.04 (m, 2H); 3.33 (m, 2H); 2.65 (s, 3H); 2.42 (s, 3H); 1.22 (t, J=7.2 Hz, 3H); 0.76 (s, 9H)).

Preparation of (S)-2-tert-butoxy-2-((R)-1-(2,3-dihydropyrano[4,3,2-de]quinolin-7-yl)-3,6-dimethylnaphthalen-2-yl) acetic acid. (S)-2-tert-butoxy-2-((R)-1-(2,3-dihydropyrano[4,3,2-de]quinolin-7-yl)-3,6-dimethylnaphthalen-2-yl) acetic acid was prepared in a similar fashion to (S)-2-tert-butoxy-2-((S)-1-(2,3-dihydropyrano[4,3,2-de]quinolin-7-yl)-3,6-dimethylnaphthalen-2-yl)acetic acid of Example 16 substituting (S)-ethyl 2-tert-butoxy-2-((S)-1-(2,3-dihydropyrano[4,3,2-de]quinolin-7-yl)-3,6-dimethylnaphthalen-2-yl) acetate with (S)-ethyl 2-tert-butoxy-2-((R)-1-(2,3-dihydropyrano[4,3,2-de]quinolin-7-yl)-3,6-dimethylnaphthalen-2-yl)acetate (0.90 g, 1.9 mmol) with appropriate adjustments to scale to (S)-2-tert-butoxy-2-((R)-1-(2,3-dihydropyrano[4,3,2-de]quinolin-7-yl)-3,6-dimethylnaphthalen-2-yl)acetic acid (TFA salt). LCMS-ESI$^+$ (m/z): [M+H]$^+$ calcd for $C_{29}H_{30}NO_4$: 456.5. found: 456.5. $^1$H-NMR: 400 MHz, (CD$_3$CN) δ: 8.55 (d, J=5.6 Hz, 1H); 7.85 (s, 1H); 7.79 (d, J=8 Hz, 1H); 7.68 (s, 1H); 7.62 (d, J=5.6 Hz, 1H); 7.37 (d, J=8 Hz, 1H); 7.11 (d, J=9 Hz, 1H); 6.78 (d, J=9 Hz, 1H); 5.15 (s, 1H); 4.69-4.58 (m, 2H); 3.54 (d, J=6 Hz, 2H); 2.67 (s, 3H); 2.45 (s, 3H); 0.93 (s, 9H).

EXAMPLE 108

The following illustrate representative pharmaceutical dosage forms, containing a compound disclosed herein ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All references, including publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

The use of the terms "a" and "an" and "the" and similar references in the context of this disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope of the claims. No language in the specification should be construed as indicating any non-claimed element as essential to the practice of the present disclosure.

Alternative embodiments of the claimed disclosure are described herein, including the best mode known to the inventors for practicing the claimed invention. Of these, variations of the disclosed embodiments will become apparent to those of ordinary skill in the art upon reading the foregoing disclosure. The inventors expect skilled artisans to employ such variations as appropriate (e.g., altering or combining features or embodiments), and the inventors intend for the invention to be practiced otherwise than as specifically described herein.

Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

The use of individual numerical values is stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Thus, recitation of ranges of values herein are merely intended to serve as a shorthand method of referring individually to each separate value falling within the range, unless otherwise indicated herein, and each separate value is incorporated into the specification as if it were individually recited herein.

It is to be understood that any ranges, ratios and ranges of ratios that can be formed by, or derived from, any of the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art most closely related to a particular range, ratio or range of ratios will appreciate that such values are unambiguously derivable from the data presented herein.

What is claimed is:

1. A compound, or a pharmaceutically acceptable salt thereof, selected from the group consisting of:

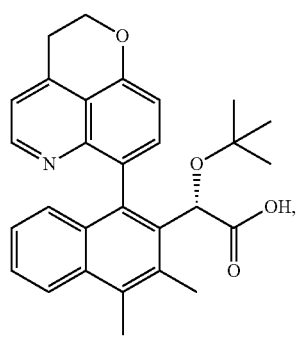

-continued

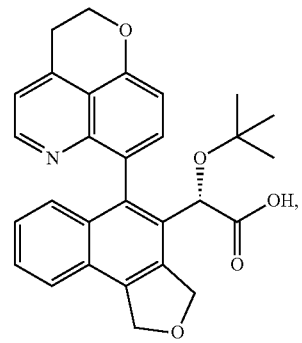

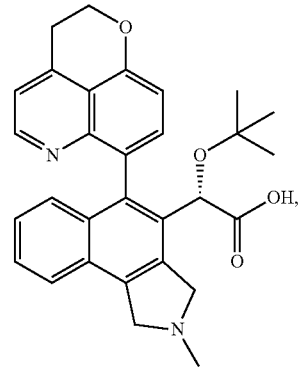

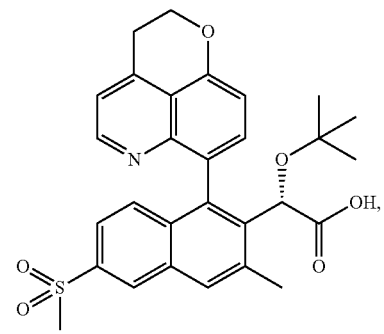

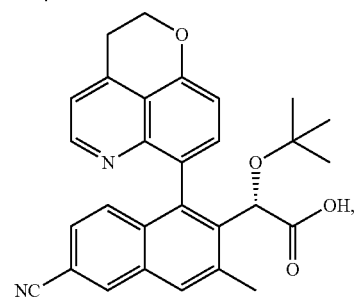

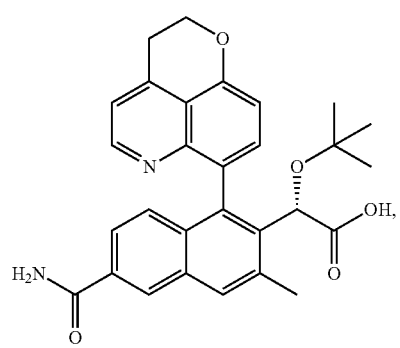

385
-continued
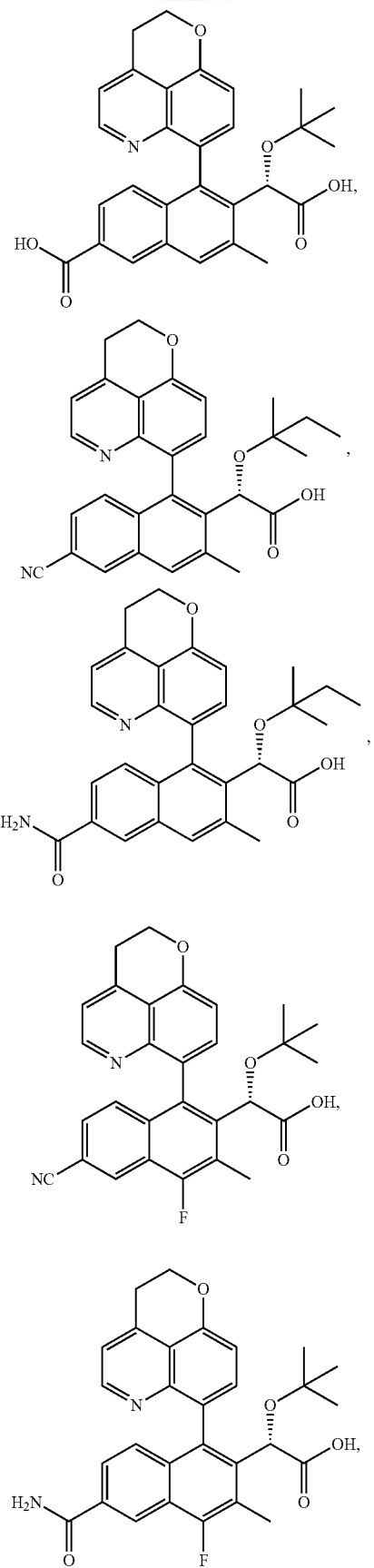
386
-continued
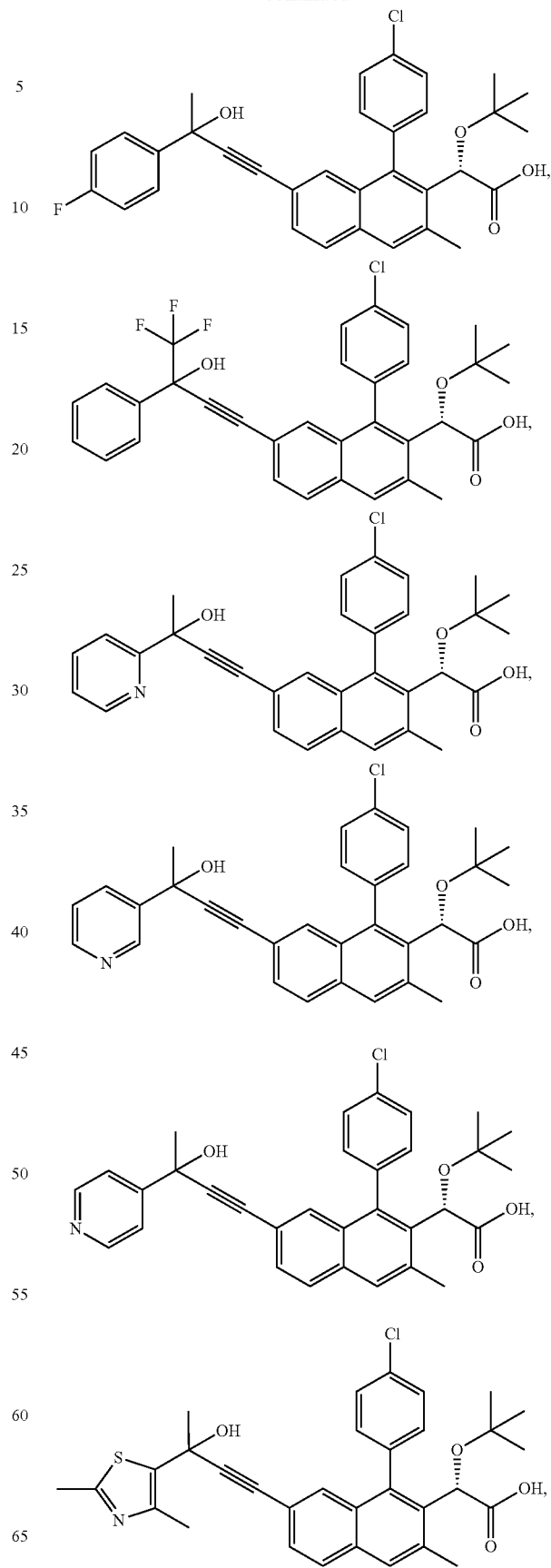

387
-continued
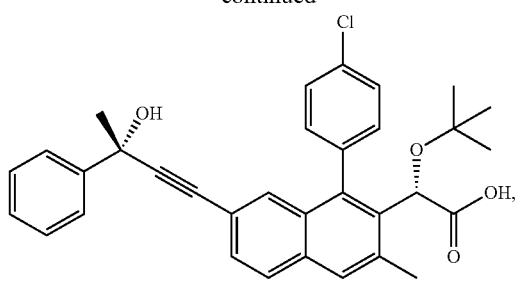
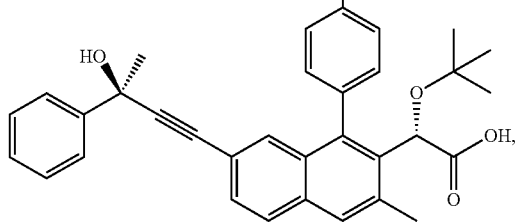
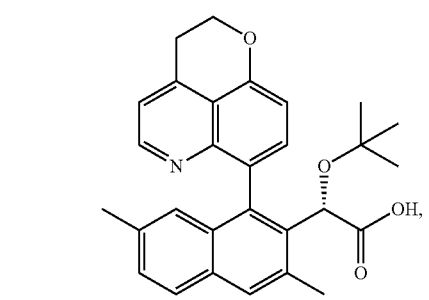
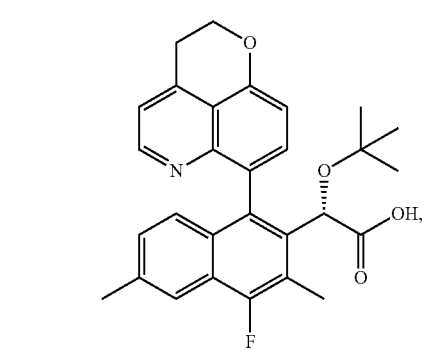
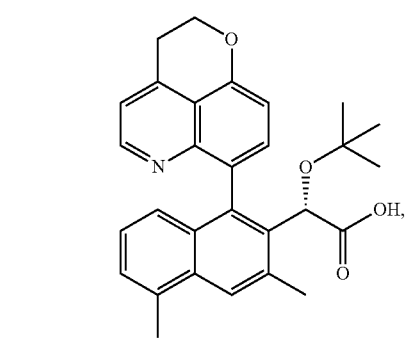
388
-continued
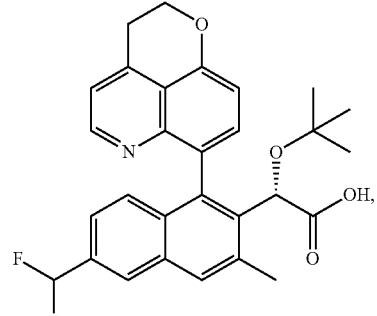
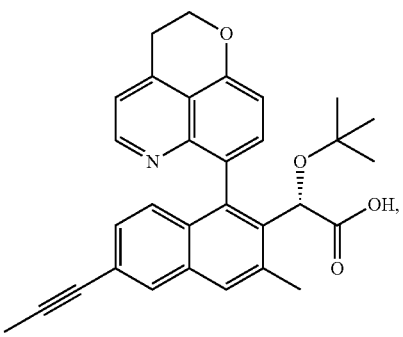
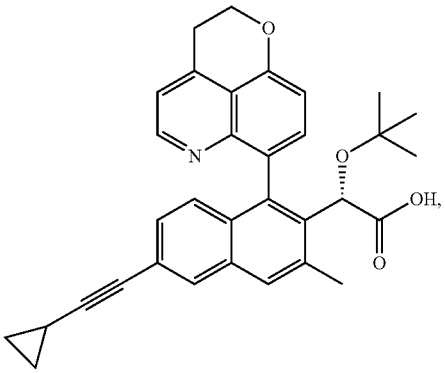
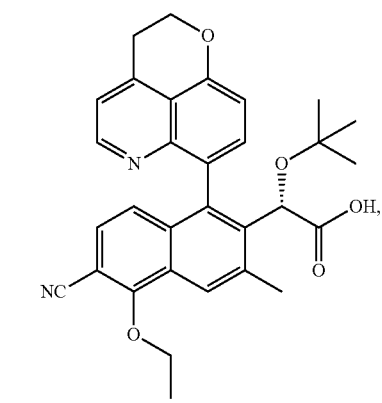

389
-continued
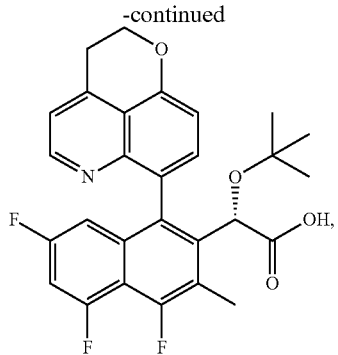
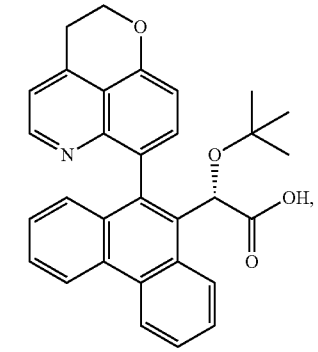
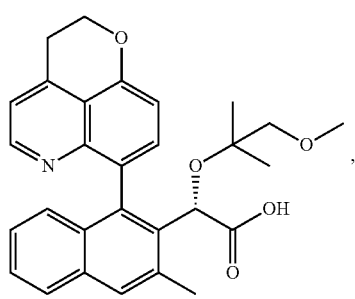
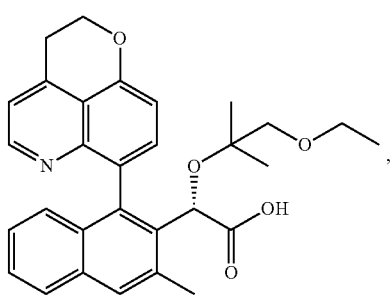
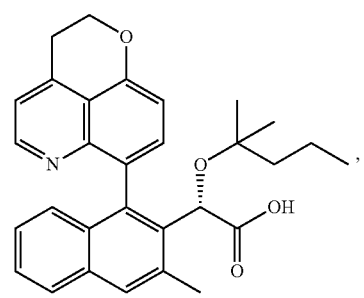
390
-continued
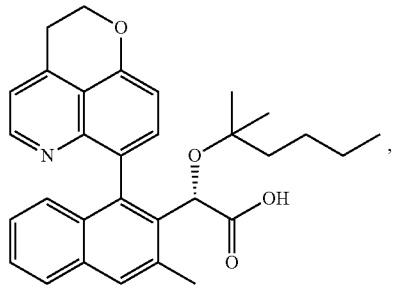
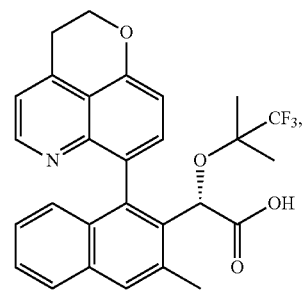
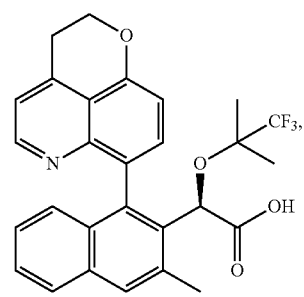
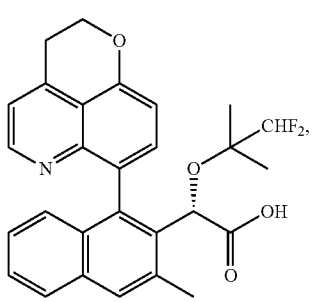
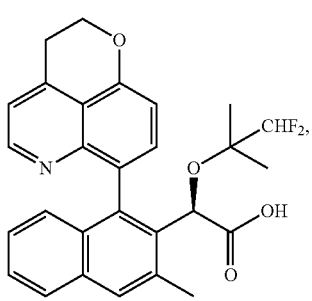

391
-continued
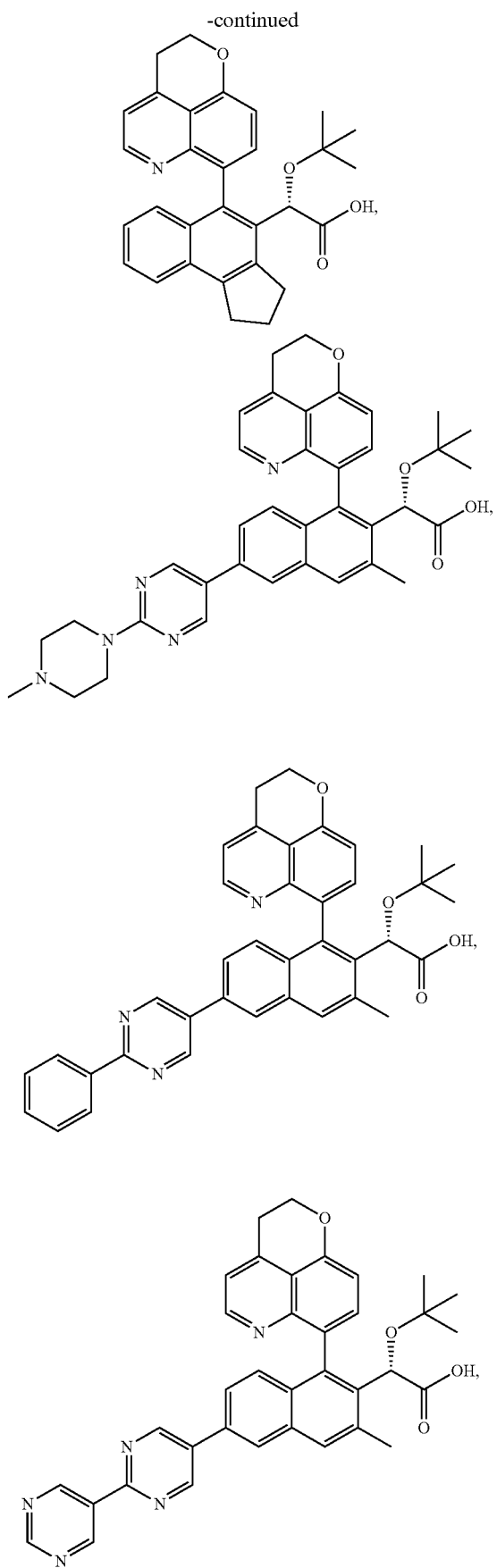
392
-continued
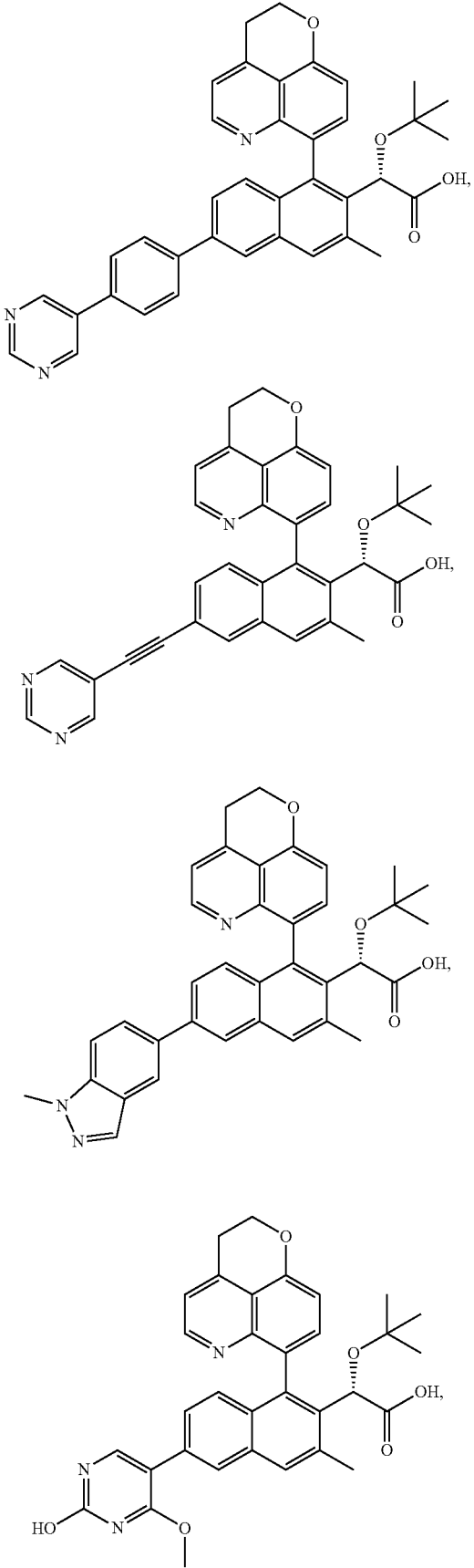

393
-continued
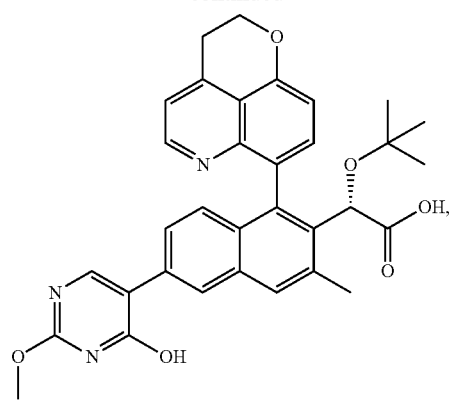
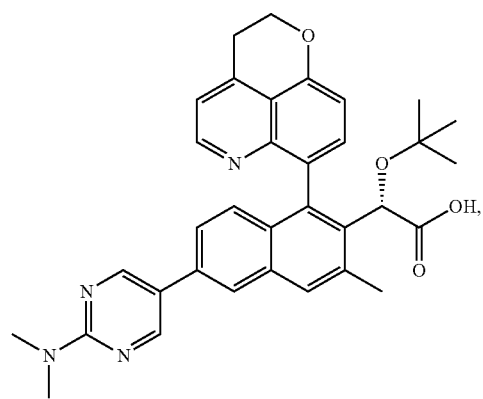
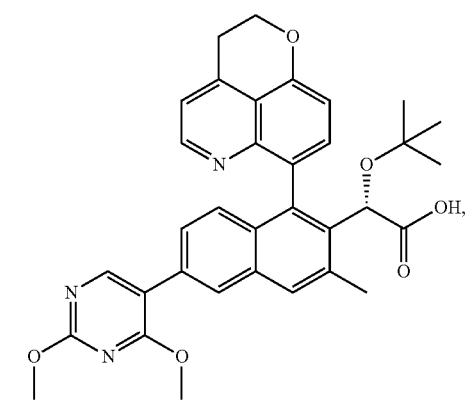
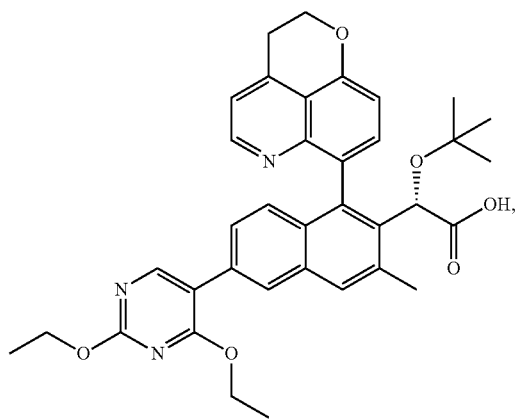
394
-continued
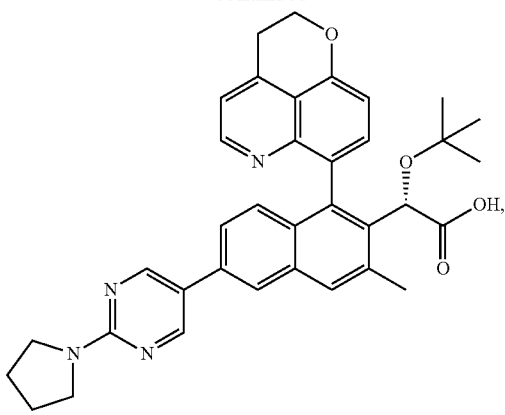
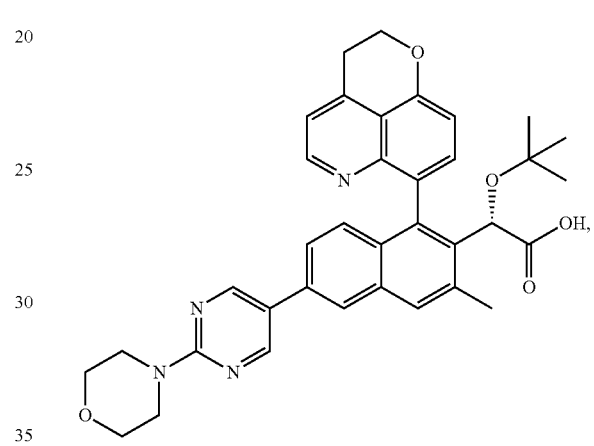
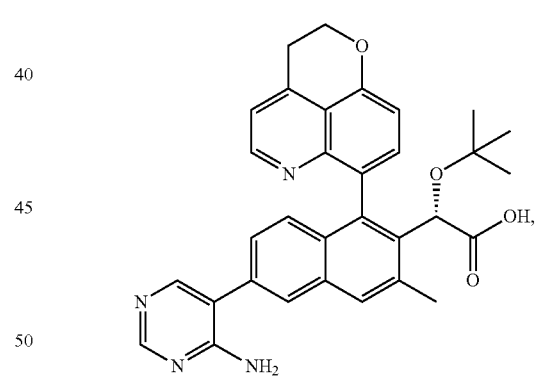
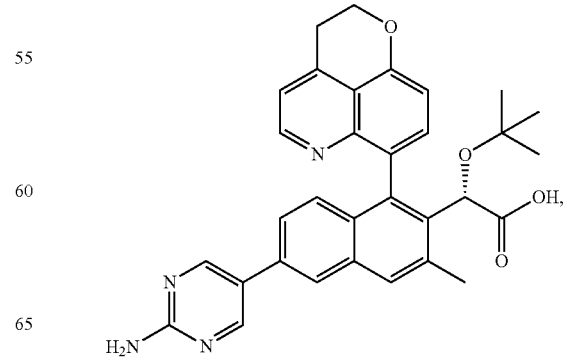

-continued
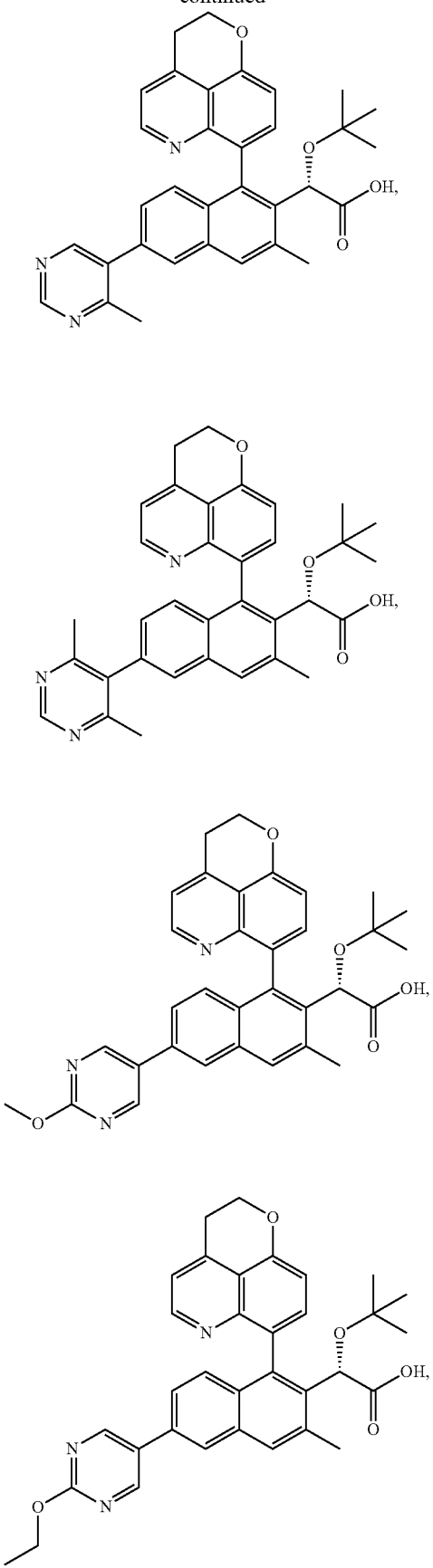
-continued
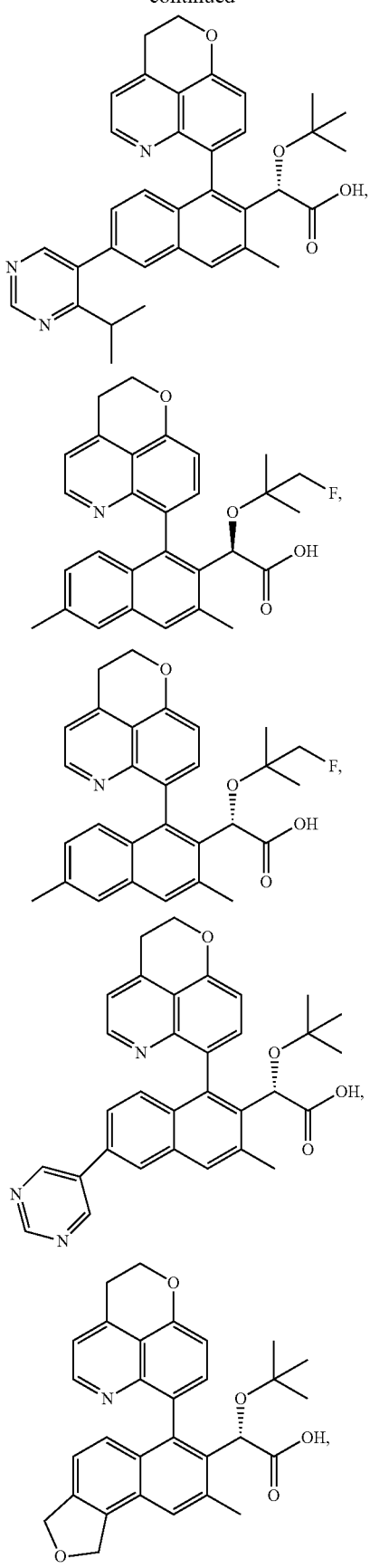

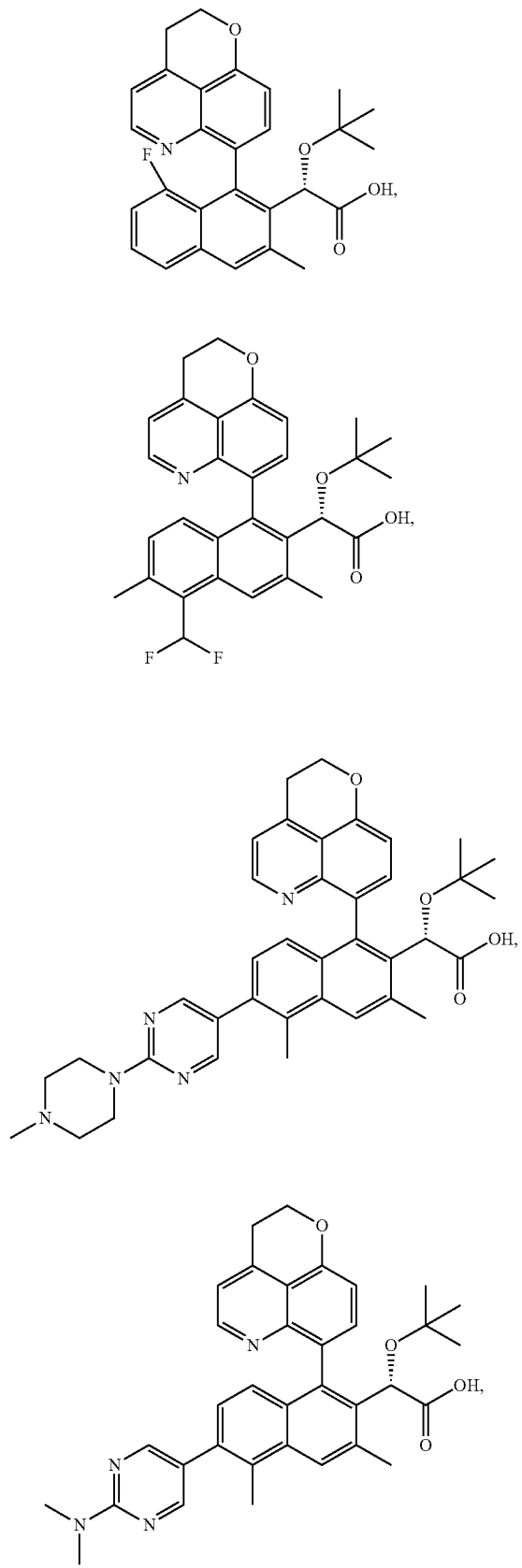
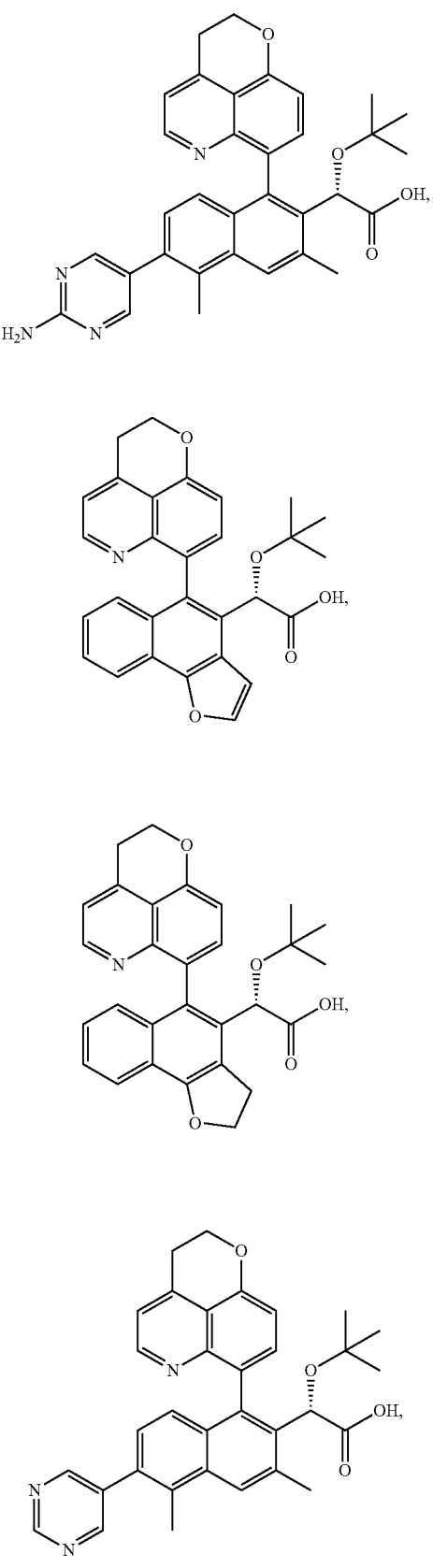

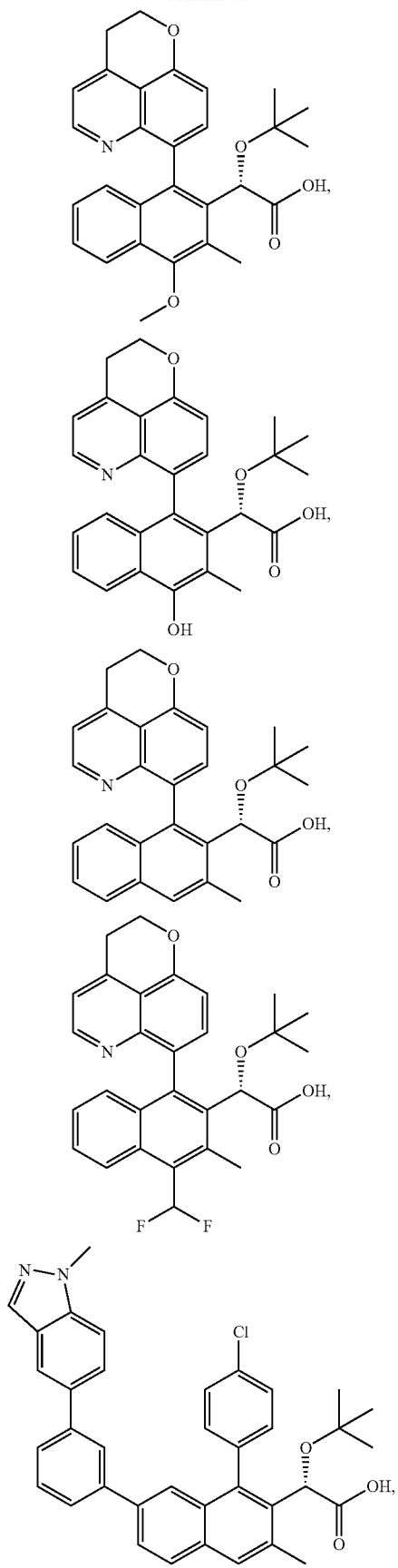
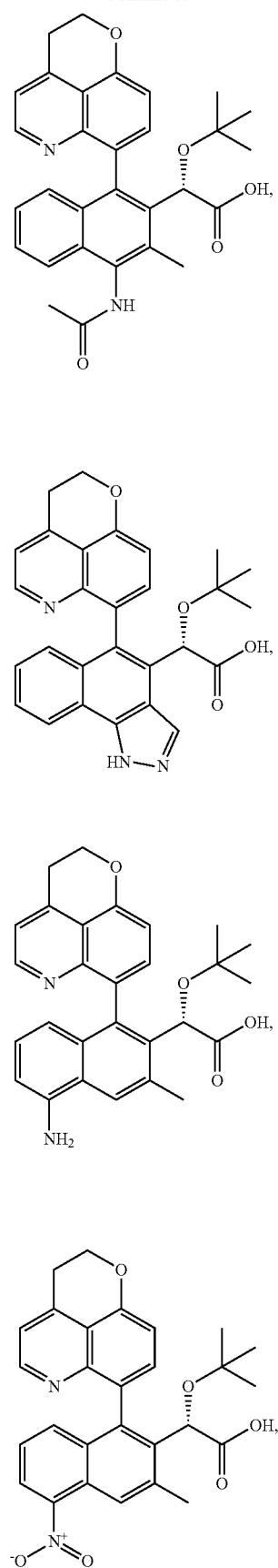

401
-continued
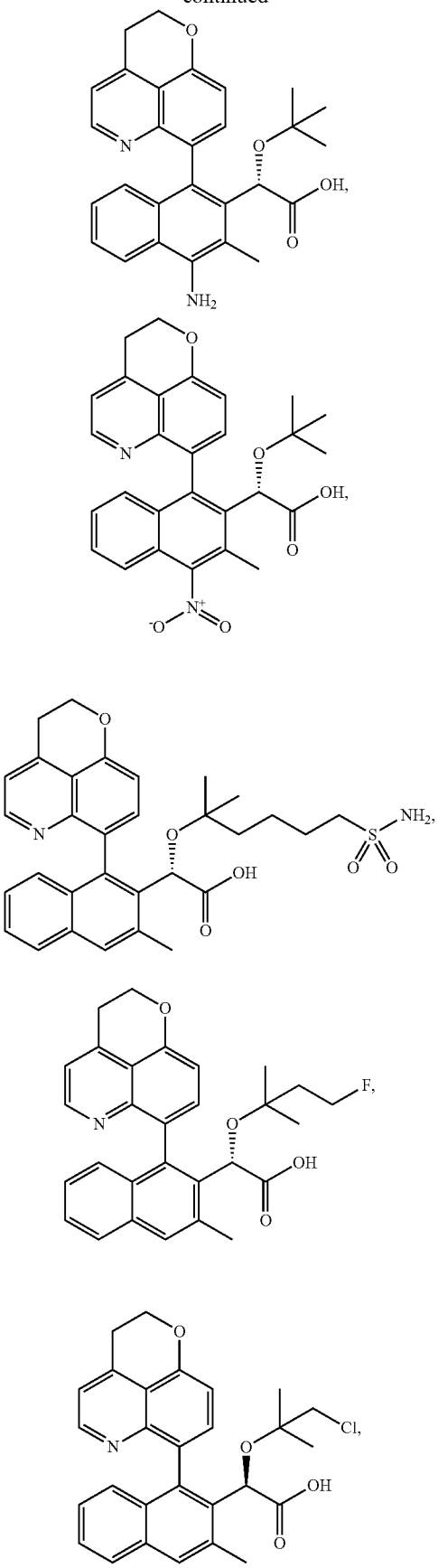
402
-continued
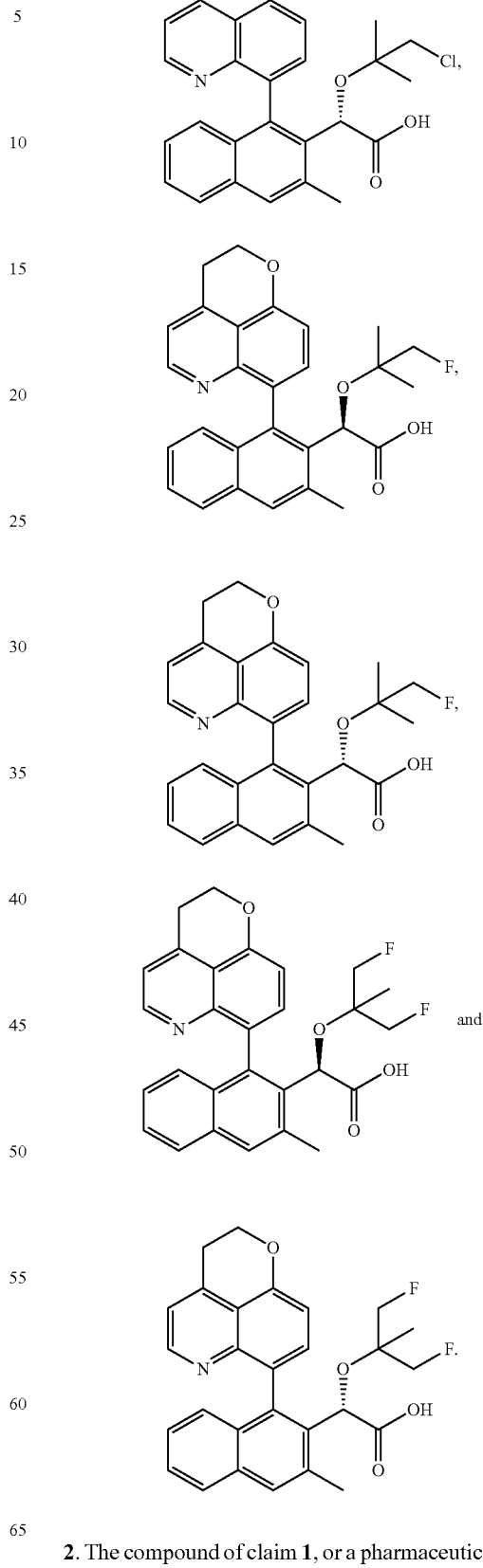
2. The compound of claim 1, or a pharmaceutically acceptable salt thereof, selected from the group consisting of:

403
404
-continued
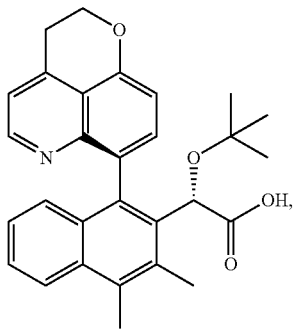
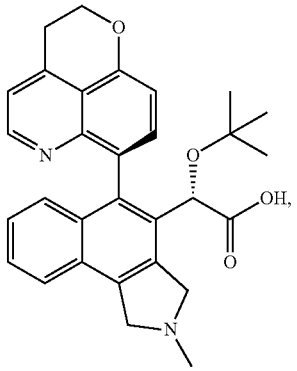

405
-continued
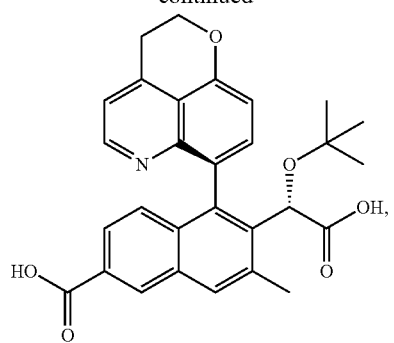
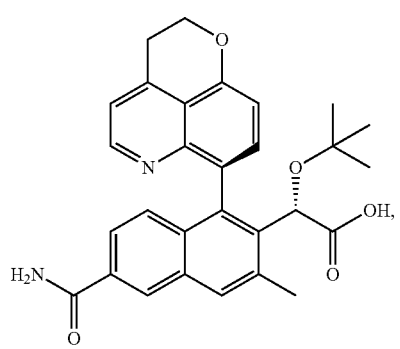
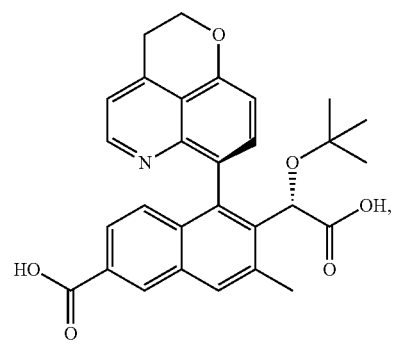
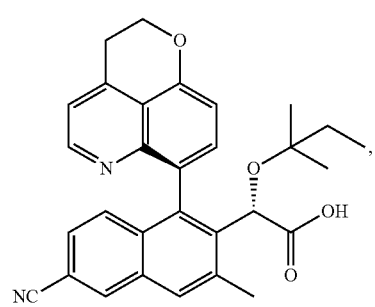
406
-continued
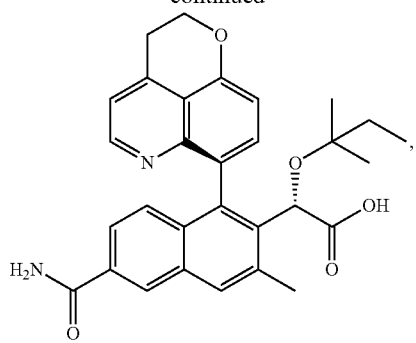
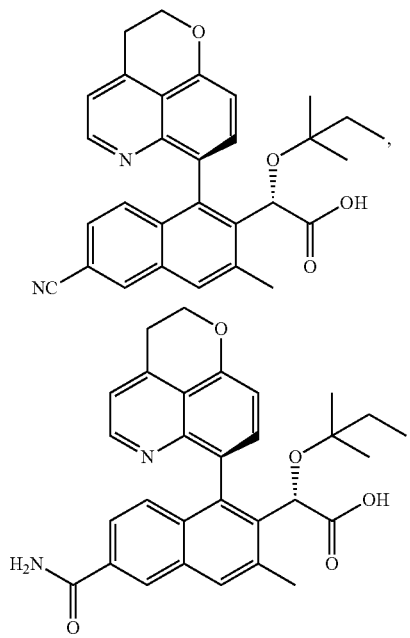
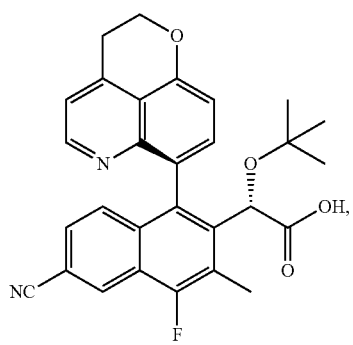
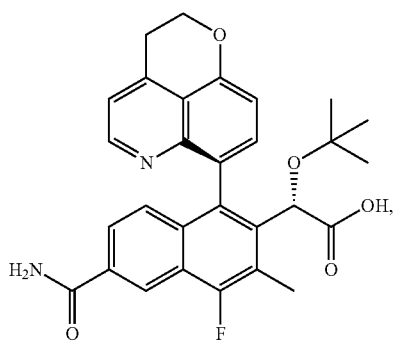

407
-continued
408
-continued
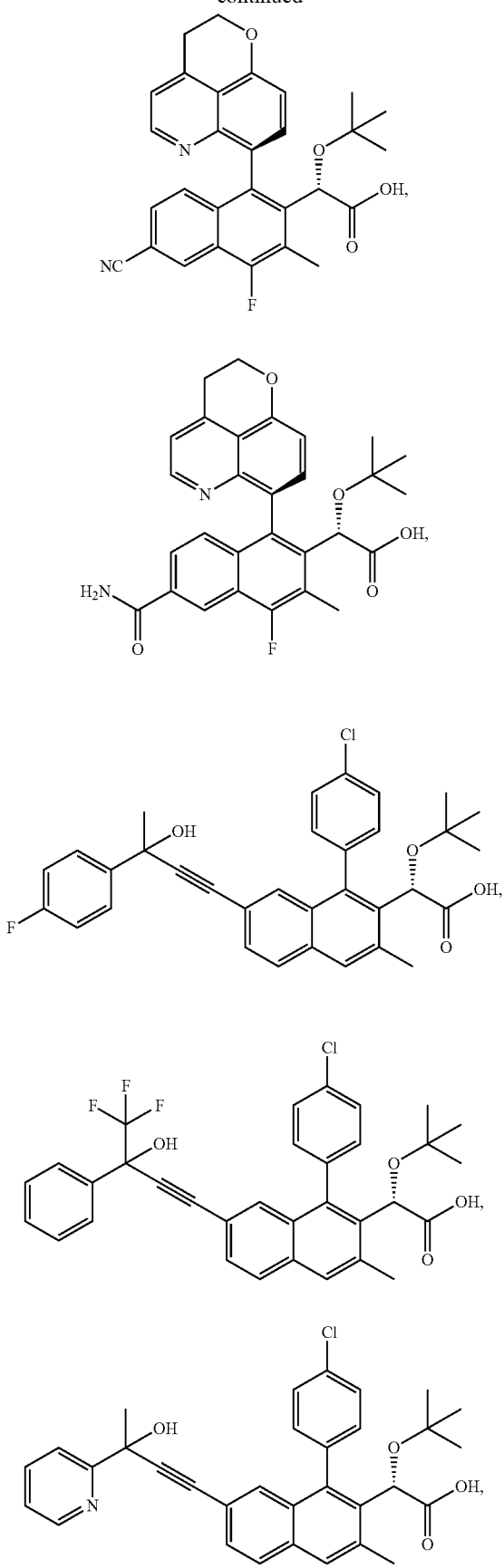
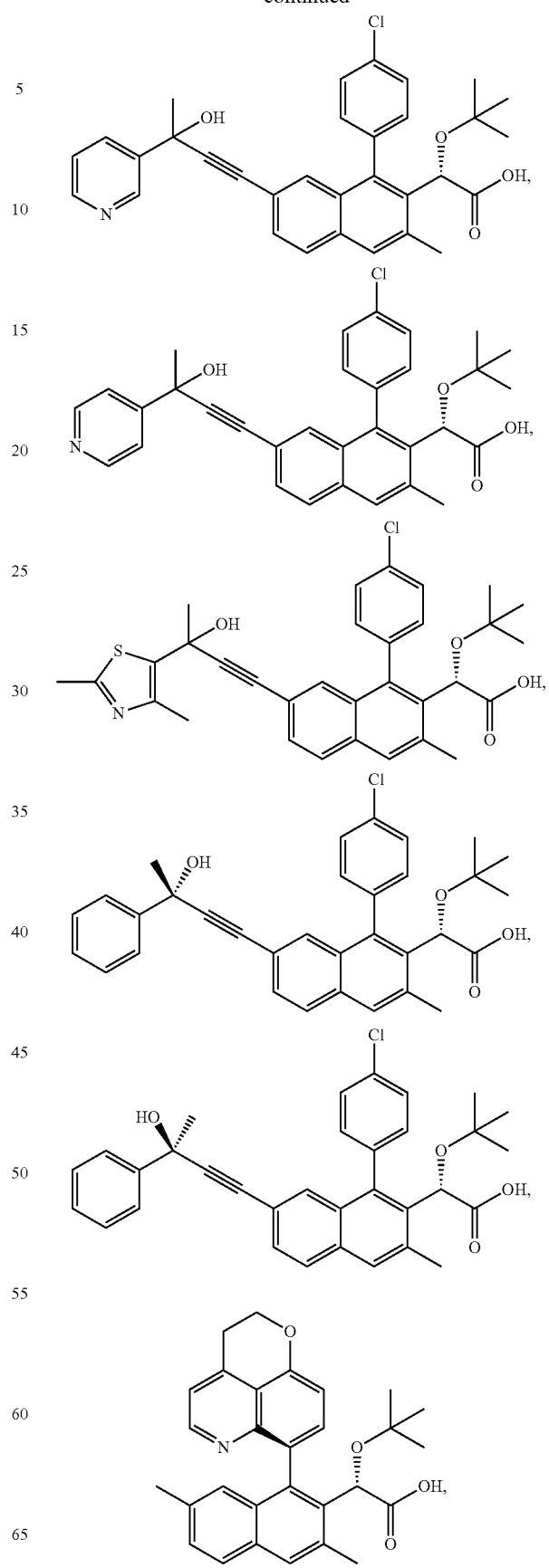

409
-continued
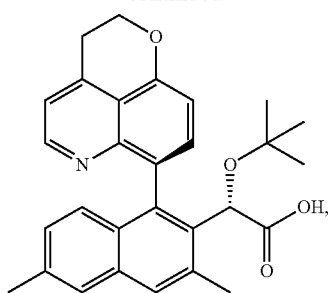
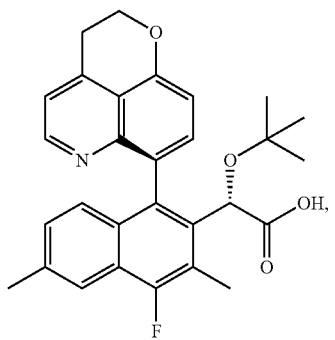
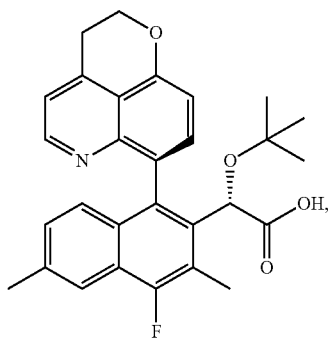
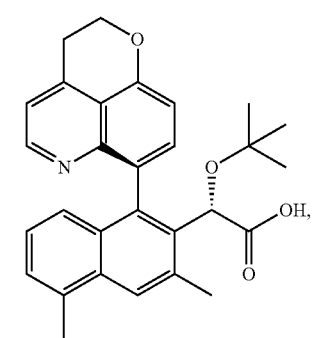
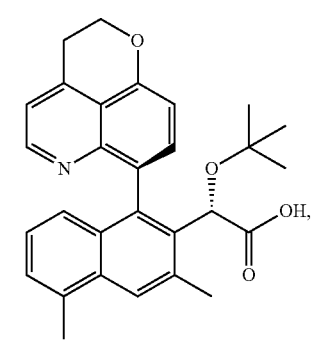
410
-continued
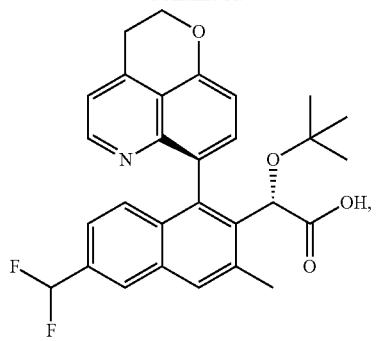
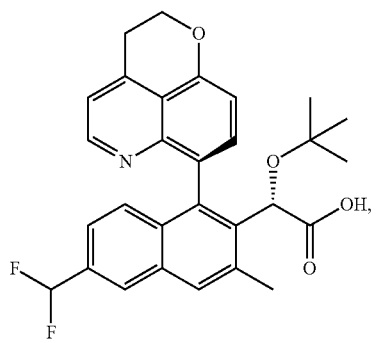
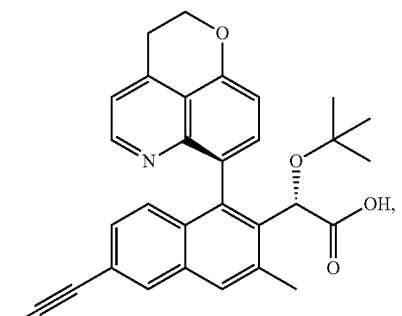
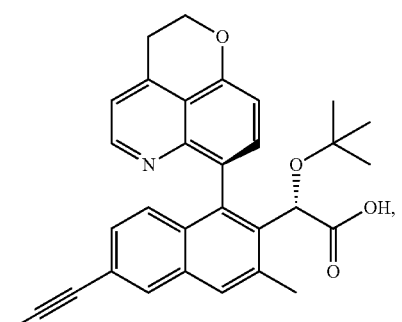
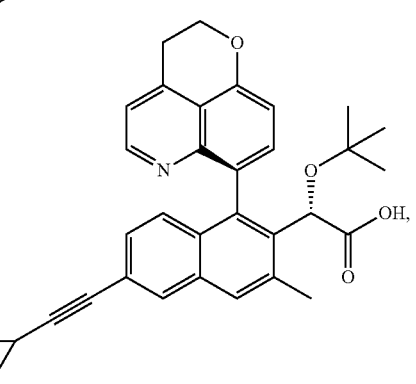

411
-continued
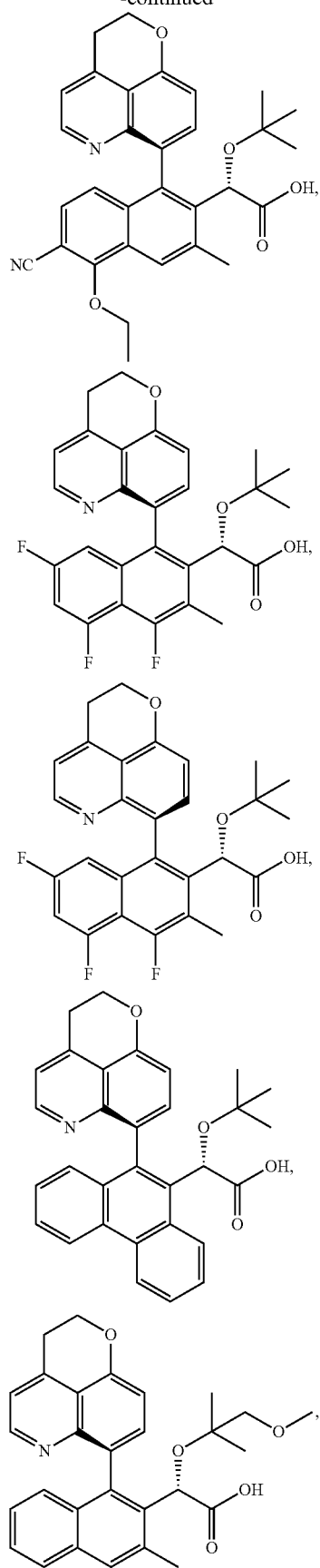
412
-continued
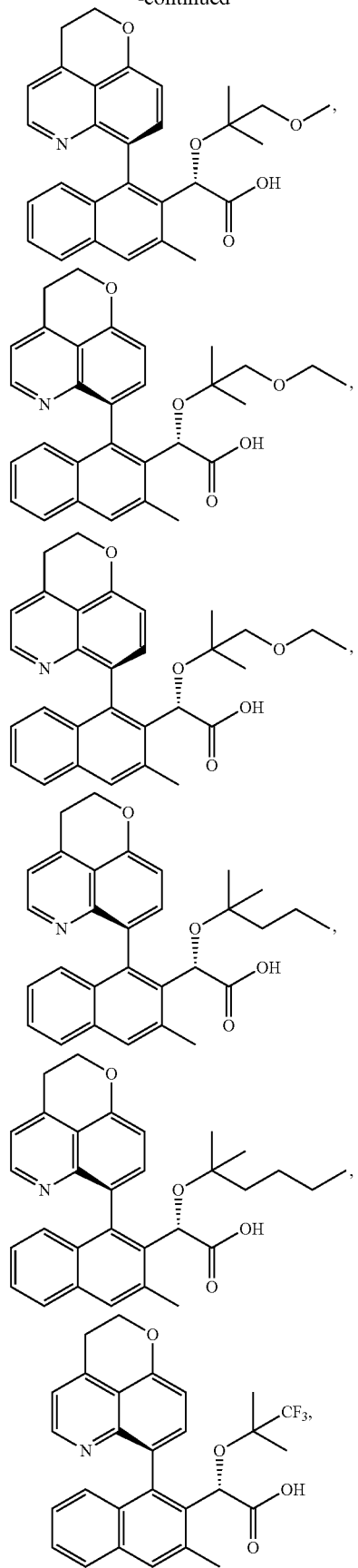

413
-continued
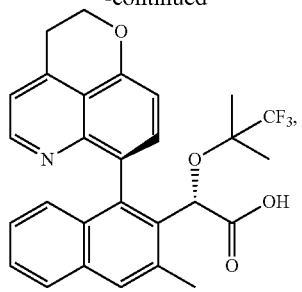
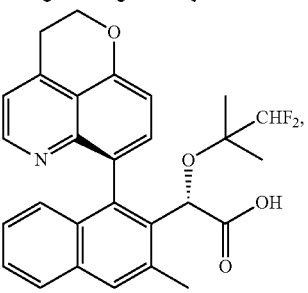
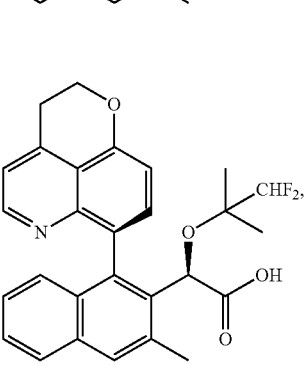
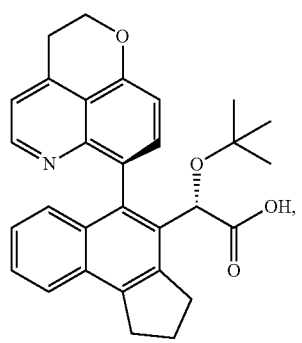
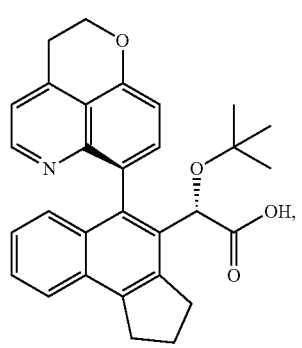
414
-continued
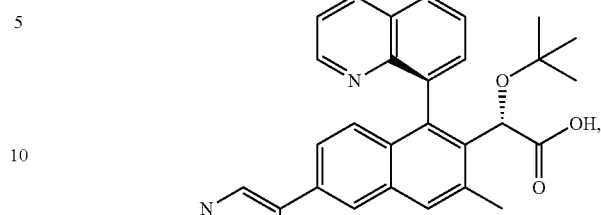
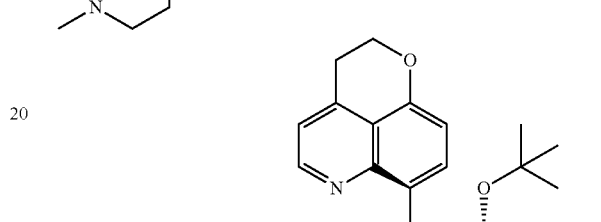
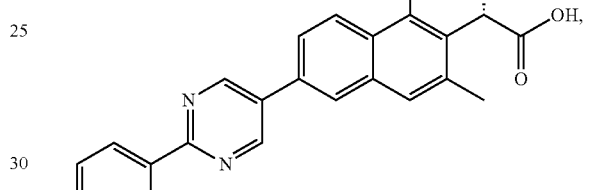
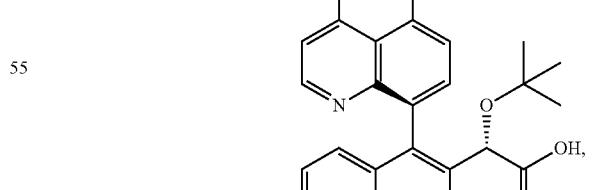

415
-continued
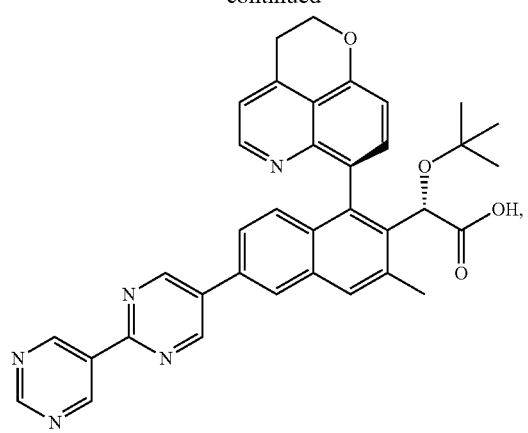
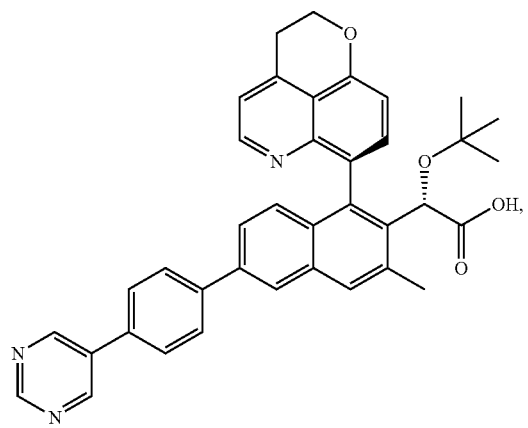
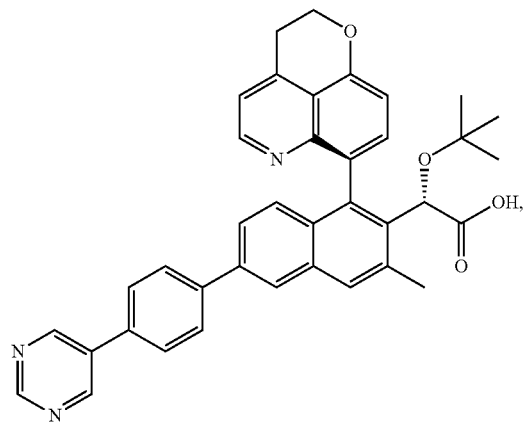
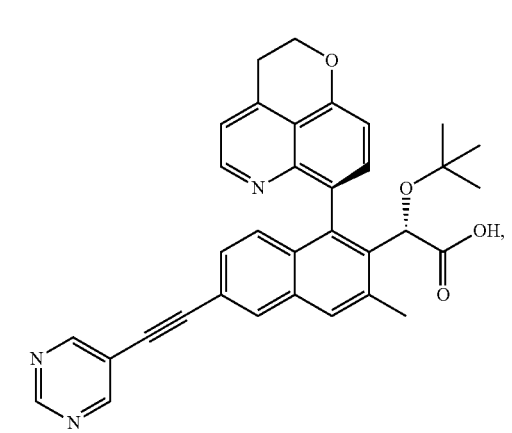
416
-continued
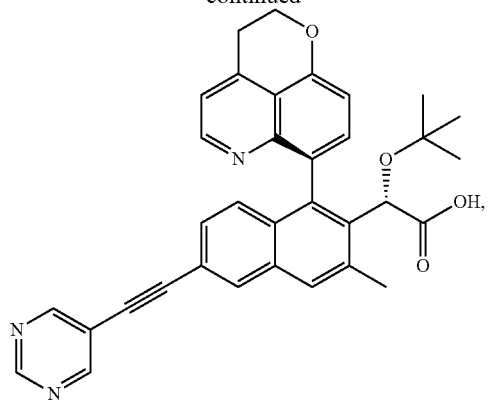
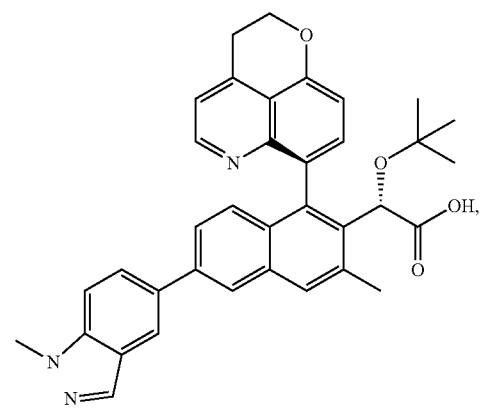
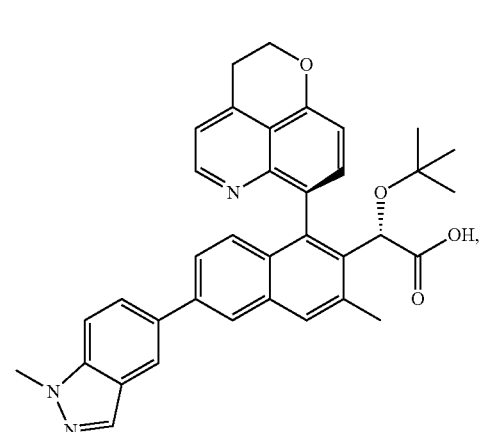
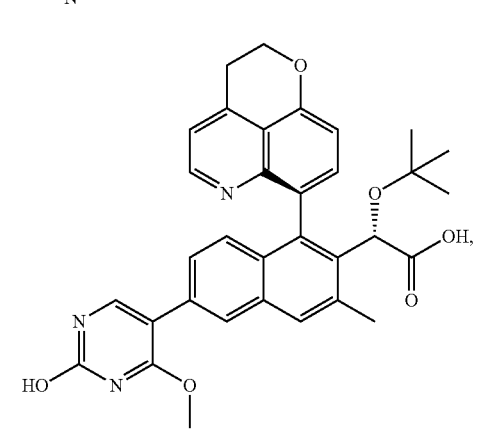

417
-continued
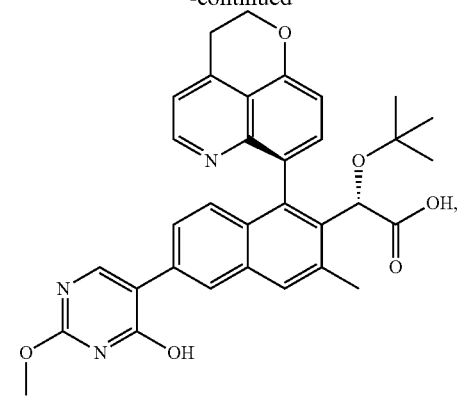
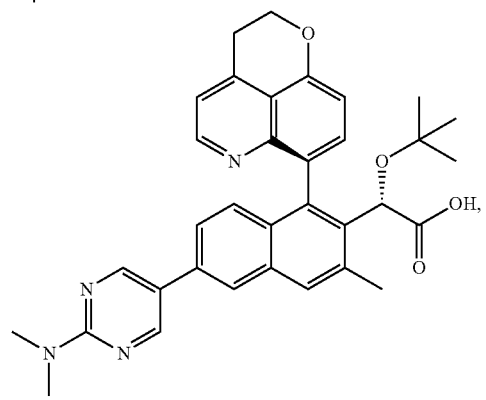
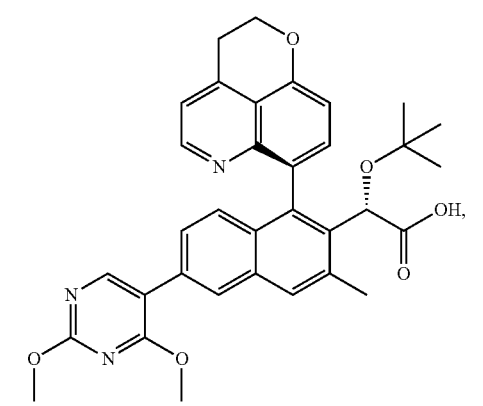
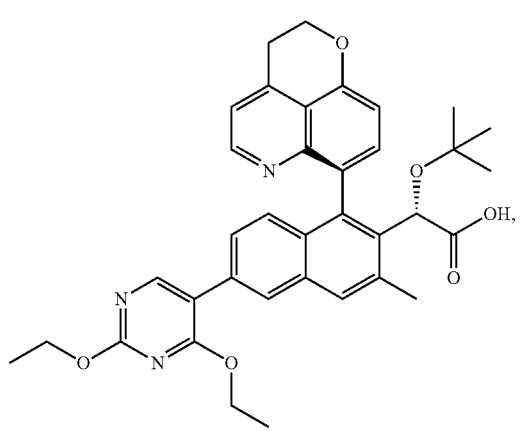
418
-continued
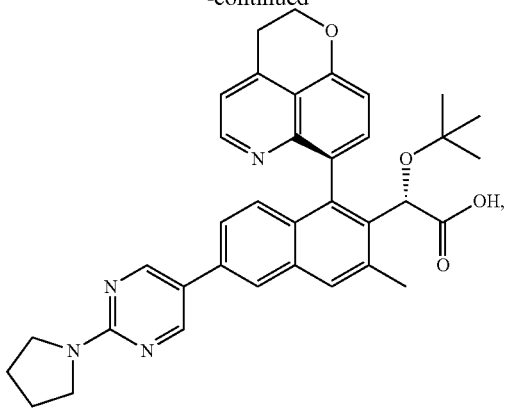
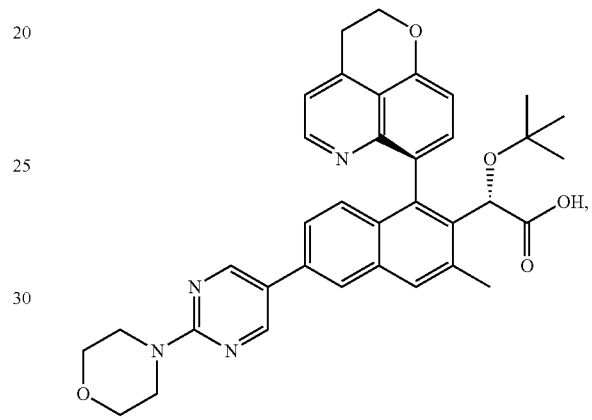
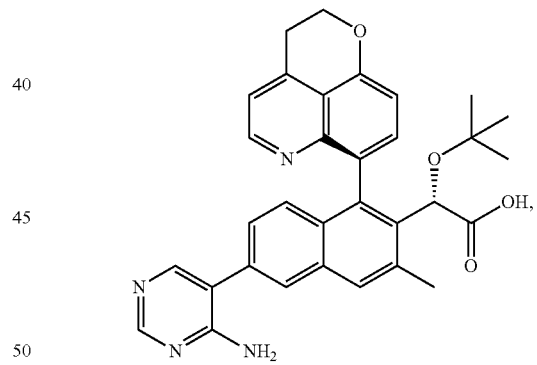
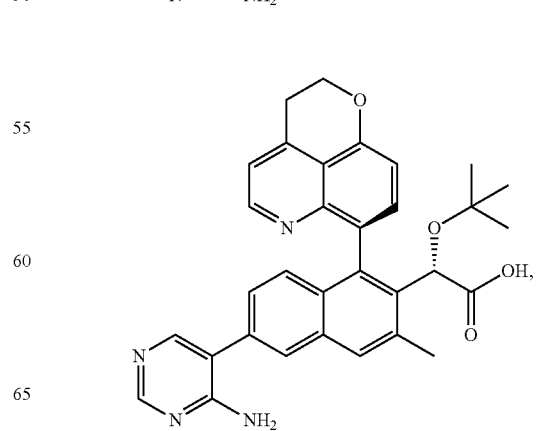

419
-continued
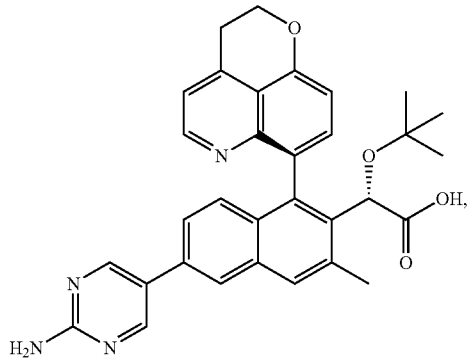
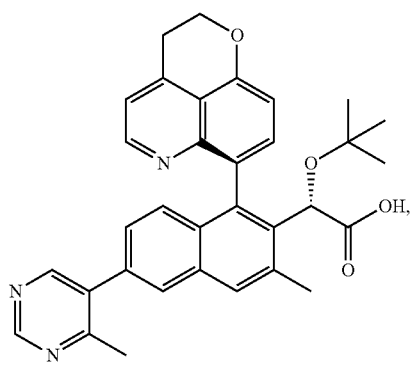
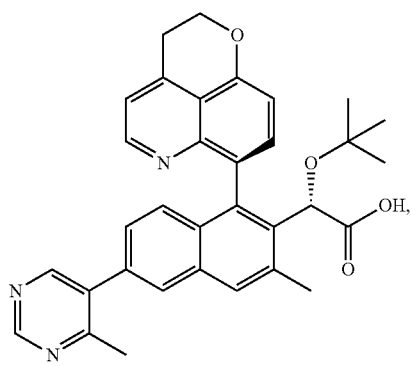
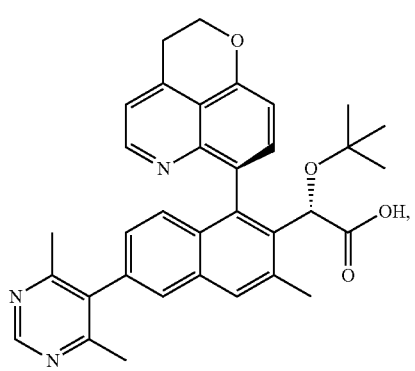
420
-continued
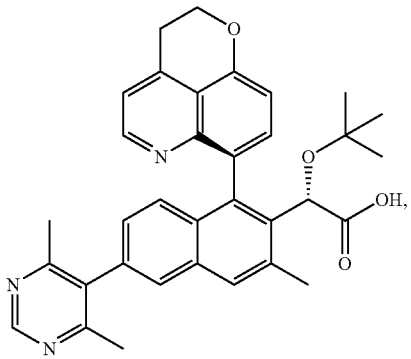
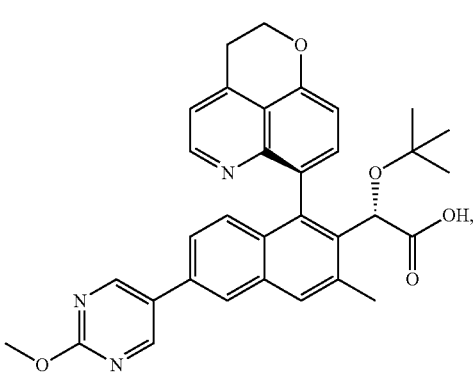
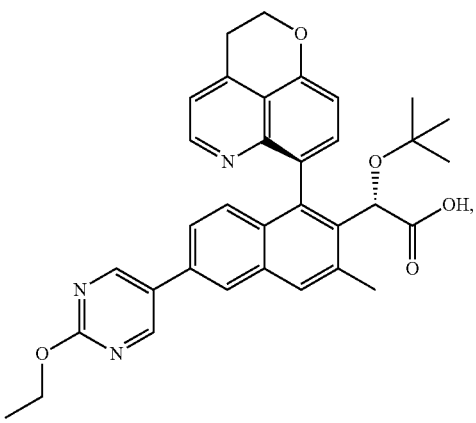
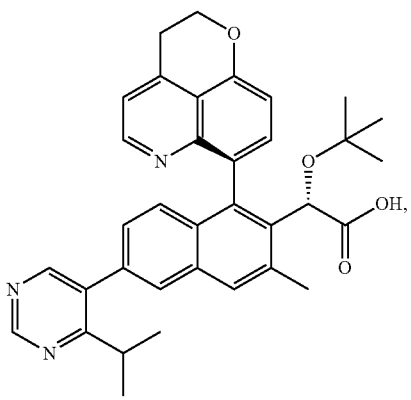

421
-continued
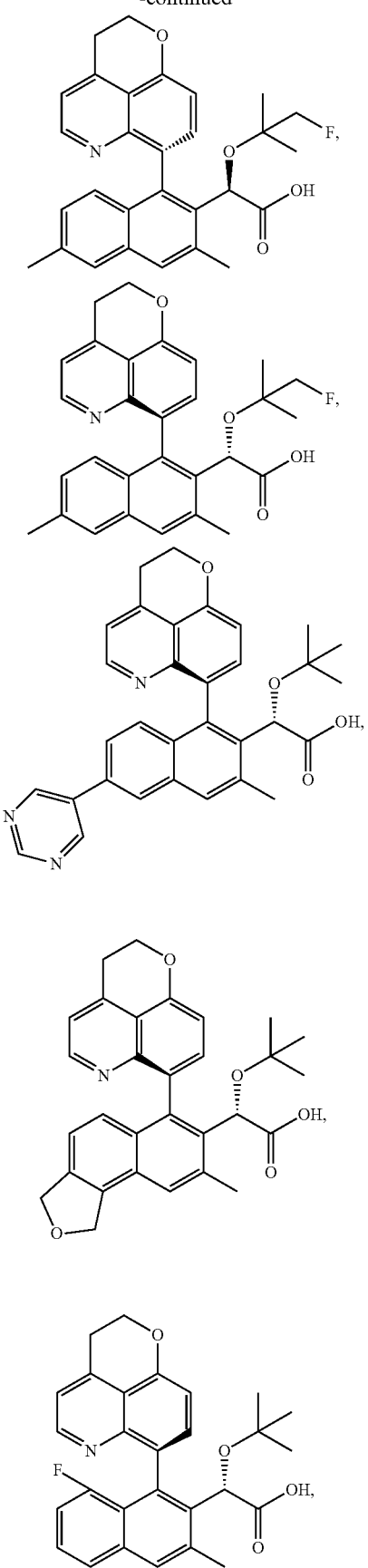
422
-continued
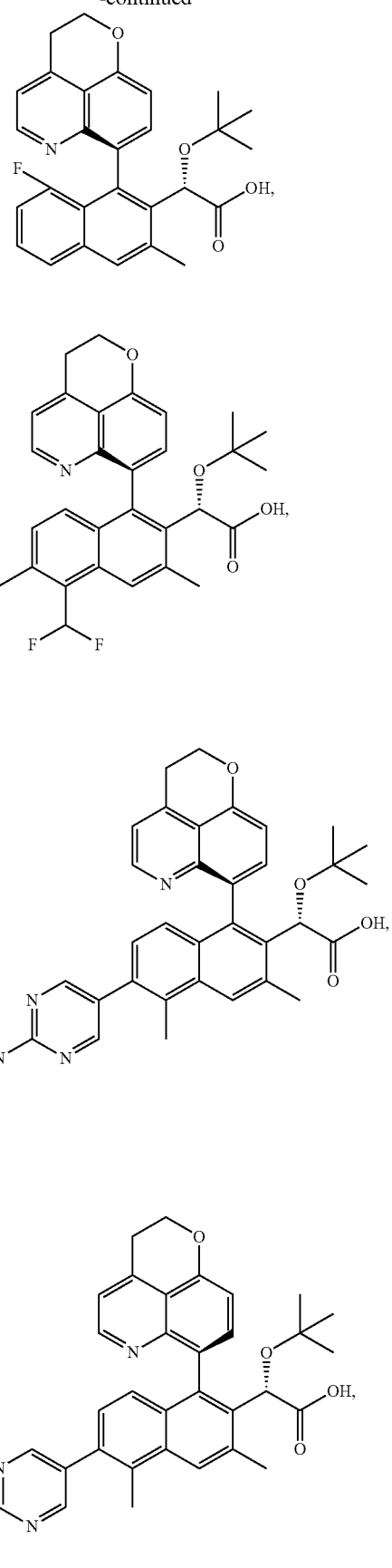

423
-continued
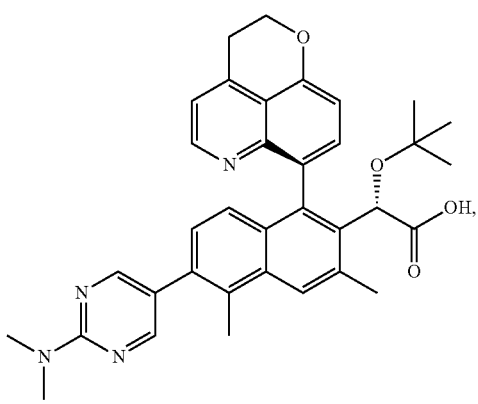
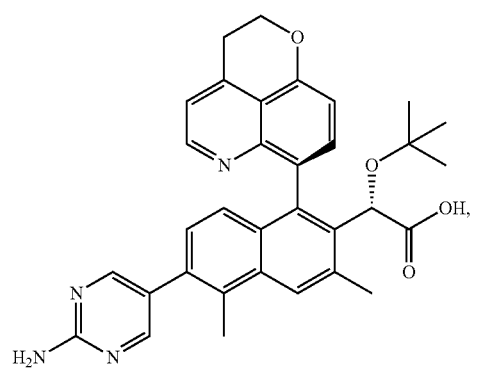
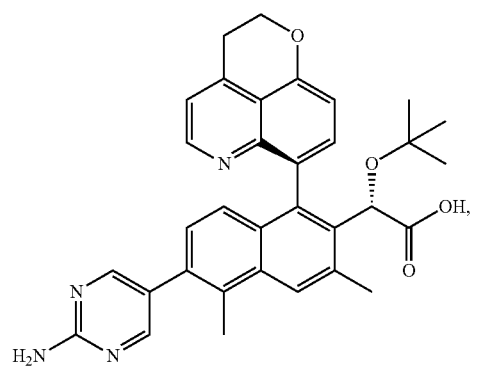
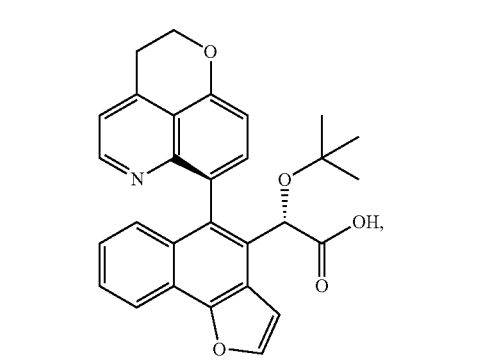
424
-continued
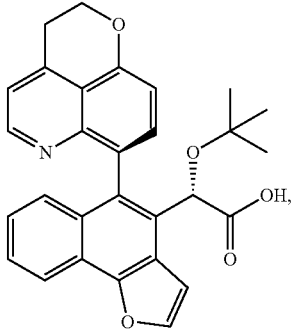
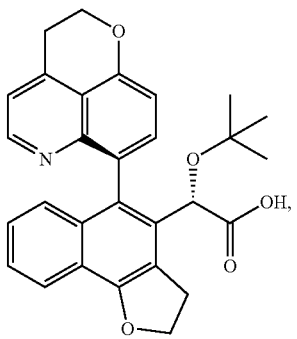
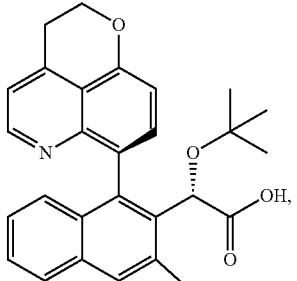
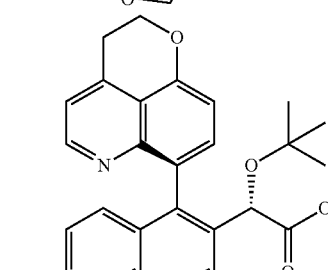
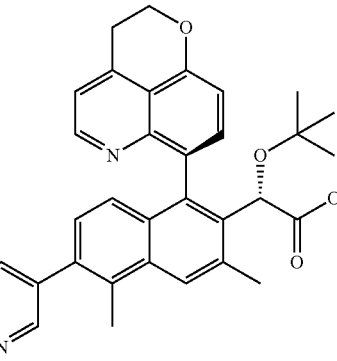

425
-continued
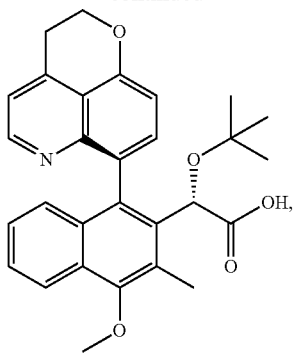
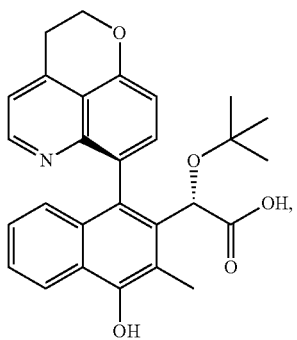
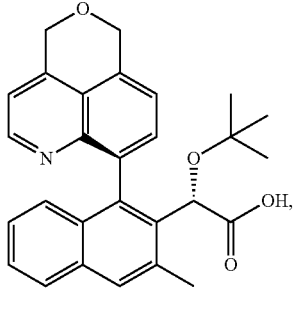
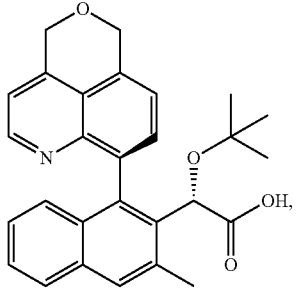
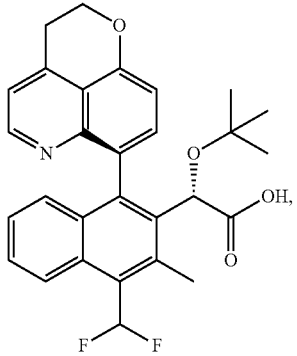
426
-continued
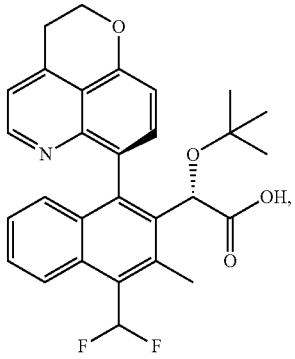
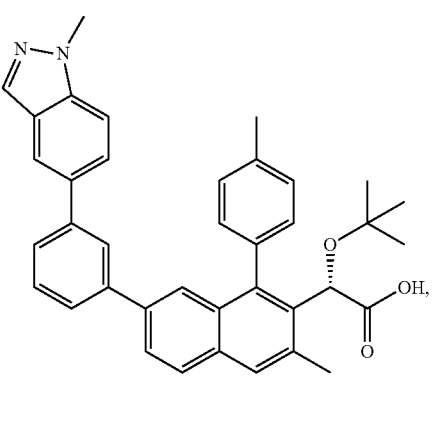
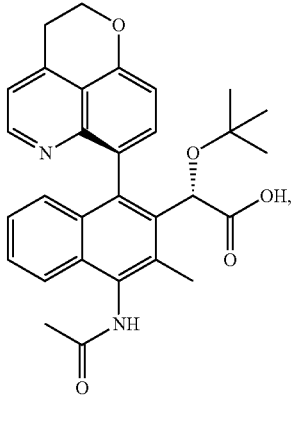
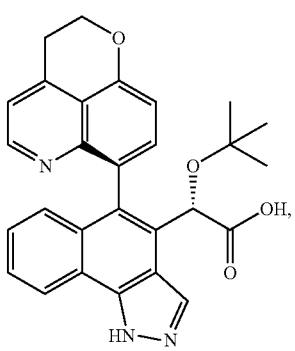

427
-continued
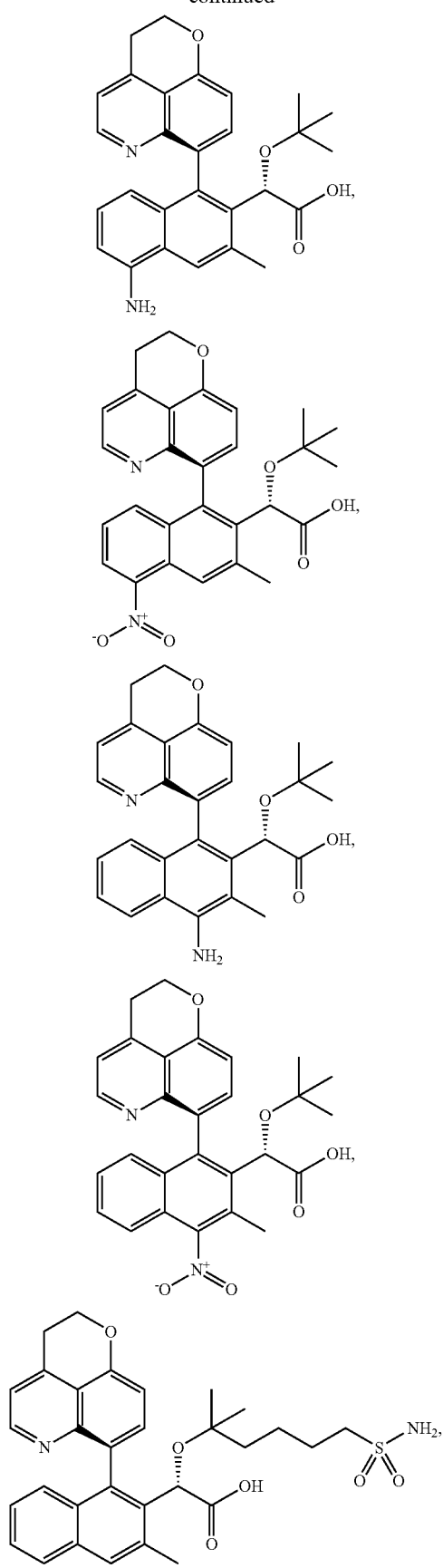
428
-continued
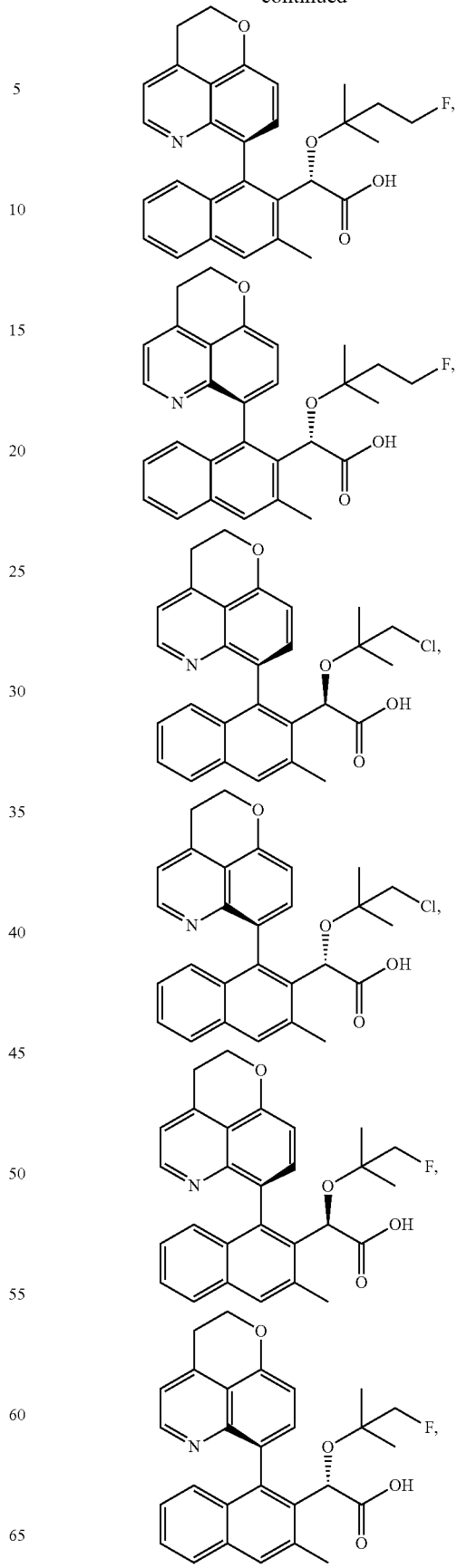

429
-continued
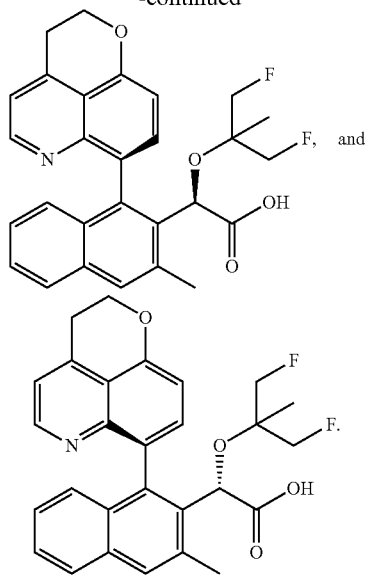
3. The compound of claim 1, or a pharmaceutically acceptable salt thereof, selected from the group consisting of:
430
-continued
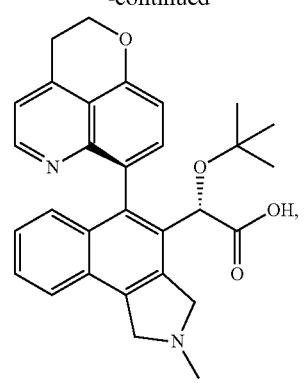
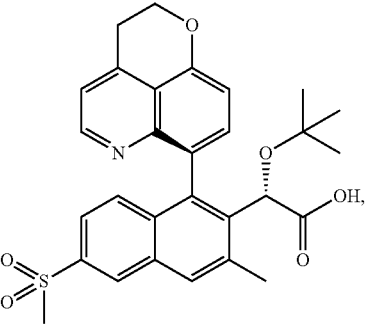
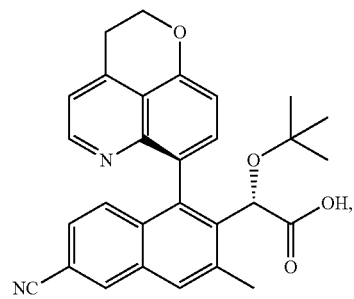
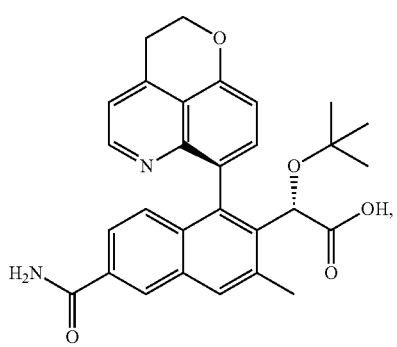
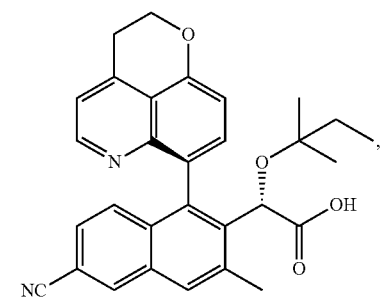

431
-continued
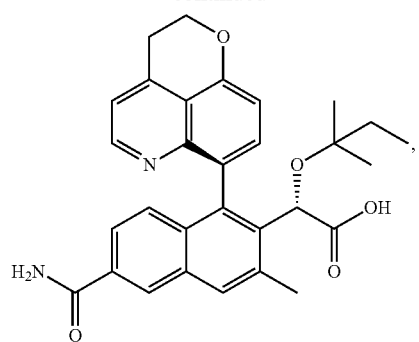
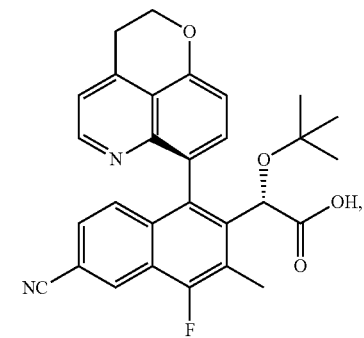
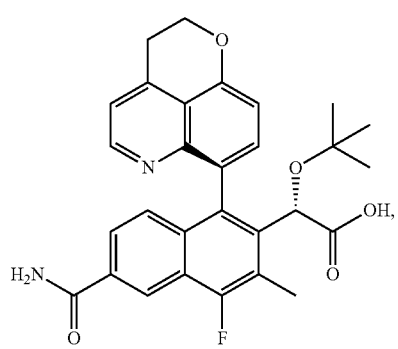
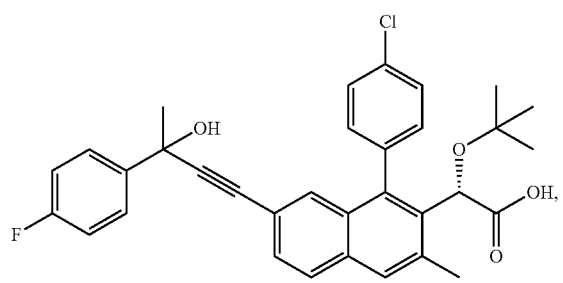
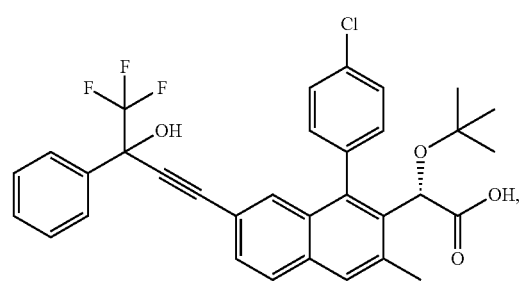
432
-continued
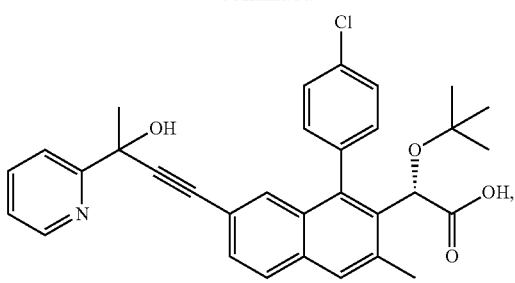
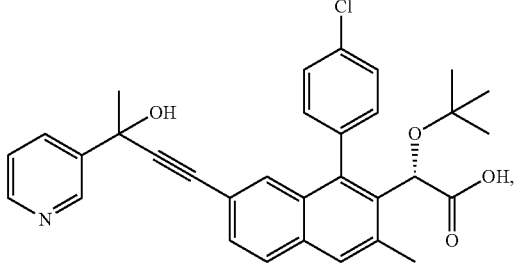
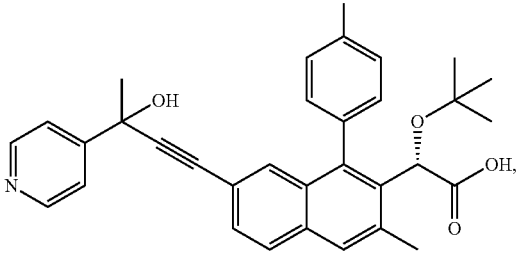
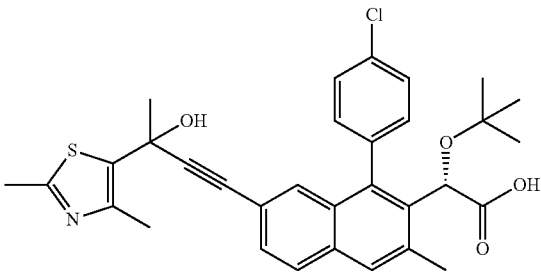
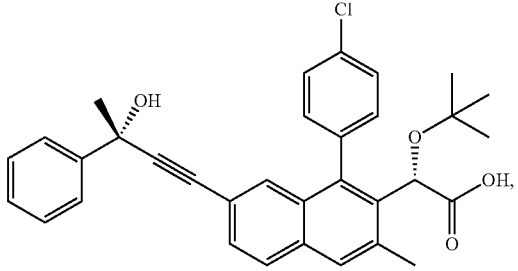
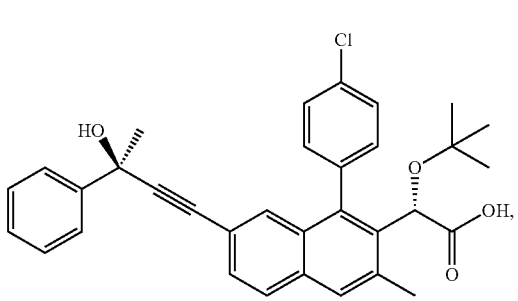

433
-continued
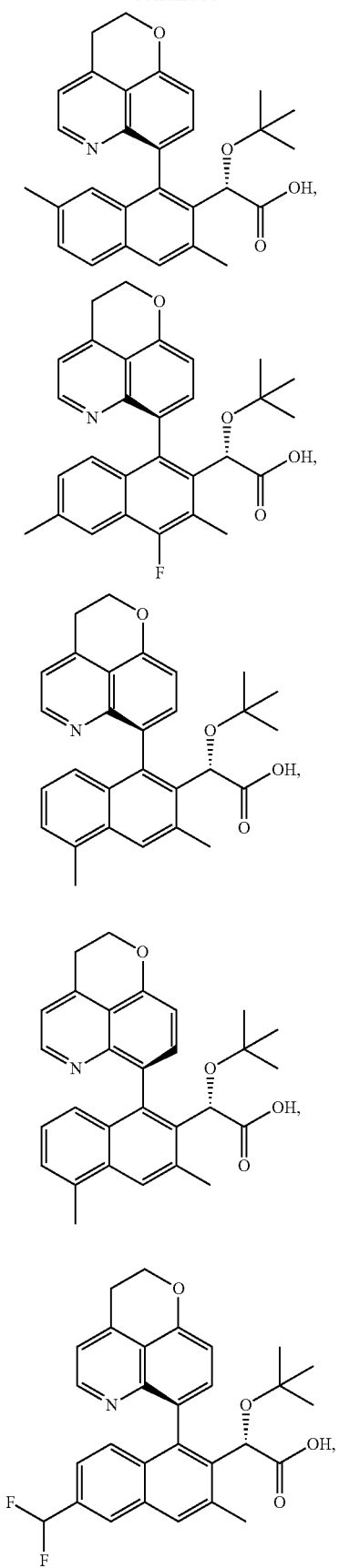
434
-continued
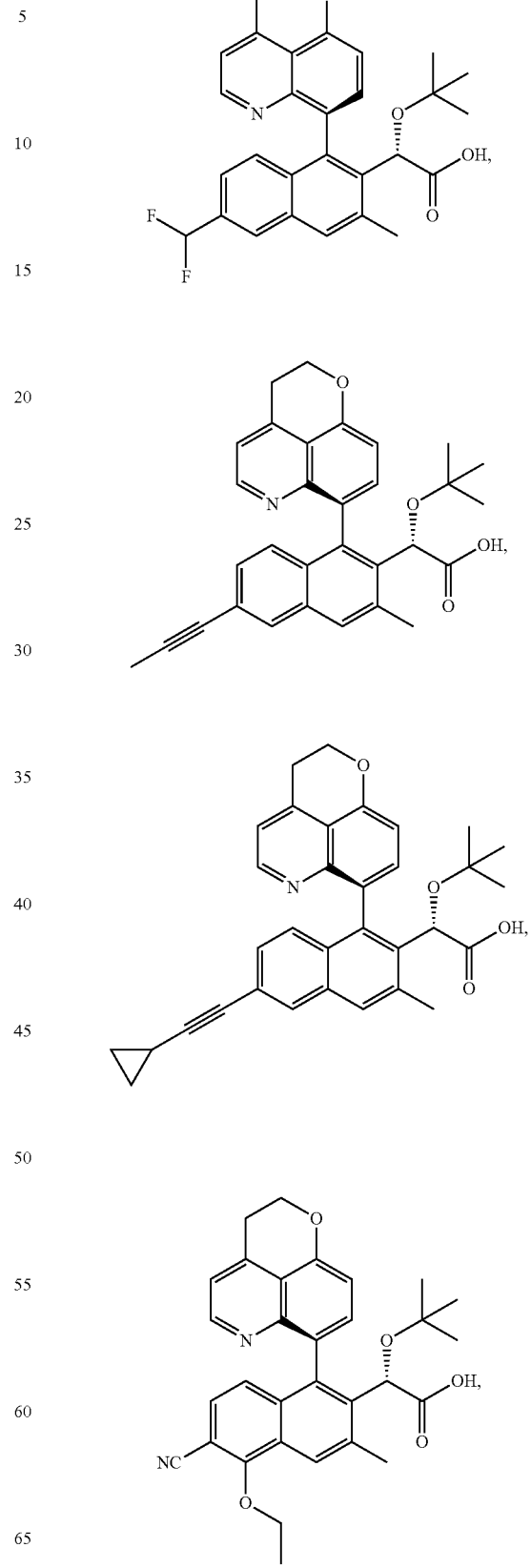

435
-continued
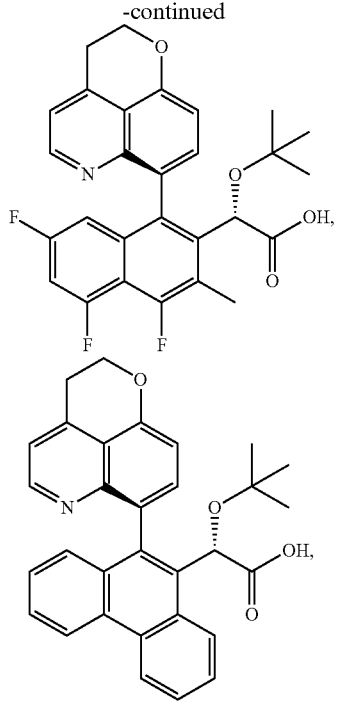
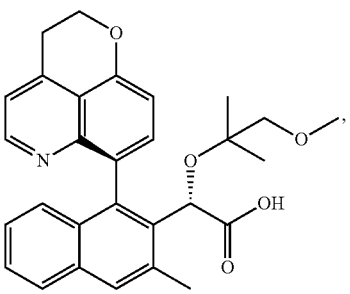
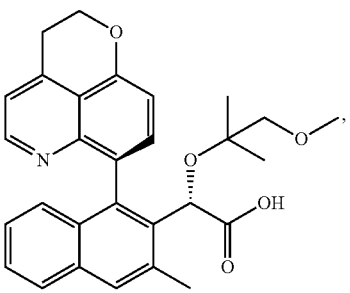
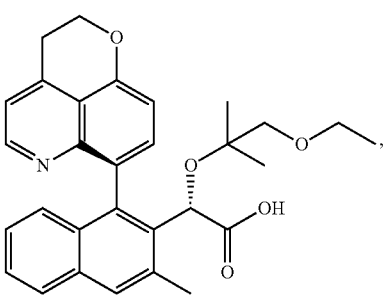
436
-continued
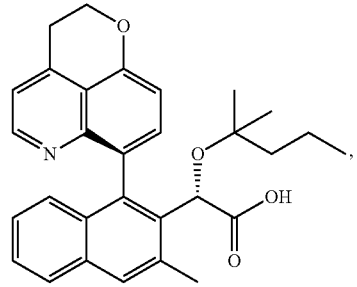
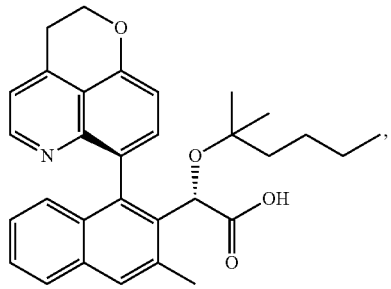
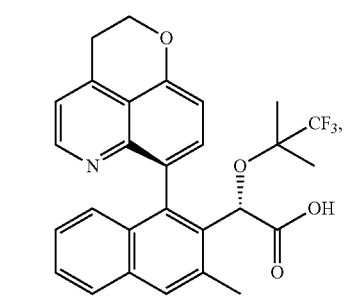
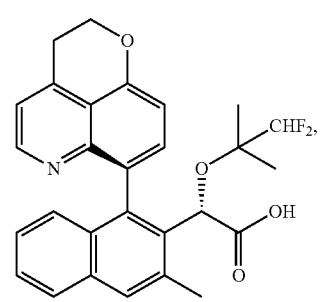
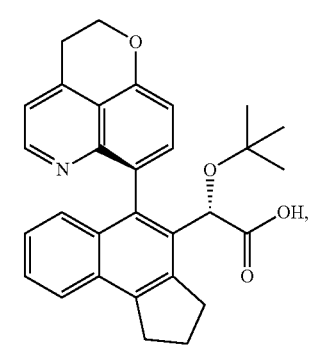

437
-continued
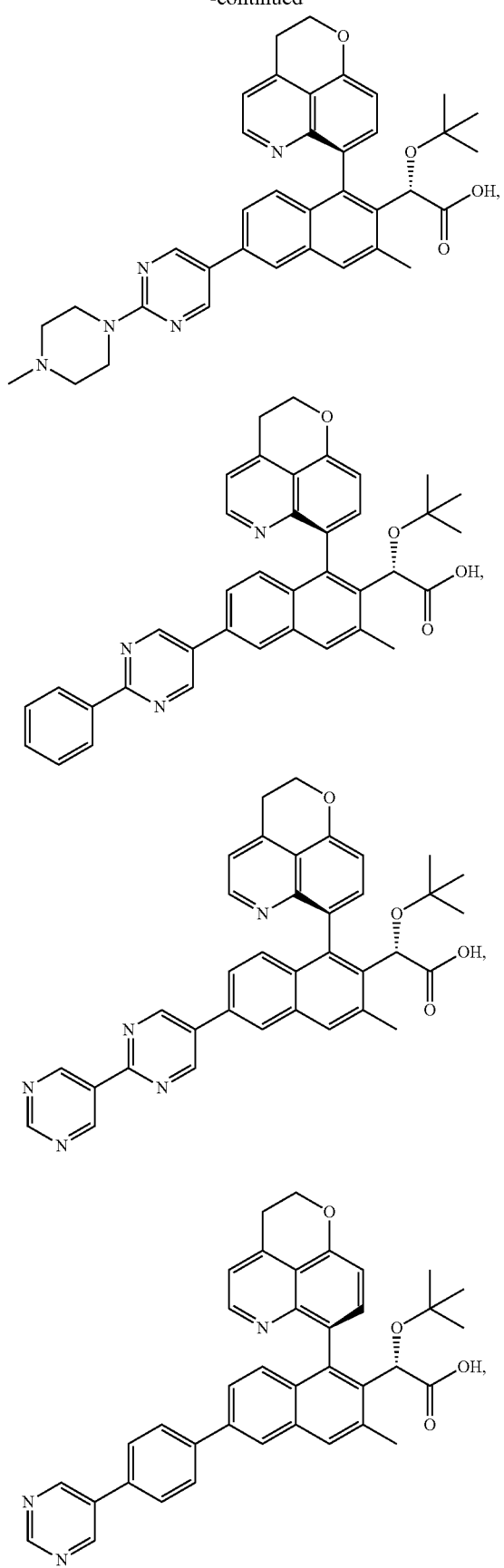
438
-continued
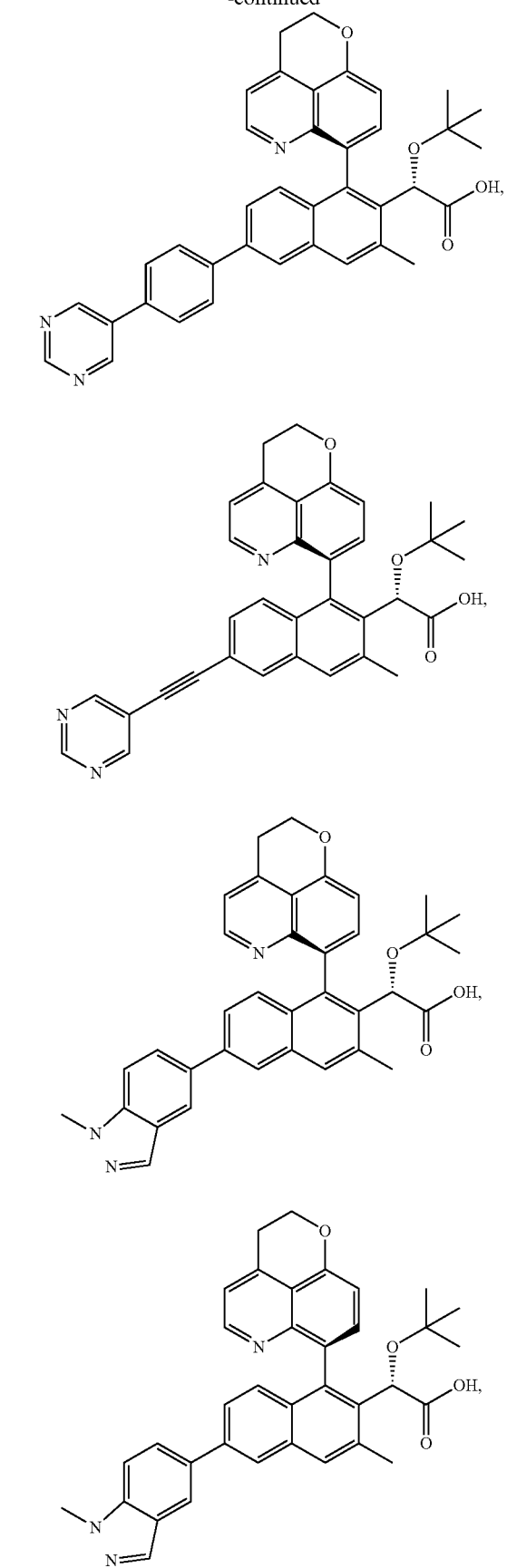

439
-continued
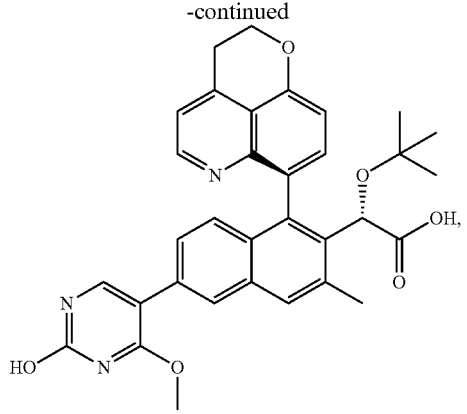
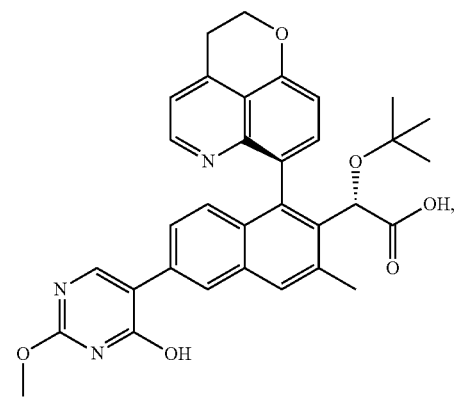
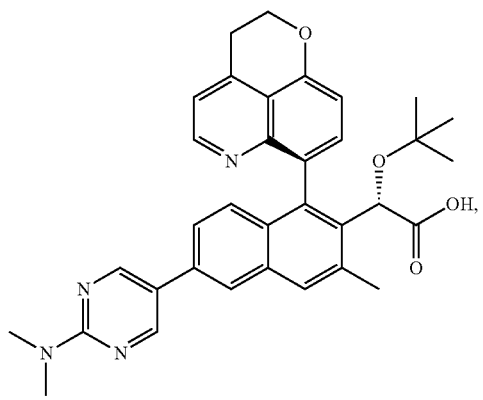
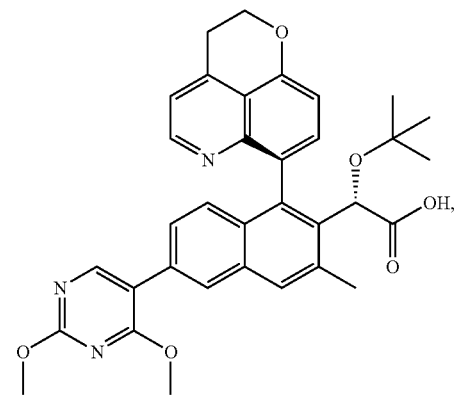
440
-continued
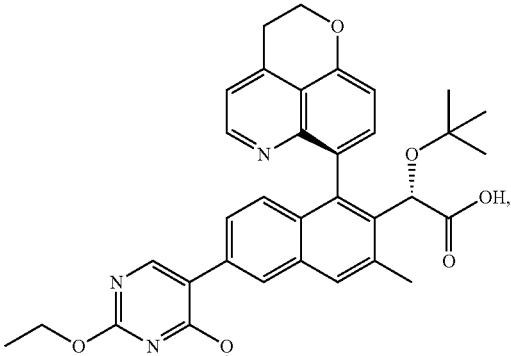
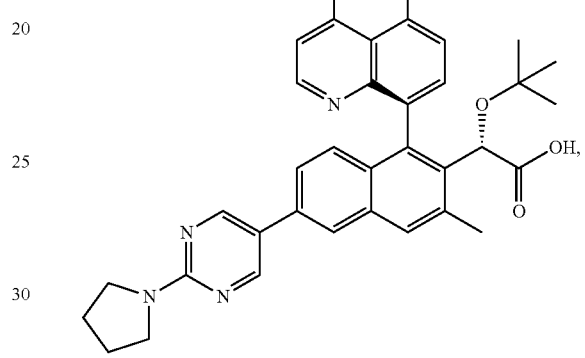
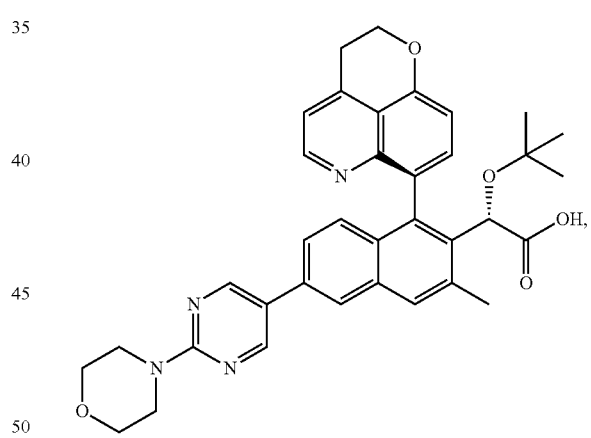
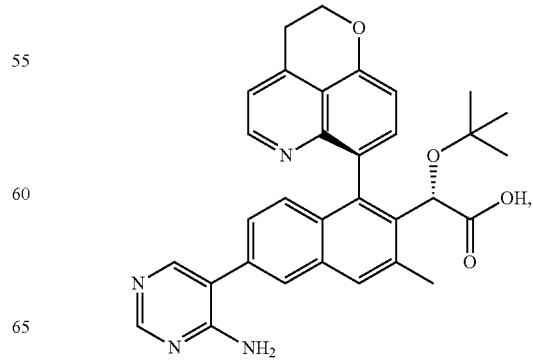

441
-continued
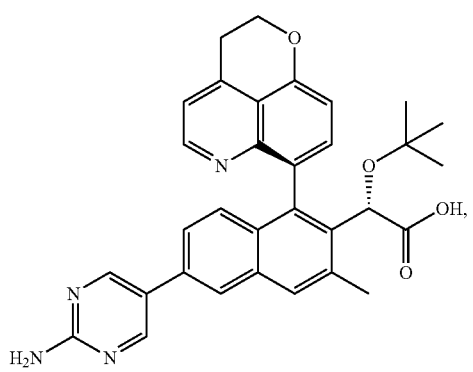
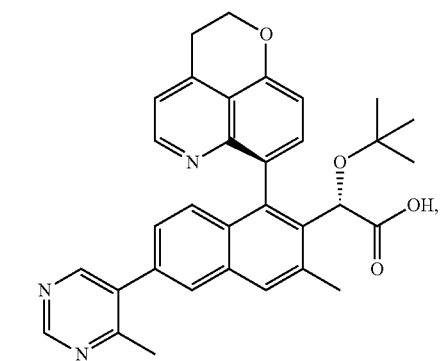
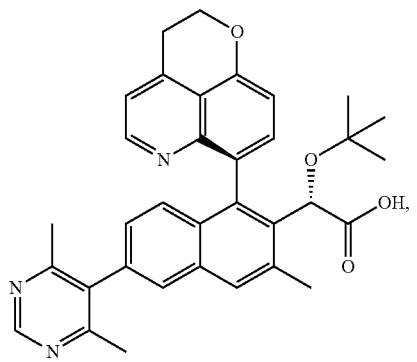
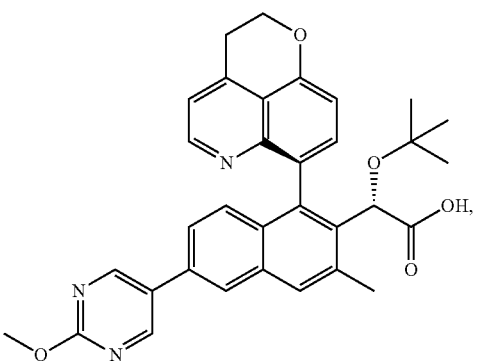
442
-continued
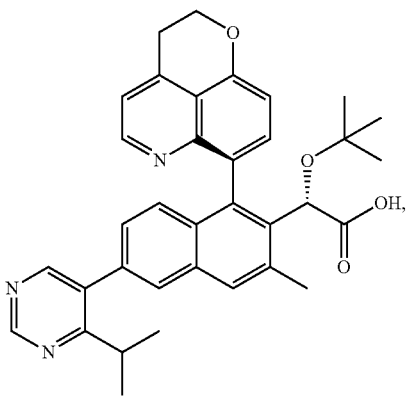
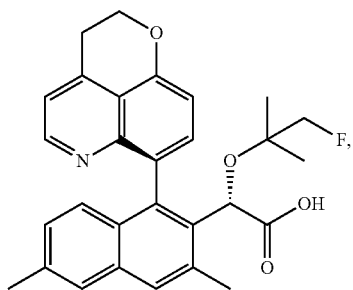
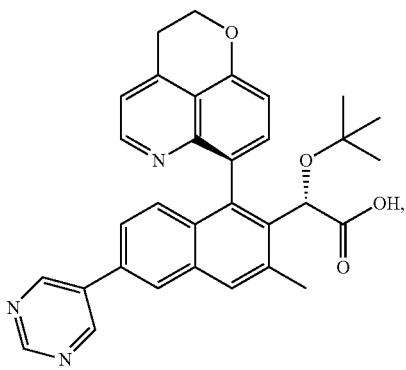
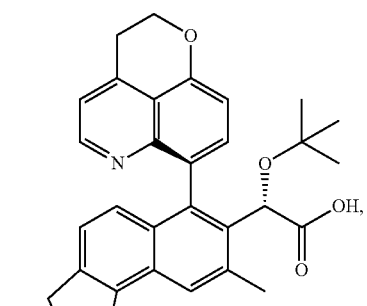
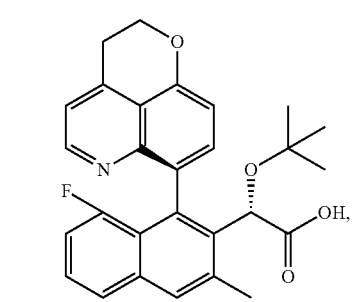

443
-continued
444
-continued
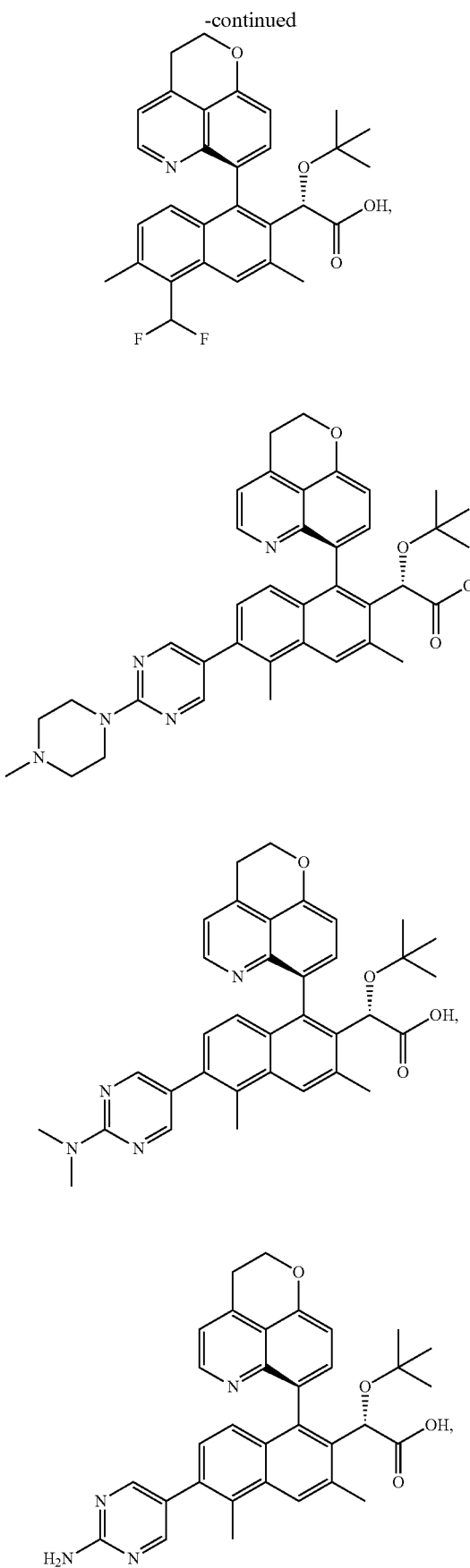
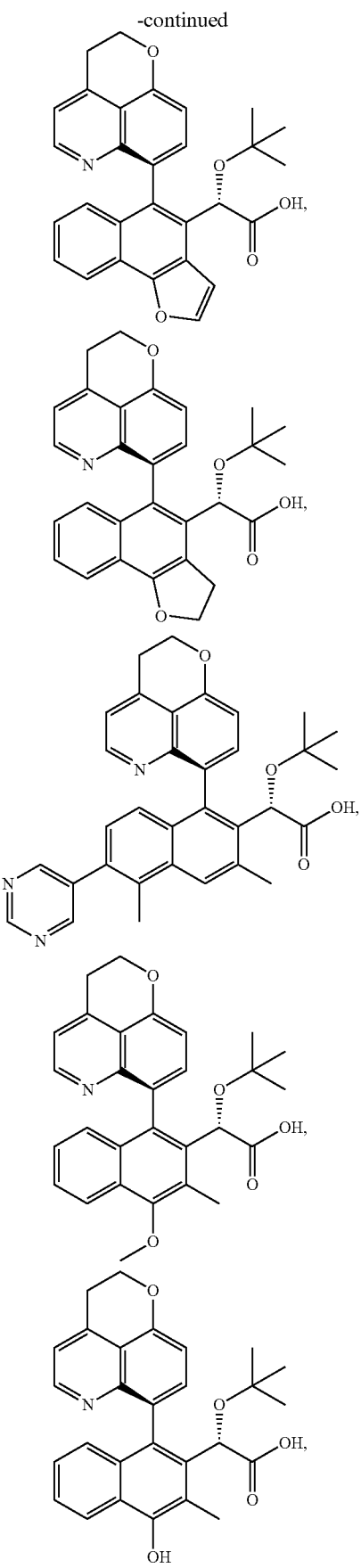

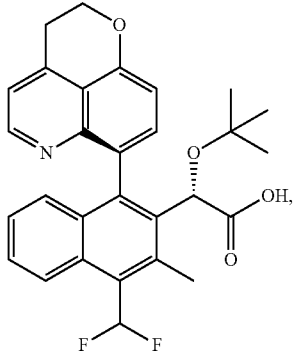
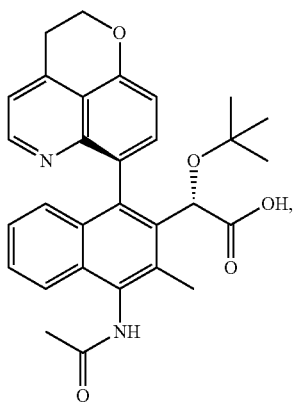
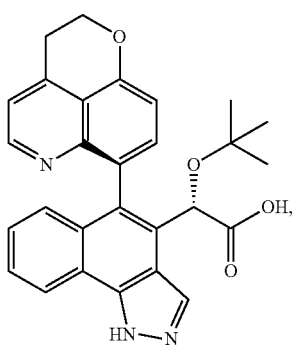
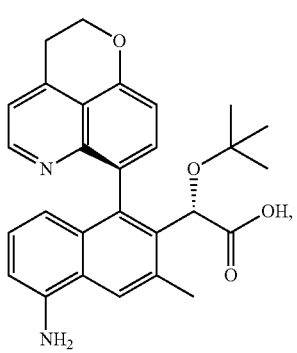
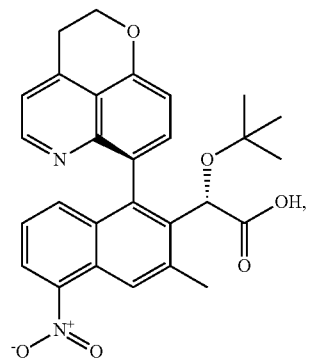
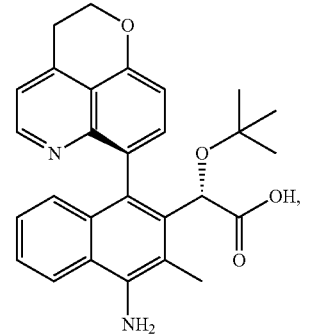
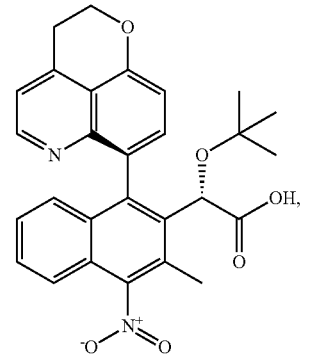
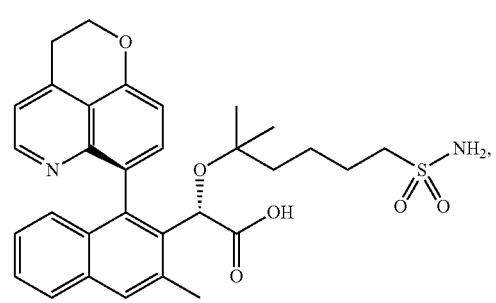
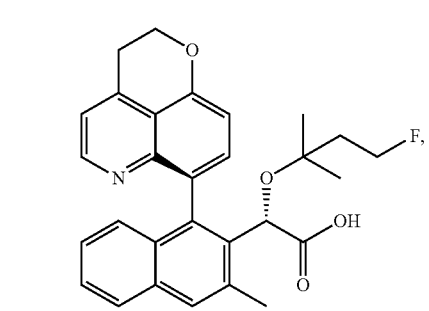

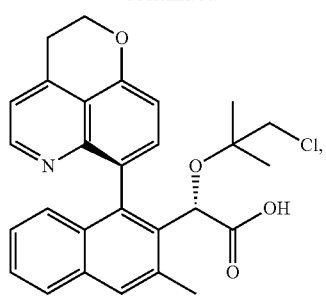
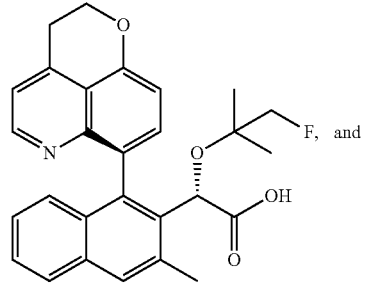
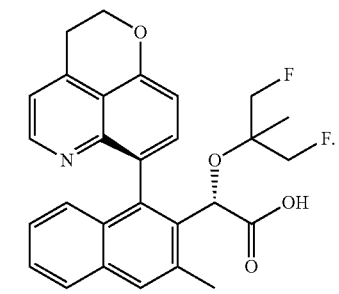
4. The compound of claim 1, or a pharmaceutically acceptable salt thereof, selected from the group consisting of:
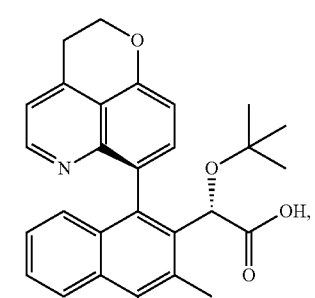
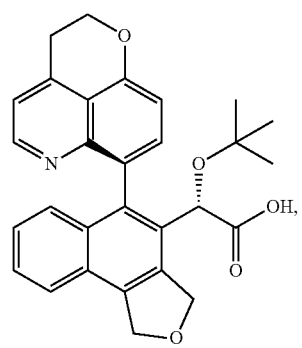
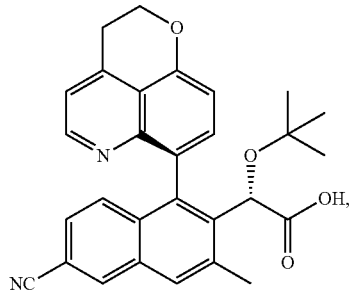
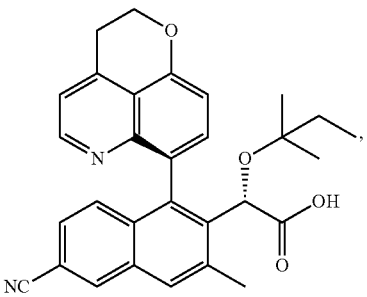
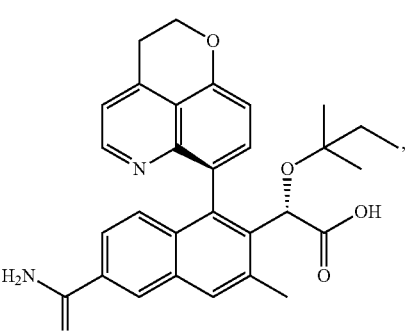
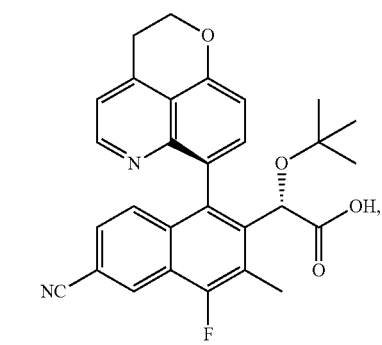
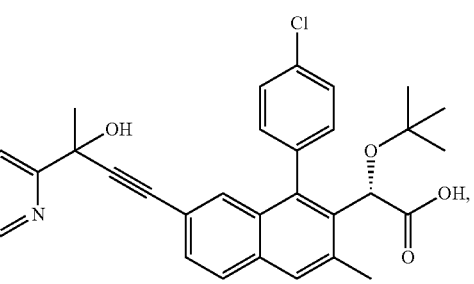

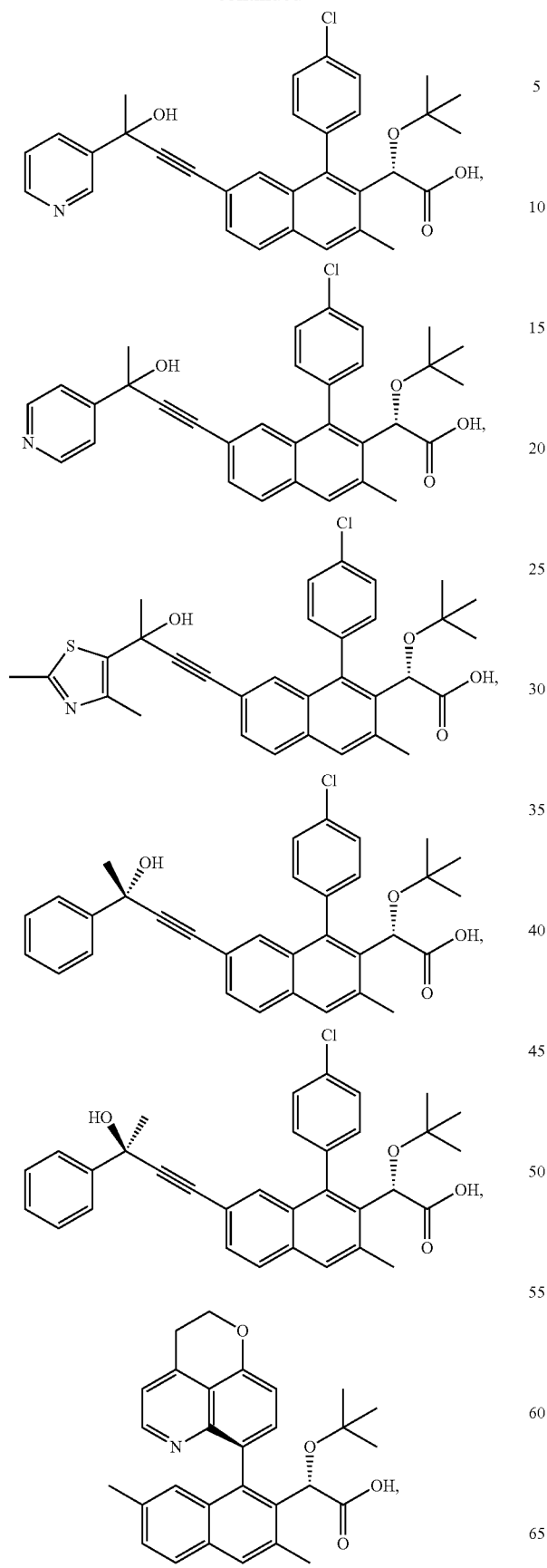
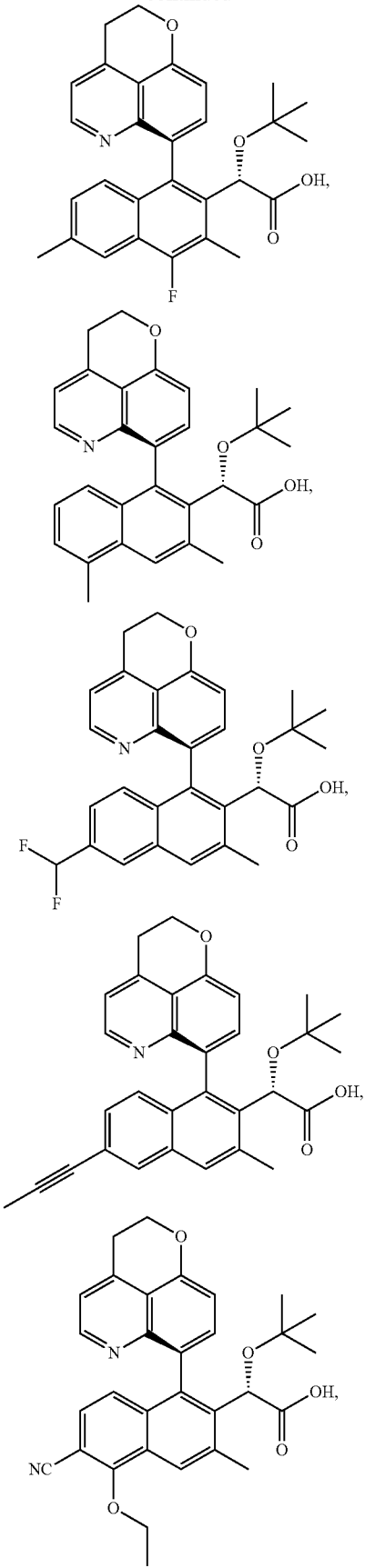

451
-continued
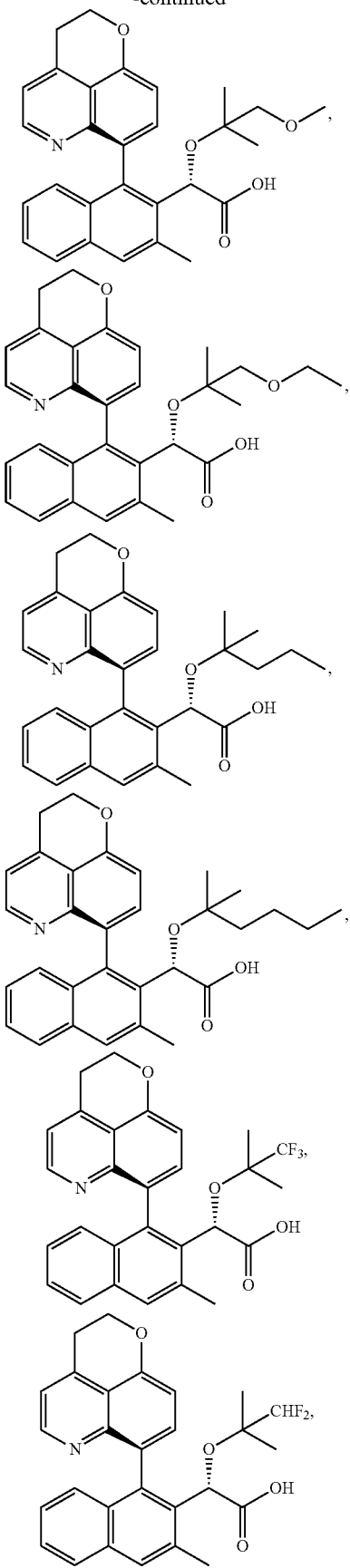
452
-continued
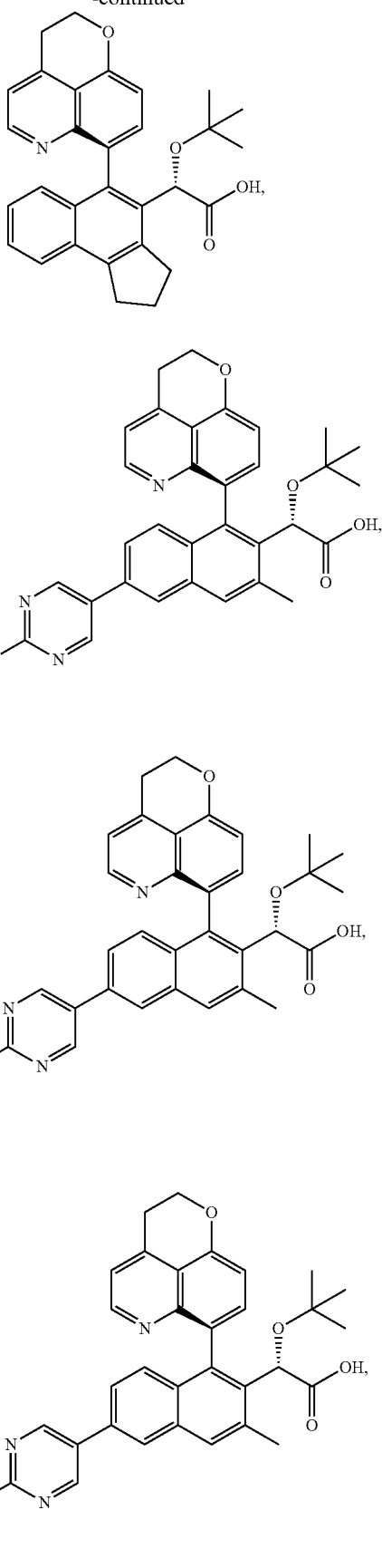

453
-continued
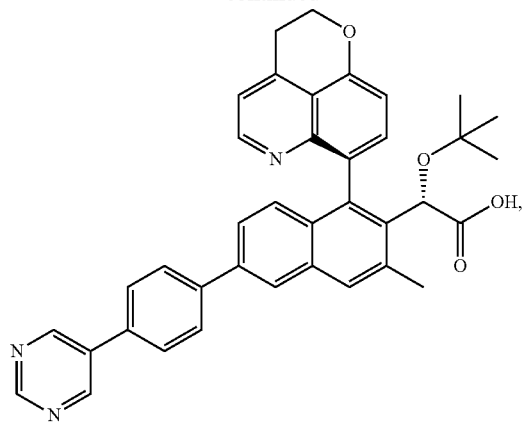
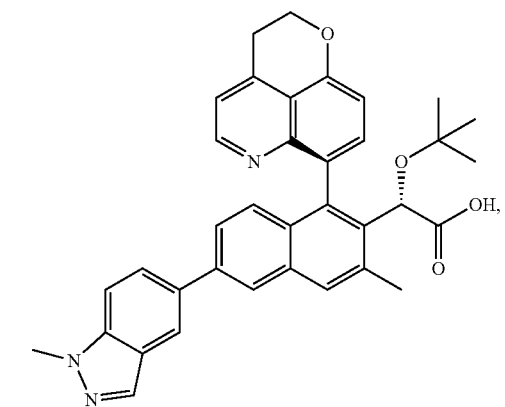
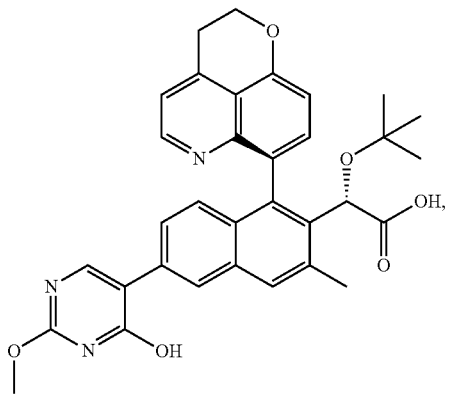
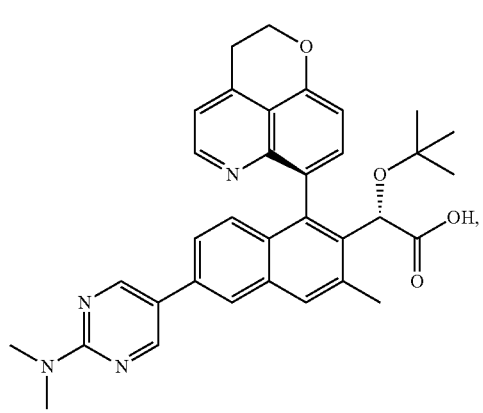
454
-continued
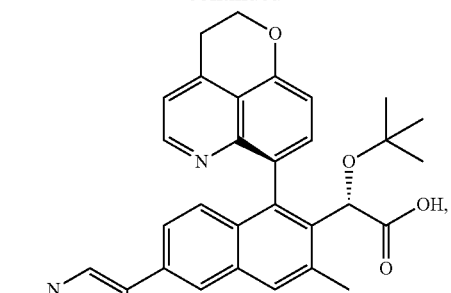
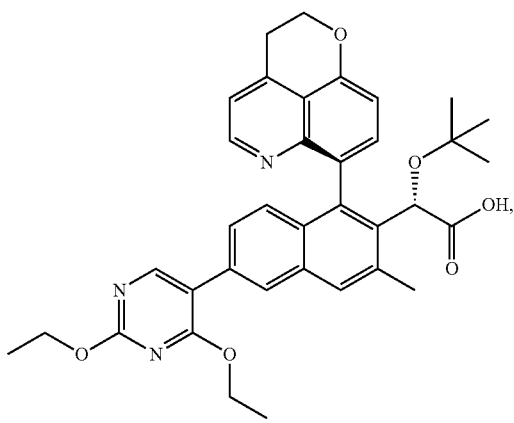
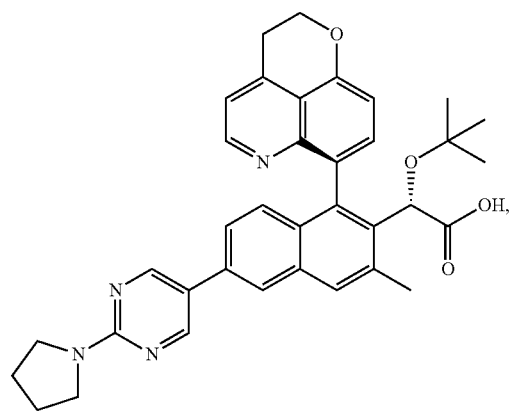
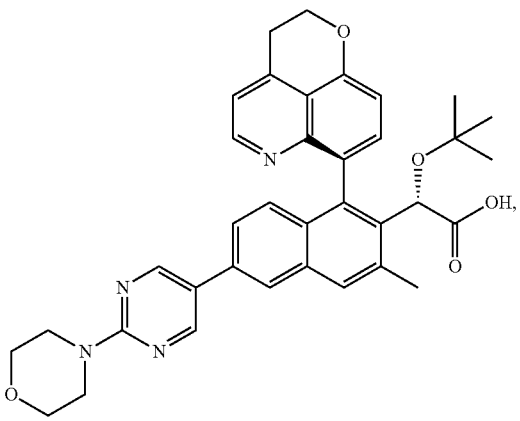

455
-continued
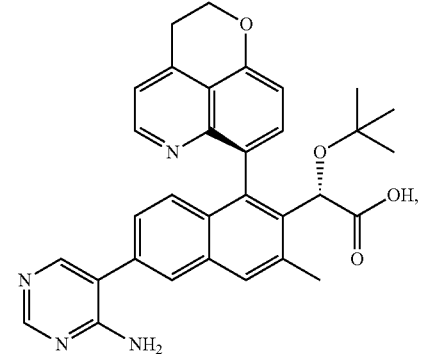
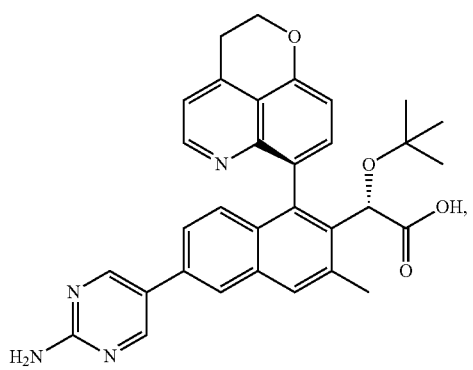
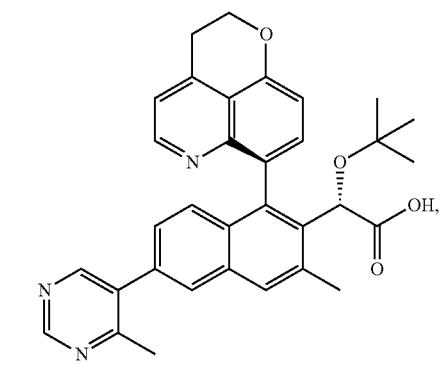
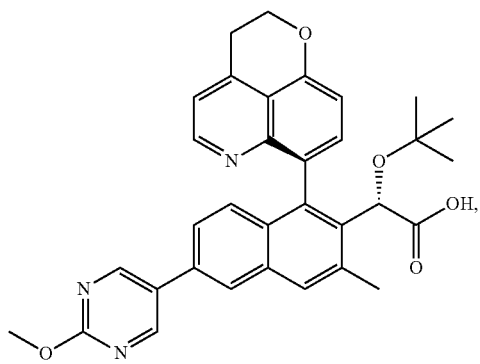
456
-continued
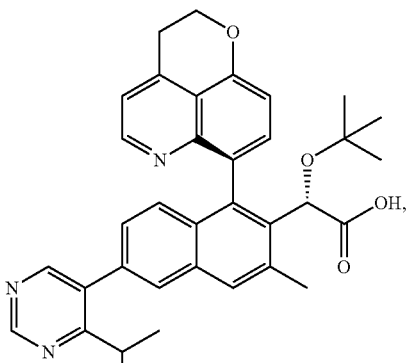
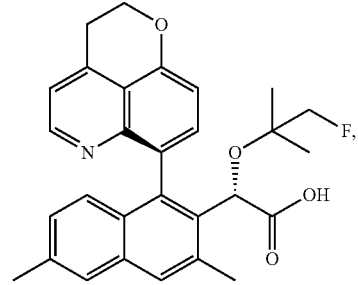
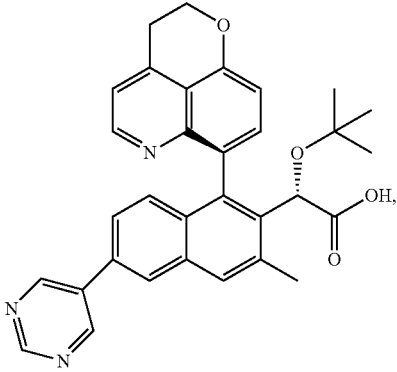
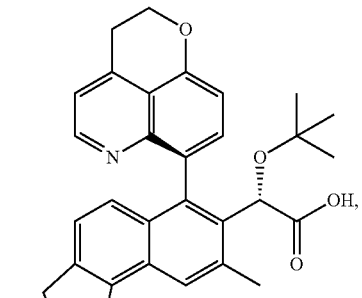
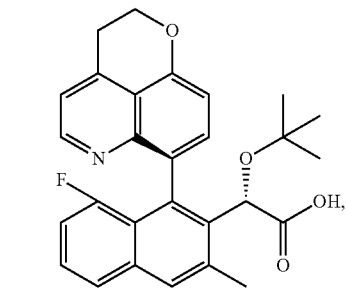

457
-continued
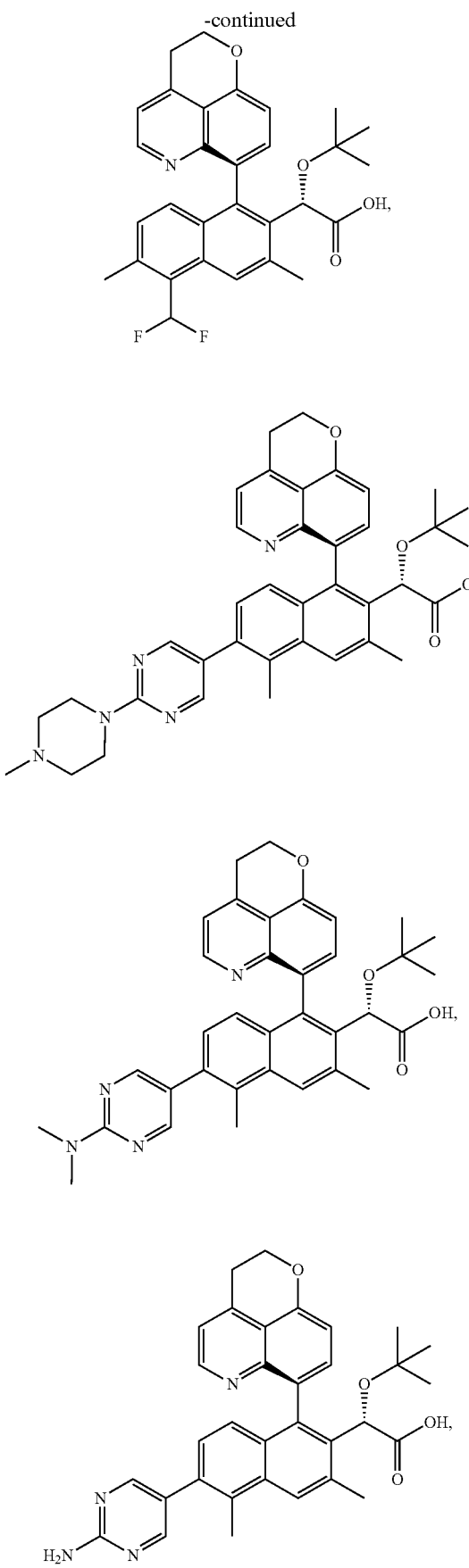
458
-continued
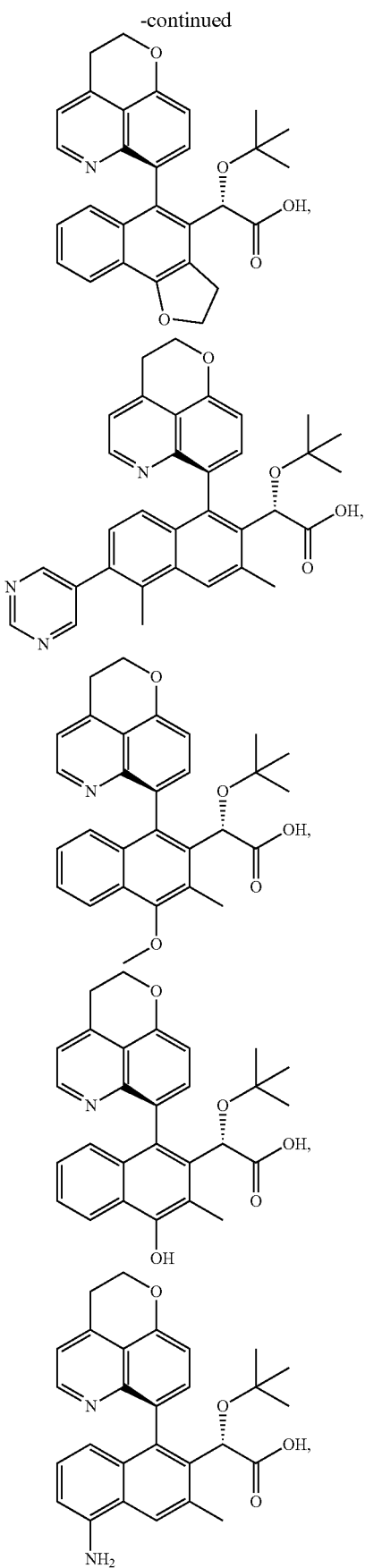

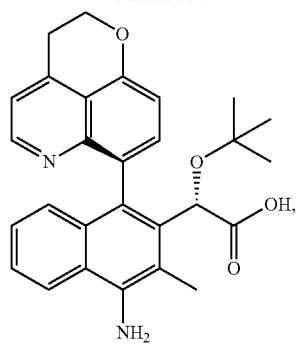
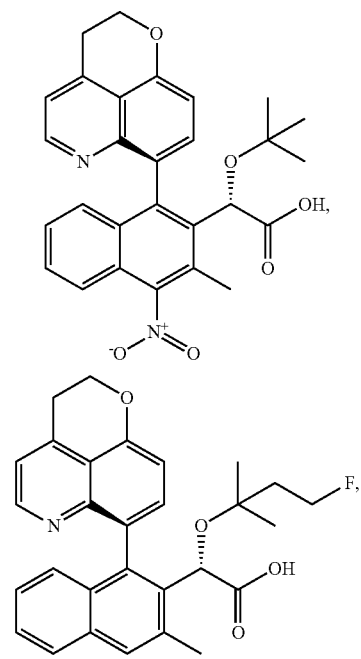
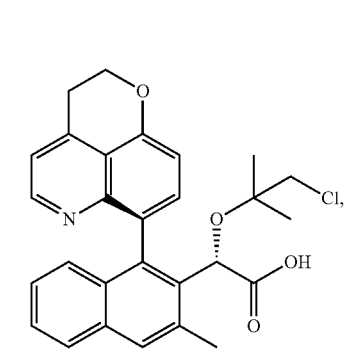
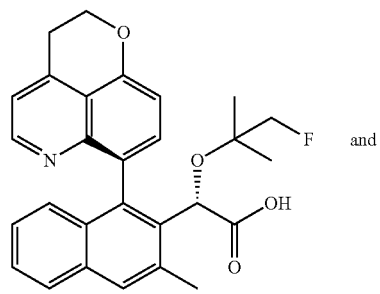
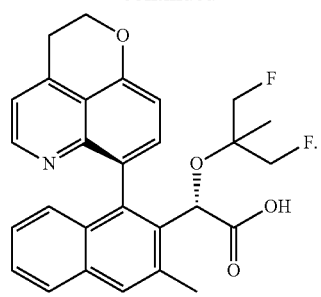
5. The compound of claim 1, or a pharmaceutically acceptable salt thereof, selected from the group consisting of:
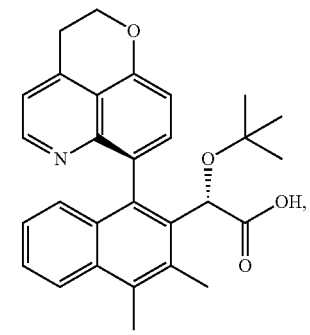

461
-continued
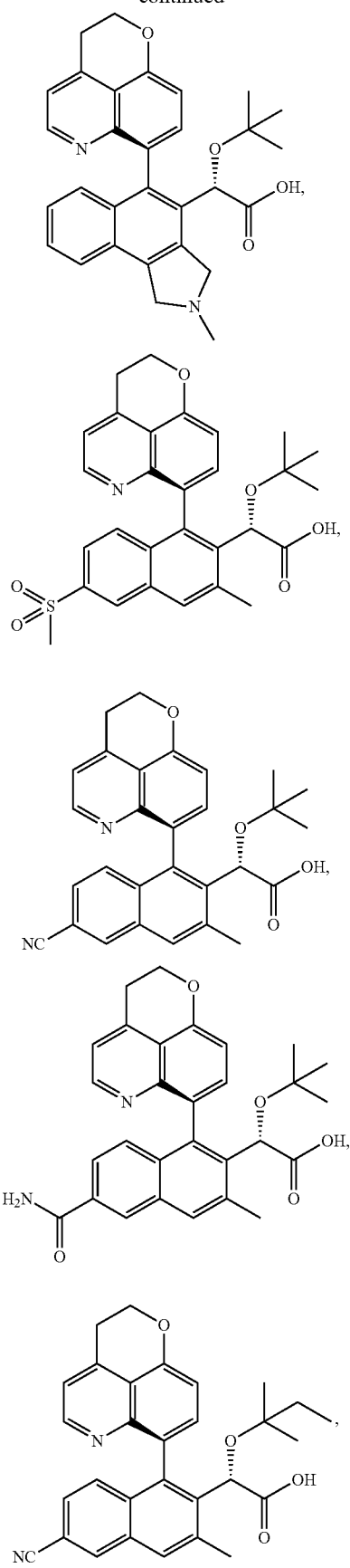
462
-continued
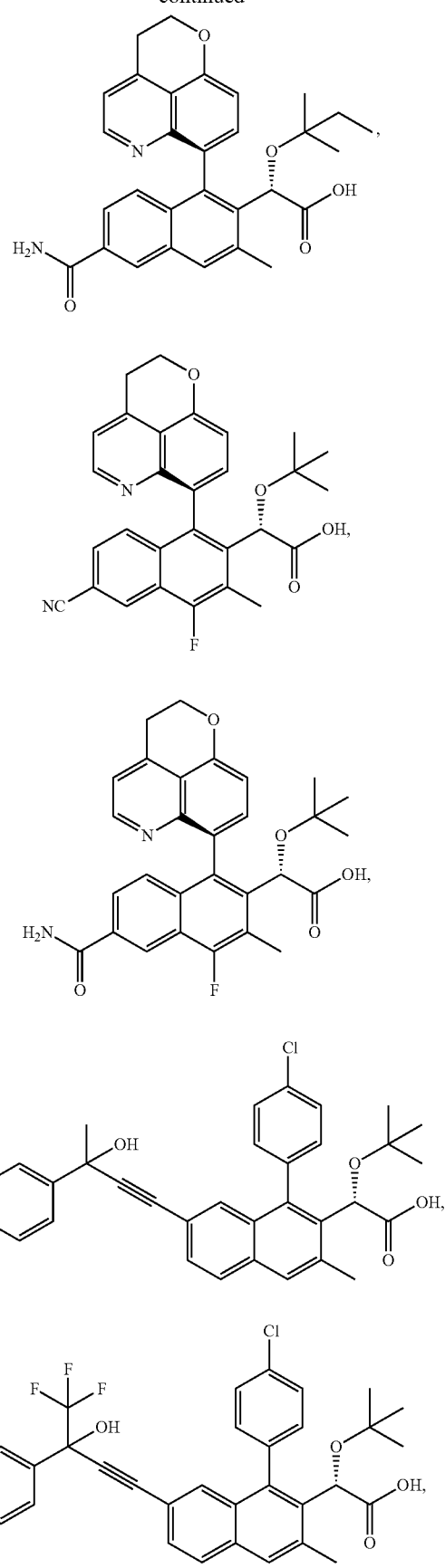

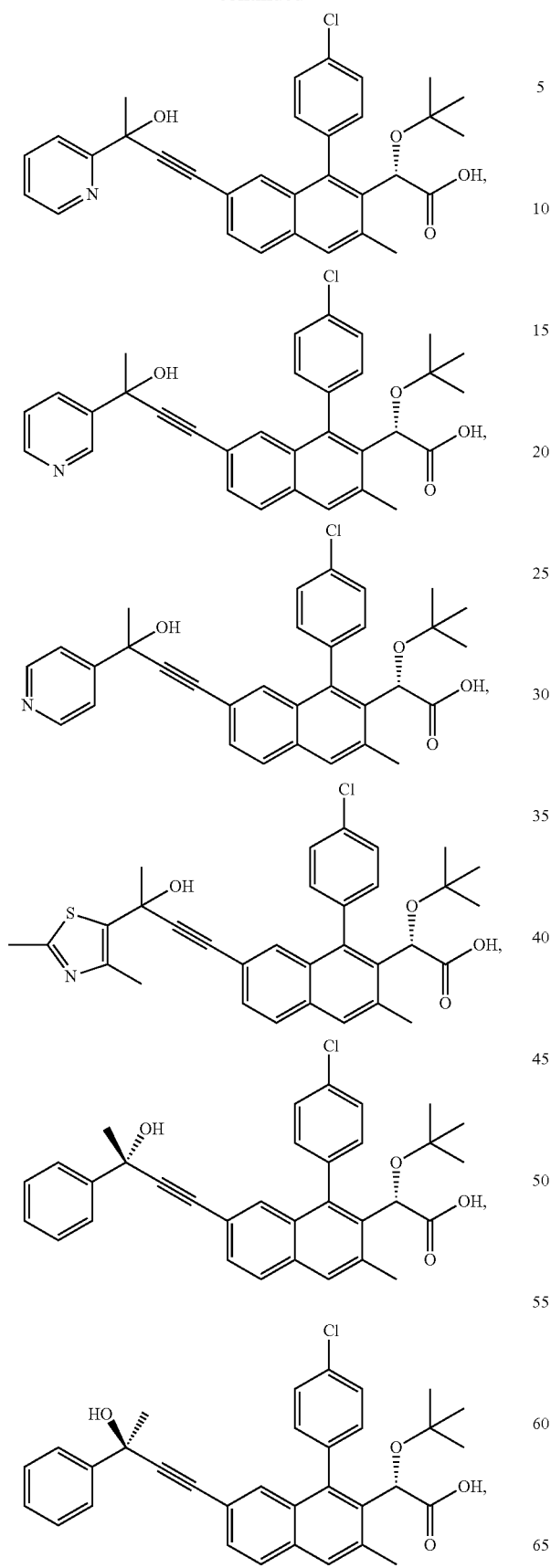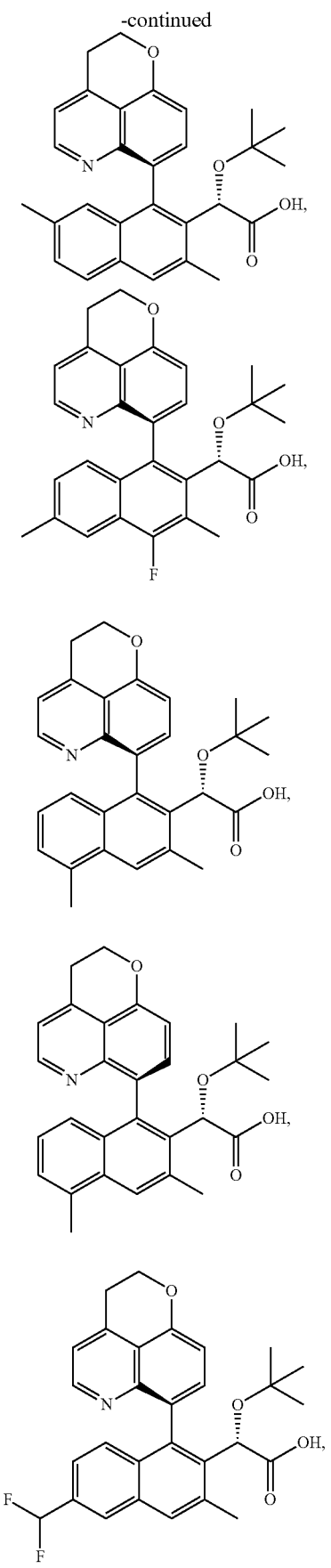

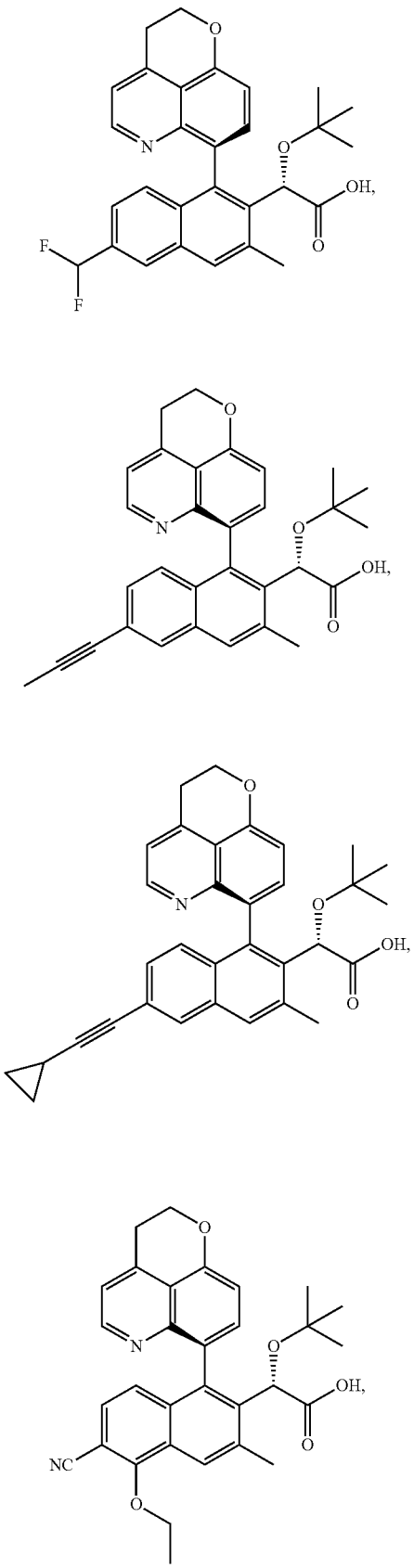
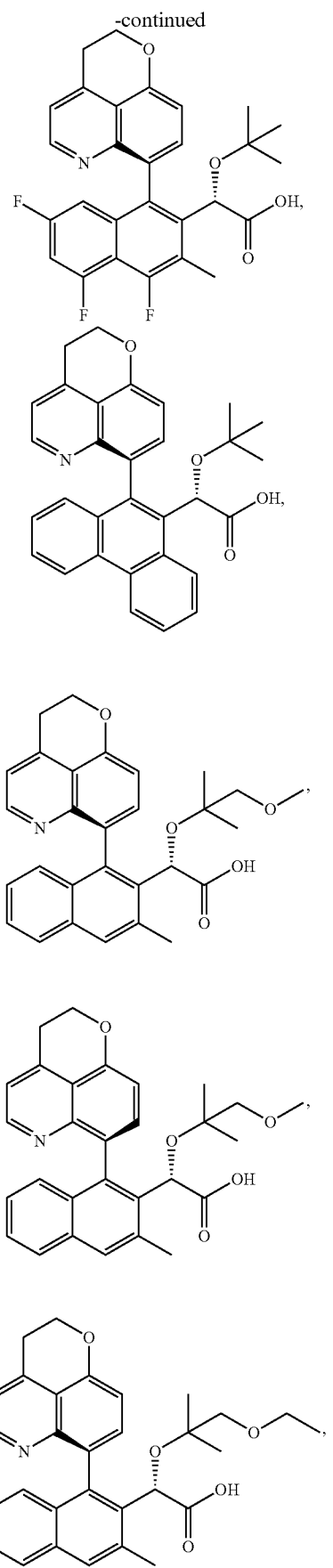

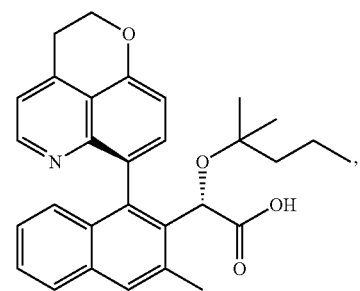
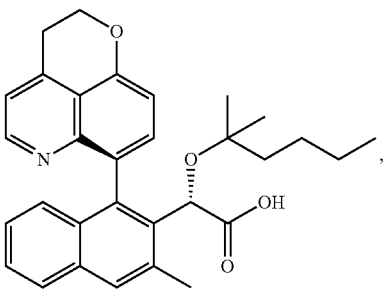
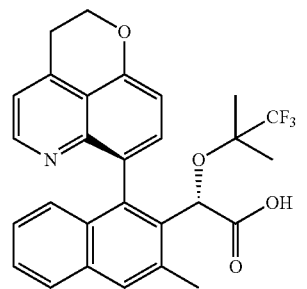
and
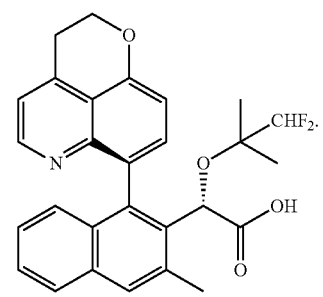
6. The compound of claim 1, or a pharmaceutically acceptable salt thereof, selected from the group consisting of:
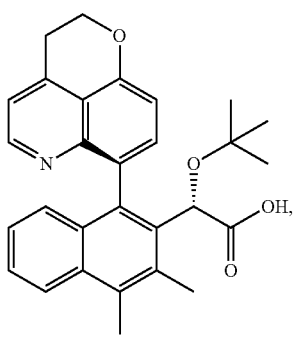
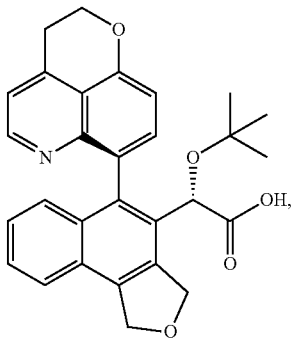
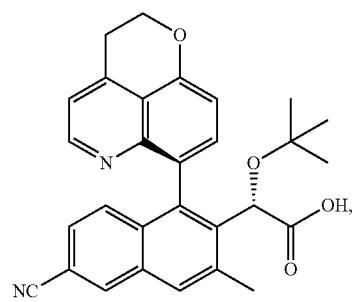
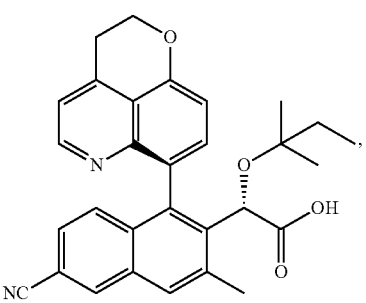
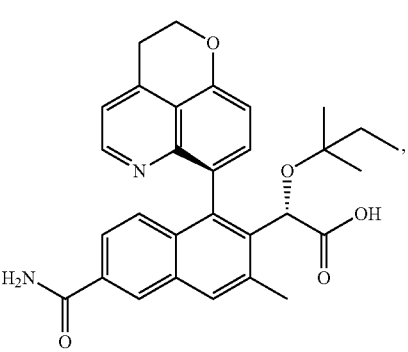
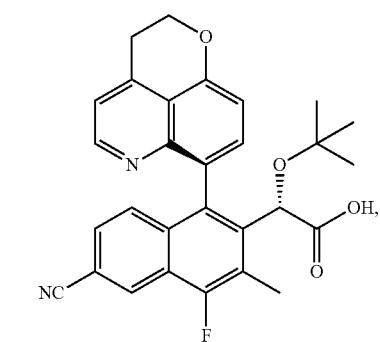

-continued
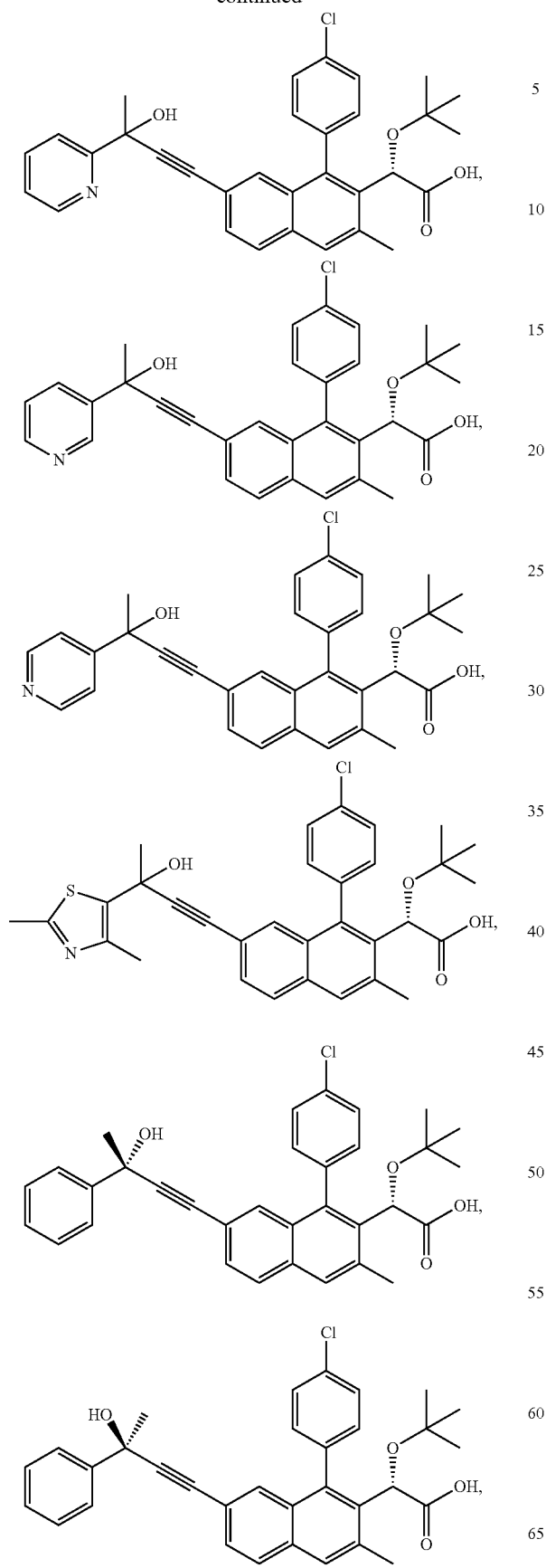
-continued
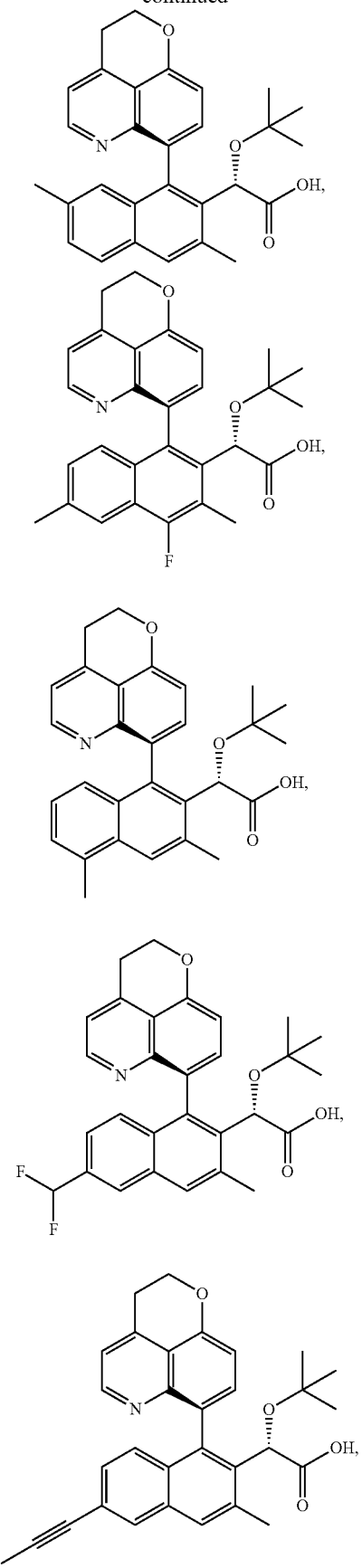

471
-continued
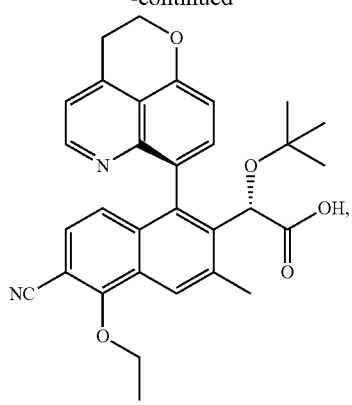
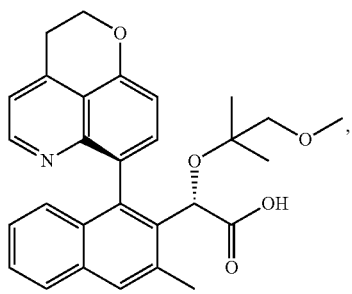
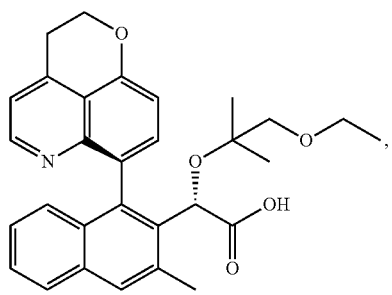
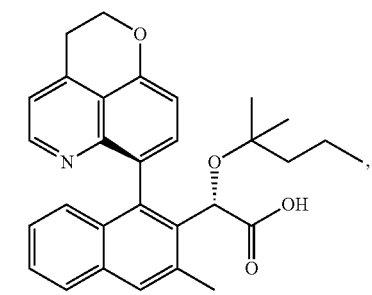
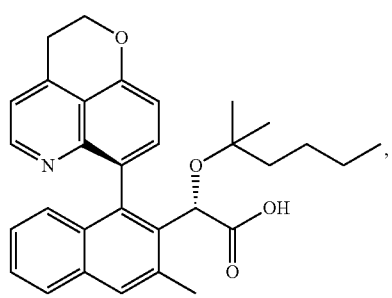
472
-continued
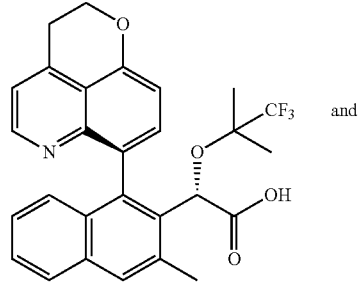
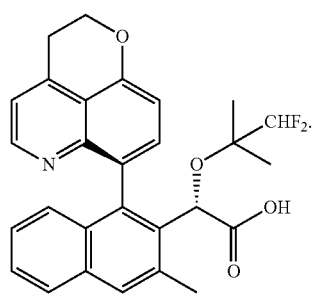
7. The compound of claim 1, or a pharmaceutically acceptable salt thereof, selected from the group consisting of:
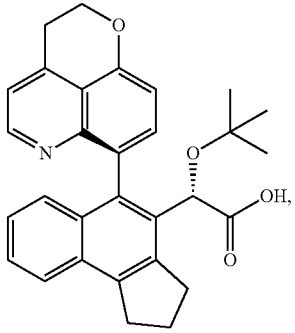
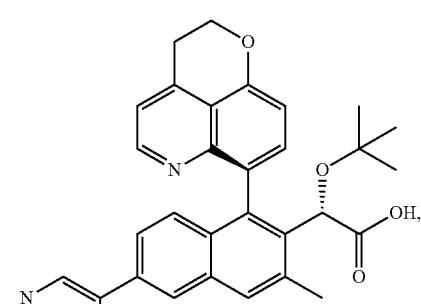
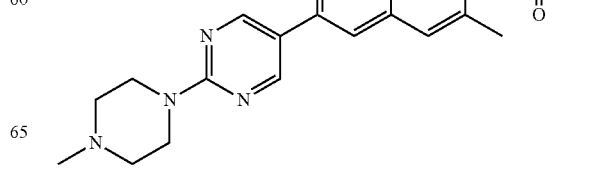

473
-continued
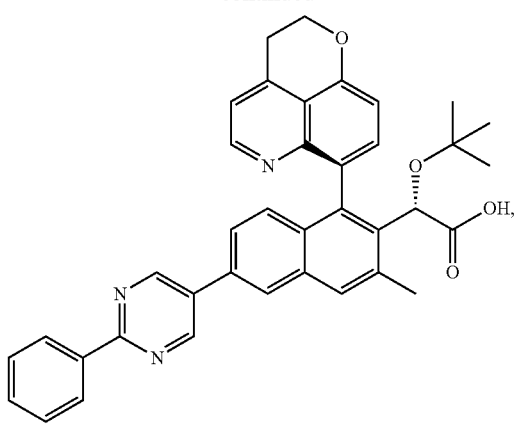
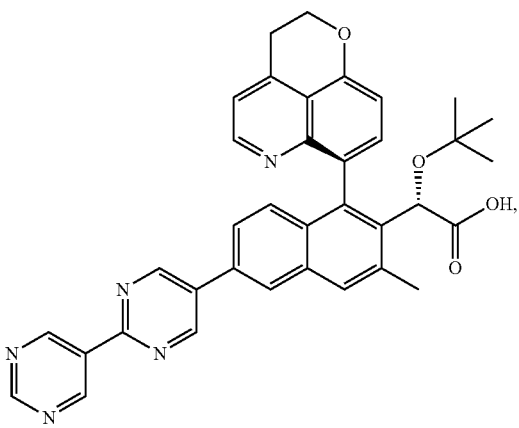
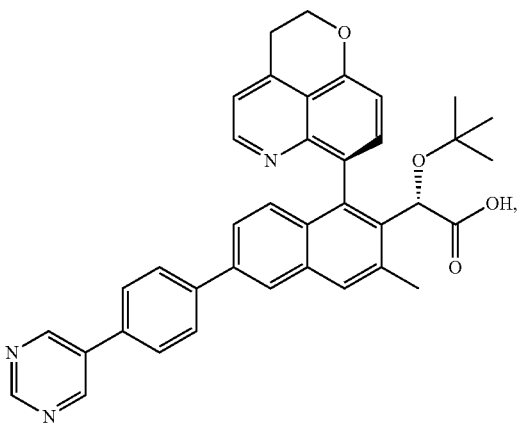
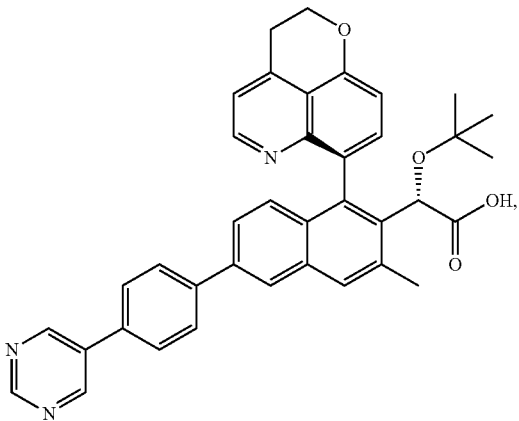
474
-continued
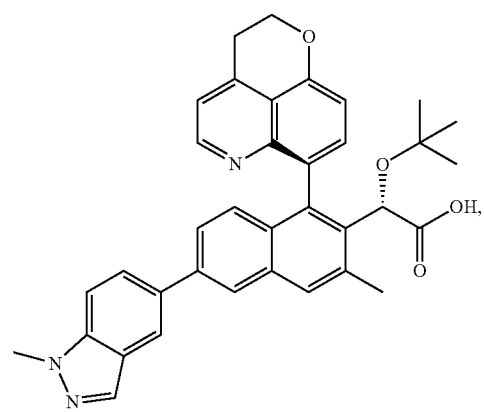
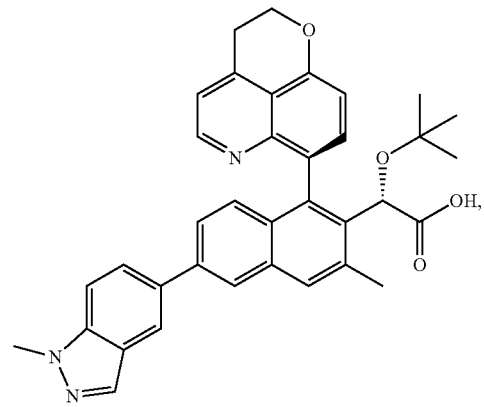
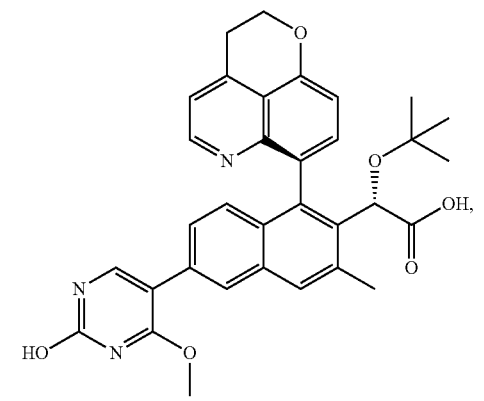

475
-continued
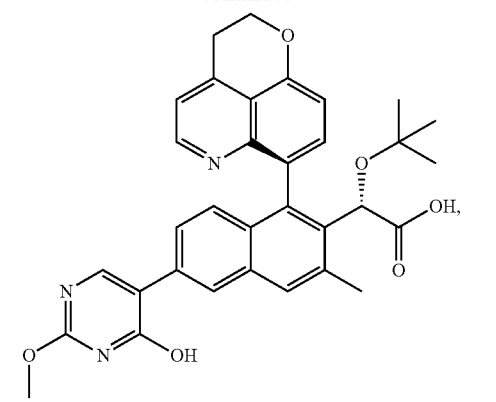
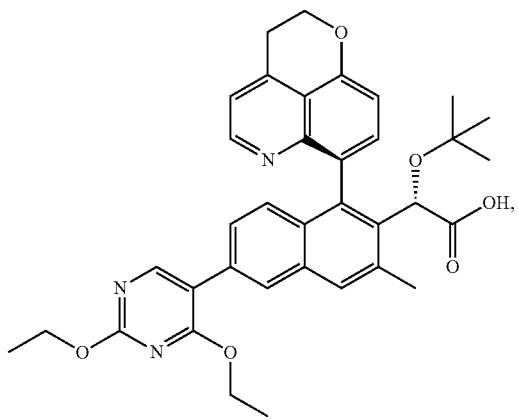
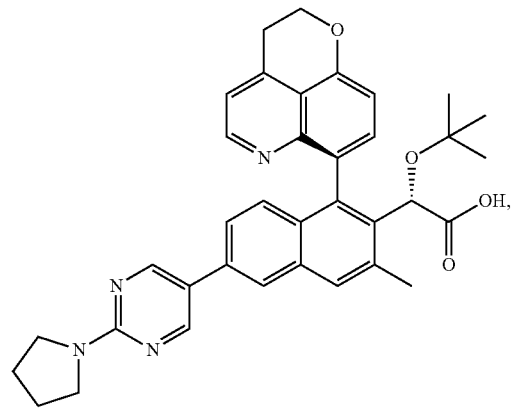
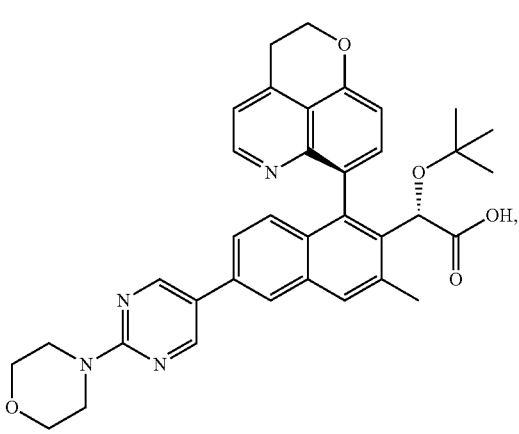
476
-continued
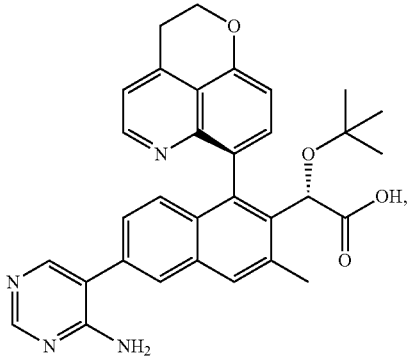
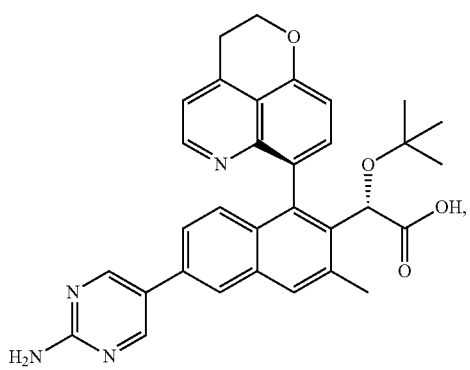
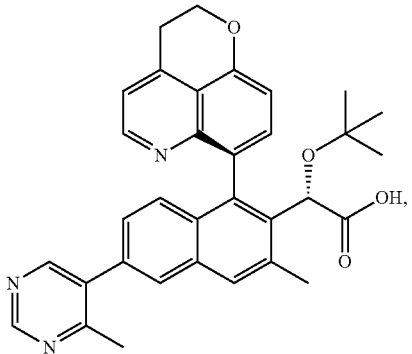
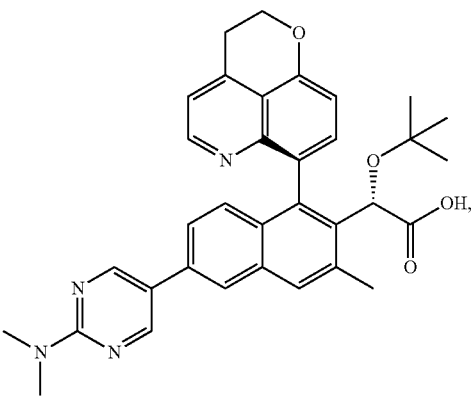

477
-continued
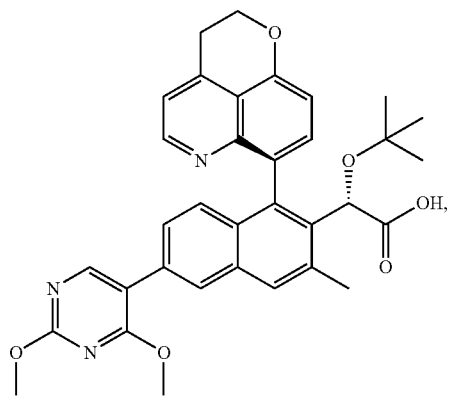
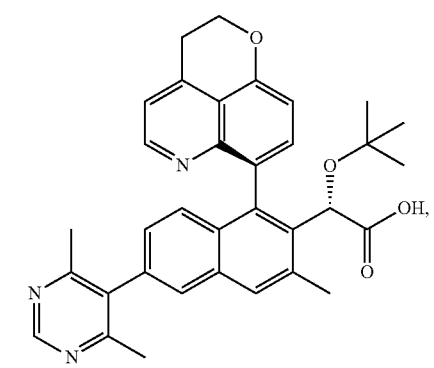
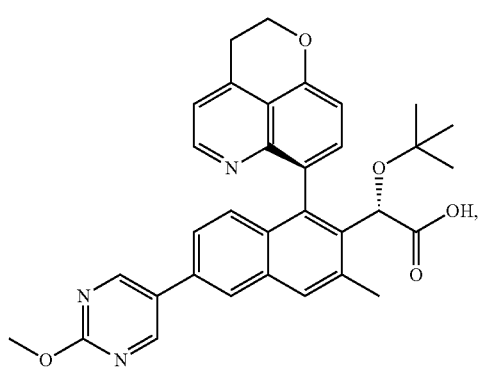
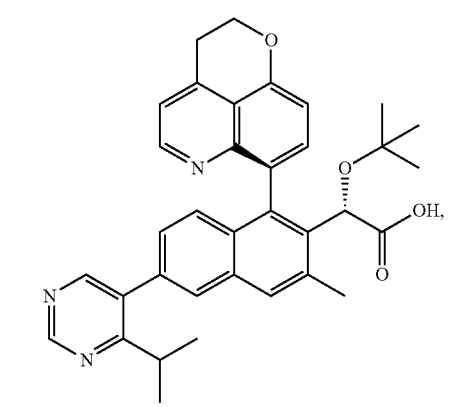
478
-continued
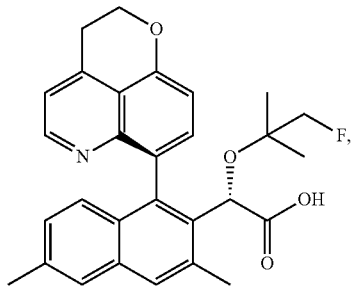
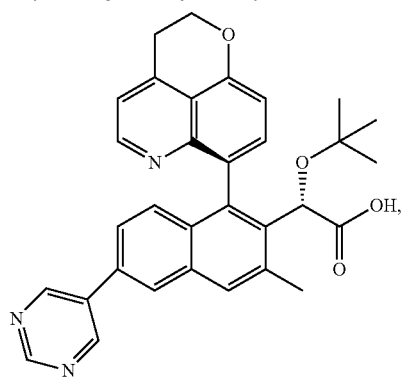
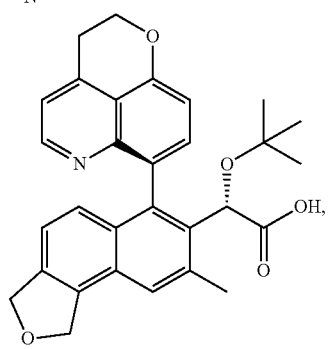
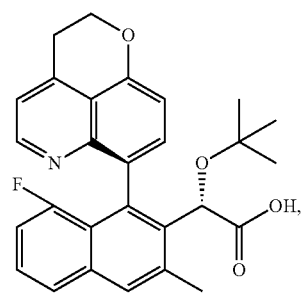
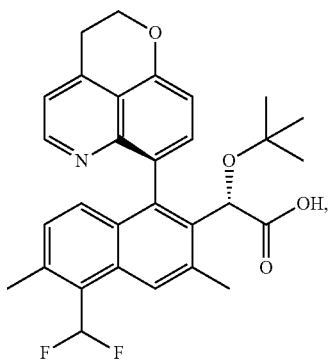

479
-continued
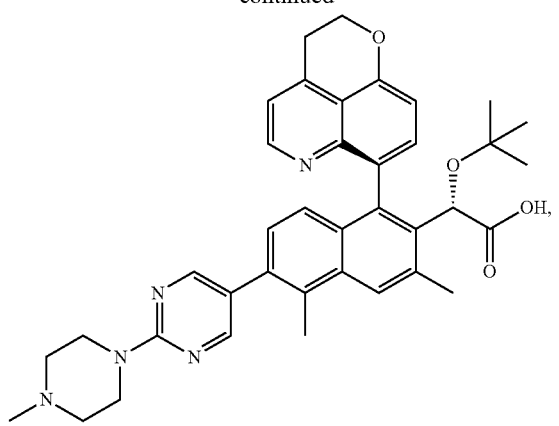
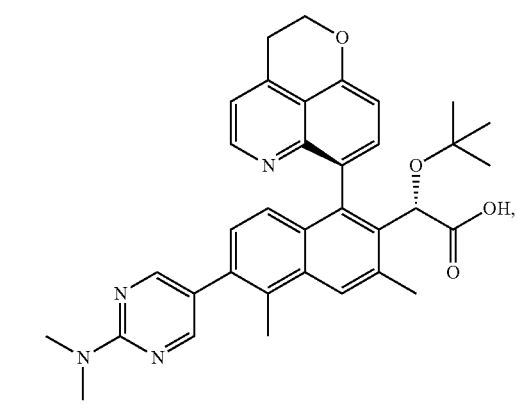
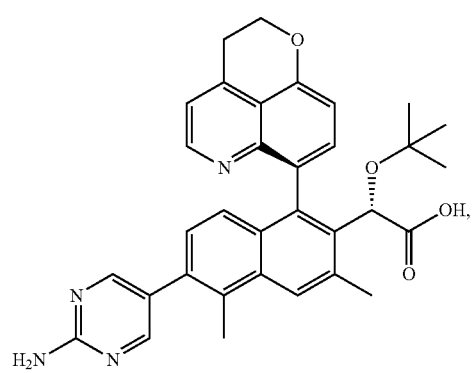
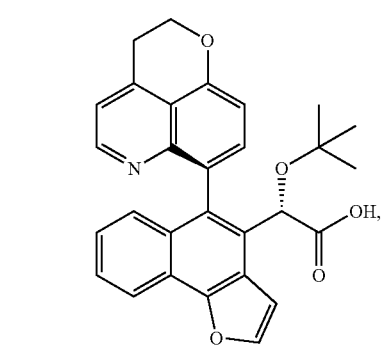
480
-continued
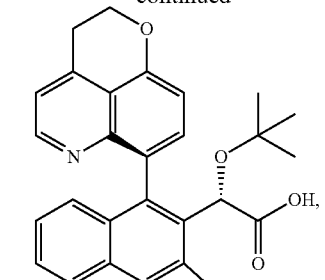
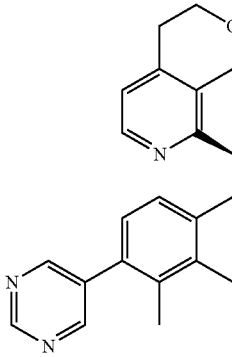
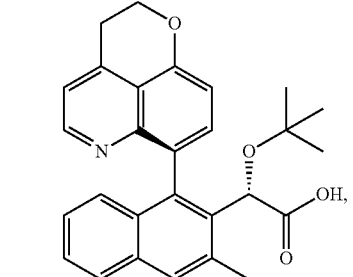
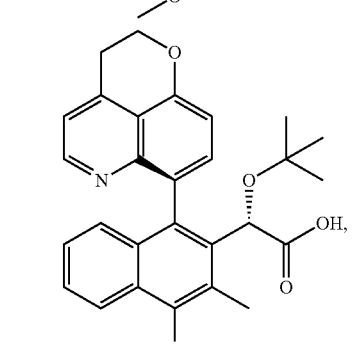
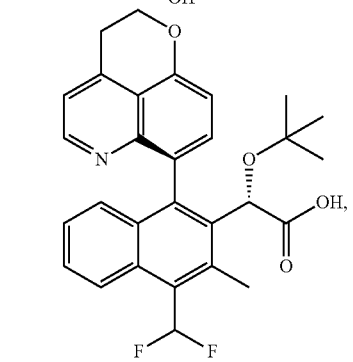

-continued
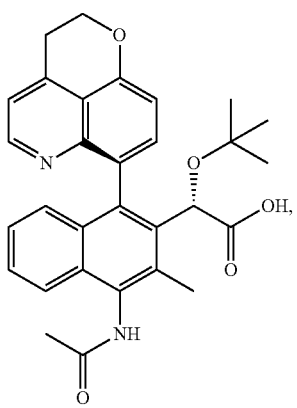
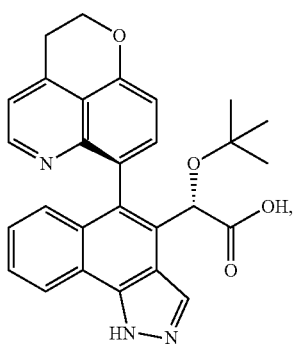
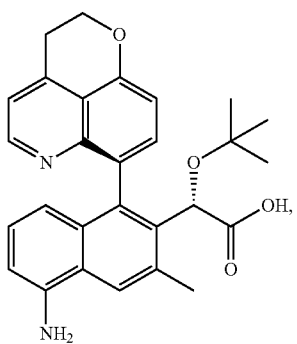
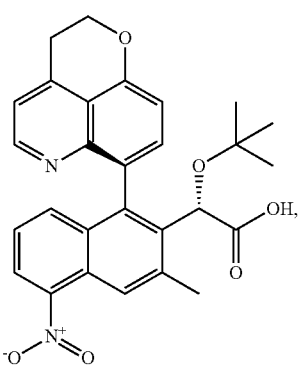
-continued
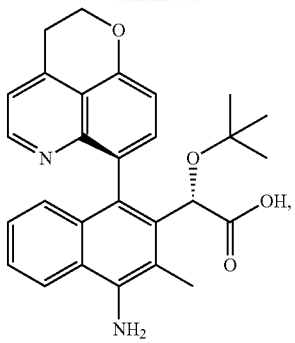
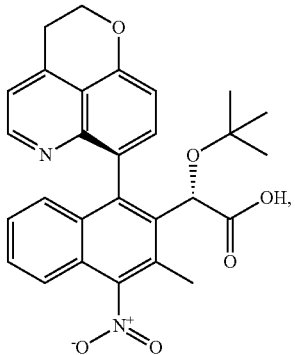
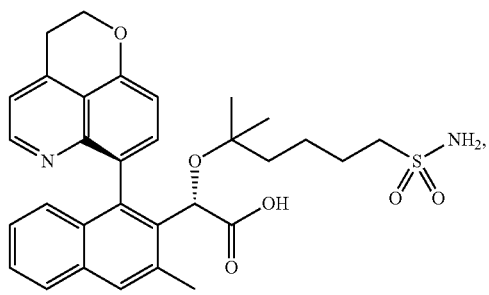
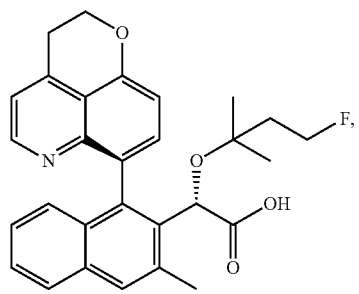
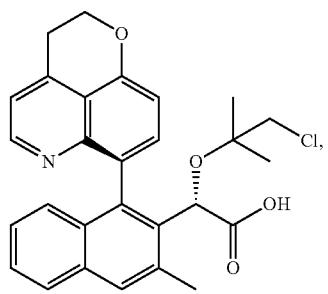

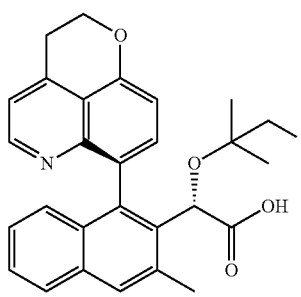
and
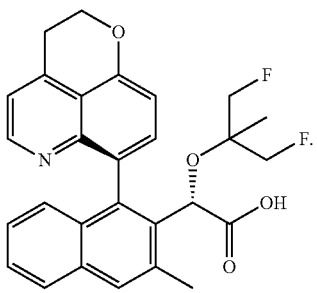
8. The compound of claim 1, or a pharmaceutically acceptable salt thereof, selected from the group consisting of:
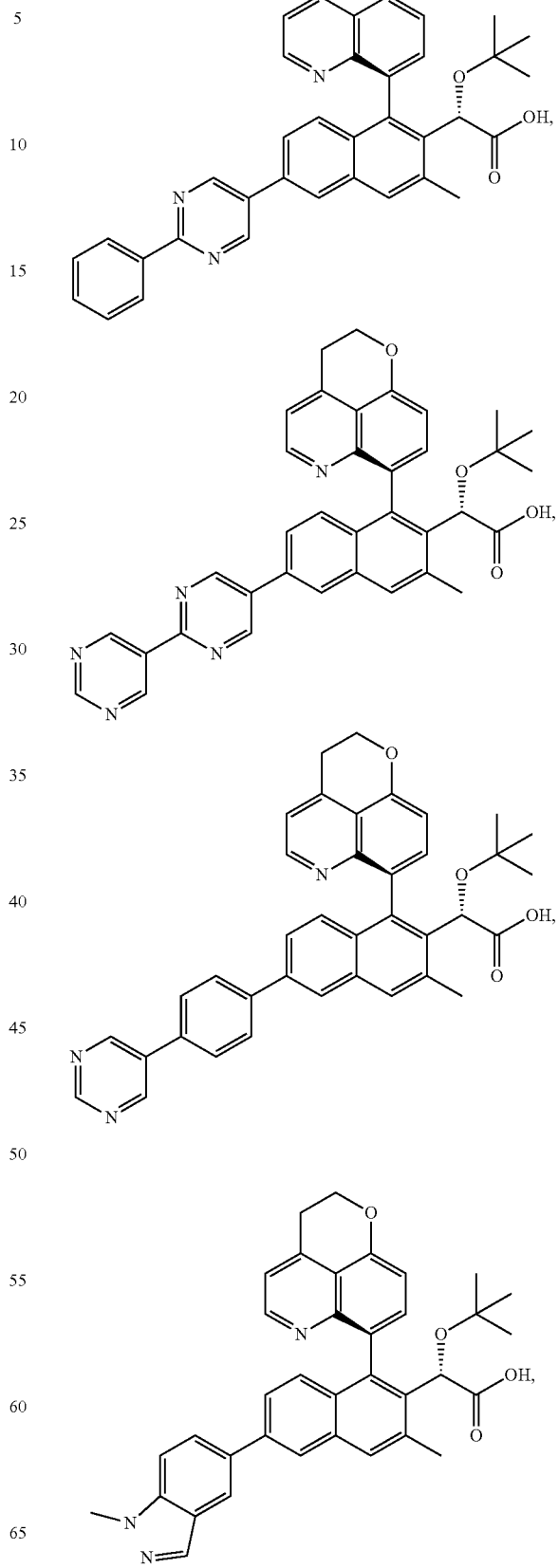

485
-continued
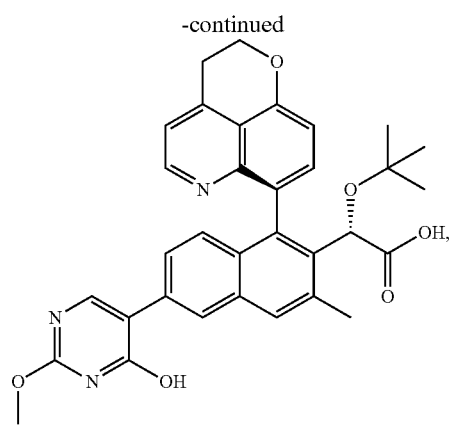
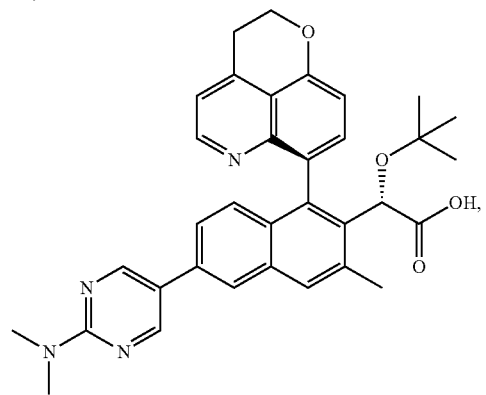
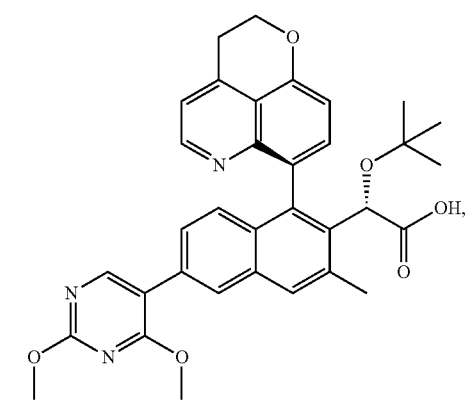
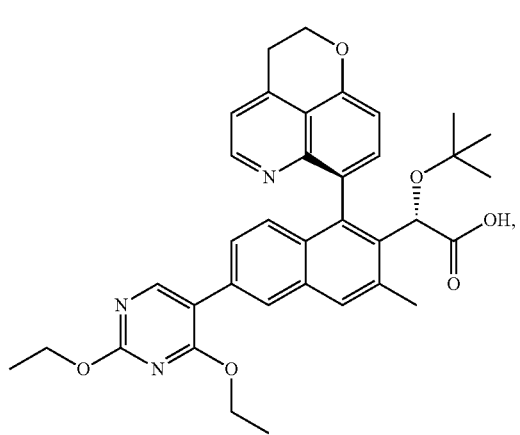
486
-continued
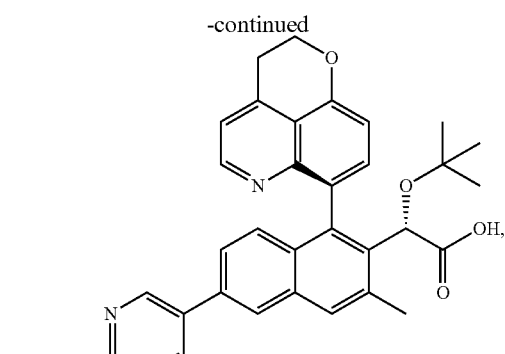
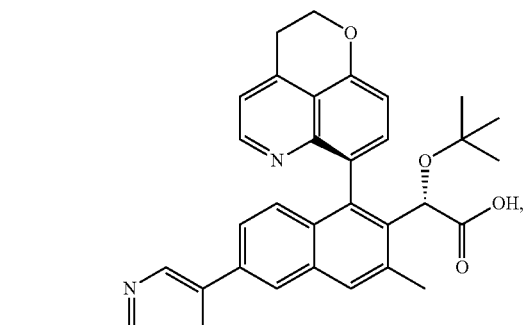
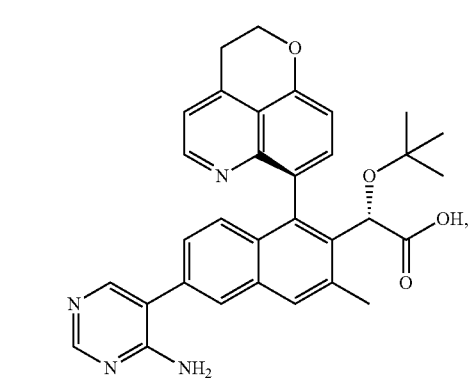
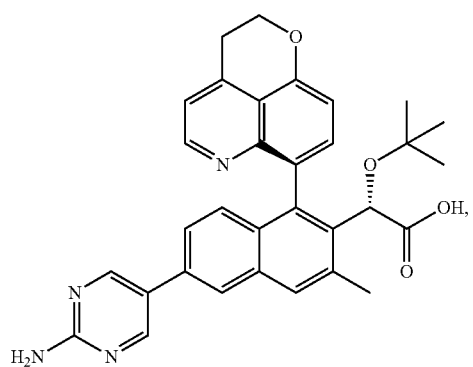

487
-continued
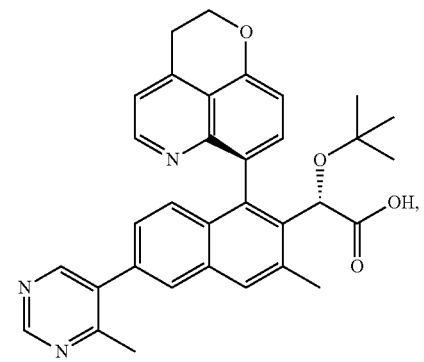
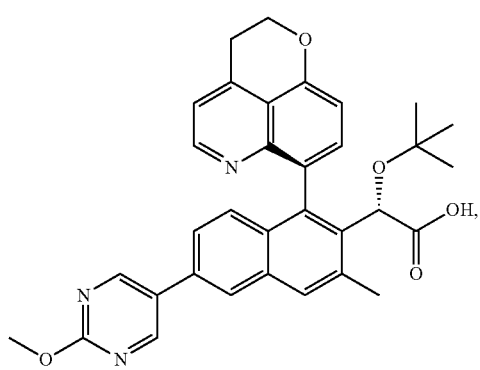
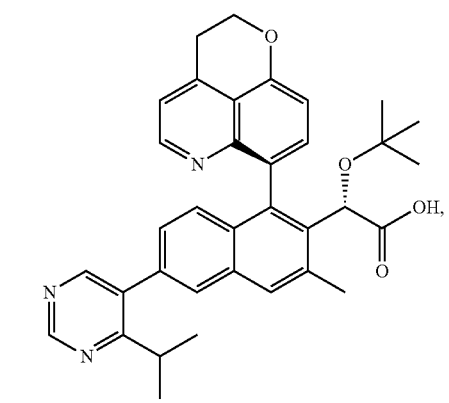
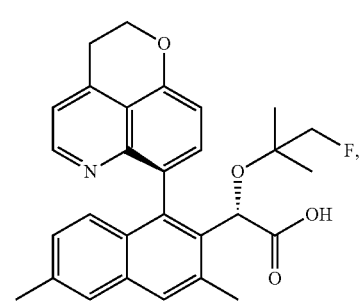
488
-continued
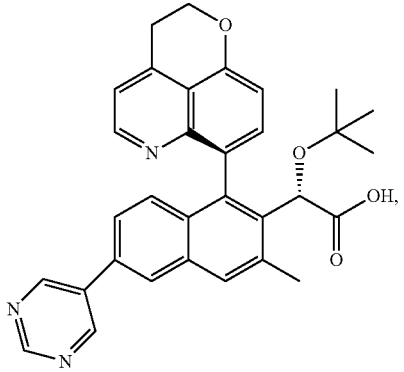
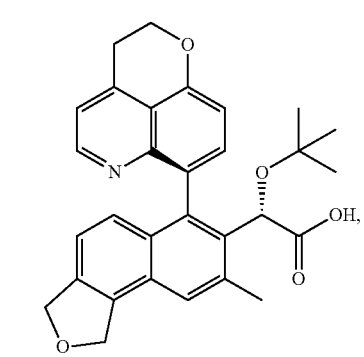
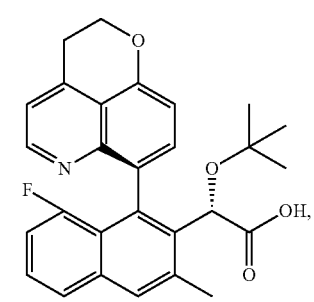
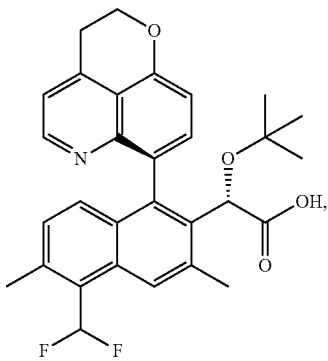

489
-continued
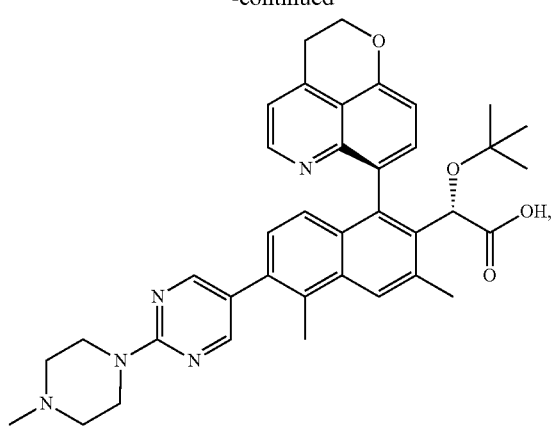
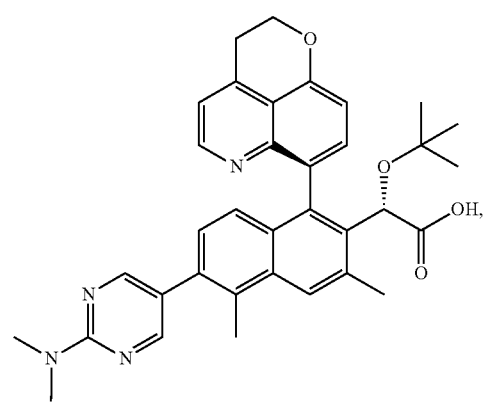
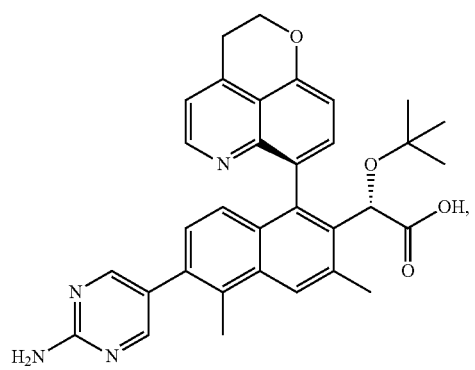
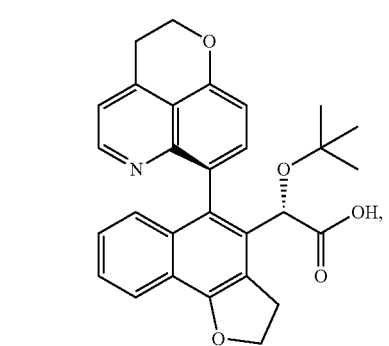
490
-continued
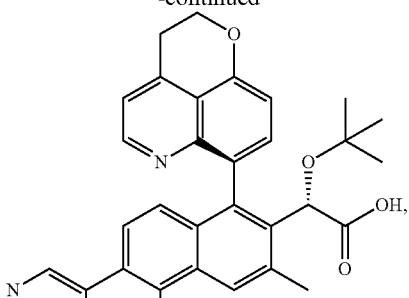
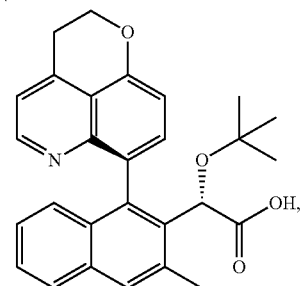
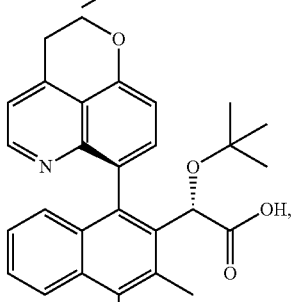
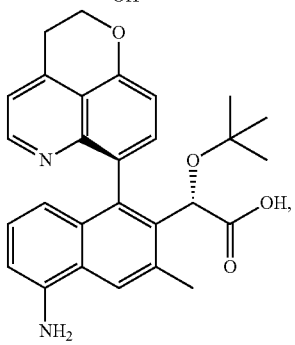

491
-continued
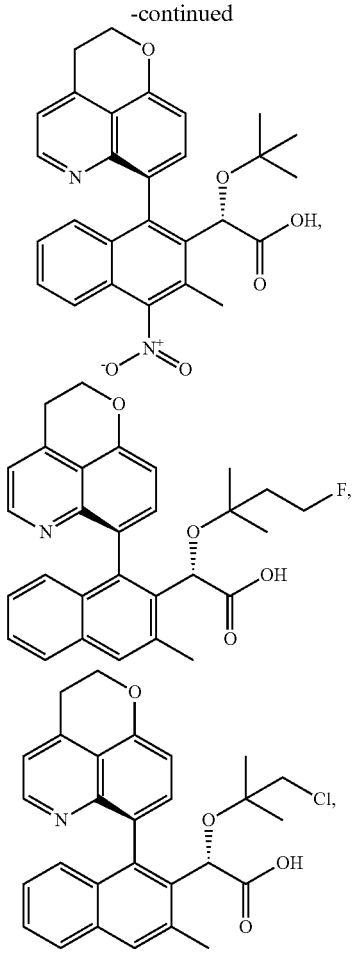
492
-continued
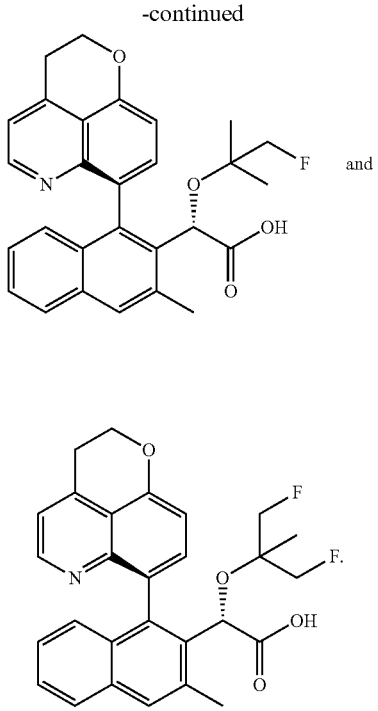
9. A pharmaceutical composition comprising a compound as described in claim 1, or a pharmaceutically acceptable salt thereof, and a pharmaceutically acceptable carrier.
10. A pharmaceutical composition comprising a compound as described in claim 2, or a pharmaceutically acceptable salt thereof, and a pharmaceutically acceptable carrier.
* * * * *